US011905281B2

(12) United States Patent
Lanman et al.

(10) Patent No.: US 11,905,281 B2
(45) Date of Patent: Feb. 20, 2024

(54) KRAS G12C INHIBITORS AND METHODS OF USING THE SAME

(71) Applicant: Amgen Inc., Thousand Oaks, CA (US)

(72) Inventors: Brian Alan Lanman, Thousand Oaks, CA (US); Jian Chen, Thousand Oaks, CA (US); Anthony B. Reed, Thousand Oaks, CA (US); Victor J. Cee, Thousand Oaks, CA (US); Longbin Liu, Thousand Oaks, CA (US); David John Kopecky, Thousand Oaks (CA); Patricia Lopez, Thousand Oaks, CA (US); Ryan Paul Wurz, Thousand Oaks, CA (US); Thomas T. Nguyen, Thousand Oaks, CA (US); Shon Booker, Thousand Oaks, CA (US); Nobuko Nishimura, Thousand Oaks, CA (US); Youngsook Shin, Thousand Oaks, CA (US); Nuria A. Tamayo, Thousand Oaks, CA (US); John Gordon Allen, Thousand Oaks, CA (US); Jennifer Rebecca Allen, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 260 days.

(21) Appl. No.: 17/031,607

(22) Filed: Sep. 24, 2020

(65) Prior Publication Data

US 2021/0009577 A1    Jan. 14, 2021

Related U.S. Application Data

(63) Continuation of application No. 16/661,907, filed on Oct. 23, 2019, now abandoned, which is a continuation of application No. 15/984,855, filed on May 21, 2018, now Pat. No. 10,519,146.

(60) Provisional application No. 62/509,629, filed on May 22, 2017.

(51) Int. Cl.
| | |
|---|---|
| *C07D 471/04* | (2006.01) |
| *C07D 213/82* | (2006.01) |
| *C07D 417/04* | (2006.01) |
| *A61K 38/07* | (2006.01) |
| *C07D 487/08* | (2006.01) |
| *C07D 417/12* | (2006.01) |
| *C07D 513/04* | (2006.01) |
| *C07D 487/10* | (2006.01) |
| *C07D 487/04* | (2006.01) |
| *C07D 401/04* | (2006.01) |
| *C07D 239/80* | (2006.01) |
| *C07D 401/14* | (2006.01) |
| *C07D 237/34* | (2006.01) |
| *C07D 403/04* | (2006.01) |
| *A61K 31/496* | (2006.01) |
| *A61K 31/416* | (2006.01) |
| *A61K 31/55* | (2006.01) |
| *A61K 31/454* | (2006.01) |
| *A61K 31/519* | (2006.01) |
| *A61K 31/502* | (2006.01) |
| *A61K 31/517* | (2006.01) |
| *A61K 31/5025* | (2006.01) |
| *A61P 35/00* | (2006.01) |
| *A61K 31/7068* | (2006.01) |

(Continued)

(52) U.S. Cl.
CPC .......... *C07D 417/04* (2013.01); *A61K 31/416* (2013.01); *A61K 31/454* (2013.01); *A61K 31/496* (2013.01); *A61K 31/502* (2013.01); *A61K 31/5025* (2013.01); *A61K 31/517* (2013.01); *A61K 31/519* (2013.01); *A61K 31/55* (2013.01); *A61K 31/7068* (2013.01); *A61K 38/07* (2013.01); *A61P 35/00* (2018.01); *C07D 237/34* (2013.01); *C07D 239/80* (2013.01); *C07D 275/04* (2013.01); *C07D 401/04* (2013.01); *C07D 401/14* (2013.01); *C07D 403/04* (2013.01); *C07D 417/12* (2013.01); *C07D 471/04* (2013.01); *C07D 475/00* (2013.01); *C07D 487/04* (2013.01); *C07D 487/08* (2013.01); *C07D 487/10* (2013.01); *C07D 513/04* (2013.01)

(58) Field of Classification Search
CPC ... C07D 213/82; C07D 471/04; C07D 487/04
See application file for complete search history.

(56) References Cited

U.S. PATENT DOCUMENTS

| | | | |
|---|---|---|---|
| 4,232,027 | A | 11/1980 | Turk et al. |
| 5,100,883 | A | 3/1992 | Schiehser |
| 5,118,677 | A | 6/1992 | Caufield |

(Continued)

FOREIGN PATENT DOCUMENTS

| | | |
|---|---|---|
| DE | 19629652 A1 | 1/1998 |
| EP | 0090505 A2 | 10/1983 |

(Continued)

OTHER PUBLICATIONS 4-methyl-2-(1-methylethyl)-3-Pyridinamine, STN Registry, CAS RN 1698293-93-4, STN entry date May 5, 2015 (May 5, 2015).

(Continued)

*Primary Examiner* — Noble E Jarrell
(74) *Attorney, Agent, or Firm* — Markus Bergauer

(57) ABSTRACT

Provided herein are KRAS G12C inhibitors, composition of the same, and methods of using the same. These inhibitors are useful for treating a number of disorders, including pancreatic, colorectal, and lung cancers.

16 Claims, No Drawings

(51) Int. Cl.
   *C07D 275/04* (2006.01)
   *C07D 475/00* (2006.01)

(56) References Cited

U.S. PATENT DOCUMENTS

| | | | |
|---|---|---|---|
| 5,118,678 A | 6/1992 | Kao et al. |
| 5,120,842 A | 6/1992 | Failli et al. |
| 5,151,413 A | 9/1992 | Caufield et al. |
| 5,256,790 A | 10/1993 | Nelson |
| 5,258,389 A | 11/1993 | Goulet et al. |
| 5,521,184 A | 5/1996 | Zimmerman |
| 5,650,415 A | 7/1997 | Tang et al. |
| 5,656,643 A | 8/1997 | Spada et al. |
| 5,712,291 A | 1/1998 | D'Amato |
| 5,728,813 A | 3/1998 | Lyman et al. |
| 5,747,498 A | 5/1998 | Schnur et al. |
| 5,770,599 A | 6/1998 | Gibson |
| 5,789,427 A | 8/1998 | Chen et al. |
| 5,792,783 A | 8/1998 | Tang et al. |
| 5,861,510 A | 1/1999 | Piscopio et al. |
| 5,863,949 A | 1/1999 | Robinson et al. |
| 5,892,112 A | 4/1999 | Levy et al. |
| 5,969,110 A | 10/1999 | Beckmann et al. |
| 5,981,245 A | 11/1999 | Fox et al. |
| 5,990,141 A | 11/1999 | Hirth et al. |
| 6,057,124 A | 5/2000 | Bartley et al. |
| 6,111,090 A | 8/2000 | Gorman et al. |
| 6,232,447 B1 | 5/2001 | Cerretti |
| 6,235,764 B1 | 5/2001 | Larson et al. |
| 6,258,812 B1 | 7/2001 | Bold et al. |
| 6,413,932 B1 | 7/2002 | Cerretti et al. |
| 6,515,004 B1 | 2/2003 | Misra et al. |
| 6,596,852 B2 | 7/2003 | Cerretti et al. |
| 6,630,500 B2 | 10/2003 | Gingrich et al. |
| 6,656,963 B2 | 12/2003 | Firestone et al. |
| 6,713,485 B2 | 3/2004 | Carter et al. |
| 6,727,225 B2 | 4/2004 | Wiley |
| 7,025,962 B1 | 4/2006 | Gorman et al. |
| 7,354,944 B2 | 4/2008 | Zeng et al. |
| 7,361,760 B2 | 4/2008 | Sircar et al. |
| 7,514,566 B2 | 4/2009 | Zeng et al. |
| 7,618,632 B2 | 11/2009 | Collins et al. |
| 7,700,636 B2 | 4/2010 | Monenschein et al. |
| 7,812,135 B2 | 10/2010 | Smith et al. |
| 7,897,619 B2 | 3/2011 | Zeng et al. |
| 7,919,504 B2 | 4/2011 | Zeng et al. |
| 7,919,514 B2 | 4/2011 | Monenschein et al. |
| 8,388,967 B2 | 3/2013 | Smith et al. |
| 8,586,023 B2 | 11/2013 | Shiku et al. |
| 8,591,886 B2 | 11/2013 | Ponath et al. |
| 10,519,146 B2 * | 12/2019 | Lanman ............... C07D 513/04 |
| 10,532,042 B2 | 1/2020 | Lanman et al. |
| 10,640,504 B2 | 5/2020 | Lanman et al. |
| 10,988,485 B2 | 4/2021 | Minatti et al. |
| 11,045,484 B2 | 6/2021 | Wurz et al. |
| 11,053,226 B2 | 7/2021 | Shin et al. |
| 11,090,304 B2 | 8/2021 | Allen et al. |
| 11,096,939 B2 | 8/2021 | Booker et al. |
| 11,236,091 B2 | 2/2022 | Chaves et al. |
| 11,285,135 B2 | 3/2022 | Lanman et al. |
| 11,285,156 B2 | 3/2022 | Allen et al. |
| 11,299,491 B2 | 4/2022 | Parsons et al. |
| 11,306,087 B2 | 4/2022 | Lanman et al. |
| 11,426,404 B2 | 8/2022 | Henary et al. |
| 11,439,645 B2 | 9/2022 | Lipford et al. |
| 2002/0042368 A1 | 4/2002 | Fanslow, III et al. |
| 2003/0105091 A1 | 6/2003 | Riedl et al. |
| 2003/0162712 A1 | 8/2003 | Cerretti et al. |
| 2009/0012085 A1 | 1/2009 | Baum et al. |
| 2009/0023761 A1 | 1/2009 | Chen et al. |
| 2009/0030002 A1 | 1/2009 | Chen et al. |
| 2009/0054405 A1 | 2/2009 | Booker et al. |
| 2009/0137581 A1 | 5/2009 | Chen et al. |
| 2009/0163489 A1 | 6/2009 | Booker et al. |
| 2009/0270445 A1 | 10/2009 | Zeng et al. |
| 2010/0273764 A1 | 10/2010 | Andrews et al. |
| 2010/0331293 A1 | 12/2010 | Chushing et al. |
| 2010/0331306 A1 | 12/2010 | Bui et al. |
| 2011/0092504 A1 | 4/2011 | Bo et al. |
| 2011/0097305 A1 | 4/2011 | Connors et al. |
| 2014/0288045 A1 | 9/2014 | Ren et al. |
| 2015/0239900 A1 | 8/2015 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2018/0015087 A1 | 1/2018 | Liu et al. |
| 2018/0072723 A1 | 3/2018 | Blake et al. |
| 2018/0177767 A1 | 6/2018 | Lanman et al. |
| 2018/0334454 A1 | 11/2018 | Lanman et al. |
| 2019/0077801 A1 | 3/2019 | Lanman et al. |
| 2019/0336514 A1 | 11/2019 | Wurz et al. |
| 2019/0343838 A1 | 11/2019 | Allen et al. |
| 2019/0345169 A1 | 11/2019 | Minatti et al. |
| 2019/0374542 A1 | 12/2019 | Allen et al. |
| 2019/0375749 A1 | 12/2019 | Chen et al. |
| 2020/0030324 A1 | 1/2020 | Booker et al. |
| 2020/0055845 A1 | 2/2020 | Lanman et al. |
| 2020/0069657 A1 | 5/2020 | Lanman et al. |
| 2020/0165231 A1 | 5/2020 | Shin et al. |
| 2020/0207766 A1 | 7/2020 | Lanman et al. |
| 2020/0216446 A1 | 7/2020 | Parsons et al. |
| 2020/0222407 A1 | 7/2020 | Lipford et al. |
| 2020/0360374 A1 | 11/2020 | Henary et al. |
| 2020/0369662 A1 | 11/2020 | Chaves et al. |
| 2022/0002298 A1 | 1/2022 | Chen et al. |
| 2022/0106313 A1 | 4/2022 | Chaves et al. |
| 2022/0168280 A1 | 6/2022 | Lanman et al. |
| 2022/0175782 A1 | 6/2022 | Allen et al. |
| 2022/0213101 A1 | 7/2022 | Lanman et al. |
| 2022/0220112 A1 | 7/2022 | Parsons et al. |
| 2022/0235045 A1 | 7/2022 | Chaves et al. |
| 2022/0378787 A1 | 12/2022 | Henary et al. |
| 2022/0395504 A1 | 12/2022 | Allen et al. |
| 2023/0028414 A1 | 1/2023 | Henary et al. |
| 2023/0121955 A1 | 4/2023 | Lipford et al. |

FOREIGN PATENT DOCUMENTS

| | | |
|---|---|---|
| EP | 404355 A1 | 12/1990 |
| EP | 511792 A2 | 11/1992 |
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1999 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 3401314 A1 | 11/2019 |
| EP | 3055290 B1 | 12/2019 |
| JP | 02233610 A | 9/1990 |
| JP | 2019031476 A | 2/2019 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002136 A1 | 2/1994 |
| WO | 1994002485 A1 | 2/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |

(56) References Cited

FOREIGN PATENT DOCUMENTS

| | | |
|---|---|---|
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 1/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1998034918 A1 | 8/1998 |
| WO | 1999007675 A1 | 2/1999 |
| WO | 1999007701 A1 | 2/1999 |
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |
| WO | 1999052889 A1 | 10/1999 |
| WO | 1999052910 A1 | 10/1999 |
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2004063195 A1 | 7/2004 |
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2008118454 A2 | 10/2008 |
| WO | 2008118455 A1 | 10/2008 |
| WO | 2008118468 A1 | 10/2008 |
| WO | 2008153947 A2 | 12/2008 |
| WO | 2009036082 A2 | 3/2009 |
| WO | 2009055730 A1 | 4/2009 |
| WO | 2009085185 A1 | 7/2009 |
| WO | 2010003118 A1 | 1/2010 |
| WO | 2010083246 A1 | 7/2010 |
| WO | 2010096314 A1 | 8/2010 |
| WO | 2010108074 A2 | 9/2010 |
| WO | 2010126895 A1 | 11/2010 |
| WO | 2010132598 A1 | 11/2010 |
| WO | 2010149786 A1 | 12/2010 |
| WO | 2010151735 A2 | 12/2010 |
| WO | 2010151737 A2 | 12/2010 |
| WO | 2010151740 A2 | 12/2010 |
| WO | 2010151791 A1 | 12/2010 |
| WO | 2011028683 A1 | 3/2011 |
| WO | 2011031842 A1 | 3/2011 |
| WO | 2011051726 A2 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014023385 A1 | 2/2014 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |
| WO | 2015109285 A1 | 7/2015 |
| WO | 2016035008 A1 | 3/2016 |
| WO | 2016044772 A1 | 3/2016 |
| WO | 2016049524 A1 | 3/2016 |
| WO | 2016049565 A1 | 3/2016 |
| WO | 2016049568 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A2 | 6/2018 |
| WO | 2018119183 A3 | 6/2018 |
| WO | 2018140598 A1 | 8/2018 |
| WO | 2018217651 A1 | 11/2018 |
| WO | 2018218069 A1 | 11/2018 |
| WO | 2019051291 A1 | 3/2019 |
| WO | 2019213516 A1 | 11/2019 |
| WO | 2019213526 A1 | 11/2019 |
| WO | 2019217691 A1 | 11/2019 |
| WO | 2019232419 A1 | 12/2019 |
| WO | 2019241157 A1 | 12/2019 |
| WO | 2019243533 A1 | 12/2019 |
| WO | 2019243535 A1 | 12/2019 |
| WO | 2020050890 A2 | 3/2020 |
| WO | 2020102730 A1 | 5/2020 |
| WO | 2020106640 A1 | 5/2020 |
| WO | 2020232130 A1 | 11/2020 |
| WO | 2020236947 A1 | 11/2020 |
| WO | 2020236948 A1 | 11/2020 |
| WO | 2021081212 A1 | 4/2021 |
| WO | 2021097207 A1 | 5/2021 |
| WO | 2021097212 A1 | 5/2021 |
| WO | 2021126816 A1 | 6/2021 |
| WO | 2002006213 A2 | 1/2022 |

(56) References Cited

OTHER PUBLICATIONS

Hirayama, "Handbook for Making Crystal of Organic Compound,— Principles and Know-how-", Maruzen Co., Ltd., Jul. 25, 2008, pp. 57-84 (incl. English translation).
International Search Report for PCT/US2020/056874, dated Feb. 12, 2021, 7 pages.
International Search Report for PCT/US2020/060415, dated Feb. 3, 2021, 7 pages.
International Search Report for PCT/US2020/065050, dated Mar. 29, 2021, 7 pages.
Kojima, "Aiming to Improve the Efficiency of Crystallization Selection in Drug Development", Pharmaceutics, Sep. 1, 2008, vol. 68, No. 5, pp. 344-349 (incl. English translation).
Noriyuki, "API Form Screening and Selection at the Drug Discovery Stage", Pharm Stage, vol. 6, No. 10, Jan. 15, 2007, pp. 20-25 (incl. English translation).
Notice of Allowance dated Jun. 30, 2021 for U.S. Appl. No. 16/438,349, pp. 1-9.
Notice of Allowance, dated Apr. 19, 2021, for U.S. Appl. No. 16/428,163, 9 pages.
Notice of Allowance, dated Sep. 22, 2021, for U.S. Appl. No. 16/878,824, 8 pages.
Notice of Allowance, dated Sep. 9, 2021, for U.S. Appl. No. 16/675,121, 7 pages.
PubChem CID 108190520, 2-isopropyl-4-methylpyridin-3-amine, available at https://pubchem.ncbi.nlm.nih.gov/compound/108190520 (last accessed Aug. 30, 2021).
Written Opinion for PCT/US2020/056874, dated Feb. 12, 2021, 10 pages.
Written Opinion for PCT/US2020/060415, dated Feb. 3, 2021, 9 pages.
Written Opinion for PCT/US2020/065050, dated Mar. 29, 2021, 8 pages.
Notice of Allowance, dated Oct. 20, 2021, for U.S. Appl. No. 16/438,349, 9 pages.
Final Office Action for U.S. Appl. No. 16/436,647, dated Mar. 24, 2021, 7 pages.
Notice of Allowance, dated Mar. 30, 2021, for U.S. Appl. No. 16/402,538, 8 pages.
"A Phase 1/2, Study Evaluating the Safety, Tolerability, PK, and Efficacy of AMG 510 in Subjects With Solid Tumor With a Specific KRAS Mutation (CodeBreak 100)," Clinical Trials Identifier NCT03600883 (2018).
"Acute Leukemia," *The Merck Manual* (Online Edition), pp. 1-6 (2013).
"KRASG12C Inhibitor," Mirati Therapeutics, retrieved on Nov. 27, 2018, from https://www.mirati.com/mrtx849/, 5 pages.
Ahmadian, et al., "Guanosine triphosphatase stimulation of oncogenic Ras mutants," *PNAS*, 96: 7065-7070, 1999.
Airoldi, et al., "Glucose-Derived Ras Pathway Inhibitors: Evidence of Ras-Ligand Binding and Ras-GEF (Cdc25) Interaction Inhibition," *ChemBioChem*, 8: 1376-1379 (2007).
ATTC "Organism: Mus musculus (B cell); Mus musculus (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.
Barnett, et al., "Identification and characterization of pleckstrin-holomogy-domain- dependent and isoenzyme specific Akt inhibitors," *Biochem. J.*, 385 (2): 399-408 (2005).
Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).
Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).
Canon, et al., "The clinical KRAS(G12C) inhibitor AMG 510 drives anti-tumour immunity," *Nature*, 575(7781): 217-223 (2019).

*Cecil Textbook of Medicine*, edited by Bennett, J.C., and Plum, F., 20th edition, vol. 1: 1004-1010 (1996).
Cohen, "The development and therapeutic potential of protein kinase inhibitors," *Current Opinion in Chemical Biology*, 3:459-465 (1999).
Cowen Slide deck -Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).
Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res.* 10(15): 5242-5252 (2004).
Dermer, et al., "Another Anniversary for the War on Cancer," *Bio/Technology*, 12: 320 (1994).
Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).
Erkkilä, et al., "Mild Organocatalytic a-Methylenation of Aldehydes," *J. Org. Chem.*, 71 (6), 2538-2541 (2006).
Freshney, et al., Culture of Animal Cells, *A Manual of Basic Technique*, Alan R. Liss, Inc, New York, p. 4 (1983).
Gentile, et al., "Discovery and Structural Investigation of Novel Binders to the Ras Switch II Pocket," NCI Initiative Symposium Poster (2015).
Gills and Dennis, "The development of phosphatidylinositol ether lipid analogues as inhibitors of the serine/threonine kinase, Akt," *Expert. Opin. Investig. Drugs*, 13: 787-797 (2004).
Goldberg, et al., "Role of PD-1 and its ligand, B7-H1, in early fate decisions of CD8 T cells," *Blood*,110(1): 186-192 (2007).
Goldstein, et al., "Biological efficacy of a chimeric antibody to the epidermal growth factor receptor in a human tumor xenograft model," *Clin. Cancer Res.*, 1: 1311-1318 (1995).
Govindan, et al., "Phase 1 Study of AMG 510, a Novel Kras G12C Inhibitor, in Advanced Solid Tumors with KRAS p.G12C Mutation," Poster, ESMO Congress, Barcelona, Spain, Sep. 27, 2019-Oct. 1, 2019.
Gura, "Cancer Models: Systems for Identifying New Drugs are Often Faulty," Science, 278(5340): 1041-1042 (1997).
Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).
Hansen, et al., "Abstract 686: Drugging an undruggable pocket: the biochemical mechanism of covalent KRAS$^{G12C}$ inhibitors," Proceedings of the American Association for Cancer Research Annual Meeting 2018; Apr. 14-18, 2018; Chicago, IL; AACR; *Cancer Res.*, 78(13 Suppl): Abstract 686 (2018).
Hichri, et al., "A Convenient Synthesis of 1,3,2-Benzodiazaphophorine-2-Oxide," *Phosphorus, Sulfur, and Silicon*, 190: 29-35 (2015).
Hichri, et al., CAPLUS Abstract, 162:245378 (2015).
Hocker, et al., "Andrographolide derivatives inhibit guanine nucleotide exchange and abrogate oncogenic Ras function," *PNAS*, 110(25): 10201-10206 (2013).
Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).
International Search Report for PCT/US2017/067801, dated Jul. 25, 2018, 6 pages.
International Search Report for PCT/US2018/033714, dated Jul. 17, 2018, 3 pages.
International Search Report for PCT/US2018/050044, dated Oct. 30, 2018, 7 pages.
International Search Report for PCT/US2019/030593, dated Aug. 6, 2019, 4 pages.
International Search Report for PCT/US2019/030606, dated Jul. 23, 2019, 5 pages.
International Search Report for PCT/US2019/031535, dated Jul. 25, 2019, 7 pages.
International Search Report for PCT/US2019/034974, dated Aug. 9, 2019, 5 pages.
International Search Report for PCT/US2019/036397, dated Aug. 26, 2019, 5 pages.

(56) References Cited

OTHER PUBLICATIONS

Janes, et al., "Targeting KRAS Mutant Cancers with a Covalent G12C-Specific Inhibitor," *Cell*, 172: 578-589 (2018).
Jarvis, "Notorious KRAS: Taking down cancer researchers' biggest foe," *Chemical & Engineering News*, 97(37), 9 pages (2019).
Jin, et al., "Inhibition of AKT survival pathway by a small molecule inhibitor in human endometrial cancer cells," *Br. J. Cancer*, 91: 1808-1812 (2004).
Johnson et al., "Relationships between drug activity in NCI preclinical in vitro and in vivo models and early clinical trials," *British Journal of Cancer*, 84(10): 1424-1431 (2001).
Lanman, et al., "Discovery of a Covalent Inhibitor of KRAS$^{G12C}$ (AMG 510) for the Treatment of Solid Tumors," *J. Med. Chem.*, 63: 52-65 (2020).
Lim, et al., "Therapeutic Targeting of Oncogenic K-Ras by a Covalent Catalytic Site Inhibitor," *Angew. Chem. Int. Ed*, 53: 199-204 (2014).
Liu, Y., "Session SY28—Transformative Small Molecule Therapies—Targeting KRAS mutant cancers with a covalent G12C—specific inhibitor," Presentation on Apr. 4, 2017, AACR Annual Meeting Presentation, Apr. 1-5, 2017, Washington, D.C. (2017).
Lu, et al., "KRAS G12C Drug Development: Discrimination between Switch II Pocket Configurations Using Hydrogen/Deuterium-Exchange Mass Spectrometry," *Structure*, 25: 1-7 (2017).
Maurer, et al., "Small-molecule ligands bind to a distinct pocket in Rad and inhibit SOS-mediated nucleotide exchange activity," *PNAS*, 109(14): 5299-5304 (2012).
McGregor, et al., "Expanding the Scope of Electrophiles Capable of Targeting K-Ras Oncogenes," *ACS Bio. Chem.*, 56: 3179-3183 (2017).
Mirati Therapeutics, "Corporate Presentation Nov. 2017," Slides 1-41 (2017).
Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).
National Cancer Institute identifier: NSC 154020, retrieved on Nov. 29, 2018, from https://cactus.nci.nih.gov/ncidb2.2/.
NCBI Reference Sequence, "GTPase KRas isoform a [*Homo sapiens*]," GenBank Accession No. NM 203524.1, Retrieved on Nov. 29, 2018 from https://www.ncbi.nlm.nih.gov/protein/15718763?sat=4&satkey=234448549, 4 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).
Paez, et al., "EGFR Mutations in Lung Cancer Correlation with Clinical Response to Gefitinib Therapy," *Science*, 304(5676): 1497-500 (2004).
Palmioli, et al., "First experimental identification of Ras-inhibitor binding interface using a water-soluble Ras ligand," *Bioorg. Med. Chem. Lett.*, 19: 4217-4222 (2009).
Patricelli, et al., "Selective Inhibition of Oncogenic KRAS Output with Small Molecules Targeting the Inactive State," *Cancer Discov*, 6 (3): 316-329 (2016).
Pearce, et al., "Failure modes in anticancer drug discovery and development," *Cancer Drug Design and Discovery*, Edited by Stephen Neidle, Chapter 18, pp. 424-435 (2008).
Peri, et al., "Design, Synthesis and Biological Evaluation of Sugar-Derived Ras Inhibitors," *ChemBioChem*, 6: 1839-1848 (2005).
Peri, et al., "Sugar-Derived Ras Inhibitors: Group Epitope Mapping by NMR Spectroscopy and Biological Evaluation," *Eur. J. Org. Chem.*, 16: 3707-3720 (2006).
Peters, et al., "Selective inhibition of K-Ras G12C through allosteric control of GTP affinity and effector interactions," EORTC Poster (2013).
Remington's Pharmaceutical Sciences, 1435-1712 (18th ed., Mack Publishing Co, Easton, Pennsylvania, 1990 (Table of Contents Only).
Rex et al., "KRAS-AACR 2018," Amgen Collection of Information published at Proceedings of the American Association for Cancer Research Annual Meeting 2018; Apr. 14-18, 2018; Chicago, IL; AACR; slides 1-24 (2018).
Sarkar, et al., "Indole-3-Carbinol and Prostate Cancer[1,2]," *J. Nutr.*, 134(12 Suppl): 3493S-3498S (2004).
Shima, et al., "In silico discovery of small-molecule Ras inhibitors that display antitumor activity by blocking the Ras-effector interaction," *PNAS*, 110(20): 8182-8187 (2013).
Simone, "Part XIV Oncology: Introduction," *Cecil Textbook of Medicine*, 20th Edition, 1:1004-1010 (1996).
Singh, et al., "Improving Prospects for Targeting RAS," *J. Clinc. Oncl*, 33(31): 3650-3660 (2015).
Sun, et al., "Discovery of Small Molecules that Bind to K-Ras and Inhibit Sos-Mediated Activation," *Angew. Chem. Int. Ed.*, 51: 6140-6143 (2012).
Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.*,, 5(1): 125-133 (1997).
Teramoto, et al., 1996, Cancer 77 (4):639-645.
The ASCO Post Staff, "AACR-NCI-EORTC: Investigational Kras G12C Inhibitor for KRAS-Mutant Solid Tumors," The ASCO Post (2019).
Thompson, et al., "PD-1 is Expressed by Tumor-Infiltrating Immune Cells and is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part II)," *Exp. Opin. Ther. Patents*, 8(12): 1599-1625 (1998).
U.S. Appl. No. 60/528,340, filed Dec. 9, 2003.
Wang, et al., "Ras inhibition via direct Ras binding—is there a path forward?," *Bioorg. Med. Chem. Lett.*, 22: 5766-5776 (2012).
Written Opinion for PCT/US2017/067801, dated Jul. 25, 2018, 10 pages.
Written Opinion for PCT/US2018/033714, dated Jul. 17, 2018, 5 pages.
Written Opinion for PCT/US2018/050044, dated Oct. 30, 2018, 7 pages.
Written Opinion for PCT/US2019/030593, dated Aug. 6, 2019, 5 pages.
Written Opinion for PCT/US2019/030606, dated Jul. 23, 2019, 6 pages.
Written Opinion for PCT/US2019/031535, dated Jul. 25, 2019, 7 pages.
Written Opinion for PCT/US2019/034974, dated Aug. 9, 2019, 5 pages.
Written Opinion for PCT/US2019/036397, dated Aug. 26, 2019, 5 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).
Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS-PDES interaction impairs oncogenic KRAS signaling," *Nature*, 1-5 (2017).
Bhatia, et al., "A Review on Bioisosterism: A Rational Approach for Drug Design and Molecular Modification," *Pharmacologyonline*, 1:272-299 (2011).
Canon, et al., "The clinical KRAS(G12C) inhibitor AMG 510 drives anti-tumour immunity," *Nature*, 575(7781): 217-223 (2019) (Supplementary Material, pp. 1-55).

(56) References Cited

OTHER PUBLICATIONS

Database Registry [Online], Chemical Abstracts Service, Columbus, Ohio, US; Jul. 31, 2017 (Jul. 31, 2017), XP002801805, retrieved from STN Database accession No. 2105944-09-8.
Extended European Search Report for European Patent Application No. 19208193.2, dated Jun. 3, 2020, pp. 1-8.
Final Office Action for U.S. Appl. No. 15/984,855, dated Mar. 28, 2019, 7 pages.
Final Office Action for U.S. Appl. No. 16/661,907, dated Mar. 27, 2020, 29 pages.
Golub, et al., "Molecular Classification of Cancer: Class Discovery and Class Prediction by Gene Expression Monitoring," *Science*, 286: 531-537(1999).
International Search Report for PCT/US2019/036626, dated Jun. 2, 2020, 5 pages.
International Search Report for PCT/US2019/061815, dated Mar. 5, 2020, 6 pages.
International Search Report for PCT/US2019/062051, dated Mar. 2, 2020, 3 pages.
International Search Report for PCT/US2019/62064, dated Oct. 29, 2020, 9 pages.
International Search Report for PCT/US2020/032686, dated Aug. 14, 2020, 4 pages.
International Search Report for PCT/US2020/033831, dated Jul. 9, 2020, 6 pages.
International Search Report for PCT/US2020/033832, dated Jul. 8, 2020, 4 pages.
Janeway et al., "Immunobiology: The Immune System in Health and Disease", Elsevier Science Ltd./Garland Publishing, 4th ed. (1999). Table of contents.
Meanwell, "Synopsis of Some Recent Tactical Application of Bioisosteres in Drug Design," *J. Med. Chem.* 54:2529-2591 (2011).
Morrissey et al., "Immunotherapy and Novel Combinations in Oncology: Current Landscape, Challenges, and Opportunities," *Clin. Transl. Sci.*, 9(2):89-104 (2016).
Non-Final Office Action (Corrected) for U.S. Appl. No. 16/125,359, dated Apr. 8, 2019, 13 pages.
Non-Final Office Action for U.S. Appl. No. 15/849,905, dated Mar. 20, 2019, 18 pages.
Non-Final Office Action for U.S. Appl. No. 15/984,855, dated Sep. 27, 2018, 25 pages.
Non-Final Office Action for U.S. Appl. No. 16/125,359, dated Apr. 5, 2019, 13 pages.
Non-Final Office Action for U.S. Appl. No. 16/402,538, dated Oct. 30, 2019, 12 pages.
Non-Final Office Action for U.S. Appl. No. 16/402,589, dated Mar. 6, 2020, 17 pages.
Non-Final Office Action for U.S. Appl. No. 16/407,889, dated Jul. 1, 2020, 6 pages.
Non-Final Office Action for U.S. Appl. No. 16/428,163, dated Sep. 15, 2020, 6 pages.
Non-Final Office Action for U.S. Appl. No. 16/436,647, dated Aug. 7, 2020, 19 pages.
Non-Final Office Action for U.S. Appl. No. 16/438,349, dated Dec. 13, 2019, 15 pages.
Non-Final Office Action for U.S. Appl. No. 16/661,907, dated Nov. 18, 2019, 20 pages.
Non-Final Office Action for U.S. Appl. No. 16/675,121, dated Feb. 2, 2021, 10 pages.
Non-Final Office Action for U.S. Appl. No. 16/817,109, dated Mar. 3, 2021, 12 pages.
Notice of Allowance dated Jan. 14, 2021 for U.S. Appl. No. 16/402,589, 5 pages.
Notice of Allowance, dated Dec. 21, 2020, for U.S. Appl. No. 16/407,889, 5 pages.
Notice of Allowance, dated Feb. 18, 2021, for U.S. Appl. No. 16/687,546, 9 pages.
Notice of Allowance, dated Jan. 26, 2021, for U.S. Appl. No. 16/438,349, 9 pages.
Notice of Allowance, dated Jan. 27, 2021, for U.S. Appl. No. 16/428,163, 9 pages.
Notice of Allowance, dated Nov. 16, 2020, for U.S. Appl. No. 16/402,538, 8 pages.
Shibata et al., "A Convenient Synthesis of 3-Cyano-2-methylpyridines under Ultrasonic Irradiation," *Bull. Chem. Soc. Jpn.*, 61:2199-2200 (1988).
Stanetty et al., "Synthesis of Aza Analogs of the Herbicide Sindone B," *Monatshefte Fuer Chemie*, 130:441-450 (1999).
Statsyuk, "Let K-Ras activate its own inhibitor," *Nature Structural & Molecular Biology*, 25:435-439 (2018).
Written Opinion for PCT/US2019/036626, dated Jun. 2, 2020, 12 pages.
Written Opinion for PCT/US2019/061815, dated Mar. 5, 2020, 4 pages.
Written Opinion for PCT/US2019/062051, dated Mar. 2, 2020, 5 pages.
Written Opinion for PCT/US2019/62064, dated Oct. 29, 2020, 14 pages.
Written Opinion for PCT/US2020/032686, dated Aug. 14, 2020, 6 pages.
Written Opinion for PCT/US2020/033831, dated Jul. 9, 2020, 7 pages.
Written Opinion for PCT/US2020/033832, dated Jul. 8, 2020, 6 pages.
Brauswetter et al., "Molecular subtype specific efficacy of MEK inhibitors in pancreatic cancers", *PLOS ONE*, 12(9): e0185687 (pp. 1-13) (2017).
Communication Pursuant to Rule 114(2) EPC, Third Party Observation, European Patent Application No. 21183032.8, Apr. 3, 2023, 6 pages.
Dimartino et al., "Preparation and Physical Characterization of Forms II and III of Paracetamol," *Journal of Thermal Analysis*, 48:447-458 (1997).
Examiner-Initiated Interview Summary, dated Dec. 9, 2021, for U.S. Appl. No. 16/817,109, 1 page.
International Search Report for PCT/US2020/060421, dated Feb. 18, 2021, 4 pages.
Knapman, "Polymorphic Predictions: Understanding the nature of crystalline compounds can be critical in drug development and manufacture", *Modern Drug Discovery*, 53-57 (2000).
Non-Final Office Action for U.S. Appl. No. 15/930,606, dated Jan. 13, 2022, 4 pages.
Non-Final Office Action for U.S. Appl. No. 17/553,598, dated Apr. 26, 2023, 4 pages.
Non-Final Office Action for U.S. Appl. No. 17/692,026, dated May 11, 2023, 17 pages.
Notice of Allowance, dated Mar. 29, 2023, for U.S. Appl. No. 17/363,878.
Office Communication (Ex Parte Quayle) for U.S. Appl. No. 16/687,563, dated Jan. 14, 2022, 5 pages.
Written Opinion for PCT/US2020/060421, dated Feb. 18, 2021, 5 pages.

\* cited by examiner

KRAS G12C INHIBITORS AND METHODS OF USING THE SAME

CROSS REFERENCES TO RELATED APPLICATIONS

This application is a continuation application of U.S. patent application Ser. No. 16/661,907, filed Oct. 23, 2019, which is a continuation application of U.S. patent application Ser. No. 15/984,855, filed May 21, 2018, now U.S. Pat. No. 10,519,146, which claims the benefit of U.S. Provisional Application No. 62/509,629, filed on May 22, 2017, all of which are hereby incorporated by reference in their entireties and for all purposes as if fully set forth herein.

FIELD OF INVENTION

Provided herein are KRAS G12C inhibitors, composition of the same, and methods of using the same. These inhibitors are useful for treating a number of disorders, including pancreatic, colorectal, and lung cancers.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation, and including those who have progressed after chemotherapy.

SUMMARY

Provided herein are compound having a structure of formula (I)

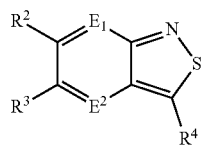

wherein $E^1$ and $E^2$ are each independently N or $CR^1$;

$R^1$ is independently H, hydroxy, $C_{1-6}$alkyl, $C_{1-6}$haloalkyl, $C_{1-6}$alkoxy, NH—$C_{1-6}$ alkyl, N($C_{1-6}$alkyl)$_2$, cyano, or halo;

$R^2$ is halo, $C_{1-6}$ alkyl, $C_{1-6}$haloalkyl, OR', N(R')$_2$, $C_{2-3}$alkenyl, $C_{2-3}$alkynyl, $C_{0-3}$ alkylene-$C_{3-14}$cycloalkyl, $C_{0-3}$alkylene-$C_{2-14}$heterocycloalkyl, aryl, heteroaryl, $C_{0-3}$ alkylenearyl, or $C_{0-3}$ alkyleneheteroaryl, and each R' is independently H, $C_{1-6}$ alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-3}$alkyl, $C_{1-2}$haloalkyl, $C_{1-3}$alkoxy, $C_{3-4}$cycloalkyl, $C_{2-3}$ alkenyl, $C_{2-3}$alkynyl, aryl, or heteroaryl;

$R^4$ is

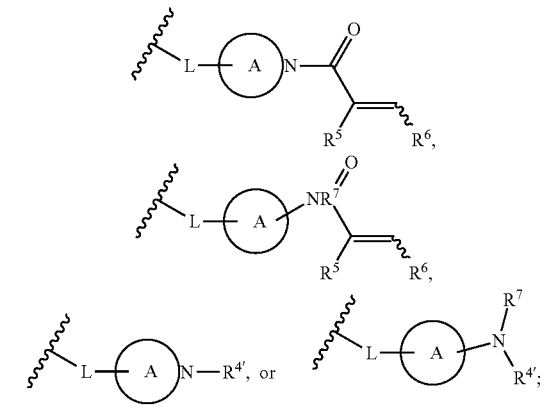

ring A is a monocyclic 4-7 membered ring or a bicyclic, bridged, fused, or spiro 6-11 membered ring;

L is a bond, $C_{1-6}$ alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$ alkylene, one carbon atom of the alkylene group can optionally be replaced with O, S, or NH;

$R^4$ is H, $C_{3-6}$alkyl, $C_{2-6}$alkynyl, $C_{1-6}$alkylene-O—$C_{1-4}$alkyl, $C_{1-6}$alkylene-OH, $C_{1-6}$ haloalkyl, cycloalklyl, heterocycloalkyl, $C_{0-3}$alkylene-$C_{3-4}$cycloalkyl, $C_{0-3}$alkylene-$C_{2-14}$heterocycloalkyl, aryl, heteroaryl, $C_{0-3}$alkylene-$C_{6-14}$aryl, or selected from

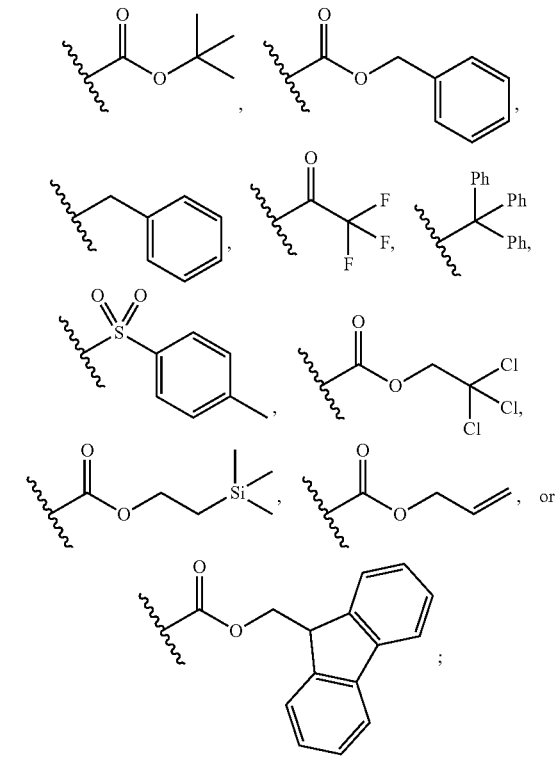

$R^5$ and $R^6$ are each independently H, halo, $C_{1-6}$alkyl, $C_{2-6}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)OC$_{1-4}$alkyl, $C_{1-6}$alkylene-O-aryl, $C_{0-3}$alkylene-C(O)C$_{1-4}$alkylene-OH, cycloalkyl, heterocycloalkyl, aryl, heteroaryl, $C_{0-3}$alkylene-$C_{3-14}$cycloalkyl, $C_{0-3}$alkylene-$C_{2-14}$heterocycloalkyl, $C_{0-3}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring; and $R^7$ is H or $C_{1-8}$alkyl, or $R^7$ and $R^5$, together with the atoms to which they are attached, form a 4-6 membered ring, or a pharmaceutically acceptable salt thereof.

In another embodiment, provided herein are compounds having a structure of formula (I)

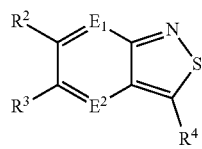

(I)

wherein $E^1$ and $E^2$ are each independently N or $CR^1$;

$R^1$ is independently H, hydroxy, $C_{1-6}$alkyl, $C_{1-6}$haloalkyl, $C_{1-6}$alkoxy, NH—$C_{1-6}$alkyl, N($C_{1-4}$alkyl)$_2$, cyano, or halo;

$R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-3}$alkyl, $C_{1-2}$haloalkyl, $C_{1-3}$alkoxy, $C_{3-14}$cycloalkyl, $C_{2-3}$alkenyl, $C_{2-3}$alkynyl, aryl, or heteroaryl;

$R^4$ is

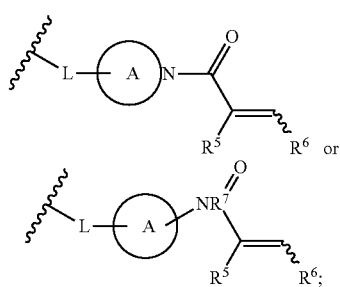

ring A is a monocyclic 4-7 membered ring or a bicyclic, bridged, fused, or spiro 6-11 membered ring;

L is a bond, $C_{1-6}$alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH;

$R^5$ and $R^6$ are each independently H, halo, $C_{1-8}$alkyl, $C_{2-5}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)OC$_{1-4}$alkyl, $C_{1-6}$alkylene-O-aryl, $C_{0-3}$alkylene-C(O)C$_{1-4}$alkylene-OH, cycloalkyl, heterocycloalkyl, aryl, heteroaryl, $C_{0-3}$alkylene-$C_{3-14}$cycloalkyl, $C_{0-3}$alkylene-$C_{2-14}$heterocycloalkyl, $C_{0-3}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring; and $R^7$ is H or $C_{1-6}$alkyl, or $R^7$ and $R^5$, together with the atoms to which they are attached, form a 4-6 membered ring, or a pharmaceutically acceptable salt thereof.

Further provided are compounds of formula (II), or a pharmaceutically acceptable salt thereof:

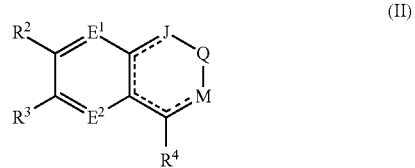

(II)

wherein $E^1$ and $E^2$ are each independently N or $CR^1$; J is N, $NR^{10}$, or $CR^{10}$; M is N, $NR^{13}$, or $CR^{13}$; === is a single or double bond as necessary to give every atom its normal valence; $R^1$ is independently H, hydroxy, $C_{1-6}$alkyl, $C_{1-4}$haloalkyl, $C_{1-4}$alkoxy, NH—$C_{1-4}$alkyl, N($C_{1-4}$alkyl)$_2$, cyano, or halo; $R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-5}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring; $R^3$ is halo, $C_{1-3}$alkyl, $C_{1-2}$haloalkyl, $C_{1-3}$alkoxy, $C_{3-4}$ cycloalkyl, $C_{2-14}$heterocycloalkyl, $C_{2-3}$ alkenyl, $C_{2-3}$alkynyl, aryl, or heteroaryl;

$R^4$ is

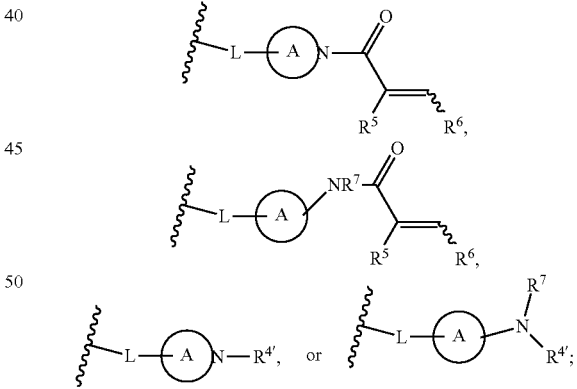

ring A is a monocyclic 4-7 membered ring or a bicyclic, bridged, fused, or spiro 6-11 membered ring; L is a bond, $C_{1-6}$alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$ alkylene, one carbon atom of the alkylene group can optionally be replaced with O, S, or NH; $R^{4'}$ is H, $C_{1-8}$alkyl, $C_{2-5}$alkynyl, $C_{1-6}$alkylene-O—$C_{1-4}$alkyl, $C_{1-6}$alkylene-OH, $C_{1-6}$ haloalkyl, cycloalklyl, heterocycloalkyl, $C_{0-3}$alkylene-$C_{3-14}$cycloalkyl, $C_{0-3}$alkylene-$C_{2-14}$ heterocycloalkyl, aryl, heteroaryl, $C_{0-3}$alkylene-$C_{6-14}$aryl, or selected from

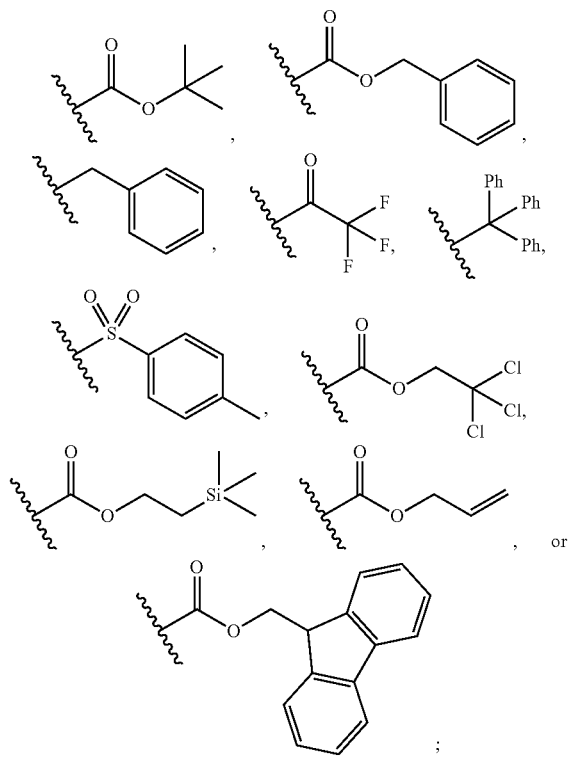

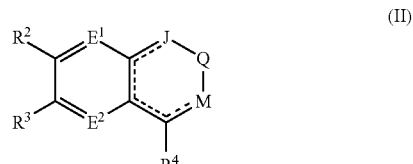

R⁵ and R⁶ are each independently H, halo, C₁₋₆alkyl, C₂₋₆alkynyl, CM alkylene-O—C₁₋₄alkyl, C₁₋₆alkylene-OH, C₁₋₆haloalkyl, C₁₋₆alkyleneamine, C₀₋₆ alkylene-amide, C₀₋₃alkylene-C(O)OH, C₀₋₃alkylene-C(O)OC₁₋₄alkyl, C₁₋₆ alkylene-O-aryl, C₀₋₃alkylene-C(O)C₁₋₄alkylene-OH, cycloalkyl, heterocycloalkyl, aryl, heteroaryl, C₀₋₃alkylene-C₃₋₁₄cycloalkyl, C₀₋₃alkylene-C₂₋₁₄heterocycloalkyl, C₀₋₃alkylene-C₆₋₁₄aryl, C₀₋₃alkylene-C₂₋₁₄heteroaryl, or cyano, or R⁵ and R⁶, together with the atoms to which they are attached, form a 4-6 membered ring; R⁷ is H or C₁₋₈alkyl, or R⁷ and R⁵, together with the atoms to which they are attached, form a 4-6 membered ring; Q is CR⁸R⁹, C=CR⁸R⁹, C=O, C=S, or C=NR⁸; R⁸ and R⁹ are each independently H, C₁₋₃alkyl, hydroxy, C₁₋₃alkoxy, cyano, nitro, or C₃₋₆cycloalkyl, or R⁸ and R⁹, taken together with the carbon atom to which they are attached, can form a 3-6 membered ring; R¹⁰ is C₁₋₈alkyl. C₀₋₃alkylene-C₆₋₁₄aryl, C₀₋₃alkylene-C₃₋₁₄heteroaryl, C₀₋₃ alkylene-C₃₋₁₄cycloalkyl, C₀₋₃alkylene-C₂₋₁₄heterocycloalkyl, C₁₋₆alkoxy, O—C₀₋₃ alkylene-C₆₋₁₄aryl, O—C₀₋₃alkylene-C₃₋₁₄heteroaryl, O—C₀₋₃ alkylene-C₅₋₁₄cycloalkyl, O—C₀₋₃ alkylene-C₂₋₁₄heterocycloalkyl, NH—C₁₋₈alkyl, N(C₁₋₈alkyl)₂, NH—C₀₋₃alkylene-C₆₋₁₄aryl, NH—C₀₋₃alkylene-C₂₋₁₄heteroaryl, NH—C₀₋₃alkylene-C₃₋₁₄cycloalkyl, NH—C₀₋₃ alkylene-C₂₋₁₄heterocycloalkyl, halo, cyano, or C₁₋₆alkylene-amine; and
R¹³ is C₁₋₆alkyl, C₁₋₆haloalkyl, C₁₋₆alkyleneamine, or C₃₋₁₄cycloalkyl,
or a pharmaceutically acceptable salt thereof, with the proviso that
(1) when J is NR¹⁰, M is N or CR¹³;
(2) when M is NR¹³, J is N or CR¹⁰;
(3) when J is CR¹⁰, M is N or NR¹³; and
(4) when M is CR¹³, J is N or NR¹⁰.
In some embodiments, when Q is C=O, and E¹ and E² are each CR¹; then either (1) R¹⁰ is C₁₋₈alkylenearyl, C₁₋₈alkyleneheteroaryl, C₀₋₃alkylene-C₃₋₈cycloalkyl, C₁₋₃alkylene-C₂₋₇heterocycloalkyl, or halo; or (2) R¹³ is C₁₋₃haloalkyl or C₃₋₅cycloalkyl. In various embodiments, J is NR¹⁰ and M is CR¹³. In some embodiments, J is CR¹⁰ and M is NR¹³. In some embodiments, J is N and M is NR¹³. In various embodiments, J is NR¹⁰ and M is N.

Further provided are compounds having a structure of formula (II)

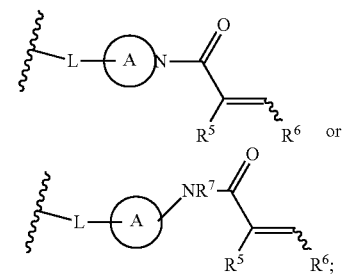

(II)

wherein
E¹ and E² are each independently N or CR¹;
J is N, NR¹⁰, or CR¹⁰;
M is N, NR¹³, or CR¹³;
≡ is a single or double bond as necessary to give every atom its normal valence;
R¹ is independently H, hydroxy, C₁₋₄alkyl, C₁₋₄haloalkyl, C₁₋₄alkoxy, NH—C₁₋₄alkyl, N(C₁₋₄alkyl)₂, cyano, or halo;
R² is halo, C₁₋₆alkyl, C₁₋₆haloalkyl, OR', N(R')₂, C₂₋₃alkenyl, C₂₋₃alkynyl, C₀₋₃alkylene-C₃₋₁₄cycloalkyl, C₀₋₃alkylene-C₂₋₁₄heterocycloalkyl, aryl, heteroaryl, C₀₋₃alkylene-C₆₋₁₄aryl, or C₀₋₃alkylene-C₂₋₁₄heteroaryl, and each R' is independently H, C₁₋₆alkyl, C₁₋₆haloalkyl, C₃₋₁₄cycloalkyl, C₂₋₁₄heterocycloalkyl, C₁₋₆alkenyl, C₂₋₃alkynyl, aryl, or heteroaryl, or two R' substituents, together with the nitrogen atom to which they are attached, form a 3-7-membered ring;
R³ is halo, C₁₋₃alkyl, C₁₋₂haloalkyl, C₁₋₃alkoxy, C₃₋₄cycloalkyl, C₂₋₃alkenyl, C₂₋₃alkynyl, aryl, or heteroaryl;
R⁴ is

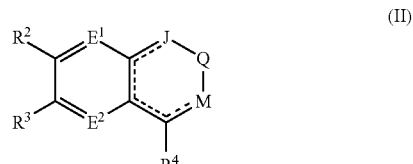

ring A is a monocyclic 4-7 membered ring or a bicyclic, bridged, fused, or spiro 6-11 membered ring;
L is a bond, C₁₋₆alkylene, —OC₀₋₅alkylene, —S—C₀₋₅alkylene, or —NH—C₀₋₅ alkylene, and for C₁₋₆alkylene, —O—C₁₋₈alkylene, —S—C₁₋₈alkylene, and NH—C₂₀ alkylene, one carbon atom of the alkylene group can optionally be replaced with O, S, or NH;
R⁵ and R⁶ are each independently H, halo, C₁₋₆alkyl, C₁₋₆alkynyl, C₁₋₆ alkylene-O—C₁₋₄alkyl, C₁₋₆alkylene-OH, C₁₋₆haloalkyl, C₁₋₆alkyleneamine, C₀₋₆ alkylene-amide, C₀₋₃alkylene-C(O)OH, C₀₋₃alkylene-C(O)OC₁₋₄alkyl, C₁₋₆alkylene-O-aryl, C₀₋₃alkylene-C(O)C₁₋₄alkylene-OH, cycloalkyl, heterocycloalkyl, aryl, heteroaryl, C₀₋₃alkylene-C₃₋₁₄cycloalkyl, C₀₋₃alkylene-C₂₋₁₄heterocycloalkyl, C₀₋₃alkylene-C₆₋₁₄aryl, C₀₋₃alkylene-C₂₋₁₄heteroaryl, or cyano, or $R^5$ and $R^6$, together with the atoms to which they are attached, form a 4-6 membered ring;

$R^7$ is H or $C_{1-8}$alkyl, or $R^7$ and $R^5$, together with the atoms to which they are attached, form a 4-6 membered ring;

Q is $CR^8R^9$, $C=CR^8R^9$, $C=O$, $C=S$, or $C=NR^8$;

$R^8$ and $R^9$ are each independently H, $C_{1-3}$alkyl, hydroxy, $C_{1-3}$alkoxy, cyano, nitro, or $C_{3-6}$cycloalkyl, or $R^8$ and $R^9$, taken together with the carbon atom to which they are attached, can form a 3-6 membered ring;

$R^{10}$ is $C_{1-8}$alkyl, $C_{0-5}$alkylene-$C_{6-14}$aryl, $C_{0-3}$alkylene-$C_{3-14}$heteroaryl, $C_{0-3}$ alkylene-$C_{3-14}$cycloalkyl, $C_{0-3}$alkylene-$C_{2-14}$heterocycloalkyl, $C_{1-6}$alkoxy, O—$C_{0-3}$alkylene-$C_{6-14}$aryl, O—$C_{0-3}$alkylene-$C_{3-14}$heteroaryl, O—$C_{0-3}$alkylene-$C_{3-14}$cycloalkyl, O—$C_{0-3}$ alkylene-$C_{2-14}$heterocycloalkyl, NH—$C_{1-8}$alkyl, N($C_{1-8}$alkyl)$_2$, NH—$C_{0-5}$alkylene-$C_{6-14}$aryl, NH—$C_{0-3}$alkylene-$C_{2-14}$heteroaryl, NH—$C_{0-3}$alkylene-$C_{3-14}$cycloalkyl, NH—$C_{0-3}$ alkylene-$C_{2-14}$heterocycloalkyl, halo, cyano, or $C_{1-6}$alkylene-amine:
with the proviso that
(1) when J is $NR^{10}$, M is N or $CR^{13}$;
(2) when M is $NR^{13}$, J is N or $CR^{10}$;
(3) when J is $CR^{10}$, M is N or $NR^{13}$; and
(4) when M is $CR^{13}$, J is N or $NR^{10}$.

In some embodiments, when Q is C=O, and $E^1$ and $E^2$ are each $CR^1$; then either (1) $R^{10}$ is $C_{1-8}$alkylenearyl. $C_{1-8}$alkyleneheteroaryl. $C_{0-3}$alkylene-$C_{3-8}$cycloalkyl, $C_{1-3}$alkylene-$C_{2-7}$heterocycloalkyl, or halo; or (2) $R^{13}$ is $C_{1-3}$haloalkyl or $C_{3-5}$cycloalkyl. In various embodiments, J is $NR^{10}$ and M is $CR^{13}$. In some embodiments, J is $CR^{10}$ and M is $NR^{13}$. In some embodiments, J is N and M is $NR^{13}$. In various embodiments, J is $NR^{10}$ and M is N.

Further provided are compounds of formula (III) or (HE), or a pharmaceutically acceptable salt thereof:

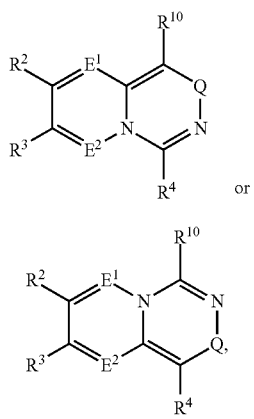

(III)

(III')

wherein $E^1$ and $E^2$ are each independently N or $CR^1$;

$R^1$ is independently H, hydroxy, $C_{1-6}$alkyl, $C_{1-4}$haloalkyl, $C_{1-4}$alkoxy, NH—$C_{1-4}$alkyl, N($C_{1-4}$alkyl)$_2$, cyano, or halo;

$R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-5}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-6}$alkyl, $C_{1-2}$haloalkyl, $C_{1-3}$alkoxy, $C_{3-4}$cycloalkyl, $C_{2-14}$heterocycloalkyl, $C_{2-3}$ alkenyl, $C_{2-3}$alkynyl, aryl, or heteroaryl;

$R^4$ is

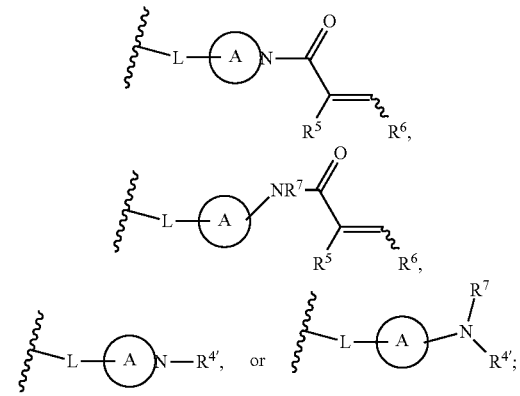

ring A is a monocyclic 4-7 membered ring or a bicyclic, bridged, fused, or spiro 6-11 membered ring;

L is a bond, $C_{1-6}$ alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$ alkylene, one carbon atom of the alkylene group can optionally be replaced with O, S, or NH;

$R^4$ is H, $C_{1-8}$alkyl, $C_{2-8}$alkynyl, $C_{1-6}$alkylene-O—$C_{1-4}$alkyl, $C_{1-6}$alkylene-OH, $C_{1-6}$ haloalkyl, cycloalklyl, heterocycloalkyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or selected from

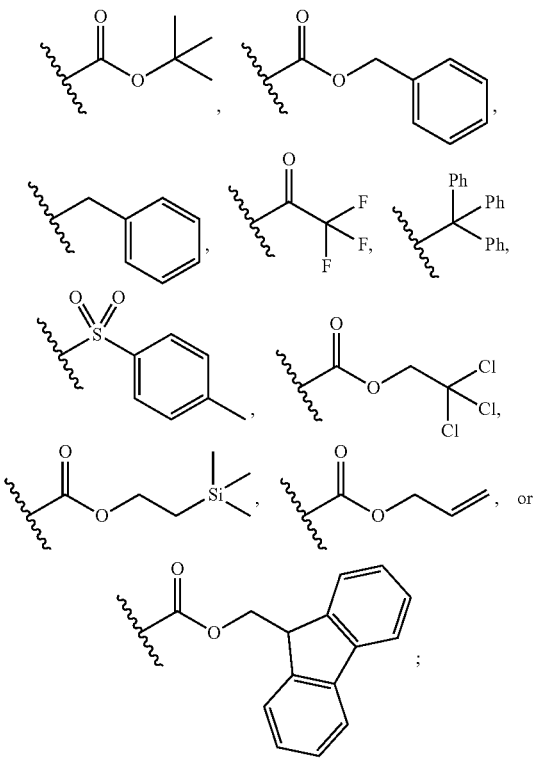

$R^5$ and $R^6$ are each independently H, halo, $C_{1-6}$alkyl, $C_{2-6}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)O$C_{1-4}$alkyl, $C_{1-6}$ alkylene-O-aryl, $C_{0-3}$alkylene-C(O)$C_{1-4}$alkylene-OH, cycloalkyl, heterocycloalkyl, aryl, heteroaryl, $C_{0-3}$alkylene-$C_{3-14}$cycloalkyl, $C_{0-3}$alkylene-$C_{2-14}$heterocycloalkyl, $C_{0-3}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring;

$R^7$ is H or $C_{1-8}$alkyl, or $R^7$ and $R^5$, together with the atoms to which they are attached, form a 4-6 membered ring;

Q is $CR^8R^9$, $C=CR^8R^9$, C=O, C=S, or $C=NR^8$;

$R^8$ and $R^9$ are each independently H, $C_{1-6}$ alkyl, hydroxy, $C_{1-6}$alkoxy, cyano, nitro, or $C_{3-14}$cycloalkyl, or $R^8$ and $R^9$, taken together with the carbon atom to which they are attached, can form a 3-6 membered ring;

$R^{10}$ is $C_{1-8}$alkyl, $C_{0-5}$alkylene-$C_{6-14}$aryl, $C_{0-3}$alkylene-$C_{3-14}$heteroaryl, $C_{0-3}$ alkylene-$C_{3-14}$cycloalkyl, $C_{0-3}$alkylene-$C_{2-14}$heterocycloalkyl, $C_{1-6}$alkoxy, O—$C_{0-3}$alkylene-$C_{6-14}$aryl, O—$C_{0-3}$alkylene-$C_{3-14}$heteroaryl, O—$C_{0-3}$ alkylene-$C_{3-14}$cycloalkyl, O—$C_{0-3}$ alkylene-$C_{2-14}$heterocycloalkyl, NH—$C_{1-8}$alkyl, N($C_{1-8}$alkyl)$_2$, NH—$C_{0-5}$alkylene-$C_{6-14}$aryl, NH—$C_{0-3}$alkylene-$C_{2-14}$heteroaryl, NH—$C_{0-3}$alkylene-$C_{3-14}$cycloalkyl, NH—$C_{0-3}$alkylene-$C_{2-14}$heterocycloalkyl, halo, cyano, or $C_{1-6}$alkylene-amine.

Further provided are compounds of formula (III) or (III'), or a pharmaceutically acceptable salt thereof:

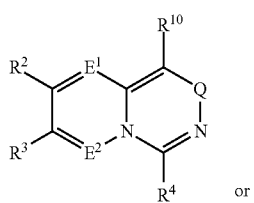

(III)

or

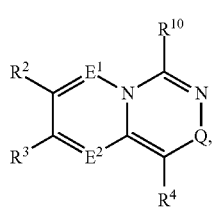

(III')

wherein $E^1$ and $E^2$ are each independently N or $CR^1$;

$R^1$ is independently H, hydroxy, $C_{1-6}$alkyl, $C_{1-4}$haloalkyl, $C_{1-4}$alkoxy, NH—$C_{1-4}$alkyl, N($C_{1-4}$alkyl)$_2$, cyano, or halo;

$R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-3}$alkyl, $C_{1-2}$haloalkyl, $C_{1-3}$alkoxy, $C_{3-4}$cycloalkyl, $C_{2-14}$heterocycloalkyl, $C_{2-3}$ alkenyl, $C_{2-3}$alkynyl, aryl, or heteroaryl;

$R^4$ is

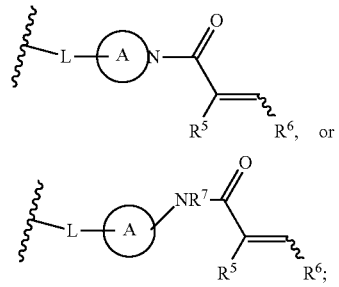

ring A is a monocyclic 4-7 membered ring or a bicyclic, bridged, fused, or spiro 6-11 membered ring;

L is a bond, $C_{1-6}$ alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$ alkylene, one carbon atom of the alkylene group can optionally be replaced with O, S, or NH;

$R^5$ and $R^6$ are each independently H, halo, $C_{1-6}$alkyl, $C_{2-6}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)O$C_{1-4}$alkyl, $C_{1-6}$ alkylene-O-aryl, $C_{0-3}$alkylene-C(O)$C_{1-4}$alkylene-OH, cycloalkyl, heterocycloalkyl, aryl, heteroaryl, $C_{0-5}$alkylene-$C_{3-14}$cycloalkyl, $C_{0-3}$alkylene-$C_{2-14}$heterocycloalkyl, $C_{0-5}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring;

$R^7$ is H or $C_{1-8}$alkyl, or $R^7$ and $R^5$, together with the atoms to which they are attached, form a 4-6 membered ring;

Q is $CR^8R^9$, $C=CR^8R^9$, C=O, C=S, or $C=NR^8$;

$R^8$ and $R^9$ are each independently H, $C_{1-6}$alkyl, hydroxy, $C_{1-6}$alkoxy, cyano, nitro, or $C_{3-14}$cycloalkyl, or $R^8$ and $R^9$, taken together with the carbon atom to which they are attached, can form a 3-6 membered ring;

$R^{10}$ is $C_{1-8}$alkyl. $C_{0-5}$alkylene-$C_{6-14}$aryl, $C_{0-3}$alkylene-$C_{3-14}$heteroaryl, $C_{0-3}$alkylene-$C_{3-14}$cycloalkyl, $C_{0-3}$alkylene-$C_{2-14}$heterocycloalkyl, $C_{1-6}$alkoxy, O—$C_{0-3}$alkylene-$C_{6-14}$aryl, O—$C_{0-3}$alkylene-$C_{3-14}$heteroaryl, O—$C_{0-3}$ alkylene-$C_{3-14}$cycloalkyl, O—$C_{0-3}$ alkylene-$C_{2-14}$heterocycloalkyl, NH—$C_{1-8}$alkyl, N($C_{1-8}$alkyl)$_2$, NH—$C_{0-5}$alkylene-$C_{6-14}$aryl, NH—$C_{0-3}$alkylene-$C_{2-14}$heteroaryl, NH—$C_{0-5}$alkylene-$C_{3-14}$cycloalkyl, NH—$C_{0-3}$alkylene-$C_{2-14}$heterocycloalkyl, halo, cyano, or $C_{1-6}$alkylene-amine.

In some embodiments, the compounds have a structure of formula (III). In other embodiments, the compounds have a structure of formula (III').

The compounds of formula (II) or (III) as disclosed herein can have one or more of the following features. In some embodiments, Q is C=O. In some embodiments, Q is C=S. In some embodiments, Q is $C=NR^8$. In various embodiments, $R^8$ is $C_{1-2}$alkyl. In some embodiments, Q is $CR^8R^9$. In various embodiments, Q is $C=CR^8R^9$. In some embodiments, $R^8$ and $R^9$, taken together with the carbon atom to which they are attached, form a 3-4 membered ring. In some embodiments, $R^8$ is $C_{1-2}$alkyl, and $R^9$ is H.

Also provided are compounds of formula (IV) or (IV'), or a pharmaceutically acceptable salt thereof:

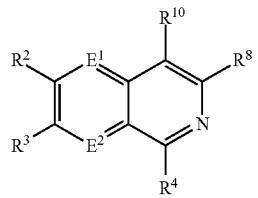

(IV)

or

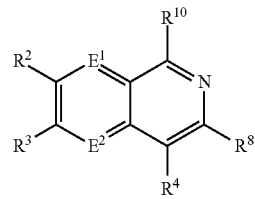

(IV')

$E^1$ and $E^2$ are each independently $CR^1$ or N;

$R^1$ is independently H, hydroxy, $C_{1-6}$alkyl, $C_{1-6}$haloalkyl, $C_{1-6}$alkoxy, NH—$C_{1-6}$alkyl, N($C_{1-6}$alkyl)$_2$, cyano, or halo;

$R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-5}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-2}$haloalkyl, $C_{1-8}$alkoxy, cycloalkyl, $C_{2-3}$alkenyl. $C_{2-3}$alkynyl, aryl, or heteroaryl;

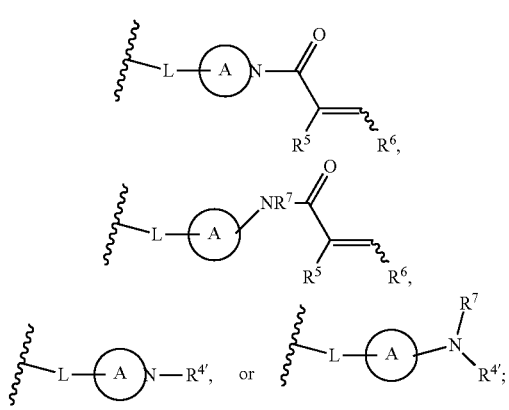

ring A is a monocyclic 4-7 membered ring or a bicyclic, bridged, fused, or spiro 6-11 membered ring;

L is a bond, $C_{1-6}$ alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH;

$R^4$ is H, $C_{1-8}$ alkyl, $C_{2-5}$alkynyl, $C_{1-6}$ alkylene-O—$C_{1-4}$ alkyl, $C_{1-6}$alkene-OH, $C_{1-6}$ haloalkyl, cycloalklyl, heterocycloalkyl, $C_{0-3}$alkylene-$C_{3-14}$cycloalkyl, $C_{0-3}$alkylene-$C_{2-14}$ heterocycloalkyl, aryl, heteroaryl, $C_{0-3}$alkylene-$C_{6-14}$aryl, or selected from

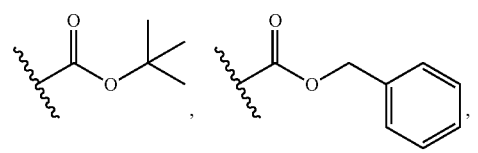

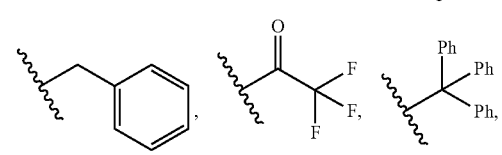

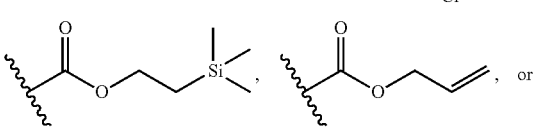

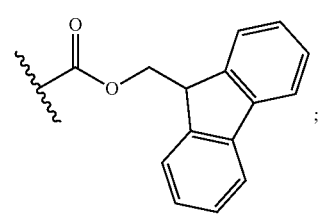

$R^5$ and $R^6$ are each independently H, halo, $C_{1-6}$alkyl, $C_{2-6}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)O$C_{1-4}$alkyl, $C_{1-6}$ alkylene-O-aryl, $C_{0-3}$alkylene-C(O)$C_{1-4}$alkylene-OH, cycloalkyl, heterocycloalkyl, aryl, heteroaryl, $C_{0-3}$alkylene-$C_{3-14}$cycloalkyl, $C_{0-3}$alkylene-$C_{2-14}$heterocycloalkyl, $C_{0-3}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring;

$R^7$ is H or $C_{1-8}$alkyl, or $R^7$ and $R^5$, together with the atoms to which they are attached, form a 4-6 membered ring;

$R^8$ is H, $C_{1-3}$alkyl, hydroxy, $C_{1-3}$alkoxy, halo, cyano, nitro, $C_{3-14}$ cycloalkyl, or $NR^{11}R^{12}$;

$R^{11}$ and $R^{12}$ are each independently H, $C_{1-8}$alkyl, or $C_{3-14}$cycloalkyl; and $R^{10}$ is $C_{1-8}$alkyl, $C_{0-5}$alkylene-$C_{6-14}$aryl, $C_{0-3}$alkylene-$C_{2-14}$heteroaryl, $C_{0-5}$alkylene-$C_{3-14}$cycloalkyl, $C_{0-3}$alkylene-$C_{2-14}$heterocycloalkyl, $C_{1-6}$alkoxy, 0-$C_{0-3}$alkylene-$C_{6-14}$aryl, O—$C_{0-3}$alkylene-$C_{2-14}$heteroaryl, 0-$C_{0-3}$alkylene-$C_{3-14}$ cycloalkyl, 0-$C_{0-3}$alkylene-$C_{2-14}$heterocycloalkyl, NH—$C_{1-8}$alkyl, N($C_{1-5}$alkyl)$_2$, NH—$C_{0-3}$alkylene-$C_{6-14}$aryl, NH—$C_{0-3}$alkylene-$C_{2-14}$heteroaryl, N—$C_{0-3}$alkylene-$C_{3-14}$ cycloalkyl, N—$C_{0-3}$alkylene-$C_{2-14}$heterocycloalkyl, halo, cyano, or $C_{1-6}$ alkylene-amine;

In some embodiments, the compounds disclosed herein have a structure of formula (IV). In various embodiments, the compounds disclosed herein have a structure of formula (IV'). In some embodiments, $E^1$ and $E^2$ are each $CR^1$, and $R^8$ is hydroxy, halo, nitro, or $C_{3-6}$cycloalkyl.

In some embodiments, $R^8$ is methyl.

Further provided are compounds having a structure of formula (IV) or (IV'):

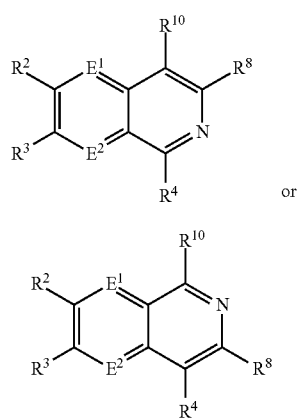

wherein $E^1$ and $E^2$ are each independently $CR^1$ or N;

$R^1$ is independently H, hydroxy, $C_{1-6}$alkyl, $C_{1-6}$haloalkyl, $C_{1-6}$alkoxy, NH—$C_{1-6}$alkyl, $N(C_{1-6}$alkyl$)_2$, cyano, or halo;

$R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-2}$haloalkyl, $C_{1-3}$alkoxy, $C_{3-14}$cycloalkyl, $C_{2-3}$alkenyl, $C_{2-3}$alkynyl, aryl, or heteroaryl;

$R^4$ is

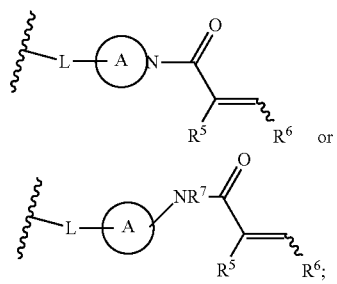

ring A is a monocyclic 4-7 membered ring or a bicyclic, bridged, fused, or spiro 6-11 membered ring;

L is a bond, $C_{1-6}$ alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH;

$R^5$ and $R^6$ are each independently H, halo, $C_{1-6}$alkyl, $C_{2-6}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)O$C_{1-4}$alkyl, $C_{1-6}$alkylene-O-aryl, $C_{0-3}$alkylene-C(O)$C_{1-4}$alkyl-OH, cycloalkyl, heterocycloalkyl, aryl, heteroaryl, $C_{0-3}$alkylene-$C_{3-14}$cycloalkyl, $C_{0-3}$alkylene-$C_{2-14}$heterocycloalkyl, $C_{0-3}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring;

$R^7$ is H or $C_{1-8}$alkyl, or $R^7$ and $R^5$, together with the atoms to which they are attached, form a 4-6 membered ring;

$R^8$ is H, $C_{1-3}$alkyl, hydroxy, $C_{1-3}$alkoxy, halo, cyano, nitro, $C_{3-14}$ cycloalkyl, or $NR^{11}R^{12}$;

$R^{11}$ and $R^{12}$ are each independently H, $C_{1-8}$alkyl, or $C_{3-15}$cycloalkyl; and $R^{10}$ is $C_{1-8}$alkyl, $C_{0-3}$alkylene-$C_{6-14}$aryl, $C_{0-3}$alkylene-$C_{3-14}$heteroaryl, $C_{0-3}$ alkylene-$C_{3-14}$cycloalkyl, $C_{0-3}$alkylene-$C_{2-14}$heterocycloalkyl, $C_{1-6}$alkoxy, O—$C_{0-3}$alkylene-$C_{6-14}$aryl, O—$C_{0-3}$alkylene-$C_{3-14}$heteroaryl, O—$C_{0-3}$ alkylene-$C_{3-14}$cycloalkyl, O—$C_{0-3}$ alkylene-$C_{2-14}$heterocycloalkyl, NH—$C_{1-8}$alkyl, $N(C_{1-5}$alkyl$)_2$, NH—$C_{0-5}$alkylene-$C_{6-14}$aryl, NH—$C_{0-3}$alkylene-$C_{2-14}$heteroaryl, NH—$C_{0-3}$alkylene-$C_{3-14}$cycloalkyl, NH—$C_{0-3}$ alkylene-$C_{2-14}$heterocycloalkyl, halo, cyano, or $C_{1-6}$alkylene-amine;

or a pharmaceutically acceptable salt thereof.

In some embodiments, the compounds disclosed herein have a structure of formula (IV). In various embodiments, the compounds disclosed herein have a structure of formula (IV'). In some embodiments, $E^1$ and $E^2$ are each $CR^1$, and $R^8$ is hydroxy, halo, nitro, or $C_{3-6}$cycloalkyl.

In some embodiments, $R^8$ is methyl.

Further provided are compounds having a structure of formula (V), or a pharmaceutically acceptable salt thereof:

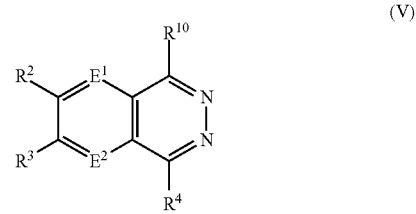

wherein $E^1$ and $E^2$ are each independently $CR^1$ or N;

$R^1$ is independently H, hydroxy, $C_{1-6}$alkyl, $C_{1-6}$haloalkyl, $C_{1-6}$alkoxy, NH—$C_{1-6}$alkyl, $N(C_{1-6}$alkyl$)_2$, cyano, or halo;

$R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-6}$alkyl, $C_{1-6}$haloalkyl, $C_{1-6}$alkoxy, $C_{3-14}$cycloalkyl, $C_{2-6}$alkenyl, $C_{2-6}$alkynyl, aryl, or heteroaryl;

$R^4$ is

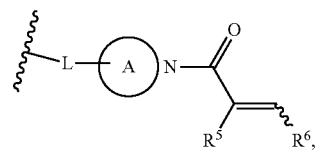

-continued

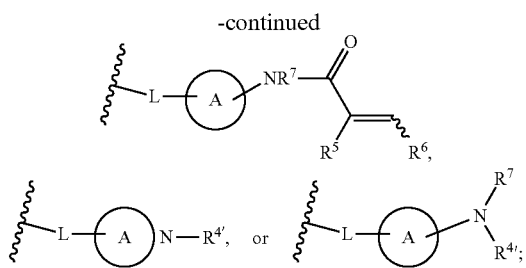

ring A is a monocyclic 4-7 membered ring or a bicyclic, bridged, fused, or spiro 6-11 membered ring;

L is a bond, $C_{1-6}$ alkylene, —O—$C_{0-5}$alkylene, —S—$C_{0-5}$alkylene, or —NH—$C_{0-5}$ alkylene, and for $C_{2-6}$alkylene, —O—$C_{2-5}$alkylene, —S—$C_{2-5}$alkylene, and NH—$C_{2-5}$ alkylene, one carbon atom of the alkylene group can optionally be replaced with O, S, or NH;

$R^4$ is H, $C_{1-8}$alkyl, $C_{2-8}$alkynyl, $C_{1-6}$alkylene-O—$C_{1-4}$alkyl, $C_{1-6}$alkylene-OH, $C_{1-6}$ haloalkyl, cycloalklyl, heterocycloalkyl, $C_{0-3}$alkylene-$C_{6-14}$cycloalkyl, $C_{0-3}$alkylene-$C_{2-14}$ heterocycloalkyl, aryl, heteroaryl, $C_{0-5}$alkylene-$C_{6-14}$aryl, or selected from

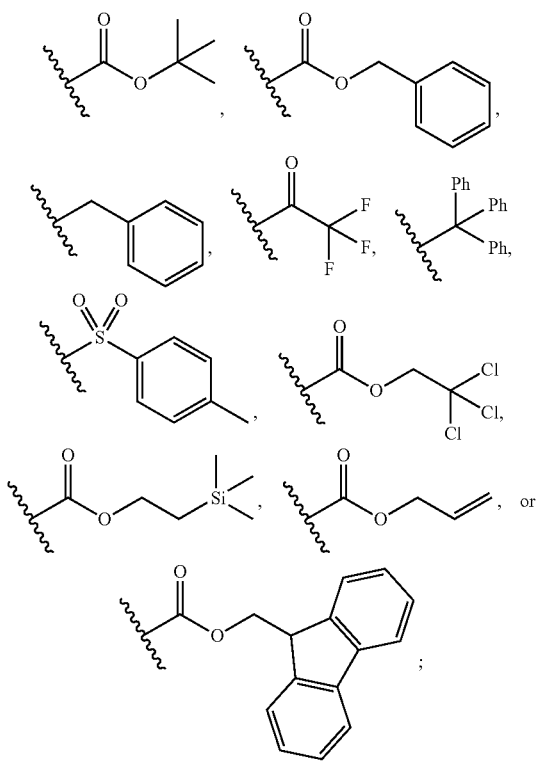

$R^5$ and $R^6$ are each independently H, halo, $C_{1-6}$alkyl, $C_{2-6}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)OC$_{1-4}$alkyl, $C_{1-6}$alkylene-O-aryl, $C_{0-3}$alkylene-C(O)C$_{1-4}$alkylene-OH, cycloalkyl, heterocycloalkyl, aryl, heteroaryl, $C_{0-3}$alkylene-$C_{3-14}$cycloalkyl, $C_{0-3}$alkylene-$C_{2-14}$heterocycloalkyl, $C_{0-3}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring;

$R^7$ is H or $C_{1-8}$alkyl, or $R^7$ and $R^5$, together with the atoms to which they are attached, form a 4-6 membered ring; and $R^{10}$ is $C_{1-8}$alkyl. $C_{0-3}$alkylene-$C_{6-14}$aryl, $C_{0-3}$alkylene-$C_{3-14}$heteroaryl, $C_{0-3}$alkylene-$C_{3-14}$cycloalkyl, $C_{0-3}$alkylene-$C_{2-14}$heterocycloalkyl, $C_{1-6}$alkoxy, O—$C_{0-3}$ alkylene-$C_{6-14}$aryl, O—$C_{0-3}$alkylene-$C_{3-14}$heteroaryl, O—$C_{0-3}$ alkylene-$C_{3-14}$cycloalkyl, O—$C_{0-3}$ alkylene-$C_{2-14}$heterocycloalkyl, NH—$C_{1-8}$alkyl, N($C_{1-8}$alkyl)$_2$, NH—$C_{0-3}$alkylene-$C_{6-14}$aryl, NH—$C_{0-5}$alkylene-$C_{2-14}$heteroaryl, NH—$C_{0-3}$alkylene-$C_{3-14}$cycloalkyl, NH—$C_{0-3}$ alkylene-$C_{2-14}$heterocycloalkyl, halo, cyano, or $C_{1-6}$alkylene-amine; or a pharmaceutically acceptable salt thereof.

Further provided are compounds having a structure of formula (V):

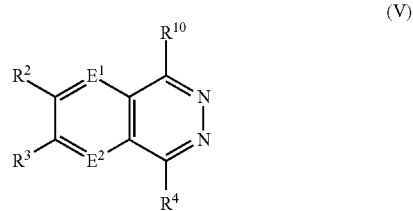

(V)

wherein $E^1$ and $E^2$ are each independently $CR^1$ or N;

$R^1$ is independently H, hydroxy, $C_{1-6}$alkyl, $C_{1-6}$haloalkyl, $C_{1-6}$alkoxy, NH—$C_{1-6}$alkyl, N($C_{1-6}$alkyl)$_2$, cyano, or halo;

$R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-14}$cycloalkyl, $C_{0-3}$alkylene-$C_{2-14}$heterocycloalkyl, aryl, heteroaryl, $C_{0-3}$alkylene-$C_{6-14}$aryl, or $C_{0-3}$alkylene-$C_{2-14}$heteroaryl, and each R' is independently H, $C_{1-6}$alkyl, $C_{1-6}$haloalkyl, $C_{3-14}$cycloalkyl, $C_{2-14}$heterocycloalkyl, $C_{2-3}$alkenyl, $C_{2-3}$alkynyl, aryl, or heteroaryl, or two R' substituents, together with the nitrogen atom to which they are attached, form a 3-7-membered ring;

$R^3$ is halo, $C_{1-6}$alkyl, $C_{1-6}$haloalkyl, $C_{1-6}$alkoxy, $C_{3-14}$cycloalkyl, $C_{2-5}$alkenyl, $C_{2-8}$alkynyl, aryl, or heteroaryl;

$R^4$ is

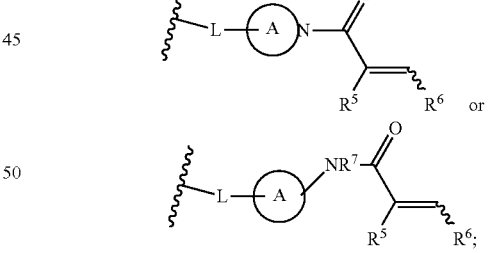

ring A is a monocyclic 4-7 membered ring or a bicyclic, bridged, fused, or spiro 6-11 membered ring;

L is a bond, $C_{1-6}$alkylene, —O—$C_{0-5}$alkylene, —S—$C_{0-5}$alkylene, or —NH—$C_{0-5}$alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH;

$R^5$ and $R^6$ are each independently H, halo, $C_{1-6}$alkyl, $C_{2-6}$alkynyl, $C_{1-6}$ alkylene-O—$C_{1-4}$alkyl, $C_{1-6}$alkylene-OH, $C_{1-6}$haloalkyl, $C_{1-6}$alkyleneamine, $C_{0-6}$ alkylene-amide, $C_{0-3}$alkylene-C(O)OH, $C_{0-3}$alkylene-C(O)OC$_{1-4}$alkyl, $C_{1-6}$alkylene-O-aryl, $C_{0-3}$alkylene-C(O)C$_{1-4}$alkylene-OH, cycloalkyl, heterocycloalkyl, aryl, heteroaryl, $C_{0-3}$alkylene- $C_{3-14}$cycloalkyl, $C_{0-3}$alkylene-$C_{2-14}$heterocycloalkyl, $C_{0-3}$alkylene-$C_{6-14}$aryl, $C_{0-3}$alkylene-$C_{2-14}$heteroaryl, or cyano, or $R^5$ and $R^6$, together with the atoms to which they are attached, form a 4-6 membered ring;

$R^7$ is H or $C_{1-8}$alkyl, or $R^7$ and $R^5$, together with the atoms to which they are attached, form a 4-6 membered ring; and $R^{10}$ is $C_{1-8}$alkyl, $C_{0-3}$alkylene-$C_{6-14}$aryl, $C_{0-3}$alkylene-$C_{3-14}$heteroaryl, $C_{0-3}$alkylene-$C_{3-14}$cycloalkyl, $C_{0-3}$alkylene-$C_{2-14}$heterocycloalkyl, $C_{1-6}$alkoxy, O—$C_{0-3}$alkylene-$C_{6-14}$aryl, O—$C_{0-3}$alkylene-$C_{3-14}$heteroaryl, O—$C_{0-3}$ alkylene-$C_{3-14}$cycloalkyl, O—$C_{0-3}$ alkylene-$C_{2-14}$heterocycloalkyl, NH—$C_{1-8}$alkyl, N($C_{1-8}$alkyl)$_2$, NH—$C_{0-3}$alkylene-$C_{6-14}$aryl, NH—$C_{0-3}$alkylene-$C_{2-14}$heteroaryl, NH—$C_{0-3}$alkylene-$C_{3-14}$cycloalkyl, NH—$C_{0-3}$alkylene-$C_{2-14}$heterocycloalkyl, halo, cyano, or $C_{1-6}$alkylene-amine; or a pharmaceutically acceptable salt thereof.

The compounds of formula (I), (II), (III), (III'), (IV), (IV'), or (V) as disclosed herein can have one or more of the following features. In some embodiments, each of $E^1$ and $E^2$ is $CR^1$. In other embodiments, $E^1$ is $CR^1$ and $E^2$ is N. In some embodiments, $E^1$ is N and $E^2$ is $CR^1$. In various embodiments, each of $E^1$ and $E^2$ is N.

The compounds of formula (II), (III), (HE), (IV), (IV'), or (V) as disclosed herein can have one or more of the following features. In various embodiments, $R^{10}$ is $C_{1-6}$ alkyl, aryl, heteroaryl, $C_{3-14}$cycloalkyl, $C_{2-14}$ heterocycloalkyl, $C_{1-6}$alkoxy, O—$C_{0-6}$alkylene-$C_{6-14}$aryl, O—$C_{0-6}$alkylene-$C_{2-14}$ heteroaryl, O—$C_{0-6}$alkylene-$C_{6-14}$cycloalkyl, O—$C_{0-6}$alkylene-$C_{2-14}$heterocycloalkyl, N—$C_{1-8}$alkyl, N($C_{1-5}$alkyl)$_2$, NH—$C_{0-6}$alkylene-$C_{6-14}$aryl, NH—$C_{0-6}$alkylene-$C_{2-14}$ heteroaryl, NH—$C_{0-6}$alkylene-$C_{3-14}$cycloalkyl, or NH—$C_{0-6}$alkylene-$C_{2-14}$ heterocycloalkyl. In various embodiments, $R^{10}$ is $C_{1-8}$alkyl. In some embodiments, $R^{10}$ is $C_{0-5}$alkylene-$C_{6-14}$aryl. In some embodiments, $R^{10}$ is $C_{0-3}$alkylene-$C_{2-14}$heteroaryl. In some embodiments, $R^{10}$ is $C_{0-3}$alkylene-$C_{3-14}$ cycloalkyl. In some embodiments, $R^{10}$ is $C_{0-3}$alkylene-$C_{2-14}$heterocycloalkyl. In other embodiments, $R^{10}$ is $C_{0-6}$alkyleneamine. For example, $R^{10}$ can be z-Pr, t-Bu, phenyl,

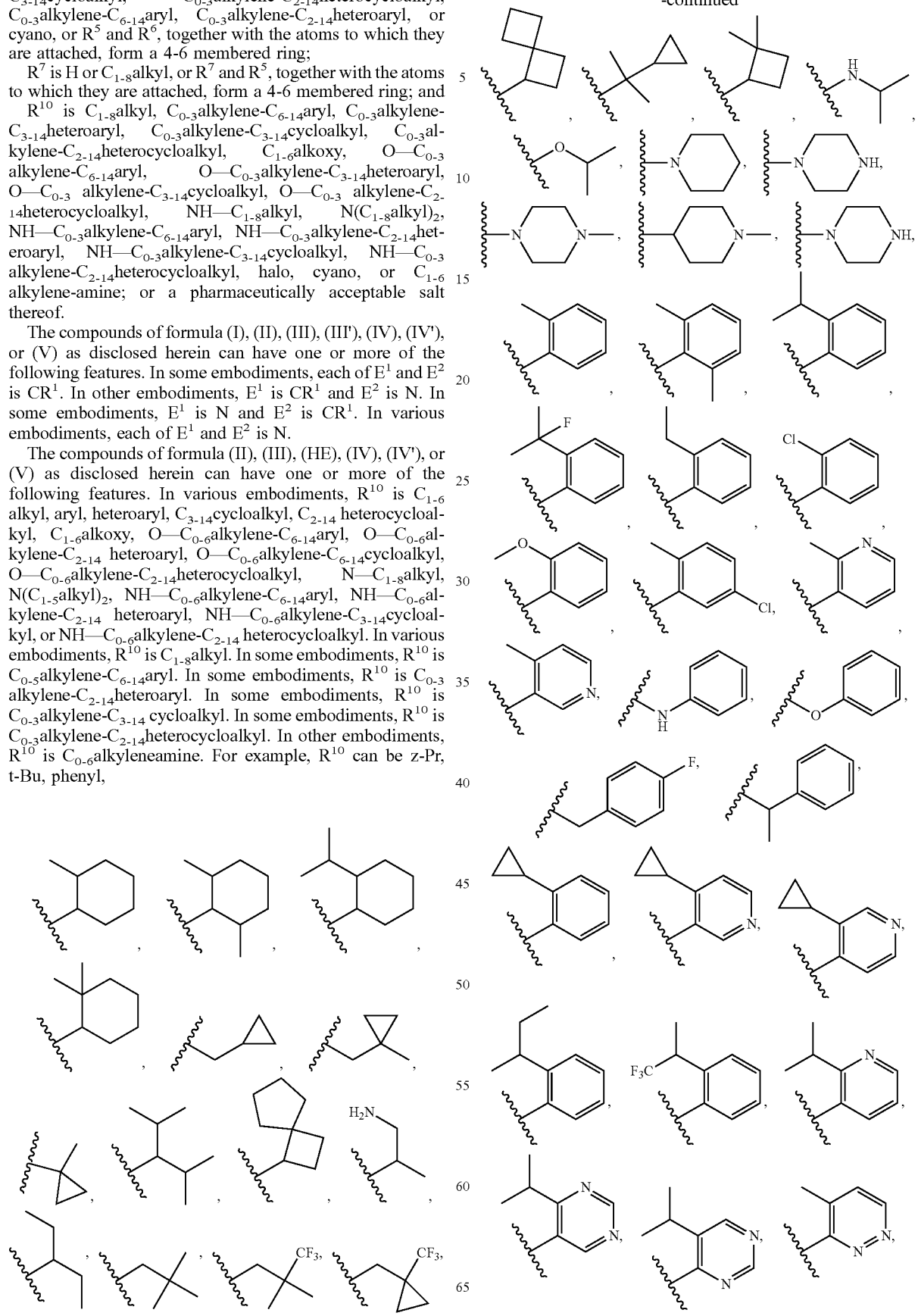

-continued
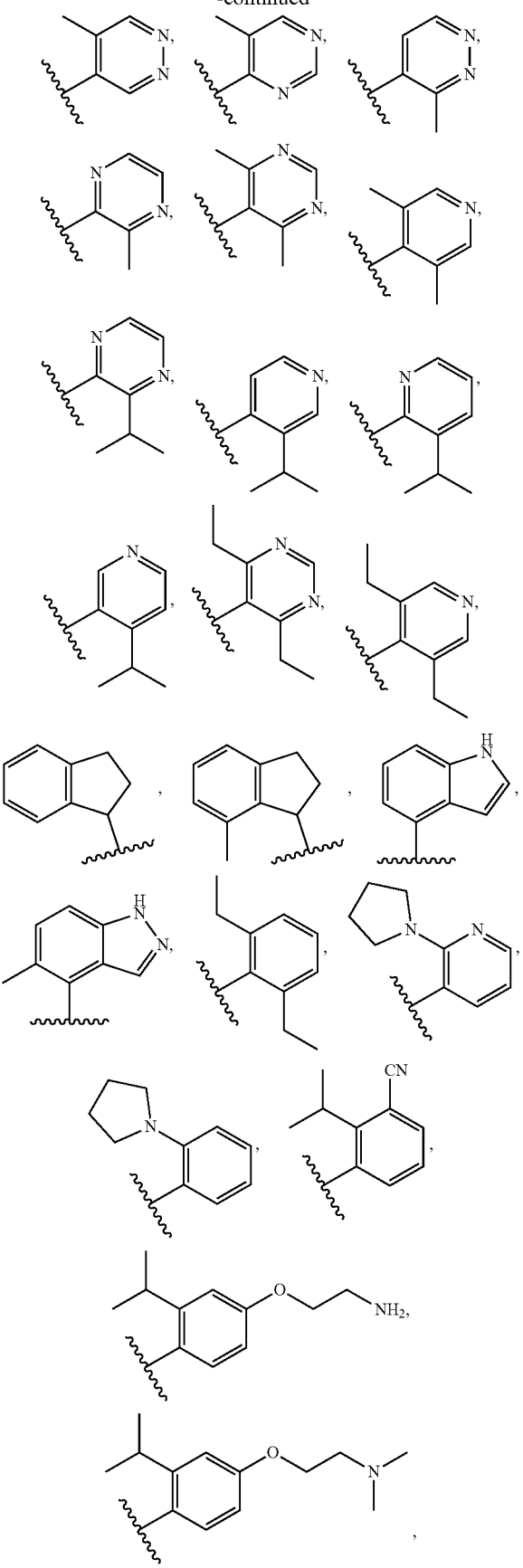
-continued
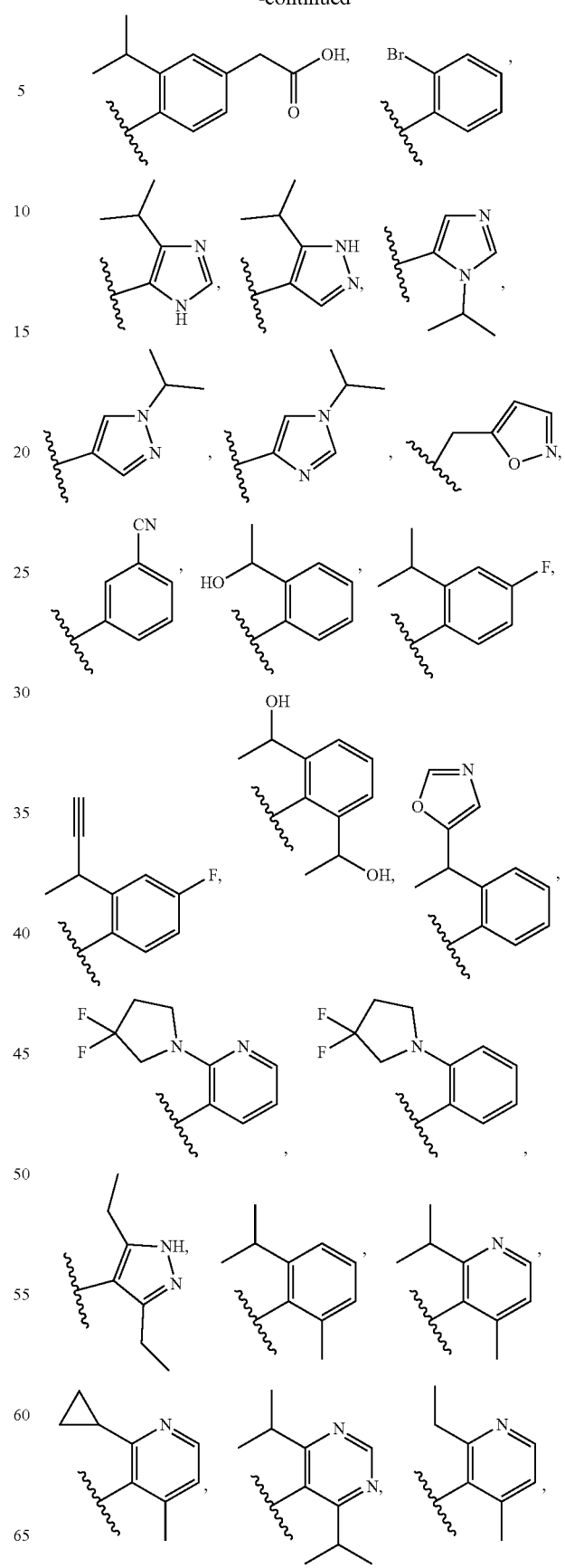

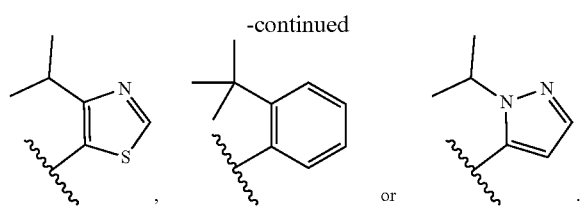

In some embodiments, $R^{10}$ comprises an ortho-substituted aryl, ortho-substituted heteroaryl, or 2-substituted cyclohexyl. For example, $R^{10}$ can be

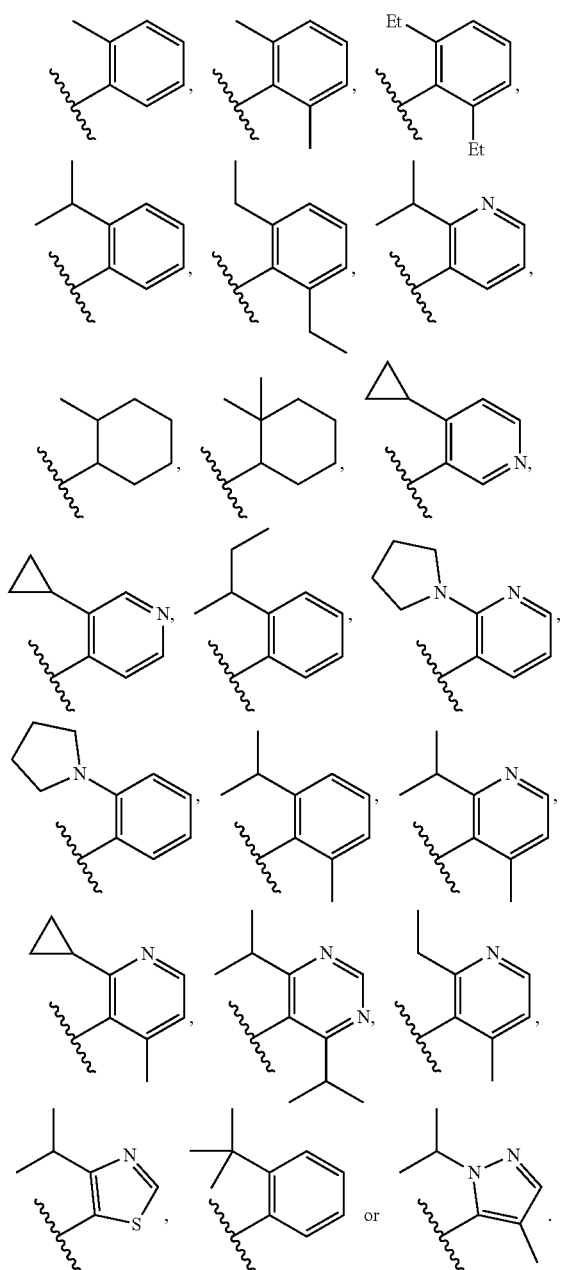

The compounds of formula (I), (II), (III), (III'), (IV), (IV'), or (V) as disclosed herein can have one or more of the following features. In some embodiments, $R^1$ is H. In some embodiments, $R^1$ is F. In some embodiments, $R^1$ is methyl.

The compounds of formula (I), (II), (III), (III'), (IV), (IV'), or (V) as disclosed herein can have one or more of the following features. In various embodiments, $R^2$ is aryl. In some embodiments, $R^2$ is heteroaryl. In various embodiments, $R^2$ is phenyl, naphthyl, pyridyl, indazolyl, indolyl, azaindolyl, indolinyl, benzotriazolyl, benzoxadiazolyl, imidazolyl, cinnolinyl, imidazopyridyl, pyrazolopyridyl, quinolinyl, isoquinolinyl, quinazolinyl, quinazolinonyl, indolinonyl, isoindolinonyl, tetrahydronaphthyl, tetrahydroquinolinyl, or tetrahydroisoquinolinyl. For example, $R^2$ can be Cl, Br, $CF_3$, cyclopropyl, cyclobutyl, cyclopentyl, cyclohexyl, piperidine, pyrrolidine, azetidine, $OCH_3$, $OCH_2CH_3$, phenyl,

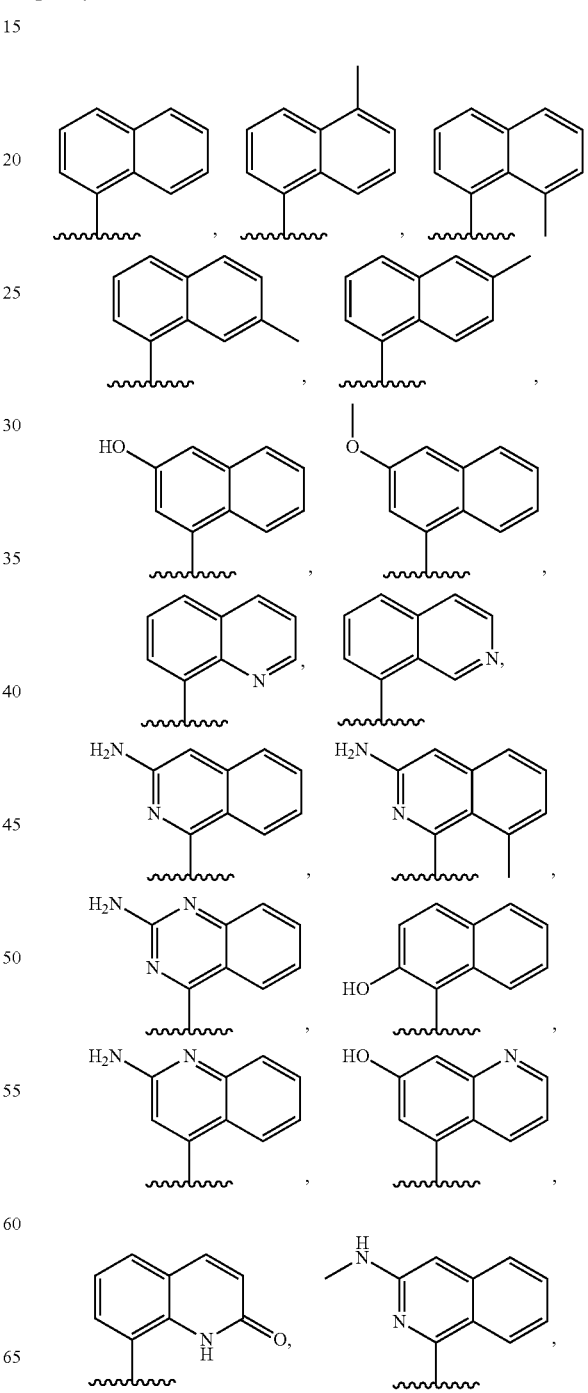

23
-continued
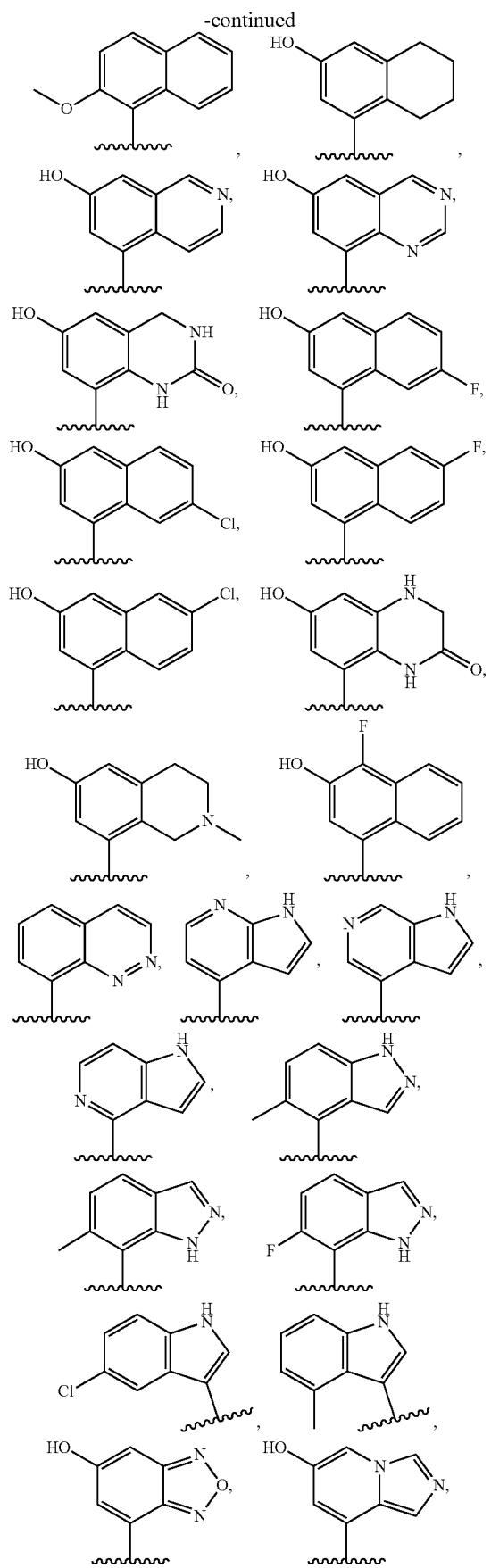
24
-continued
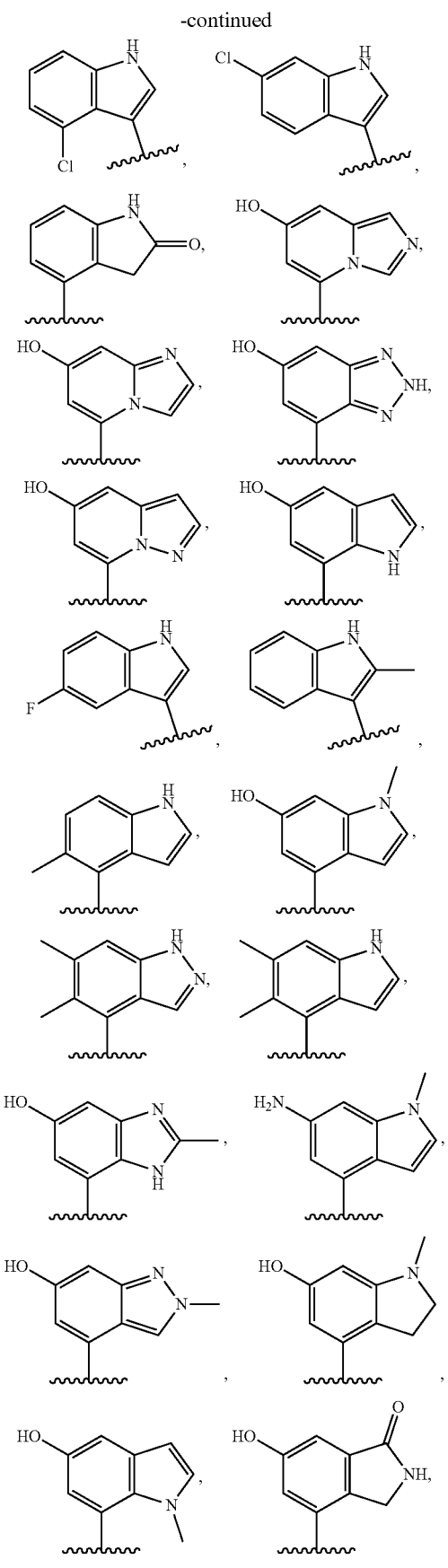

-continued
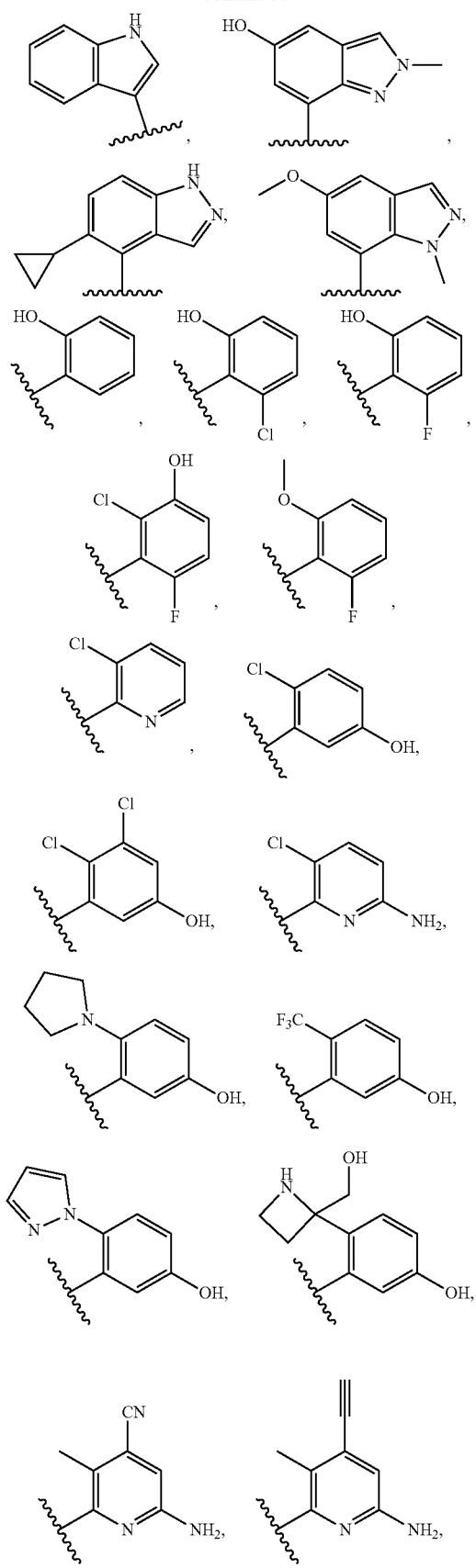
-continued
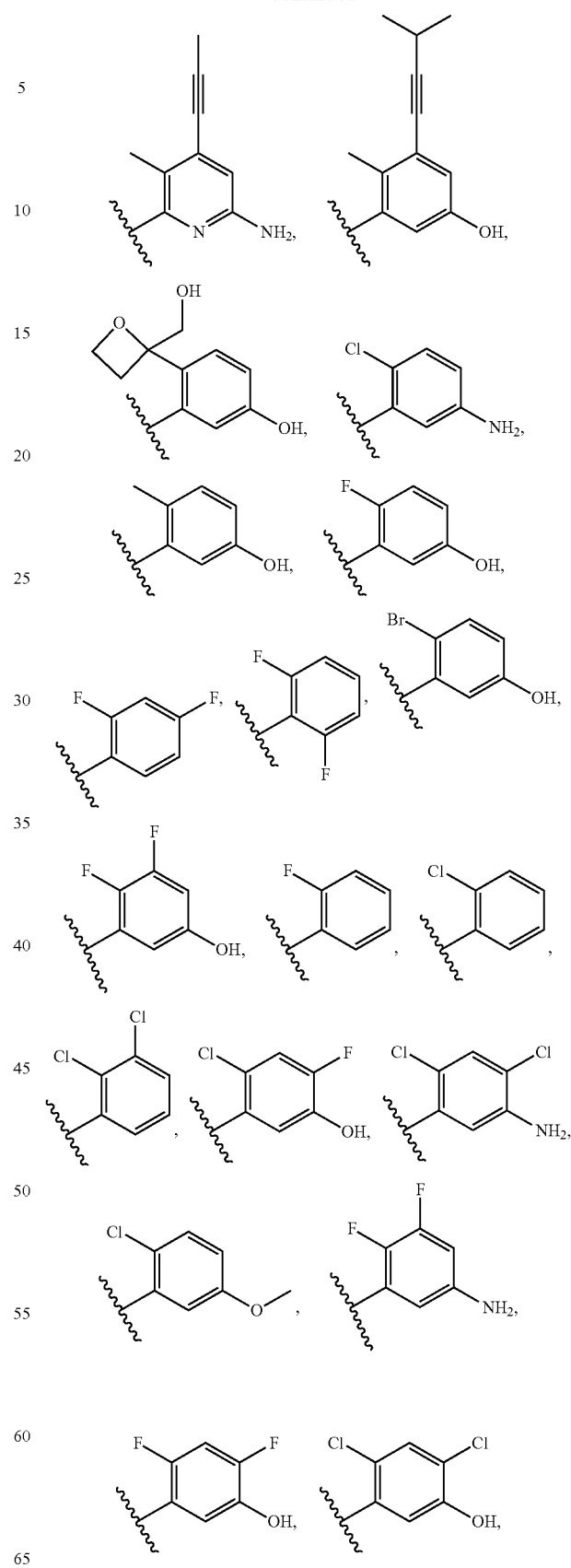

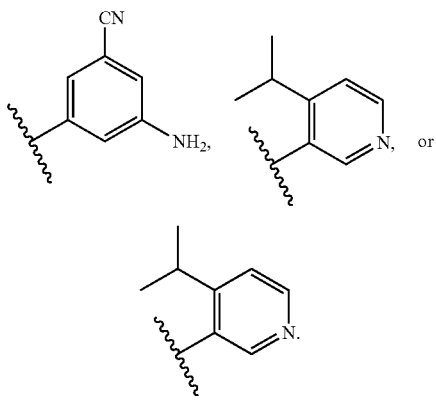

In various embodiments, $R^2$ can be bromine,

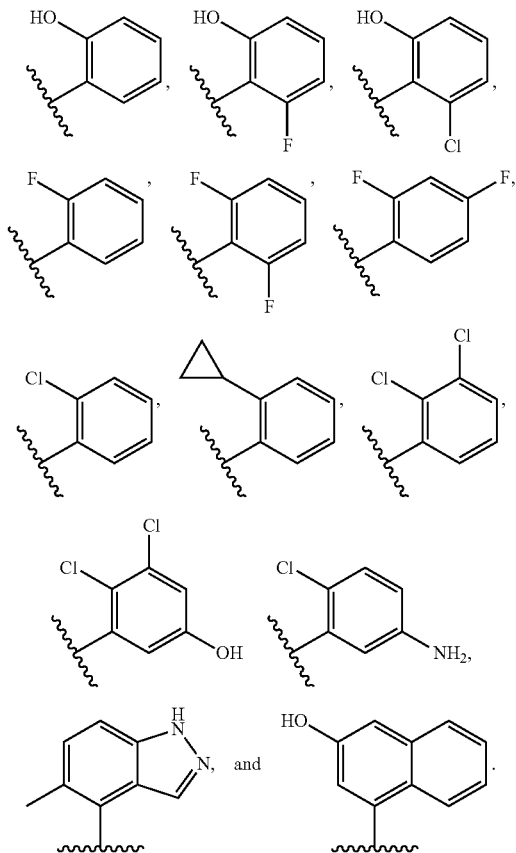

The compounds of formula (I), (II), (III), (III'), (IV), (IV'), or (V) as disclosed herein can have one or more of the following features. In various embodiments, $R^3$ is halo. In various embodiments, $R^3$ is $C_1$. In various embodiments, $R^3$ is F. In some embodiments, $R^3$ is $C_{1-2}$alkyl. In some embodiments, $R^3$ is methyl. In some embodiments, $R^3$ is $C_{1-2}$haloalkyl. In various embodiments, $R^3$ is $CF_3$.

The compounds of formula (I), (II), (III), (III'), (IV), (IV'), or (V) as disclosed herein can have one or more of the following features. In some embodiments, $R^4$ is

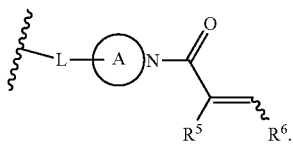

In various embodiments, $R^4$ is

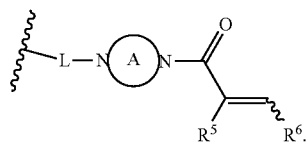

In some embodiments, $R^4$ is

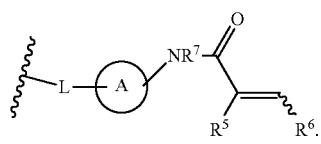

In some embodiments, $R^4$ is

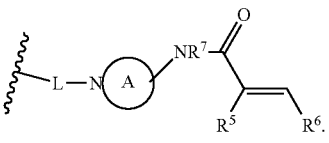

In some embodiments, $R^4$ is

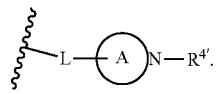

In some embodiments, $R^4$ is

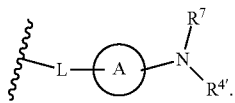

In some embodiments, $R^4$ can be

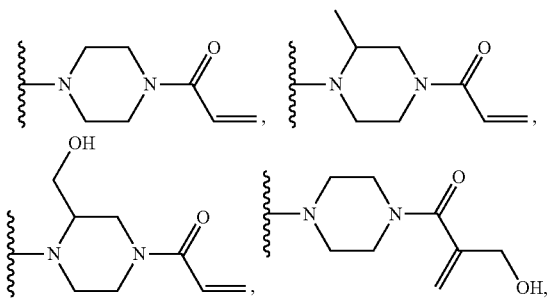

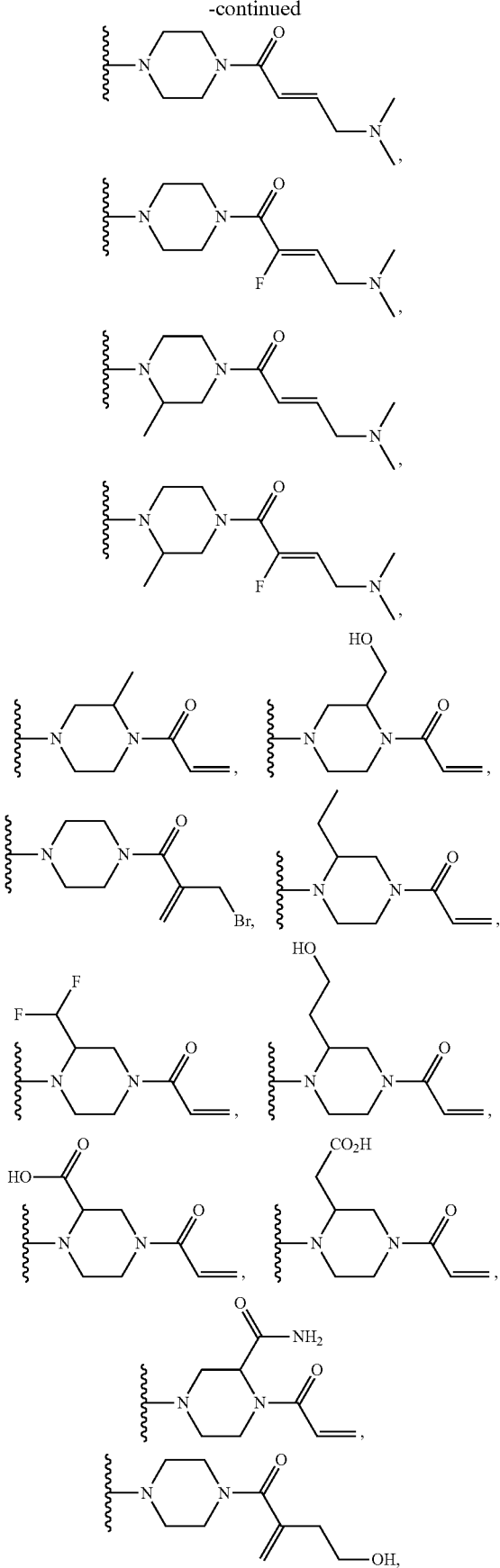
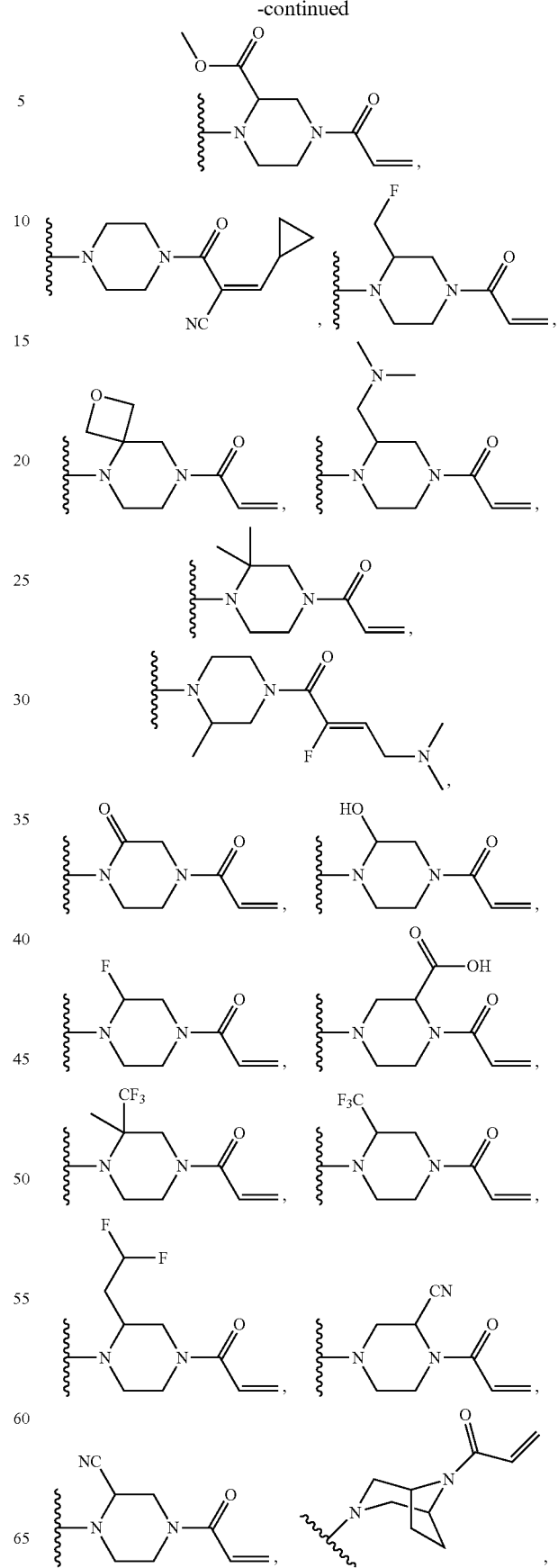

-continued
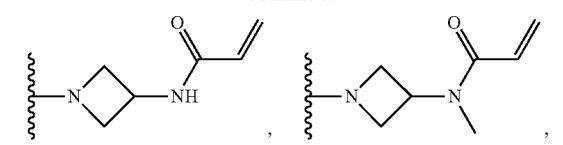
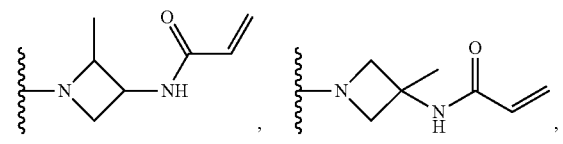
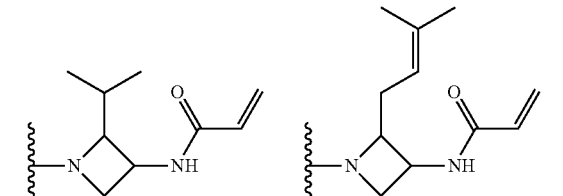
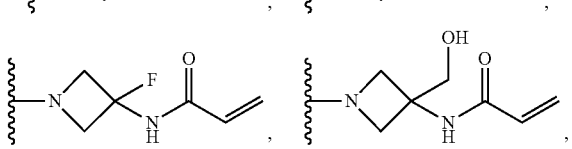
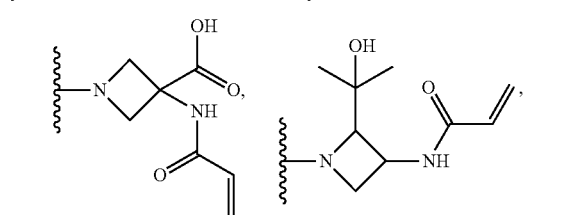
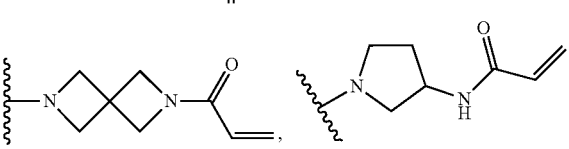
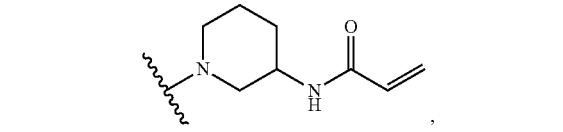
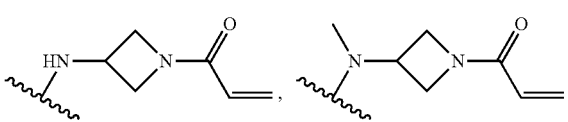
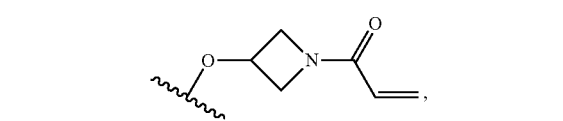
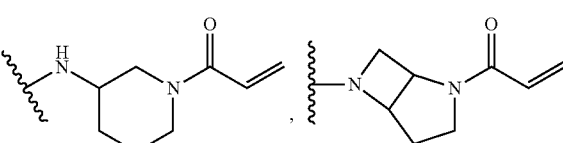
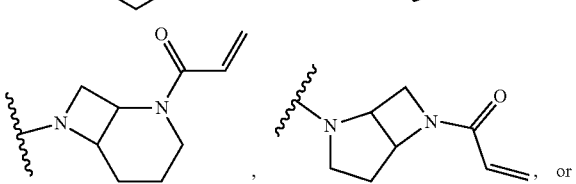, or
-continued
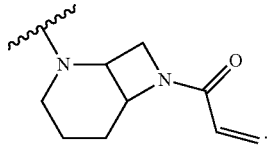
In various embodiments $R^4$ is H, $C_{1-8}$alkyl, $C_{2-8}$alkynyl, $C_{1-6}$alkylene-O—$C_{1-4}$alkyl, $C_{1-6}$alkylene-OH, $C_{1-6}$haloalkyl, $C_{0-3}$alkylene-$C_{3-8}$cycloalkyl, $C_{0-3}$alkylene-$C_{2-7}$heterocycloalkyl, $C_{0-3}$alkylene-$C_{6-14}$aryl, or selected from
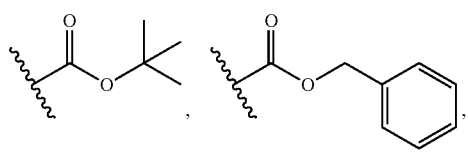
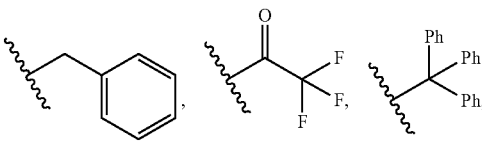
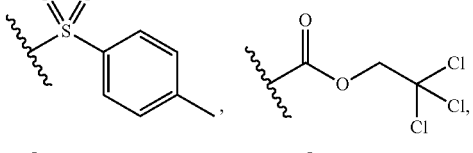
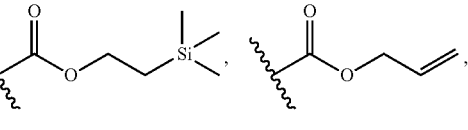
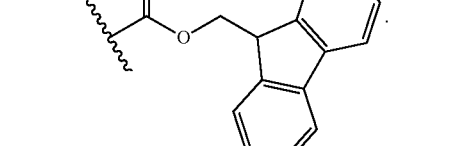, or
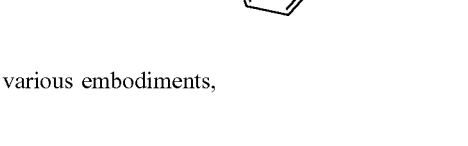
In various embodiments,
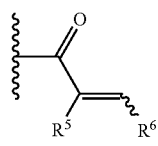
can be
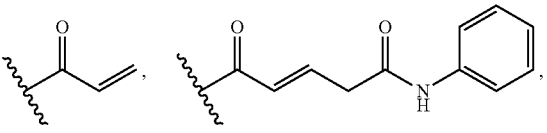

-continued
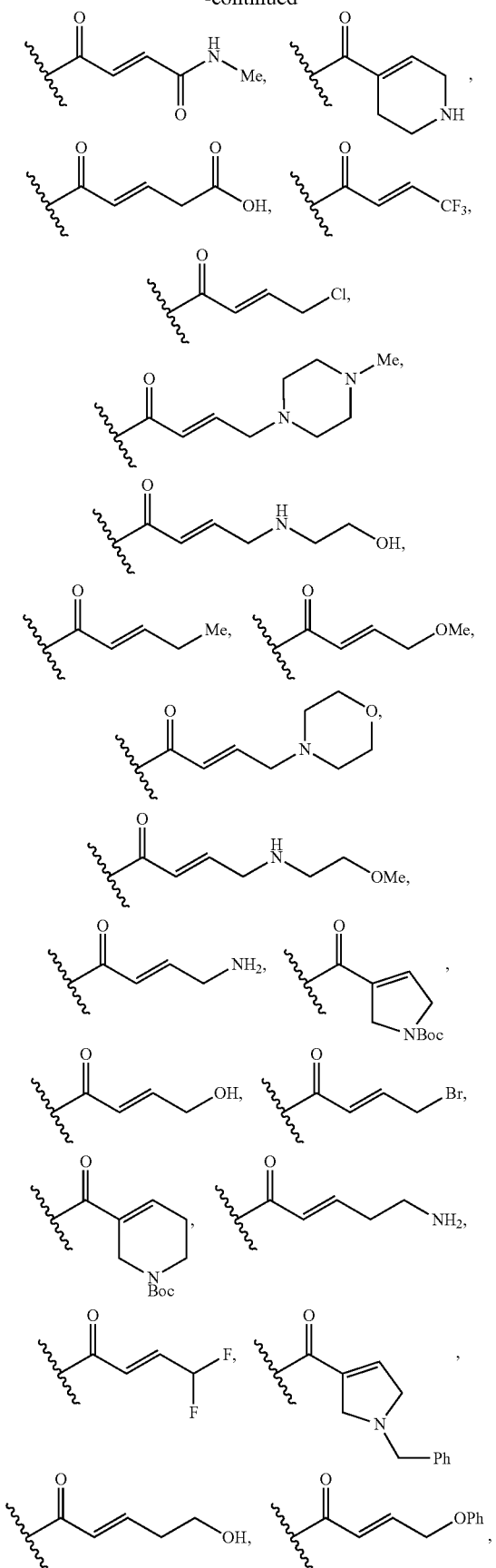
-continued
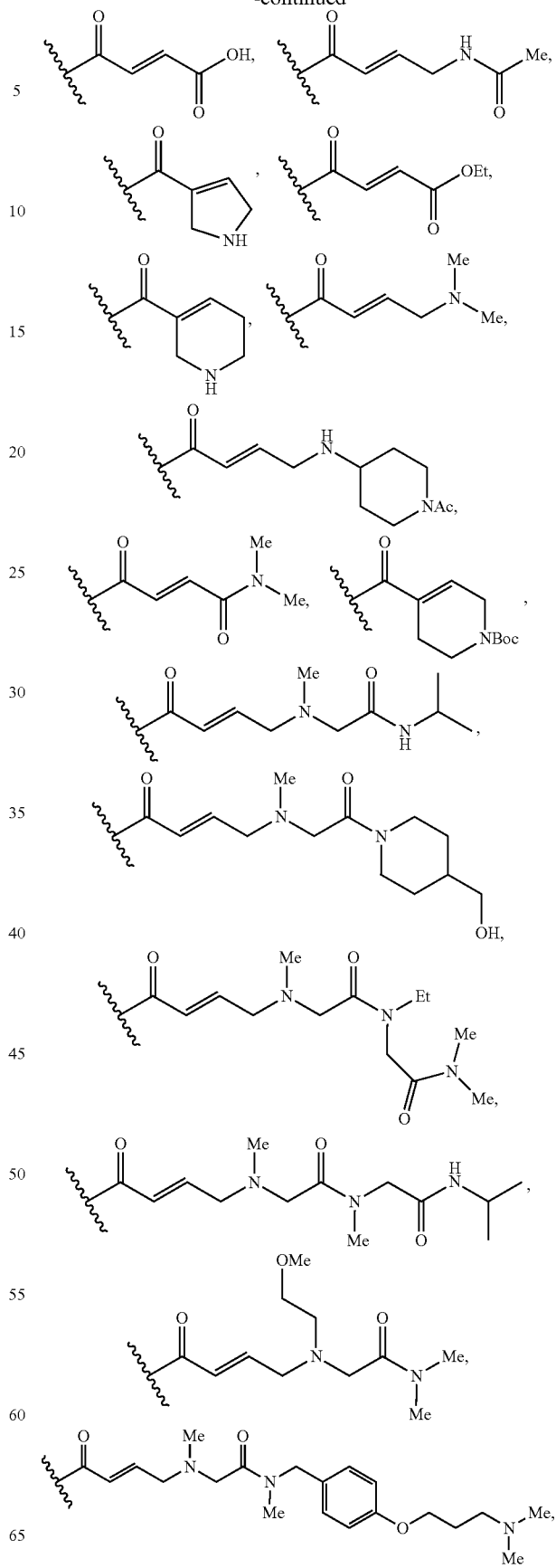

-continued
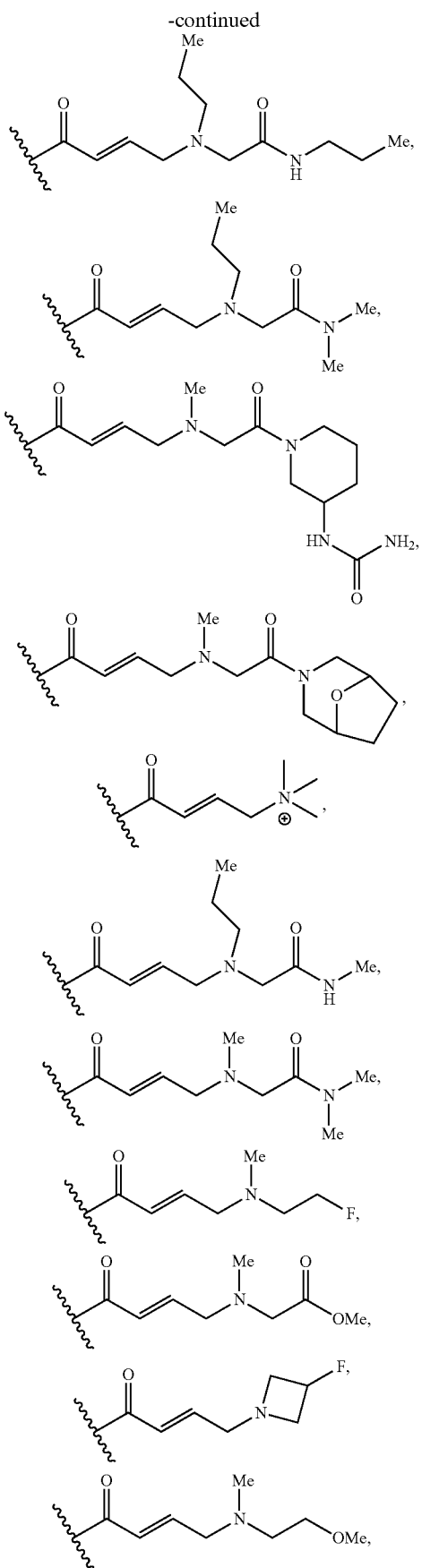
-continued
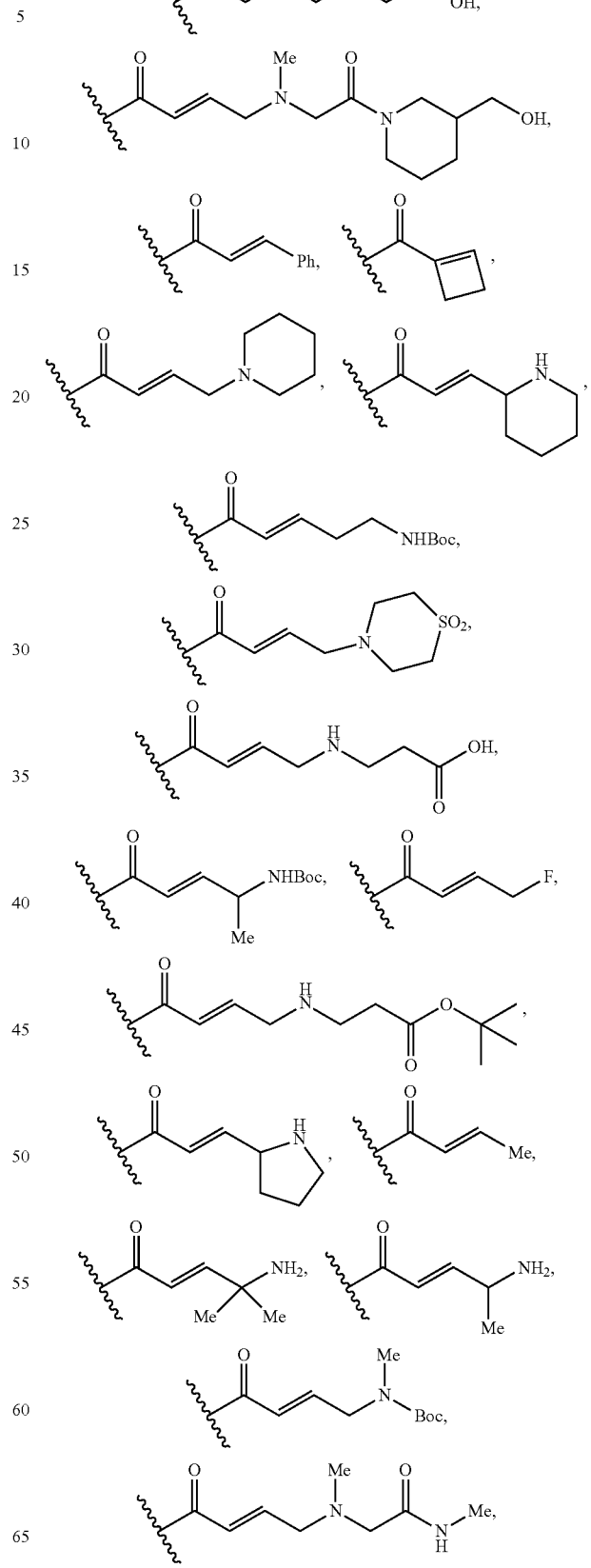

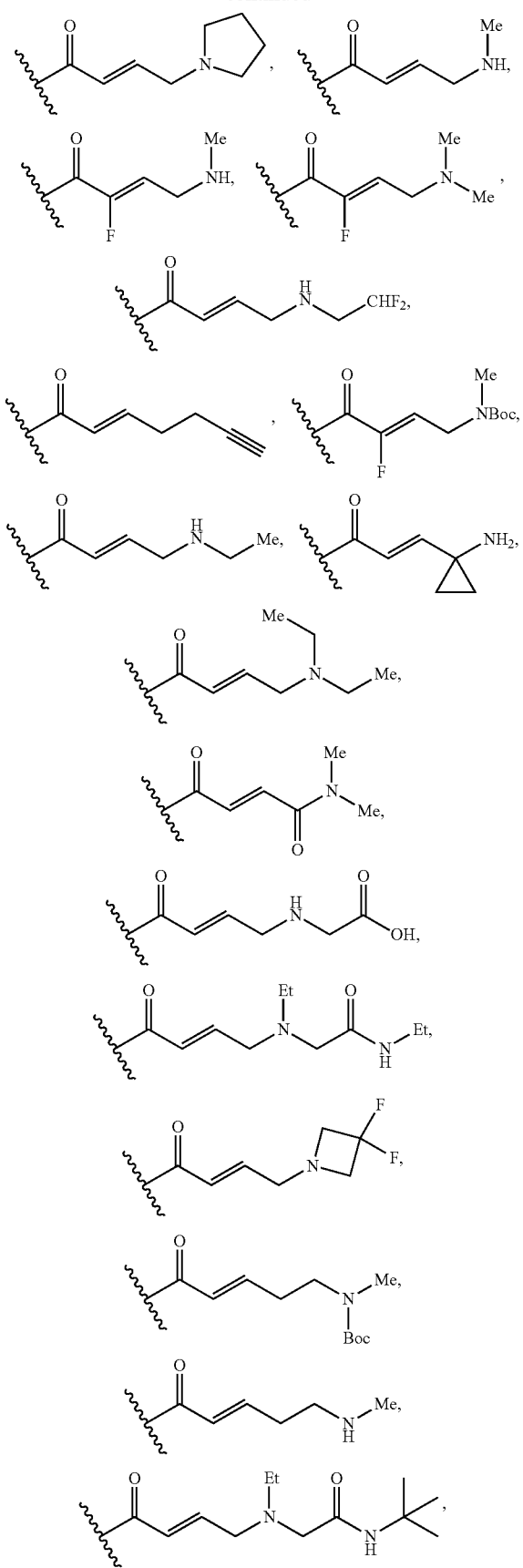
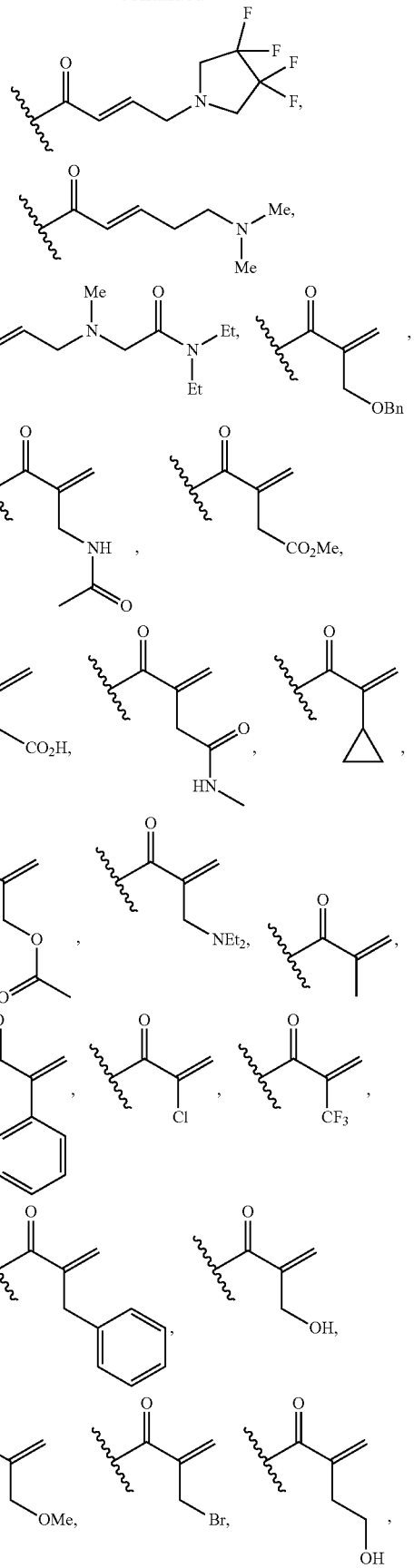

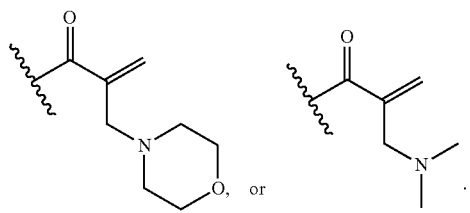
In some embodiments, ring A is
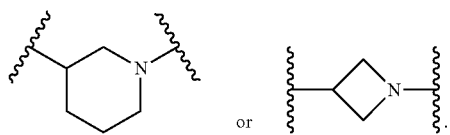 [SMILES: *C1CCCN(*)C1 ; *C1CN(*)C1]
In some embodiments, ring A comprises piperidinyl, piperazinyl, pyrrolidinyl, or azetidinyl. In some embodiments, ring A comprises piperidinyl.
In various embodiments, ring A can be
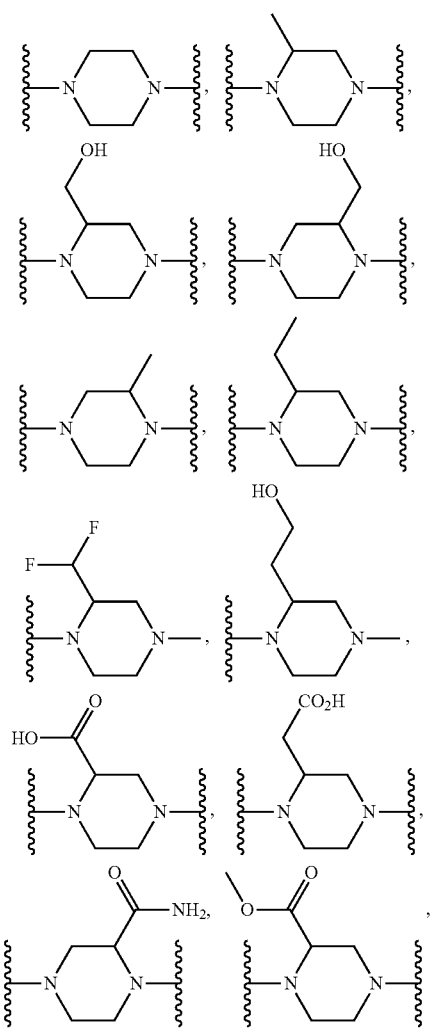
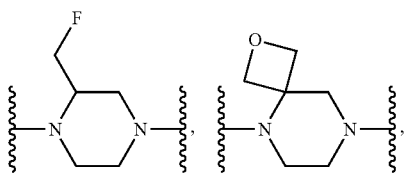
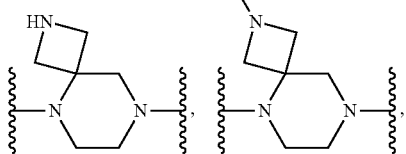
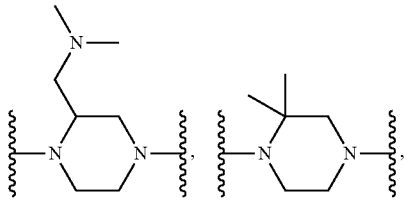
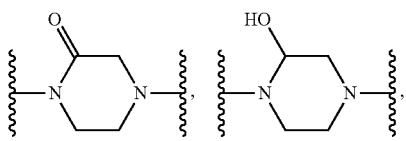
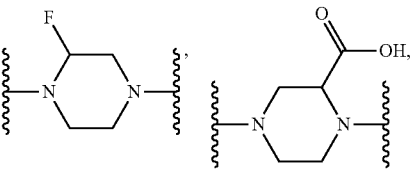
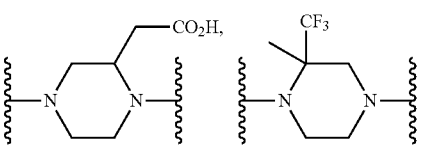
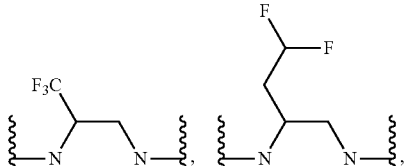
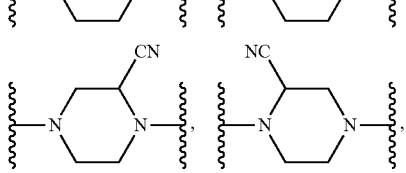
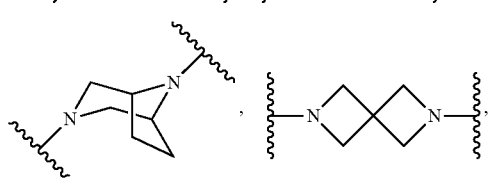
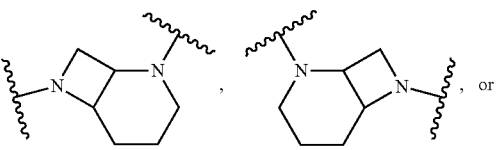

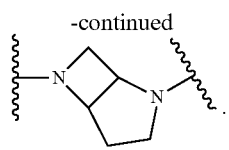

In various embodiments, ring A can be

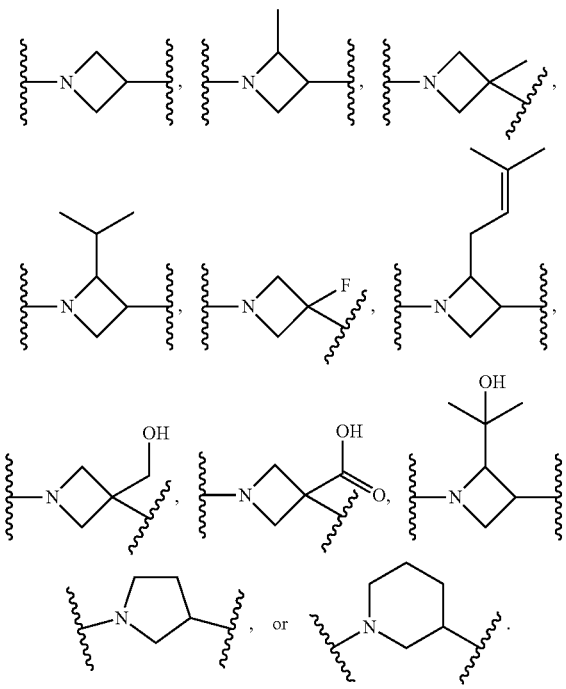

The compounds of formula (I), (II), (III), (III'), (IV), (IV'), or (V) as disclosed herein can have one or more of the following features.

In some embodiments, L is a bond.
In some embodiments, L is $C_{1-2}$alkylene.
In various embodiments, L is O. In some embodiments, L is S.
In various embodiments, L is NH.
In some embodiments, $R^5$ is H or halo.
In some embodiments, $R^5$ is H, Br, Cl, F, CN, $CH_3$, $CF_3$, $CH_2Br$, $CH_2OH$, $CH_2CH_2OH$, $CH_2OCH_2$phenyl, cyclopropyl, phenyl, $CH_2$phenyl, $CH_2OCH_3$, $CH_2N(CH_3)_2$, $CH_2N(CH_2CH_3)_2$, $CH_2CO_2H$, $CH_2CO_2CH_3$, $CH_2C(O)NHCH_3$, $CH_2OC(O)CH_3$, or

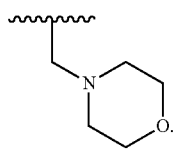 [SMILES: *CN1CCOCC1]

In some embodiments, $R^6$ is $C_{1-6}$alkyl, $C_{1-6}$alkylene-O—$C_{1-6}$alkyl, $C_{1-6}$alkylene-OH, $C_{1-3}$haloalkyl, $C_{1-6}$alkylene-amine, $C_{0-6}$alkylene-amide, $C_{0-1}$alkylene C(O)O$C_{1-3}$alkyl, $C_{0-1}$alkylene-$C_{2-14}$heterocycloalkyl, $C_{0-1}$alkylene-$C_{3-14}$cycloalkyl, or $C_{0-5}$alkylene-$C_{6-14}$aryl.

In various embodiments, $R^6$ is $C_{0-6}$alkylene-amine or $C_{0-5}$alkylene-amide and is $CH_2NH_2$, $CH(CH_3)NH_2$, $CH(CH_3)_2NH_2$, $CH_2CH_2NH_2$, $CH_2CH_2N(CH_3)_2$, $CH_2NHCH_3$, $C(O)NHCH_3$, $C(O)N(CH_3)_2$, $CH_2C(O)NH$-phenyl, $CH_2NHC(O)CH_3$, $CH_2NHCH_2CH_2OH$, $CH_2NHCH_2CO_2H$, $CH_2NH(CH_3)CH_2C_{02}CH_3$, $CH_2NHCH_2CH_2OCH_3$, $CH_2NH(CH_3)CH_2CH_2OCH_3$, $CH_2NH(CH_3)CH_2C(O)N(CH_3)_2$, $CH_2NH(CH_3)CH_2C(O)NHCH_3$, $CH_2NMe_2$, $CH_2NH(CH_3)CH_2CH_2OH$, $CH_2NH(CH_3)CH_2CH_2F$, $CH_2N^+(CH_3)_3$, $CH_2NHCH_2CHF_2$, $CH_2NHCH_2CH_3$,

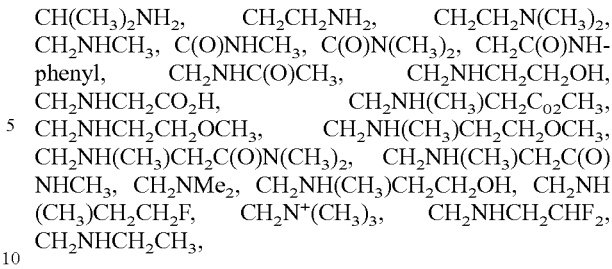

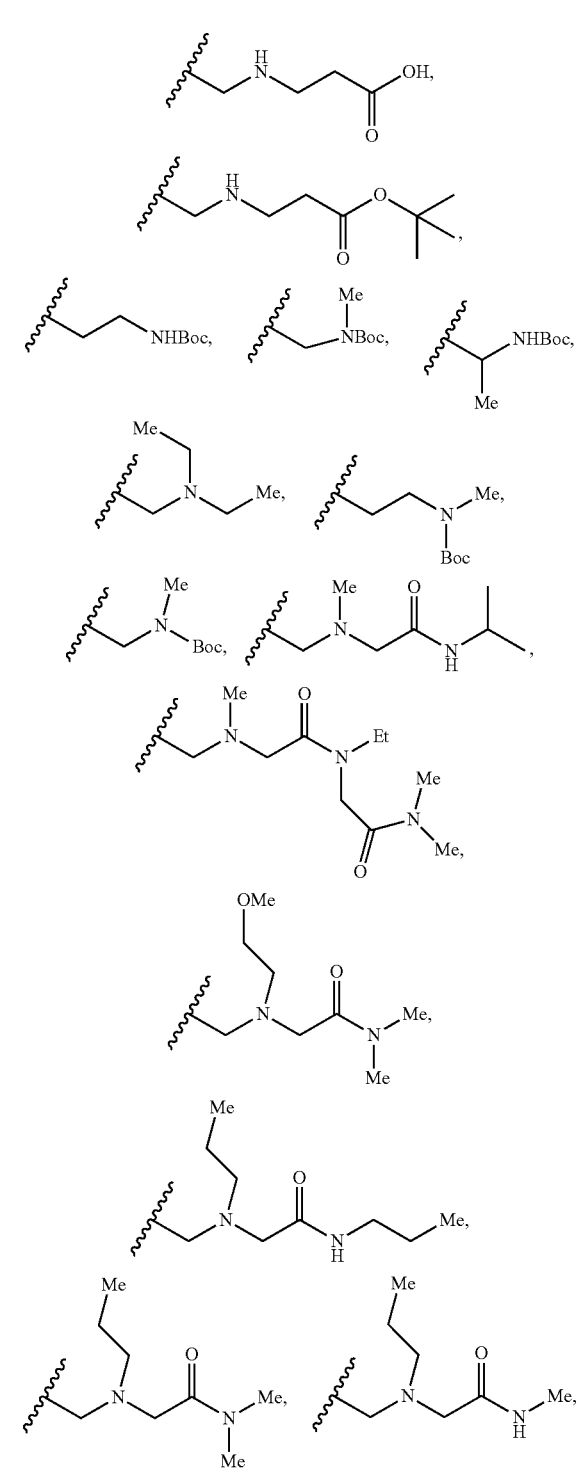

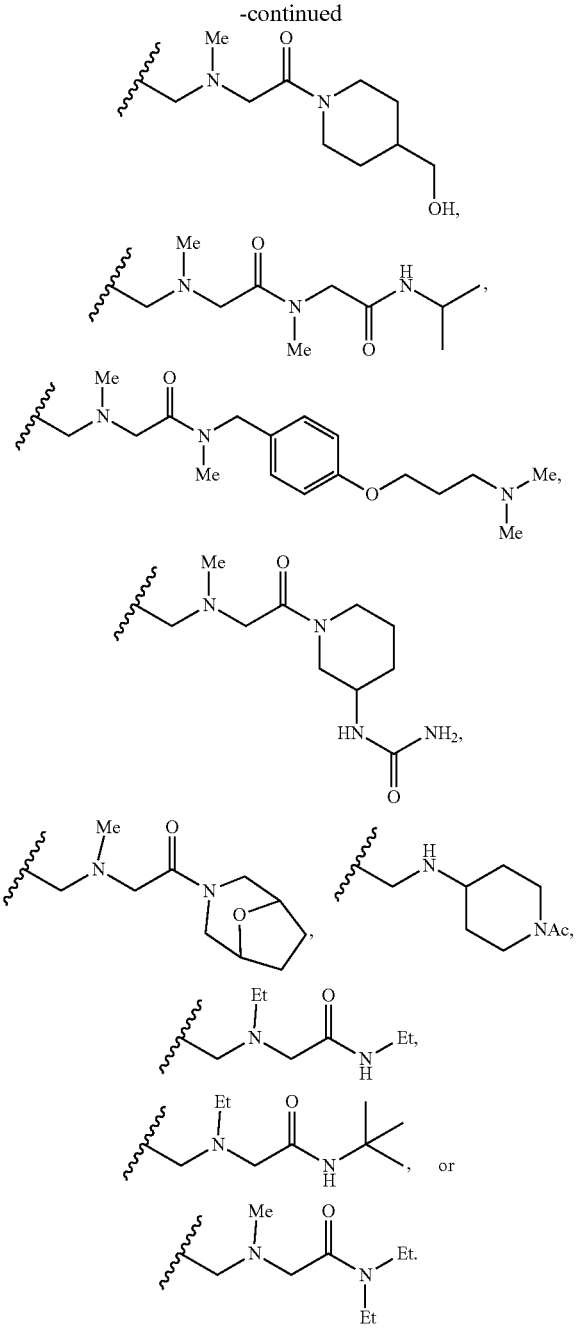
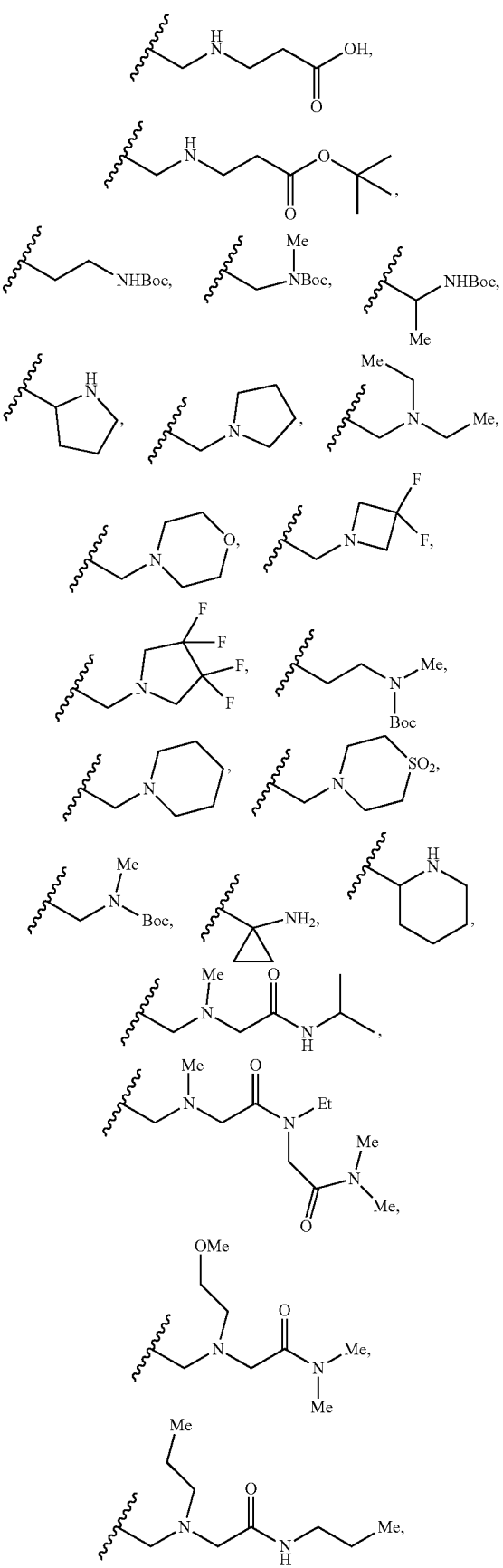

In various embodiments, $R^6$ is phenyl, cyclopropyl, $CH_3$, $CF_3$, $CH_2CH_3$, $CH_2NH_2$, $CH(CH_3)NH_2$, $CH(CH_3)_2NH_2$, $CH_2Cl$, $CH_2Br$, $CH_2OCH_3$, $CH_2Ophenyl$, $CH_2OH$, $CO_2H$, $CO_2CH_2CH_3$, $CH_2CO_2H$, $CH_2CH_2NH_2$, $CH_2CH_2OH$, $CH_2CH_2N(CH_3)_2$, $CH_2NHCH_3$, $C(O)NHCH_3$, $C(O)N(CH_3)_2$, $CH_2C(O)NHphenyl$, $CH_2CHF_2$, $CH_2F$, $CHF_2$, $CH_2NHC(O)CH_3$, $CH_2NHCH_2CH_2OH$, $CH_2NHCH_2CO_2H$, $CH_2NH(CH_3)CH_2CO_2CH_3$, $CH_2NHCH_2CH_2OCH_3$, $CH_2NH(CH_3)CH_2CH_2OCH_3$, $CH_2NH(CH_3)CH_2C(O)N(CH_3)_2$, $CH_2NH(CH_3)CH_2C(O)NHCH_3$, $CH_2CH_2CCH$, $CH_2NMe_2$, $CH_2NH(CH_3)CH_2CH_2OH$, $CH_2NH(CH_3)CH_2CH_2F$, $CH_2N^+(CH_3)_3$, $CH_2NHCH_2CHF_2$, $CH_2NHCH_2CH_3$, -continued

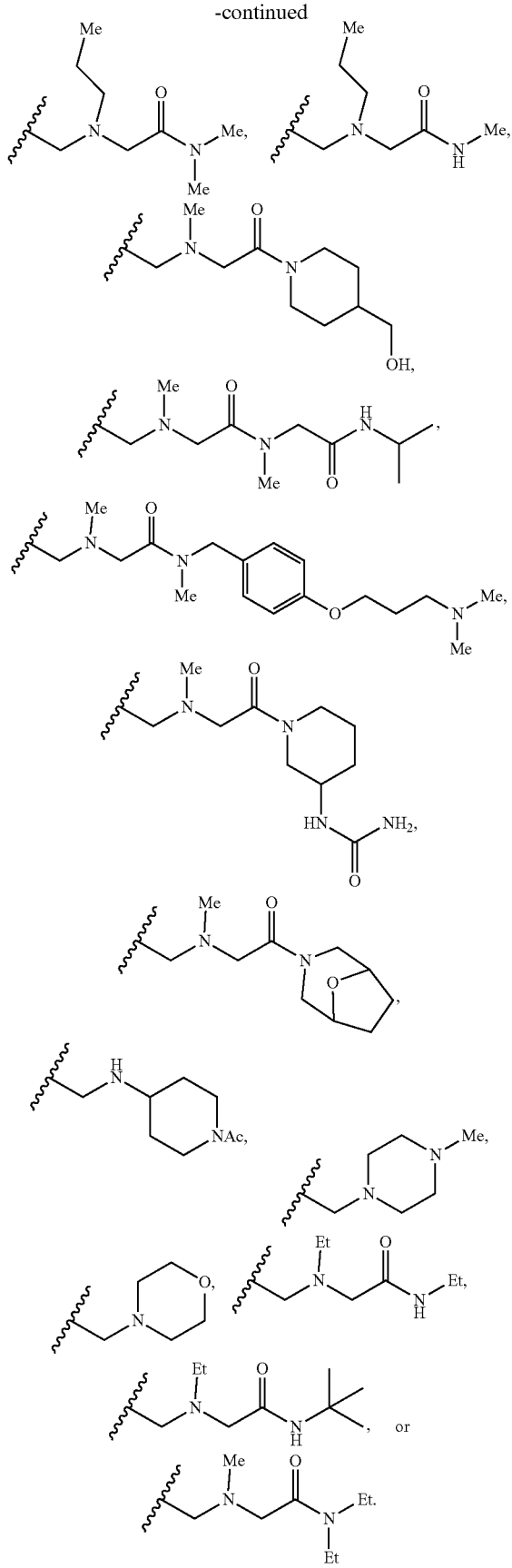

In various embodiments, $R^5$ and $R^6$ together are

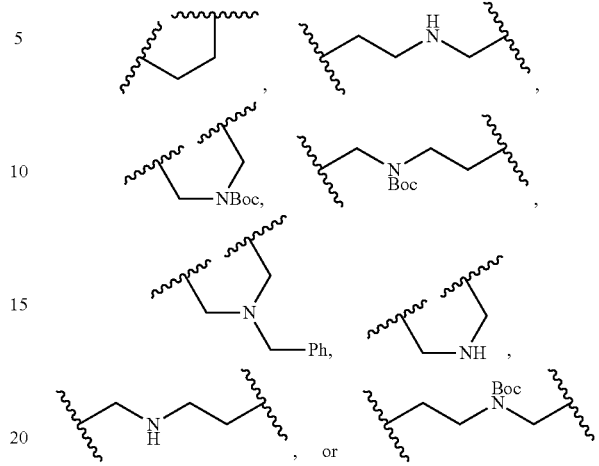

In some embodiments, each of $R^5$ and $R^6$ is H.
In some embodiments, $R^7$ is H.
In some embodiments, $R^7$ is methyl.
In various embodiments, $R^7$ and $R^5$ together are —$CH_2$— or —$C(O)CH_2$—.

The compounds disclosed herein can be in the form of a pharmaceutically acceptable salt. The compounds provided can be formulated into a pharmaceutical formulation comprising a compound disclosed herein and a pharmaceutically acceptable excipient.

Also provided is a method of inhibiting KRAS G12C in a cell, comprising contacting the cell with a compound or composition disclosed herein. Further provided is a method of treating cancer in a subject comprising administering to the subject a therapeutically effective amount of a compound or composition disclosed herein. In some embodiments, the cancer is lung cancer, pancreatic cancer, or colorectal cancer.

DETAILED DESCRIPTION

Definitions

Abbreviations

The following abbreviations may be used herein:

| | |
|---|---|
| AcOH | acetic acid |
| aq or aq. | Aqueous |
| BOC or Boc | tert-butyloxycarbonyl |
| cpme | cyclopentyl methyl ether |
| DCE | 1,2-dichloroethane |
| DABCO | 1,4-diazabicyclo[2.2.2]octane |
| DCM | Dichloromethane |
| DMA | N,N-Dimethylacetamide |
| DMAP | 4-dimethylaminopyridine |
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | Equivalent |
| ESI or ES | electrospray ionization |
| Et | Ethyl |
| $Et_2O$ | diethyl ether |
| EtOAc | ethyl acetate |
| g | Grams |
| h | Hour |
| HPLC | high pressure liquid chromatography |
| iPr | Isopropyl |
| $iPr_2NEt$ or DIPEA | N-ethyl diisopropylamine (Hünig's base) |

| | |
|---|---|
| | -continued |
| KHMDS | potassium hexamethyldisilazide |
| KOAc | potassium acetate |
| Lawesson's reagent | 2,4-bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide |
| LC MS, LCMS, LC-MS or LC/MS | liquid chromatography mass spectroscopy |
| LG | Leaving group (e.g., halogen, mesylate, triflate) |
| LHMDS or LiHMDS | lithium hexamethyldisilazide |
| m/z | mass divided by charge |
| Me | Methyl |
| MeCN | Acetonitrile |
| MeOH | Methanol |
| Met | Metal species for cross-coupling (e.g., MgX, ZnX, SnR$_3$, SiR$_3$, B(OR)$_2$) |
| mg | Milligrams |
| min | Minutes |
| mL | Milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| Pd$_2$(dba)$_3$ | tris(dibenzylideneacetone)dipalladium(0) |
| Pd(dppf)Cl$_2$ · DCM | [1,1'-Bis(diphenylphosphino)ferrocene]dichloropalladium(II), complex with dichloromethane |
| Pd(PPh$_3$)$_4$ | Tetrakis(triphenylphosphine)palladium(0) |
| Ph | Phenyl |
| PR or PG or Prot. group | protecting group |
| rbf | round-bottom flask |
| RP-HPLC | reverse phase high pressure liquid chromatography |
| RT or rt | room temperature |
| sat. or satd. | saturated |
| SFC | supercritical fluid chromatography |
| SPhos Pd G3 or SPhos G3 | (2-Dicyclohexylphosphino-2',6'-dimethoxybiphenyl)[2-(2'-amino-1,1'-biphenyl)]palladium(II) methanesulfonate |
| TBAF | tetra-n-butylammonium fluoride |
| TBTU | N,N,N',N'-Tetramethyl-O-(benzotriazol-1-yl)uronium tetrafluoroborate |
| t-BuOH | tert-butanol |
| TEA or Et$_3$N | Trimethylamine |
| TFA | trifluoroacetic acid |
| THF | Tetrahydrofuran |
| UV | Ultraviolet |

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched C1-C$_8$ hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl. The term Cm-n means the alkyl group has "m" to "n" carbon atoms. The term "alkylene" refers to an alkyl group having a substituent. An alkyl (e.g., methyl), or alkylene (e.g., —CH$_2$—), group can be substituted with one or more, and typically one to three, of independently selected, for example, halo, trifluoromethyl, trifluoromethoxy, hydroxy, alkoxy, nitro, cyano, alkylamino, C$_{1-8}$ alkyl, C$_{2-8}$alkenyl, C$_{2-8}$ alkynyl, —NC, amino, —CO$_2$H, —CO$_2$C$_1$-C$_8$alkyl, —OCOC$_1$-C$_8$alkyl, C$_3$-C$_{10}$ cycloalkyl, C$_3$-C$_{10}$ heterocycloalkyl, C$_5$-C$_{14}$aryl, and C$_5$-C$_{14}$ heteroaryl. The term "haloalkyl" specifically refers to an alkyl group wherein at least one, e.g., one to six, or all of the hydrogens of the alkyl group are substituted with halo atoms.

The terms "alkenyl" and "alkynyl" indicate an alkyl group that further includes a double bond or a triple bond, respectively.

As used herein, the term "halo" refers to fluoro, chloro, bromo, and iodo. The term "alkoxy" is defined as —OR, wherein R is alkyl.

As used herein, the term "amino" or "amine" interchangeably refers to a —NR$_2$ group, wherein each R is, e.g., H or a substituent. In some embodiments, the amino group is further substituted to form an ammonium ion, e.g., NR$_3^+$. Ammonium moieties are specifically included in the definition of "amino" or "amine." Substituents can be, for example, an alkyl, alkoxy, cycloalkyl, heterocycloalkyl, amide, or carboxylate. An R group may be further substituted, for example, with one or more, e.g., one to four, groups selected from halo, cyano, alkenyl, alkynyl, alkyl, cycloalkyl, heterocycloalkyl, aryl, heteroaryl, urea, carbonyl, carboxylate, amine, and amide. An "amide" or "amido" group interchangeably refers to a group similar to an amine or amino group but further including a C(O), e.g., —C(O) NR$_2$. Some contemplated amino or amido groups (some with optional alkylene groups, e.g., alkylene-amino, or alkylene-amido) include CH$_2$NH$_2$, CH(CH$_3$)NH$_2$, CH(CH$_3$)$_2$NH$_2$, CH$_2$CH$_2$NH$_2$, CH$_2$CH$_2$N(CH$_3$)$_2$, CH$_2$NHCH$_3$, C(O)NHCH$_3$, C(O)N(CH$_3$)$_2$, CH$_2$C(O)NH-phenyl, CH$_2$NHC(O)CH$_3$, CH$_2$NHCH$_2$CH$_2$OH, CH$_2$NHCH$_2$CO$_2$H, CH$_2$NH(CH$_3$)CH$_2$C$_{02}$CH$_3$, CH$_2$NHCH$_2$CH$_2$OCH$_3$, CH$_2$NH(CH$_3$)CH$_2$CH$_2$OCH$_3$, CH$_2$NH(CH$_3$)CH$_2$C(O)N(CH$_3$)$_2$, CH$_2$NH(CH$_3$)CH$_2$C(O) NHCH$_3$, CH$_2$CH$_2$CCH, CH$_2$NMe$_2$, CH$_2$NH(CH$_3$) CH$_2$CH$_2$OH, CH$_2$NH(CH$_3$)CH$_2$CH$_2$F, CH$_2$N$^+$(CH$_3$)$_3$, CH$_2$NHCH$_2$CHF$_2$, CH$_2$NHCH$_2$CH$_3$,

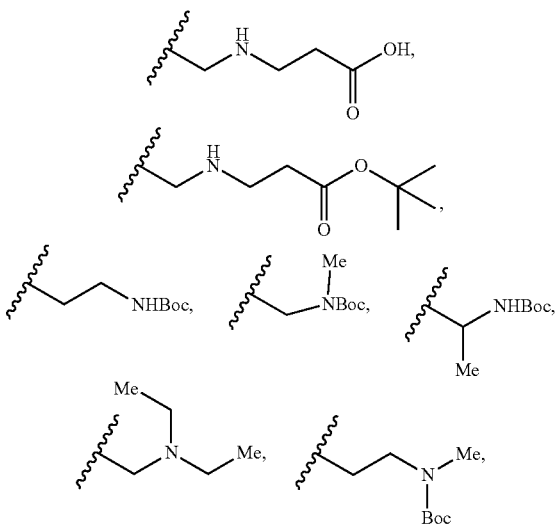

-continued

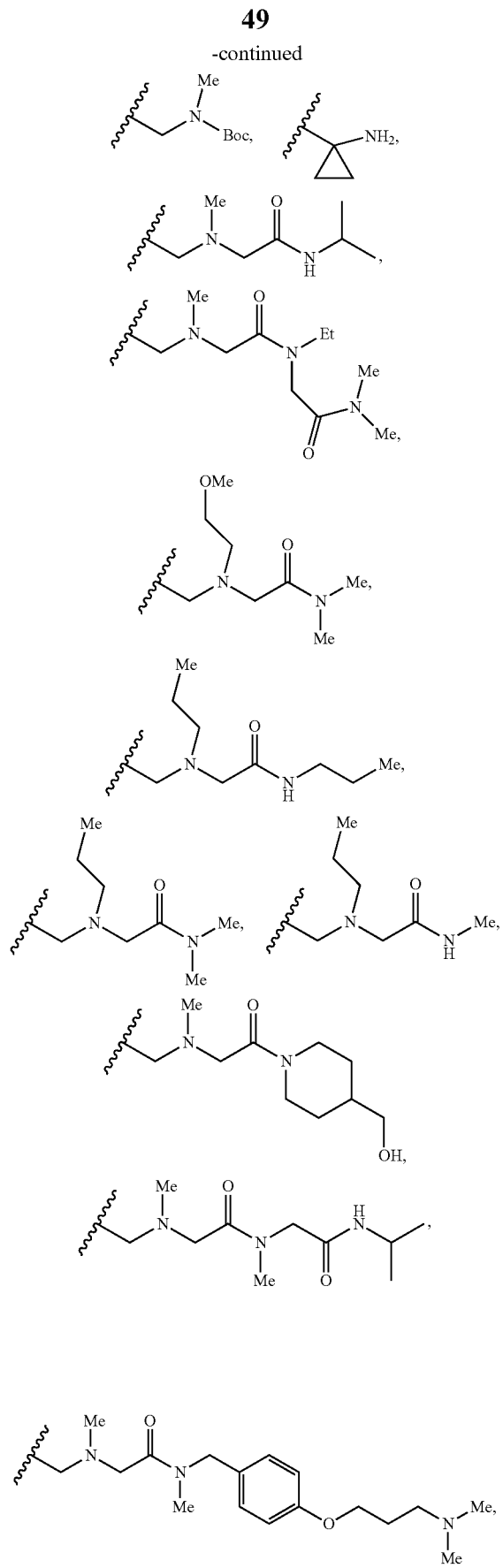

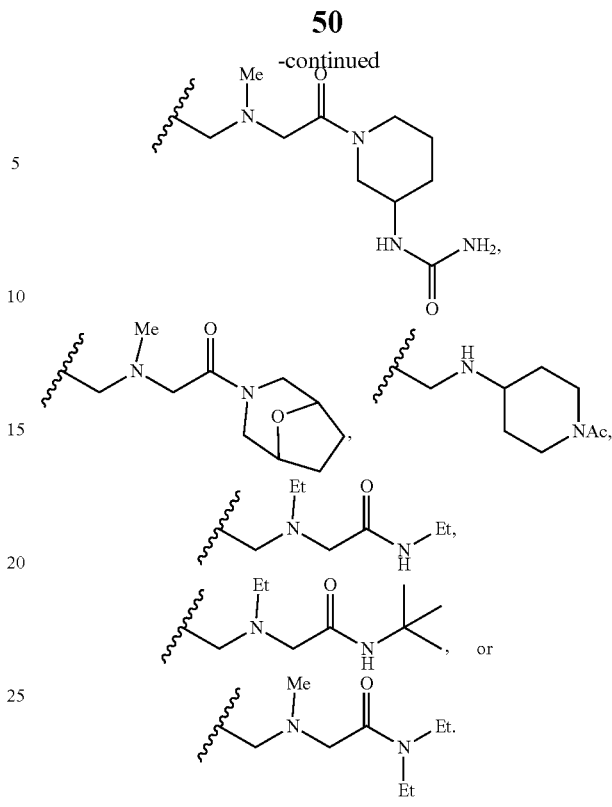

As used herein, the term "aryl" refers to a $C_{6-14}$ monocyclic or polycyclic aromatic group, preferably a $C_{6-10}$ monocyclic or bicyclic aromatic group, or CM-M polycyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to $C_{10-14}$ bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, $C_{1-8}$alkyl, $C_{2-8}$alkenyl, $C_{2-5}$alkynyl, —$CF_3$, —$OCF_3$, —$NO_2$, —CN, —NC, —OH, alkoxy, amino, —$CO_2H$, —$CO_2C_1$-$C_8$alkyl, —$OCOC_1$-$C_8$alkyl, $C_3$-$C_{10}$ cycloalkyl, $C_3$-$C_{10}$ heterocycloalkyl, $C_5$-$C_{10}$aryl, and $C_5$-$C_{14}$ heteroaryl.

As used herein, the term "cycloalkyl" refers to a monocyclic or polycyclic non-aromatic carbocyclic ring, where the polycyclic ring can be fused, bridged, or spiro. The carbocyclic ring can have 3 to 10 carbon ring atoms. Contemplated carbocyclic rings include, but are not limited to, cyclopropyl, cyclobutyl, cyclopentyl, cyclohexyl, cycloheptyl, cyclooctyl, and cyclononyl.

As used herein, the term "heterocycloalkyl" means a monocyclic or polycyclic (e.g., bicyclic), saturated or partially unsaturated, ring system containing 3 or more (e.g., 3 to 12, 4 to 10, 4 to 8, or 5 to 7) total atoms, of which one to five (e.g., 1, 2, 3, 4, or 5) of the atoms are independently selected from nitrogen, oxygen, and sulfur. Nonlimiting examples of heterocycloalkyl groups include azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, and diazacycloheptyl.

Unless otherwise indicated, a cycloalkyl or heterocycloalkyl group can be unsubstituted or substituted with one or more, and in particular one to four, groups. Some contemplated substituents include halo, $C_{1-8}$alkyl, $C_{2-5}$alkenyl. $C_{2-5}$alkynyl. —$OCF_3$, —$NO_2$, —CN, —NC, —OH, alkoxy, amino, —$CO_2H$, —$CO_2C_1$-$C_8$alkyl, —$OCOC_1$-$C_8$alkyl, $C_3$-$C_{10}$ cycloalkyl, $C_3$-$C_{10}$ heterocycloalkyl, $C_5$-$C_{10}$aryl, and $C_5$-$C_{14}$ heteroaryl.

As used herein, the term "heteroaryl" refers to a monocyclic or polycyclic ring system (for example, bicyclic) containing one to three aromatic rings and containing one to four (e.g., 1, 2, 3, or 4) heteroatoms selected from nitrogen, oxygen, and sulfur in an aromatic ring. In certain embodiments, the heteroaryl group has from 5 to 20, from 5 to 15, from 5 to 10 ring, or from 5 to 7 atoms. Heteroaryl also refers to $C_{10-14}$ bicyclic and tricyclic rings, where one ring is aromatic and the others are saturated, partially unsaturated, or aromatic. Examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four or one or two, substituents. Contemplated substituents include halo, $C_{1-8}$alkyl, $C_{2-8}$alkenyl, $C_{2-8}$alkynyl, —$OCF_3$, —$NO_2$, —CN, —NC, —OH, alkoxy, amino, —$CO_2H$, —$C_{02}C_1$-$C_8$alkyl, —$OCOC_1$-$C_8$alkyl, $C_3$-$C_{10}$ cycloalkyl, $C_3$-$C_{10}$ heterocycloalkyl, $C_5$-$C_{14}$aryl, and $C_5$-$C_{14}$ heteroaryl.

As used herein, the term Boc refers to the structure

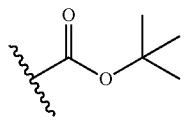

As used herein, the term Cbz refers to the structure

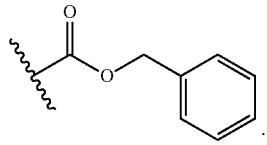 [SMILES: *C(=O)OCc1ccccc1]

As used herein, the term Bn refers to the structure

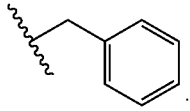 [SMILES: *Cc1ccccc1]

As used herein, the term trifluoroacetamide refers to the structure

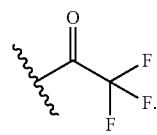 [SMILES: *C(=O)C(F)(F)F]

As used herein, the term trityl refers to the structure

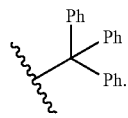

As used herein, the term tosyl refers to the structure

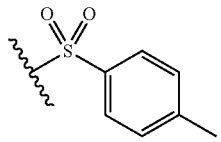

As used herein, the term Troc refers to the structure

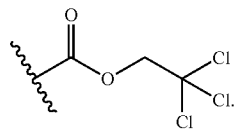 [SMILES: *C(=O)OCC(Cl)(Cl)Cl]

As used herein, the term Teoc refers to the structure

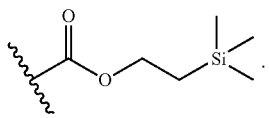 [SMILES: *C(=O)OCC[Si](C)(C)C]

As used herein, the term Teoc refers to the structure

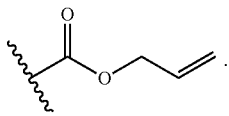 [SMILES: *C(=O)OCC=C]

As used herein, the term Alloc refers to the structure

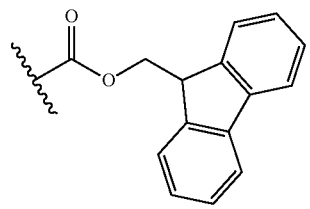

As used herein, the term Fmoc refers to the structure

Compounds of the Disclosure

Provided herein are KRAS inhibitors having structures of one of Formulas I-V, discussed in more detail below.

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. For example, groups such as, but not limited to, the following $R^{10}$ groups

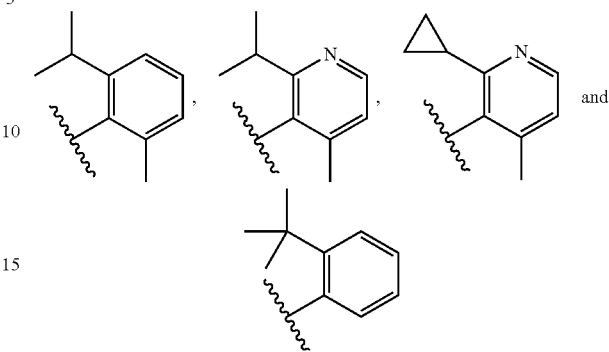

may exhibit restricted rotation.

The disclosure provides a compound having a structure of formula (I)

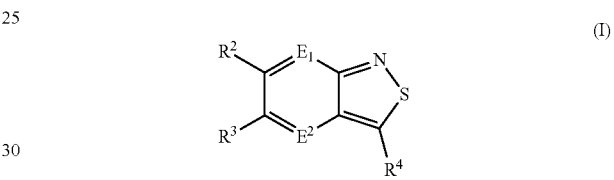

wherein $E^1$ and $E^2$ are each independently N or $CR^1$; $R^1$ is independently H, hydroxy, $C_{1-4}$ alkyl, $C_{1-4}$haloalkyl, $C_{1-4}$alkoxy, NH—$C_{1-4}$alkyl, N($C_{1-4}$alkyl)$_2$, cyano, or halo; $R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-8}$cycloalkyl, $C_{0-3}$alkylene-$C_{2-7}$heterocycloalkyl, $C_{0-5}$alkylenearyl, or $C_{0-5}$alkyleneheteroaryl, and each R' is independently H, $C_{1-6}$alkyl, $C_{1-6}$haloalkyl, $C_{3-4}$cycloalkyl, $C_{2-3}$alkenyl, $C_{2-3}$alkynyl, aryl, or heteroaryl, or two R' substituents, together with the nitrogen atom to which they are attached, form a 3-7-membered ring; $R^3$ is halo, $C_{1-3}$alkyl, $C_{1-2}$haloalkyl, $C_{1-3}$alkoxy, $C_{3-4}$cycloalkyl, $C_{2-3}$ alkenyl, $C_{2-3}$alkynyl, aryl, or heteroaryl; $R^4$ is ring A is a monocyclic 4-7 membered ring or a bicyclic, bridged, fused, or spiro 6-11 membered ring; L is a bond, $C_{1-6}$alkylene, —O—$C_{0-5}$alkylene, —S—$C_{0-5}$alkylene, or —NH—$C_{0-5}$alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH; $R^4$ is H, $C_{1-8}$alkyl, $C_{2-5}$alkynyl, $C_{1-6}$alkylene-O—$C_{1-4}$alkyl, $C_{1-6}$alkylene-OH, $C_{1-6}$haloalkyl, $C_{0-5}$alkylene-$C_{3-8}$cycloalkyl, $C_{0-3}$alkylene-$C_{2-7}$heterocycloalkyl, $C_{0-5}$alkylenearyl, or selected from

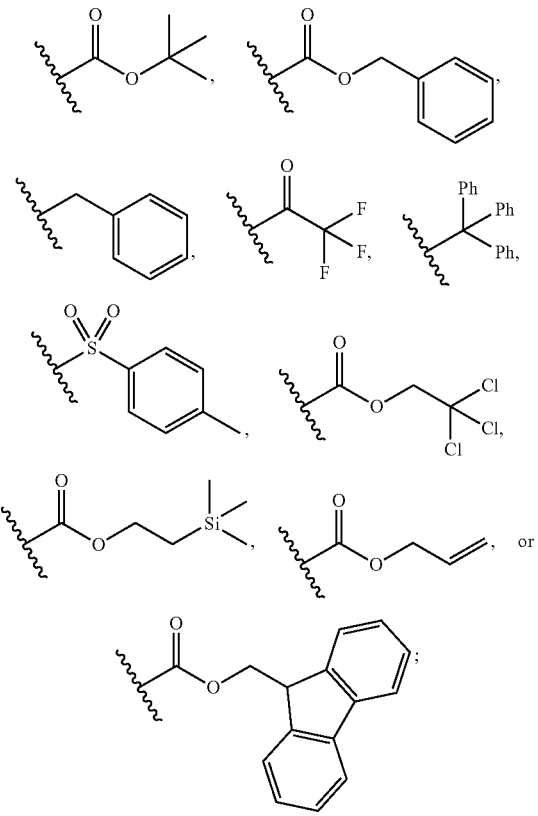

$R^5$ and $R^6$ are each independently H, halo, $C_{1-8}$alkyl, $C_{2-8}$alkynyl, $C_{1-6}$alkylene-O—$C_{1-4}$alkyl, $C_{1-6}$alkylene-OH, $C_{1-6}$haloalkyl, $C_{1-6}$alkyleneamine, $C_{0-6}$alkyleneamide, $C_{0-3}$alkylene-C(O)OH, $C_{0-3}$alkylene-C(O)O$C_{1-4}$ alkyl, $C_{1-6}$alkylene-O-aryl, $C_{0-3}$alkylene-C(O)$C_{1-4}$alkylene-OH, $C_{0-5}$alkylene-$C_{5-8}$cycloalkyl, $C_{0-3}$alkylene-$C_{2-7}$heterocycloalkyl, $C_{0-5}$alkylenearyl, or cyano, or $R^5$ and $R^6$, together with the atoms to which they are attached, form a 4-6 membered ring; and $R^7$ is H or $C_{1-8}$alkyl, or $R^7$ and $R^5$, together with the atoms to which they are attached, form a 4-6 membered ring, or a pharmaceutically acceptable salt thereof.

A compound of formula I, can be in the form of formula (I-A), (I-B), (I-C), or (I-D):

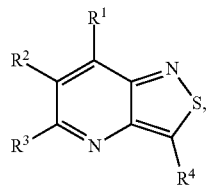
(I-A)

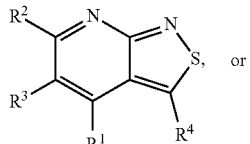
(I-B)

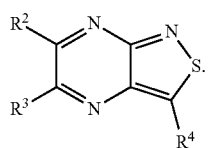
(I-C)

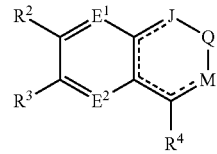
(I-D)

The disclosure also provides a compound having a structure of formula (II)

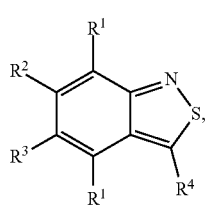
(II)

wherein $E^1$ and $E^2$ are each independently N or $CR^1$; J is N, $NR^{10}$, or $CR^{10}$; M is N, $NR^{13}$, or $CR^{13}$; ═══ is a single or double bond as necessary to give every atom its normal valence; $R^1$ is independently H, hydroxy, $C_{1-6}$alkyl, $C_{1-4}$haloalkyl, $C_{1-4}$alkoxy, NH—$C_{1-4}$alkyl, N($C_{1-4}$alkyl)$_2$, cyano, or halo; $R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-8}$cycloalkyl, $C_{0-3}$alkylene-$C_{2-7}$heterocycloalkyl, $C_{0-5}$alkylenearyl, or $C_{0-5}$alkyleneheteroaryl, and each R' is independently H, $C_{1-6}$alkyl, $C_{1-6}$haloalkyl, $C_{3-4}$cycloalkyl, $C_{2-3}$alkenyl, $C_{2-3}$alkynyl, aryl, or heteroaryl, or two R' substituents, together with the nitrogen atom to which they are attached, form a 3-7-membered ring; $R^3$ is halo, $C_{1-8}$alkyl, $C_{1-2}$haloalkyl, $C_{1-3}$alkoxy, $C_{3-4}$cycloalkyl, $C_{2-3}$alkenyl, $C_{2-3}$alkynyl, aryl, or heteroaryl; $R^4$ is

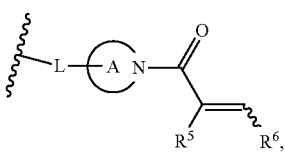

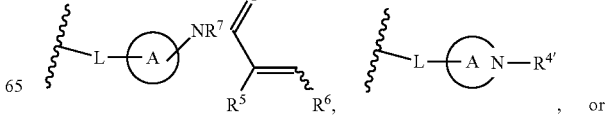
, or

-continued

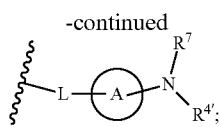

ring A is a monocyclic 4-7 membered ring or a bicyclic, bridged, fused, or spiro 6-11 membered ring; L is a bond, $C_{1-6}$alkylene, —O—$C_{0-5}$alkylene, —S—$C_{0-5}$alkylene, or —NH—$C_{0-5}$alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH; $R^4$ is H, $C_{1-8}$alkyl, $C_{2-8}$alkynyl, $C_{1-6}$alkylene-O—$C_{1-4}$alkyl, $C_{1-6}$alkylene-OH, $C_{1-6}$haloalkyl, $C_{0-5}$alkylene-$C_{3-8}$cycloalkyl, $C_{0-3}$alkylene-$C_{2-7}$heterocycloalkyl, $C_{0-5}$alkylenearyl, or selected from

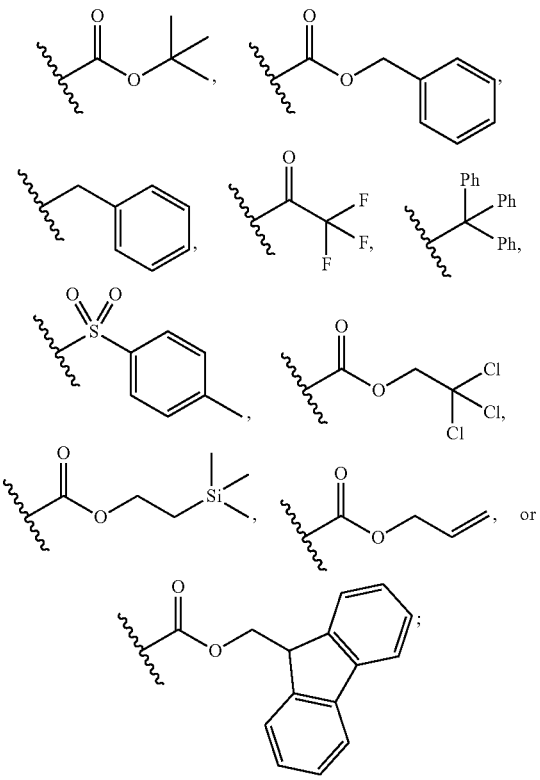

$R^5$ and $R^6$ are each independently H, halo, $C_{1-8}$alkyl, $C_{2-8}$alkynyl, $C_{1-6}$alkylene-O—$C_{1-4}$alkyl, $C_{1-6}$alkylene-OH, $C_{1-6}$haloalkyl, $C_{1-6}$alkyleneamine, $C_{0-6}$alkyleneamide, $C_{0-3}$alkylene-C(O)OH, $C_{0-3}$alkylene-C(O)O$C_{1-4}$ alkyl, $C_{1-6}$alkylene-O-aryl, $C_{0-3}$alkylene-C(O)$C_{1-4}$alkylene-OH, $C_{0-5}$alkylene-$C_{3-8}$cycloalkyl, $C_{0-5}$alkylene-$C_{2-7}$heterocycloalkyl, $C_{0-5}$alkylenearyl, or cyano, or $R^5$ and $R^6$, together with the atoms to which they are attached, form a 4-6 membered ring; $R^7$ is H or $C_{1-8}$alkyl, or $R^7$ and $R^5$, together with the atoms to which they are attached, form a 4-6 membered ring; Q is $CR^8R^9$, C=$CR^8R^9$, C=O, C=S, or C=$NR^8$; $R^8$ and $R^9$ are each independently H, $C_{1-8}$alkyl, hydroxy, $C_{1-8}$alkoxy, cyano, nitro, or $C_{3-6}$cycloalkyl, or $R^8$ and $R^9$, taken together with the carbon atom to which they are attached, can form a 3-6 membered ring; $R^{10}$ is $C_{1-8}$alkyl, $C_{0-3}$alkylenearyl, $C_{0-3}$alkyleneheteroaryl, $C_{0-3}$alkylene-$C_{3-8}$cycloalkyl, $C_{0-3}$alkylene-$C_{2-7}$heterocycloalkyl, $C_{1-6}$alkoxy, O—$C_{0-3}$alkylenearyl, O—$C_{0-3}$alkylenehet- eroaryl, O—$C_{0-3}$alkylene-$C_{3-8}$cycloalkyl, O—$C_{0-3}$alkylenearyl, O—$C_{0-3}$alkylene-$C_{2-7}$heterocycloalkyl, NH—$C_{1-8}$alkyl, N($C_{1-8}$alkyl)$_2$, NH—$C_{0-3}$alkylenearyl, NH—$C_{0-3}$alkyleneheteroaryl, NH—$C_{0-3}$alkylene-$C_{3-8}$cycloalkyl, NH—$C_{0-3}$alkylene-$C_{2-7}$heterocycloalkyl, halo, cyano, or $C_{1-6}$alkyleneamine; and $R^{13}$ is $C_{1-4}$alkyl, $C_{1-3}$haloalkyl, $C_{1-3}$alkyleneamine, and $C_{3-8}$cycloalkyl, or a pharmaceutically acceptable salt thereof, with the proviso that (1) when J is $NR^{10}$, M is N or $CR^{13}$; (2) when M is $NR^{13}$, J is N or $CR^{10}$; (3) when J is $CR^{10}$, M is N or $NR^{13}$; and (4) when M is $CR^{13}$, J is N or $NR^{10}$.

In various embodiments, J is $NR^{10}$ and M is $CR^{13}$. In some embodiments, J is $CR^{10}$ and M is $NR^{13}$. In some embodiments, J is $CR^{10}$ and M is N. In various embodiments, J is N and M is $NR^{13}$. In some embodiments, J is N and M is $CR^{13}$. Some specifically contemplated $R^{13}$ include methyl, ethyl, propyl, isopropyl, butyl, sec-butyl, trifluormethyl, $CH_2NH_2$, and cyclopropyl. In some embodiments, J is $NR^{10}$ and M is N. In some embodiments, when Q is C=O and each of $E^1$ and $E^2$ is $CR^1$, then either (1) $R^{10}$ is $C_{1-3}$alkylenearyl, $C_{1-3}$alkyleneheteroaryl, $C_{0-3}$alkylene-$C_{3-8}$cycloalkyl, $C_{1-3}$alkylene-$C_{2-7}$heterocycloalkyl, or halo; or (2) $R^{13}$ is $C_{1-3}$haloalkyl or $C_{3-5}$cycloalkyl.

A compound of formula II can be in the form of formula (II-A), (II-B), (II-C), (II-D), (II-E), (II-F), (II-G), (II-H), (II-J), (II-K), (II-L), (II-M), (II-N), (II-O), (II-P), or (II-Q):

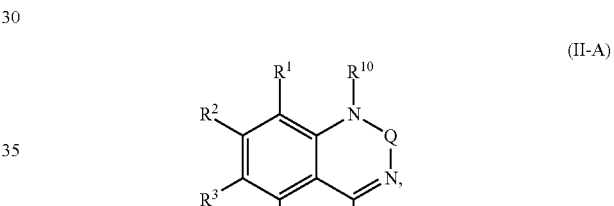
(II-A)

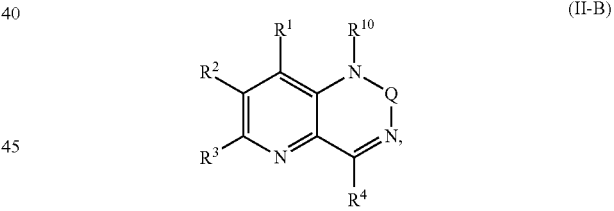
(II-B)

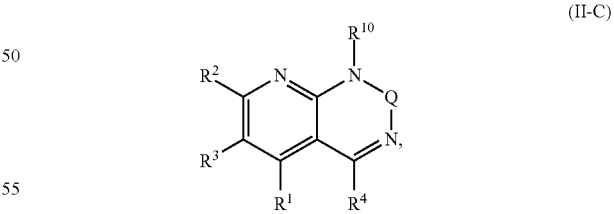
(II-C)

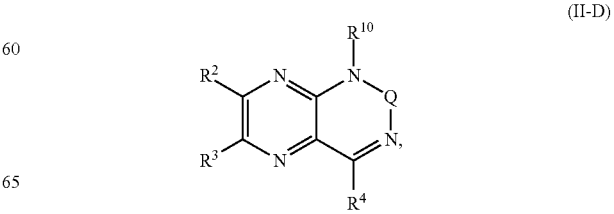
(II-D)

(II-E) 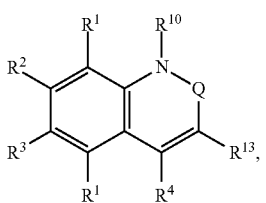

(II-F) 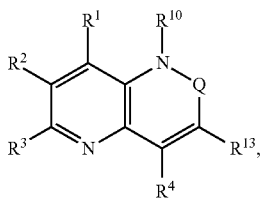

(II-G) 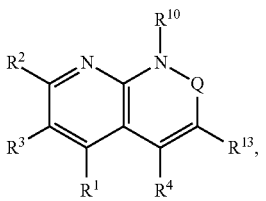

(II-H) 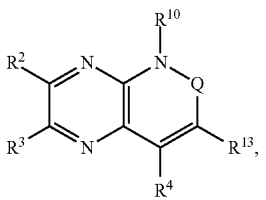

(II-J) 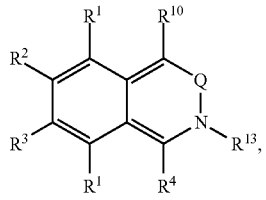

(II-K) 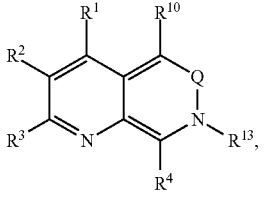

(II-L) 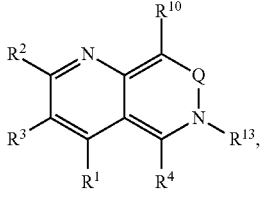

(II-M) 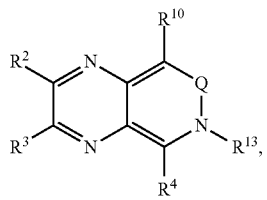

(II-N) 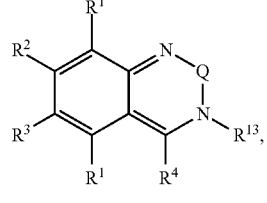

(II-O) 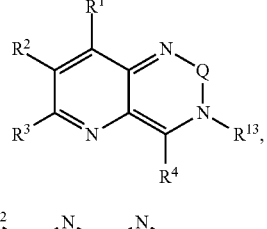

(II-P) 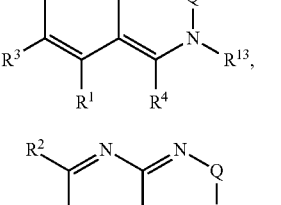

or (II-Q) 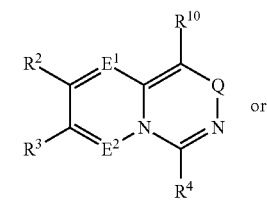

The disclosure also provides a compound having a structure of formula (III) or formula (III'):

(III) 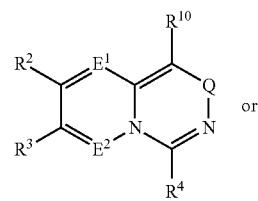

or (III') 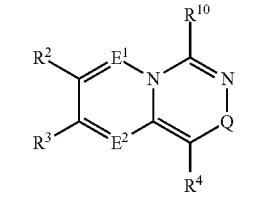

wherein each $R^1$ is independently H, hydroxy, $C_{1-4}$alkyl, $C_{1-4}$haloalkyl, $C_{1-4}$alkoxy, NH—$C_{1-4}$alkyl, N($C_{1-4}$alkyl)$_2$, cyano, or halo; $R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-8}$cycloalkyl, $C_{0-3}$alkylene-$C_{2-7}$heterocycloalkyl, $C_{0-3}$alkylenearyl, or $C_{0-3}$alkyleneheteroaryl, and each R' is independently H, $C_{1-6}$alkyl, $C_{1-6}$haloalkyl, $C_{3-4}$ cycloalkyl, $C_{2-3}$alkenyl, $C_{2-3}$alkynyl, aryl, or heteroaryl, or two R' substituents, together with the nitrogen atom to which they are attached, form a 3-7-membered ring; $R^3$ is halo, $C_{1-6}$alkyl, $C_{1-2}$haloalkyl, $C_{1-3}$alkoxy, $C_{3-4}$ cycloalkyl, $C_{2-3}$alkenyl, $C_{2-3}$alkynyl, aryl, or heteroaryl; $R^4$ is

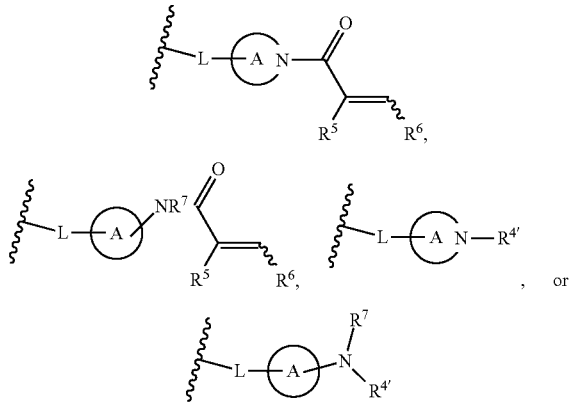

ring A is a monocyclic 4-7 membered ring or a bicyclic, bridged, fused, or spiro 6-11 membered ring; L is a bond, $C_{1-6}$alkylene, —O—$C_{0-5}$alkylene, —S—$C_{0-5}$alkylene, or —NH—$C_{0-5}$alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH; $R^4$ is H, $C_{1-8}$alkyl, $C_{2-8}$alkynyl, $C_{1-6}$alkylene-O—$C_{1-4}$alkyl, $C_{1-6}$alkylene-OH, $C_{1-6}$haloalkyl, $C_{0-5}$alkylene-$C_{3-8}$cycloalkyl, $C_{0-3}$alkylene-$C_{2-7}$heterocycloalkyl, $C_{0-5}$alkylenearyl, or selected from

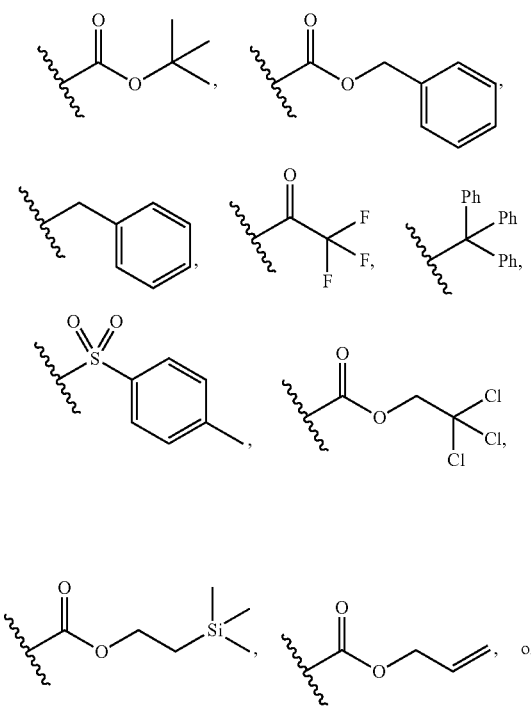

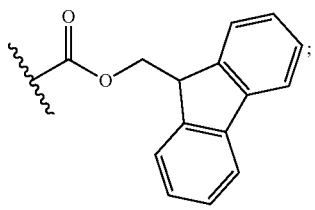 [SMILES: *C(=O)OCC1c2ccccc2-c2ccccc21]

$R^5$ and $R^6$ are each independently H, halo, $C_{1-8}$alkyl, $C_{2-5}$alkynyl, $C_{1-6}$alkylene-O—$C_{1-4}$alkyl, $C_{1-6}$alkylene-OH, $C_{1-6}$haloalkyl, $C_{1-6}$alkyleneamine, $C_{0-6}$alkyleneamide, $C_{0-3}$alkylene-C(O)OH, $C_{0-3}$alkylene-C(O)OC$_{1-4}$alkyl, $C_{1-6}$alkylene-O-aryl, $C_{0-3}$alkylene-C(O)C$_{1-4}$alkylene-OH, $C_{0-5}$alkylene-$C_{3-8}$cycloalkyl, $C_{0-5}$alkylene-$C_{2-7}$heterocycloalkyl, $C_{0-5}$alkylenearyl, or cyano, or $R^5$ and $R^6$, together with the atoms to which they are attached, form a 4-6 membered ring; $R^7$ is H or $C_{1-3}$alkyl, or $R^7$ and $R^5$, together with the atoms to which they are attached, form a 4-6 membered ring; Q is $CR^8R^9$, $C=CR^8R^9$, C=O, C=S, or $C=NR^8$; each of $R^8$ and $R^9$ independently is H, $C_{1-3}$alkyl, hydroxy, $C_{1-3}$alkoxy, cyano, nitro, or $C_{3-6}$cycloalkyl, or $R^8$ and $R^9$, taken together with the carbon atom to which they are attached, can form a 3-6 membered ring; and $R^{10}$ is $C_{1-8}$alkyl. $C_{0-5}$alkylenearyl, $C_{0-3}$alkyleneheteroaryl, $C_{0-3}$alkylene-$C_{3-5}$cycloalkyl, $C_{0-3}$alkylene-$C_{2-7}$heterocycloalkyl, $C_1$alkoxy, $C_{1-6}$alkoxy, O—$C_{0-5}$alkylenearyl, O—$C_{0-5}$alkyleneheteroaryl, O—$C_{0-5}$alkylene-$C_{5-8}$ cycloalkyl, O—$C_{0-3}$alkylene-$C_{2-7}$heterocycloalkyl, NH—$C_{1-8}$alkyl, N($C_{1-8}$alkyl)$_2$, NH—$C_{0-5}$alkylenearyl, NH—$C_{0-5}$alkyleneheteroaryl, NH—$C_{0-5}$alkylene-$C_{3-8}$cycloalkyl, NH—$C_{0-5}$alkylene-$C_{2-7}$heterocycloalkyl, halo, cyano, or $C_{1-6}$alkyleneamine, or a pharmaceutically acceptable salt thereof.

A compound of formula III can be in the form of formula (III-A), (III-B), (III-C), or (III-D):

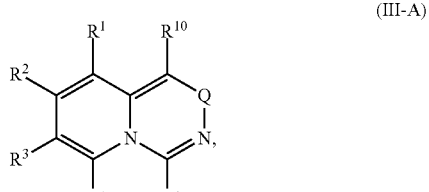

(III-A)

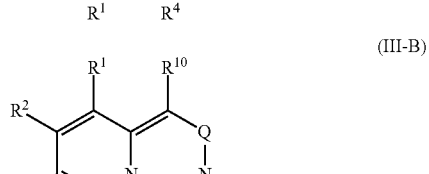

(III-B)

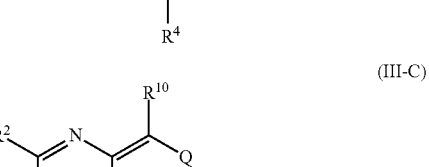

(III-C)

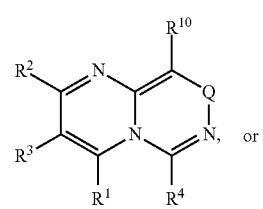

-continued

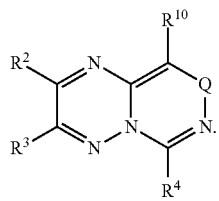
(III-D)

A compound of formula III' can be in the form of formula (III-A'), (III-B'), (III-C'), or (III-D'):

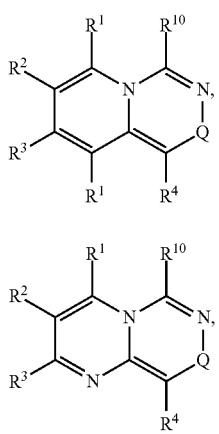
(III-A')
(III-B')
(III-C')

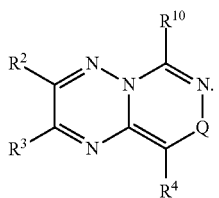
(III-D')

The disclosure also provides a compound having a structure of formula (IV) or formula (IV'):

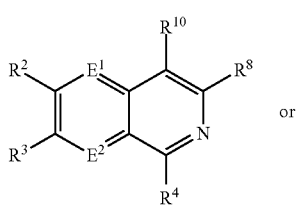
(IV)

-continued

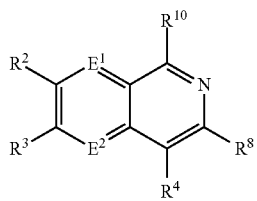
(IV')

wherein $E^1$ and $E^2$ are each independently $CR^1$ or N; $R^1$ is independently H, hydroxy, $C_{1-4}$alkyl, $C_{1-4}$haloalkyl, $C_{1-4}$alkoxy, NH—$C_{1-4}$alkyl, N($C_{1-4}$alkyl)$_2$, cyano, or halo; $R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-8}$cycloalkyl, $C_{0-3}$alkylene-$C_{2-7}$heterocycloalkyl, $C_{0-3}$alkylenearyl, or $C_{0-3}$alkyleneheteroaryl, and each R' is independently H, $C_{1-6}$alkyl, $C_{1-6}$haloalkyl, $C_{3-4}$cycloalkyl, $C_{2-3}$alkenyl, $C_{2-3}$alkynyl, aryl, or heteroaryl, or two R' substituents, together with the nitrogen atom to which they are attached, form a 3-7-membered ring; $R^3$ is halo, $C_{1-2}$haloalkyl, $C_{1-3}$alkoxy, $C_{3-4}$cycloalkyl, $C_{2-3}$alkenyl, $C_{2-3}$alkynyl, aryl, or heteroaryl; $R^4$ is

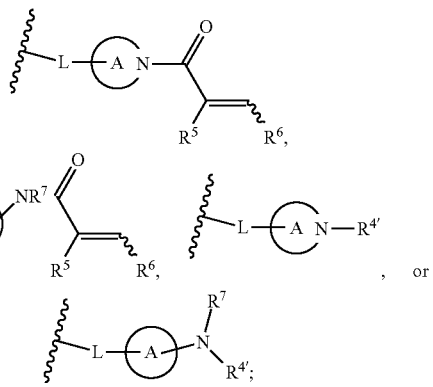

ring A is a monocyclic 4-7 membered ring or a bicyclic, bridged, fused, or spiro 6-11 membered ring; L is a bond, $C_{1-6}$alkylene, —O—$C_{0-5}$alkylene, —S—$C_{0-5}$alkylene, or —NH—$C_{0-5}$alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH; $R^4$ is H, $C_{1-8}$alkyl, $C_{2-5}$alkynyl, $C_{1-6}$alkylene-O—$C_{1-4}$alkyl, $C_1$alkylene-OH, $C_{1-6}$haloalkyl, $C_{0-3}$alkylene-$C_{3-5}$cycloalkyl, $C_{0-3}$alkylene-$C_{2-7}$heterocycloalkyl, $C_{0-3}$alkylenearyl, or selected from

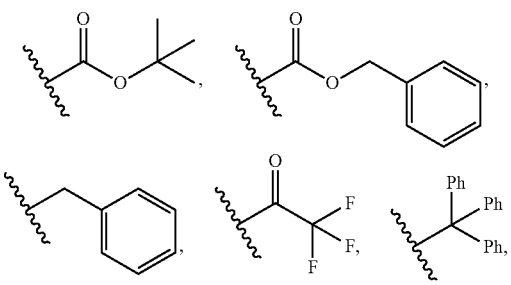

-continued

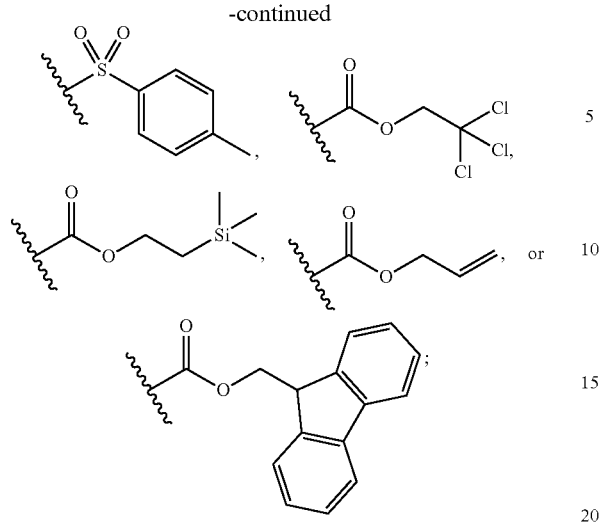

$R^5$ and $R^6$ are each independently H, halo, $C_{1-8}$alkyl, $C_{2-8}$alkynyl, $C_{1-6}$alkylene-O—$C_{1-4}$alkyl, $C_{1-6}$alkylene-OH, $C_{1-6}$haloalkyl, $C_{1-6}$alkyleneamine, $C_{0-6}$alkyleneamide, $C_{0-3}$alkylene-C(O)OH, $C_{0-3}$alkylene-C(O)OC$_{1-4}$alkyl, $C_{1-6}$alkylene-O-aryl, $C_{0-3}$alkylene-C(O)C$_{1-4}$alkylene-OH, $C_{0-3}$alkylene-C$_{3-5}$cycloalkyl, $C_{0-3}$alkylene-C$_{2-7}$heterocycloalkyl, $C_{0-3}$alkylenearyl, or cyano, or $R^5$ and $R^6$, together with the atoms to which they are attached, form a 4-6 membered ring; $R^7$ is H or $C_{1-3}$alkyl, or $R^7$ and $R^5$, together with the atoms to which they are attached, form a 4-6 membered ring; $R^8$ is $C_{1-3}$alkyl, hydroxy, $C_{1-3}$alkoxy, halo, cyano, nitro, $C_{3-6}$cycloalkyl, or $NR^{11}R^{12}$; $R^{11}$ and $R^{12}$ are each independently H, $C_{1-4}$alkyl, or $C_{3-5}$cycloalkyl; and $R^{10}$ is $C_{1-8}$alkyl, $C_{0-5}$alkylenearyl, $C_{0-5}$alkyleneheteroaryl, $C_{0-5}$alkylene-C$_{3-8}$cycloalkyl, $C_{0-3}$alkylene-C$_{2-7}$heterocycloalkyl, $C_{1}$alkoxy, O—$C_{0-5}$alkylenearyl, O—$C_{0-5}$alkyleneheteroaryl, O—$C_{0-5}$alkylene-C$_{1-8}$cycloalkyl, O—$C_{0-3}$alkylene-C$_{2-7}$heterocycloalkyl, NH—$C_{1-8}$alkyl, $N(C_{1-8}$alkyl$)_2$, NH—$C_{0-5}$alkylenearyl, NH—$C_{0-3}$alkyleneheteroaryl, NH—$C_{0-5}$alkylene-C$_{3-8}$cycloalkyl, NH—$C_{0-3}$alkylene-C$_{2-7}$heterocycloalkyl, halo, cyano, or $C_{1-6}$alkyleneamine, or a pharmaceutically acceptable salt thereof. In some embodiments, $E^1$ and $E^2$ are each $CR^1$, and $R^8$ is hydroxy, halo, nitro, or $C_{3-6}$cycloalkyl. In some embodiments, $R^8$ is methyl. The compound can have a structure of formula (IV-A), (IV'-A), (IV-B), (IV'—B), (IV-C), (IV'—C), (IV-D), or (IV'-D):

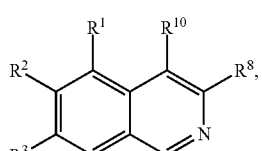

(IV-A)

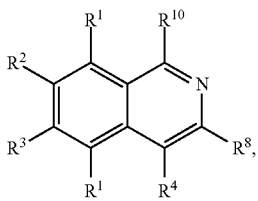

(IV'-A)

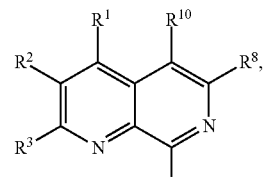

(IV-B)

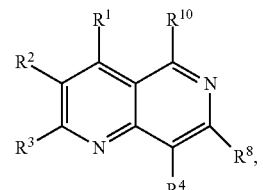

(IV'-B)

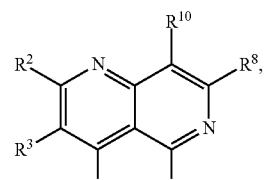

(IV-C)

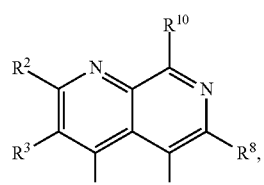

(IV'-C)

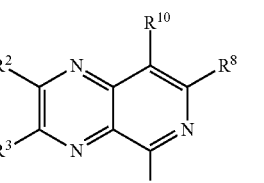

(IV-D)

or

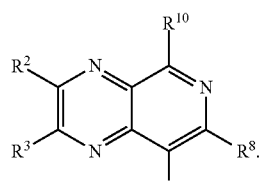

(IV'-D)

Also provided herein are compounds having a structure of formula (V):

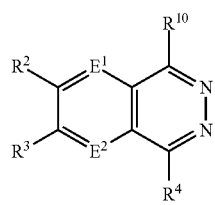

(V)

wherein $E^1$ and $E^2$ are each independently $CR^1$ or N; $R^1$ is independently H, hydroxy, $C_{1-4}$alkyl, $C_{1-4}$haloalkyl, $C_{1-4}$alkoxy, NH—$C_{1-4}$alkyl, N($C_{1-4}$alkyl)$_2$, cyano, or halo; $R^2$ is halo, $C_{1-6}$alkyl, $C_{1-6}$haloalkyl, OR', N(R')$_2$, $C_{2-3}$alkenyl, $C_{2-3}$alkynyl, $C_{0-3}$alkylene-$C_{3-8}$cycloalkyl, $C_{0-3}$alkylene-$C_{2-7}$heterocycloalkyl, $C_{0-3}$alkylenearyl, or $C_{0-3}$alkyleneheteroaryl, and each R' is independently H, $C_{1-6}$alkyl, $C_{1-6}$haloalkyl, $C_{3-4}$cycloalkyl, $C_{2-3}$alkenyl, $C_{2-3}$alkynyl, aryl, or heteroaryl, or two R' substituents, together with the nitrogen atom to which they are attached, form a 3-7-membered ring; $R^3$ is halo, $C_{1-3}$alkyl, $C_{1-2}$haloalkyl, $C_{1-3}$alkoxy, $C_{3-4}$ cycloalkyl, $C_{2-3}$ alkenyl, $C_{2-3}$alkynyl, aryl, or heteroaryl; $R^4$ is

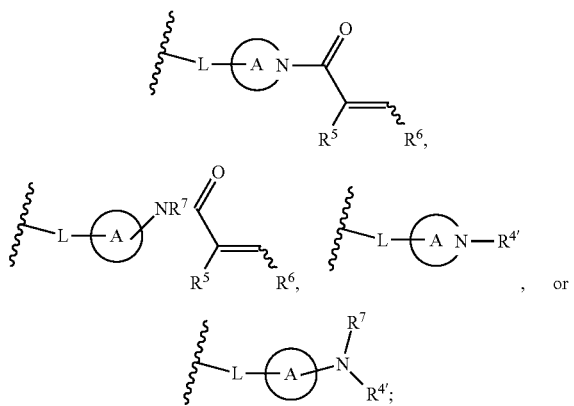

ring A is a monocyclic 4-7 membered ring or a bicyclic, bridged, fused, or spiro 6-11 membered ring; L is a bond, $C_{1-6}$alkylene, —O—$C_{0-5}$alkylene, —S—$C_{0-5}$alkylene, or —NH—$C_{0-5}$alkylene, and for $C_{2-6}$alkylene, —O—$C_{2-5}$alkylene, —S—$C_{2-5}$alkylene, and NH—$C_{2-5}$alkylene, one carbon atom of the alkylene group can optionally be replaced with O, S, or NH; $R^4$ is H, $C_{1-8}$alkyl, $C_{2-5}$alkynyl, $C_{1-6}$alkylene-O—$C_{1-4}$ alkyl, $C_{1-6}$alkylene-OH, $C_{1-6}$haloalkyl, $C_{0-3}$alkylene-$C_{3-8}$cycloalkyl, $C_{0-3}$alkylene-$C_{2-7}$ heterocycloalkyl, $C_{0-3}$alkylenearyl, or selected from

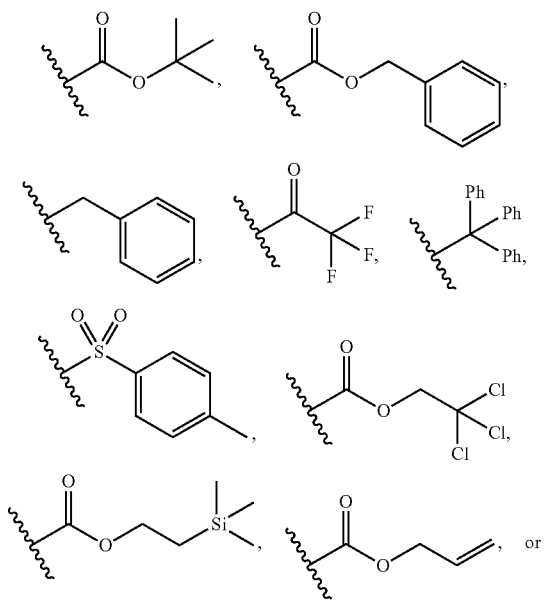

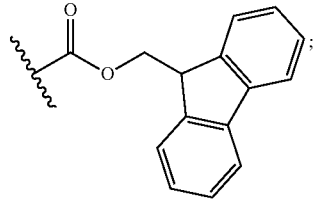

$R^5$ and $R^6$ are each independently H, halo, $C_{1-8}$alkyl, $C_{2-5}$alkynyl, $C_{1-6}$alkylene-O—$C_{1-4}$ alkyl, $C_{1-6}$alkylene-OH, $C_{1-6}$haloalkyl, $C_{1-6}$alkyleneamine, $C_{0-6}$alkyleneamide, $C_{0-3}$alkylene-C(O)OH, $C_{0-3}$alkylene-C(O)O$C_{1-4}$alkyl, $C_{1-6}$alkylene-O-aryl, $C_{0-3}$alkylene-C(O)$C_{1-4}$alkylene-OH, $C_{0-3}$alkylene-$C_{3-8}$cycloalkyl, $C_{0-3}$alkylene-$C_{2-7}$heterocycloalkyl, $C_{0-3}$alkylenearyl, or cyano, or $R^5$ and $R^6$, together with the atoms to which they are attached, form a 4-6 membered ring; $R^7$ is H or $C_{1-3}$alkyl, or $R^7$ and $R^5$, together with the atoms to which they are attached, form a 4-6 membered ring; and $R^{10}$ is $C_{1-8}$alkyl, $C_{0-3}$alkylenearyl, $C_{0-3}$alkyleneheteroaryl, $C_{0-3}$alkylene-$C_{3-8}$ cycloalkyl, $C_{0-3}$alkylene-$C_{2-7}$heterocycloalkyl, $C_{1-6}$alkoxy, O—$C_{0-3}$alkylenearyl, O—$C_{0-3}$alkyleneheteroaryl, O—$C_{0-3}$alkylene-$C_{3-8}$cycloalkyl, O—$C_{0-3}$alkylene-$C_{2-7}$heterocycloalkyl, NH—$C_{1-8}$alkyl, N—$C_{1-8}$alkyl, NH—$C_{0-5}$alkylenearyl, NH—$C_{0-3}$alkyleneheteroaryl, NH—$C_{0-3}$alkylene-$C_{3-8}$cycloalkyl, NH—$C_{0-3}$alkylene-$C_{2-7}$heterocycloalkyl, halo, cyano, or $C_{1-6}$alkyleneamine; or a pharmaceutically acceptable salt thereof.

For compounds of formulas (II), (III), and (III'): In some embodiments, Q is C=O. In some embodiments, Q is C=S. In some embodiments, Q is C=NR$^8$. $R^8$ can be $C_{1-2}$alkyl, e.g. methyl.

Q can be CR$^8$R$^9$ or C=CR$^8$R$^9$. $R^8$ and $R^9$, taken together with the carbon atom to which they are attached, can form a 3-4 membered ring, e.g., a cyclopropyl ring. In some embodiments, $R^8$ is $C_{1-2}$alkyl (e.g., methyl), and $R^9$ is H.

For compounds of formulas (II), (III), (III'), (IV), (IV'), and (V): In various embodiments, $R^{10}$ is $C_{1-6}$alkyl, aryl, heteroaryl, $C_{3-6}$cycloalkyl, $C_{3-6}$heterocycloalkyl, $C_{1-4}$alkoxy, or aryloxy. In various embodiments, $R^{10}$ is $C_{1-8}$alkyl, $C_{1-5}$alkyl, or $C_{1-3}$alkyl. In various embodiments, $R^{10}$ is $C_{0-5}$alkylenearyl, $C_{0-1}$alkylenearyl, or phenyl. In various embodiments, $R^{10}$ is $C_{0-5}$alkyleneheteroaryl, or $C_{0-1}$alkyleneheteroaryl, and the heteoraryl can be, e.g., pyridyl. In various embodiments, $R^{10}$ is $C_{0-3}$alkylene-$C_{3-8}$cycloalkyl, $C_{0-1}$alkylene-$C_{1-8}$cycloalkyl, or $C_{3-8}$cycloalkyl, and the cycloalkyl can be, e.g., cyclohexyl. In various embodiments, $R^{10}$ is $C_{0-5}$alkylene-$C_{3-8}$heterocycloalkyl or $C_{0-1}$alkylene-$C_{3-8}$heterocycloalkyl. In various embodiments, $R^{10}$ is $C_{0-6}$alkyleneamine or $C_{0-3}$alkyleneamine or amine. Some specifically contemplated $R^{10}$ include i-Pr, t-Bu, phenyl, benzyl, OCH$_3$, Cl, cyclopropyl, cyclobutyl, cyclopentyl, cyclohexyl,

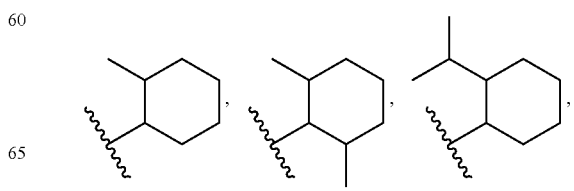

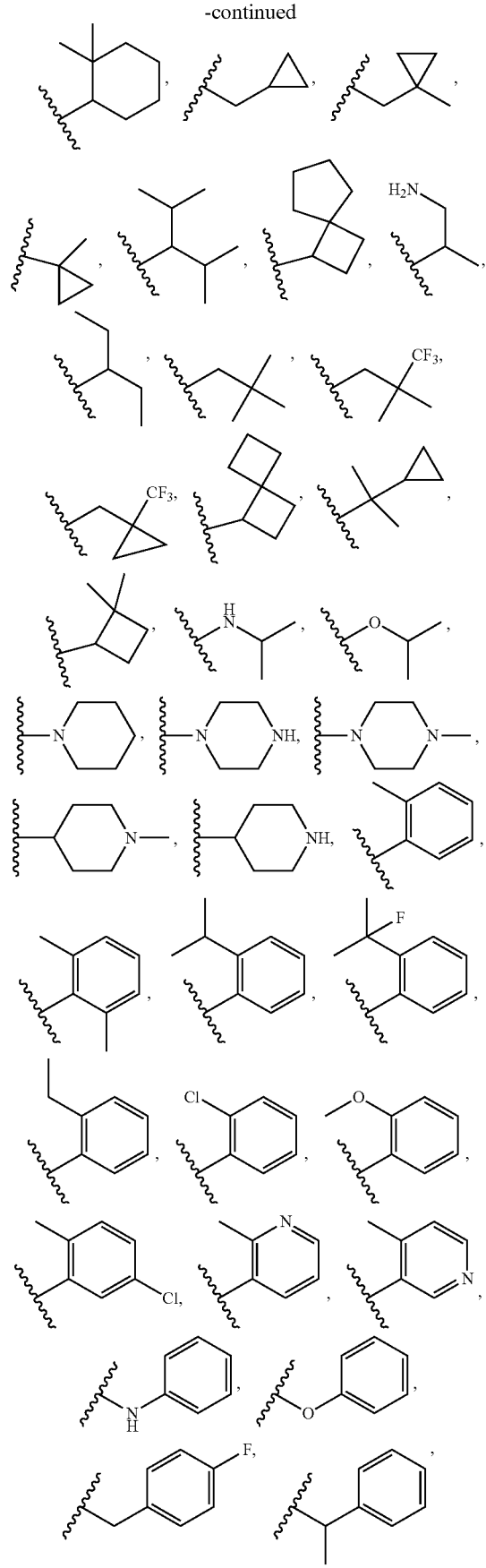
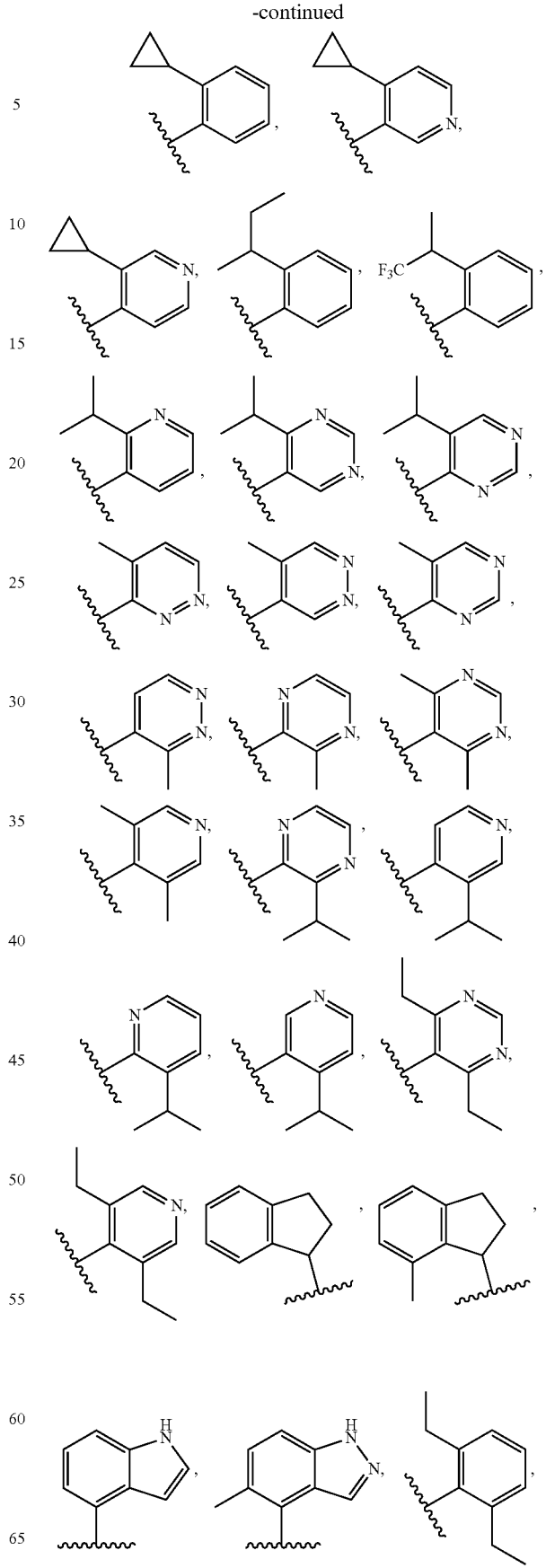

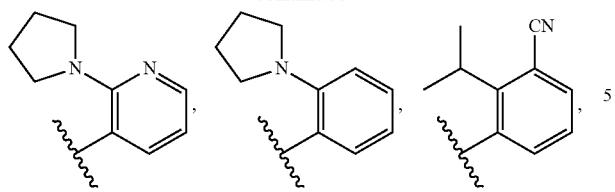
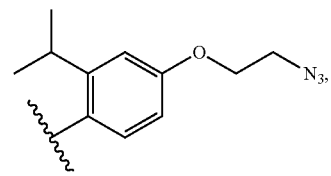
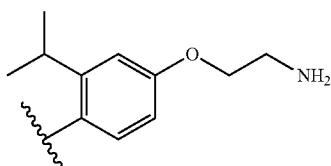
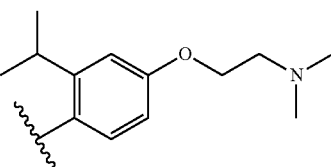
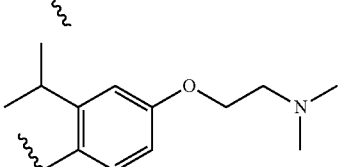
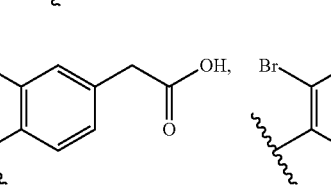
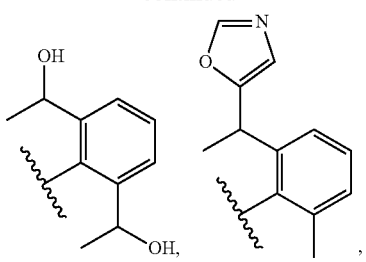
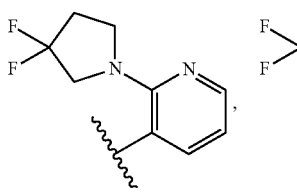
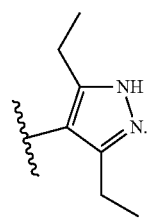
$R^{10}$ can comprise an ortho-substituted aryl, ortho-substituted heteroaryl, or 2-substituted cyclohexyl, such as, for example,
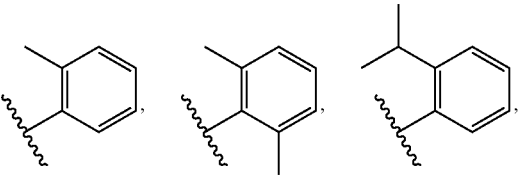
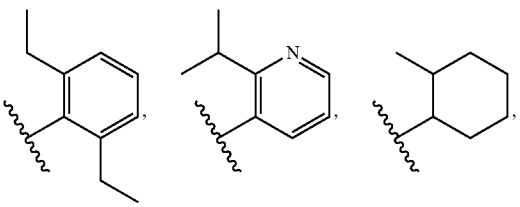
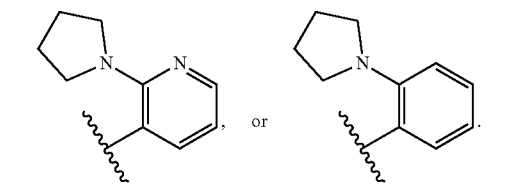

embodiment, $R^{10}$ can comprise

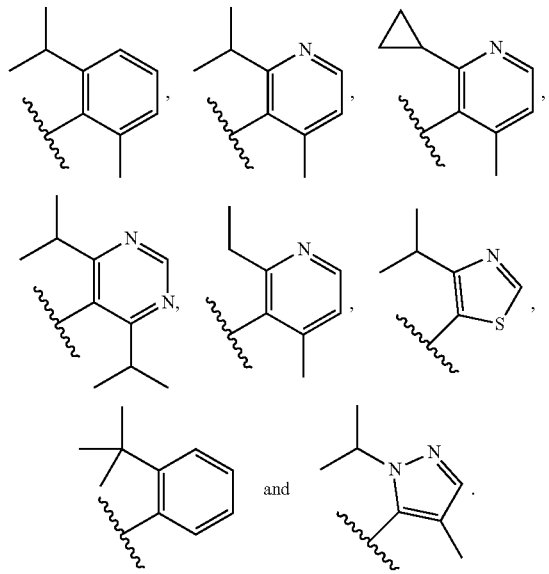

For all compounds:

$R^1$ can be a small moiety. For example, $R^1$ can be H, $C_{1-2}$alkyl (e.g., methyl), $C_{1-2}$haloalkyl (e.g., $CF_3$), or halo (e.g., F). Some specifically contemplated $R^1$ include H, F, Me, Cl, and $CF_3$.

$R^2$ can be $C_{1-3}$alkyl, $C_{1-3}$haloalkyl, $C_{1-3}$alkoxy, $C_{0-1}$alkylene-$C_{3-8}$cycloalkyl, $C_{3-6}$cycloalkyl, $C_{0-1}$alkylenearyl (e.g., aryl), or $C_{0-1}$alkyleneheteroaryl (e.g., heteroaryl). Some specifically contemplated $R^2$ groups include phenyl, naphthyl, pyridyl, indazolyl, indolyl, azaindolyl, indolinyl, benzotriazolyl, benzoxadiazolyl, imidazolyl, cinnolinyl, imidazopyridyl, pyrazolopyridyl, quinolinyl, isoquinolinyl, quinazolinyl, quinazolinonyl, indolinonyl, isoindolinonyl, tetrahydronaphthyl, tetrahydroquinolinyl, or tetrahydroisoquinolinyl. Some other specific $R^2$ include Cl, Br, $CF_3$, cyclopropyl, cyclobutyl, cyclopentyl, cyclohexyl, piperidine, pyrrolidine, azetidine, $OCH_3$, $OCH_2CH_3$, phenyl,

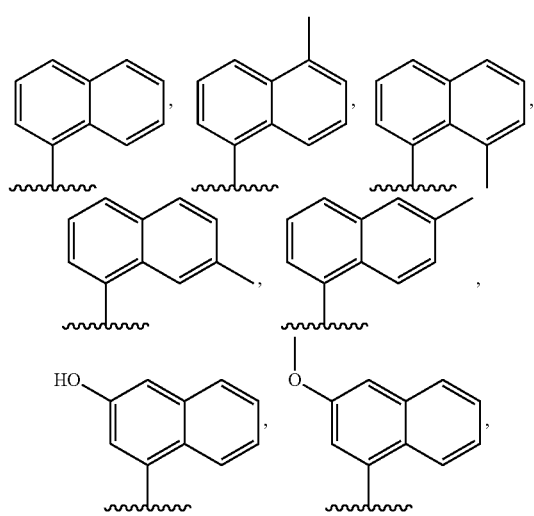

-continued

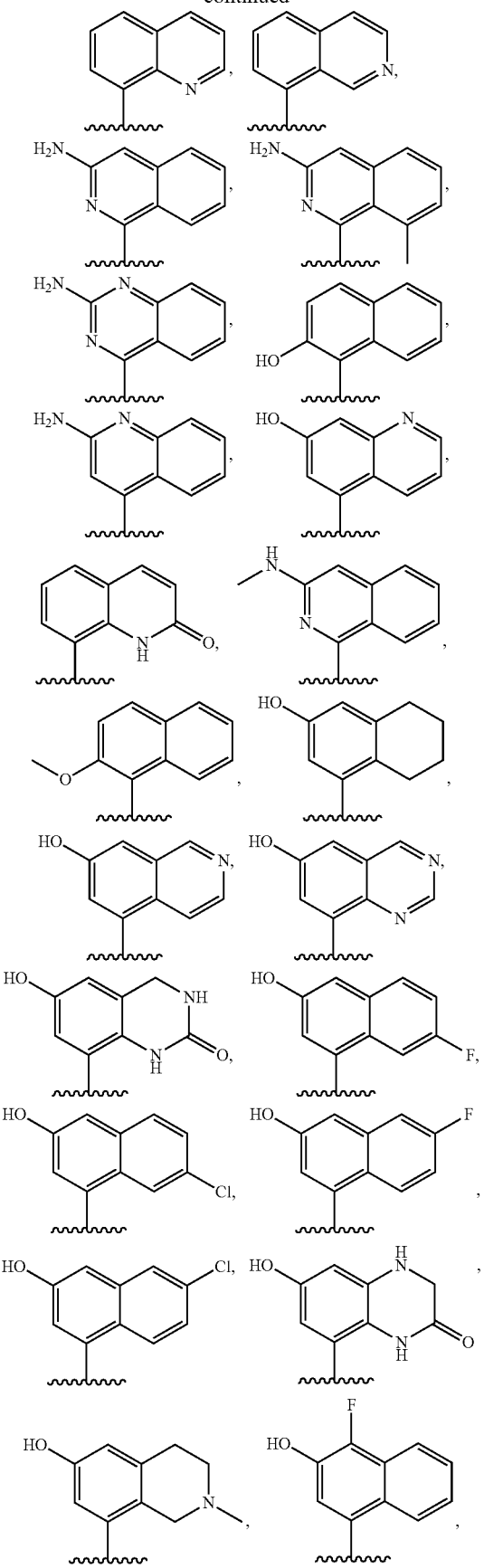

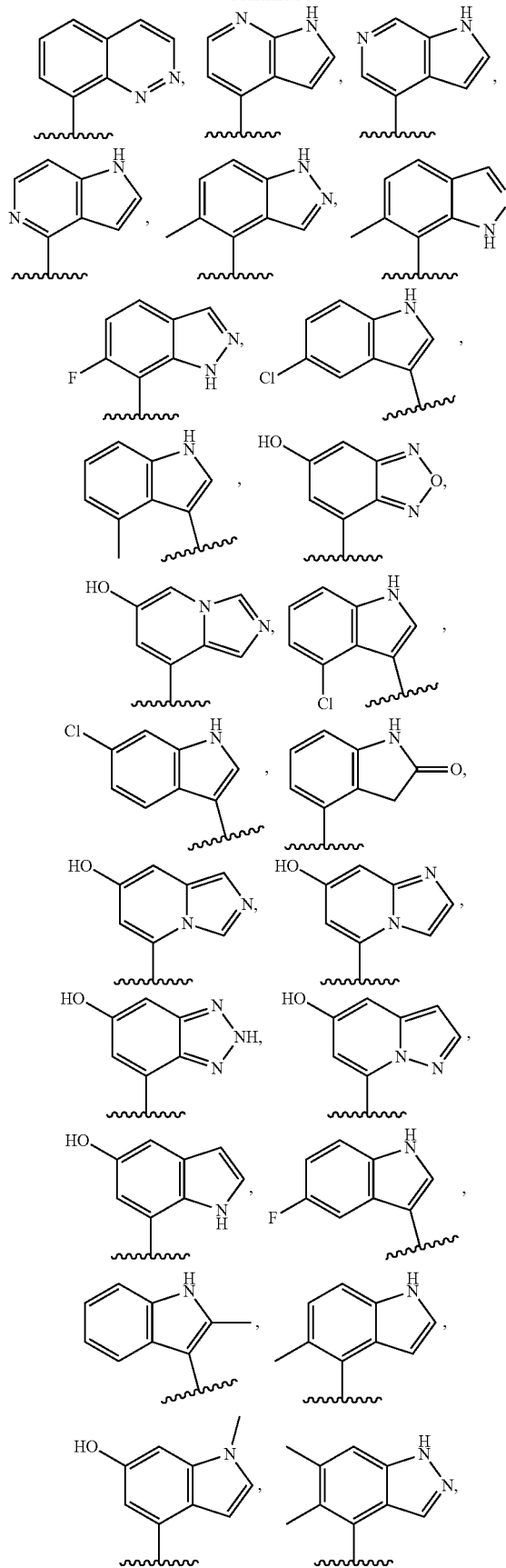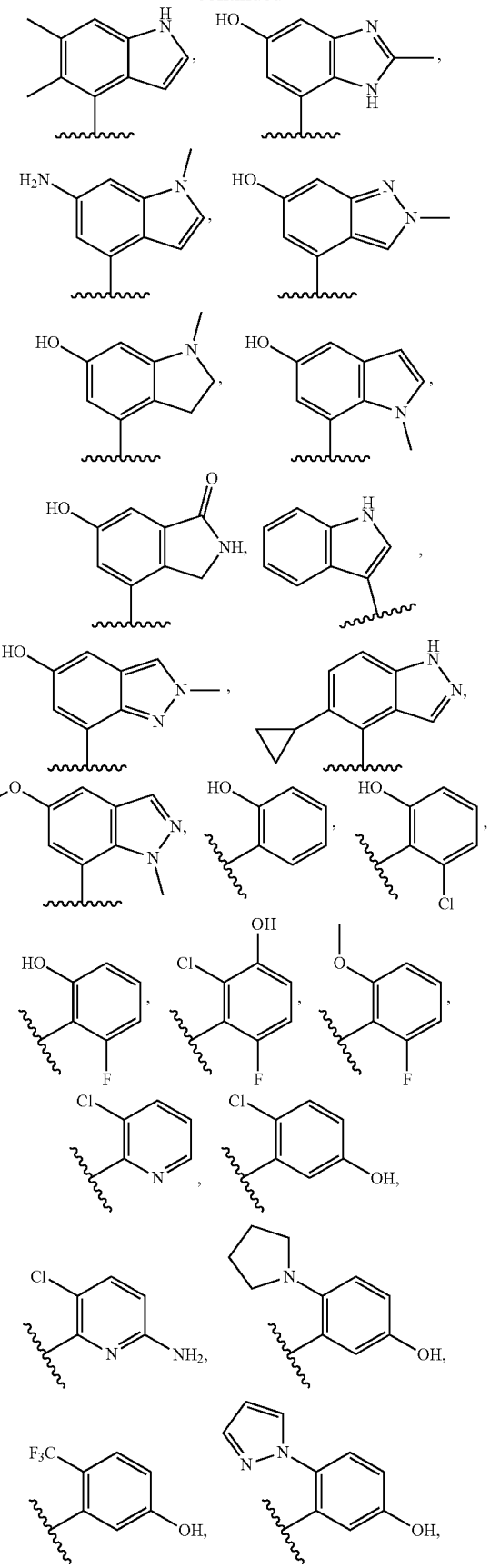

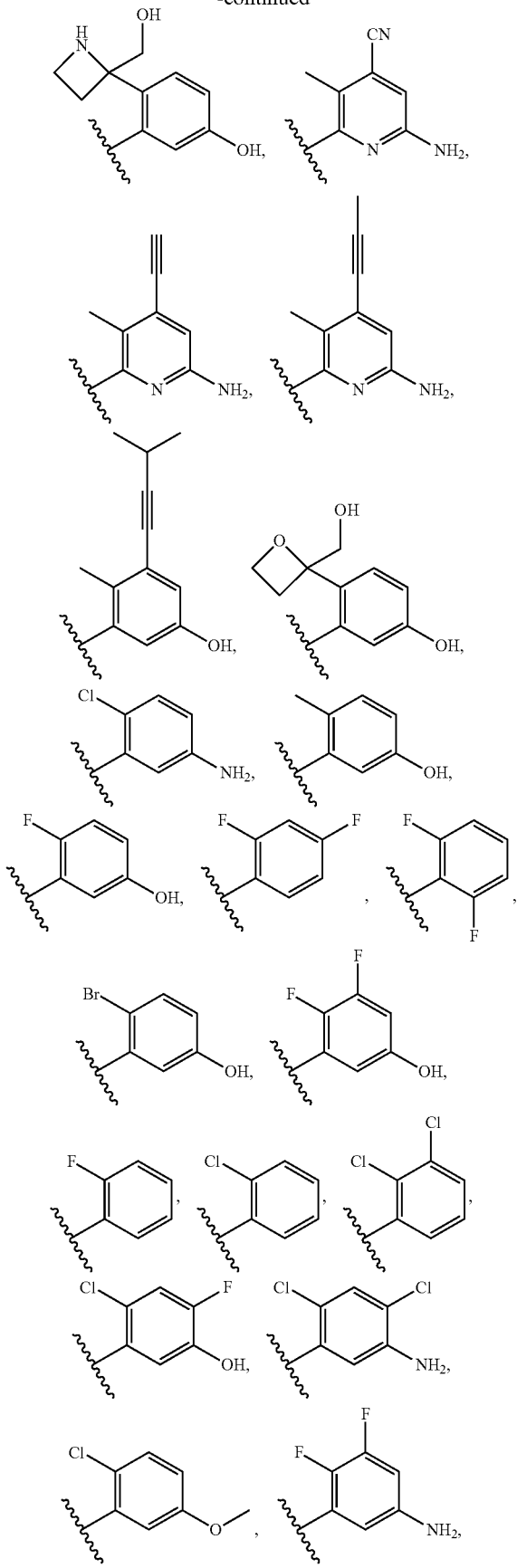

In some embodiments, $R^2$ is

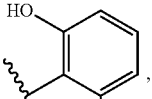

$R^3$ can be halo (e.g., Cl, F), C$_{1}$alkyl (e.g., methyl), or C$_{1-2}$haloalkyl (e.g., CF$_3$). Some specifically contemplated $R^3$ include Cl, F, Me, CF$_3$, OMe, Et, C=CH$_2$, and cyclopropyl.

L can be a bond, C$_{1-6}$alkylene, —O—C$_{0-5}$alkylene, —S—C$_{0-5}$alkylene, or —NH—C$_{0-5}$ alkylene, and for C$_{2-6}$ alkylene, —O—C$_{2-5}$alkylene, —S—C$_{2-5}$alkylene, and NH—C$_{2-5}$alkylene, one carbon atom of the alkylene group can optionally be replaced with O, S, or NH. For example, L can be —CH$_2$—NH— when a carbon on a C$_2$ alkylene group is replaced with NH, or —O—CH$_2$CH$_2$—O—, when a carbon on a O—C$_3$alkylene group is replaced with a O. Other options with substitution of C$_3$, C$_4$, C$_5$, or C$_6$ alkylene with O, S, or NH are specifically contemplated. In some embodiments, L is C$_{1-2}$alkylene, O, S, or NH. In some embodiments, L is a bond.

Ring A is a monocyclic 4-7 membered ring or a bicyclic, bridged, fused, or spiro 6-11 membered ring. Some specifically contemplated rings include cyclobutyl, cyclopentyl, cyclohexyl, cycloheptyl, pyrrolidinyl, piperidinyl, azepanyl, imidazolidinyl, hexahydropyrimidinyl, hexahydropyridazinyl, tetrahydrofuranyl, tetrahydrothiofuranyl, azetidinyl, spiroheptyl, spirooctyl, spirononyl, spirodecyl, diazabicyclodecyl, diazabicyclononyl, diazabicyclooctyl, diazabicycloheptyl, hexahydropyrrolopyridyl, octahydropyrrolopyridyl, and octahydropyrrolopyrimidinyl. In various embodiments, ring A can comprise piperidinyl, piperazinyl, pyrrolidinyl, or azetidinyl. In some embodiments, ring A comprises piperidinyl. Ring A can be further substituted with one to three substituents. Some non-limiting examples of substitutions on ring A include one to three substituents selected from alkyl, alkenyl, alkynyl, hydroxy alkyl, carboxylic acid or ester, haloalkyl, alkylamine, $C(O)NH_2$, oxo, halo, cyano, and isocyano.

When $R^4$ is

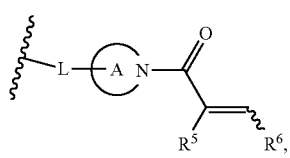

ring A can be, for example,

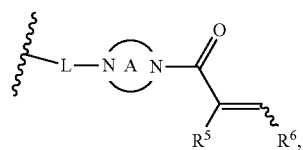

More specifically, when $R^4$ is

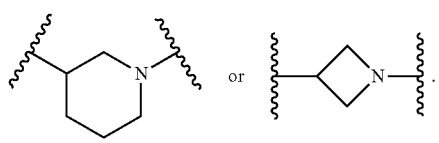 [SMILES: *C1CCCN(*)C1 ; *C1CN(*)C1]

ring A can be, for example,

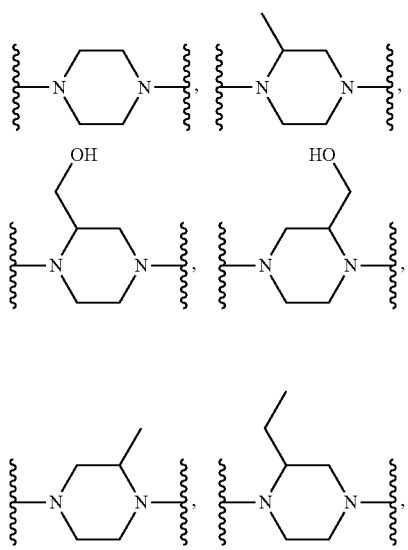

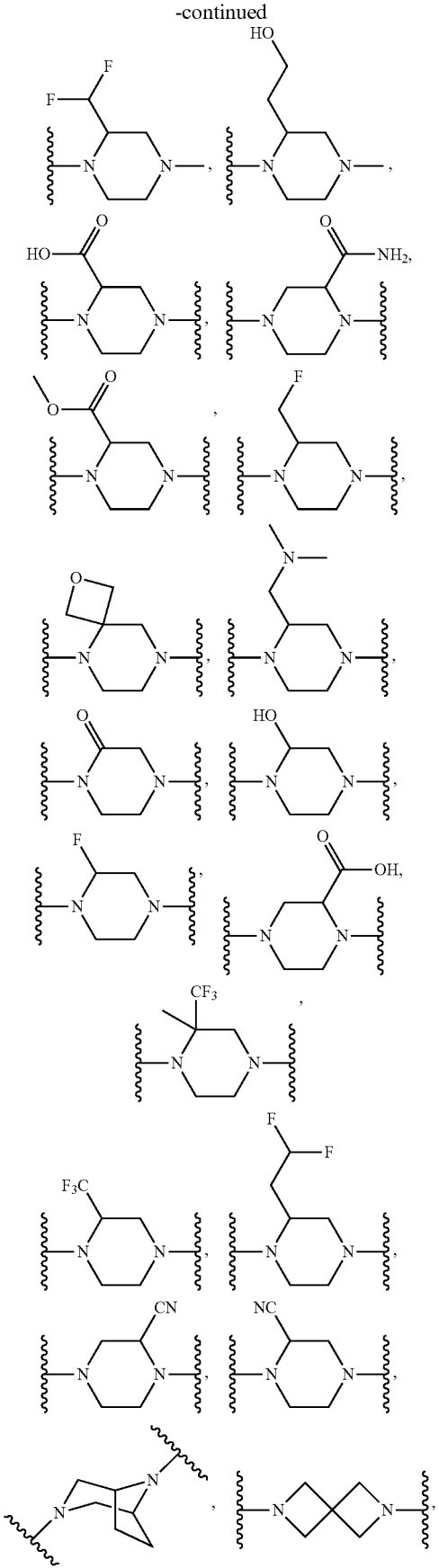

-continued

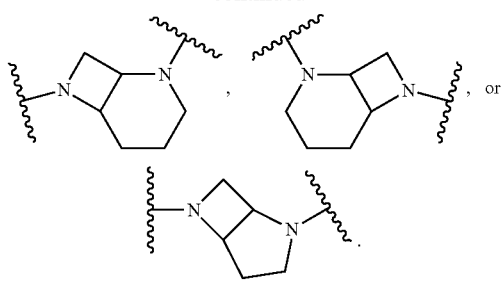

When R⁴ is

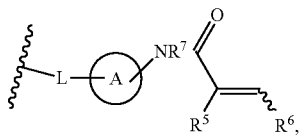

it can more specifically be

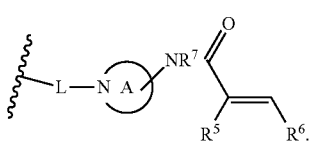

In such embodiments, ring A can be, for example,

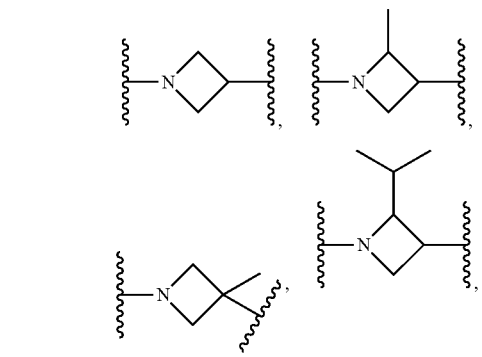

-continued

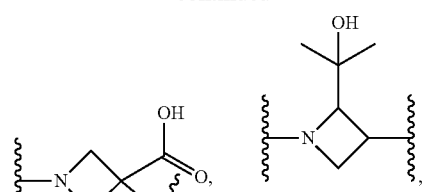

R⁵ and R⁶ are substituents on the acrylamide moiety of the KRAS inhibitors disclosed herein. In some embodiments, each of R⁵ and R⁶ is H. Some specifically contemplated R⁵ substituents include H, Br, Cl, F, CN, $CH_3$, $CF_3$, $CH_2Br$, $CH_2OH$, $CH_2CH_2OH$, $CH_2OCH_2phenyl$, cyclopropyl, phenyl, $CH_2phenyl$, $CH_2OCH_3$, $CH_2N(CH_3)_2$, $CH_2N(CH_2CH_3)_2$, $CH_2CO_2H$, $CH_2CO_2CH_3$, $CH_2NHC(O)CH_3$, $CH_2C(O)NHCH_3$, $CH_2OC(O)CH_3$, or

Some specifically contemplated R⁶ substituents include phenyl, cyclopropyl, $CH_3$, $CF_3$, $CH_2CH_3$, $CH_2NH_2$, $CH(CH_3)NH_2$, $CH(CH_3)_2NH_2$, $CH_2C_1$, $CH_2Br$, $CH_2OCH_3$, $CH_2Ophenyl$, $CH_2OH$, $CO_2H$, $CO_2CH_2CH_3$, $CH_2CO_2H$, $CH_2CH_2NH_2$, $CH_2CH_2OH$, $CH_2CH_2N(CH_3)_2$, $CH_2NHCH_3$, $C(O)NHCH_3$, $C(O)N(CH_3)_2$, $CH_2C(O)NH$-phenyl, $CH_2CHF_2$, $CH_2F$, $CHF_2$, $CH_2NHC(O)CH_3$, $CH_2NHCH_2CH_2OH$, $CH_2NHCH_2CO_2H$, $CH_2NH(CH_3)CH_2CO_2CH_3$, $CH_2NHCH_2CH_2OCH_3$, $CH_2NH(CH_3)CH_2CH_2OCH_3$, $CH_2NH(CH_3)CH_2C(O)N(CH_3)_2$, $CH_2NH(CH_3)CH_2C(O)NHCH_3$, $CH_2CH_2CCH$, $CH_2NMe_2$, $CH_2NH(CH_3)CH_2CH_2OH$, $CH_2NH(CH_3)CH_2CH_2F$, $CH_2N^+(CH_3)_3$, $CH_2NHCH_2CHF_2$, $CH_2NHCH_2CH_3$,

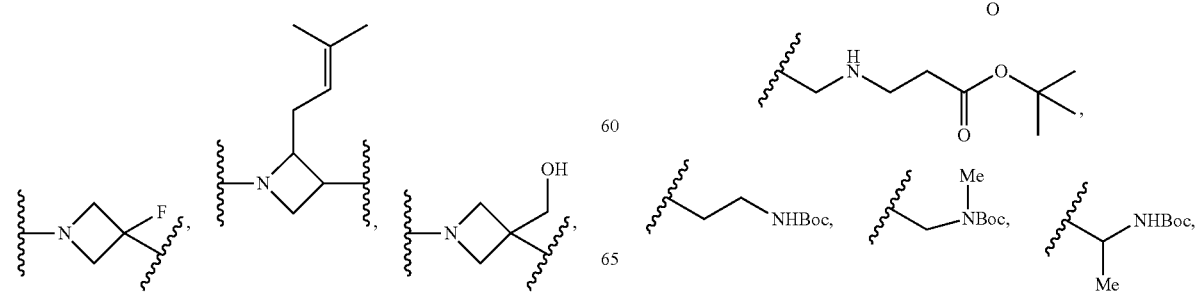

-continued
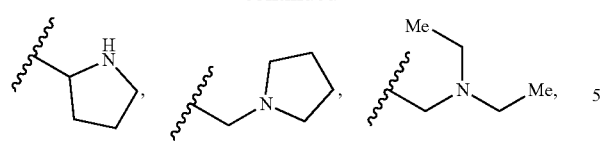
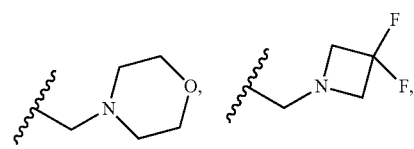
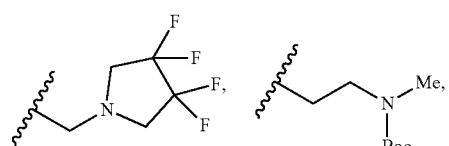
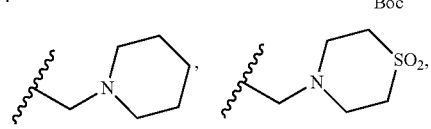
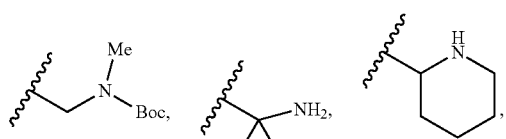
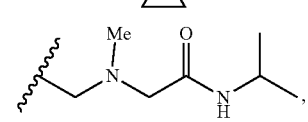
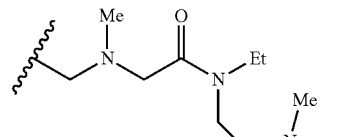
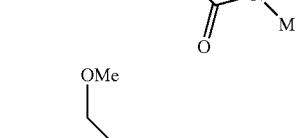
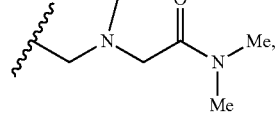
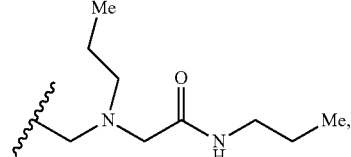
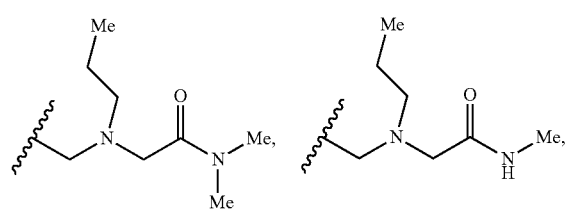
-continued
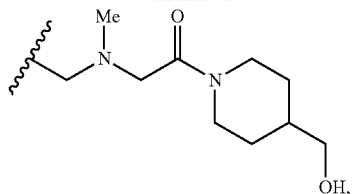
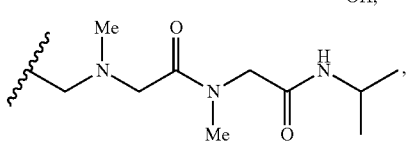
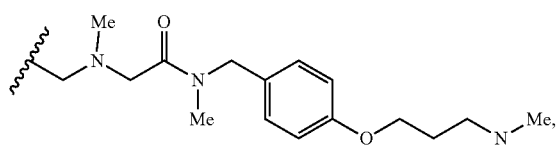
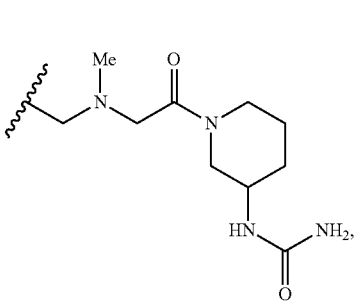
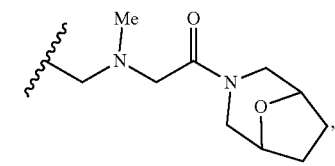
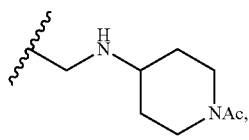
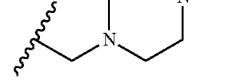
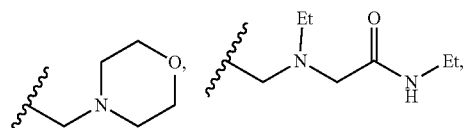
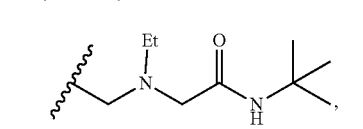, or
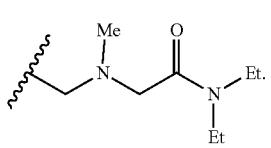

$R^5$ and $R^6$, together with the atoms to which they are attached, can form a 4-6 membered ring, e.g., a 5- or 6-membered ring. Such rings include $R^5$ and $R^6$ together being
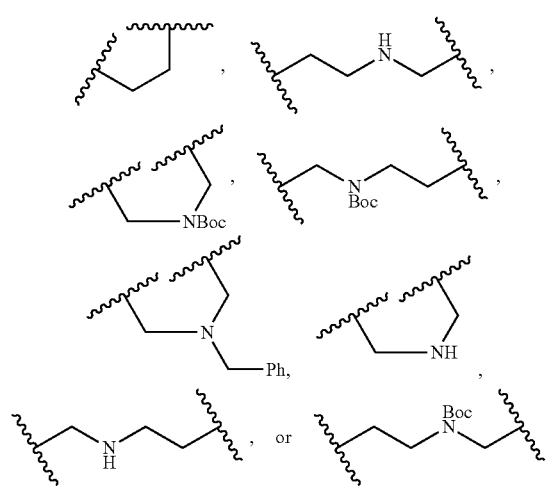
In most embodiments, $R^7$ is H. However, in some embodiments, $R^7$ is methyl. In other embodiments, $R^7$ and $R^5$ together are —CH$_2$— or —C(O)CH$_2$—.
Some specifically contemplated options for the moiety
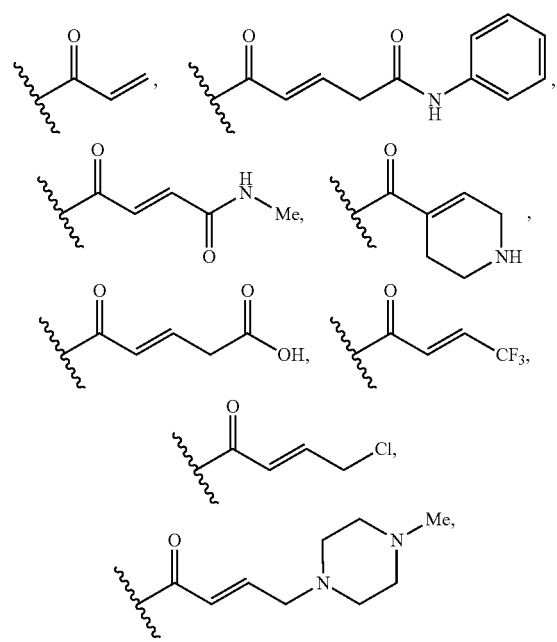
include
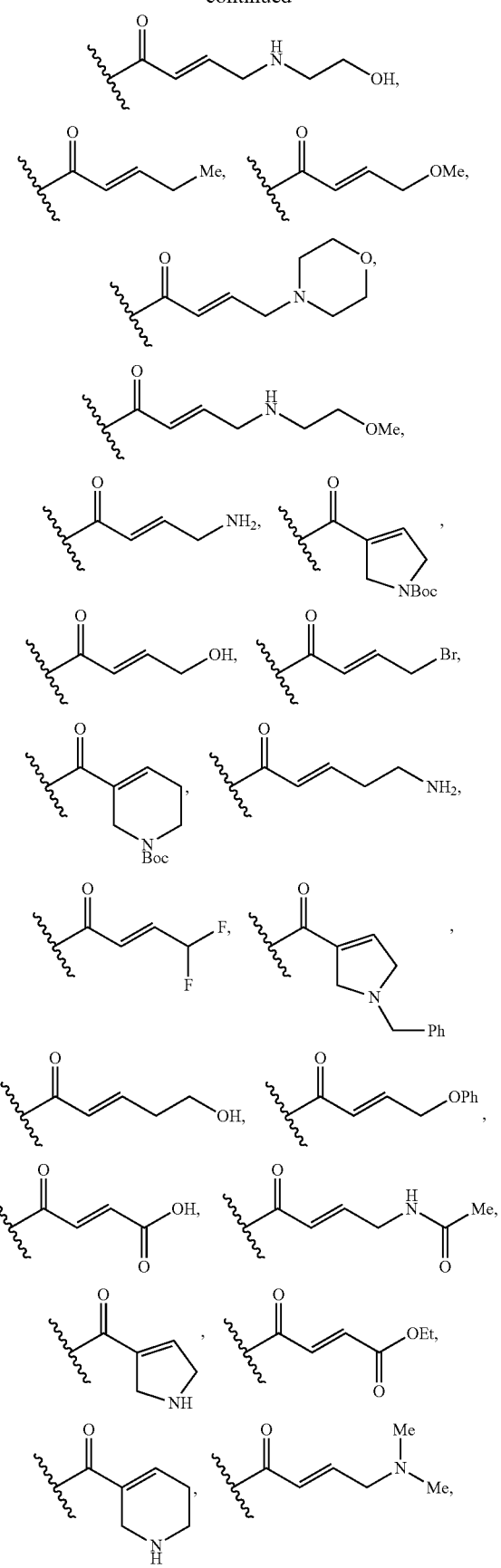

87
-continued
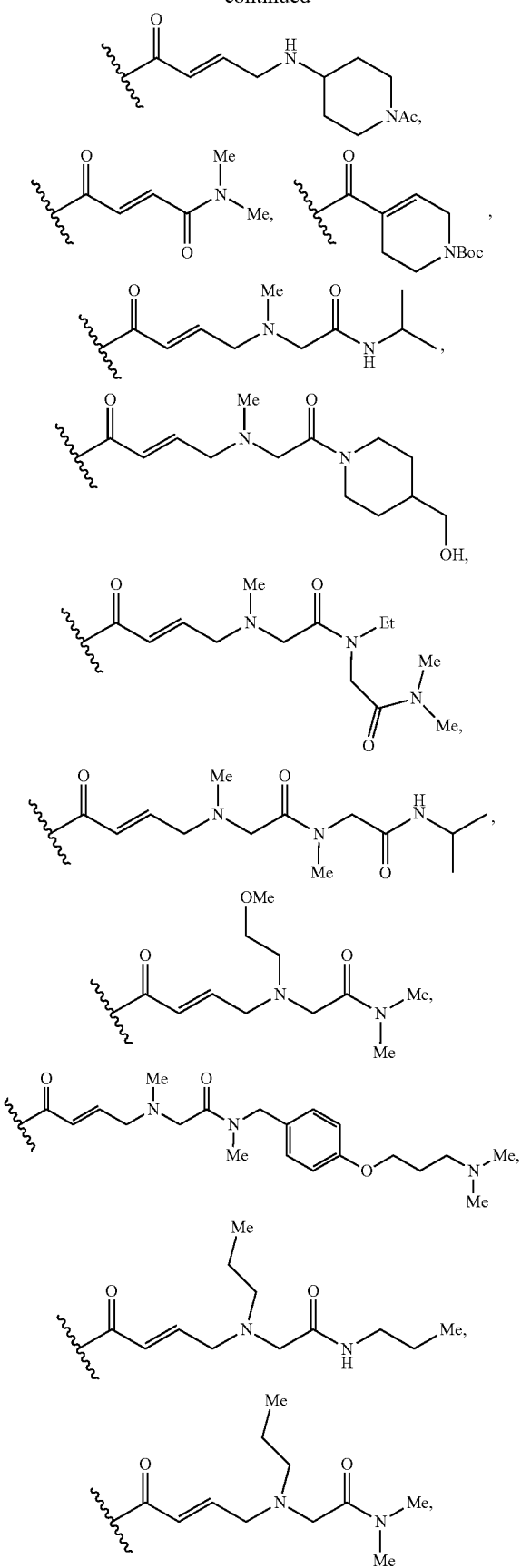
88
-continued
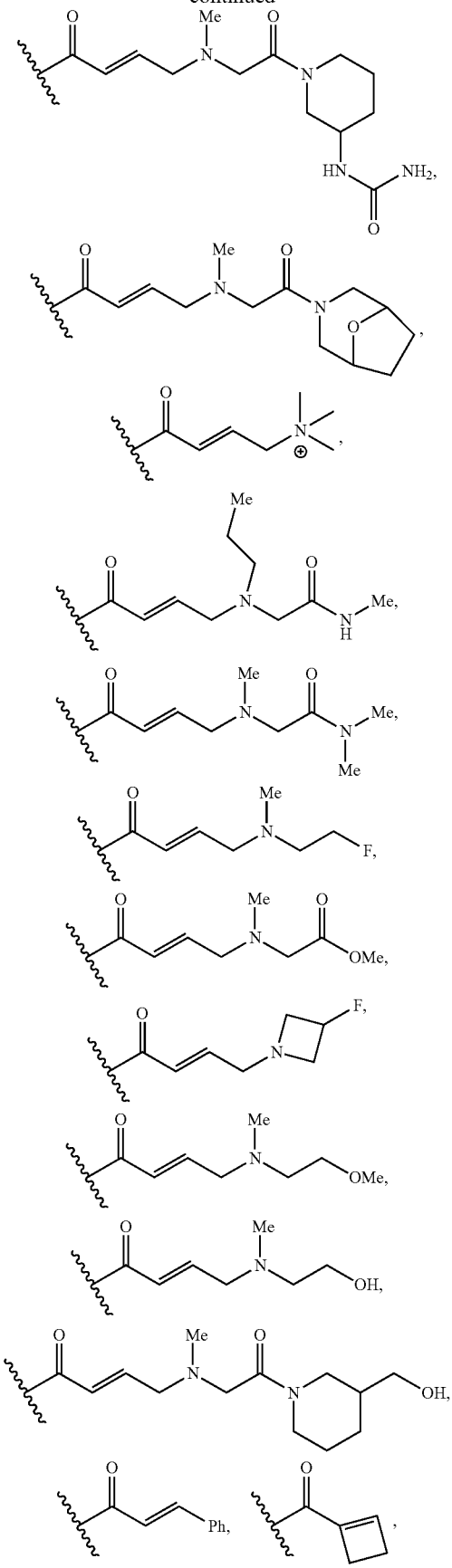

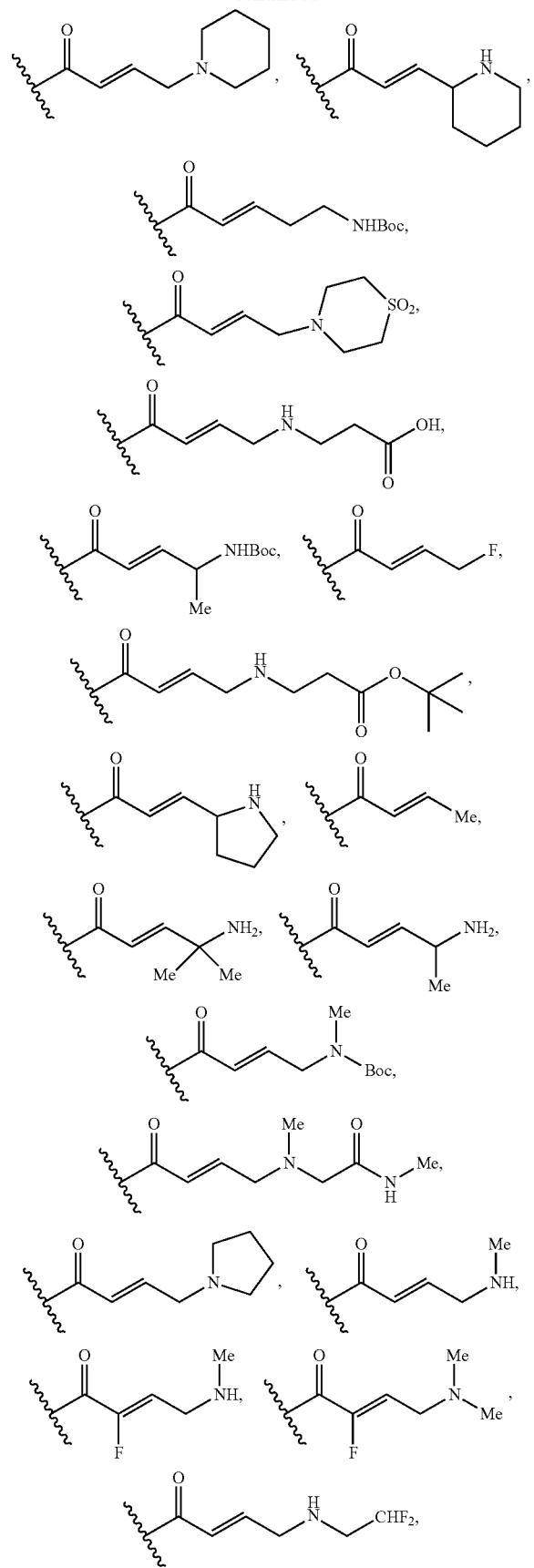
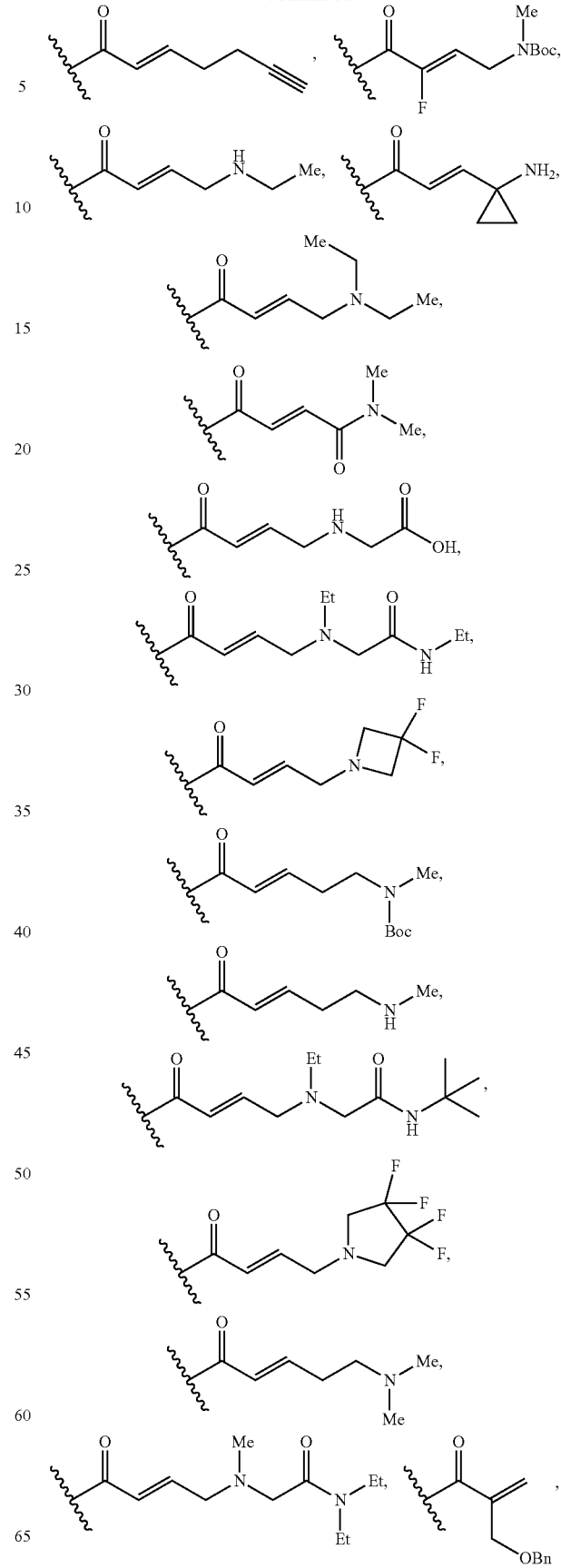

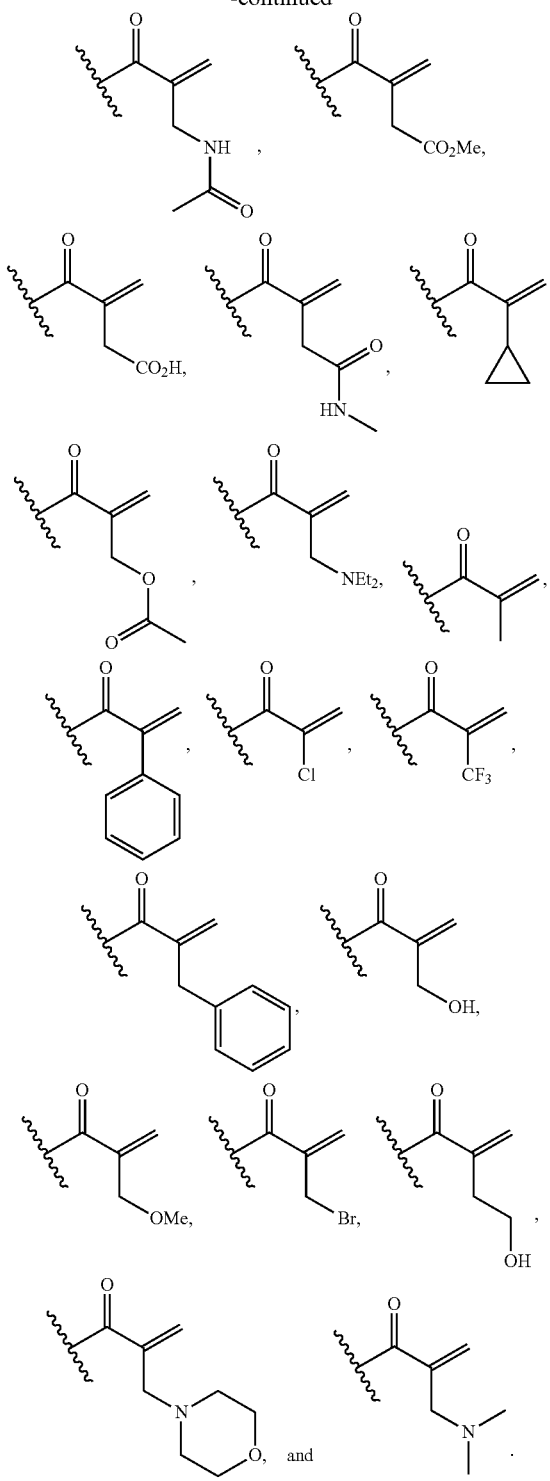
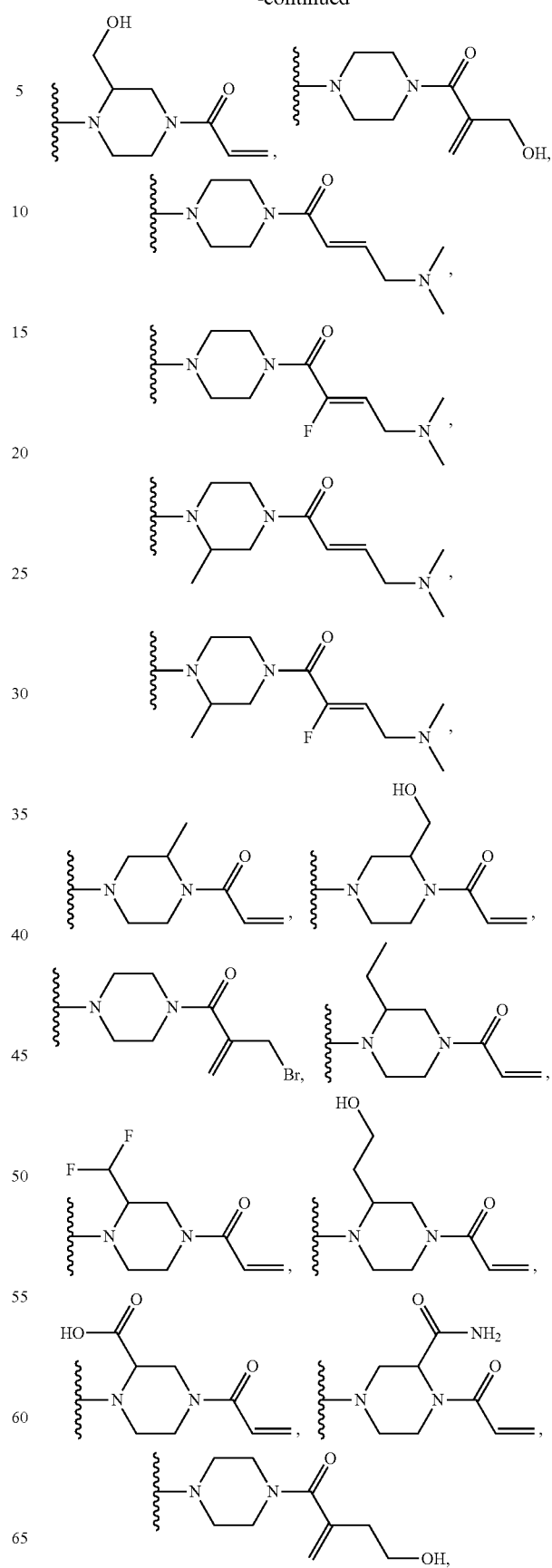
Some specifically contemplated R[4] substituents include
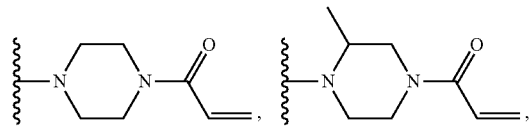

-continued
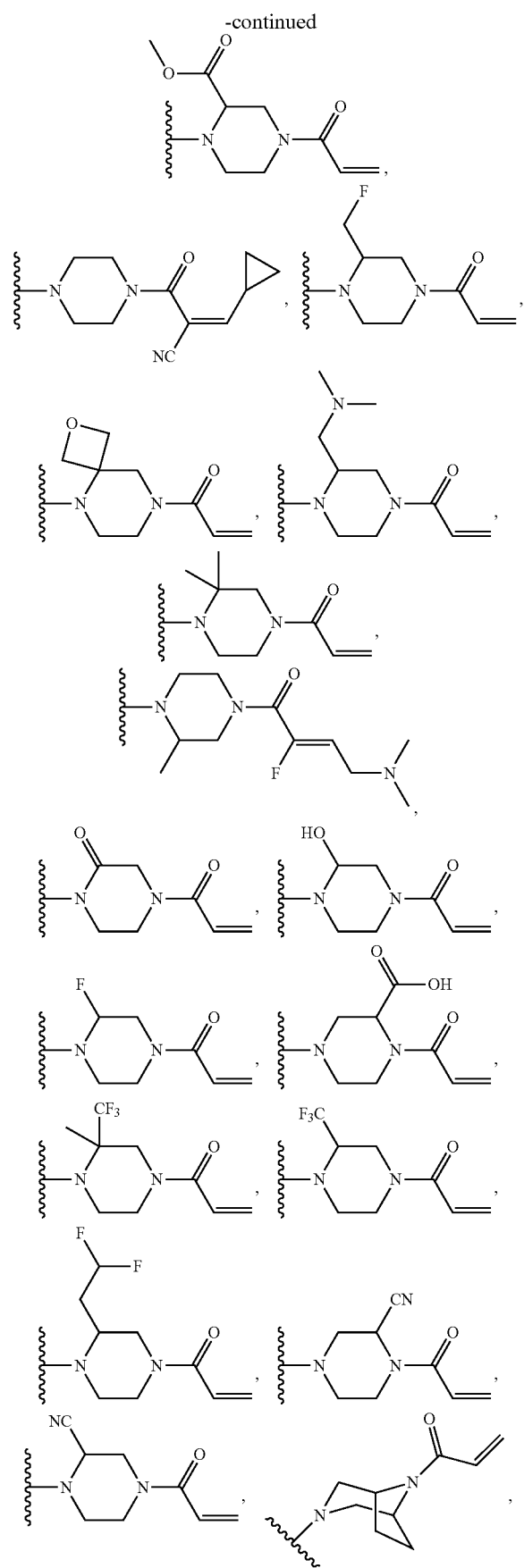
-continued
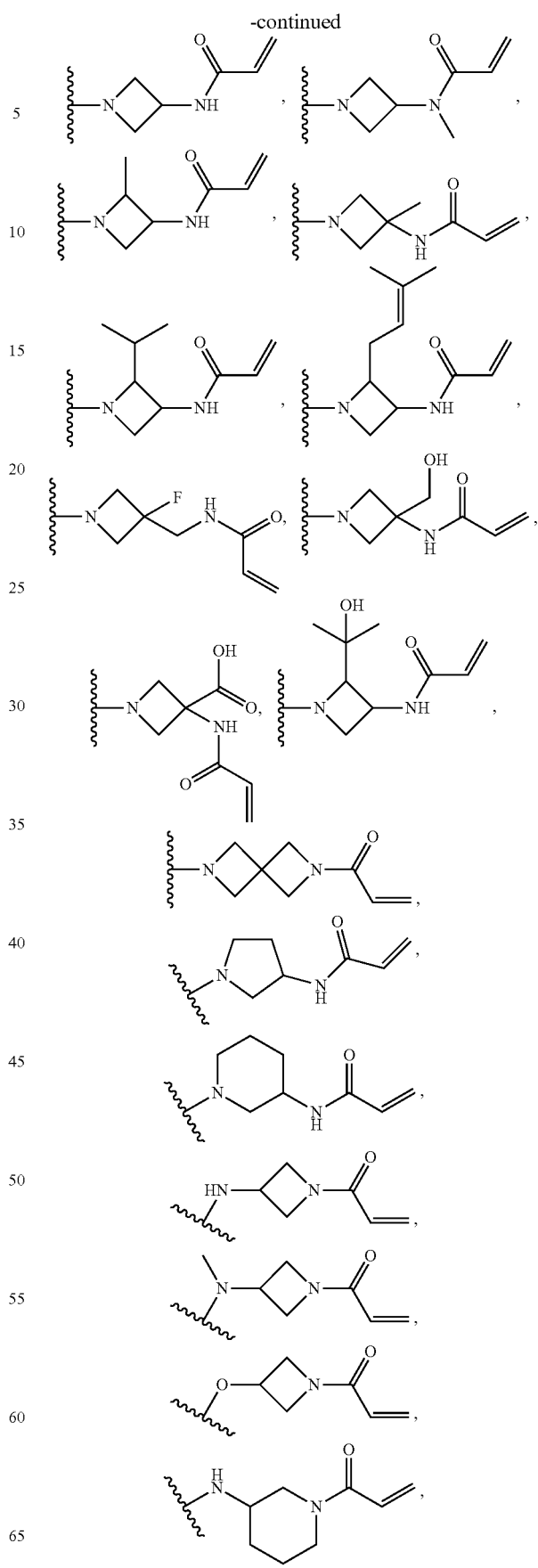

-continued
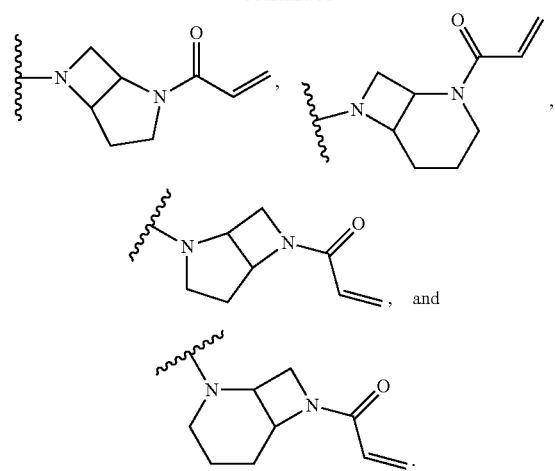
Some specifically contemplated R⁴ substituents can include
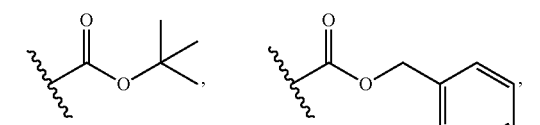
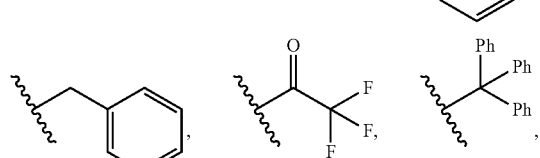
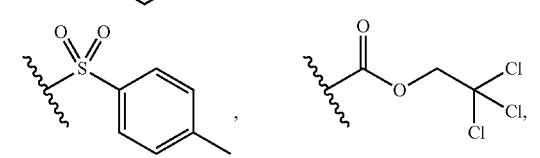
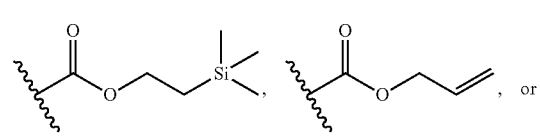, or
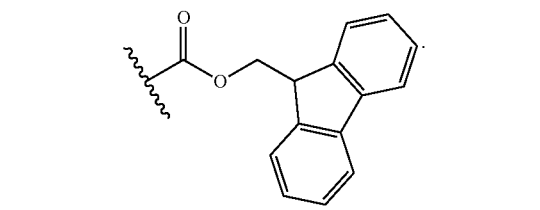
In another embodiment, the present invention discloses compounds having a structure selected from:
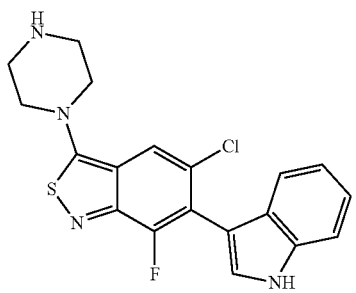
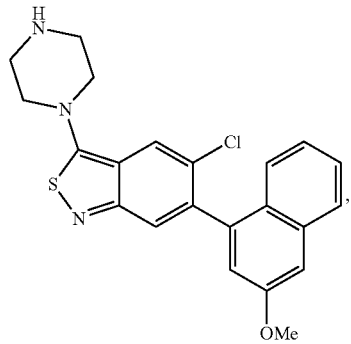
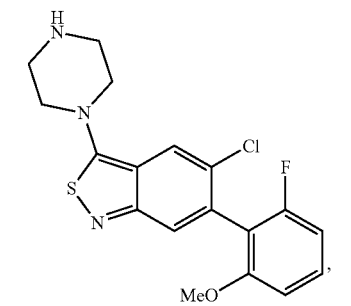
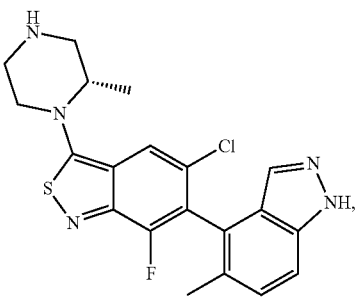
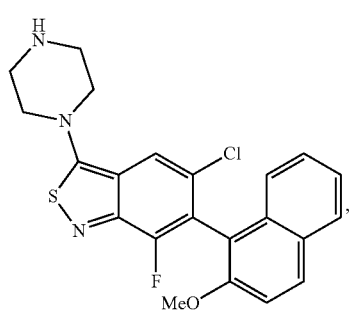

97
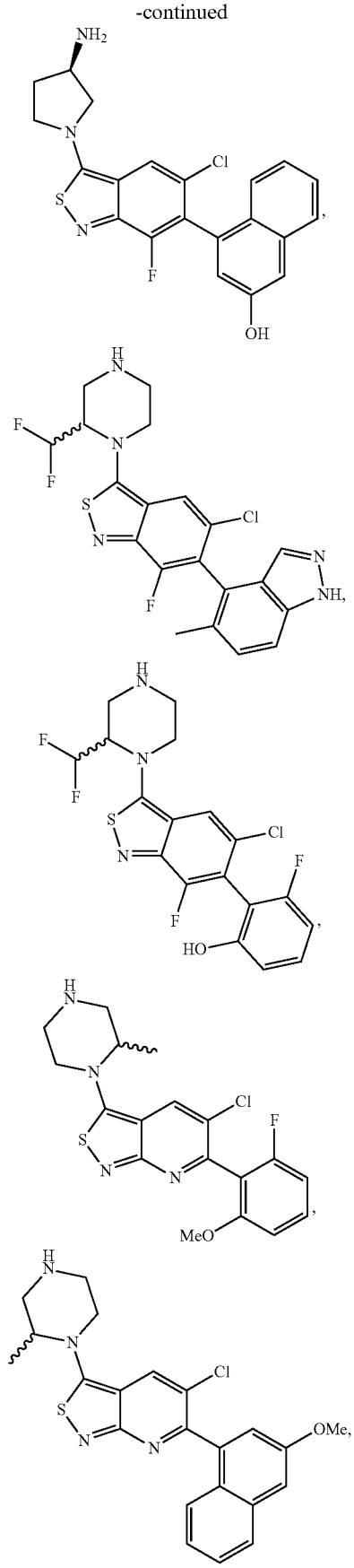
98
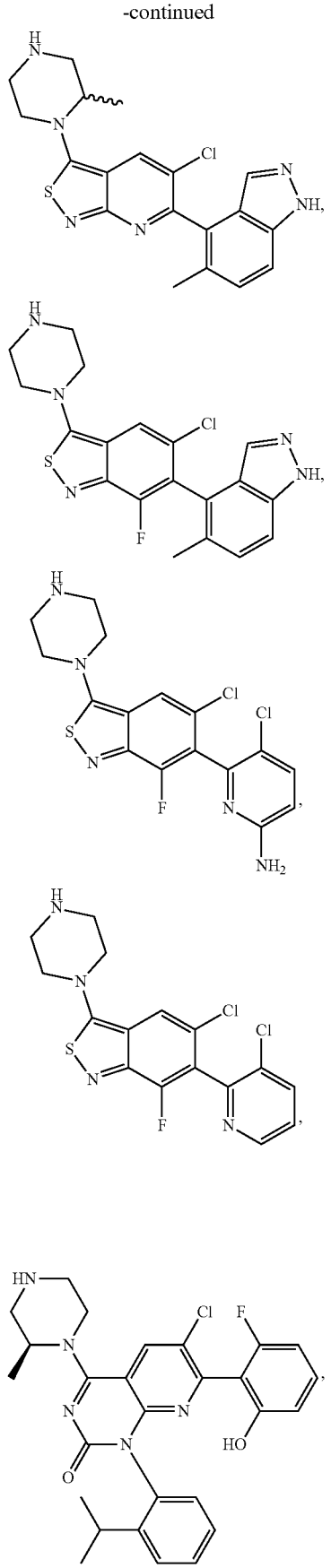

99
-continued
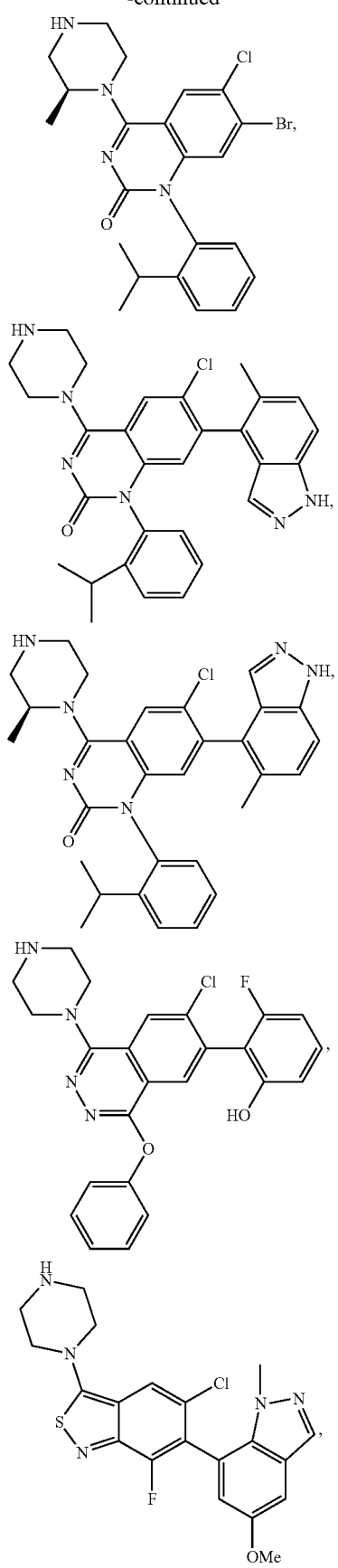
100
-continued
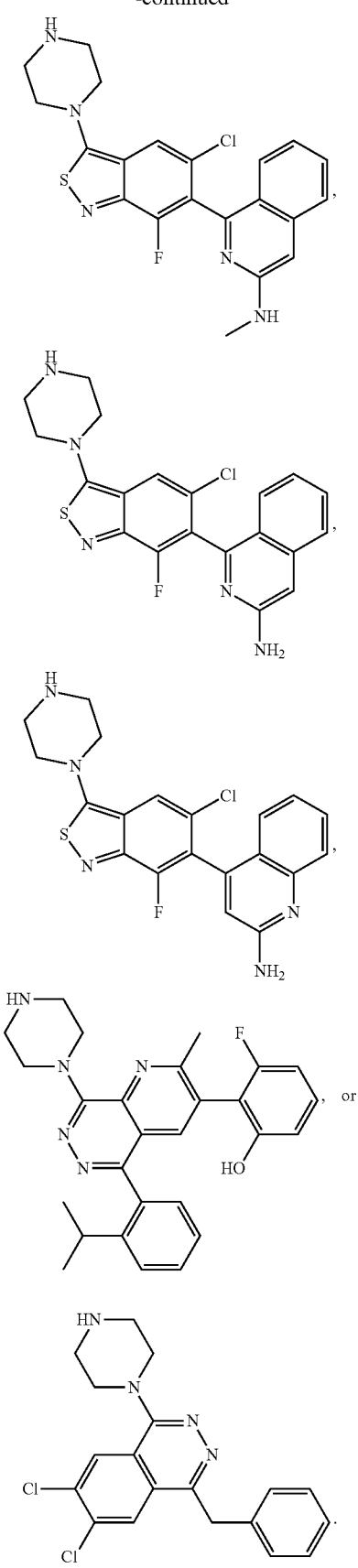

In another embodiment, the present invention discloses compounds having a structure selected from:
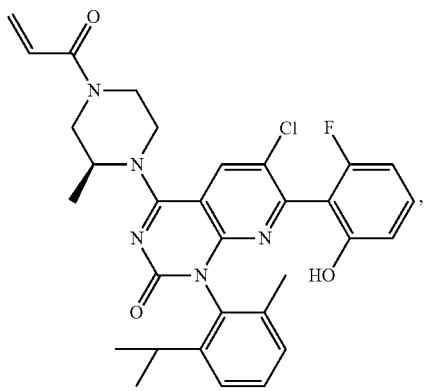
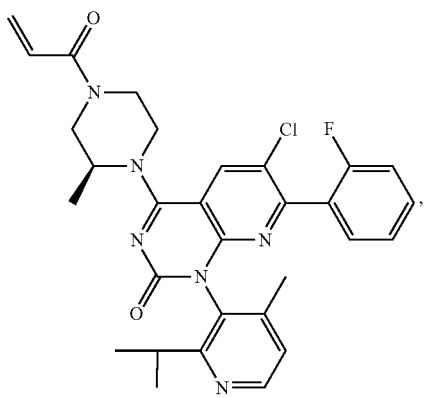
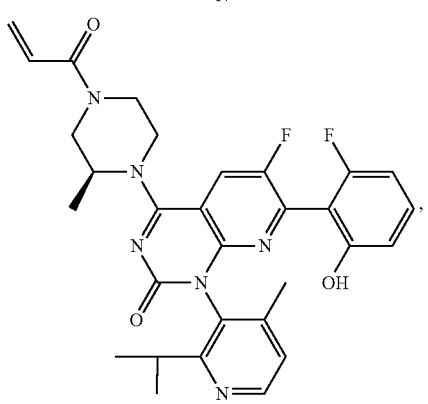
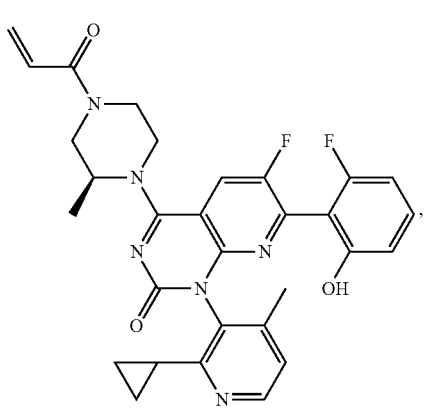
-continued
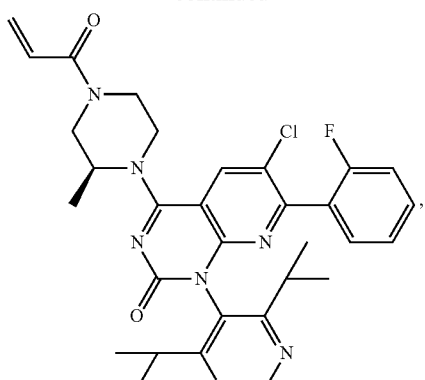
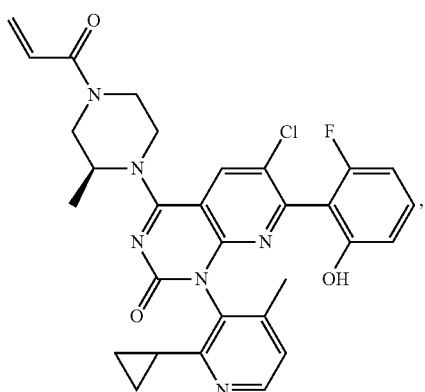
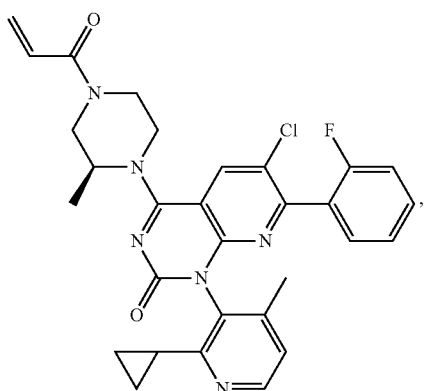
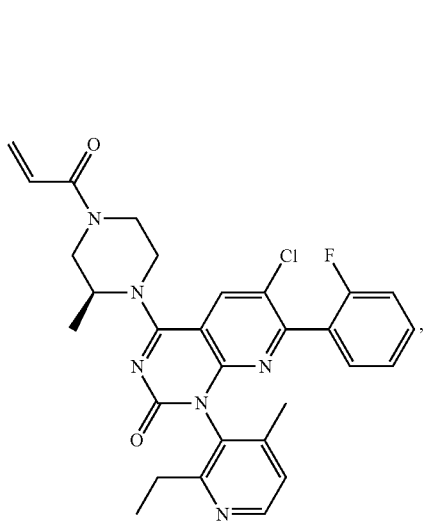

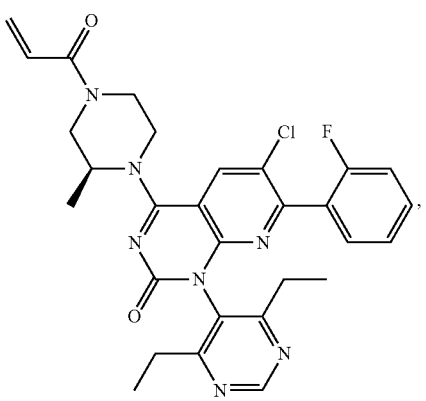
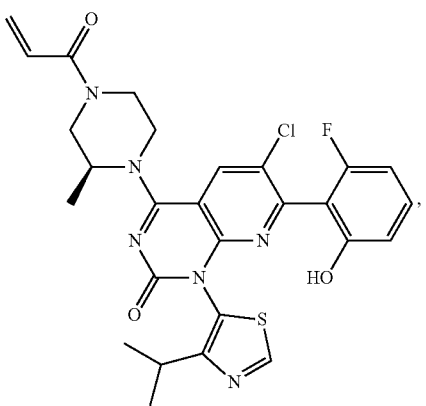
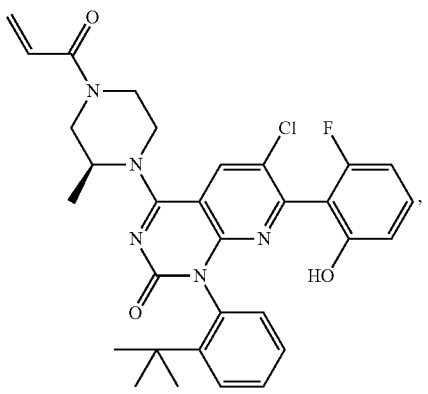
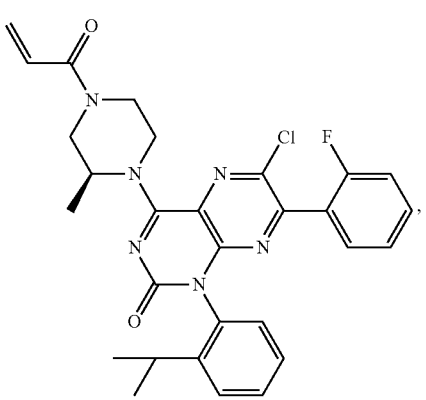
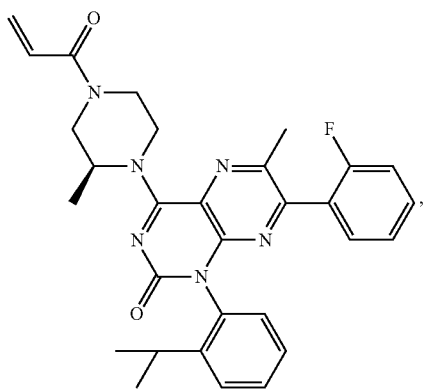
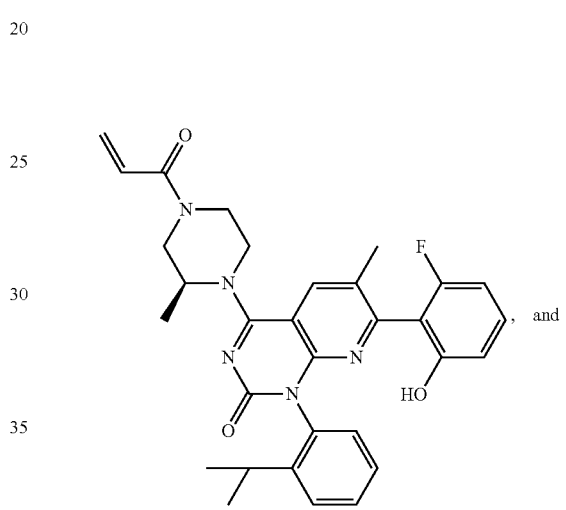
or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

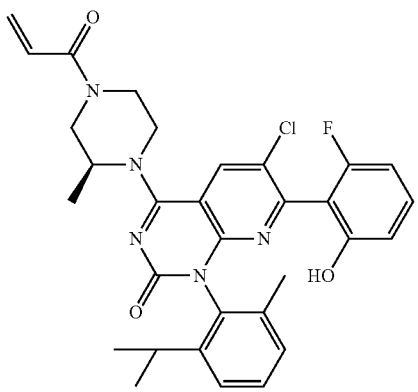 [SMILES: C=CC(=O)N1CCN(c2nc(=O)n(-c3c(C)cccc3C(C)C)c3nc(-c4c(O)cccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

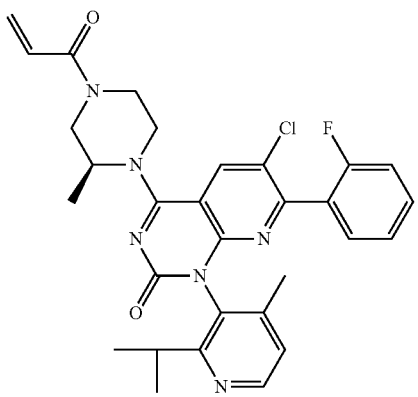 [SMILES: C=CC(=O)N1CCN(c2nc(=O)n(-c3c(C)ccnc3C(C)C)c3nc(-c4ccccc4F)c(Cl)cc23)[C@@H](C)C1]

or a stereoisomer thereof, an atropisJomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

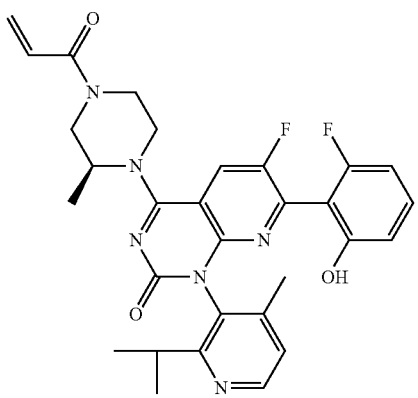 [SMILES: C=CC(=O)N1CCN(c2nc(=O)n(-c3c(C)ccnc3C(C)C)c3nc(-c4c(O)cccc4F)c(F)cc23)[C@@H](C)C1]

or a stereoisomer thereof, an atropisomer Jthereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

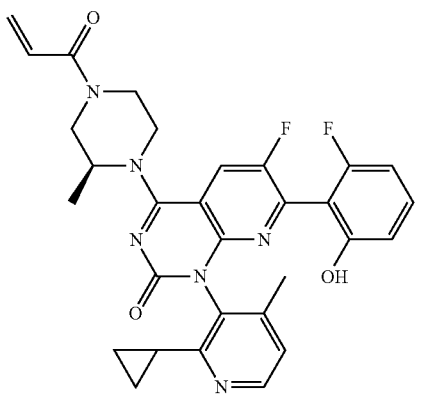 [SMILES: C=CC(=O)N1CCN(c2nc(=O)n(-c3c(C)ccnc3C3CC3)c3nc(-c4c(O)cccc4F)c(F)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

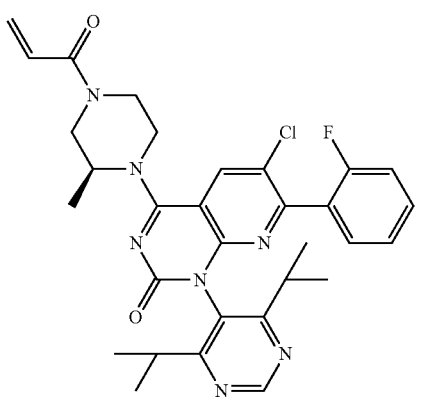 [SMILES: C=CC(=O)N1CCN(c2nc(=O)n(-c3c(C(C)C)ncnc3C(C)C)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

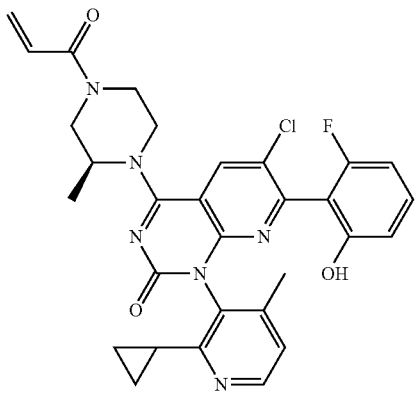

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

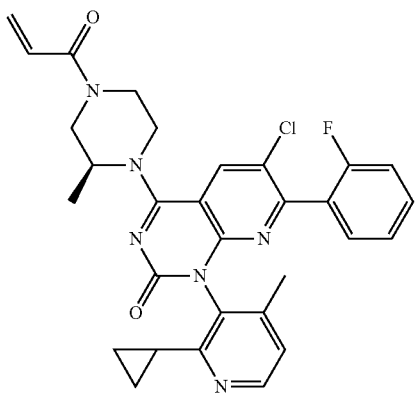 [SMILES: C=CC(=O)N1CCN(c2nc(=O)n(-c3c(C)ccnc3C3CC3)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

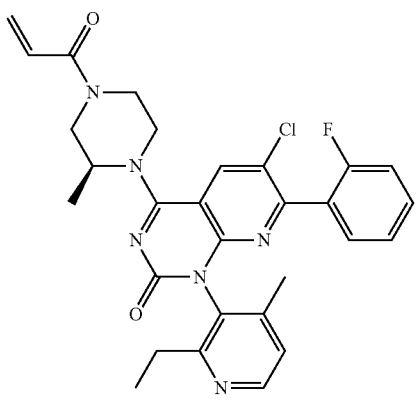 [SMILES: C=CC(=O)N1CCN(c2nc(=O)n(-c3c(C)ccnc3CC)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

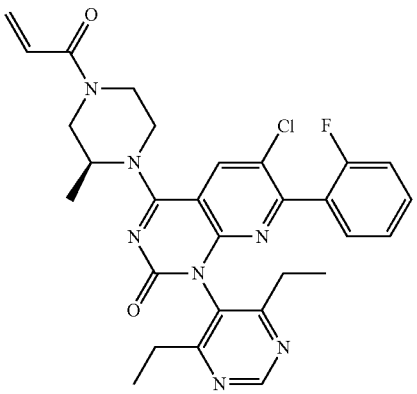 [SMILES: C=CC(=O)N1CCN(c2nc(=O)n(-c3c(CC)ncnc3CC)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

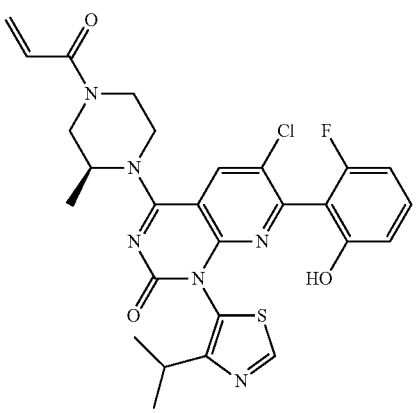 [SMILES: C=CC(=O)N1CCN(c2nc(=O)n(-c3scnc3C(C)C)c3nc(-c4c(O)cccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

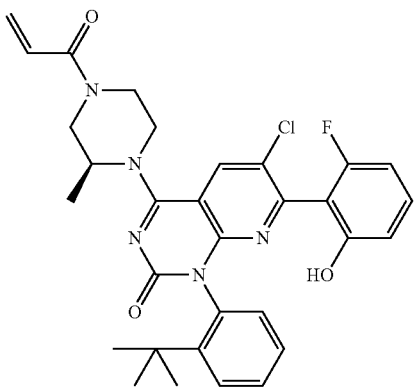 [SMILES: C=CC(=O)N1CCN(c2nc(=O)n(-c3ccccc3C(C)(C)C)c3nc(-c4c(O)cccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

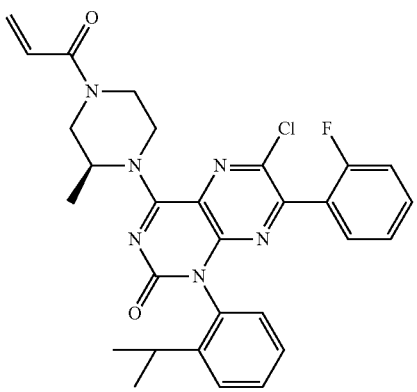 [SMILES: C=CC(=O)N1CCN(c2nc(=O)n(-c3ccccc3C(C)C)c3nc(-c4ccccc4F)c(Cl)nc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

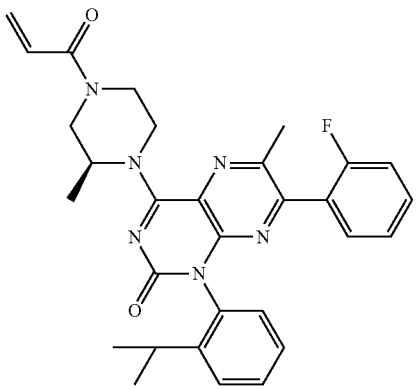 [SMILES: C=CC(=O)N1CCN(c2nc(=O)n(-c3ccccc3C(C)C)c3nc(-c4ccccc4F)c(C)nc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

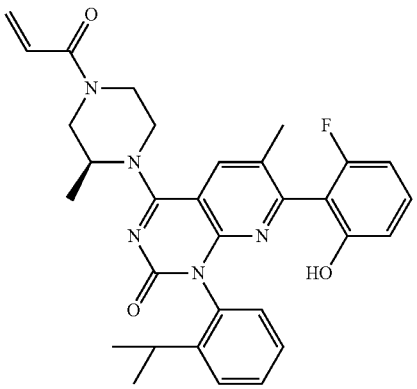 [SMILES: C=CC(=O)N1CCN(c2nc(=O)n(-c3ccccc3C(C)C)c3nc(-c4c(O)cccc4F)c(C)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, the present invention discloses compounds having a structure selected from:

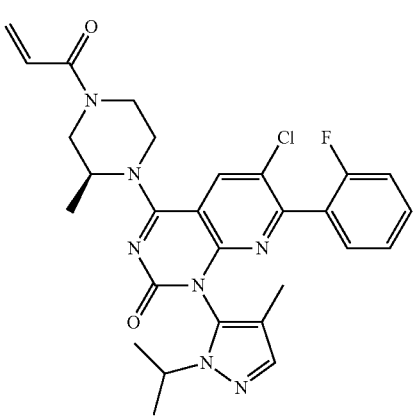 [SMILES: C=CC(=O)N1CCN(c2nc(=O)n(-c3c(C)cnn3C(C)C)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

In another embodiment, these compounds can be used as intermediates in the process of making compounds in the present application.

In another embodiment, these compounds can be in the form of a pharmaceutically acceptable salt.

In another embodiment, these compounds can be in a pharmaceutical formulation comprising any one or more of the compounds and a pharmaceutically acceptable excipient.

In another embodiment, these compounds can be used in a method of inhibiting KRAS G12C in a cell, comprising contacting the cell with the compound of any one of compounds or the pharmaceutical formulation.

In another embodiment, these compounds can be used in a method of treating cancer in a subject comprising administering to the subject a therapeutically effective amount of any of the compounds or the compositions.

In another embodiment, the cancer is lung cancer, pancreatic cancer, or colorectal cancer.

In another embodiment, the cancer is lung cancer.

In another embodiment, the cancer is pancreatic cancer.

In another embodiment, the cancer is colorectal cancer.

In another embodiment, the method further comprises administering to the patient in need thereof a therapeutically effective amount of an additional pharmaceutically active compound.

In another embodiment, the additional pharmaceutically active compound is carfdzomib.

In another embodiment, the additional pharmaceutically active compound is cytarabine.

In another embodiment, the present invention comprises the use of one or more of the compounds for treating cancer in a subject.

In another embodiment, the present invention comprises the use of one or more of the compounds in the preparation of a medicament for treating cancer.

In another embodiment, the cancer is a hematologic malignancy.

In another embodiment, the present invention comprises the use of one or more of the compounds for treating cancer, wherein the cancer is a hematologic malignancy.

The following examples 1-11 are labeled using a classification system in which the first number refers to the method used to synthesize the compound, the second number is an identifying number, and the third number, if present, refers to the compound's order of elution in a chromatographic separation process. If third number is absent, the compound is a single compound or mixture of isomers. Examples 12-53 use a classification system in which the first number is an identifying number, and the second number, if present, refers to the compound's order of elution in a chromatographic separation process. If the second number is absent, the compound is a single compound or mixture of isomers. The sequential numbering of the Examples is interrupted and certain Example numbers are intentionally omitted due to formatting considerations. The denotes that no changes were made, or no entries are in the relevant box. Specifically contemplated compounds include those as listed in Table 1 and Table 1(a):

TABLE 1

| Ex. # | Chemical Structure |
|---|---|
| 1-1 | 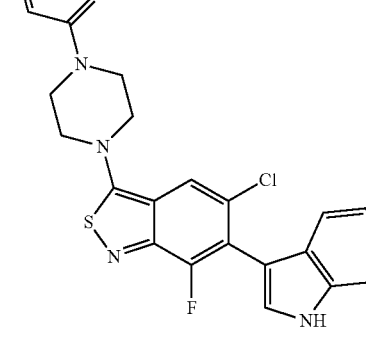 |
| 1-2 | 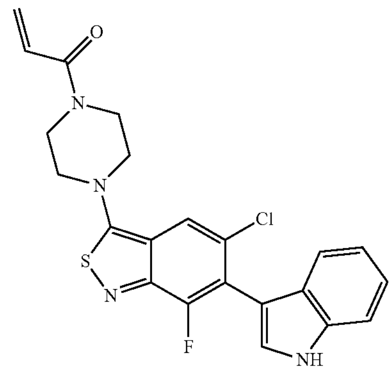 [SMILES: C=CC(=O)N1CCN(c2snc3c(F)c(-c4c[nH]c5ccccc45)c(Cl)cc23)CC1] |
| 1-3 | 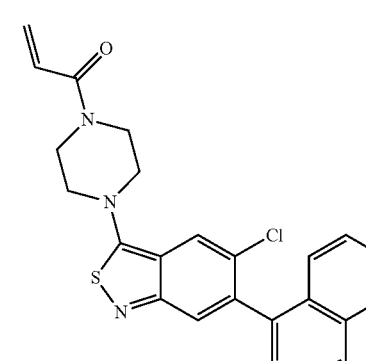 |
| 1-6 | 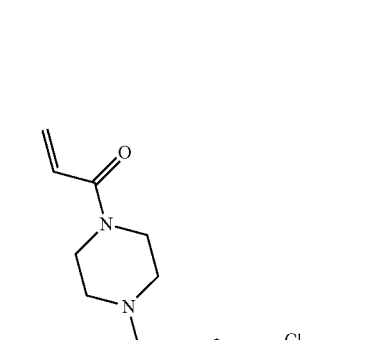 |

TABLE 1-continued
| Ex. # | Chemical Structure |
|---|---|
| 1-7 | 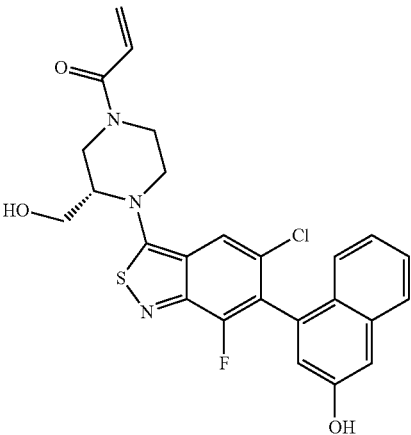 [SMILES: C=CC(=O)N1CCN(c2snc3c(F)c(-c4cc(O)cc5ccccc45)c(Cl)cc23)[C@H](CO)C1] |
| 1-8 | 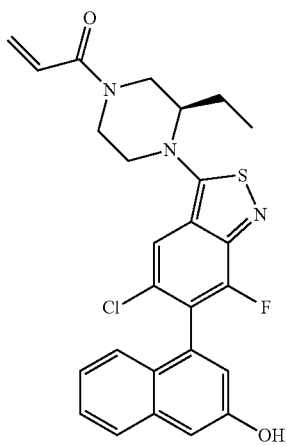 [SMILES: C=CC(=O)N1CCN(c2snc3c(F)c(-c4cc(O)cc5ccccc45)c(Cl)cc23)[C@H](CC)C1] |
| 1-9 | 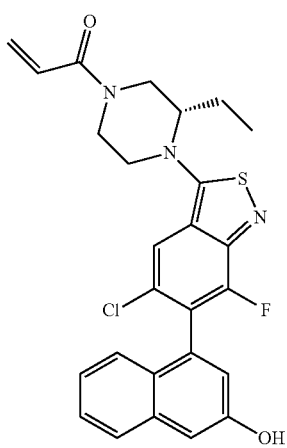 [SMILES: C=CC(=O)N1CCN(c2snc3c(F)c(-c4cc(O)cc5ccccc45)c(Cl)cc23)[C@@H](CC)C1] |
TABLE 1-continued
| Ex. # | Chemical Structure |
|---|---|
| 1-11 | 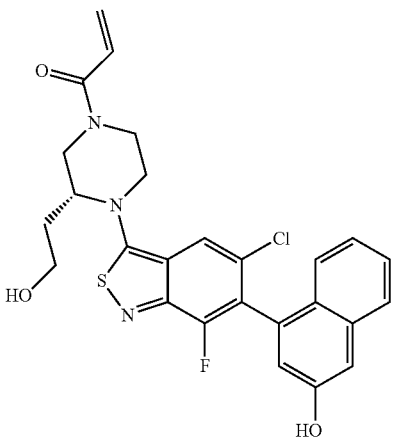 [SMILES: C=CC(=O)N1CCN(c2snc3c(F)c(-c4cc(O)cc5ccccc45)c(Cl)cc23)[C@H](CCO)C1] |
| 1-12 | 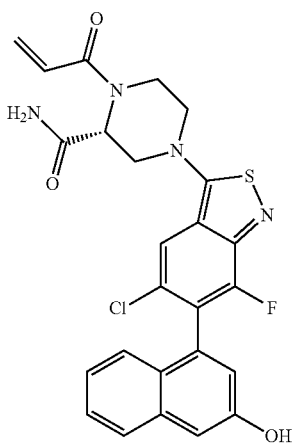 [SMILES: C=CC(=O)N1CCN(c2snc3c(F)c(-c4cc(O)cc5ccccc45)c(Cl)cc23)C[C@@H]1C(N)=O] |
| 1-13 | 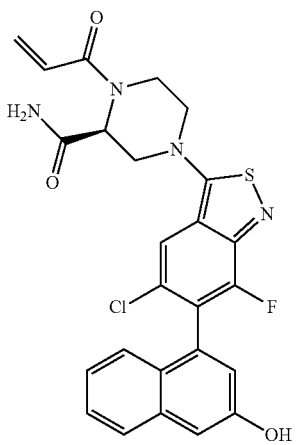 [SMILES: C=CC(=O)N1CCN(c2snc3c(F)c(-c4cc(O)cc5ccccc45)c(Cl)cc23)C[C@H]1C(N)=O] |

TABLE 1-continued

| Ex. # | Chemical Structure |
|---|---|
| 1-13 | 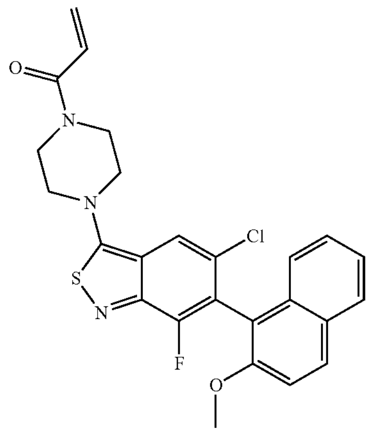 [SMILES: C=CC(=O)N1CCN(c2snc3c(F)c(-c4c(OC)ccc5ccccc45)c(Cl)cc23)CC1] |
| 1-4 | 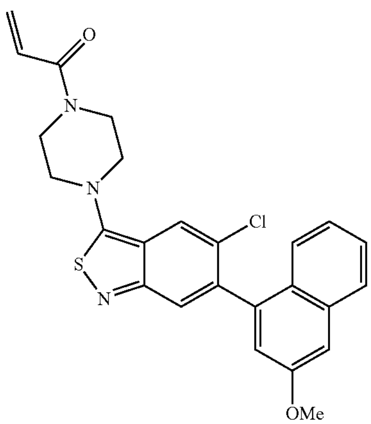 [SMILES: C=CC(=O)N1CCN(c2snc3cc(-c4cc(OC)cc5ccccc45)c(Cl)cc23)CC1] |
| 1-5 | 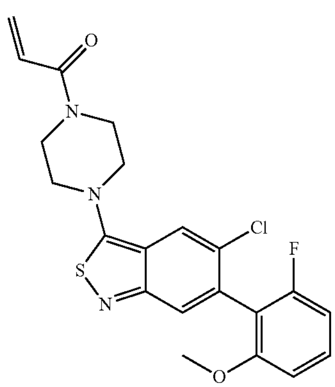 [SMILES: C=CC(=O)N1CCN(c2snc3cc(-c4c(F)cccc4OC)c(Cl)cc23)CC1] |
| 1-9 | |

TABLE 1-continued
| Ex. # | Chemical Structure |
|---|---|
| 1-10 | 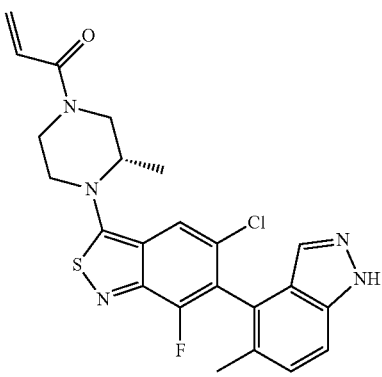 [SMILES: C=CC(=O)N1CCN(c2snc3c(F)c(-c4c(C)ccc5[nH]ncc45)c(Cl)cc23)[C@@H](C)C1] |
| 1-14 | 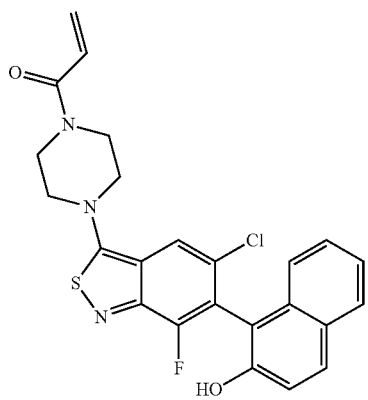 [SMILES: C=CC(=O)N1CCN(c2snc3c(F)c(-c4c(O)ccc5ccccc45)c(Cl)cc23)CC1] |
| 1-15 | 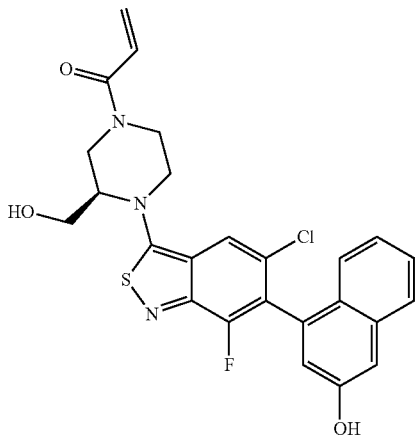 [SMILES: C=CC(=O)N1CCN(c2snc3c(F)c(-c4cc(O)cc5ccccc45)c(Cl)cc23)[C@@H](CO)C1] |
TABLE 1-continued
| Ex. # | Chemical Structure |
|---|---|
| 1-16 | 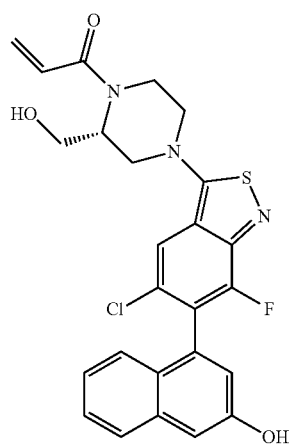 [SMILES: C=CC(=O)N1CCN(c2snc3c(F)c(-c4cc(O)cc5ccccc45)c(Cl)cc23)C[C@@H]1CO] |
| | 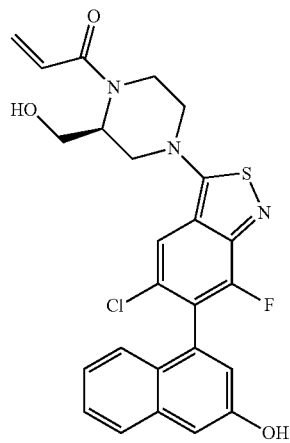 [SMILES: C=CC(=O)N1CCN(c2snc3c(F)c(-c4cc(O)cc5ccccc45)c(Cl)cc23)C[C@H]1CO] |
| 1-17 | 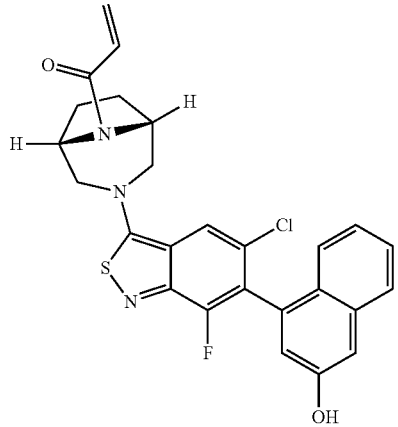 [SMILES: C=CC(=O)N1[C@@H]2CC[C@H]1CN(c1snc3c(F)c(-c4cc(O)cc5ccccc45)c(Cl)cc13)C2] |

TABLE 1-continued
| Ex. # | Chemical Structure |
|---|---|
| 1-19-2 | 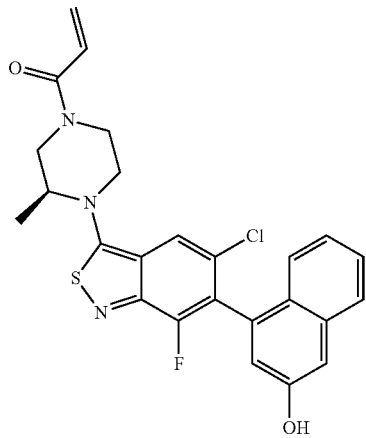 [SMILES: C=CC(=O)N1CCN(c2snc3c(F)c(-c4cc(O)cc5ccccc45)c(Cl)cc23)[C@@H](C)C1] |
| 1-20 | 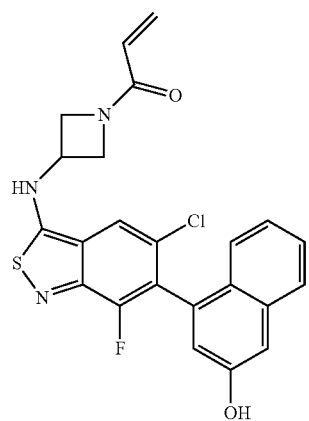 [SMILES: C=CC(=O)N1CC(Nc2snc3c(F)c(-c4cc(O)cc5ccccc45)c(Cl)cc23)C1] |
| 2-7 | 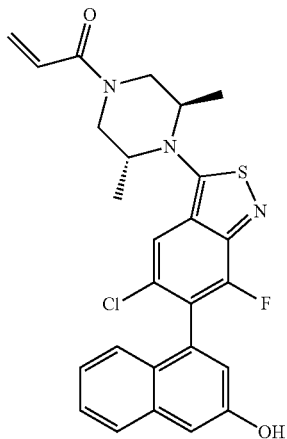 [SMILES: C=CC(=O)N1C[C@@H](C)N(c2snc3c(F)c(-c4cc(O)cc5ccccc45)c(Cl)cc23)[C@H](C)C1] |
TABLE 1-continued
| Ex. # | Chemical Structure |
|---|---|
| | 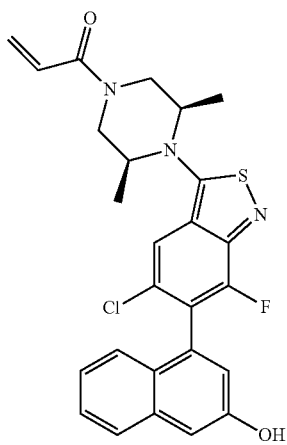 [SMILES: C=CC(=O)N1C[C@@H](C)N(c2snc3c(F)c(-c4cc(O)cc5ccccc45)c(Cl)cc23)[C@@H](C)C1] |
| | 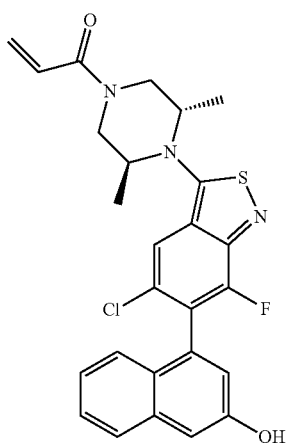 [SMILES: C=CC(=O)N1C[C@H](C)N(c2snc3c(F)c(-c4cc(O)cc5ccccc45)c(Cl)cc23)[C@@H](C)C1] |
| 2-8 | 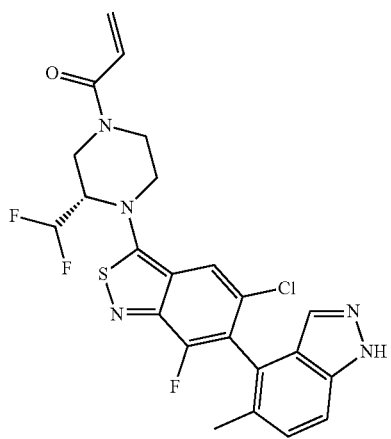 [SMILES: C=CC(=O)N1CCN(c2snc3c(F)c(-c4c(C)ccc5[nH]ncc45)c(Cl)cc23)[C@H](C(F)F)C1] |

TABLE 1-continued
| Ex. # | Chemical Structure |
|---|---|
| | 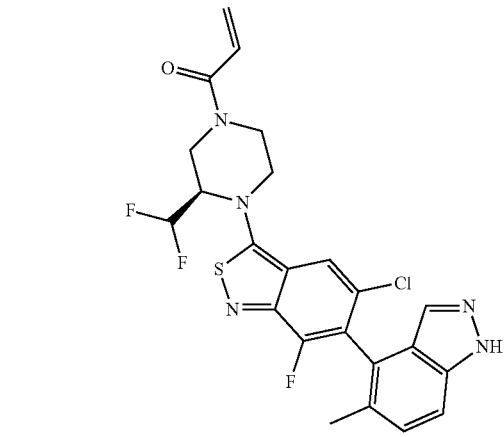 [SMILES: C=CC(=O)N1CCN(c2snc3c(F)c(-c4c(C)ccc5[nH]ncc45)c(Cl)cc23)[C@@H](C(F)F)C1] |
| 1-18 | 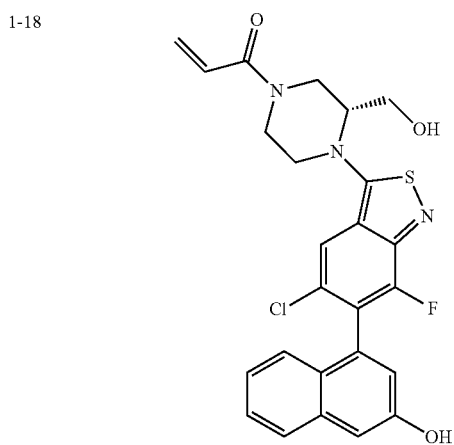 |
TABLE 1-continued
| Ex. # | Chemical Structure |
|---|---|
| 1-19 | 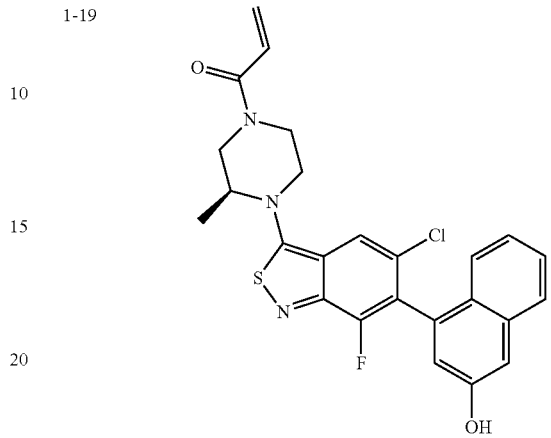 |
| 1-19-1 | 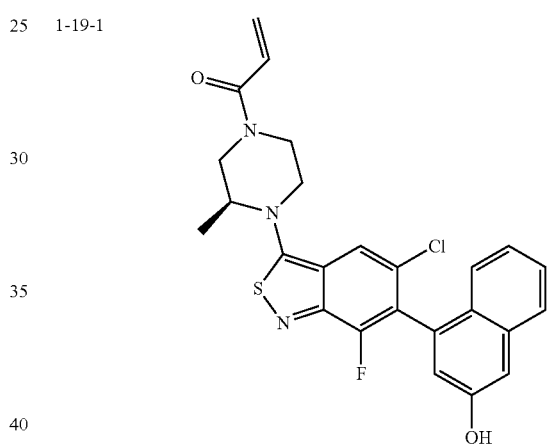 |
| 1-21 | 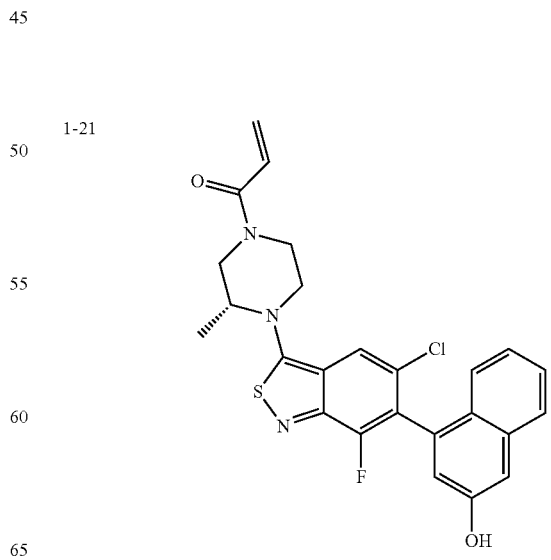 |

TABLE 1-continued
| Ex. # | Chemical Structure |
|---|---|
| 1-22 | 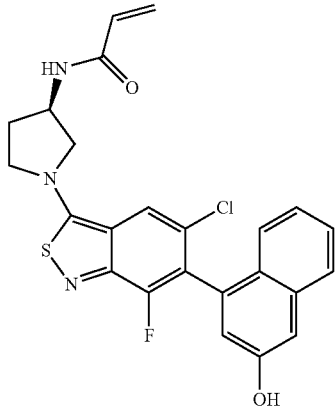 [SMILES: C=CC(=O)N[C@@H]1CCN(c2snc3c(F)c(-c4cc(O)cc5ccccc45)c(Cl)cc23)C1] |
| 1-23 | 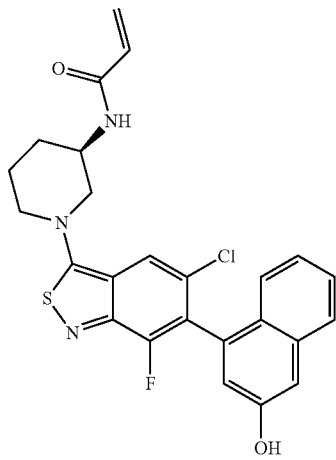 [SMILES: C=CC(=O)N[C@@H]1CCCN(c2snc3c(F)c(-c4cc(O)cc5ccccc45)c(Cl)cc23)C1] |
| 2-9 | 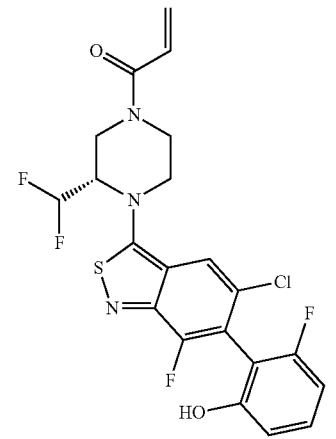 [SMILES: C=CC(=O)N1CCN(c2snc3c(F)c(-c4c(O)cccc4F)c(Cl)cc23)[C@H](C(F)F)C1] |
TABLE 1-continued
| Ex. # | Chemical Structure |
|---|---|
| | 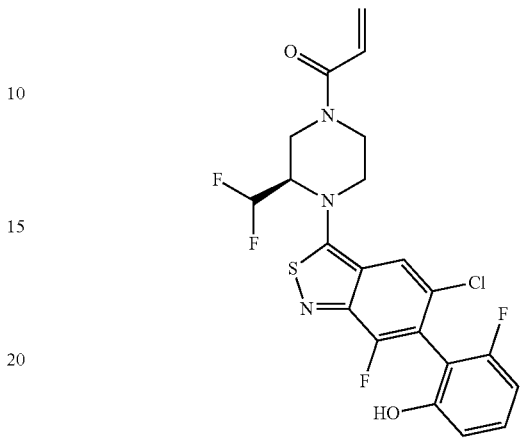 |
| 2-10 | 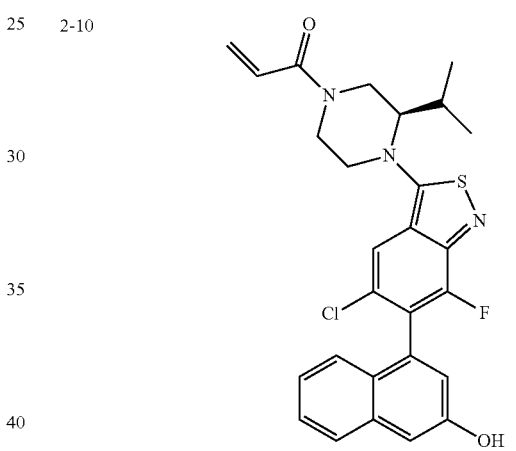 |
| | 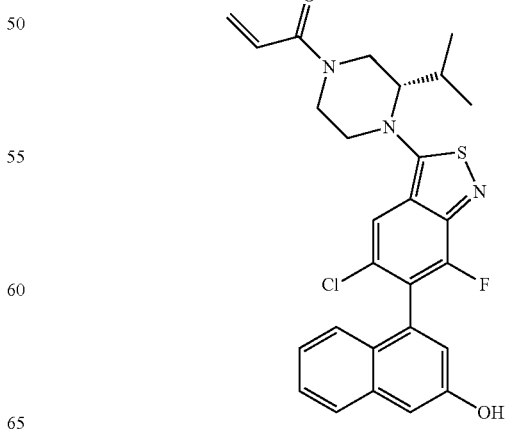 |

TABLE 1-continued
| Ex. # | Chemical Structure |
|---|---|
| 1-28 | 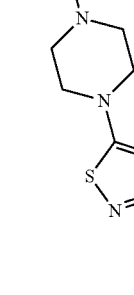 |
| 2-2 | 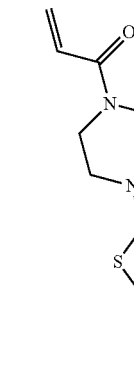 |
| 2-3 | 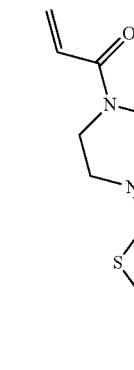 |
TABLE 1-continued
| Ex. # | Chemical Structure |
|---|---|
| | 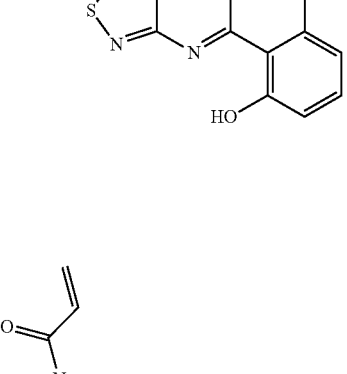 |
| 2-4 | 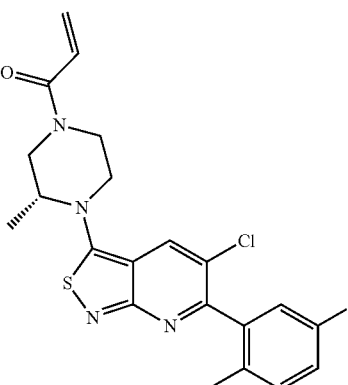 |
| | 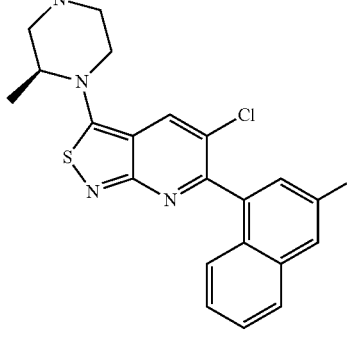 |

TABLE 1-continued

| Ex. # | Chemical Structure |
|---|---|
| 2-5-2 | 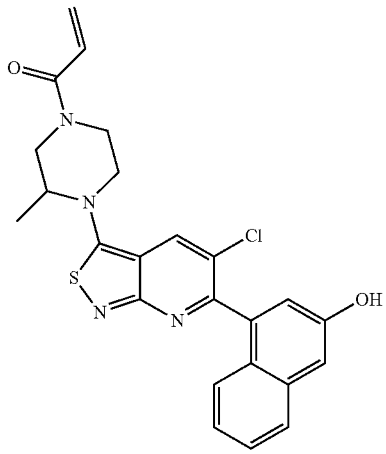 [SMILES: C=CC(=O)N1CCN(c2snc3nc(-c4cc(O)cc5ccccc45)c(Cl)cc23)C(C)C1] |
| 2-6 | 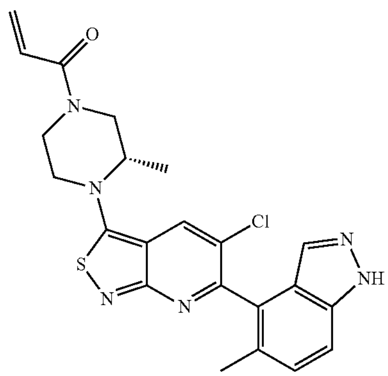 [SMILES: C=CC(=O)N1CCN(c2snc3nc(-c4c(C)ccc5[nH]ncc45)c(Cl)cc23)[C@@H](C)C1] |
| 2-6-1 | 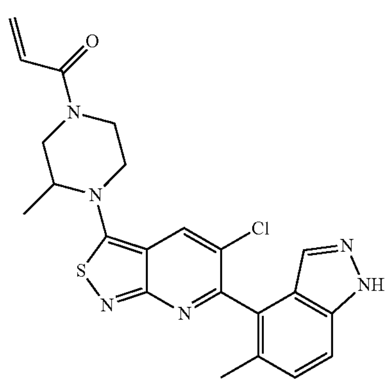 [SMILES: C=CC(=O)N1CCN(c2snc3nc(-c4c(C)ccc5[nH]ncc45)c(Cl)cc23)C(C)C1] |
| 3-1-1 | |
| 3-1-2 | |
| 3-2 | |

TABLE 1-continued
| Ex. # | Chemical Structure |
|---|---|
| 2-5 | 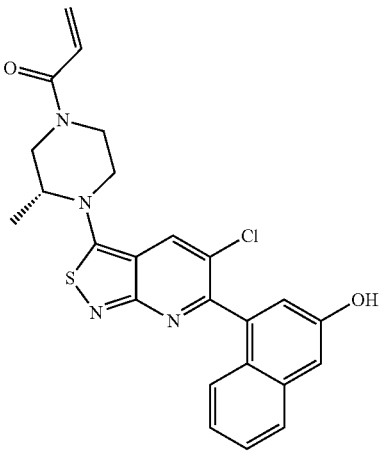 [SMILES: C=CC(=O)N1CCN(c2snc3nc(-c4cc(O)cc5ccccc45)c(Cl)cc23)[C@H](C)C1] |
| 2-5-1 | 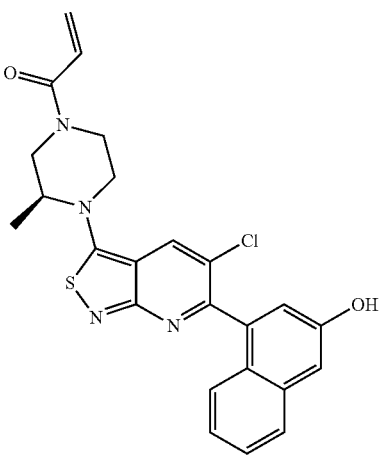 [SMILES: C=CC(=O)N1CCN(c2snc3nc(-c4cc(O)cc5ccccc45)c(Cl)cc23)[C@@H](C)C1] |
| 2-5-1 | 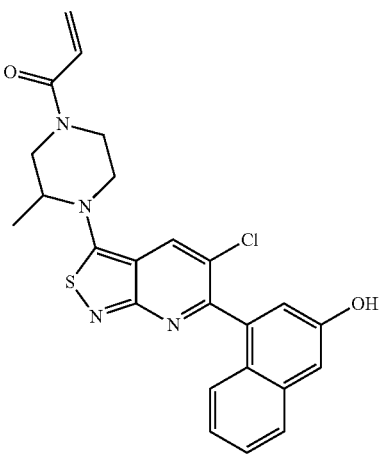 [SMILES: C=CC(=O)N1CCN(c2snc3nc(-c4cc(O)cc5ccccc45)c(Cl)cc23)C(C)C1] |
TABLE 1-continued
| Ex. # | Chemical Structure |
|---|---|
| 3-5 | 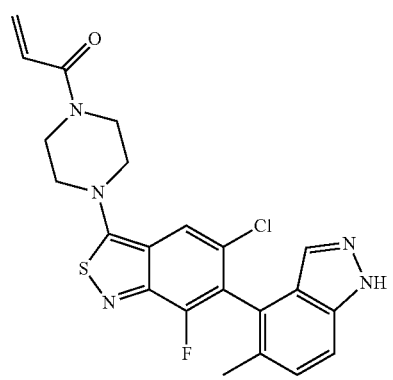 [SMILES: C=CC(=O)N1CCN(c2snc3c(F)c(-c4c(C)ccc5[nH]ncc45)c(Cl)cc23)CC1] |
| 3-6 | 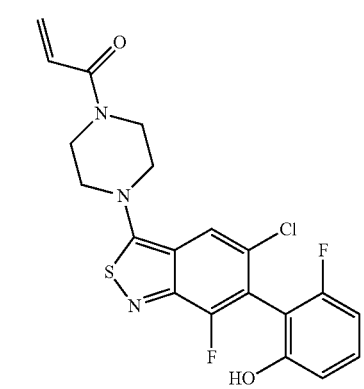 [SMILES: C=CC(=O)N1CCN(c2snc3c(F)c(-c4c(O)cccc4F)c(Cl)cc23)CC1] |
| 3-7 | 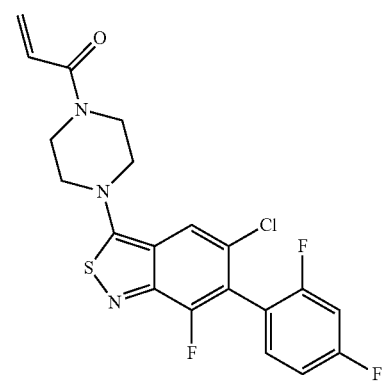 [SMILES: C=CC(=O)N1CCN(c2snc3c(F)c(-c4ccc(F)cc4F)c(Cl)cc23)CC1] |
| 2-6-2 | 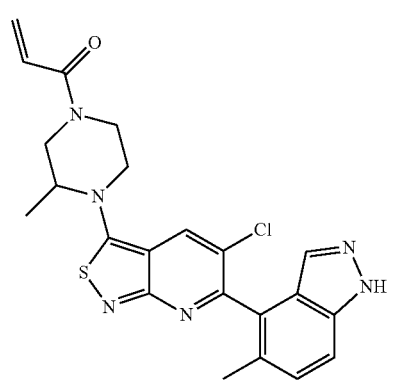 [SMILES: C=CC(=O)N1CCN(c2snc3nc(-c4c(C)ccc5[nH]ncc45)c(Cl)cc23)C(C)C1] |

TABLE 1-continued
| Ex. # | Chemical Structure |
|---|---|
| 3-1 | 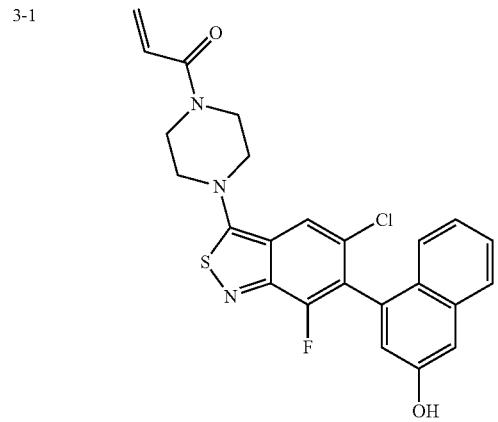 |
| 3-10 | 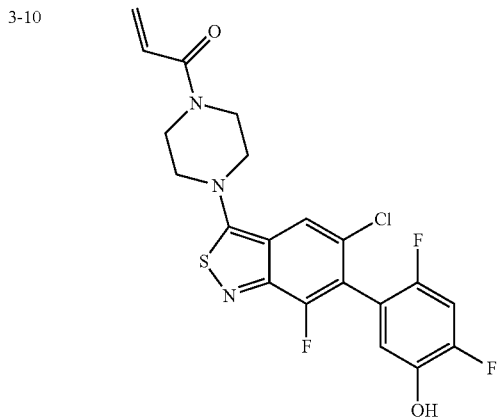 |
| 3-11 | 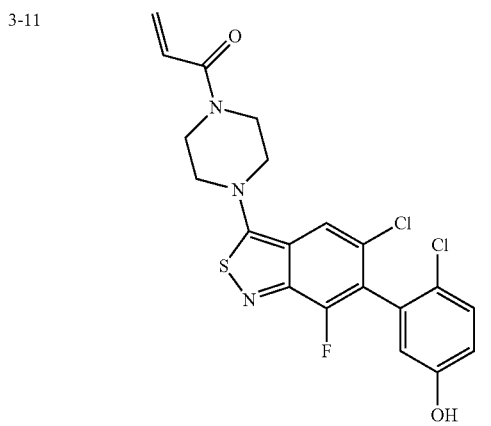 |
TABLE 1-continued
| Ex. # | Chemical Structure |
|---|---|
| 3-12 | 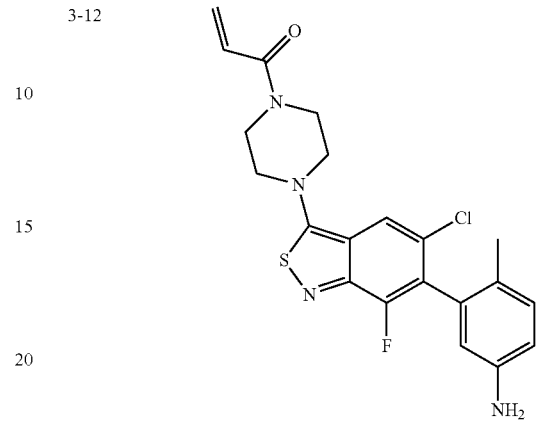 |
| 3-3 | 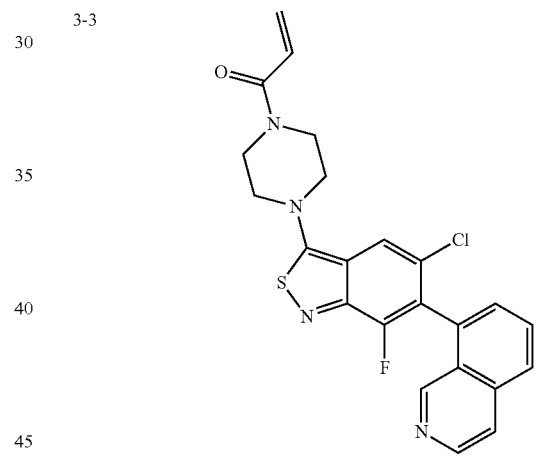 |
| 3-4 | 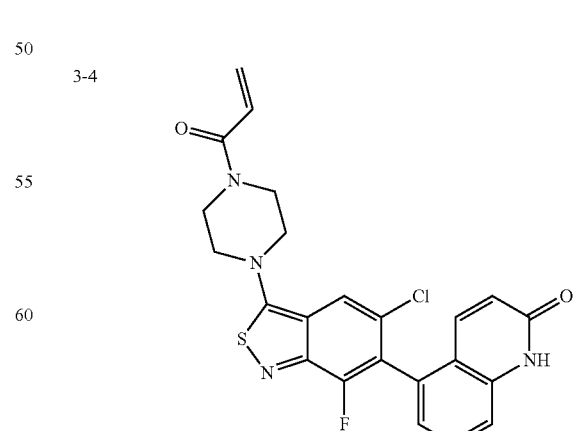 |

TABLE 1-continued
| Ex. # | Chemical Structure |
|---|---|
| 3-15 | 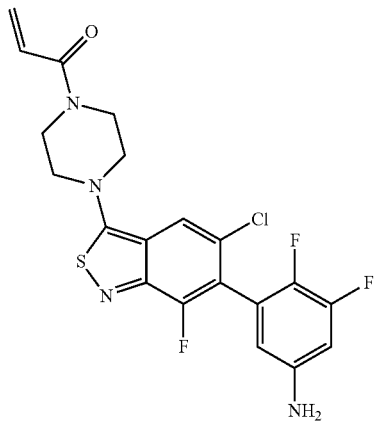 [SMILES: C=CC(=O)N1CCN(c2snc3c(F)c(-c4cc(N)cc(F)c4F)c(Cl)cc23)CC1] |
| 3-16 | 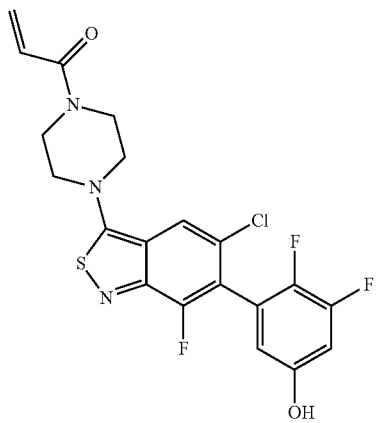 [SMILES: C=CC(=O)N1CCN(c2snc3c(F)c(-c4cc(O)cc(F)c4F)c(Cl)cc23)CC1] |
| 3-17 | 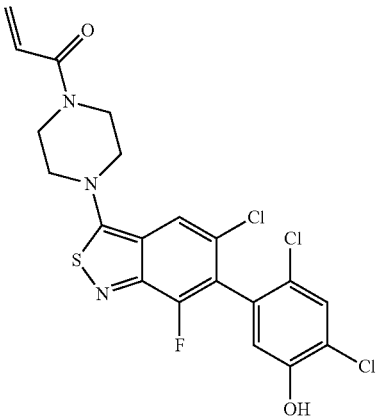 [SMILES: C=CC(=O)N1CCN(c2snc3c(F)c(-c4cc(O)c(Cl)cc4Cl)c(Cl)cc23)CC1] |
TABLE 1-continued
| Ex. # | Chemical Structure |
|---|---|
| 3-8 | 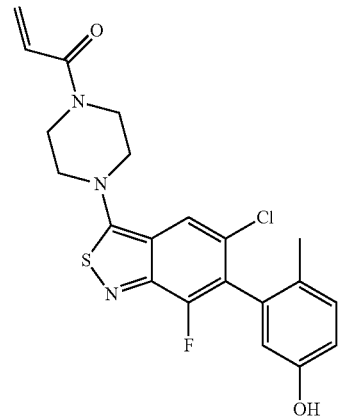 [SMILES: C=CC(=O)N1CCN(c2snc3c(F)c(-c4cc(O)ccc4C)c(Cl)cc23)CC1] |
| 3-9 | 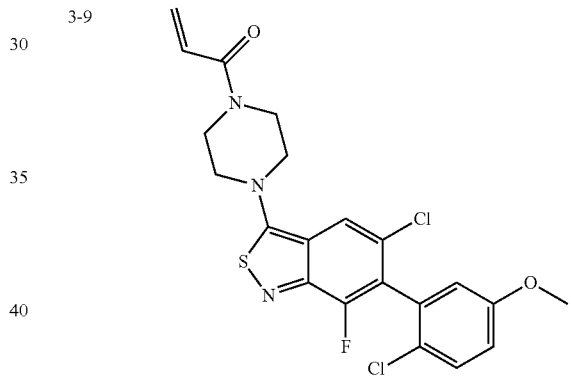 |
| 3-20 | 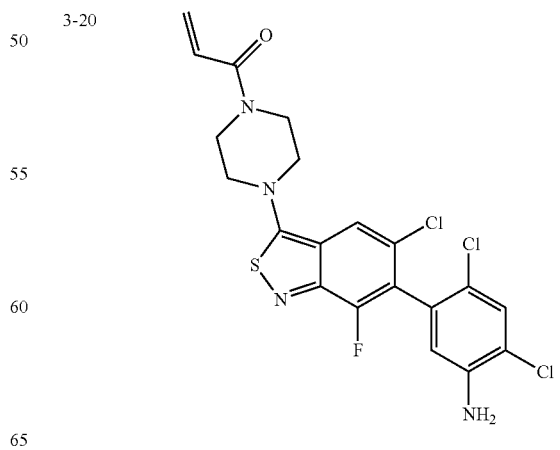 |

TABLE 1-continued
| Ex. # | Chemical Structure |
|---|---|
| 3-21 | 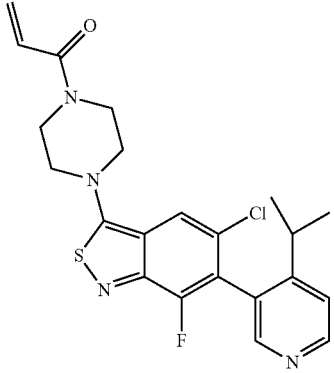 [SMILES: C=CC(=O)N1CCN(c2snc3c(F)c(-c4cnccc4C(C)C)c(Cl)cc23)CC1] |
| 3-22 | 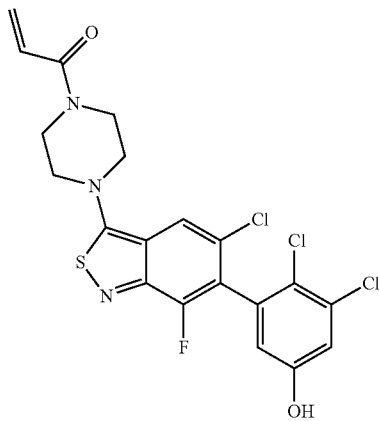 [SMILES: C=CC(=O)N1CCN(c2snc3c(F)c(-c4cc(O)cc(Cl)c4Cl)c(Cl)cc23)CC1] |
| 3-23 | 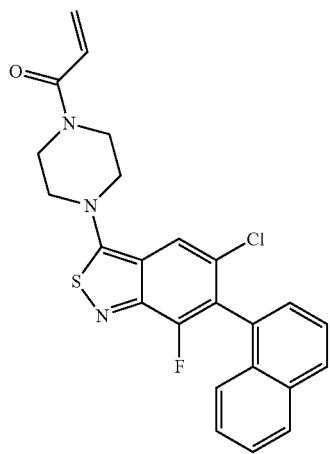 [SMILES: C=CC(=O)N1CCN(c2snc3c(F)c(-c4cccc5ccccc45)c(Cl)cc23)CC1] |
TABLE 1-continued
| Ex. # | Chemical Structure |
|---|---|
| 3-13 | 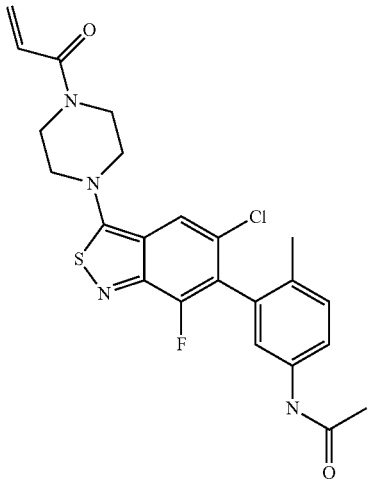 [SMILES: C=CC(=O)N1CCN(c2snc3c(F)c(-c4cc(NC(C)=O)ccc4C)c(Cl)cc23)CC1] |
| 3-14 | 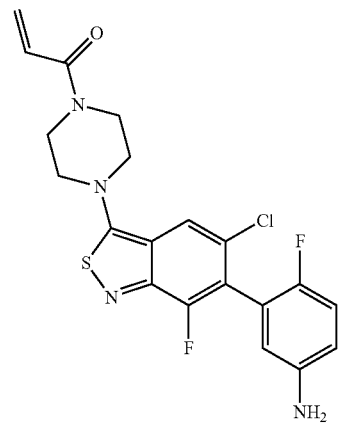 |
| 3-25 | 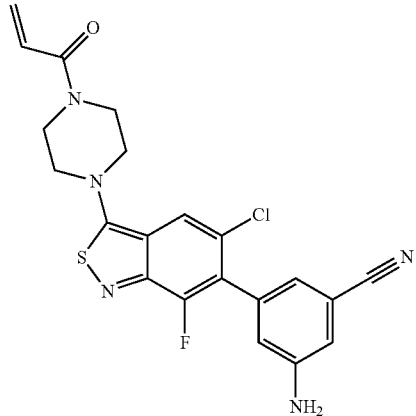 [SMILES: C=CC(=O)N1CCN(c2snc3c(F)c(-c4cc(N)cc(C#N)c4)c(Cl)cc23)CC1] |

TABLE 1-continued
| Ex. # | Chemical Structure |
|---|---|
| 4-1 | 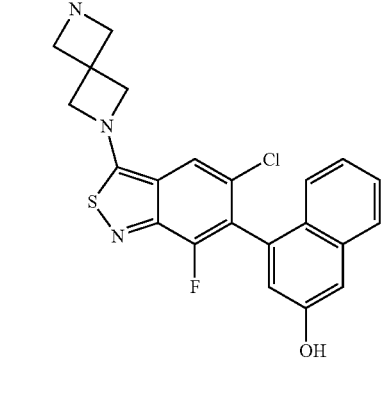 |
| 4-2 | 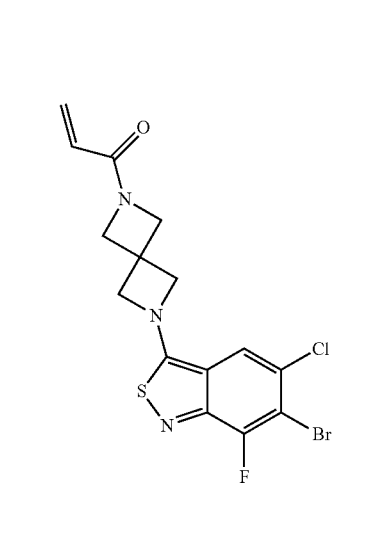 [SMILES: C=CC(=O)N1CC2(C1)CN(c1snc3c(F)c(Br)c(Cl)cc13)C2] |
| 4-3 | 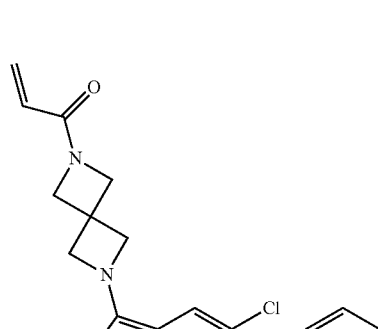 |
TABLE 1-continued
| Ex. # | Chemical Structure |
|---|---|
| 3-18 | 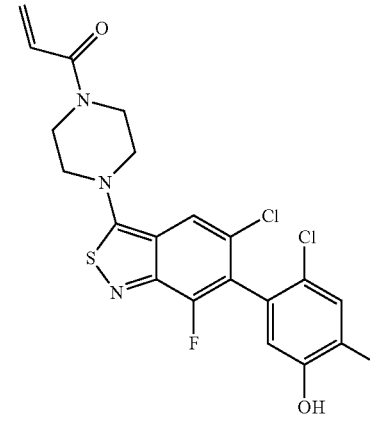 |
| 3-19 | 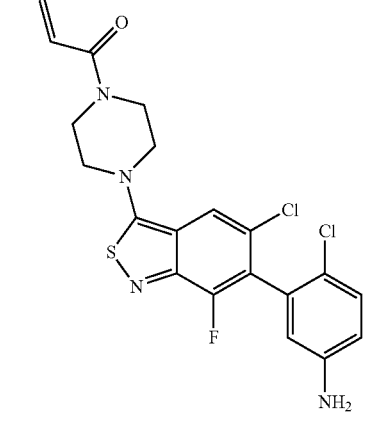 |
| 4-5 | 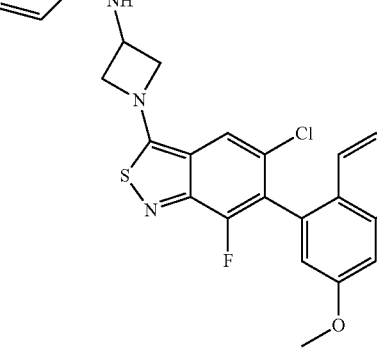 |

TABLE 1-continued

| Ex. # | Chemical Structure |
|---|---|
| 4-6 | 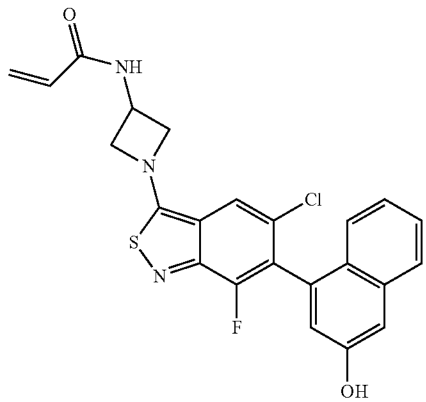 [SMILES: C=CC(=O)NC1CN(c2snc3c(F)c(-c4cc(O)cc5ccccc45)c(Cl)cc23)C1] |
| 4-7 | 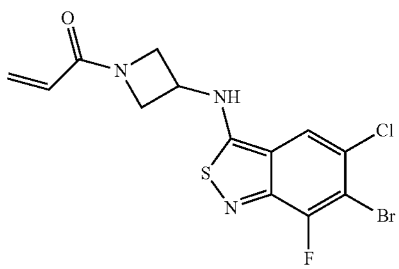 [SMILES: C=CC(=O)N1CC(Nc2snc3c(F)c(Br)c(Cl)cc23)C1] |
| 4-8 | 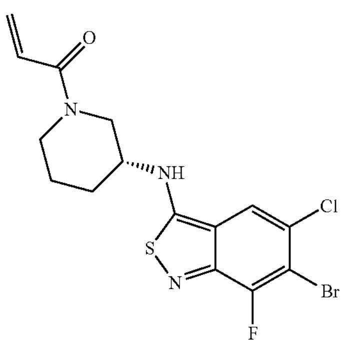 [SMILES: C=CC(=O)N1CCC[C@@H](Nc2snc3c(F)c(Br)c(Cl)cc23)C1] |
| 3-24 | 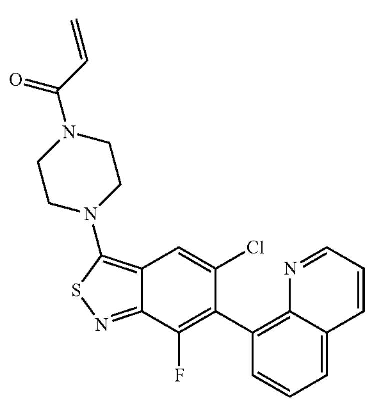 [SMILES: C=CC(=O)N1CCN(c2snc3c(F)c(-c4cccc5cccnc45)c(Cl)cc23)CC1] |
| 5-1 | |
| 5-2 | |
| 4-4 | |
| 5-6 | |

TABLE 1-continued
| Ex. # | Chemical Structure |
|---|---|
| 5-7 | 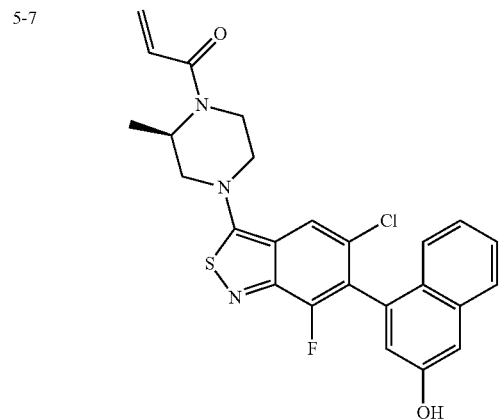 |
| 4-9 | 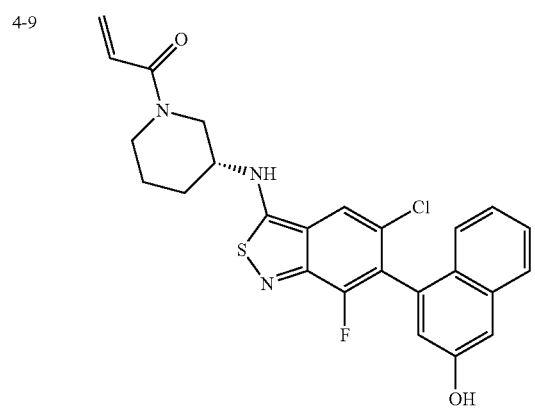 |
| 6-2 | 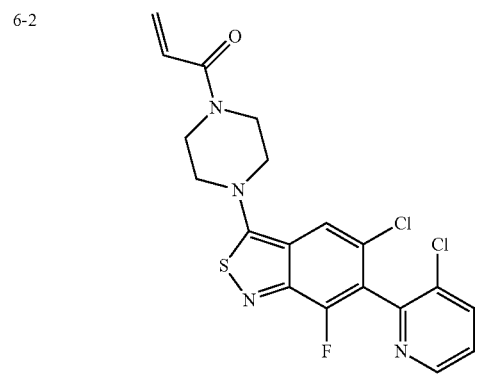 |
| 7-1 | 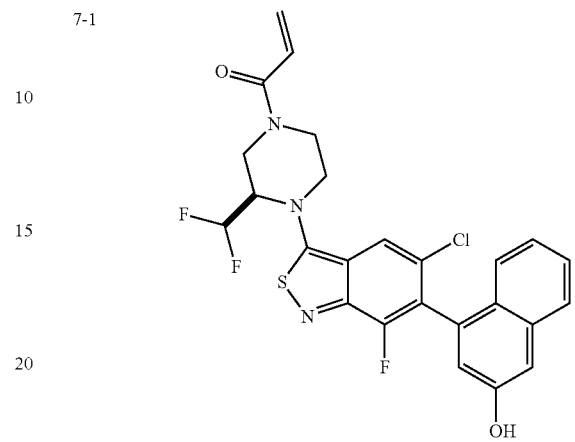 |
| 7-2 | 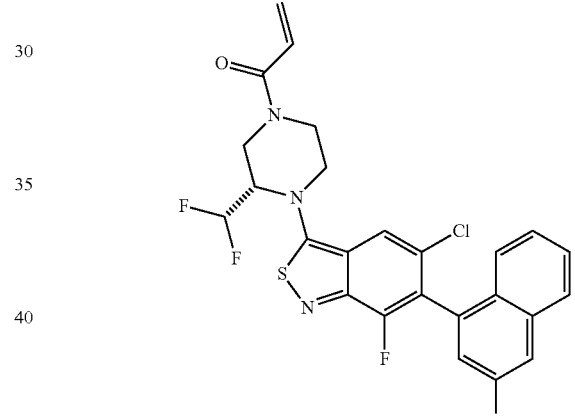 |
| 5-3 | 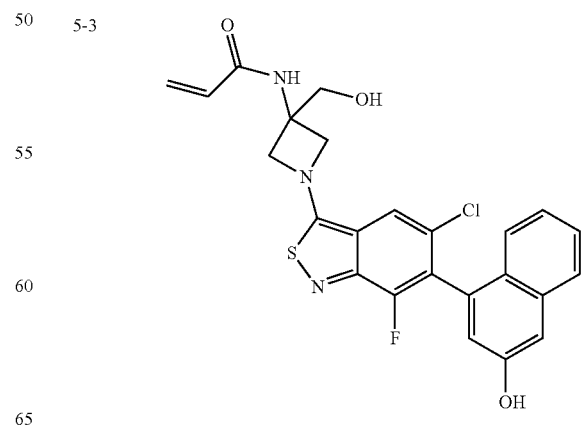 |

TABLE 1-continued

| Ex. # | Chemical Structure |
|---|---|
| 5-4 | 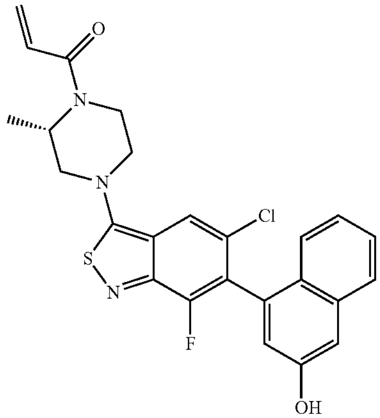 [SMILES: C=CC(=O)N1CCN(c2snc3c(F)c(-c4cc(O)cc5ccccc45)c(Cl)cc23)C[C@@H]1C] |
| 5-5 | 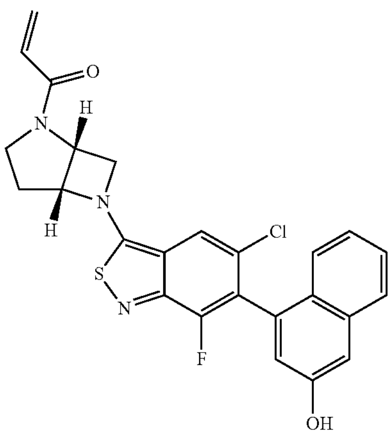 [SMILES: C=CC(=O)N1CC[C@@H]2[C@H]1CN2c1snc2c(F)c(-c3cc(O)cc4ccccc34)c(Cl)cc12] |
| 5-8 | 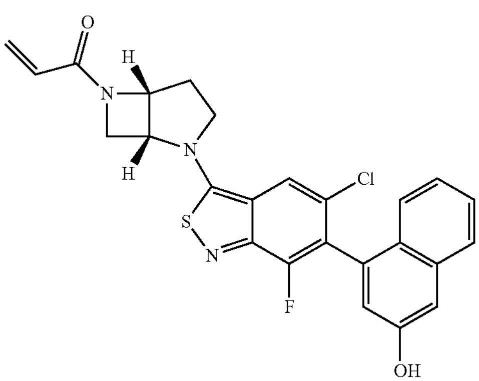 [SMILES: C=CC(=O)N1C[C@@H]2[C@H]1CCN2c1snc2c(F)c(-c3cc(O)cc4ccccc34)c(Cl)cc12] |
| 5-9 | |
| 6-1 | |
| 7-2 | |

TABLE 1-continued
| Ex. # | Chemical Structure |
|---|---|
|  | 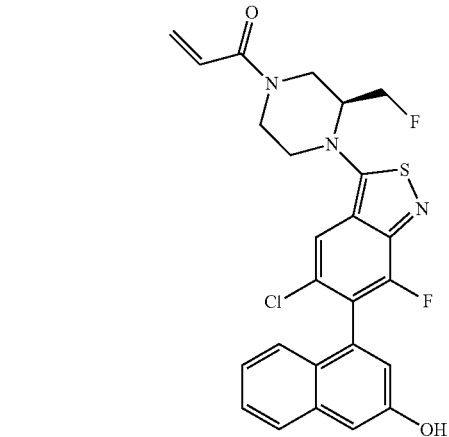 [SMILES: C=CC(=O)N1CCN(c2snc3c(F)c(-c4cc(O)cc5ccccc45)c(Cl)cc23)[C@H](CF)C1] |
| 7-3 | 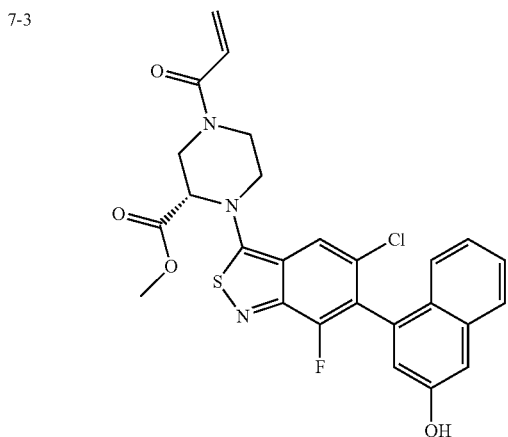 |
TABLE 1-continued
| Ex. # | Chemical Structure |
|---|---|
| 8-1 | 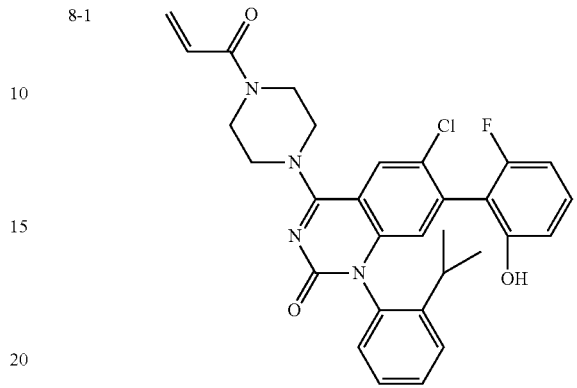 |
| 8-1-1 | 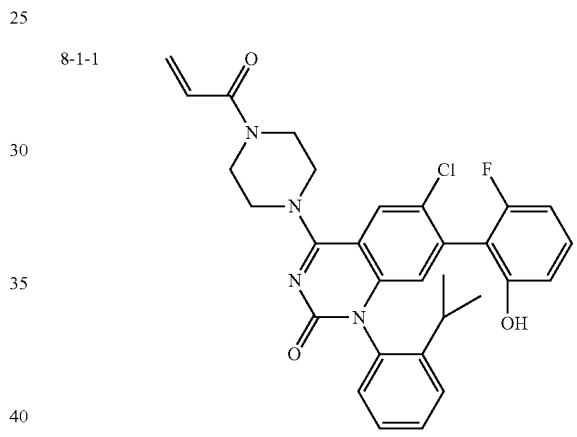<br>1st eluting isomer |
| 8-1-2 | 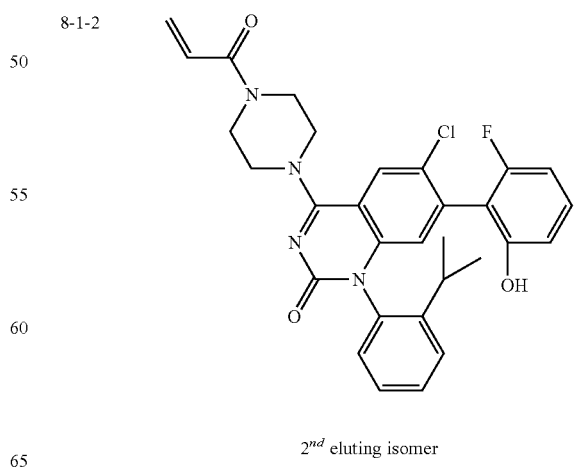<br>2nd eluting isomer |

TABLE 1-continued
| Ex. # | Chemical Structure |
|---|---|
| 8-2 | 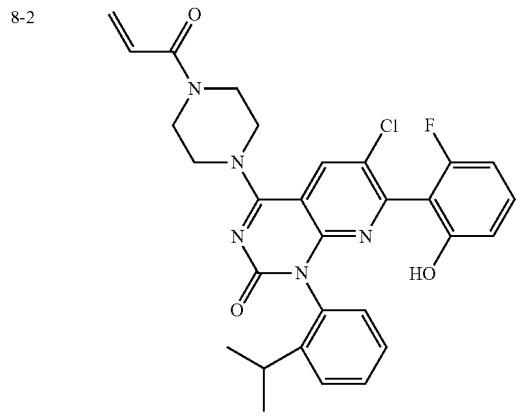 |
| 8-3 | 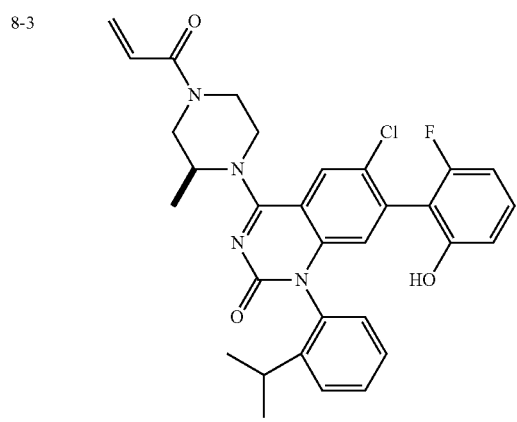 |
| 8-3-2 | 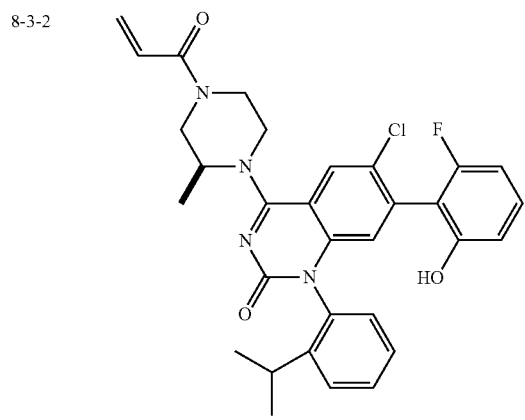<br>2nd eluting isomer |
TABLE 1-continued
| Ex. # | Chemical Structure |
|---|---|
| 8-4 | 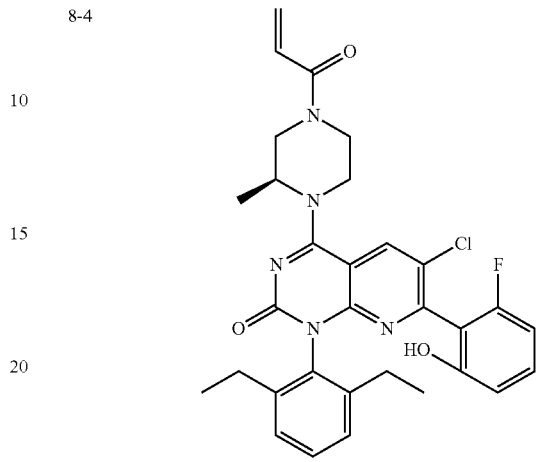 |
| 8-5 | 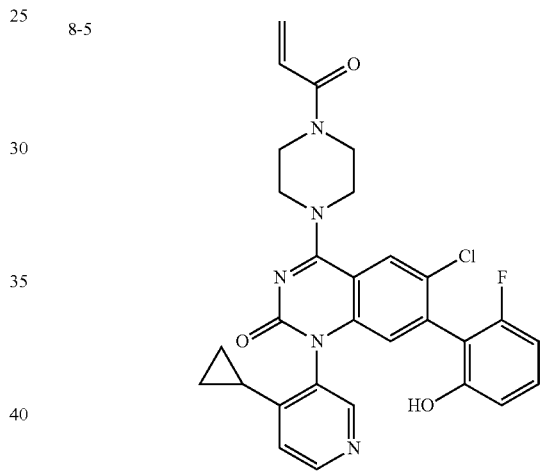 |
| 8-6 | 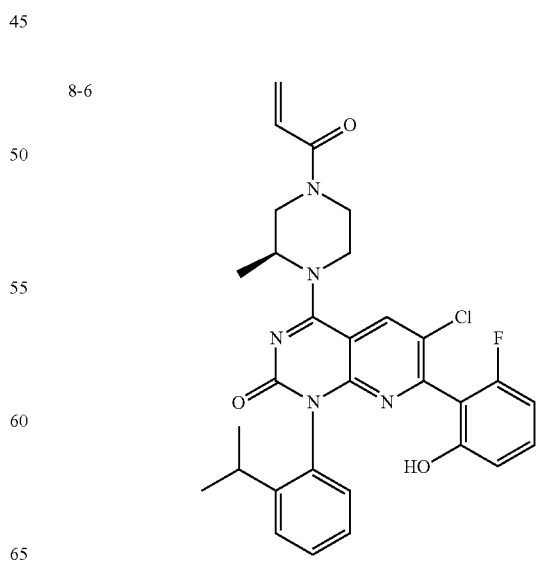 |

TABLE 1-continued
| Ex. # | Chemical Structure |
|---|---|
| 8-6-2 | 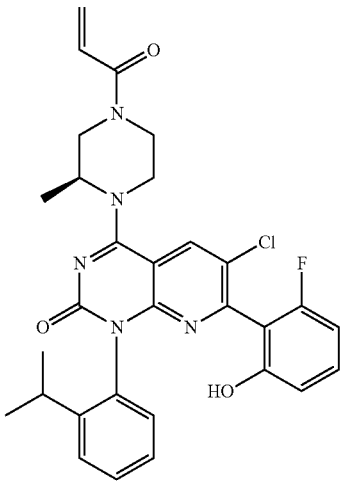 [SMILES: C=CC(=O)N1CCN(c2nc(=O)n(-c3ccccc3C(C)C)c3nc(-c4c(O)cccc4F)c(Cl)cc23)[C@@H](C)C1]<br>2nd eluting isomer |
| 9-1 | 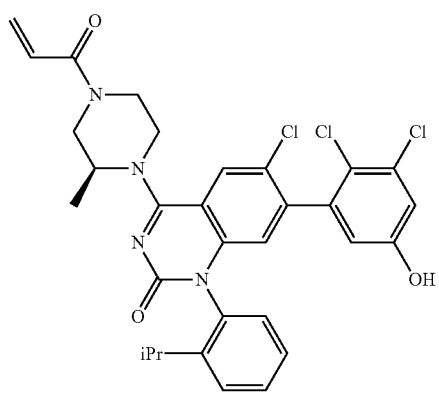 [SMILES: C=CC(=O)N1CCN(c2nc(=O)n(-c3ccccc3C(C)C)c3cc(-c4cc(O)cc(Cl)c4Cl)c(Cl)cc23)[C@@H](C)C1] |
| 9-2 | 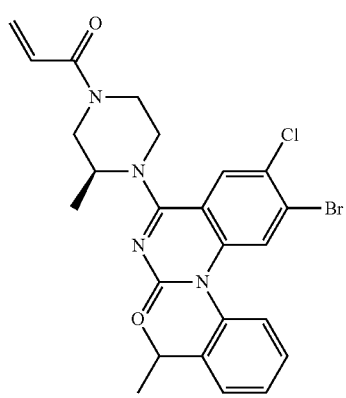 |
| 9-3 | 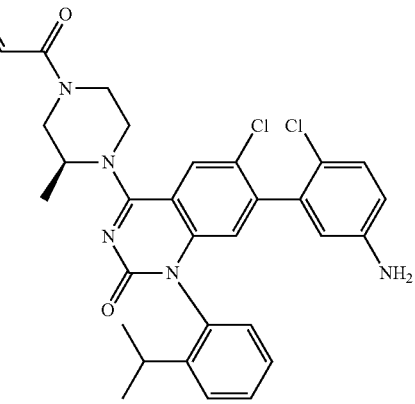 |
| 8-3-1 | 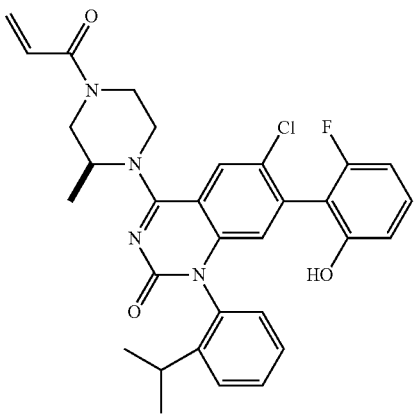 [SMILES: C=CC(=O)N1CCN(c2nc(=O)n(-c3ccccc3C(C)C)c3cc(-c4c(O)cccc4F)c(Cl)cc23)[C@@H](C)C1]<br>1st eluting isomer |
| 9-5 | 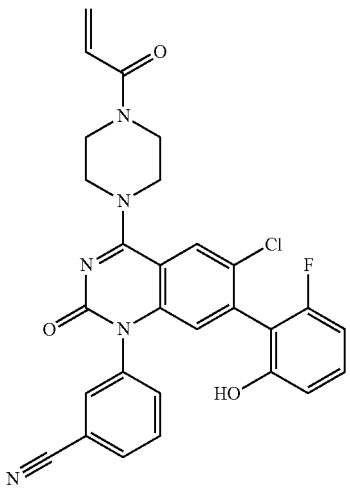 [SMILES: C=CC(=O)N1CCN(c2nc(=O)n(-c3cccc(C#N)c3)c3cc(-c4c(O)cccc4F)c(Cl)cc23)CC1] |

TABLE 1-continued
| Ex. # | Chemical Structure |
|---|---|
| 9-6 | 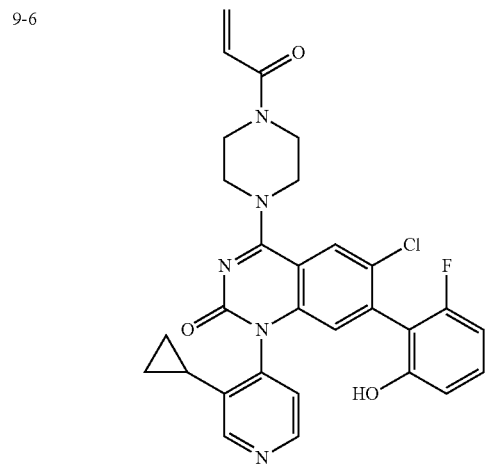 |
| 9-7-2 | 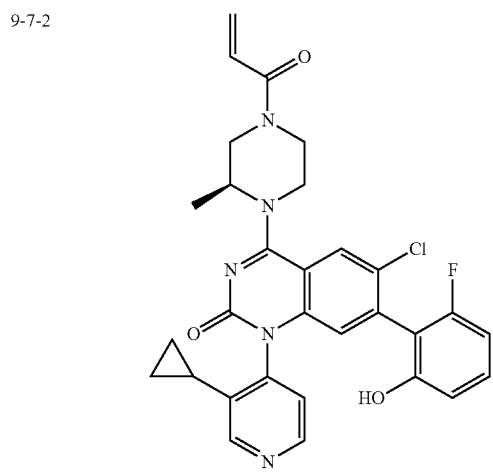 2nd eluting isomer |
| 8-6-1 | 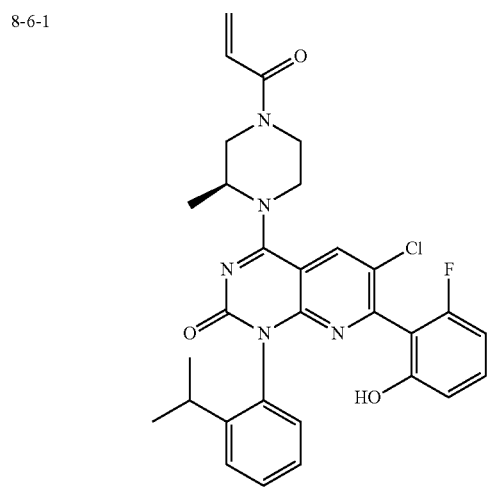 1st eluting isomer |
| 9-10 | 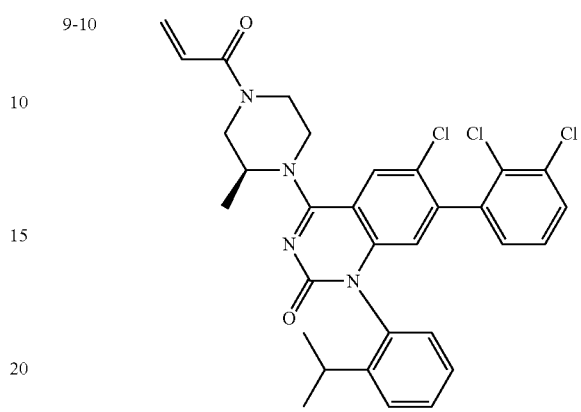 |
| 9-11 | 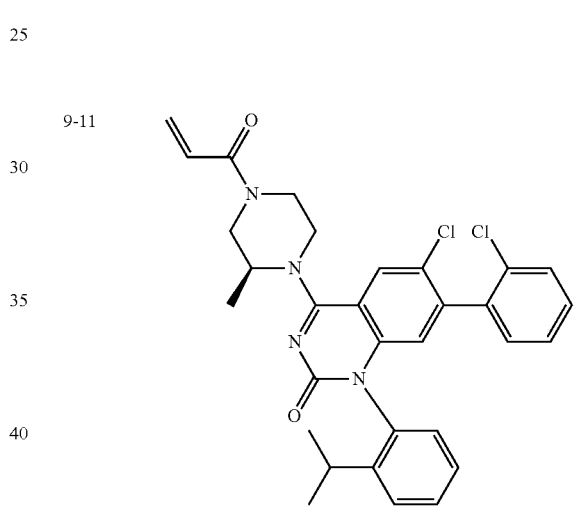 |
| 9-12 | 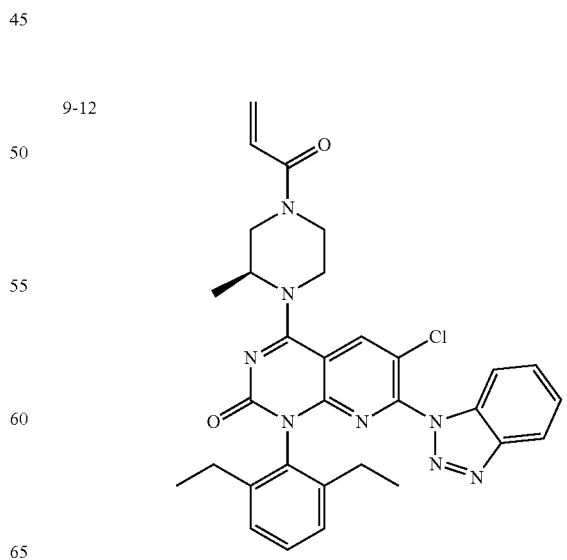 |

TABLE 1-continued

| Ex. # | Chemical Structure |
|---|---|
| 9-4 | 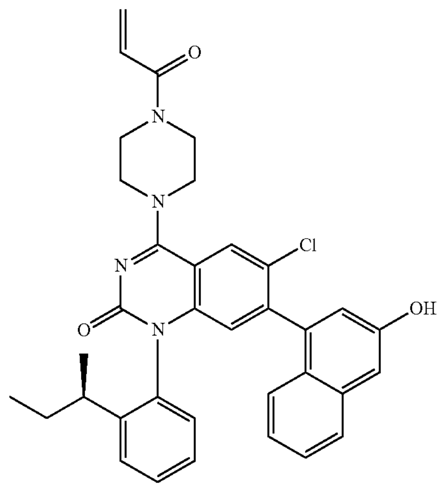 [SMILES: C=CC(=O)N1CCN(c2nc(=O)n(-c3ccccc3[C@H](C)CC)c3cc(-c4cc(O)cc5ccccc45)c(Cl)cc23)CC1] |
| 10-1 | 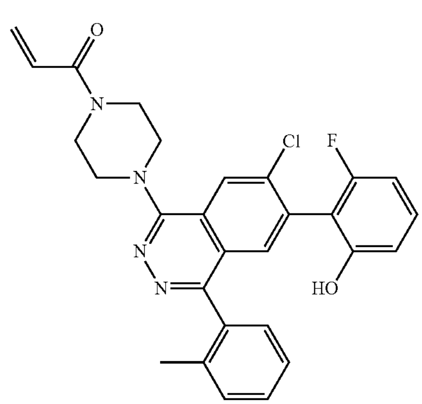 [SMILES: C=CC(=O)N1CCN(c2nnc(-c3ccccc3C)c3cc(-c4c(O)cccc4F)c(Cl)cc23)CC1] |

TABLE 1-continued

| Ex. # | Chemical Structure |
|---|---|
| 10-2 | 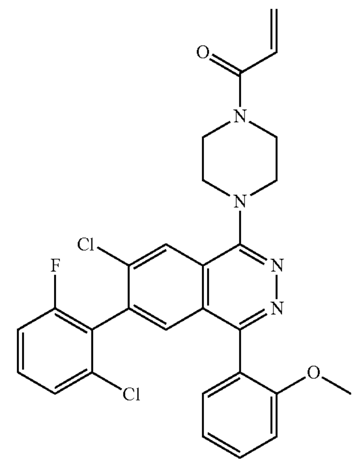 [SMILES: C=CC(=O)N1CCN(c2nnc(-c3ccccc3OC)c3cc(-c4c(F)cccc4Cl)c(Cl)cc23)CC1] |
| 10-3 | 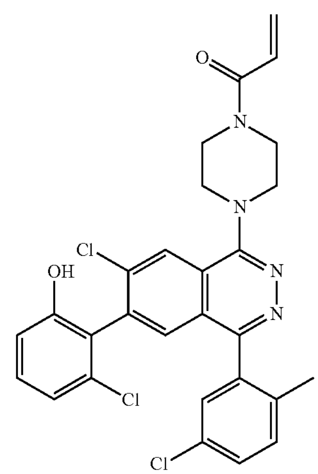 |
| 9-7-1 | 1st eluting isomer |

TABLE 1-continued
| Ex. # | Chemical Structure |
|---|---|
| 9-9 | 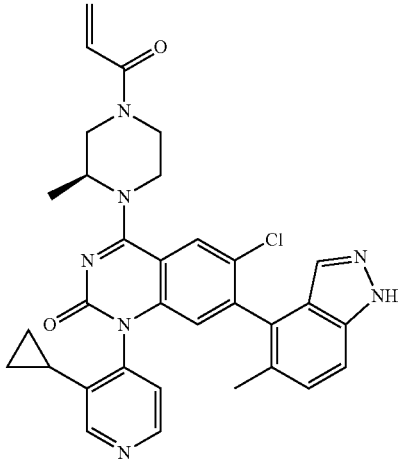 [SMILES: C=CC(=O)N1CCN(c2nc(=O)n(-c3ccncc3C3CC3)c3cc(-c4c(C)ccc5[nH]ncc45)c(Cl)cc23)[C@@H](C)C1] |
| 10-6 | 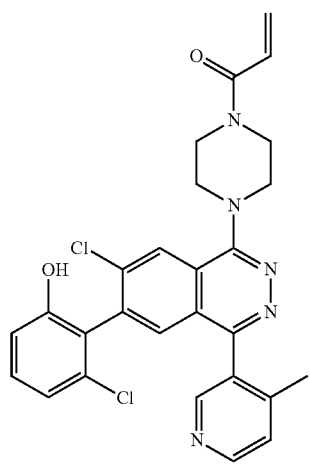 |
| 10-7 | 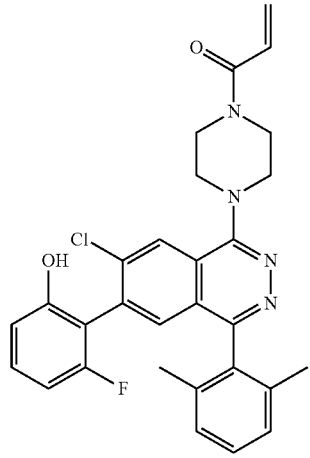 [SMILES: C=CC(=O)N1CCN(c2nnc(-c3c(C)cccc3C)c3cc(-c4c(O)cccc4F)c(Cl)cc23)CC1] |
TABLE 1-continued
| Ex. # | Chemical Structure |
|---|---|
| 9-13 | 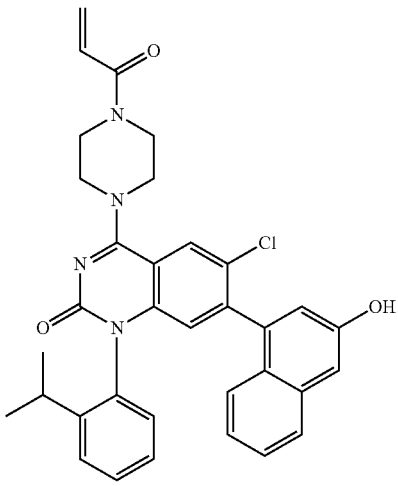 [SMILES: C=CC(=O)N1CCN(c2nc(=O)n(-c3ccccc3C(C)C)c3cc(-c4cc(O)cc5ccccc45)c(Cl)cc23)CC1] |
| 9-14 | 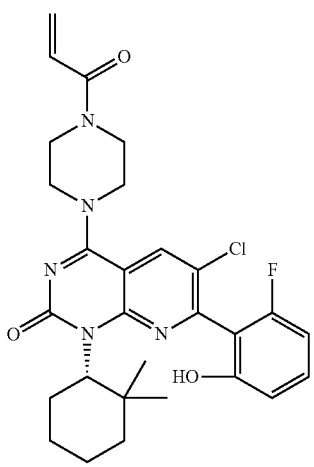 [SMILES: C=CC(=O)N1CCN(c2nc(=O)n([C@H]3CCCCC3(C)C)c3nc(-c4c(O)cccc4F)c(Cl)cc23)CC1] |
| | 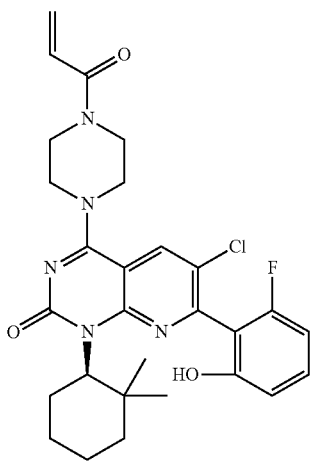 [SMILES: C=CC(=O)N1CCN(c2nc(=O)n([C@@H]3CCCCC3(C)C)c3nc(-c4c(O)cccc4F)c(Cl)cc23)CC1] |

TABLE 1-continued

| Ex. # | Chemical Structure |
|---|---|
| 10-11 | 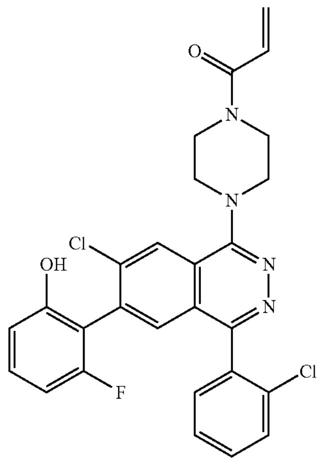 [SMILES: C=CC(=O)N1CCN(c2nnc(-c3ccccc3Cl)c3cc(-c4c(O)cccc4F)c(Cl)cc23)CC1] |
| 10-12 | 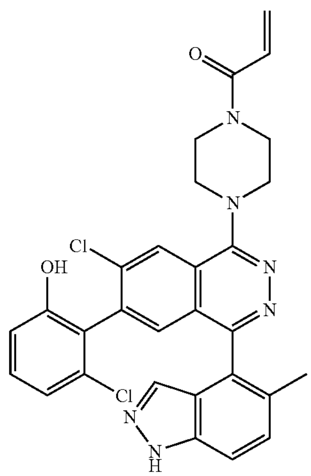 |
| 10-4 | 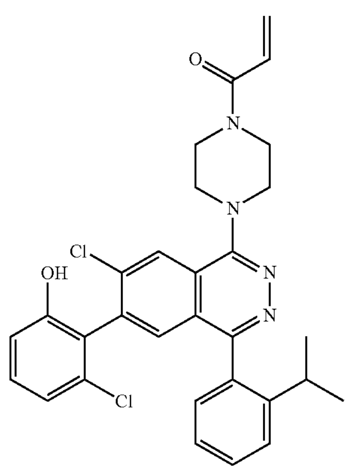 |
| 10-5 | |
| 11-2-1 | (1st eluting isomeric mixture) |
| 11-2-2 | (2nd eluting isomeric mixture) |

TABLE 1-continued
| Ex. # | Chemical Structure |
|---|---|
| 10-8 | 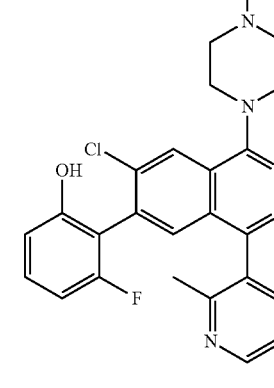 |
| 10-9 | 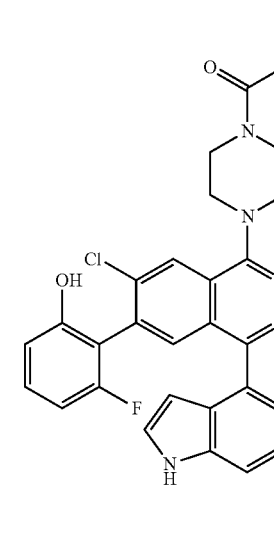 |
| 10-10 | 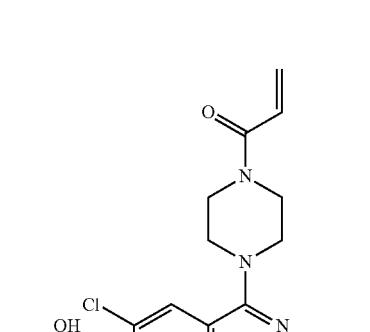 |
| 15 | 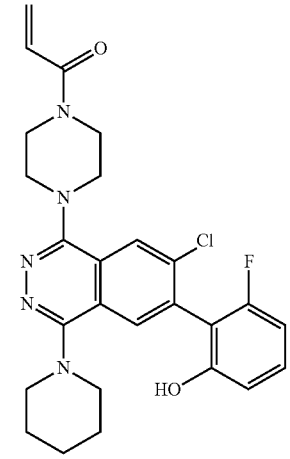 [SMILES: C=CC(=O)N1CCN(c2nnc(N3CCCCC3)c3cc(-c4c(O)cccc4F)c(Cl)cc23)CC1] |
| 16 | 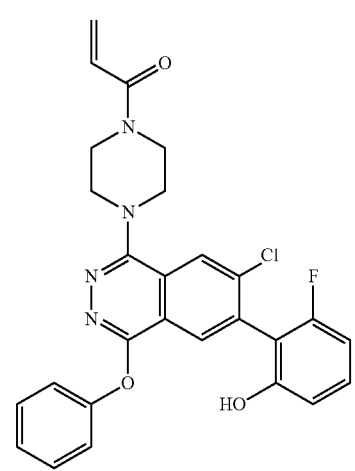 [SMILES: C=CC(=O)N1CCN(c2nnc(Oc3ccccc3)c3cc(-c4c(O)cccc4F)c(Cl)cc23)CC1] |
| 10-13 | 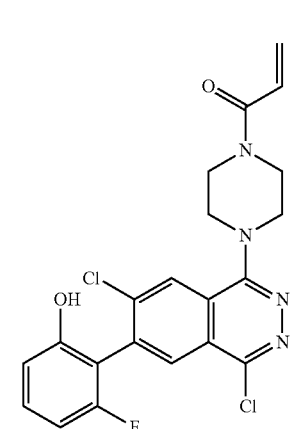 |

TABLE 1-continued
| Ex. # | Chemical Structure |
|---|---|
| 11-1-1 | 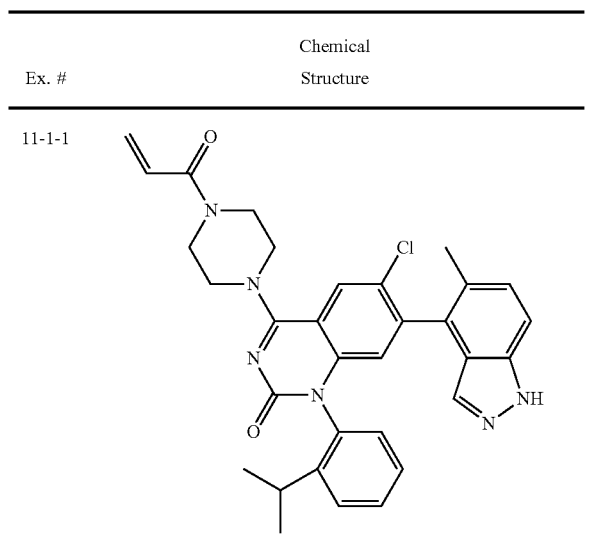<br>1st eluting isomeric mixture |
| 11-1-2 | 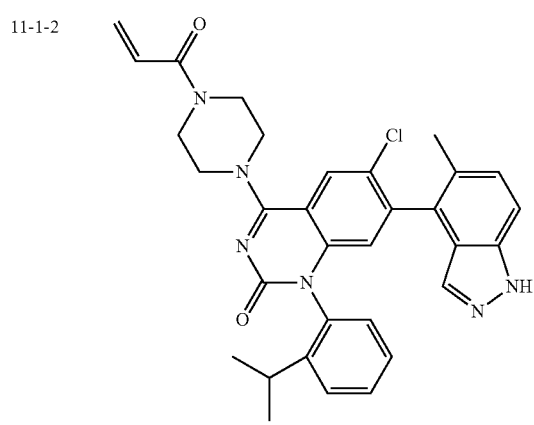<br>2nd eluting isomeric mixture |
| 18-2 | 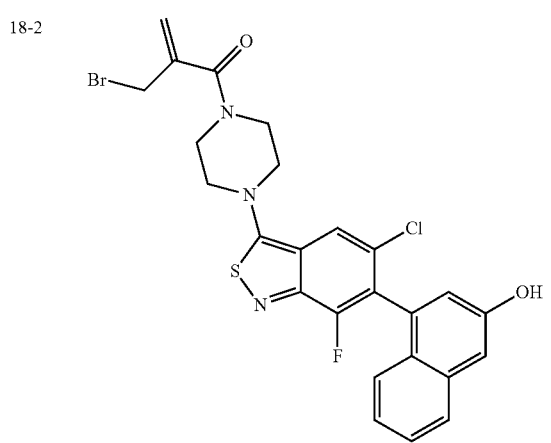 |
TABLE 1-continued
| Ex. # | Chemical Structure |
|---|---|
| 18-3 | 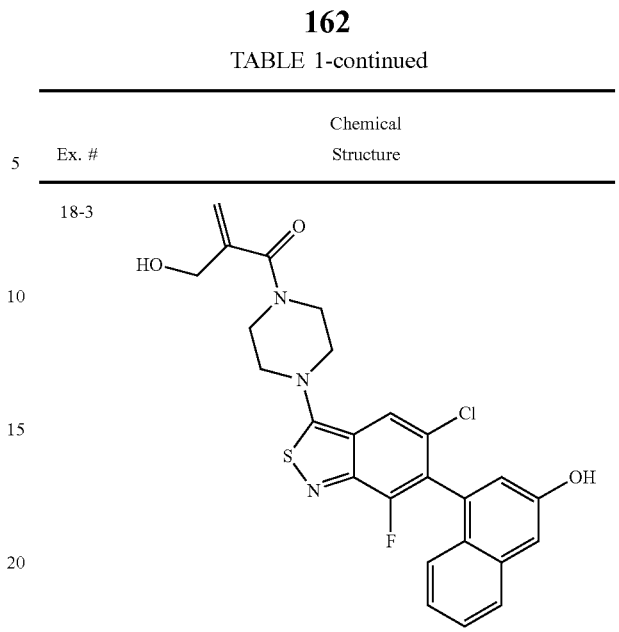 |
| 12 | 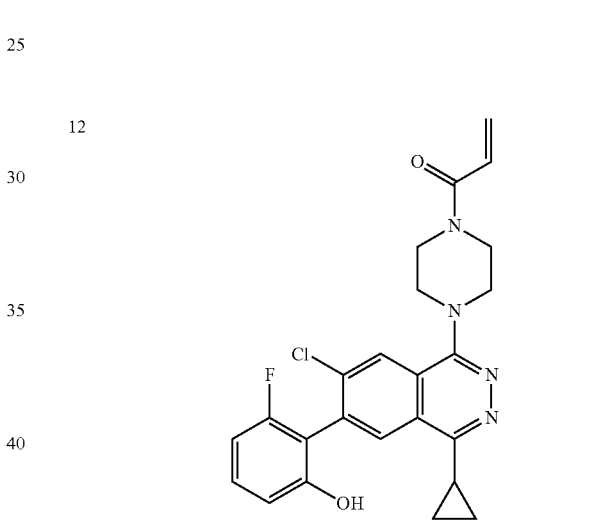 |
| 13 | 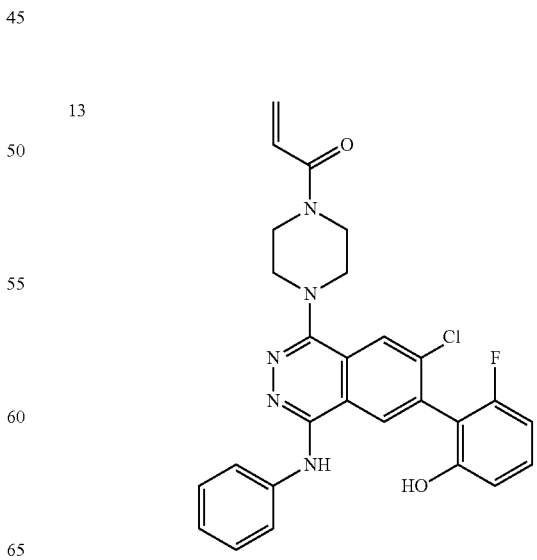 |

TABLE 1-continued
| Ex. # | Chemical Structure |
|---|---|
| 14 | 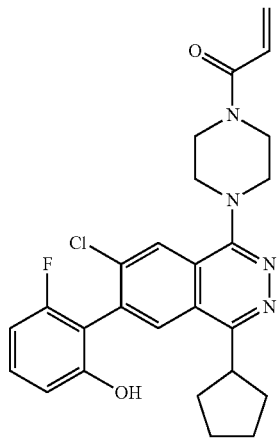 [SMILES: C=CC(=O)N1CCN(c2nnc(C3CCCC3)c3cc(-c4c(O)cccc4F)c(Cl)cc23)CC1] |
| 20 | 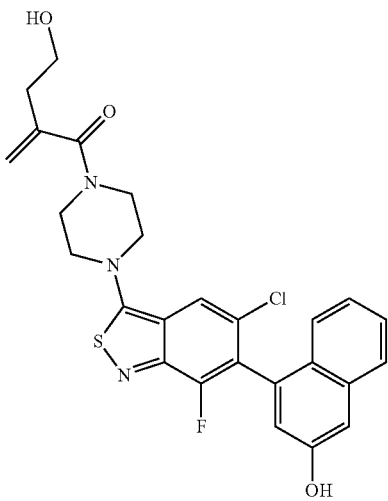 [SMILES: C=C(CCO)C(=O)N1CCN(c2snc3c(F)c(-c4cc(O)cc5ccccc45)c(Cl)cc23)CC1] |
| 21 | 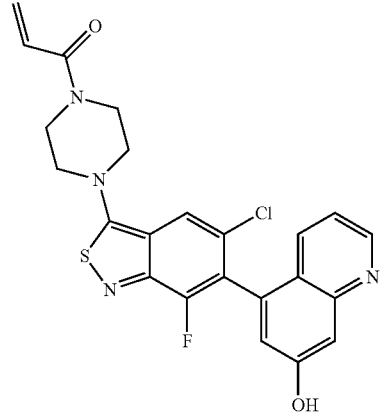 [SMILES: C=CC(=O)N1CCN(c2snc3c(F)c(-c4cc(O)cc5ncccc45)c(Cl)cc23)CC1] |
TABLE 1-continued
| Ex. # | Chemical Structure |
|---|---|
| 17-1 | 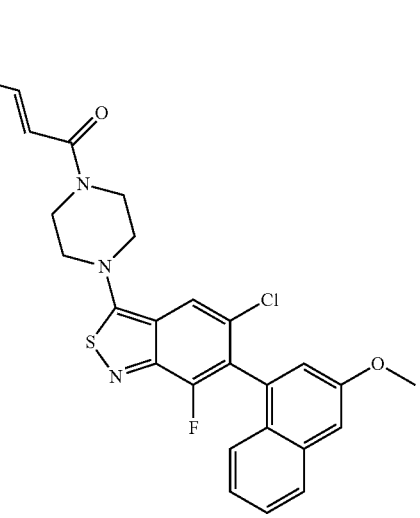 |
| 17-2 | 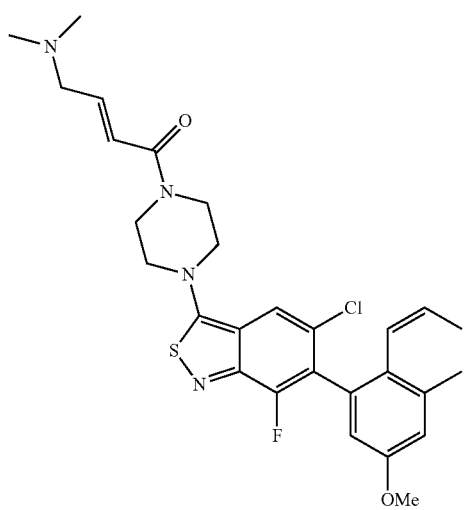 [SMILES: C/C=C\c1c(C)cc(OC)cc1-c1c(Cl)cc2c(N3CCN(C(=O)/C=C/CN(C)C)CC3)snc2c1F] |
| 18-1 | 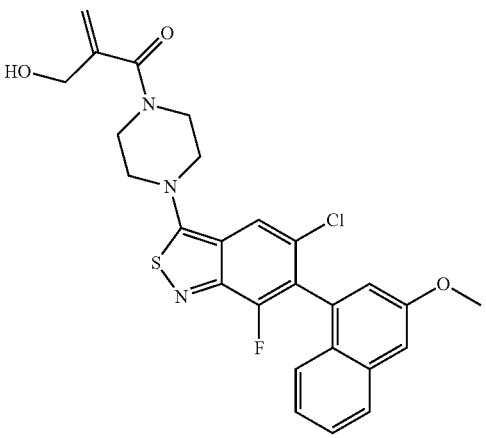 [SMILES: C=C(CO)C(=O)N1CCN(c2snc3c(F)c(-c4cc(OC)cc5ccccc45)c(Cl)cc23)CC1] |

TABLE 1-continued
| Ex. # | Chemical Structure |
|---|---|
| 25 | 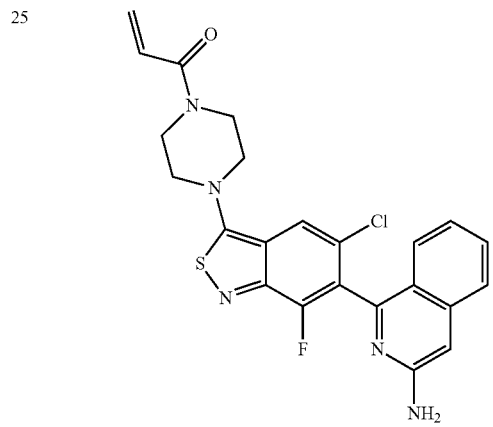 |
| 26 | 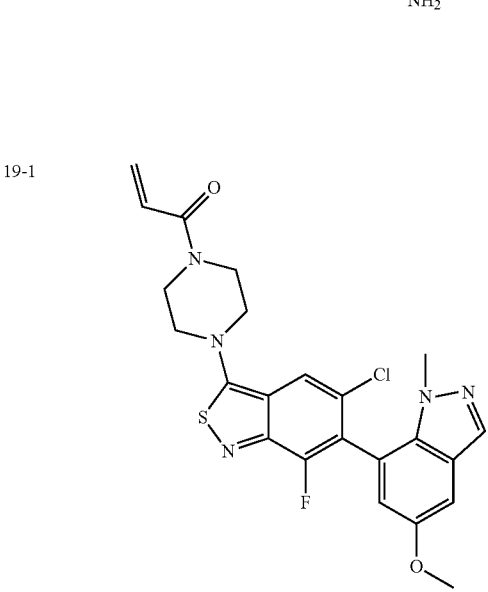 |
| 19-1 | 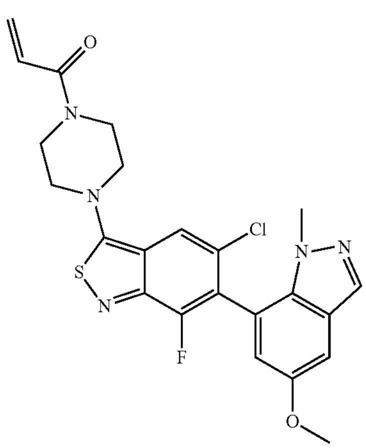 [SMILES: C=CC(=O)N1CCN(c2snc3c(F)c(-c4cc(OC)cc5cnn(C)c45)c(Cl)cc23)CC1] |
TABLE 1-continued
| Ex. # | Chemical Structure |
|---|---|
| 19-2 | 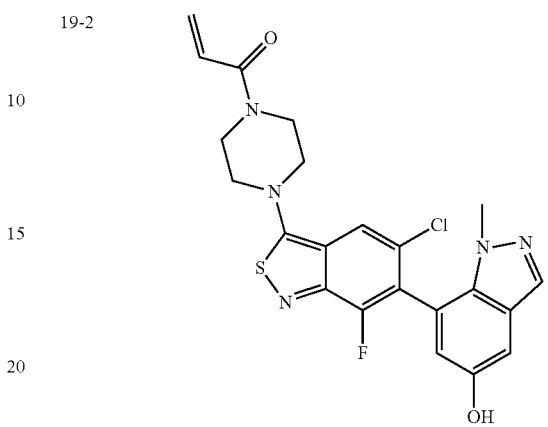 |
| 19-3 | 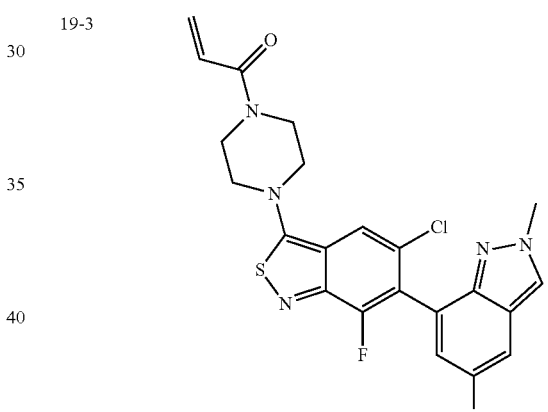 |
| 30 | 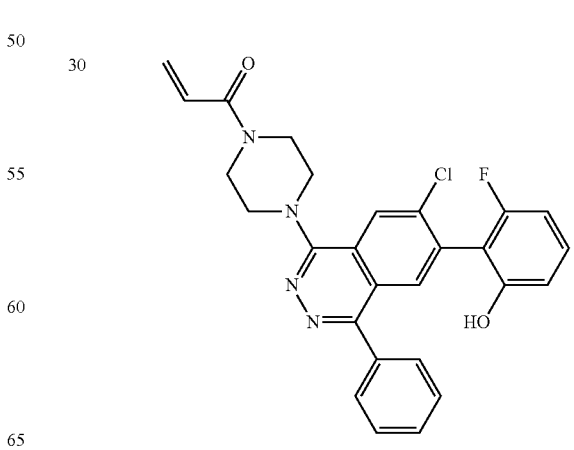 |

TABLE 1-continued
| Ex. # | Chemical Structure |
|---|---|
| 31 | 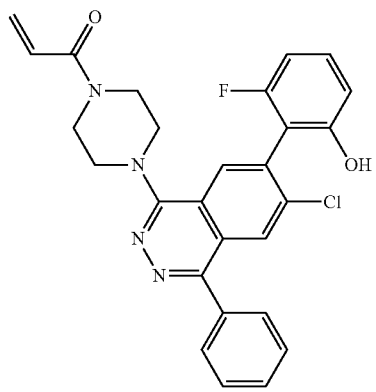 [SMILES: C=CC(=O)N1CCN(c2nnc(-c3ccccc3)c3cc(Cl)c(-c4c(O)cccc4F)cc23)CC1] |
| 22 | 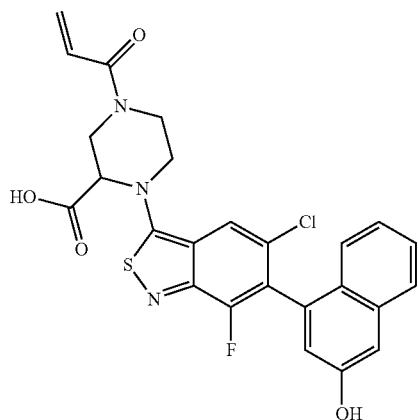 [SMILES: C=CC(=O)N1CCN(c2snc3c(F)c(-c4cc(O)cc5ccccc45)c(Cl)cc23)C(C(=O)O)C1] |
| 23 | 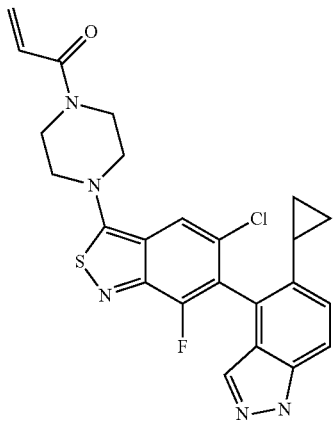 [SMILES: C=CC(=O)N1CCN(c2snc3c(F)c(-c4c(C5CC5)ccc5[nH]ncc45)c(Cl)cc23)CC1] |
TABLE 1-continued
| Ex. # | Chemical Structure |
|---|---|
| 24 | 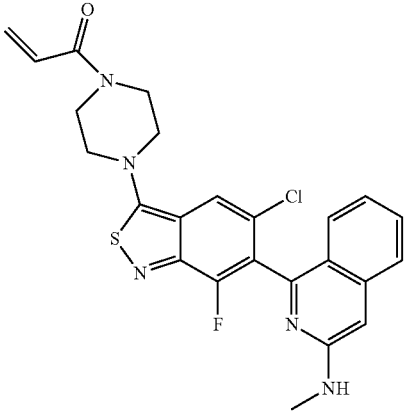 [SMILES: C=CC(=O)N1CCN(c2snc3c(F)c(-c4nc(NC)cc5ccccc45)c(Cl)cc23)CC1] |
| 35 | 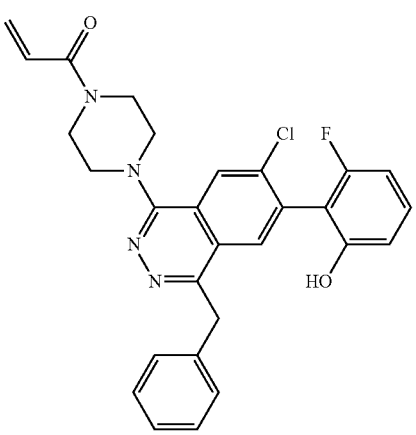 [SMILES: C=CC(=O)N1CCN(c2nnc(Cc3ccccc3)c3cc(-c4c(O)cccc4F)c(Cl)cc23)CC1] |
| 36 | 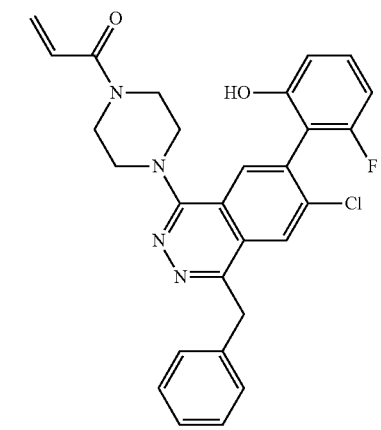 [SMILES: C=CC(=O)N1CCN(c2nnc(Cc3ccccc3)c3cc(Cl)c(-c4c(O)cccc4F)cc23)CC1] |

TABLE 1-continued
| Ex. # | Chemical Structure |
|---|---|
| 27 | 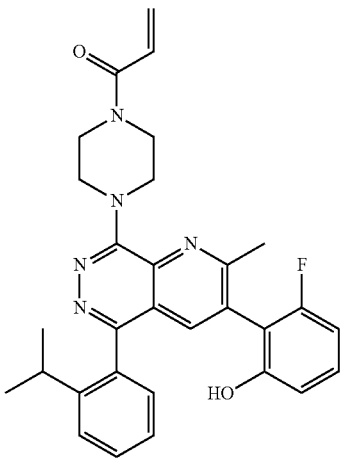 [SMILES: C=CC(=O)N1CCN(c2nnc(-c3ccccc3C(C)C)c3cc(-c4c(O)cccc4F)c(C)nc23)CC1] |
| 28 | 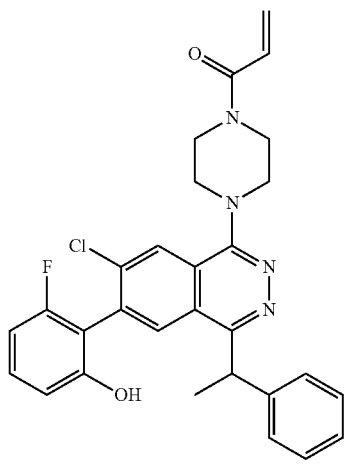 [SMILES: C=CC(=O)N1CCN(c2nnc(C(C)c3ccccc3)c3cc(-c4c(O)cccc4F)c(Cl)cc23)CC1] |
| 29 | 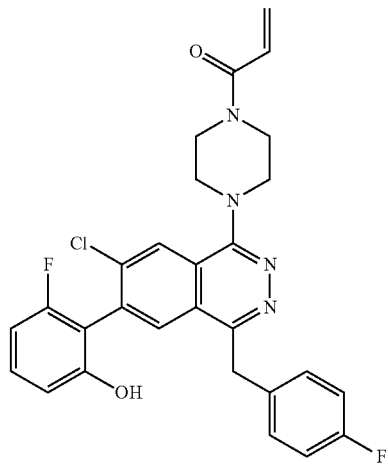 [SMILES: C=CC(=O)N1CCN(c2nnc(Cc3ccc(F)cc3)c3cc(-c4c(O)cccc4F)c(Cl)cc23)CC1] |
| 32 | 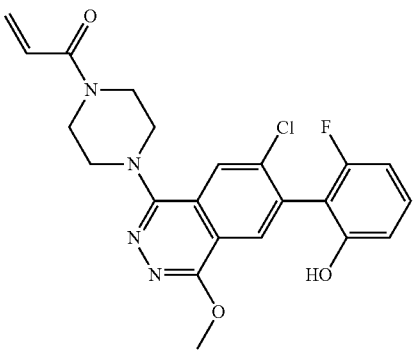 [SMILES: C=CC(=O)N1CCN(c2nnc(OC)c3cc(-c4c(O)cccc4F)c(Cl)cc23)CC1] |
| 33 | 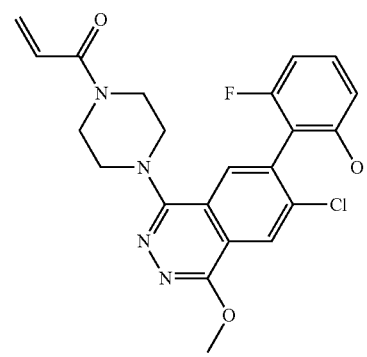 [SMILES: C=CC(=O)N1CCN(c2nnc(OC)c3cc(Cl)c(-c4c(O)cccc4F)cc23)CC1] |
| 34 | 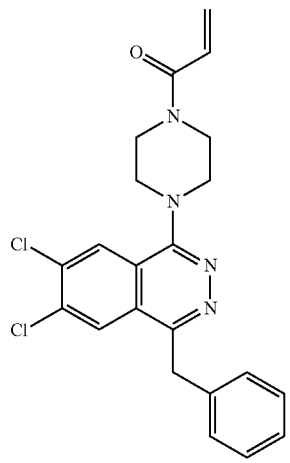 [SMILES: C=CC(=O)N1CCN(c2nnc(Cc3ccccc3)c3cc(Cl)c(Cl)cc23)CC1] |
| 37 | 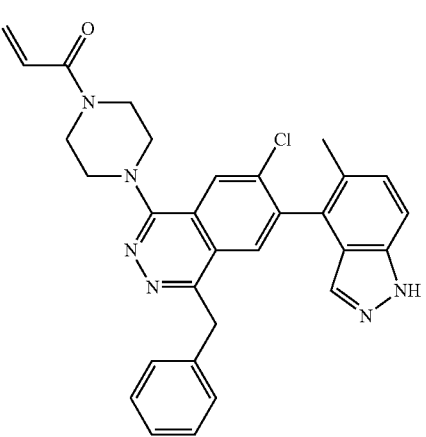 [SMILES: C=CC(=O)N1CCN(c2nnc(Cc3ccccc3)c3cc(-c4c(C)ccc5[nH]ncc45)c(Cl)cc23)CC1] |

TABLE 1-continued

| Ex. # | Chemical Structure |
|---|---|
|  | (acryloyl-piperazinyl phthalazine with chloro, methyl-indazole, benzyl substituents) |
| 38 | (acryloyl-piperazinyl pyrido-pyrimidinone with chloro, fluoro-hydroxyphenyl, cyclopropylmethyl substituents) |
| NA | NA |

TABLE 1(a)

| Ex. # | Chemical Structure |
|---|---|
| 39-1 | (acryloyl-methylpiperazinyl pyrido-pyrimidinone with chloro, fluoro-hydroxyphenyl, isopropyl-methylphenyl substituents) 1st-eluting isomer |
| 39-2 | (same as 39-1) 2nd-eluting isomer |
| 40-1 | (acryloyl-methylpiperazinyl pyrido-pyrimidinone with chloro, fluorophenyl, isopropyl-methylpyridyl substituents) 1st-eluting isomer |
| 40-2 | (same as 40-1) 2nd-eluting isomer |

TABLE 1(a)-continued
| Ex. # | Chemical Structure |
|---|---|
| 41-1 | 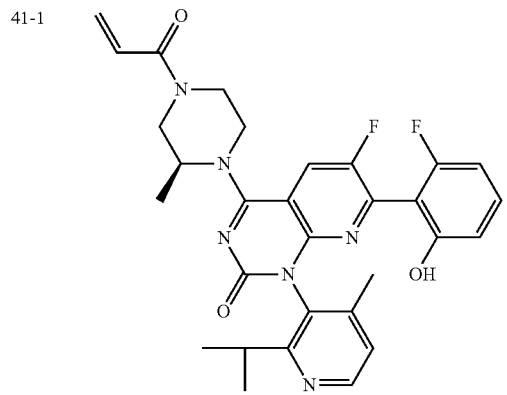<br>1st-eluting isomer |
| 41-2 | 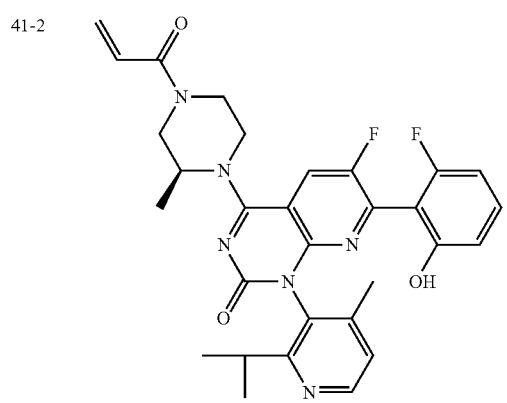<br>2nd-eluting isomer |
| 42-1 | 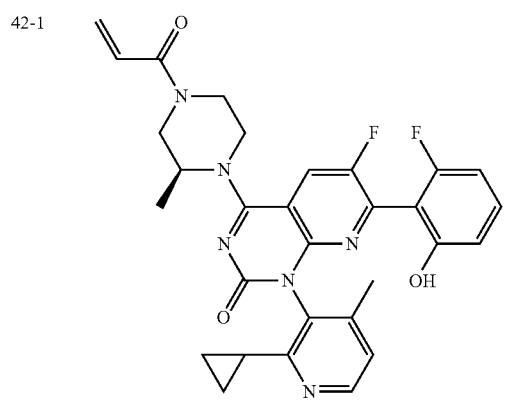<br>1st-eluting isomer |
| 42-2 | 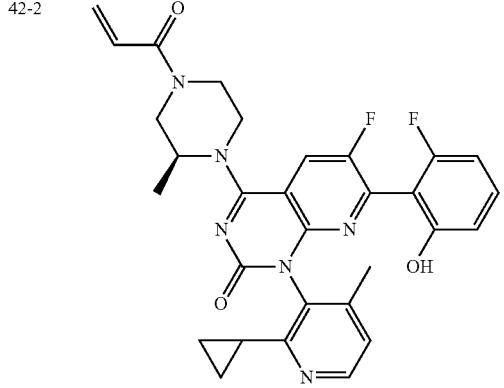<br>2nd-eluting isomer |
| 44-1 | 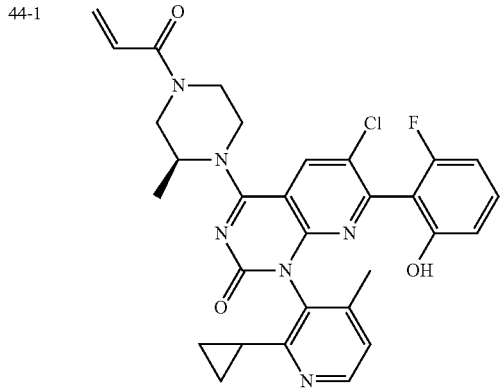<br>1st-eluting isomer |
| 44-2 | 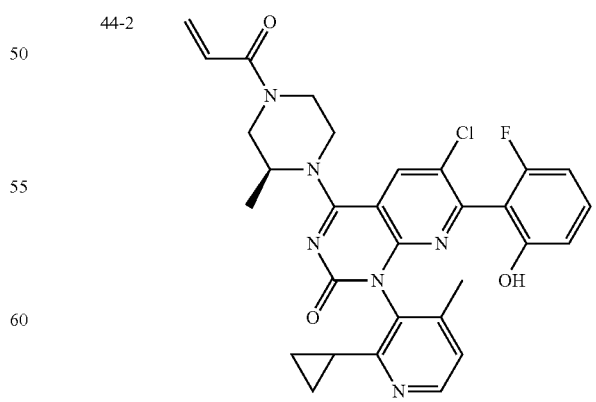<br>2nd-eluting isomer |

TABLE 1(a)-continued
| Ex. # | Chemical Structure |
|---|---|
| 45-1 | 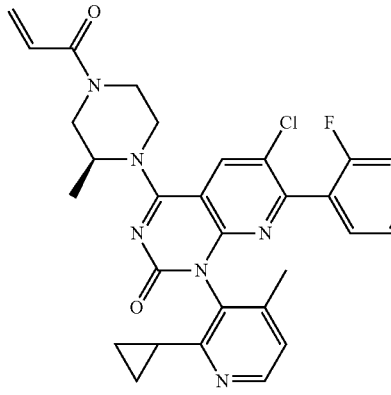<br>1st-eluting isomer |
| 45-2 | 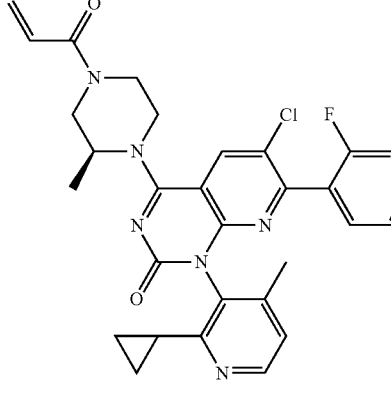<br>2nd-eluting isomer |
| 46-1 | 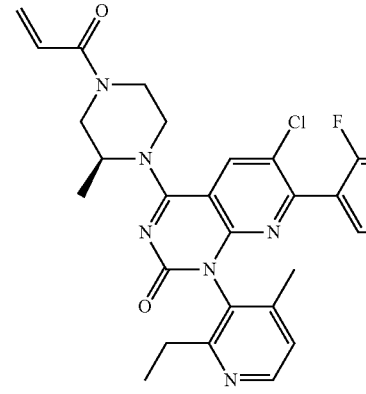<br>1st-eluting isomer |
TABLE 1(a)-continued
| Ex. # | Chemical Structure |
|---|---|
| 46-2 | 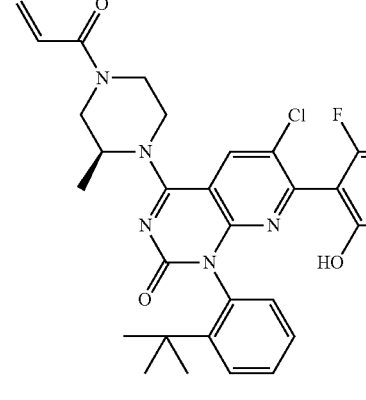<br>2nd-eluting isomer |
| 49-1 | 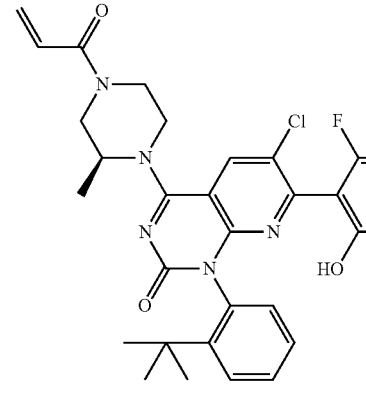<br>1st-eluting isomer |
| 49-2 | <br>2nd-eluting isomer |

TABLE 1(a)-continued
| Ex. # | Chemical Structure |
|---|---|
| 50-1 | 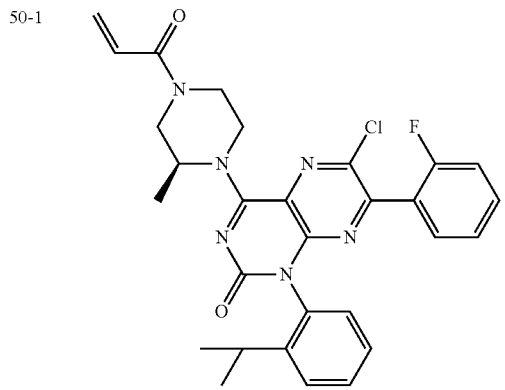<br>1st-eluting isomer |
| 50-2 | 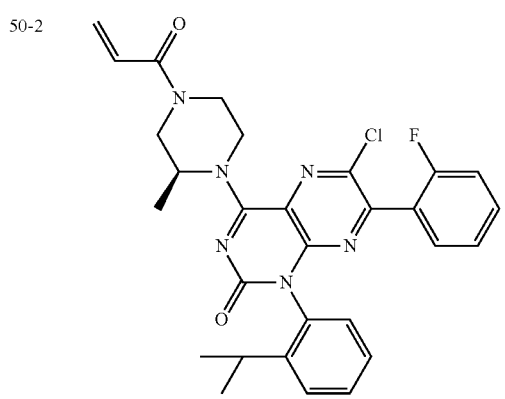<br>2nd-eluting isomer |
| 51-1 | 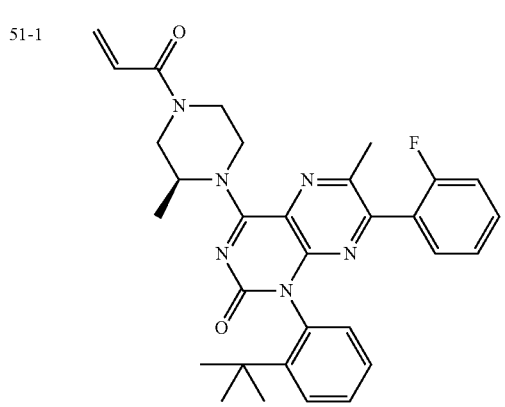<br>1st-eluting isomer |
| 51-2 | 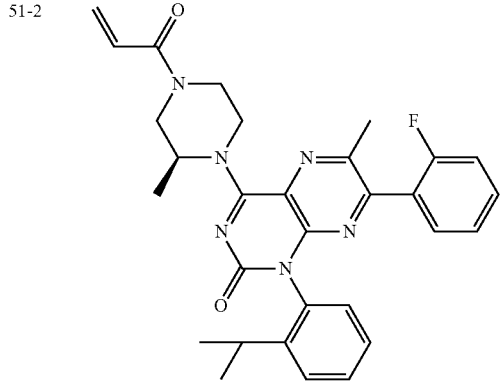<br>2nd-eluting isomer |
| 52-1 | 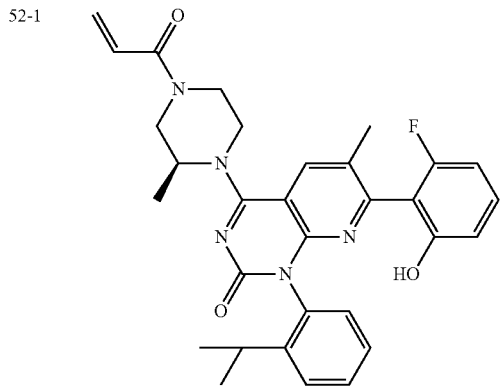<br>1st-eluting isomer |
| 52-2 | 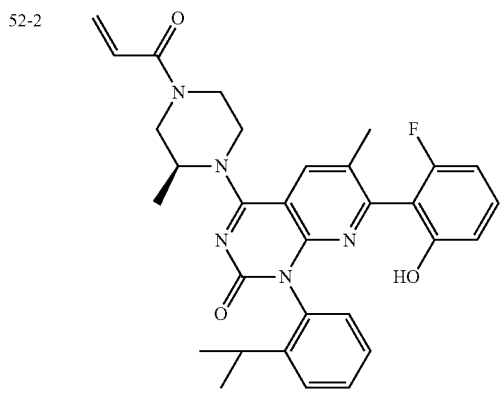<br>2nd-eluting isomer |

TABLE 1(a)-continued

| Ex. # | Chemical Structure |
|---|---|
| 53-1 | 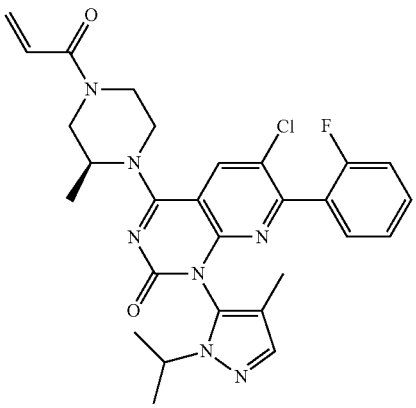 [SMILES: C=CC(=O)N1CCN(c2nc(=O)n(-c3c(C)cnn3C(C)C)c3nc(-c4ccccc4F)c(Cl)cc23)[C@@H](C)C1]<br>1st-eluting isomer |
| 53-2 | 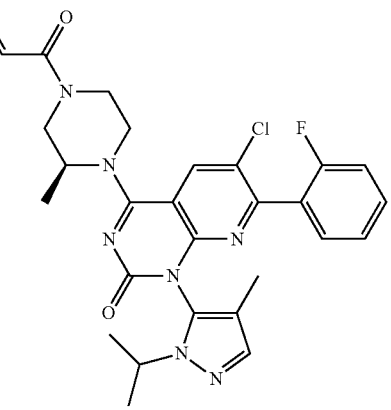<br>2nd-eluting isomer |

Synthesis of Disclosed Compounds

Compounds as disclosed herein can be synthesized via a number of specific methods. The examples which outline specific synthetic routes, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

Method 1

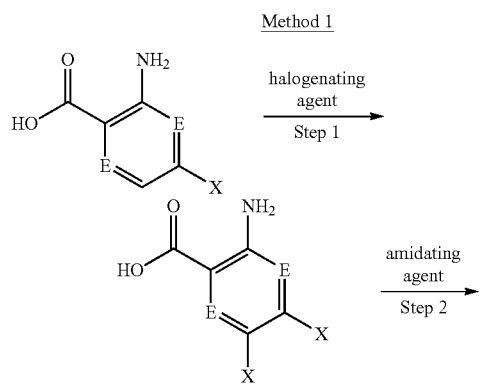

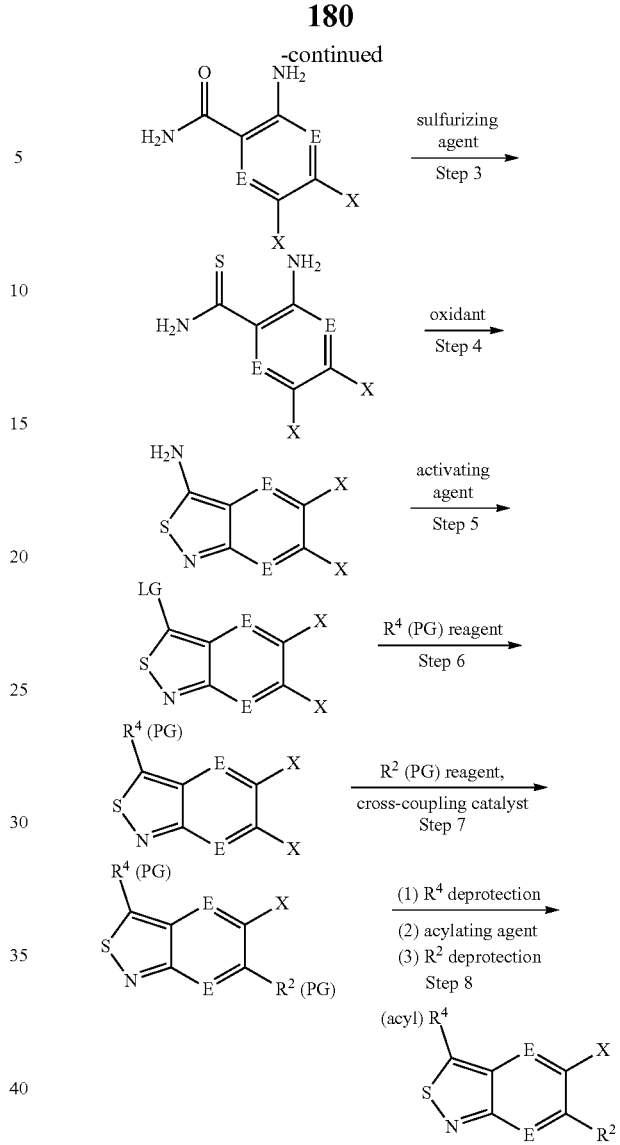

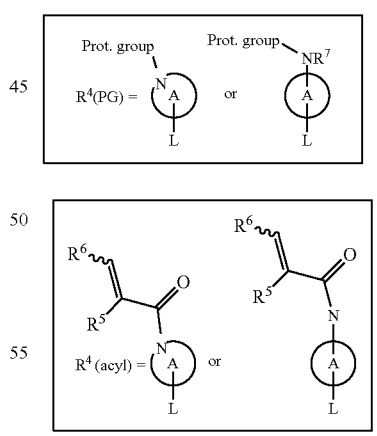

Method 1 synthesis: A compound of Formula (I) as disclosed herein can be synthesized as outlined in Method 1. An appropriate aromatic or heteroaromatic acid is reacted with a halogenating agent in Step 1 to form a halogenated aromatic or heteroaromatic acid. The acid is then reacted with an amidating agent in Step 2 to form an amide intermediate. The amide intermediate is then reacted with a sulfurizing agent in Step 3 to form a thioamide intermediate.

Next, the thioamide intermediate is reacted with an oxidant in Step 4 to form the thiazole ring as shown. The amine of the thiazole is then converted to a leaving group in Step 5 using an activating agent. The leaving group is then replaced with an $R^4$ protected group, as shown in Step 6. The $R^2$ moiety is then introduced in Step 7 by a cross-coupling reaction with the appropriate $R^2$ (protected) reagent with the X halide on the thiazole intermediate. Then, in Step 8, the $R^4$ group is deprotected under appropriate conditions, depending upon the protecting group used, the $R^4$ group is then acylated to introduce the acrylamide moiety as shown, and lastly, $R^2$ is deprotected. Appropriate protecting groups and deprotection reagents are known to those skilled in the art, e.g., as discussed in Greene's Protective Groups in Organic Synthesis.

Contemplated halogenating agents include, but are not limited to, chlorine, bromine, N-chlorosuccinimide, and N-bromosuccinimide, optionally in the presence of a catalyst, e.g., iron or aluminum. The ordinarily skilled synthetic chemist will readily understand that other halogenating agents and catalysts can be used.

Contemplated amidating agents include, but are not limited to, N, N'-diisopropylcarbodiimide, N-(3-dimethylaminopropyl)-N'-ethylcarbodiimide, benzotriazol-1-yloxytripyrrolidinophosphonium hexafluorophosphate, 0-(benzotriazol-1-yl)-N,N,N',N'-tetramethyluronium hexafluorophosphate, thionyl chloride, isobutyl chloroformate, diethyl cyanophosphonate, carbonyl diimidazole, and polyphosphonic anhydride. The ordinarily skilled synthetic chemist will readily understand that other amidating agents can be used.

Contemplated sulfurizing agents include, but are not limited to, sulfur, phosphorus pentasulfide, and Lawesson's reagent. The ordinarily skilled synthetic chemist will readily understand that other sulfurizing agents can be used.

Contemplated oxidants include, but are not limited to, hydrogen peroxide, iodobenzene diacetate, t-butyl hydroperoxide, N-bromosuccinimide, and ammonium peroxodisulfate. The ordinarily skilled synthetic chemist will readily understand that other oxidants can be used.

Contemplated activating agents include, but are not limited to, sodium nitrite and t-butyl nitrite. The ordinarily skilled synthetic chemist will readily understand that other activating agents can be used.

Contemplated cross-coupling reactions include, but are not limited to, Suzuki coupling, Negishi coupling, Hiyama coupling, Kumada coupling, and Stille coupling. The ordinarily skilled chemist will readily understand that couplings as shown in Method 1 can be performed under a number of conditions.

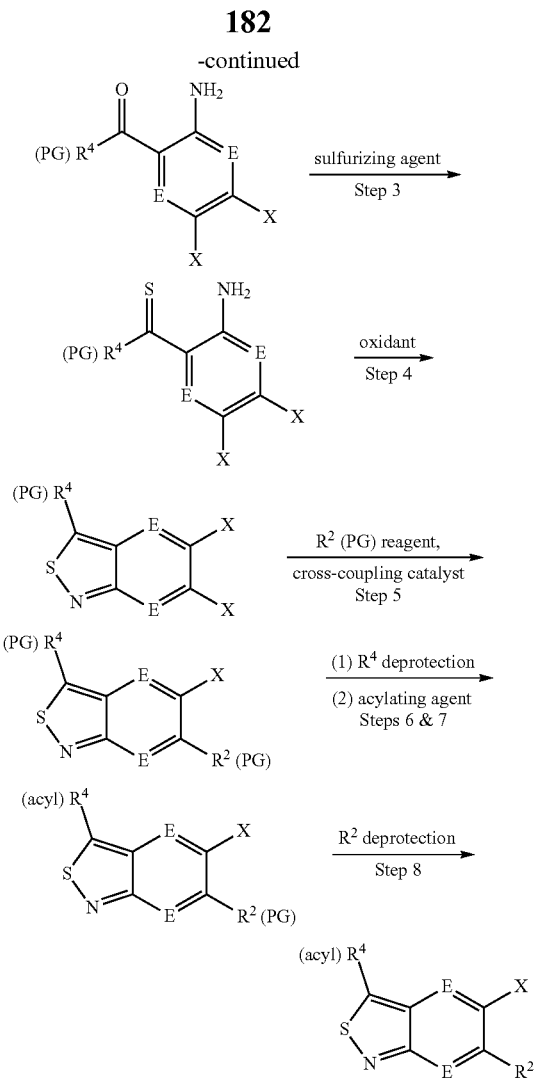

Method 2 synthesis: Method 2 provides an alternative method for formation of compounds of Formula (I) as disclosed herein. After halogenation in Step t, the $R^4$ protected group is introduced by reaction with the acid in a coupling reaction in Step 2. The oxo group is transformed to a sulfur using a sulfurizing agent in Step 3. Then the thiazole ring is formed in the presence of an oxidant in Step 4. The remaining steps 5-8 are analogous to steps 7 and 8 in Method 1 described above.

Method 2

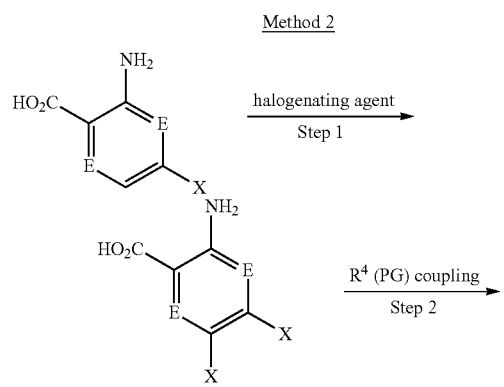

Method 3

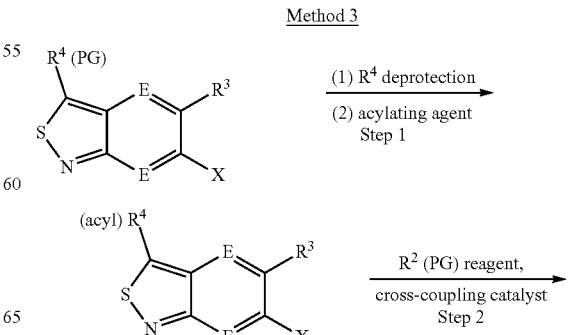

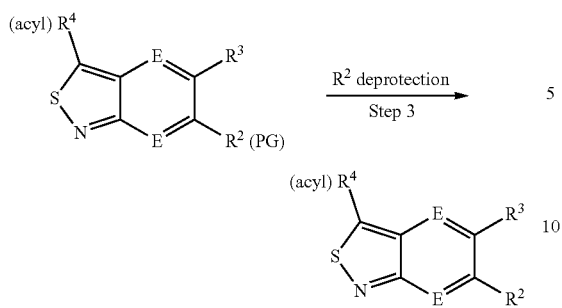

Method 3 synthesis: Method 3 provides an alternative method for formation of compounds of Formula (I) as disclosed herein. The $R^4$ group of the isothiazole intermediate is deprotected and acylated in Step 1 to introduce the acrylamide moiety. The $R^2$ moiety is then introduced in Step 2 by a cross-coupling reaction with the appropriate $R^2$ (protected) reagent with the X halide on the isothiazole intermediate. Lastly, the $R^2$ group is deprotected in Step 3.

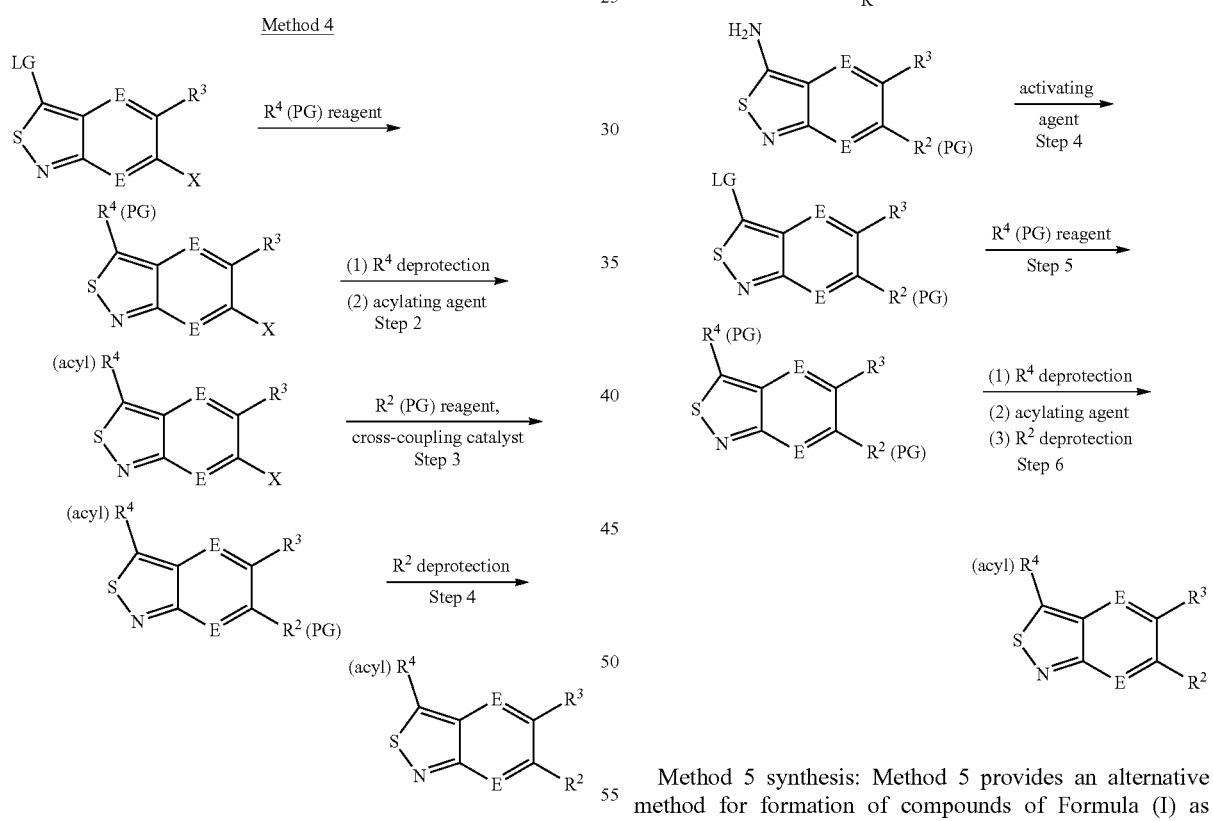

Method 4 synthesis: Method 4 provides an alternative method for formation of compounds of Formula (I) as disclosed herein. After substituting a leaving group on an isothiazole intermediate with a protected $R^4$ group, as depicted in Step 1, the $R^4$ group intermediate is deprotected and acylated in Step 2 to introduce the acrylamide moiety. The $R^2$ moiety is introduced by a cross-coupling reaction in Step 3, as in Method 1, and the $R^2$ group is deprotected in Step 4.

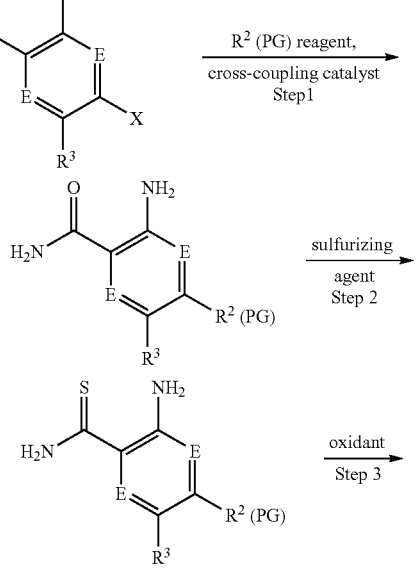

Method 5 synthesis: Method 5 provides an alternative method for formation of compounds of Formula (I) as disclosed herein. In this alternative, the $R^2$ moiety is first introduced by a cross-coupling with the X halide on the aromatic or heteroaromatic amide intermediate shown in Step 1. The amide intermediate is then reacted with a sulfurizing agent in Step 2 to form a thioamide intermediate. Oxidation of this intermediate provides the isothiazole ring in Step 3. The amine group is then converted to a leaving group in Step 4 and subsequently substituted with a protected $R^4$ group in Step 5. Finally, in Step 6, the $R^4$ group is deprotected and reacted with an acylating agent, and then the $R^2$ group is deprotected.

Method 6

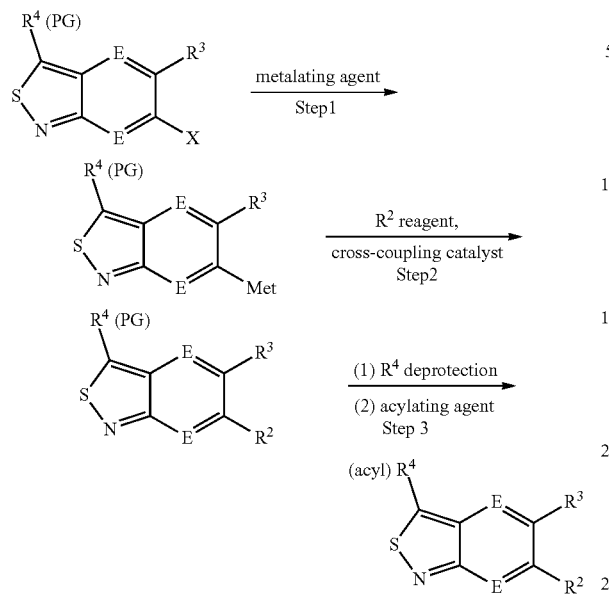

Method 6 synthesis: Method 6 provides an alternative method for formation of compounds of Formula (I) as disclosed herein. In this alternative, an isothiazole intermediate is reacted with a metalating agent to activate the X halide. The $R^2$ group is then introduced by reacting the activated intermediate with the appropriate $R^2$ (protected) reagent. In the last step, the $R^4$ group is deprotected and acylated to introduce the acrylamide moiety.

Contemplated metalating agents include, but are not limited to, bis(pinacolato)diboron, magnesium, zinc, hexamethyldistannane, and n-butyllithium. The ordinarily skilled synthetic chemist will readily understand that other metalating agents and catalysts can be used.

Method 7

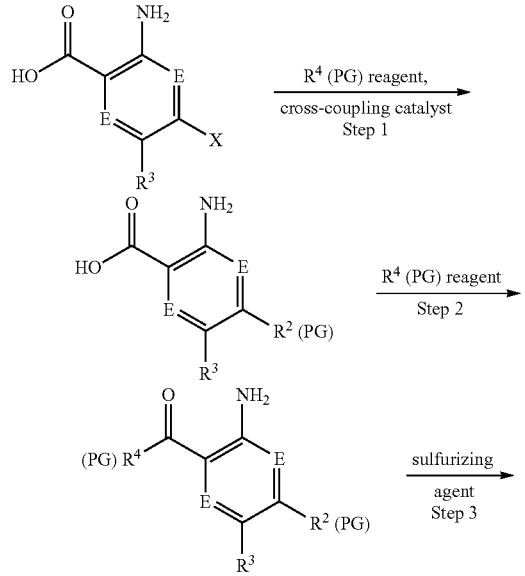

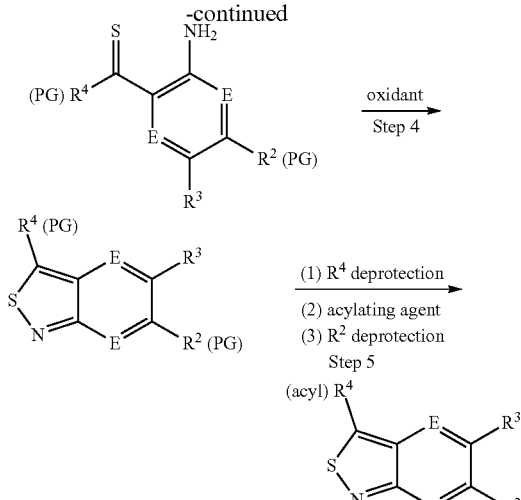

Method 7 synthesis: Method 7 provides an alternative method for formation of compounds of Formula (I) as disclosed herein. The $R^2$ moiety is first introduced by a cross-coupling with the X halide on the aromatic or heteroaromatic acid intermediate shown in Step 1. The acid moiety is then reacted with the appropriate $R^4$ (protected) reagent in the presence of an amidating agent in Step 2. The carbonyl group of the acid derivative is then converted to a thiocarbonyl group in Step 3 using a sulfurizing agent. The thioacid derivative is then reacted with an oxidant to form the isothiazole intermediate in Step 4. Lastly, the $R^4$ group is deprotected and acylated to introduce the acrylamide moiety, and the $R^2$ group is deprotected.

Method 8

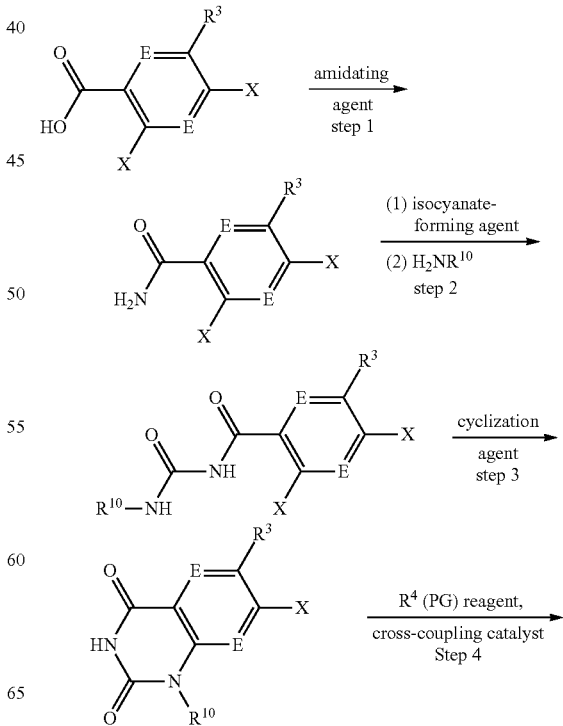

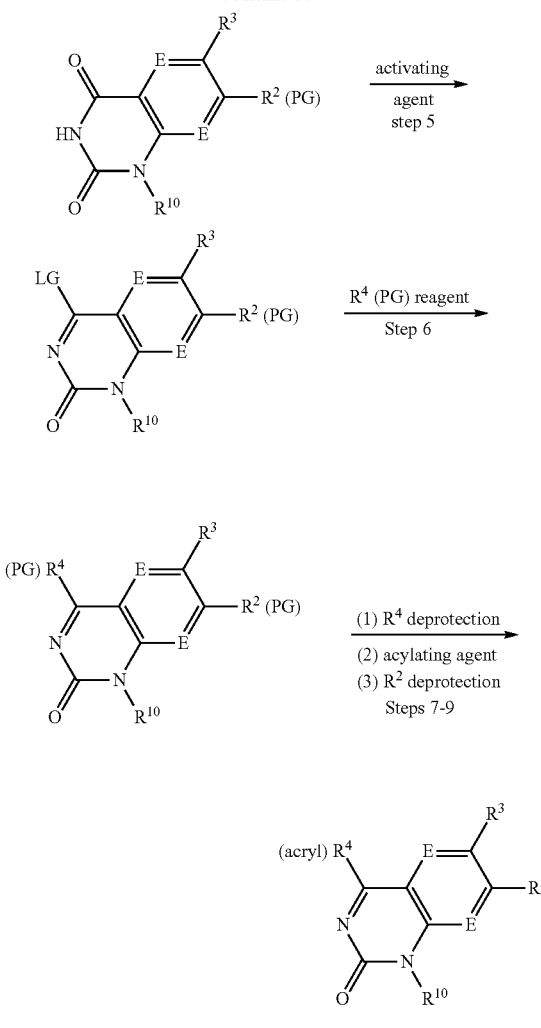

Method 8 synthesis: A compound of Formula (II) as disclosed herein can be synthesized as outlined in Method 8. An appropriate aromatic or heteroaromatic acid is reacted with an amidating agent in Step 1 to form a primary amide intermediate. The amide is then reacted with an isocyanate-forming reagent and a $R^{10}$-substituted amine to form a urea intermediate. Contemplated isocyanate-forming agents include oxalyl chloride, thionyl chloride, and phosphorus oxychloride. The urea intermediate is then reacted with a cyclization agent in Step 3 to form the quinazolinedione ring shown. Contemplated cyclization agents include, but are not limited to, bases such as potassium hexamethyldisilazide, potassium tert-butoxide, sodium hydride, and phosphazene bases. The $R^2$ moiety is then introduced in Step 4 by a cross-coupling reaction with the appropriate $R^2$ (protected) reagent with the X halide on the quinazolinedione intermediate. An oxo group of the quinazolinedione is then converted to a leaving group in Step 5 using an activating agent. Contemplated activating agents include, but are not limited to, thionyl chloride, triflic anhydride, phosphorus oxychloride, and phosphorus pentachloride. The leaving group is then replaced with an $R^4$ protected group to form a substituted quinazolinone, as shown in Step 6. The remaining deprotection-acylation-deprotection sequence shown in Steps 7-9 are analogous to Step 8 in Method 1.

Method 9 synthesis: Method 9 provides an alternative method for formation of compounds of Formula (II) as disclosed herein. An oxo group of the quinazolinedione is converted to a leaving group in Step 1. Step 2 involves the introduction of the $R^4$ (protected) group, deprotection of the $R^4$ group, and acylation of the free $R^4$ group. The $R^2$ group is introduced in Step 3 by a cross-coupling reaction with the appropriate $R^2$ (protected) reagent with the X halide on the quinazolinedione intermediate. Finally, the $R^2$ group is deprotected.

Method 10

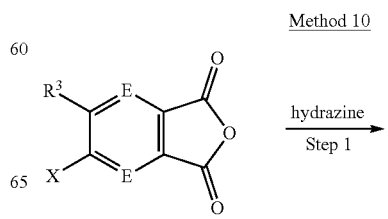

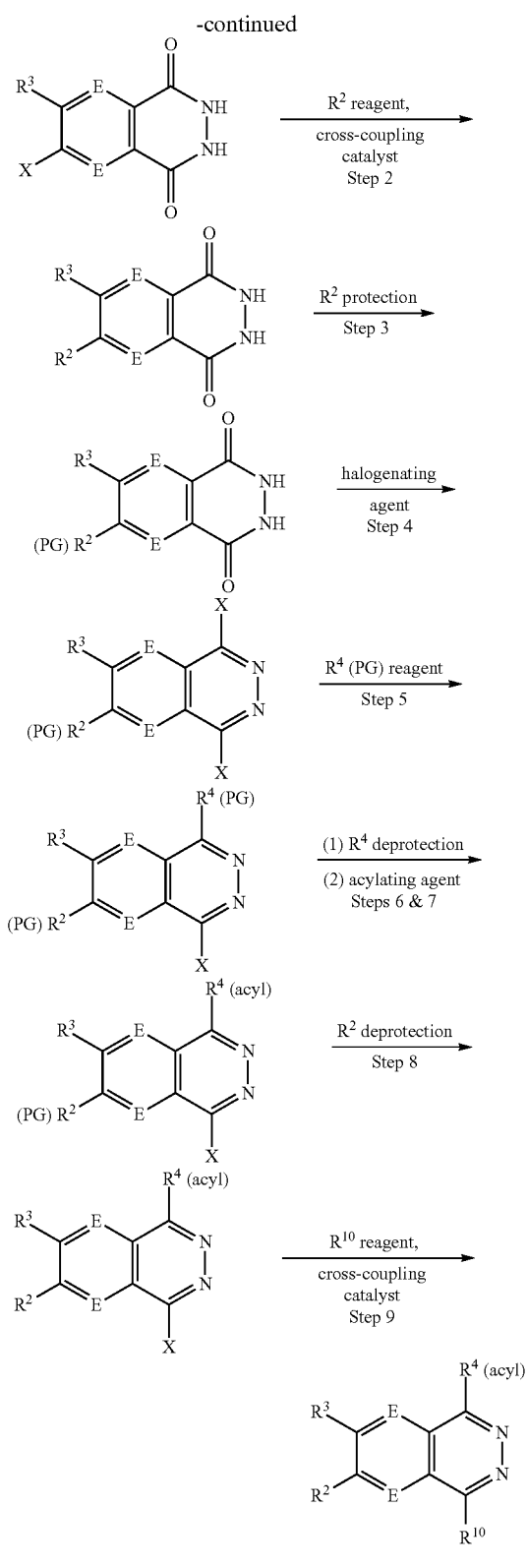

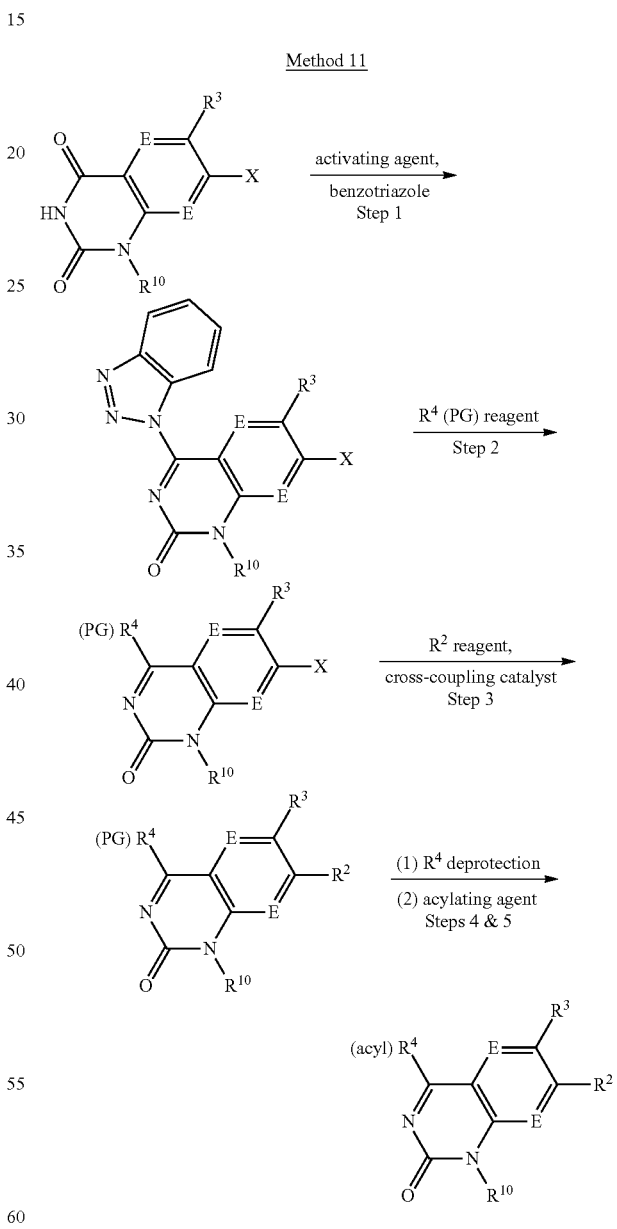

quinazolinedione intermediate. The $R^2$ group is then protected in Step 3. The phthalazinedione ring is halogenated twice. Contemplated halogenating agent include thionyl chloride, phosphorus oxychloride, and oxalyl chloride. One of the halogen groups is then replaced with an $R^4$ protected group to form a substituted phthalazine ring, as shown in Step 5. Then, in Steps 6 and 7, the $R^4$ group is deprotected under appropriate conditions, depending upon the protecting group used, and the free $R^4$ group is then acylated to introduce the acrylamide moiety. The $R^2$ is deprotected in Step 8. Lastly, the $R^{10}$ moiety is introduced in Step 9 by a cross-coupling reaction with the appropriate $R^{10}$ reagent with the X halide on the phthalazine intermediate.

Method 10 synthesis: A compound of Formula (V) as disclosed herein can be synthesized as outlined in Method 10. The appropriate anhydride is reacted with hydrazine to form the phthalazinedione ring as shown in Step 1. The $R^2$ moiety is introduced in Step 2 by a cross-coupling reaction with the appropriate $R^2$ reagent with the X halide on the Method 11 synthesis: Method 11 provides an alternative method for formation of compounds of Formula (II) as disclosed herein. An oxo group of the quinazolinedione is converted to a leaving group in Step 1. The $R^4$ (protected) group is introduced in Step 2. The $R^2$ group is introduced in Step 3 by a cross-coupling reaction with the appropriate $R^2$ (protected) reagent with the X halide on the quinazolinedione intermediate. Lastly, the $R^4$ group is deprotected and subsequently acylated in Steps 4 and 5.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pennsylvania, 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable e" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxy maleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or it may be divided into multiple doses.

Methods of Using KRAS G12C Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, mi dime tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastema, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In some embodiments, the methods for treatment are directed to treating lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C Mutant KRAS, HRAS or NRAS protein with an effective amount of a compound of the disclosure in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, HRAS or NRAS G12C activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C in said human. The present disclosure provides methods of treating a disease mediated by KRAS, HRAS or NRAS G12C activity in a subject in need of such treatment.

Combination Therapy:

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylomithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Sabnosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of 1-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EPOS 18442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No. EP1181017, United States Publication No. US20090012085, United States Publication U.S. Pat. No. 5,863,949, United States Publication U.S. Pat. No. 5,861, 510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflomithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, barozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aetema), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, EDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RE 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al, U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland);

2-methoxyestradiol, (EntreMed, USA); TEC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC: anti angiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxy estradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and Medlmmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived anti angiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Sobering AG, Germany); tissue factor pathway inhibitors, (EntreMed, USA); pegaptanib (Finn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aetema, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxy estradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAh, KDR, (ImClone Systems, USA); MAh, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); T etrathiomoly bdate, (University of Michigan, USA); GCS 100, (Wayne State University, USA) CV 247, (Ivy Medical, UK); CKD 732, (Chong Kun Dang, South Korea); MAh, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafdomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfdgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracydines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiprobferative/antimitotic antimetabobtes such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirobmus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutrabzing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CSl (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zamestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds or pharmaceutical compositions of the disclosure can also be used in combination with an amount of one or more substances selected from EGFR inhibitors, MEK inhibitors, PI3K inhibitors, AKT inhibitors, TOR inhibitors, and immune therapies, including anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., *Pharmacogenetics and Pharmacogenomics In Oncology Therapeutic Antibody Development*, BioTechniques 2005; 39(4): 565-8, and Paez J G, et. al., *EGFR Mutations In Lung Cancer Correlation With Clinical Response To Gefitinib Therapy*, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCX International Publication WO 97/30034, published Aug. 21, 1997; PCX International Publication WO 97/30044, published Aug. 21, 1997; PCX International Publication WO 97/38994, published Oct. 23, 1997; PCX International Publication WO 97/49688, published Dec. 31, 1997; European Patent Application EP 837063, published Apr. 22, 1998; PCX International Publication WO 98/02434, published Jan. 22, 1998; PCX International Publication WO 97/38983, published Oct. 23, 1997; PCX International Publication WO 95/19774, published Jul. 27, 1995; PCX International Publication WO 95/19970, published Jul. 27, 1995; PCX International Publication WO 97/13771, published Apr. 17, 1997; PCX International Publication WO 98/02437, published Jan. 22, 1998; PCX International Publication WO 98/02438, published Jan. 22, 1998; PCX International Publication WO 97/32881, published Sep. 12, 1997; German Application DE 19629652, published Jan. 29, 1998; PCX International Publication WO 98/33798, published Aug. 6, 1998; PCX International Publication WO 97/32880, published Sep. 12, 1997; PCX International Publication WO 97/32880 published Sep. 12, 1997; European Patent Application EP 682027, published Nov. 15, 1995; PCX International Publication WO 97/02266, published Jan. 23, 197; PCX International Publication WO 97/27199, published Jul. 31, 1997; PCX International Publication WO 98/07726, published Feb. 26, 1998; PCX International Publication WO 97/34895, published Sep. 25, 1997; PCX International Publication WO 96/31510', published Oct. 10, 1996; PCX International Publication WO 98/14449, published Apr. 9, 1998; PCX International Publication WO 98/14450, published Apr. 9, 1998; PCX International Publication WO 98/14451, published Apr. 9, 1998; PCX International Publication WO 95/09847, published Apr. 13, 1995; PCX International Publication WO 97/19065, published May 29, 1997; PCX International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCX International Publication WO 99/35146, published Jul. 15, 1999; PCX International Publication WO 99/35132, published Jul. 15, 1999; PCX International Publication WO 99/07701, published Feb. 18, 1999; and PCX International Publication WO 92/20642 published Nov. 26, 1992. Additional non-limiting examples of small molecule EGFR inhibitors include any of the EGFR inhibitors described in Xraxler, P., 1998, Exp. Opin. Xher. Patents 8(12): 1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8): 1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morphobne (also known as GDC 0941 and described in PCX Publication Nos. WO 09/036,082 and WO 09/055,730), 2-Methyl-2-[4-[3-methyl-2-oxo-8-(quinobn-3-yl)-2,3-dihydroimidazo[4,5-c]quinobn-1-yl]phenyl]propionitrile (also known as BEZ 235 or NVP-BEZ 235, and described in PCX Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCX Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazobn-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazobdine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL 147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) Biochem. J., 385 (Pt. 2), 399-408); Akt-1-1,2 (inhibits Ak1 and 2) (Barnett et al. (2005) Biochem. J 385 (Pt. 2), 399-408); API-59CJ-Ome (e.g., Jin et al. (2004) Br. J Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

Immune therapies include, but are not limited to, anti-PD-1 agents, anti-PDL-1 agents, anti-CTLA-4 agents, anti-LAG1 agents, and anti-OX40 agents. Exemplary anti-PD-1 antibodies and methods for their use are described by Goldberg et al., Blood 110(1): 186-192 (2007), Thompson et al., Clin. Cancer Res. 13(6): 1757-1761 (2007), and Korman et al., International Application No. PCT/JP2006/309606 (publication no. WO 2006/121168 A1), each of which are expressly incorporated by reference herein, include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090 box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In some embodiments, the compound having the structure

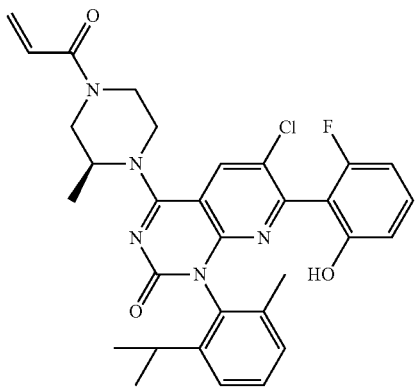 [SMILES: C=CC(=O)N1CCN(c2nc(=O)n(-c3c(C)cccc3C(C)C)c3nc(-c4c(O)cccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

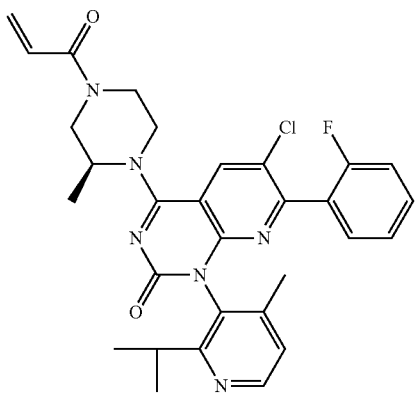 [SMILES: C=CC(=O)N1CCN(c2nc(=O)n(-c3c(C)ccnc3C(C)C)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

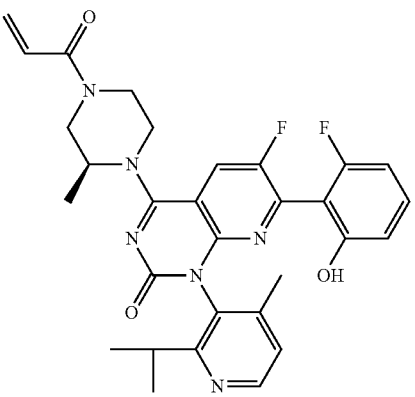

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

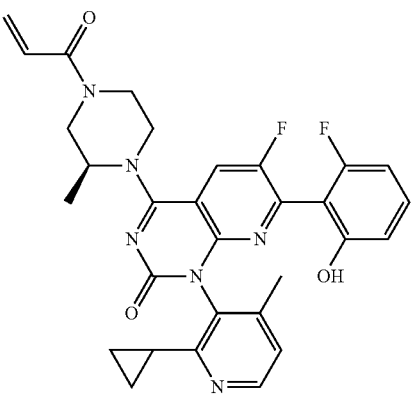

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is admin- In some embodiments, the compound having the structure

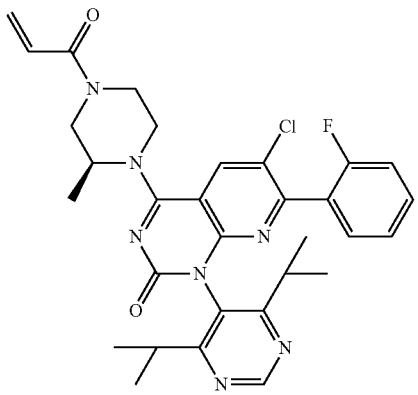 [SMILES: C=CC(=O)N1CCN(c2nc(=O)n(-c3c(C(C)C)ncnc3C(C)C)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

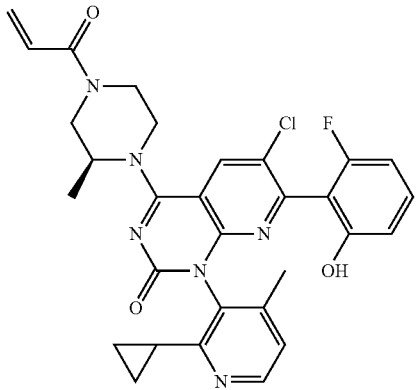

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

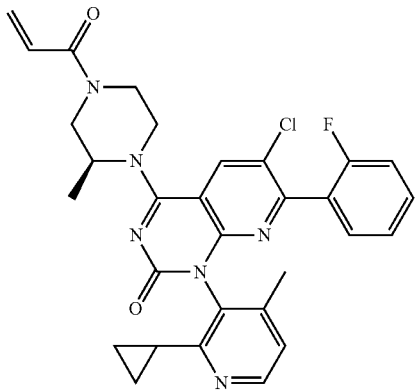 [SMILES: C=CC(=O)N1CCN(c2nc(=O)n(-c3c(C)ccnc3C3CC3)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-r inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

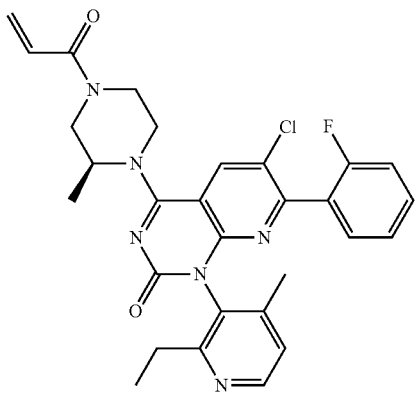 [SMILES: C=CC(=O)N1CCN(c2nc(=O)n(-c3c(C)ccnc3CC)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

215

In some embodiments, the compound having the structure

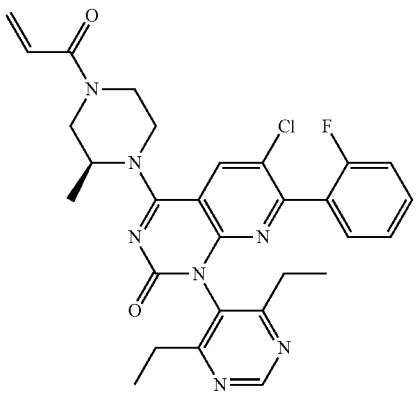 [SMILES: C=CC(=O)N1CCN(c2nc(=O)n(-c3c(CC)ncnc3CC)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BCl-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

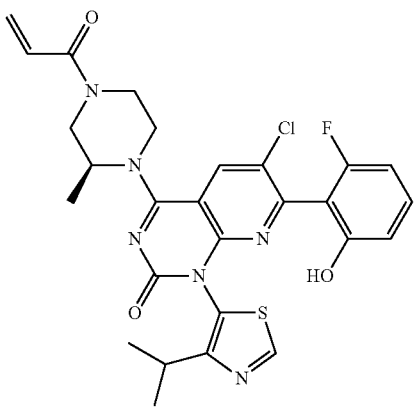 [SMILES: C=CC(=O)N1CCN(c2nc(=O)n(-c3scnc3C(C)C)c3nc(-c4c(O)cccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BCl-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

216

In some embodiments, the compound having the structure

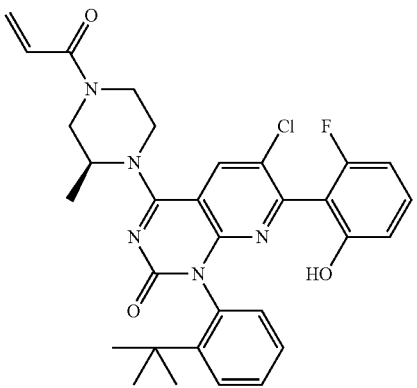 [SMILES: C=CC(=O)N1CCN(c2nc(=O)n(-c3ccccc3C(C)(C)C)c3nc(-c4c(O)cccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BCl-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

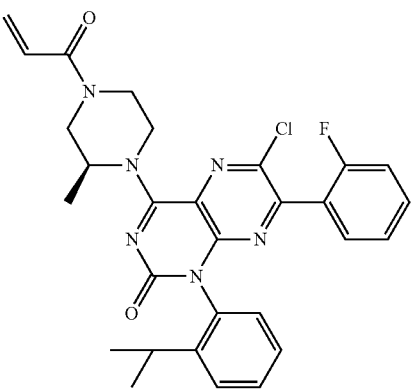 [SMILES: C=CC(=O)N1CCN(c2nc(=O)n(-c3ccccc3C(C)C)c3nc(-c4ccccc4F)c(Cl)nc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BCl-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

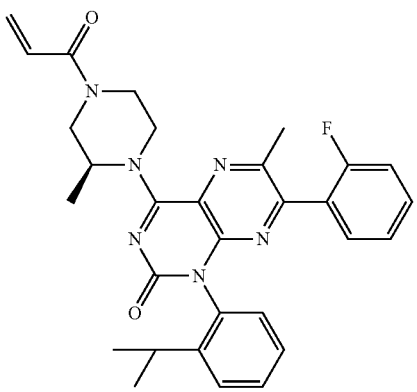

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

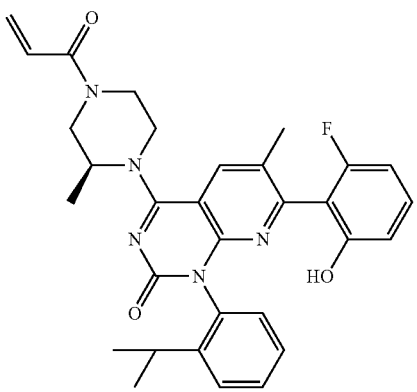 [SMILES: C=CC(=O)N1CCN(c2nc(=O)n(-c3ccccc3C(C)C)c3nc(-c4c(O)cccc4F)c(C)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

In some embodiments, the compound having the structure

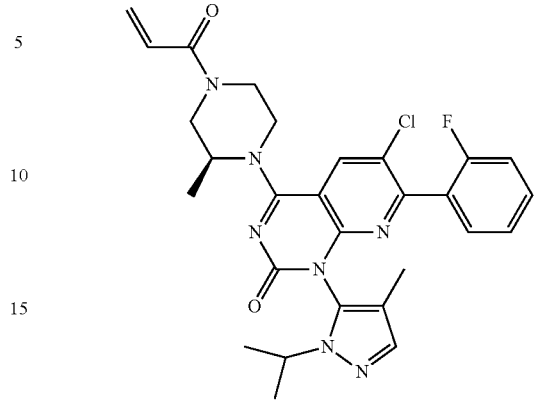

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, is administered to a patient in need thereof a therapeutically effective amount of an additional pharmaceutically active compound, for example, cytarabine, a proteasome inhibitor, such as carfilzomib or oprozomib, a BC1-2 inhibitor, such as venetoclax, an MCl-1 inhibitor, such as AMG-176, a monoconal antibody, such as daratumumab, and an immunomodulatory imide drug (IMiD), such as thalidomide, lenalidomide, pomalidomide and apremilast.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXAMPLES

Method 1

Example 1-1: 1-(4-(6-(2-bromo-5-hydroxyphenyl)-5-chloro-7-fluorobenzo[c]isothiazol-3-yl)piperazin-1-yl)prop-2-en-1-one

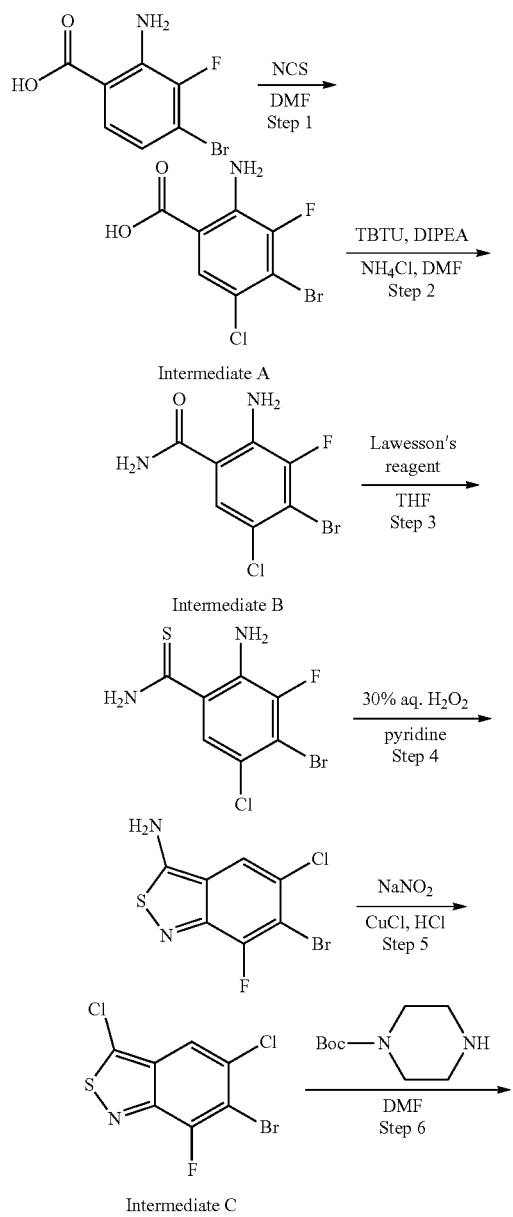

Intermediate A

Intermediate B

Intermediate C

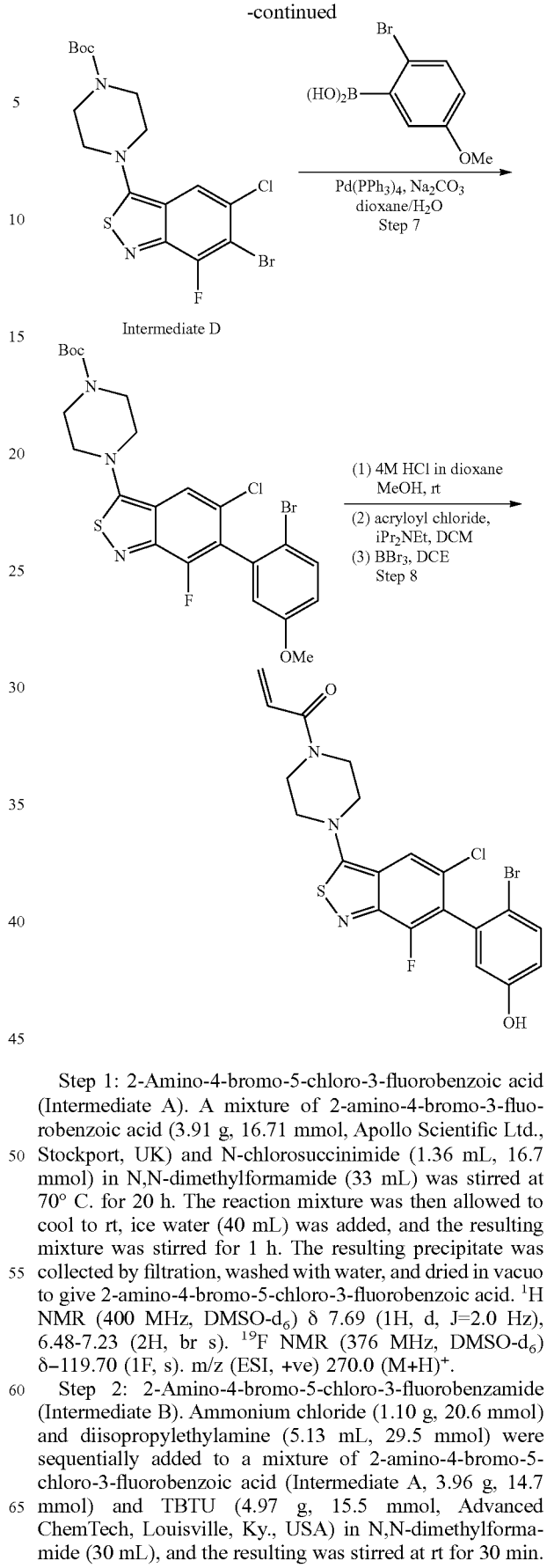

Intermediate D

Step 1: 2-Amino-4-bromo-5-chloro-3-fluorobenzoic acid (Intermediate A). A mixture of 2-amino-4-bromo-3-fluorobenzoic acid (3.91 g, 16.71 mmol, Apollo Scientific Ltd., Stockport, UK) and N-chlorosuccinimide (1.36 mL, 16.7 mmol) in N,N-dimethylformamide (33 mL) was stirred at 70° C. for 20 h. The reaction mixture was then allowed to cool to rt, ice water (40 mL) was added, and the resulting mixture was stirred for 1 h. The resulting precipitate was collected by filtration, washed with water, and dried in vacuo to give 2-amino-4-bromo-5-chloro-3-fluorobenzoic acid. $^1$H NMR (400 MHz, DMSO-$d_6$) δ 7.69 (1H, d, J=2.0 Hz), 6.48-7.23 (2H, br s). $^{19}$F NMR (376 MHz, DMSO-$d_6$) δ−119.70 (1F, s). m/z (ESI, +ve) 270.0 (M+H)$^+$.

Step 2: 2-Amino-4-bromo-5-chloro-3-fluorobenzamide (Intermediate B). Ammonium chloride (1.10 g, 20.6 mmol) and diisopropylethylamine (5.13 mL, 29.5 mmol) were sequentially added to a mixture of 2-amino-4-bromo-5-chloro-3-fluorobenzoic acid (Intermediate A, 3.96 g, 14.7 mmol) and TBTU (4.97 g, 15.5 mmol, Advanced ChemTech, Louisville, Ky., USA) in N,N-dimethylformamide (30 mL), and the resulting was stirred at rt for 30 min.

The reaction mixture was then added to saturated aqueous sodium bicarbonate and stirred for 15 min. The resulting precipitate was collected by filtration, washed with water, and dried in vacuo to give 2-amino-4-bromo-5-chloro-3-fluorobenzamide. $^1$H NMR (400 MHz, DMSO-d$_6$) δ 8.03 (1H, br s), 7.72 (1H, d, J=2.0 Hz), 7.47 (1H, br s), 6.86 (2H, s). $^{19}$F NMR (376 MHz, DMSO-d$_6$) δ−120.79 (1F, s). m/z (ESI, +ve) 268.9 (M+H)$^+$.

Step 3: 2-Amino-4-bromo-5-chloro-3-fluorobenzothioamide Lawesson's reagent (2.81 g, 6.95 mmol) was added to 2-amino-4-bromo-5-chloro-3-fluorobenzamide (Intermediate B, 3.10 g, 11.59 mmol) in THF (77 mL), and the resulting mixture was stirred at rt for 1 h. The reaction mixture was then diluted with EtOAc (75 mL) and sequentially washed with aqueous 2 M HCl (50 mL), saturated aqueous sodium bicarbonate solution (50 mL), and brine (50 mL). The organic extract was then dried over Na$_2$SO$_4$, collected by filtration, and concentrated in vacuo. Chromatographic purification of the residue (silica gel, 0-3% MeOH in DCM) provided 2-amino-4-bromo-5-chloro-3-fluorobenzothioamide: $^1$H NMR (400 MHz, DMSO-d$_6$) δ 9.93-10.15 (1H, m), 9.63 (1H, br s), 7.28 (1H, d, J=1.96 Hz), 6.34 (2H, s). $^{19}$F NMR (376 MHz, DMSO-d$_6$) δ−119.52 (1° F., s). m/z (ESI, +ve) 284.8 (M+H)$^+$.

Step 4: 6-Bromo-5-chloro-7-fluorobenzo[c]isothiazol-3-amine Hydrogen peroxide (30% by wt. in water, 2.93 mL, 28.7 mmol) was added dropwise to an ice-cooled solution of 2-amino-4-bromo-5-chloro-3-fluorobenzothioamide (2.71 g, 9.55 mmol) in pyridine (32 mL), and the resulting mixture was subsequently allowed to warm to rt and stir for 24 h. Water (50 mL) was added, and the precipitated solid was collected by filtration, washed with water, and dried in vacuo to give 6-bromo-5-chloro-7-fluorobenzo[c]isothiazol-3-amine: $^1$H NMR (400 MHz, DMSO-d$_6$) δ 8.12-8.26 (2H, m), 7.95-8.06 (1H, m). $^{19}$F NMR (376 MHz, DMSO-d$_6$) δ−114.32 (1° F., s). m/z (ESI, +ve) 283.0 (M+H)$^+$.

Step 5: 6-Bromo-3,5-dichloro-7-fluorobenzo[c]isothiazole (Intermediate C) To an ice-cooled mixture of 6-bromo-5-chloro-7-fluorobenzo[c]isothiazol-3-amine (2.47 g, 8.78 mmol), water (12 mL), and concentrated hydrochloric acid (37 wt %, 12 mL, 395 mmol) was slowly added a solution of sodium nitrite (0.788 g, 11.4 mmol) in water (2.0 mL). The resulting mixture was stirred at 0° C. for 2.5 h, and a mixture of copper (I) chloride (1.39 g, 14.1 mmol) in concentrated hydrochloric (37 wt %, 12 mL, 395 mmol) was then added at 0° C. The reaction mixture was subsequently allowed to warm to rt and stir for 20 h. The reaction mixture was diluted with water (50 mL), and the precipitated solid was collected by filtration and dried in vacuo. The collected material was taken up in (3:1) DCM:MeOH (200 mL) and sequentially washed with water (200 mL) and brine (100 mL). The organic layer was then dried over Na$_2$SO$_4$, filtered, and concentrated in vacuo. Chromatographic purification of the residue (silica gel, 0-20% EtOAc in heptane) gave 6-bromo-3,5-dichloro-7-fluorobenzo[c]isothiazole: $^1$H NMR (400 MHz, DMSO-d$_6$) δ 7.99 (1H, d, J=1.57 Hz). $^{19}$F NMR (376 MHz, DMSO-d$_6$) δ −111.48 (1° F., s). m/z (ESI, +ve) 425.0 (M+H)$^+$.

Step 6: tert-Butyl 4-(6-bromo-5-chloro-7-fluorobenzo[c]isothiazol-3-yl)piperazine-1-carboxylate (Intermediate D) A mixture of 6-bromo-3,5-dichloro-7-fluorobenzo[c]isothiazole (Intermediate C, 150 mg, 0.497 mmol) and 1-Boc-piperazine (204 mg, 1.09 mmol) in N,N-dimethylformamide (2.0 mL) was stirred at rt for 20 h. The reaction mixture was then adsorbed onto silica gel and chromatographically purified (silica gel, 0-20% EtOAc in heptane) to provide tert-butyl 4-(6-bromo-5-chloro-7-fluorobenzo[c]isothiazol-3-yl) piperazine-1-carboxylate. $^1$H NMR (400 MHz, CHLOROFORM-d) δ 7.60 (1H, d, J=1.56 Hz), 3.68-3.79 (4H, m), 3.40-3.51 (4H, m), 1.26 (9H, s). m/z (ESI, +ve) 451.8 (M+H)$^+$.

Step 7: tert-Butyl 4-(6-(2-bromo-5-methoxyphenyl)-5-chloro-7-fluorobenzo[c]isothiazol-3-yl)piperazine-1-carboxylate A mixture of tert-butyl 4-(6-bromo-5-chloro-7-fluorobenzo[c]isothiazol-3-yl)piperazine-1-carboxylate (Intermediate D, 111 mg, 0.247 mmol), 2-bromo-5-methoxybenzene boronic acid (0.114 mL, 0.494 mmol), sodium carbonate (0.041 mL, 0.988 mmol), and tetrakis (triphenylphosphine)palladium (14.3 mg, 0.012 mmol) in 1,4-dioxane (L6 mL) and water (0.4 mL) was heated at 90° C. for 21 h. The reaction mixture then concentrated in vacuo, adsorbed onto silica gel, and purified by column chromatography (silica gel, 0-20% (3:1) EtOAc/EtOH in heptane) to furnish tert-butyl 4-(6-(2-bromo-5-methoxyphenyl)-5-chloro-7-fluorobenzo[c]isothiazol-3-yl)piperazine-1-carboxylate: m/z (ESI, +ve) 558.1 (M+H)$^+$.

Step 8: 1-(4-(6-(2-bromo-5-hydroxyphenyl)-5-chloro-7-fluorobenzo[c]isothiazol-3-yl)piperazin-1-yl)prop-2-en-1-one Hydrogen chloride (4M in 1,4-dioxane, 2.0 mL, 8.0 mmol) was added to a mixture of tert-butyl 4-(6-(2-bromo-5-methoxyphenyl)-5-chloro-7-fluorobenzo[c]isothiazol-3-yl)piperazine-1-carboxylate (107 mg, 0.192 mmol) and methanol (2.0 mL), and the resulting mixture was stirred at rt for 1 h. The reaction mixture was then concentrated in vacuo to give 6-(2-bromo-5-methoxyphenyl)-5-chloro-7-fluoro-3-(piperazin-1-yl)benzo[c]isothiazole: m/z (ESI, +ve) 458.0 (M+1)$^+$.

To this material (88 mg) was added N,N-diisopropylethylamine (0.101 mL, 0.578 mmol) in dichloromethane (2 mL), and the resulting mixture was cooled to 0° C. Acryloyl chloride (0.26 M in DCM, 0.75 mL, 0.19 mmol) was added, and the resulting mixture was stirred at 0° C. for 10 min. The reaction mixture was concentrated in vacuo to provide 1-(4-(6-(2-bromo-5-methoxyphenyl)-5-chloro-7-fluorobenzo[c]isothiazol-3-yl)piperazin-1-yl)prop-2-en-1-one: m/z (ESI, +ve) 512.0 (M+H)$^+$.

For compounds without a methyl ether protecting group, the crude material was purified at this stage. For compounds bearing a methyl ether protecting group, the crude material was used in the next transformation without purification:

The resulting 1-(4-(6-(2-bromo-5-methoxyphenyl)-5-chloro-7-fluorobenzo[c]isothiazol-3-yl)piperazin-1-yl)prop-2-en-1-one was taken up in 1,2-dichloroethane (2.0 mL) and cooled to 0° C. Boron tribromide solution (1.0 M in hexanes, 0.97 mL, 0.97 mmol) was added, and the resulting mixture was stirred at 0° C. for 1 h. The reaction mixture was then added to saturated aqueous sodium bicarbonate (2.0 mL) and extracted with (2:1) DCM/MeOH (10 mL). The organic extract was dried over Na$_2$SO$_4$, filtered, and concentrated in vacuo. Chromatographic purification of the residue (silica gel, 0-3% MeOH in DCM) provided 1-(4-(6-(2-bromo-5-hydroxyphenyl)-5-chloro-7-fluorobenzo[c]isothiazol-3-yl) piperazin-1-yl)prop-2-en-1-one: $^1$H NMR (400 MHz, DMSO-de) δ 9.99 (hr s, 1H), 8.04 (s, 1H), 7.55 (d, J=8.7 Hz, 1H), 6.81-6.94 (m, 2H), 6.79 (d, J=2.9 Hz, 1H), 6.19 (dd, J=16.7, 2.2 Hz, 1H), 5.77 (dd, J=10.5, 2.2 Hz, 1H), 3.87 (br d, J=19.5 Hz, 4H), 3.63 (hr t, J=5.1 Hz, 4H). $^{19}$F NMR (376 MHz, DMSO-d$_6$) δ−124.16 (1F, s). m/z (ESI, +ve) 498.0 (M+H)$^+$ TABLE 1(b)

Compounds 1-2 to 1-28 were prepared following the procedure described in Method 1, Steps 1-8, above as follows:

| Ex.# | Chemical Structure | Name | Method changes | Reagent |
|---|---|---|---|---|
| 1-2 | 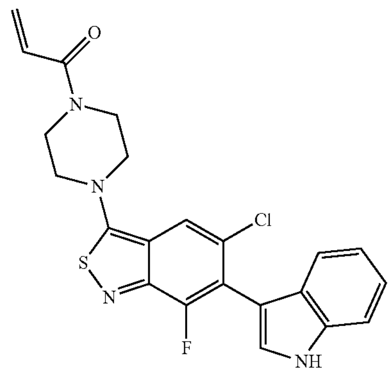 [SMILES: C=CC(=O)N1CCN(c2snc3c(F)c(-c4c[nH]c5ccccc45)c(Cl)cc23)CC1] | 1-(4-(5-chloro-7-fluoro-6-(1H-indol-3-yl)-2,1-benzothiazol-3-yl)-1-piperazinyl)-2-propen-1-one | Omit step 8-3 | Step 7: (1-tert-butoxycarbonyl)-1h-indol-3-yl)boronic acid (Combi-blocks Inc. San Diego, CA, USA), Step 8-1: TFA/DCM |
| 1-3 | 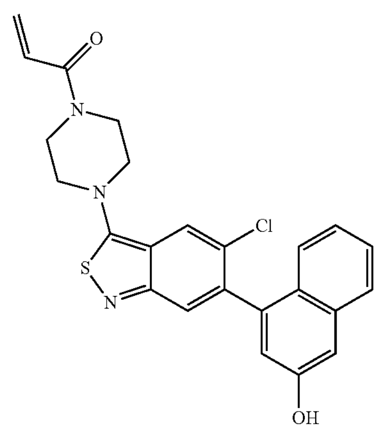 [SMILES: C=CC(=O)N1CCN(c2snc3cc(-c4cc(O)cc5ccccc45)c(Cl)cc23)CC1] | 1-(4-(5-chloro-6-(2-fluoro-6-hydroxyphenyl)-2,1-benzothiazol-3-yl)-1-piperazinyl)-2-propen-1-one | Omit step 8-3 | Step 7: (3-methoxynaphthalen-1-yl)boronic acid Cs₂CO₃, 100° C., Step 8-1: TFA/DCM |
| 1-4 | 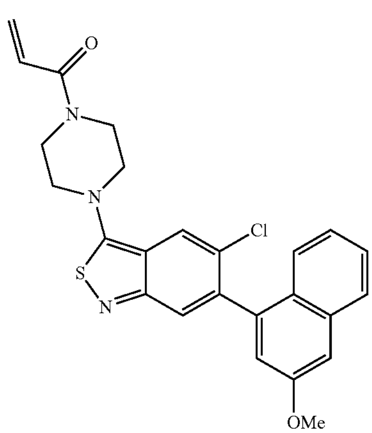 [SMILES: C=CC(=O)N1CCN(c2snc3cc(-c4cc(OC)cc5ccccc45)c(Cl)cc23)CC1] | 1-(4-(5-chloro-6-(3-methoxy-1-naphthalenyl)-2,1-benothiazol-3-yl)-1-piperazinyl)-2-propen-1-one | — | Step 7: (3-methoxynaphthalen-1-yl)boronic acid, Cs₂CO₃, 100° C., Step 8-1: TFA/DCM |

TABLE 1(b)-continued

Compounds 1-2 to 1-28 were prepared following the procedure described in Method 1, Steps 1-8, above as follows:

| Ex.# | Chemical Structure | Name | Method changes | Reagent |
|---|---|---|---|---|
| 1-5 | 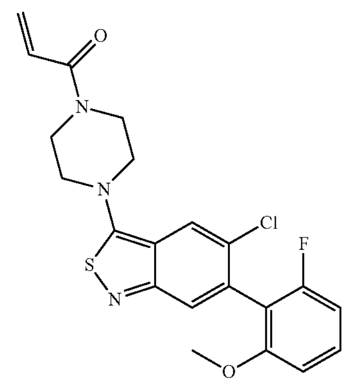 [SMILES: C=CC(=O)N1CCN(c2snc3cc(-c4c(F)cccc4OC)c(Cl)cc23)CC1] | 1-(4-(5-chloro-6-(2-fluoro-6-methoxyphenyl)-2,1-benzothiazol-3-yl)-1-piperazinyl)-2-propen-1-one | — | Step 7: (2-fluoro-6-methoxyphenyl) boronic acid, $Cs_2CO_3$, 100° C., Step 8-1: TFA/DCM |
| 1-6 | 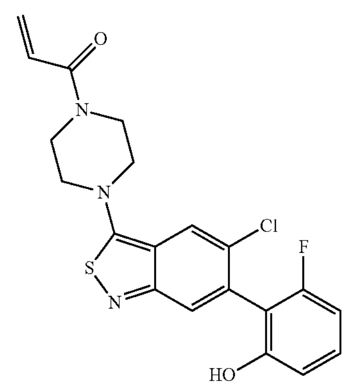 [SMILES: C=CC(=O)N1CCN(c2snc3cc(-c4c(O)cccc4F)c(Cl)cc23)CC1] | 1-(4-(5-chloro-6-(2-fluoro-6-hydroxyphenyl)-2,1-benzothiazol-3-yl)-1-piperazinyl)-2-propen-1-one | — | Step 7: (2-fluoro-6-methoxyphenyl) boronic acid, $Cs_2CO_3$, 100° C., Step 8-1: TFA/DCM |
| 1-7 | 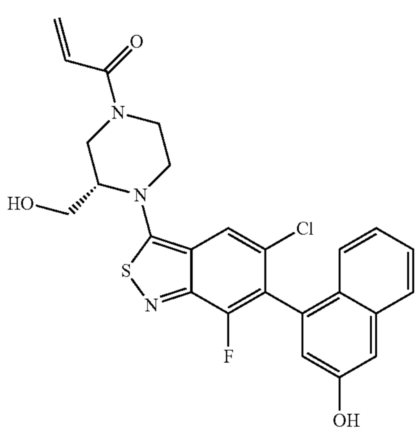 [SMILES: C=CC(=O)N1CCN(c2snc3c(F)c(-c4cc(O)cc5ccccc45)c(Cl)cc23)[C@H](CO)C1] | 1-((3R)-4-(5-chloro-7-fluoro-6-(3-hydroxy-1-naphthalenyl)-2,1-benzothiazol-3-yl)-3-(hydroxymethyl)-1-piperazinyl)-2-propen-1-one | — | Step 6: (3R)-1-(tert-butoxycarbonyl)-3-(hydroxymethyl) piperazine (Synthonix Inc., Wake Forest, NC, USA), Step 7: (3-methoxynaphthalen-1-yl)boronic acid (Ark Pharm Inc. Arlington Heights, IL, USA), Step 8-1: TFA/DCM |

TABLE 1(b)-continued

Compounds 1-2 to 1-28 were prepared following the procedure described in Method 1, Steps 1-8, above as follows:

| Ex.# | Chemical Structure | Name | Method changes | Reagent |
|---|---|---|---|---|
| 1-8 | 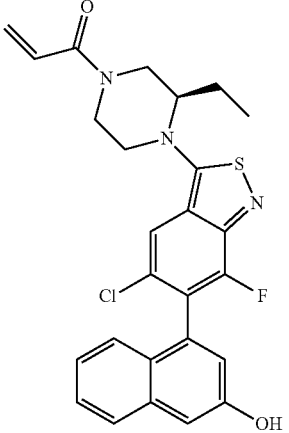 [SMILES: C=CC(=O)N1CCN(c2snc3c(F)c(-c4cc(O)cc5ccccc45)c(Cl)cc23)[C@H](CC)C1] | 1-4-(5-chloro-7-fluoro-6-(3-hydroxy-1-naphthalenyl)-2,1-benzothiazol-3-yl)-3-ethyl-1-piperazinyl)-2-propen-1-one | — | Step 6: tert-butyl 3-ethylpiperazine-1-carboxylate (Accel Pharmtech LLC, East Brunswick, NJ, USA), Step 7: (3-methoxynaphthalen-1-yl)boronic acid (Ark Pharm Inc. Arlington Heights, IL, USA), Step 8-1: TFA/DCM |
| 1-9 | 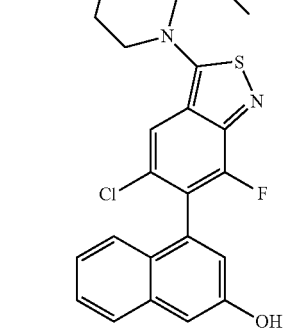 | N-(1-(5-chloro-7-fluoro-6-(3-hydroxy-1-naphthalenyl)-2,1-benzothiazol-3-yl)-2-methyl-3-azetidinyl)-2-propenamide | — | Step 6: tert-butyl (2-methylazetidin-3-yl)carbamate (pharmaBlock Nanjing, China), Step 7: (3-methoxynaphthalen-1-yl)boronic acid (Ark Pharm Inc. Arlington Heights, IL, USA), Step 8-1: TFA/DCM |

TABLE 1(b)-continued

Compounds 1-2 to 1-28 were prepared following the procedure described in
Method 1, Steps 1-8, above as follows:

| Ex.# | Chemical Structure | Name | Method changes | Reagent |
|------|--------------------|------|----------------|---------|

TABLE 1(b)-continued

Compounds 1-2 to 1-28 were prepared following the procedure described in Method 1, Steps 1-8, above as follows:

| Ex.# | Chemical Structure | Name | Method changes | Reagent |
|---|---|---|---|---|
| 1-10 | 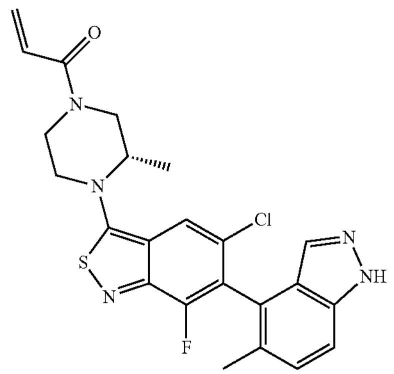 [SMILES: C=CC(=O)N1CCN(c2snc3c(F)c(-c4c(C)ccc5[nH]ncc45)c(Cl)cc23)[C@@H](C)C1] | 1-((3S)-4-(5-chloro-7-fluoro-6-(5-methyl-1H-indazol-4-yl)-2,1-benzothiazol-3-yl)-3-methyl-1-piperazinyl)-2-propen-1-one | Omit step 8-3 | Step 6: (S)-4-n-boc-2-methyl piperazine (CNH Technologies, Inc., Woburn, MA, USA), Step 7: 4-borono-5-methyl-1h-indazole (Ark Pharm Inc. Arlington Heights, IL, USA.), Step 8-1: TFA/DCM |
| 1-11 | 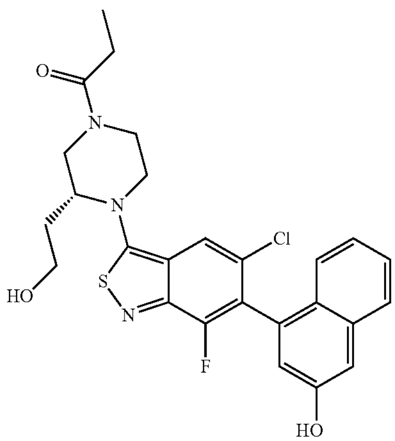 [SMILES: CCC(=O)N1CCN(c2snc3c(F)c(-c4cc(O)cc5ccccc45)c(Cl)cc23)[C@H](CCO)C1] | 1-((3S)-4-(5-chloro-7-fluoro-6-(3-hydroxy-1-naphthalenyl)-2,1-benzothiazol-3-yl)-3-(2-hydroxyethyl)-1-piperazinyl)-2-propen-1-one | — | Step 6: (S)-tert-butyl 3-(2-hydroxyethyl) piperazine-1-carboxylate (Activate Scientific GmbH, Prien, Germany), Step 7: (3-methoxynaphthalen-1-yl)boronic acid (Ark Pharm Inc. Arlington Heights, IL, USA), Step 8-1: TFA/DCM |
| 1-12 | 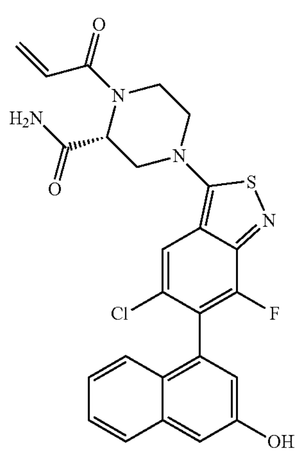 [SMILES: C=CC(=O)N1CCN(c2snc3c(F)c(-c4cc(O)cc5ccccc45)c(Cl)cc23)C[C@@H]1C(N)=O] | 4-(5-chloro-7-fluoro-6-(3-hydroxy-1-naphthalenyl)-2,1-benzothiazol-3-yl)-1-(2-propenoyl)-2-piperazinecarboxamide | — | Step 6: piperazine-2-carboxamide (Enamine, Kiev, Ukraine), Step 7: (3-methoxynaphthalen-1-yl)boronic acid (Ark Pharm Inc. Arlington Heights, IL, USA), Step 8-1: TFA/DCM |

TABLE 1(b)-continued

Compounds 1-2 to 1-28 were prepared following the procedure described in Method 1, Steps 1-8, above as follows:

| Ex.# | Chemical Structure | Name | Method changes | Reagent |
|---|---|---|---|---|
| | 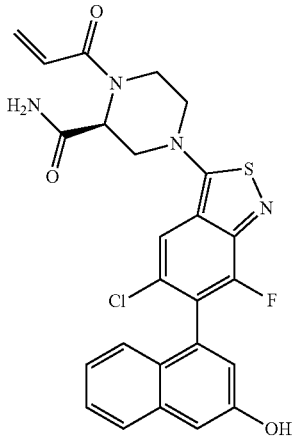 | | | |
| 1-13 | 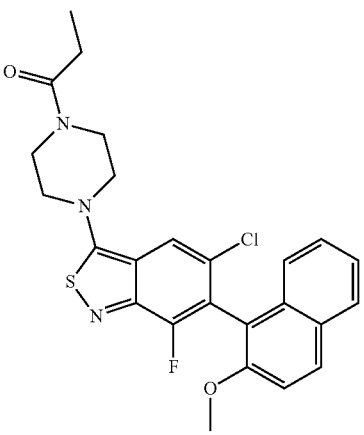 [SMILES: CCC(=O)N1CCN(c2snc3c(F)c(-c4c(OC)ccc5ccccc45)c(Cl)cc23)CC1] | 1-(4-(5-chloro-7-fluoro-6-(2-methoxy-1-naphthalenyl)-2,1-benzothiazol-3-yl)-1-piperazinyl)-2-propen-1-one | Omit step 8-3 | Step 7: (2-methoxynaphthalen-1-yl)boronic acid, Cs$_2$CO$_3$, 100° C., Step 8-1: TFA/DCM |
| 1-14 | 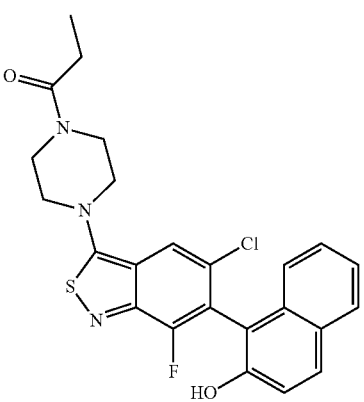 [SMILES: CCC(=O)N1CCN(c2snc3c(F)c(-c4c(O)ccc5ccccc45)c(Cl)cc23)CC1] | 1-(4-(5-chloro-7-fluoro-6-(2-hydroxy-1-naphthalenyl)-2,1-benzothiazol-3-yl)-1-piperazinyl)-2-propen-1-one | — | Step 7: (2-methoxynaphthalen-1-yl)boronic acid, Cs$_2$CO$_3$, 100° C., Step 8-1: TFA/DCM |

TABLE 1(b)-continued

Compounds 1-2 to 1-28 were prepared following the procedure described in Method 1, Steps 1-8, above as follows:

| Ex.# | Chemical Structure | Name | Method changes | Reagent |
|---|---|---|---|---|
| 1-15 | 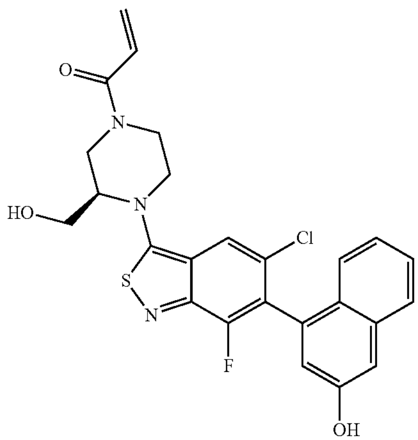 [SMILES: C=CC(=O)N1CCN(c2snc3c(F)c(-c4cc(O)cc5ccccc45)c(Cl)cc23)[C@@H](CO)C1] | 1-((3S)-4-(5-chloro-7-fluoro-6-(3-hydroxy-1-naphthalenyl)-2,1-benzothiazol-3-yl)-3-(hydroxymethyl)-1-piperazinyl)-2-propen-1-one | — | Step 6: (3S)-1-boc-3-(hydroxymethyl)-piperazine (Combi-blocks Inc., San Diego, CA, USA), Step 7: (3-methoxynaphthalen-1-yl)boronic acid, Step 8-1: TFA/DCM |
| 1-16 | 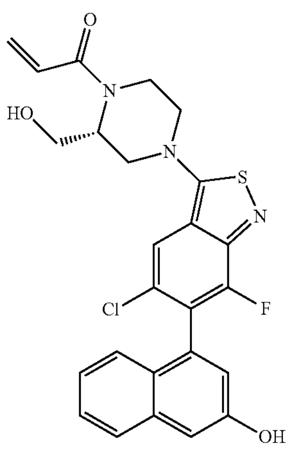 [SMILES: C=CC(=O)N1CCN(c2snc3c(F)c(-c4cc(O)cc5ccccc45)c(Cl)cc23)C[C@@H]1CO] | 1-(4-(5-chloro-7-fluoro-6-(3-hydroxy-1-naphthalenyl)-2,1-benzothiazol-3-yl)-2-(hydroxymethyl)-1-piperazinyl)-2-propen-1-one | — | Step 6: tert-butyl 3-(((tert-butyldimethylsilyl)oxy)methyl)piperazine-1-carboxylate[i], Step 7: (3-methoxynaphthalen-1-yl)boronic acid, Step 8-1: TFA/DCM |

TABLE 1(b)-continued

Compounds 1-2 to 1-28 were prepared following the procedure described in
Method 1, Steps 1-8, above as follows:

| Ex.# | Chemical Structure | Name | Method changes | Reagent |
|---|---|---|---|---|
| 1-17 | 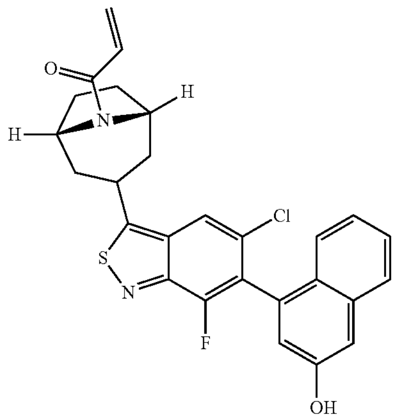 [SMILES: C=CC(=O)N1[C@@H]2CC[C@H]1CC(c1snc3c(F)c(-c4cc(O)cc5ccccc45)c(Cl)cc13)C2] | 1-((1R,5S)-3-(5-chloro-7-fluoro-6-(3-hydroxy-1-naphthalenyl)-2,1-benzothiazol-3-yl)-3,8-diazabicyclo[3.2.1]octan-8-yl)-2-propen-1-one | — | Step 6: 8-boc-3,8-diazabicyclo[3.2.1]octane (Chem-Impex International, Inc. Wood Dale, IL, USA), Step 7: (3-methoxynaphthalen-1-yl)boronic acid (Ark Pharm Inc. Arlington Heights, IL, USA), Step 8-1: TFA/DCM |
| 1-18 | | 1-(4-(5-chloro-7-fluoro-6-(3-hydroxy-1-naphthalenyl)-2,1-benzothiazol-3-yl)-3-(hydroxymethyl)-1-piperazinyl)-2-propen-1-one | — | Step 6: 4-n-boc-2-hydroxymethyl-piperazine (AstaTech, Inc., Bristol PA, USA), Step 7: (3-methoxynaphthalen-1-yl)boronic acid (Ark Pharm Inc. Arlington Heights, IL, USA), Step 8-1: TFA/DCM |

TABLE 1(b)-continued

Compounds 1-2 to 1-28 were prepared following the procedure described in Method 1, Steps 1-8, above as follows:

| Ex.# | Chemical Structure | Name | Method changes | Reagent |
|---|---|---|---|---|
| 1-19 | 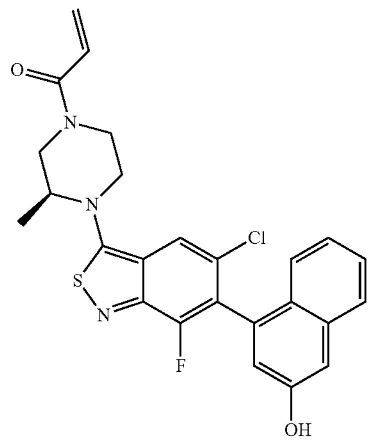 [SMILES: C=CC(=O)N1CCN(c2snc3c(F)c(-c4cc(O)cc5ccccc45)c(Cl)cc23)[C@@H](C)C1] | 1-((3S)-4-(5-chloro-7-fluoro-6-(3-hydroxy-1-naphthalenyl)-2,1-benzothiazol-3-yl)-3-methyl-1-piperazinyl)-2-propen-1-one | — | Step 6: (S)-4-n-boc-2-methyl piperazine (CNH Technologies, Inc., Woburn, MA, USA), Step 7: (3-methoxynaphthalen-1-yl)boronic acid (Ark Pharm Inc. Arlington Heights, IL, USA), Step 8-1: TFA/DCM |
| 1-20 | 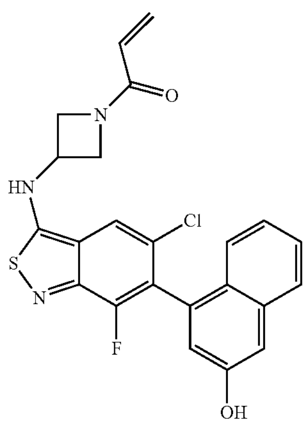 [SMILES: C=CC(=O)N1CC(Nc2snc3c(F)c(-c4cc(O)cc5ccccc45)c(Cl)cc23)C1] | 1-(3-((5-chloro-7-fluoro-6-(3-hydroxy-1-naphthalenyl)-2,1-benzothiazol-3-yl)amino)-1-azetidinyl)-2-propen-1-one | — | Step 6: 1-boc-3-aminoazetidine (Alfa Aesar, Haver Hill, MA, USA), Step 7: (3-methoxynaphthalen-1-yl)boronic acid (Ark Pharm Inc. Arlington Heights, IL, USA), Step 8-1: TFA/DCM |
| 1-21 | 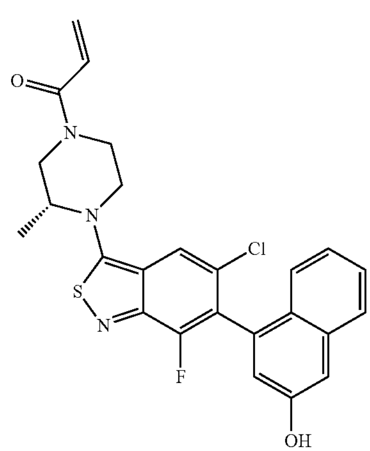 [SMILES: C=CC(=O)N1CCN(c2snc3c(F)c(-c4cc(O)cc5ccccc45)c(Cl)cc23)[C@H](C)C1] | 1-((3R)-4-(5-chloro-7-fluoro-6-(3-hydroxy-1-naphthalenyl)-2,1-benzothiazol-3-yl)-3-methyl-1-piperazinyl)-2-propen-1-one | — | Step 6: (R)-4-n-boc-2-methyl-piperazine (CNH Technologies, Inc., Woburn, MA, USA), Step 7: (3-methoxynaphthalen-1-yl)boronic acid (Ark Pharm Inc. Arlington Heights, IL, USA), Step 8-1: TFA/DCM |

TABLE 1(b)-continued

Compounds 1-2 to 1-28 were prepared following the procedure described in Method 1, Steps 1-8, above as follows:

| Ex.# | Chemical Structure | Name | Method changes | Reagent |
|---|---|---|---|---|
| 1-22 | 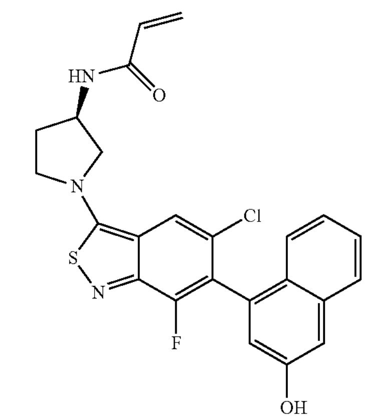 [SMILES: C=CC(=O)N[C@@H]1CCN(c2snc3c(F)c(-c4cc(O)cc5ccccc45)c(Cl)cc23)C1] | N-((3R)-1-(5-chloro-7-fluoro-6-(3-hydroxy-1-naphthalenyl)-2,1-benzothiazol-3-yl)-3-pyrrolidinyl)-2-propenamide | | Step 6: (3R)-(−)-3-tert-butoxycarbonyl-amino pyrrolidine (Oakwood Products, Inc. Estill, SC, USA), Step 7: (3-methoxynaphthalen-1-yl)boronic acid (Ark Pharm Inc. Arlington Heights, IL, USA), Step 8-1: TFA/DCM |
| 1-23 | 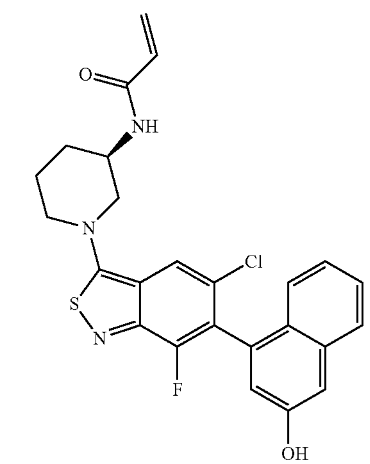 [SMILES: C=CC(=O)N[C@@H]1CCCN(c2snc3c(F)c(-c4cc(O)cc5ccccc45)c(Cl)cc23)C1] | N-((3R)-1-(5-chloro-7-fluoro-6-(3-hydroxy-1-naphthalenyl)-2,1-benzothiazol-3-yl)-3-piperidinyl)-2-propenamide | | Step 6: (R)-tert-butyl piperidin-3-ylcarbamate (Combi-blocks Inc., San Diego, CA, USA), Step 7: (3-methoxynaphthalen-1-yl)boronic acid (Ark Pharm Inc. Arlington Heights, IL, USA), Step 8-1: TFA/DCM |
| 1-28 | 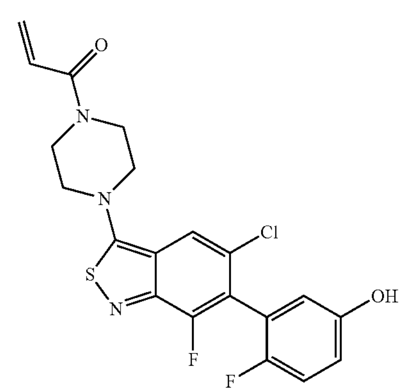 [SMILES: C=CC(=O)N1CCN(c2snc3c(F)c(-c4cc(O)ccc4F)c(Cl)cc23)CC1] | 1-(4-(5-chloro-7-fluoro-6-(2-fluoro-5-hydroxyphenyl)benzo[c]isothiazol-3-yl)piperazin-1-yl)prop-2-en-1-one | | Step 7: (2-fluoro-5-methoxyphenyl)boronic acid (Combi-blocks Inc., San Diego, CA, USA), $K_2CO_3$, Pd(DPPF)$Cl_2$•DCM, 100° C. Step 8-1: TFA/DCM |

243
Method 2
Example 2-1: 1-(4-(5-chloro-6-(3-hydroxy-1-naphthalenyl) [1,2]thiazolo[3,4-b]pyridin-3-yl)-1-piperazinyl)-2-propen-1-one
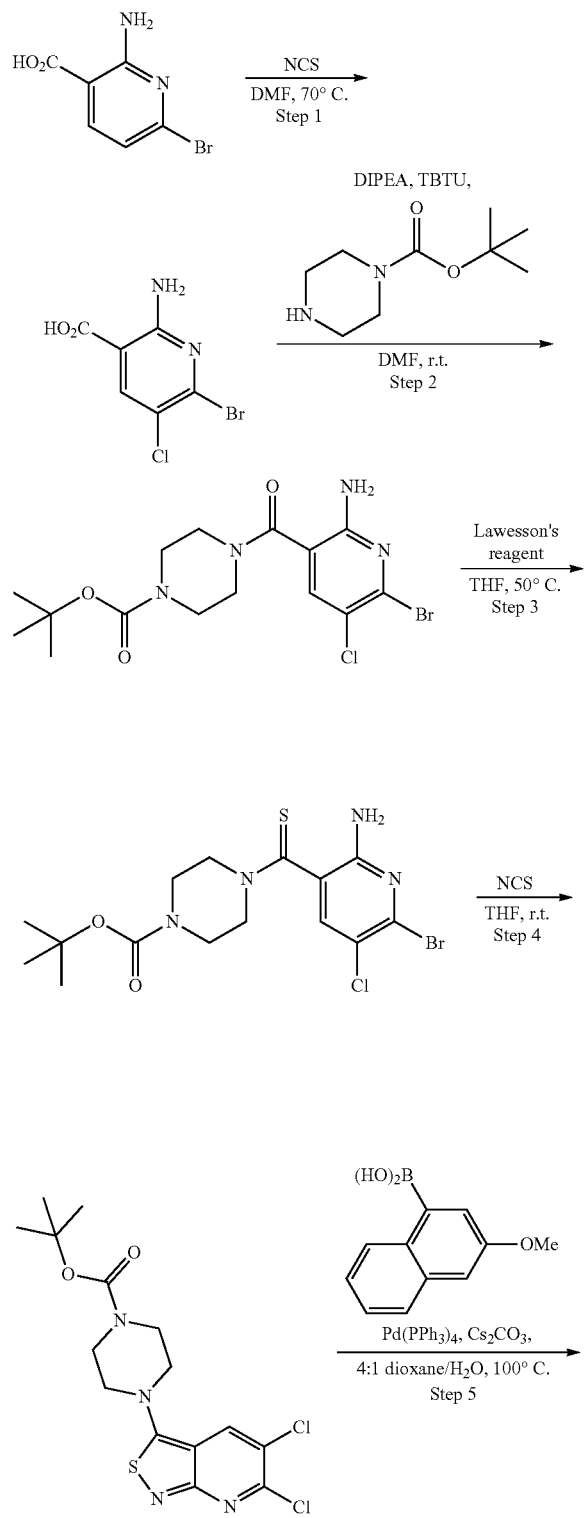
244
-continued
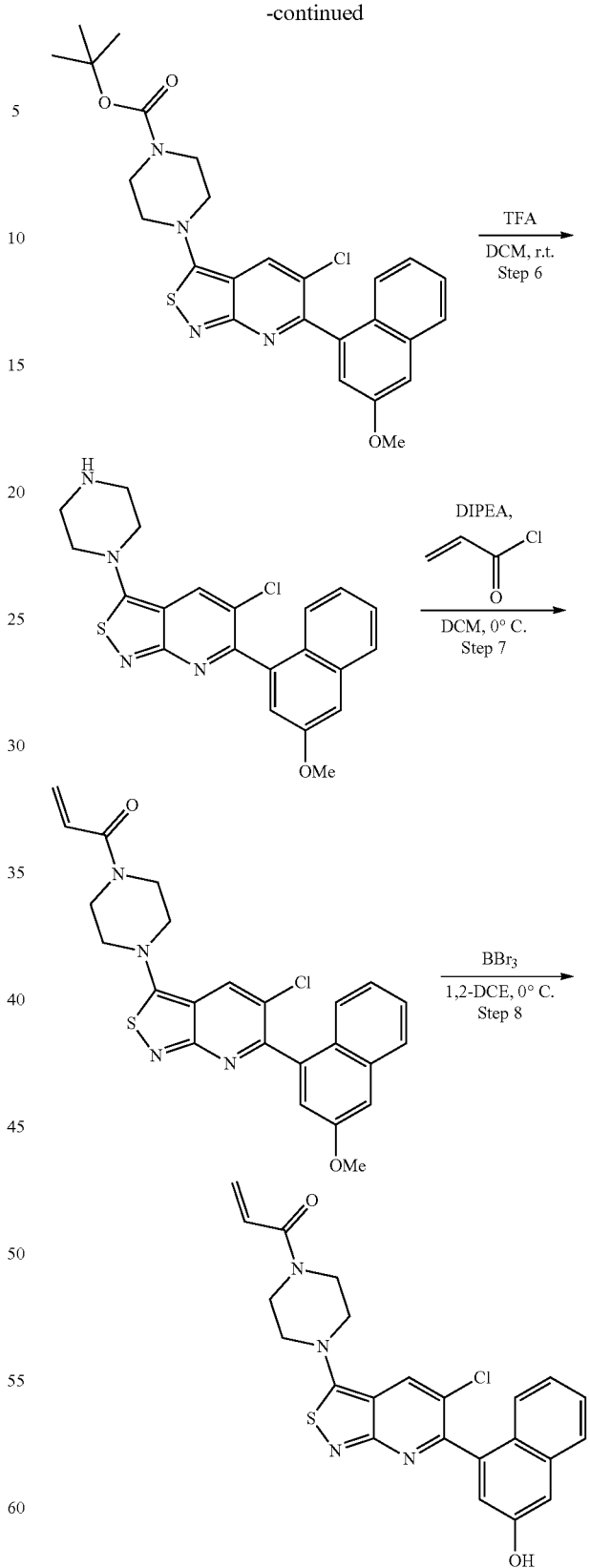
Step 1: 2-Amino-6-bromo-5-chloronicotinic acid. N-Chlorosuccinimide (2.78 g, 20.8 mmol) was added to a solution of 2-amino-6-bromonicotinic acid (4.51 g, 20.8 mmol, Ark Pharm Inc. Arlington Heights, IL, USA) in DMF (75 mL), and the resulting mixture was heated at 70° C. for 2.5 h. Heating was then stopped, and stirring was continued for 16 h. The reaction mixture was subsequently poured into ice water. After the ice had melted, the resulting slurry was filtered through a fritted glass funnel. The collected solids were air-dried, providing 2-amino-6-bromo-5-chloronicotinic acid: $^1$H NMR (400 MHz, DMSO-$d_6$) δ 8.05 (s, 1H), 7.64 (br. s, 2H). m/z (ESI, +ve) 250.9 (M+H)$^+$.

Step 2: tert-Butyl 4-(2-amino-6-bromo-5-chloronicotinoyl)piperazine-1-carboxylate. To a solution of 2-amino-6-bromo-5-chloronicotinic acid (1.12 g, 4.5 mmol) in DMF (14 mL) was added TBTU (1.93 g, 6.0 mmol). After 5 min, the reaction was sequentially treated with 1-Boc-piperazine (912 mg, 4.9 mmol) and DIPEA (2.33 mL, 13.4 mmol). The resulting solution was stirred at rt for 25 h, saturated aqueous NaHCO$_3$ solution (75 mL) was added, and the resulting mixture was extracted with DCM. The organic layer was separated and sequentially washed with water (2×), dried over anhydrous sodium sulfate, and concentrated in vacuo. Chromatographic purification of the residue (silica gel, 0 to 7% MeOH in DCM) furnished tert-butyl 4-(2-amino-6-bromo-5-chloronicotinoyl)piperazine-1-carboxylate: $^1$H NMR (400 MHz, DMSO-$d_6$) δ 7.58 (s, 1H), 6.66 (s, 2H), 3.33 (s, 8H), 1.40 (s, 9H). m/z (ESI, +ve) 419.0 (M+H)$^+$.

Step 3: tert-Butyl 4-(2-amino-6-bromo-5-chloropyridine-3-carbonothioyl)piperazine-1-carboxylate. Lawesson's reagent (353 mg, 0.87 mmol) was added to a solution of tert-butyl 4-(2-amino-6-bromo-5-chloronicotinoyl)piperazine-1-carboxylate (610 mg, 1.45 mmol) in THF (7.5 mL), and the resulting solution was stirred as 50° C. for 2.5 h. The reaction mixture was then allowed to cool to rt and sequentially treated with water (10 mL) and aqueous 1 N HCl (4 mL). The resulting mixture was extracted with EtOAc (2×), and the combined extracts were dried over anhydrous sodium sulfate, filtered, and concentrated in vacuo. Chromatographic purification of the residue (silica gel, 0-6% MeOH in DCM) provided tert-butyl 4-(2-amino-6-bromo-5-chloropyridine-3-carbonothioyl)piperazine-1-carboxylate: $^1$H NMR (400 MHz, DMSO-$d_6$) δ 7.47 (s, 1H), 6.58 (hr. s, 2H), 4.30 (ddd, J=13.3, 6.3, 3.3 Hz, 1H), 4.01-4.13 (m, 2H), 3.68-3.77 (m, 1H), 3.51-3.59 (m, 1H), 3.40-3.50 (m, 3H), 1.41 (s, 9H). m/z (ESI, +ve) 434.9 (M+H)$^+$.

Step 4: tert-Butyl 4-(5,6-dichloroisothiazolo[3,4-b]pyridin-3-yl)piperazine-1-carboxylate. NCS (116 mg, 0.87 mmol) was added to a solution of tert-butyl 4-(2-amino-6-bromo-5-chloropyridine-3-carbonothioyl)piperazine-1-carboxylate (343 mg, 0.79 mmol) in THF (8 mL), and the resulting solution was stirred at rt for 20 min. A mixture of water (10 mL) and 1 M aqueous sodium sulfite (5 mL) was then added, and the resulting mixture was extracted with EtOAc (2×). The combined extracts were dried over anhydrous sodium sulfate, filtered, and concentrated in vacuo. Chromatographic purification of the residue (silica gel, 0 to 4% MeOH in DCM) provided tert-butyl 4-(5,6-dichloroisothiazolo[3,4-b]pyridin-3-yl)piperazine-1-carboxylate: $^1$H NMR (400 MHz, CHLOROFORM-d) δ 8.10 (s, 1H), 3.69-3.80 (m, 4H), 3.50-3.57 (m, 4H), 1.51 (s, 9H). m/z (ESI, +ve) 389.0 (M+H)$^+$.

Step 5: tert-Butyl 4-(5-chloro-6-(3-methoxynaphthalen-1-yl)isothiazolo[3,4-b]pyridin-3-yl)piperazine-1-carboxylate. A mixture of tert-butyl 4-(5,6-dichloroisothiazolo[3,4-b]pyridin-3-yl)piperazine-1-carboxylate (154 mg, 0.36 mmol), (3-methoxynaphthalen-1-yl)boronic acid (287 mg, 1.42 mmol), and cesium carbonate (463 mg, 1.42 mmol) in 1,4-dioxane (8 mL) and water (2 mL) was sparged with argon before adding tetrakis(triphenylphosphine)palladium (41 mg, 0.04 mmol). The reaction mixture was again sparged with argon, then heated in a sealed tube at 100° C. for 25 h. After cooling to rt, the reaction mixture was diluted with brine (40 mL) and extracted with EtOAc (2×). The combined extracts were dried over sodium sulfate, filtered, and concentrated in vacuo. Chromatographic purification of the residue (silica gel, 0-3.5% MeOH in DCM) gave tert-butyl 4-(5-chloro-6-(3-methoxynaphthalen-1-yl)isothiazolo[3,4-b]pyridin-3-yl)piperazine-1-carboxylate: in z (ESI, +ve) 511.1 (M+H)$^+$.

Step 6: 5-Chloro-6-(3-methoxynaphthalen-1-yl)-3-(piperazin-1-yl)isothiazolo[3,4-b]pyridine. Trifluoroacetic acid (560 μL, 7.6 mmol) was added to a solution of tert-butyl 4-(5-chloro-6-(3-methoxynaphthalen-1-yl)isothiazolo[3,4-b]pyridin-3-yl)piperazine-1-carboxylate (155 mg, 0.30 mmol) in DCM (6 mL), and the resulting solution was stirred at rt for 2.3 h, then concentrated in vacuo. Chromatographic purification of the residue (silica gel, 0-25% MeOH in DCM) furnished 5-chloro-6-(3-methoxynaphthalen-1-yl)-3-(piperazin-1-yl)isothiazolo[3,4-b]pyridine as a TEA salt: $^1$H NMR (400 MHz, DMSO-$d_6$) δ 8.78 (s, 1H), 7.94 (d, J=8.2 Hz, 1H), 7.46-7.53 (m, 2H), 7.31 (d, J=3.7 Hz, 2H), 7.19 (d, J=2.4 Hz, 1H), 3.95 (s, 3H), 3.76-3.83 (m, 4H), 3.35-3.43 (m, 4H). m/z (ESI, +ve) 411.0 (M+H)$^+$.

Step 7: 1-(4-(5-Chloro-6-(3-methoxy-1-naphthalenyl)[1,2]thiazolo[3,4-b]pyridin-3-yl)-1-piperazinyl)-2-propen-1-one. To an ice-cooled slurry of 5-chloro-6-(3-methoxynaphthalen-1-yl)-3-(piperazin-1-yl)isothiazolo[3,4-b]pyridine (TEA salt; 100 mg, 0.19 mmol) in DCM (5 mL) was sequentially added DIPEA (100 μL, 0.57 mmol) and acryloyl chloride (23 μL, 0.29 mmol). The resulting solution was stirred at 0° C. for 70 min, and saturated aqueous NaHCO$_3$ solution (15 mL) was added. The resulting mixture was extracted with DCM (3×), and the combined extracts were dried over sodium sulfate, filtered, and concentrated in vacuo. Chromatographic purification of the residue (silica gel, 0 to 7% MeOH in DCM) provided 1-(4-(5-chloro-6-(3-methoxy-1-naphthalenyl)[1,2]thiazolo[3,4-b]pyridin-3-yl)-1-piperazinyl)-2-propen-1-one: $^1$H NMR (400 MHz, DMSO-$d_6$) δ 8.73 (s, 1H), 7.93 (d, J=8.2 Hz, 1H), 7.45-7.54 (m, 2H), 7.25-7.39 (m, 2H), 7.19 (d, j=2.5 Hz, 1H), 6.86 (dd, J=16.7, 10.3 Hz, 1H), 6.19 (dd, J=16.7, 2.3 Hz, 1H), 5.77 (dd, J=10.5, 2.3 Hz, 1H), 3.94 (s, 3H), 3.81-3.94 (m, 4H), 3.69-3.76 (m, 4H). m/z (ESI, +ve) 465.0 (M+H)$^+$.

Step 8: 1-(4-(5-Chloro-6-(3-hydroxy-1-naphthalenyl)[1,2]thiazolo[3,4-b]pyridin-3-yl)-1-piperazinyl)-2-propen-1-one. Boron tribromide (1.0 M in hexanes, 400 μL, 0.40 mmol) was added (dropwise) to an ice-cooled solution of 1-(4-(5-chloro-6-(3-methoxynaphthalen-1-yl)isothiazolo[3,4-b]pyridin-3-yl)piperazin-1-yl)prop-2-en-1-one (37.3 mg, 0.08 mmol) in 1,2-dichloroethane (4 mL), and the resulting mixture was stirred at 0° C. for 2.3 h. Saturated aqueous NaHCO$_3$ solution (5 mL) was then added, and the resulting mixture was extracted with (4:1) DCM:MeOH (2×). The combined extracts were dried over sodium sulfate, filtered, and concentrated in vacuo. Chromatographic purification of the residue (silica gel, 0-6% MeOH in DCM) provided 1-(4-(5-chloro-6-(3-hydroxy-1-naphthalenyl)[1,2]thiazolo[3,4-b]pyridin-3-yl)-1-piperazinyl)-2-propen-1-one: $^1$H NMR (400 MHz, DMSO-$d_6$) δ 9.97 (hr. s, 1H), 8.72 (s, 1H), 7.79 (d, J=8.6 Hz, 1H), 7.42 (t, J=7.1 Hz, 1H), 7.17-7.28 (m, 3H), 7.09 (d, 0.7=2.1 Hz, 1H), 6.86 (dd, J=16.7, 10.5 Hz, 1H), 6.19 (dd, J=16.7, 2.3 Hz, 1H), 5.74-5.79 (m, 1H), 3.81-3.95 (m, 4H), 3.68-3.76 (m, 4H). m/z (ESI, +ve) 451.0 (M+H)$^+$.

TABLE 2

Compounds 2-2 to 2-6 were prepared following the procedure described in Method 2, Steps 1-8, above as follows:

| Ex.# | Chemical Structure | Name | Method changes | Reagents |
|---|---|---|---|---|
| 2-2 | 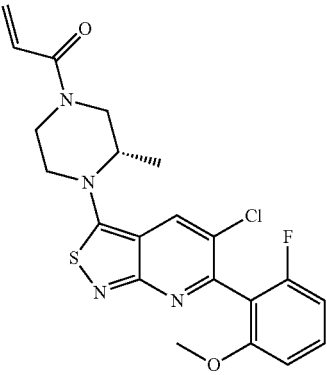 [SMILES: C=CC(=O)N1CCN(c2snc3nc(-c4c(F)cccc4OC)c(Cl)cc23)[C@@H](C)C1]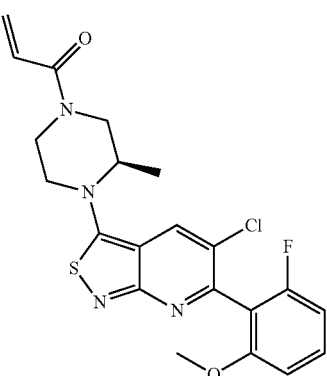 | 1-(4-(5-chloro-6-(2-fluoro-6-methoxyphenyl)[1,2]thiazolo[3,4-b]pyridin-3-yl)-3-methyl-1-piperazinyl)-2-propen-1-one | Omit Step 8 | Step 2: 1-Boc-3-methylpiperazine (Accela ChemBio Inc. San Diego, CA, USA), Step 4: N-bromosuccinimide, Step 5: 2-fluoro-6-methoxyphenyl boronic acid |
| 2-3 | 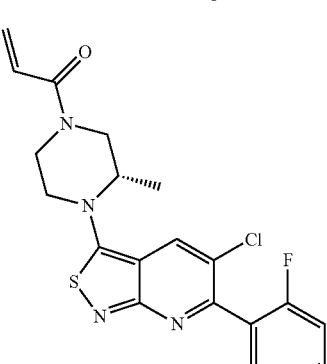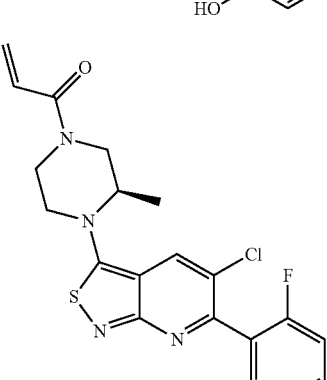 | 1-(4-(5-chloro-6-(2-fluoro-6-hydroxyphenyl)[1,2]thiazolo[2,3-b]pyridin-3-yl)-3-methyl-1-piperazinyl)-2-propen-1-one | — | Step 2: 1-Boc-3-methylpiperazine (Accela ChemBio Inc. San Diego, CA, USA), Step 4: N-bromosuccinimide, Step 5: 2-fluoro-6-methoxyphenyl boronic acid |

TABLE 2-continued

Compounds 2-2 to 2-6 were prepared following the procedure described in Method 2, Steps 1-8, above as follows:

| Ex.# | Chemical Structure | Name | Method changes | Reagents |
|---|---|---|---|---|
| 2-4 | 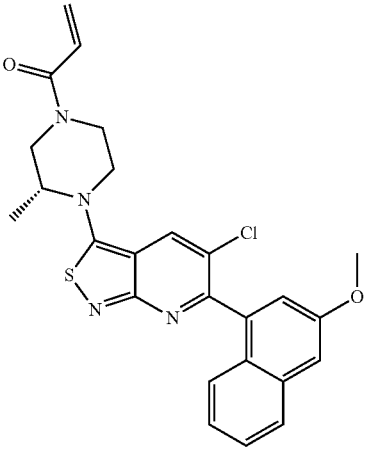 [SMILES: C=CC(=O)N1CCN(c2snc3nc(-c4cc(OC)cc5ccccc45)c(Cl)cc23)[C@H](C)C1] | 1-(4-(5-chloro-6-(3-methoxy-1-naphthalenyl)[1,2]thiazolo[3,4-b]pyridin-3-yl)-3-methyl-1-piperazinyl)-2-propen-1-one | Omit Step 8 | Step 2: 1-Boc-3-methylpiperazine (Accela ChemBio Inc. San Diego, CA, USA), Step 4: N-bromosuccinimide |
| 2-5 | 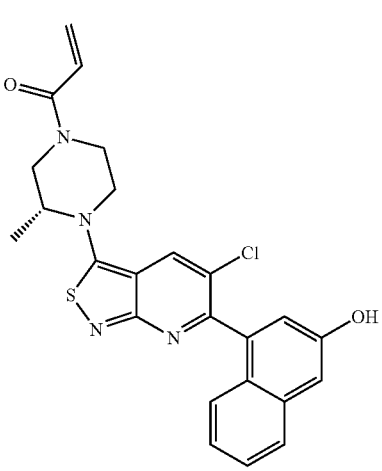 [SMILES: C=CC(=O)N1CCN(c2snc3nc(-c4cc(O)cc5ccccc45)c(Cl)cc23)[C@H](C)C1] | 1-(4-(5-chloro-6-(3-hydroxy-1-naphthalenyl)[1,2]thiazolo[3,4-b]pyridin-3-yl)-3-methyl-1-piperazinyl)-2-propen-1-one | — | Step 2: 1-Boc-3-methylpiperazine (Accela ChemBio Inc. San Diego, CA, USA), Step 4: N-bromosuccinimide |

TABLE 2-continued

Compounds 2-2 to 2-6 were prepared following the procedure described in Method 2, Steps 1-8, above as follows:

| Ex.# | Chemical Structure | Name | Method changes | Reagents |
|---|---|---|---|---|
| | 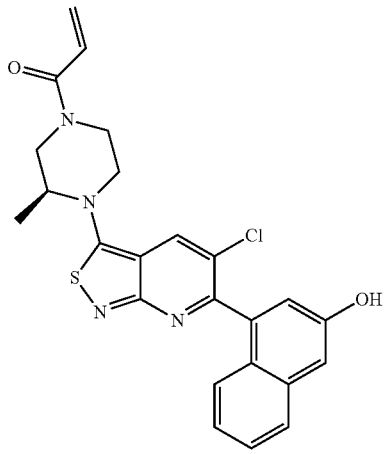 [SMILES: C=CC(=O)N1CCN(c2snc3nc(-c4cc(O)cc5ccccc45)c(Cl)cc23)[C@@H](C)C1] | | | |
| 2-6 | 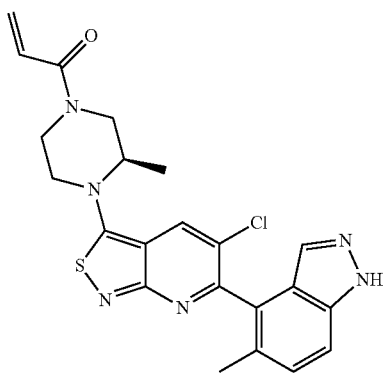 [SMILES: C=CC(=O)N1CCN(c2snc3nc(-c4c(C)ccc5[nH]ncc45)c(Cl)cc23)[C@H](C)C1] | 1-(4-(5-chloro-6-(5-methyl-1H-indazol-4-yl)[1,2]thiazolo[3,4-b]pyridin-3-yl)-3-methyl-1-piperazinyl)-2-propen-1-one | Omit Step 8 | Step 2: 1-Boc-3-methylpiperazine (Accela ChemBio Inc. San Diego, CA, USA), Step 4: N-bromosuccinimide Step 5: 4-borono-5-methyl-1h-indazole (Ark Pharm Inc. Arlington Heights, IL, USA) |

TABLE 2-continued

Compounds 2-2 to 2-6 were prepared following the procedure described in Method 2, Steps 1-8, above as follows:

| Ex.# | Chemical Structure | Name | Method changes | Reagents |
|---|---|---|---|---|
| 2-7 | 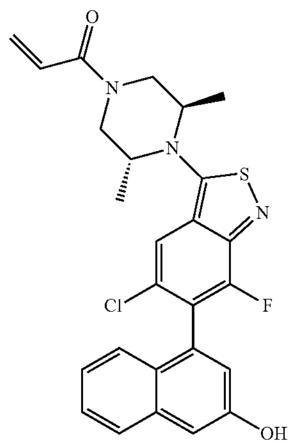 [SMILES: C=CC(=O)N1C[C@@H](C)N(c2snc3c(F)c(-c4cc(O)cc5ccccc45)c(Cl)cc23)[C@H](C)C1] | 1-(4-(5-chloro-7-fluoro-6-(3-hydroxy-1-naphthalenyl)-2,1-benzothiazol-3-yl)-3,5-dimethyl-1-piperazinyl)-2-propen-1-one | — | Step 1: 2-amino-4-bromo-3-fluorobenzoic acid (Apollo Scientific Ltd., Stockport, UK), Step 2: 1-boc-3,5-dimethylpiperazine (Combi-blocks Inc., San Diego, CA, USA), Step 7: (3-methoxynaphthalen-1-yl)boronic acid (Ark Pharm Inc. Arlington Heights, IL, USA), Step 8-1: TFA/DCM |

TABLE 2-continued

Compounds 2-2 to 2-6 were prepared following the procedure described in Method 2, Steps 1-8, above as follows:

| Ex.# | Chemical Structure | Name | Method changes | Reagents |
|---|---|---|---|---|
| 2-8 | 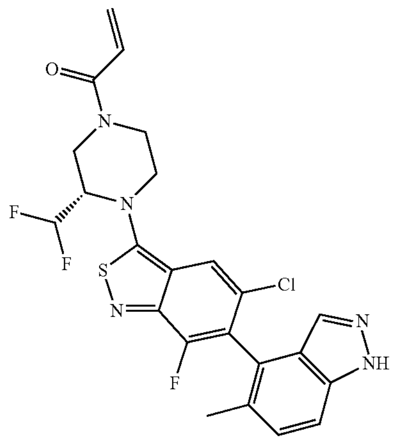 [SMILES: C=CC(=O)N1CCN(c2snc3c(F)c(-c4c(C)ccc5[nH]ncc45)c(Cl)cc23)[C@H](C(F)F)C1] | 1-(4-(5-chloro-7-fluoro-6-(5-methyl-1H-indazol-4-yl)-2,1-benzothiazol-3-yl)-3-(difluoromethyl)-1-piperazinyl)-2-propen-1-one | — | Step 1: 2-amino-4-bromo-3-fluorobenzoic acid (Apollo Scientific Ltd., Stockport, UK), Step 2: tert-butyl 3-(difluoromethyl)piperazine-1-carboxylate (Enamine, Kiev, Ukraine), Step 7: (5-methyl-1H-indazol-4-yl)boronic acid (Combi-Blocks, Inc.), Step 8-1: TFA/DCM |
| | | | | |
| 2-9 | 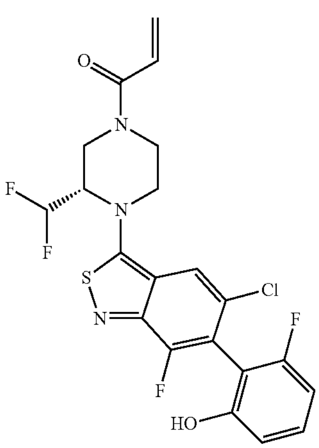 [SMILES: C=CC(=O)N1CCN(c2snc3c(F)c(-c4c(O)cccc4F)c(Cl)cc23)[C@H](C(F)F)C1] | 1-(4-(5-chloro-7-fluoro-6-(2-fluoro-6-hydroxyphenyl)-2,1-benzothiazol-3-yl)-3-(difluoromethyl)-1-piperazinyl)-2-propen-1-one | Step 8-3 performed prior to steps 8-2 | Step 1: 2-amino-4-bromo-3-fluorobenzoic acid (Apollo Scieentific Ltd., Stockport, UK), Step 2: tert-butyl 3-(difluoromethyl)piperazine-1-carboxylate (Enamine, Kiev, Ukraine), Step 7: 2-fluoro-6-methoxy-phenylboronic acid (Accela Chem Bio Inc. San Diego, CA, USA), Step 8-1: TFA/DCM |

TABLE 2-continued

Compounds 2-2 to 2-6 were prepared following the procedure described in Method 2, Steps 1-8, above as follows:

| Ex.# | Chemical Structure | Name | Method changes | Reagents |
|---|---|---|---|---|
| | (structure) | | | |
| 2-10 | (structure) | 1-(4-(5-chloro-7-fluoro-6-(3-hydroxy-1-naphthalenyl)-2,1-benzothiazol-3-yl)-3-(2-propanyl)-1-piperazinyl)-2-propen-1-one | — | Step 1: 2-amino-4-bromo-3-fluorobenzoic acid (Apollo Scientific Ltd., Stockport, UK), Step 2: 1-boc-3-isopropyl-piperazine (Ark Pharm Inc. Arlington Heights, IL, USA), Step 7: (3-methoxynaphthalen-1-yl)boronic acid (Ark Pharm Inc. Arlington Heights, IL, USA), Step 8-1: TFA/DCM |
| | (structure) | | | |

Method 3

Example 3-1: 1-(4-(5-Chloro-7-fluoro-6-(3-hydroxynaphthalen-1-yl)benzo[c]isothiazol-3-yl)piperazin-1-yl)prop-2-en-1-one

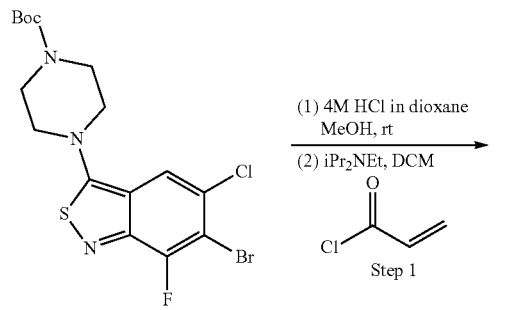

Intermediate D

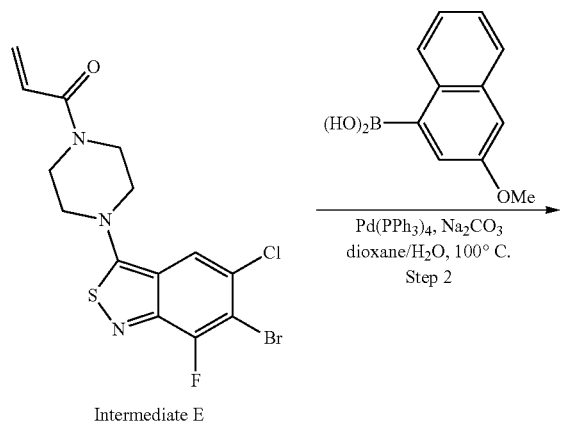

Intermediate E

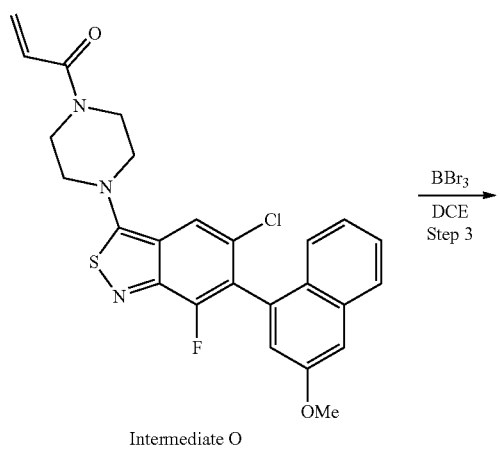

Intermediate O

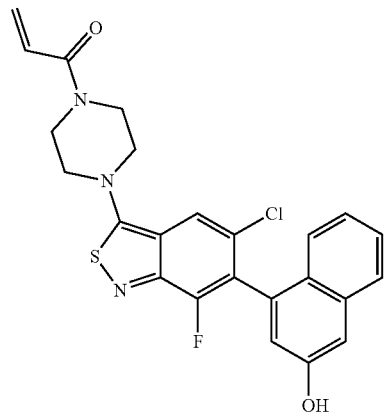

Step 1: 1-(4-(6-Bromo-5-chloro-7-fluorobenzo[c]isothiazol-3-yl)piperazin-1-yl)prop-2-en-1-one. 0.2 M acryloyl chloride in DCM (1.240 mL, 0.248 mmol) was added to an ice-cooled solution of 6-bromo-5-chloro-7-fluoro-3-(piperazin-1-yl)benzo[c]isothiazole (Intermediate D, 87 mg, 0.248 mmol) and N,N-diisopropylethylamine (0.129 mL, 0.744 mmol) in dichloromethane (2.3 mL), and the resulting mixture was stirred at 0° C. for 10 min. The mixture was then concentrated in vacuo, and the residue was sonicated in MeOH (2 mL). The suspended solid was collected by filtration, washed with MeOH, and dried in vacuo to provide 1-(4-(6-bromo-5-chloro-7-fluorobenzo[c]isothiazol-3-yl) piperazin-1-yl)prop-2-en-1-one: $^1$H NMR (400 MHz, DMSO-$d_6$) δ 8.13 (1H, d, J=1.56 Hz), 6.84 (1H, dd, J=10.47, 16.73 Hz), 6.17 (1H, dd, J=2.35, 16.63 Hz), 5.66-5.82 (1H, m), 3.73-3.93 (4H, m), 3.55-3.67 (4H, m). $^{19}$F NMR (376 MHz, DMSO-$d_6$) δ −113.39 (s, 1F), m/z (ESI, +ve) 405.8 (M+H)$^+$.

Step 2: 1-(4-(5-Chloro-7-fluoro-6-(3-methoxynaphthalen-1-yl)benzo[c]isothiazol-3-yl)piperazin-1-yl)prop-2-en-1-one (Intermediate E). A mixture of 1-(4-(6-bromo-5-chloro-7-fluorobenzo[c]isothiazol-3-yl)piperazin-1-yl)prop-2-en-1-one (Intermediate D, 79 mg, 0.20 mmol), (3-methoxynaphthalen-1-yl)boronic acid (47.3 mg, 0.234 mmol), tetrakis(triphenylphosphine)palladium (22.5 mg, 0.020 mmol) and sodium carbonate (83 mg, 0.78 mmol) in water (0.500 mL) and 1,4-dioxane (2.0 mL) was heated at 100° C. for 16 h. The reaction mixture was then adsorbed onto silica gel and chromatographically purified (silica gel, 0-3% MeOH in DCM) to give 1-(4-(5-chloro-7-fluoro-6-(3-methoxynaphthalen-1-yl)benzo[c]isothiazol-3-yl) piperazin-1-yl)prop-2-en-1-one: m/z (ESI, +ve) 482.0 (M+H)$^+$.

Step 3: 1-(4-(5-Chloro-7-fluoro-6-(3-hydroxynaphthalen-1-yl)benzo[c]isothiazol-3-yl)piperazin-1-yl)prop-2-en-1-one. Boron tribromide (1.0M in hexanes, 0.664 mL, 0.664 mmol) was added to an ice-cooled solution of 1-(4-(5-chloro-7-fluoro-6-(3-methoxynaphthalen-1-yl)benzo[c]isothiazol-3-yl)piperazin-1-yl)prop-2-en-1-one (64 mg, 0.13 mmol) in 1,2-dichloroethane (2.0 mL), and the resulting mixture was stirred at 0° C. for 1 h. The reaction mixture was then added to saturated aqueous sodium bicarbonate (2.0 mL) and the resulting mixture was extracted with (2:1) DCM:MeOH (10 mL). The organic extract was dried over Na$_2$SO$_4$, filtered, and concentrated in vacuo. Chromatographic purification of the residue (silica gel, 0-3% MeOH in DCM) gave 1-(4-(5-chloro-7-fluoro-6-(3-hydroxynaphthalen-1-yl)benzo[c]isothiazol-3-yl)piperazin-1-yl)prop-2-en-1-one: $^1$H NMR (400 MHz, DMSO-d$_6$) δ 9.90-10.04 (1H, m), 8.10 (1H, s), 7.80 (1H, d, J=8.41 Hz), 7.43 (1H, ddd, J=1.96, 6.11, 8.17 Hz), 7.16-7.31 (3H, m), 7.07 (1H, d, J=2.35 Hz), 6.87 (1H, dd, J=10.47, 16.73 Hz), 6.19 (1H, dd, J=2.25, 16.73 Hz), 5.77 (1H, dd, J=2.25, 10.47 Hz), 3.88 (4H, br d, J=19.56 Hz), 3.61-3.72 (4H, m). $^{19}$F NMR (376 MHz, DMSO-d$_6$) δ −123.78 (s, 1F), m/z (ESI, +ve) 468.0 (M+H)$^+$.

Alternate Synthesis of Intermediate E

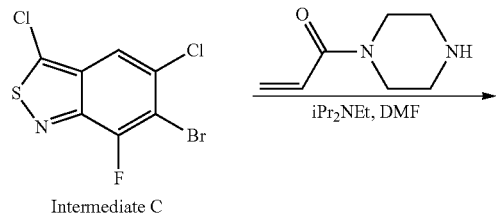

Intermediate C

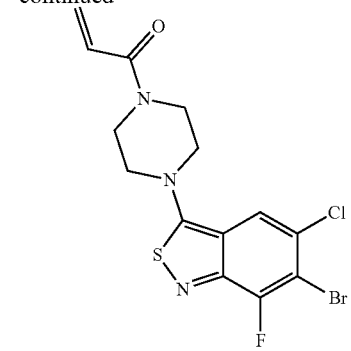

Intermediate E 1-(4-(5-Chloro-7-fluoro-6-(3-methoxynaphthalen-1-yl)benzo[c]isothiazol-3-yl)piperazin-1-yl)prop-2-en-1-one (Intermediate E, alternative synthesis): To a solution of 6-bromo-3,5-dichloro-7-fluorobenzo[c]isothiazole (Intermediate C, 715 mg, 2.37 mmol) in N,N-dimethylformamide (5.6 mL) was sequentially added a solution of 1-(piperazin-1-yl)prop-2-en-1-one bis(2,2,2-trifluoroacetate) (961 mg, 2.61 mmol, eNovation Chemicals LLC, Bridgewater, NJ, USA) in N,N-dimethylformamide (5.6 mL) and N,N-diisopropylethylamine (1.243 mL, 7.12 mmol). The resulting mixture was stirred at rt for 1 h and then heated at 50° C. for 22 h. After cooling to rt, the reaction mixture was added to ice water (10 mL), and the resulting precipitate was collected by filtration and washed with water. The collected solid was adsorbed onto silica gel and chromatographically purified (silica gel, 0-3% MeOH in DCM) to furnish 1-(4-(6-bromo-5-chloro-7-fluorobenzo[c]isothiazol-3-yl)piperazin-1-yl)prop-2-en-1-one.

TABLE 3

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-2 | (structure shown) | 8-(5-chloro-7-fluoro-3-(4-(2-propenoyl)-1-piperazinyl)-2,1-benzothiazol-6-yl)-2(1H)-quinolinone | Omit step 3 | Step 2: 8-(4,4,5,5-tetramethyl-1,3,2-dioxaborolan-2-yl)quinolin-2(1H)-one (Chem Shuttle, Hayward, CA, USA), S-Phos Pd G3, aq. K$_2$CO$_3$, 1,4-dioxane |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-3 | 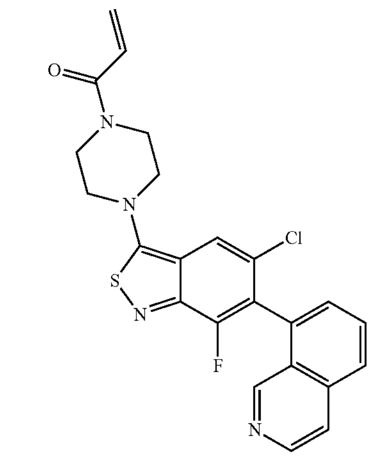 [SMILES: C=CC(=O)N1CCN(c2snc3c(F)c(-c4cccc5ccncc45)c(Cl)cc23)CC1] | 1-(4-(5-chloro-7-fluoro-6-(8-isoquinolinyl)-2,1-benzothiazol-3-yl)-1-piperazinyl)-2-propen-1-one | Omit step 3 | Step 2: 8-boronoisoquinoline (Frontier Scientific, Inc. Logan, UT, USA) |
| 3-4 | 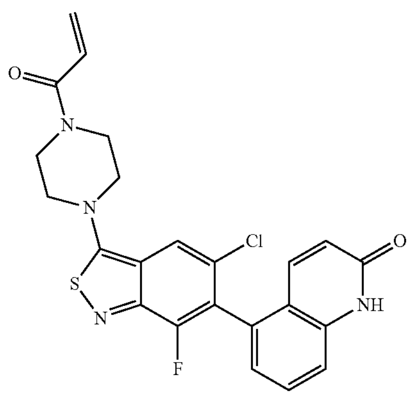 [SMILES: C=CC(=O)N1CCN(c2snc3c(F)c(-c4cccc5[nH]c(=O)ccc45)c(Cl)cc23)CC1] | 5-(5-chloro-7-fluoro-3-(4-(2-propenoyl)-1-piperazinyl)-2,1-benzothiazol-6-yl)-2(1H)-quinolinone | Omit step 3 | Step 2: 5-(4,4,5,5-tetramethyl-1,3,2-dioxaborolan-2-yl)quinolin-2(1h)-one (Ark Pharm Inc. Arlington Heights, IL, USA) |
| 3-5 | 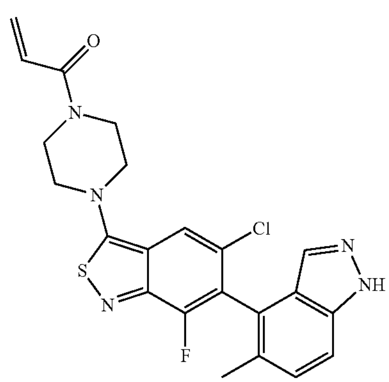 [SMILES: C=CC(=O)N1CCN(c2snc3c(F)c(-c4c(C)ccc5[nH]ncc45)c(Cl)cc23)CC1] | 1-(4-(5-chloro-7-fluoro-6-(5-methyl-1H-indazol-4-yl)-2,1-benzothiazol-3-yl)-1-piperazinyl)-2-propen-1-one | Omit step 3 | Step 2: 4-borono-5-methyl-1h-indazole (Ark Pharm Inc. Arlington Heights, IL, USA) |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-6 | 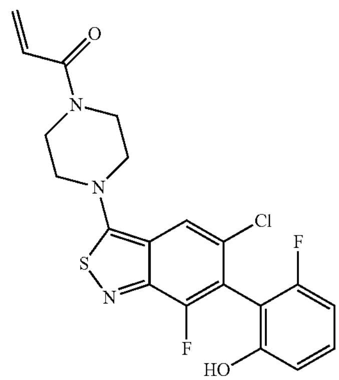 [SMILES: C=CC(=O)N1CCN(c2snc3c(F)c(-c4c(O)cccc4F)c(Cl)cc23)CC1] | 1-(4-(5-chloro-7-fluoro-6-(2-fluoro-6-hydroxyphenyl)-2,1-benzothiazol-3-yl)-1-piperazinyl)-2-propen-1-one | — | Step 2: 2-fluoro-6-methoxy-phenylboronic acid (Accela ChemBio Inc. San Diego, CA, USA) |
| 3-7 | 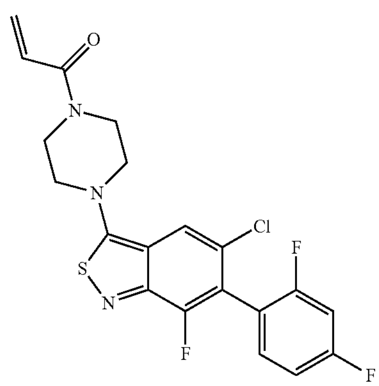 [SMILES: C=CC(=O)N1CCN(c2snc3c(F)c(-c4ccc(F)cc4F)c(Cl)cc23)CC1] | 1-(4-(5-chloro-6-(2,4-difluorophenyl)-7-fluoro-2,1-benzothiazol-3-yl)-1-piperazinyl)-2-propen-1-one | Omit step 3 | Step 2: (2,4-difluorophenyl) boronic acid (Combi-blocks Inc., San Diego, CA, USA) |
| 3-8 | 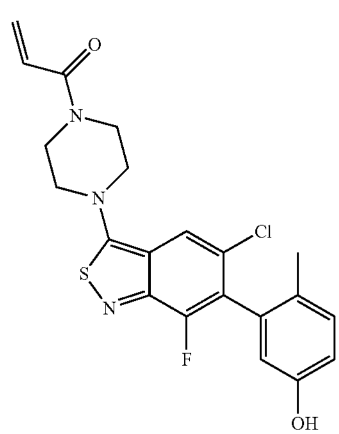 [SMILES: C=CC(=O)N1CCN(c2snc3c(F)c(-c4cc(O)ccc4C)c(Cl)cc23)CC1] | 1-(4-(5-chloro-7-fluoro-6-(5-hydroxy-2-methylphenyl)-2,1-benzothiazol-3-yl)-1-piperazinyl)-2-propen-1-one | Omit step 3 | Step 2: (5-hydroxy-2-methylphenyl boronic acid (Combi-blocks Inc., San Diego, CA, USA) |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-9 | 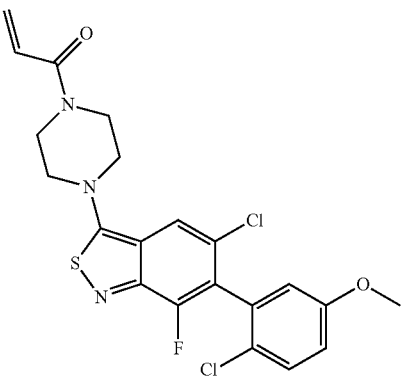 [SMILES: C=CC(=O)N1CCN(c2snc3c(F)c(-c4cc(OC)ccc4Cl)c(Cl)cc23)CC1] | 1-(4-(5-chloro-6-(2-chloro-5-methoxyphenyl)-7-fluoro-2,1-benzothiazol-3-yl)-1-piperazinyl)-2-propen-1-one | Omit step 3 | Step 2: 2-chloro-5-methoxyphenyl boronic acid (Combi-blocks Inc., San Diego, CA, USA) |
| 3-10 | 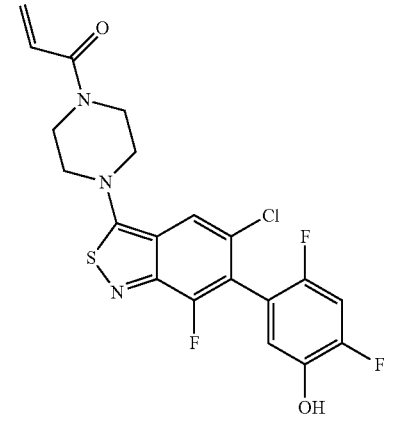 [SMILES: C=CC(=O)N1CCN(c2snc3c(F)c(-c4cc(O)c(F)cc4F)c(Cl)cc23)CC1] | 1-(4-(5-chloro-6-(2,4-difluoro-5-hydroxyphenyl)-7-fluoro-2,1-benzothiazol-3-yl)-1-piperazinyl)-2-propen-1-one | — | Step 2: 1-boronic acid-2,4-difluoro-5-methoxy-benzene (Combi-blocks Inc., San Diego, CA, USA) |
| 3-11 | 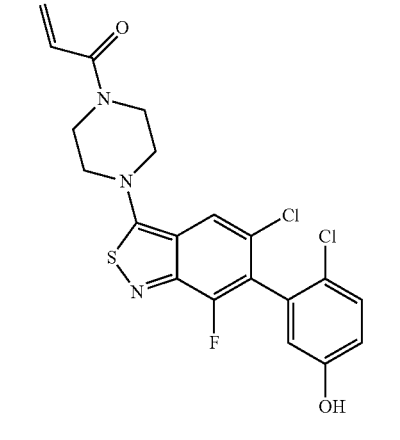 [SMILES: C=CC(=O)N1CCN(c2snc3c(F)c(-c4cc(O)ccc4Cl)c(Cl)cc23)CC1] | 1-(4-(5-chloro-6-(2-chloro-5-hydroxyphenyl)-7-fluoro-2,1-benzothiazol-3-yl)-1-piperazinyl)-2-propen-1-one | — | Step 2: 2-chloro-5-methoxyphenyl boronic acid (Combi-blocks Inc., San Diego, CA, USA) |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-12 | 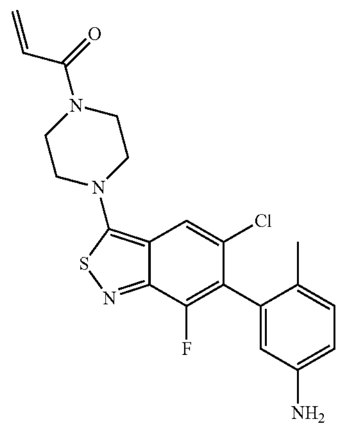 [SMILES: C=CC(=O)N1CCN(c2snc3c(F)c(-c4cc(N)ccc4C)c(Cl)cc23)CC1] | 1-(4-(6-(5-amino-2-methylphenyl)-5-chloro-7-fluoro-2,1-benzothiazol-3-yl)-1-piperazinyl)-2-propen-1-one | Omit step 3 | Step 2: (5-amino-2-methylphenyl) boronic acid (Combi-blocks Inc., San Diego, CA, USA) |
| 3-13 | 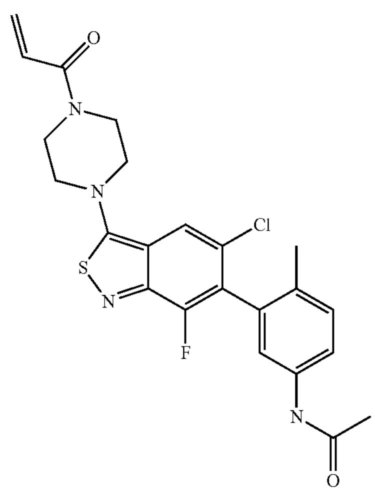 [SMILES: C=CC(=O)N1CCN(c2snc3c(F)c(-c4cc(NC(C)=O)ccc4C)c(Cl)cc23)CC1] | N-(3-(5-chloro-7-fluoro-3-(4-(2-propenoyl)-1-piperazinyl)-2,1-benzothiazol-6-yl)-4-methylphenyl) acetamide | Omit step 3 | Step 2: [5-(acetylamino)-2-methylphenyl] boronic acid (Combi-blocks Inc., San Diego, CA, USA) |
| 3-14 | 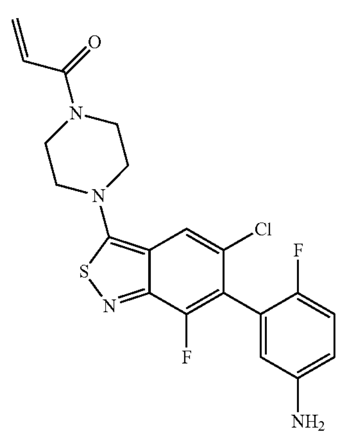 | 1-(4-(6-(5-amino-2-fluorophenyl)-5-chloro-7-fluoro-2,1-benzothiazol-3-yl)-1-piperazinyl)-2-propen-1-one | Omit step 3 | Step 2: 2-fluoro-5-aminophenyl boronic acid (Combi-blocks Inc., San Diego, CA, USA) |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-15 | 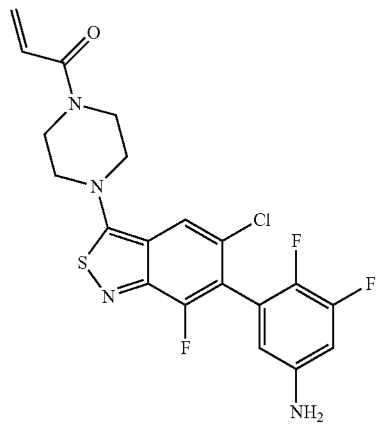 [SMILES: C=CC(=O)N1CCN(c2snc3c(F)c(-c4cc(N)cc(F)c4F)c(Cl)cc23)CC1] | 1-(4-(6-(5-amino-2,3-difluorophenyl)-5-chloro-7-fluoro-2,1-benzothiazol-3-yl)-1-piperazinyl)-2-propen-1-one | Omit step 3 | Step 2: 3-borono-4,5-difluoroaniline (Combi-blocks Inc., San Diego, CA, USA) |
| 3-16 | 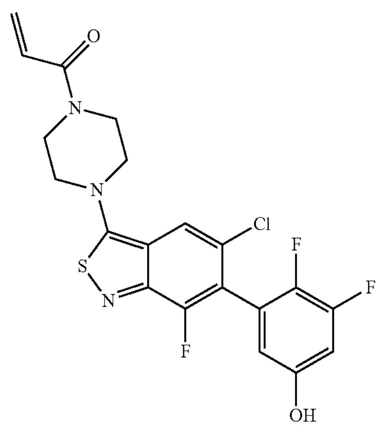 [SMILES: C=CC(=O)N1CCN(c2snc3c(F)c(-c4cc(O)cc(F)c4F)c(Cl)cc23)CC1] | 1-(4-(5-chloro-6-(2,3-difluoro-5-hydroxyphenyl)-7-fluoro-2,1-benzothiazol-3-yl)-1-piperazinyl)-2-propen-1-one | — | Step 2: 2,3-difluoro-5-methoxyphenylboronic acid (Combi-blocks Inc., San Diego, CA, USA) |
| 3-17 | 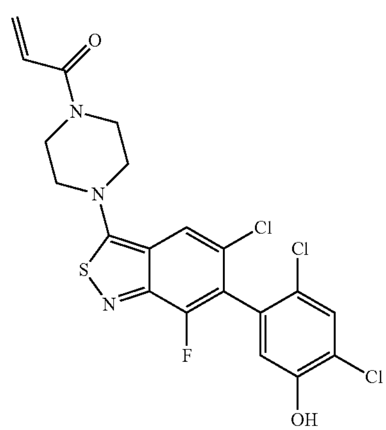 [SMILES: C=CC(=O)N1CCN(c2snc3c(F)c(-c4cc(O)c(Cl)cc4Cl)c(Cl)cc23)CC1] | 1-(4-(5-chloro-6-(2,4-dichloro-5-hydroxyphenyl)-7-fluoro-2,1-benzothiazol-3-yl)-1-piperazinyl)-2-propen-1-one | — | Step 2: (2,4-dichloro-5-methoxyphenyl)boronic acid (Combi-blocks Inc., San Diego, CA, USA) |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-18 | 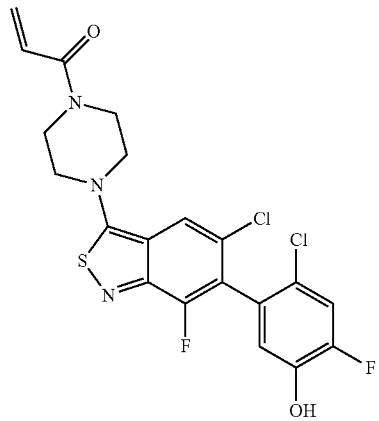 [SMILES: C=CC(=O)N1CCN(c2snc3c(F)c(-c4cc(O)c(F)cc4Cl)c(Cl)cc23)CC1] | 1-(4-(5-chloro-6-(2-chloro-4-fluoro-5-hydroxyphenyl)-7-fluoro-2,1-benzothiazol-3-yl)-1-piperazinyl)-2-propen-1-one | — | Step 2: (2-chloro-4-fluoro-5-methoxyphenyl) boronic acid (Combi-blocks Inc., San Diego, CA, USA) |
| 3-19 | 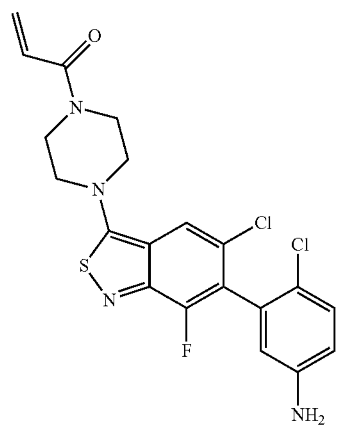 [SMILES: C=CC(=O)N1CCN(c2snc3c(F)c(-c4cc(N)ccc4Cl)c(Cl)cc23)CC1] | 1-(4-(6-(5-amino-2-chlorophenyl)-5-chloro-7-fluoro-2,1-benzothiazol-3-yl)-1-piperazinyl)-2-propen-1-one | Omit step 3 | Step 2: (5-amino-2-chlorophenyl) boronic acid hydrochloride (Combi-blocks Inc., San Diego, CA, USA) |
| 3-20 | 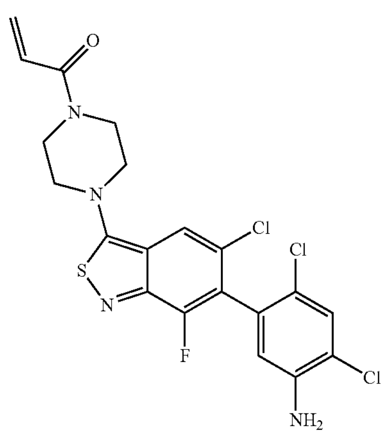 [SMILES: C=CC(=O)N1CCN(c2snc3c(F)c(-c4cc(N)c(Cl)cc4Cl)c(Cl)cc23)CC1] | 1-(4-(6-(5-amino-2,4-dichlorophenyl)-5-chloro-7-fluoro-2,1-benzothiazol-3-yl)-1-piperazinyl)-2-propen-1-one | — | Step 2: (5-amino-2,4-dichlorophenyl) boronic acid (Combi-blocks Inc., San Diego, CA, USA) |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-21 | 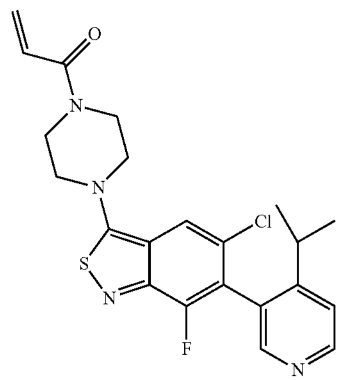 [SMILES: C=CC(=O)N1CCN(c2snc3c(F)c(-c4cnccc4C(C)C)c(Cl)cc23)CC1] | 1-(4-(5-chloro-7-fluoro-6-(4-(2-propanyl)-3-pyridinyl)-2,1-benzothiazol-3-yl)-1-piperazinyl)-2-propen-1-one | Omit step 3 | Step 2: (4-isopropylpyridin-3-yl)boronic acid (Combi-Phos Catalysts Inc. Trenton, NJ, USA) |
| 3-22 | 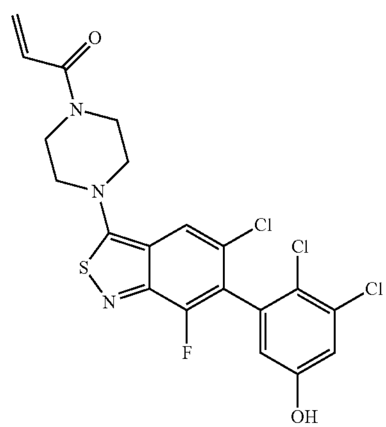 [SMILES: C=CC(=O)N1CCN(c2snc3c(F)c(-c4cc(O)cc(Cl)c4Cl)c(Cl)cc23)CC1] | 1-(4-(5-chloro-6-(2,3-dichloro-5-hydroxyphenyl)-7-fluoro-2,1-benzothiazol-3-yl)-1-piperazinyl)-2-propen-1-one | — | Step 2: 2-(2,3-dichloro-5-methoxyphenyl)-4,4,5,5-tetramethyl-1,3,2-dioxaborolane (Anisyn Inc., Kalamazoo, MI, US) |
| 3-23 | 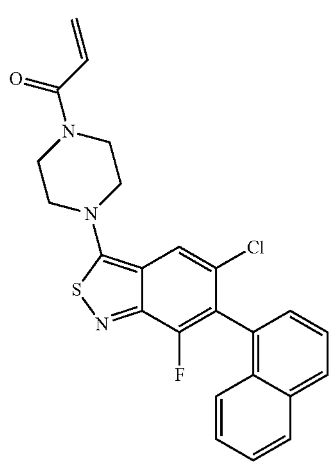 [SMILES: C=CC(=O)N1CCN(c2snc3c(F)c(-c4cccc5ccccc45)c(Cl)cc23)CC1] | 1-(4-(5-chloro-7-fluoro-6-(naphthalen-1-yl)benzo[c]isothiazol-3-yl)piperazin-1-yl)prop-2-en-1-one | Omit step 3 | Step 1-1: TFA/DCM Step 2: (1-naphthalyl)boronic acid, Cs$_2$CO$_3$, 80° C. |

TABLE 3-continued

Compounds 3-2 to 3-24 were prepared following the procedure described in Method 3, Steps 1-3, above as follows:

| Ex. # | Chemical Structure | Name | Method changes | Reagent |
|---|---|---|---|---|
| 3-24 | 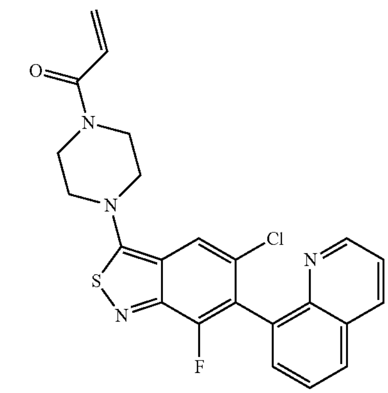 [SMILES: C=CC(=O)N1CCN(c2snc3c(F)c(-c4cccc5cccnc45)c(Cl)cc23)CC1] | 1-(4-(5-chloro-7-fluoro-6-(quinolin-8-yl)benzo[c]isothiazol-3-yl)piperazin-1-yl)prop-2-en-1-one | Omit step 3 | Step 1-1: TFA/DCM Step 2: 8-quinoline boronic acid (Frontier Scientific Inc., Logan UT, USA), $Cs_2CO_3$, 80° C. |
| 3-25 | 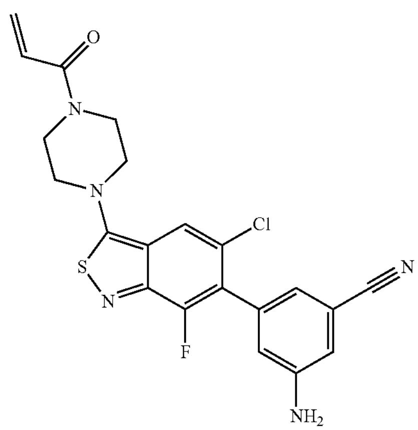 [SMILES: C=CC(=O)N1CCN(c2snc3c(F)c(-c4cc(N)cc(C#N)c4)c(Cl)cc23)CC1] | 3-amino-5-(5-chloro-7-fluoro-3-(4-(2-propenoyl)-1-piperazinyl)-2,1-benzothiazol-6-yl)benzonitrile | Omit step 3 | Step 1-1: TFA/DCM Step 2: (3-amino-5-cyanophenyl) boronic acid (Combi-blocks Inc., San Diego, CA, USA), 5-Phos Pd G3, $K_2CO_3$, 100° C. |

Method 4

Example 4-1: 1-(6-(5-Chloro-7-fluoro-6-(3-hydroxynaphthalen-1-yl)benzo[c]isothiazol-3-yl)-2,6-diazaspiro[3.3]heptan-2-yl)prop-2-en-1-one

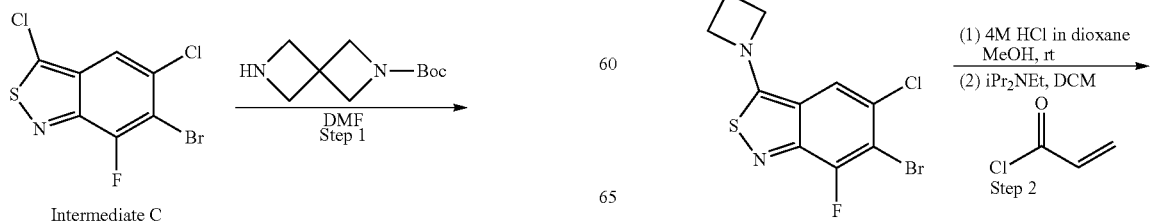

-continued

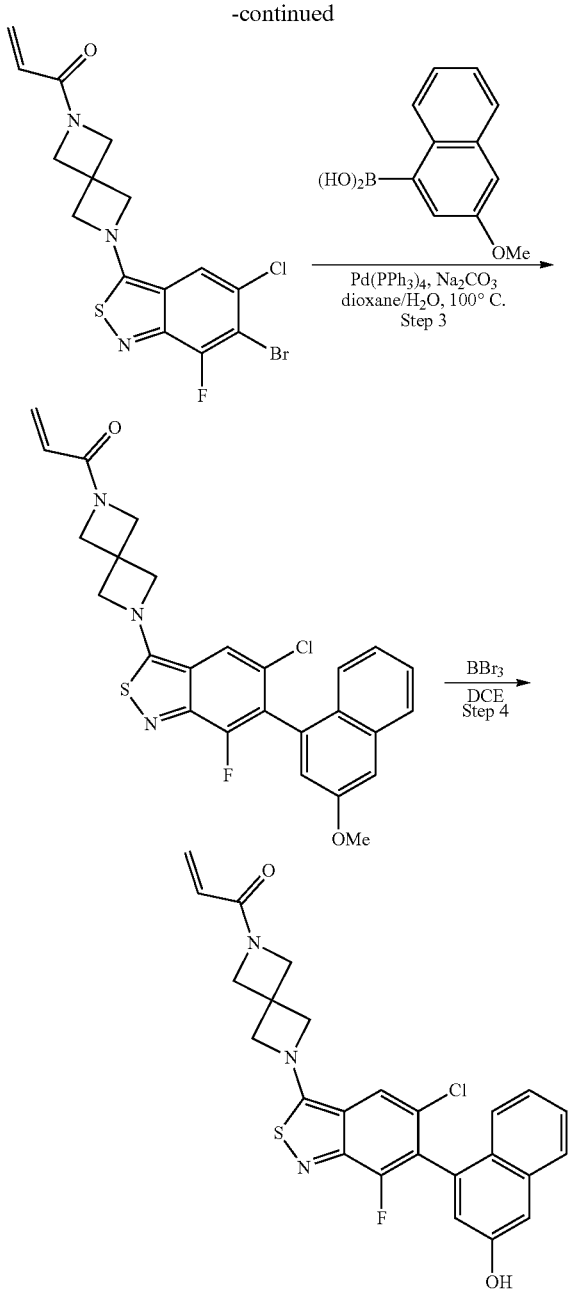

Step 1: tert-Butyl 6-(6-bromo-5-chloro-7-fluorobenzo[c]isothiazol-3-yl)-2,6-diazaspiro[3.3]heptane-2-carboxylate. A mixture of 6-bromo-3,5-dichloro-7-fluorobenzo[c]isothiazole (Intermediate C, 169 mg, 0.562 mmol) and 2-Boc-2,6-diazaspiro[3.3]heptane (212 mg, 1.07 mmol, AstaTech, Inc., Bristol, PA, USA) in DMF (3.5 mL) was stirred at rt for 5 h. Ice water (5 mL) was added, and the resulting mixture was stirred for 15 min. The resulting precipitate was collected by filtration, washed with water, and dried in vacuo to provide tert-butyl 6-(6-bromo-5-chloro-7-fluorobenzo[c]isothiazol-3-yl)-2,6-diazaspiro[3.3]heptane-2-carboxylate: $^1$H NMR (400 MHz, DMSO-d$_6$) δ 7.52-7.74 (1H, m), 4.55 (4H, s), 4.09 (4H, s), 1.38 (9H, s). $^{19}$F NMR (376 MHz, DMSO-d$_6$) δ−113.55 (1F, s). m/z (ESI, +ve) 464.0 (M+1).

Step 2: 1-(6-(6-Bromo-5-chloro-7-fluorobenzo[c]isothiazol-3-yl)-2,6-diazaspiro[3.3]heptan-2-yl)prop-2-en-1-one. Hydrogen chloride solution (4M in 1,4-dioxane, 5.0 mL, 20 mmol) was added to tert-butyl 6-(6-bromo-5-chloro-7-fluorobenzo[c]isothiazol-3-yl)-2,6-diazaspiro[3.3]heptane-2-carboxylate (249 mg, 0.538 mmol) in methanol (10 mL), and the resulting mixture was stirred at rt for 2 h. The reaction mixture was then concentrated in vacuo to provide 6-bromo-5-chloro-7-fluoro-3-(2,6-diazaspiro[3.3]heptan-2-yl)benzo[c]isothiazole: m/z (ESI, +ve) 363.8 (M+1)$^+$.

To this material was added N,N-diisopropylethylamine (0.281 mL, 1.61 mmol) in dichloromethane (3.0 mL), and the resulting mixture was cooled to 0° C. Acryloyl chloride (0.2 M in DCM, 2.69 mL, 0.538 mmol) was then added, and the resulting mixture was stirred at 0° C. for 10 min. The reaction mixture was then concentrated in vacuo, and the residue was chromatographically purified (silica gel, 0-10% (3:1) EtOAc/EtOH in DCM) to provide 1-(6-(6-bromo-5-chloro-7-fluorobenzo[c]isothiazol-3-yl)-2,6-diazaspiro[3.3]heptan-2-yl)prop-2-en-1-one: $^1$H NMR (400 MHz, DMSO-d$_6$) δ 7.65 (1H, d, J=1.4 Hz), 6.25-6.36 (1H, m), 6.10 (1H, dd, J=17.0, 2.3 Hz), 5.64-5.72 (1H, m), 4.58 (4H, s), 4.47 (2H, s), 4.18 (2H, s). $^{19}$F NMR (376 MHz, DMSO-d$_6$) δ−113.54 (1F, s). m/z (ESI, +ve) 418.0 (M+H)$^+$.

Step 3: 1-(6-(5-Chloro-7-fluoro-6-(3-methoxynaphthalen-1-yl)benzo[c]isothiazol-3-yl)-2,6-diazaspiro[3.3]heptan-2-yl)prop-2-en-1-one. A mixture of 1-(6-(6-bromo-5-chloro-7-fluorobenzo[c]isothiazol-3-yl)-2,6-diazaspiro[3.3]heptan-2-yl)prop-2-en-1-one (102 mg, 0.245 mmol), (3-methoxynaphthalen-1-yl)boronic acid (59.3 mg, 0.294 mmol), tetrakis(triphenylphosphine)palladium (28.3 mg, 0.024 mmol), and sodium carbonate (104 mg, 0.979 mmol) in water (0.5 mL) and 1,4-dioxane (2.0 mL) was heated at 100° C. for 1 h. The reaction mixture was then adsorbed onto silica gel and chromatographically purified (silica gel, 0-5% MeOH in DCM). The purified material was sonicated in MeOH, and the suspended solid was collected by filtration, washed with MeOH, and dried in vacuo to provide 1-(6-(5-chloro-7-fluoro-6-(3-methoxynaphthalen-1-yl)benzo[c]isothiazol-3-yl)-2,6-diazaspiro[3.3]heptan-2-yl)prop-2-en-1-one: $^1$H NMR (400 MHz, DMSO-d$_6$) δ 7.93 (1H, d, J=8.4 Hz), 7.67 (1H, s), 7.45-7.57 (2H, m), 7.23-7.36 (2H, m), 7.16 (1H, d, J=2.5 Hz), 6.27-6.39 (1H, m), 6.11 (1H, dd, J=17.0, 2.2 Hz), 5.65-5.76 (1H, m), 4.58-4.67 (4H, m), 4.50 (2H, s), 4.22 (2H, s), 3.93 (3H, s). $^{19}$F NMR (376 MHz, DMSO-d$_6$) δ−123.88 (1F, s). m/z (ESI, +ve) 494.0 (M+H)$^+$.

Step 4: 1-(6-(5-chloro-7-fluoro-6-(3-hydroxynaphthalen-1-yl)benzo[c]isothiazol-3-yl)-2,6-diazaspiro[3.3]heptan-2-yl)prop-2-en-1-one. Boron tribromide (1.0 M in hexanes, 0.638 mL, 0.638 mmol) was added to ice-cooled 1-(6-(5-chloro-7-fluoro-6-(3-methoxynaphthalen-1-yl)benzo[c]isothiazol-3-yl)-2,6-diazaspiro[3.3]heptan-2-yl)prop-2-en-1-one (63 mg, 0.128 mmol) in 1,2-dichloroethane (2.0 mL), and the resulting mixture was stirred at 0° C. for 2 h. The reaction mixture was then added to saturated aqueous sodium bicarbonate (2.0 mL), and the resulting mixture was extracted with (2:1) DCM:MeOH (10 mL). The organic extract was dried over Na$_2$SO$_4$, filtered, and concentrated in vacuo. Chromatographic purification of the residue (silica gel, 0-2% MeOH (with 2M ammonia) in DCM) gave 1-(6-(5-chloro-7-fluoro-6-(3-hydroxynaphthalen-1-yl)benzo[c]isothiazol-3-yl)-2,6-diazaspiro[3.3]heptan-2-yl)prop-2-en-1-one: $^1$H NMR (400 MHz, DMSO-d$_6$) δ 9.82-10.04 (1H, m), 7.79 (1H, d, J=8.2 Hz), 7.66 (1H, s), 7.43 (1H, dt, J=8.3, 4.0 Hz), 7.26 (1H, d, J=2.3 Hz), 7.22 (2H, d, J=3.7 Hz), 7.05 (1H, d, J=2.3 Hz), 6.26-6.38 (1H, m), 6.12 (1H, dd, J=16.8, 2.2 Hz), 5.66-5.72 (1H, m), 4.58-4.67 (4H, m), 4.50 (2H, s), 4.22 (2H, s). $^{19}$F NMR (376 MHz, DMSO-d$_6$) δ−123.98 (1F, s). m/z (ESI, +ve) 480.0 (M+H)$^+$.

TABLE 4

Compounds 4-2 to 4-9 were prepared following the procedure described in Method 4, Steps 1-4, above as follows:

| Ex. # | Chemical Structure | Name | Method changes | Reagent |
|---|---|---|---|---|
| 4-2 | 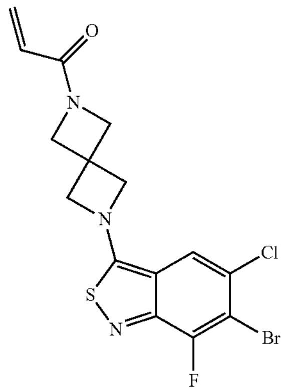 [SMILES: C=CC(=O)N1CC2(C1)CN(c1snc3c(F)c(Br)c(Cl)cc13)C2] | 1-(6-(6-bromo-5-chloro-7-fluoro-2,1-benzothiazol-3-yl)-2,6-diazaspiro[3.3]hept-2-yl)-2-propen-1-one | Omit steps 3 & 4 | — |
| 4-3 | 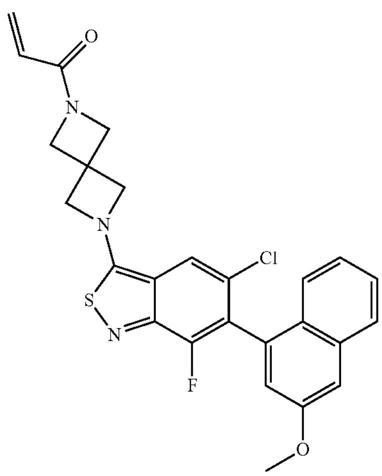 [SMILES: C=CC(=O)N1CC2(C1)CN(c1snc3c(F)c(-c4cc(OC)cc5ccccc45)c(Cl)cc13)C2] | 1-(6-(5-chloro-7-fluoro-6-(3-methoxy-1-naphthalenyl)-2,1-benzothiazol-3-yl)-2,6-diazaspiro[3.3]heptan-2-yl)-2-propen-1-one | Omit step 4 | — |
| 4-4 | 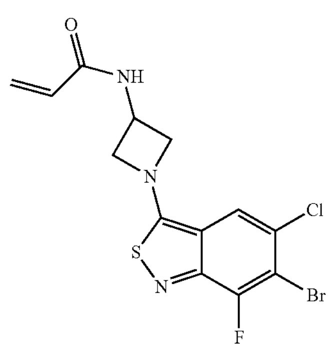 [SMILES: C=CC(=O)NC1CN(c2snc3c(F)c(Br)c(Cl)cc23)C1] | N-(1-(6-bromo-5-chloro-7-fluoro-2,1-benzothiazol-3-yl)-3-azetidinyl)-2-propenamide | Omit steps 3 & 4 | Step 1: 3-N-boc-amino-azetidine, HCl salt (Combi-blocks Inc., San Diego, CA, USA) |

TABLE 4-continued

Compounds 4-2 to 4-9 were prepared following the procedure described in
Method 4, Steps 1-4, above as follows:

| Ex. # | Chemical Structure | Name | Method changes | Reagent |
|---|---|---|---|---|
| 4-5 | 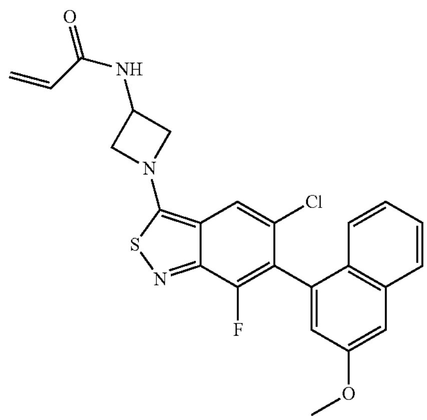 [SMILES: C=CC(=O)NC1CN(c2snc3c(F)c(-c4cc(OC)cc5ccccc45)c(Cl)cc23)C1] | N-(1-(5-chloro-7-fluoro-6-(3-methoxy-1-naphthalenyl)-2,1-benzothiazol-3-yl)-3-azetidinyl)-2-propenamide | Omit step 4 | Step 1: 3-N-boc-amino-azetidine, HCl salt (Combi-blocks Inc., San Diego, CA, USA) |
| 4-6 | 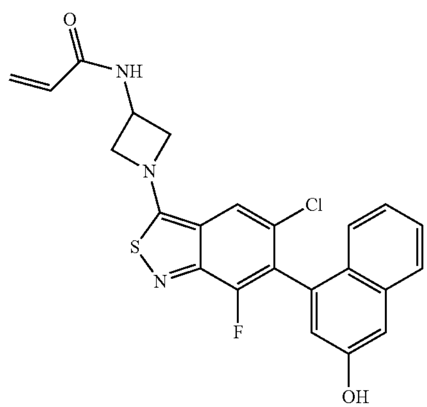 [SMILES: C=CC(=O)NC1CN(c2snc3c(F)c(-c4cc(O)cc5ccccc45)c(Cl)cc23)C1] | N-(1-(5-chloro-7-fluoro-6-(3-hydroxy-1-naphthalenyl)-2,1-benzothiazol-3-yl)-3-azetidinyl)-2-propenamide | — | Step 1: 3-N-boc-amino-azetidine, HCl salt (Combi-blocks Inc., San Diego, CA, USA) |
| 4-7 | 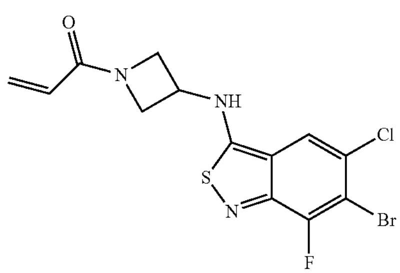 [SMILES: C=CC(=O)N1CC(Nc2snc3c(F)c(Br)c(Cl)cc23)C1] | 1-(3-((6-bromo-5-chloro-7-fluoro-2,1-benzothiazol-3-yl)amino)-1-azetidinyl)-2-propen-1-one | Omit steps 3 & 4 | Step 1: 1-boc-3-aminoazetidine (Alfa Aesar, Haver Hill, MA, USA) |
| 4-8 | 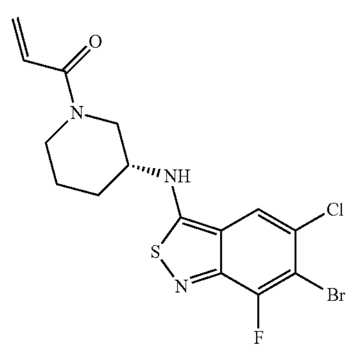 [SMILES: C=CC(=O)N1CCC[C@@H](Nc2snc3c(F)c(Br)c(Cl)cc23)C1] | 1-((3R)-3-((6-bromo-5-chloro-7-fluoro-2,1-benzothiazol-3-yl)amino)-1-piperidinyl)-2-propen-1-one | Omit steps 3 & 4 | Step 1: (R)-tert-butyl 3-aminopiperidine-1-carboxylate (AstaTech, Inc., Bristol, PA, USA) |

TABLE 4-continued

Compounds 4-2 to 4-9 were prepared following the procedure described in Method 4, Steps 1-4, above as follows:

| Ex. # | Chemical Structure | Name | Method changes | Reagent |
|---|---|---|---|---|
| 4-9 | 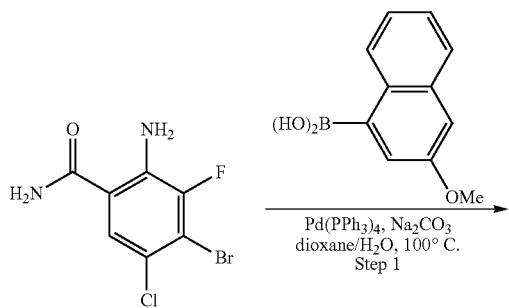 | 1-((3R)-3-((5-chloro-7-fluoro-6-(3-hydroxynaphthalen-1-yl)benzo[c]isothiazol-3-yl)amino)piperidin-1-yl)prop-2-en-1-one | — | Step 1: (R)-tert-butyl 3-aminopiperidine-1-carboxylate (AstaTech, Inc., Bristol, PA, USA) |

Method 5

Example 5-1: N-(1-(5-Chloro-7-fluoro-6-(3-hydroxy-1-naphthalenyl)-2,1-benzothiazol-3-yl)-3-azetidinyl)-N-methyl-2-propenamide

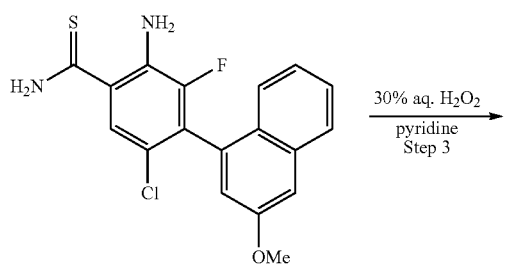

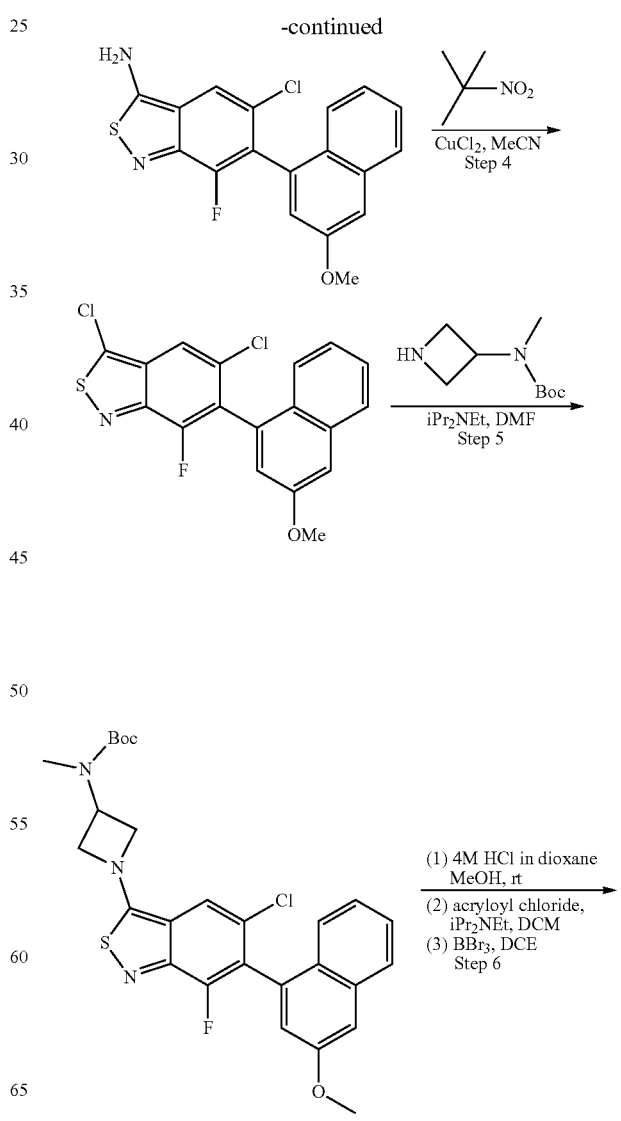

-continued

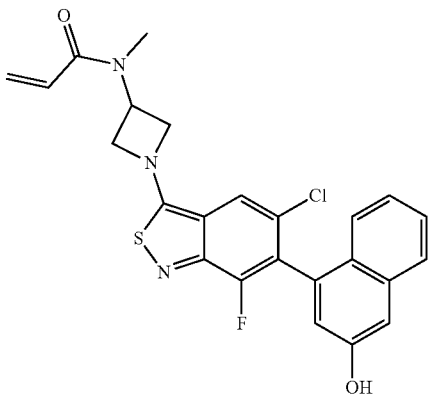

Step 1: 2-Amino-5-chloro-3-fluoro-4-(3-methoxynaphthalen-1-yl)benzamide. A mixture of (3-methoxynaphthalen-1-yl)boronic acid (2.04 g, 10.1 mmol), 2-amino-4-bromo-5-chloro-3-fluorobenzamide (Intermediate B (1.93 g, 7.20 mmol), tetrakis(triphenylphosphine)palladium (0.832 g, 0.720 mmol), sodium carbonate (1.2 mL, 28.8 mmol) in water (9.6 mL), and 1,4-dioxane (38.4 mL) was heated at 90° C. for 2 days. The reaction mixture was then filtered through a pad of Celite, washing with EtOAc. The filtrate was diluted with saturated aqueous NaHCO₃ (50 mL) and extracted with EtOAc (3×50 mL). The organic extract was washed with brine (30 mL) and dried over Na₂SO₄. The solution was then filtered and the filtrated concentrated in vacuo. The residue was suspended in MeOH (5 mL), and the suspended solid collected by filtration, washed with MeOH, and dried to give 2-amino-5-chloro-3-fluoro-4-(3-methoxynaphthalen-1-yl)benzamide. Chromatographic purification of the concentrated filtrate (silica gel, 0% to 100% (3:1) EtOAc-EtOH in heptane) provided additional 2-amino-5-chloro-3-fluoro-4-(3-methoxynaphthalen-1-yl)benzamide. $^1$H NMR (400 MHz, DMSO-$d_6$) δ 8.01-8.17 (m, 1H), 7.92 (d, J=8.2 Hz, 1H), 7.75 (s, 1H), 7.43-7.55 (m, 3H), 7.23-7.34 (m, 2H), 7.10 (d, J=2.5 Hz, 1H), 6.73 (s, 2H), 3.93 (s, 3H). m/z (ESI, +ve) 345.0 (M+H)⁺.

Step 2: 2-Amino-5-chloro-3-fluoro-4-(3-methoxynaphthalen-1-yl)benzothioamide. To a solution of 2-amino-5-chloro-3-fluoro-4-(3-methoxynaphthalen-1-yl)benzamide (2.11 g, 6.12 mmol) in tetrahydrofuran (41 mL) was added Lawesson's reagent (1.49 mL, 3.67 mmol), and the resulting mixture was stirred at rt for 1 h. The reaction mixture was then diluted with EtOAc (60 mL) and sequentially washed with 2 M HCl (60 mL), saturated aqueous NaHCO₃ (60 mL), and brine (60 mL). The organic extract was dried over Na₂SO₄, filtered, and concentrated in vacuo. The residue was sonicated in DCM (5 mL), and the resulting precipitate was collected by filtration, washed with DCM, and dried in vacuo provide 2-amino-5-chloro-3-fluoro-4-(3-methoxynaphthalen-1-yl)benzothioamide. Chromatographic purification of the filtrate (silica gel, 0% to 100% (3:1) EtOAc-EtOH in heptane) gave additional 2-amino-5-chloro-3-fluoro-4-(3-methoxynaphthalen-1-yl)benzothioamide: m/z (ESI, +ve) 361.0 (M+H)⁺.

Step 3: 5-Chloro-7-fluoro-6-(3-methoxynaphthalen-1-yl)benzo[c]isothiazol-3-amine. Hydrogen peroxide solution (30% in water, 2.2 mL, 21.3 mmol) was slowly added to an ice-cooled solution of 2-amino-5-chloro-3-fluoro-4-(3-methoxynaphthalen-1-yl)benzothioamide (1.92 g, 5.33 mmol) in pyridine (18 mL). The resulting mixture was allowed to warm to rt and stir at rt for 18 h. The reaction mixture was then diluted with water (60 mL), and the resulting precipitate was collected by filtration, sequentially washed with water and MeOH, and dried in vacuo to give 5-chloro-7-fluoro-6-(3-methoxynaphthalen-1-yl)benzo[c]isothiazol-3-amine: $^1$H NMR (400 MHz, DMSO-$d_6$) δ 8.14 (s, 2H), 7.99-8.03 (m, 1H), 7.93 (d, J=8.3 Hz, 1H), 7.48-7.55 (m, 1H), 7.47 (d, J=2.3 Hz, 1H), 7.31 (d, J=3.9 Hz, 2H), 7.16 (d, J=2.5 Hz, 1H), 3.94 (s, 3H). $^{19}$F NMR (376 MHz, DMSO-$d_6$) δ−124.71 (s, 1F). m/z (ESI, +ve) 359.0 (M+H)⁺.

Step 4: 3,5-Dichloro-7-fluoro-6-(3-methoxynaphthalen-1-yl)benzo[c]isothiazole. 5-Chloro-7-fluoro-6-(3-methoxynaphthalen-1-yl)benzo[c]isothiazol-3-amine (1.55 g, 4.31 mmol) was added portion-wise over 15 min to a suspension of copper (II) chloride (0.870 g, 6.47 mmol) and tert-butyl nitrite (0.77 mL, 6.47 mmol) in acetonitrile (43 mL) at 65° C. The resulting mixture was stirred at 65° C. for 30 min and then cooled to ambient temperature and diluted with ice water (50 mL). The precipitated solid was collected by filtration, washed with water, and dried in vacuo. The residue was sonicated in DCM (10 mL), and the suspended solid was collected by filtration, washed with DCM, and dried in vacuo to recover unreacted 5-chloro-7-fluoro-6-(3-methoxynaphthalen-1-yl)benzo[c]isothiazol-3-amine. The filtrate was concentrated in vacuo to give 3,5-dichloro-7-fluoro-6-(3-methoxynaphthalen-1-yl)benzo[c]isothiazole. $^1$H NMR (400 MHz, DMSO-$d_6$) δ 7.98 (s, 1H), 7.96 (d, J=8.2 Hz, 1H), 7.49-7.56 (m, 2H), 7.28-7.36 (m, 2H), 7.24-7.28 (m, 1H), 3.95 (s, 3H). $^{19}$F NMR (376 MHz, DMSO-$d_6$) δ−122.17 (s, 1F), m/z (ESI, +ve) 378.0 (M+H)⁺.

Step 5: tert-Butyl (1-(5-chloro-7-fluoro-6-(3-methoxynaphthalen-1-yl)benzo[c]isothiazol-3-yl)azetidin-3-yl)(methyl)carbamate. A mixture of 3,5-dichloro-7-fluoro-6-(3-methoxynaphthalen-1-yl)benzo[c]isothiazole (100 mg, 0.264 mmol), DIPEA (0.14 mL, 0.793 mmol), and 3-Boc-3-methylaminoazatidine (0.098 mL, 0.529 mmol, Beta Pharma Scientific, Inc.) in DMF (1.3 mL) was stirred at rt for 18 h. Ice water (3 mL) was then added, and the resulting mixture was stirred for 15 min. The precipitated solid was then collected by filtration, washed with water, and dried in vacuo to furnish tert-butyl (1-(5-chloro-7-fluoro-6-(3-methoxynaphthalen-1-yl)benzo[c]isothiazol-3-yl)azetidin-3-yl)(methyl)carbamate: m/z (ESI, +ve) 528.0 (M+H)⁺.

Step 6: N-(1-(5-Chloro-7-fluoro-6-(3-hydroxy-1-naphthalenyl)-2,1-benzothiazol-3-yl)-3-azetidinyl)-N-methyl-2-propenamide. The title compound was prepared from tert-butyl (1-(5-chloro-7-fluoro-6-(3-methoxynaphthalen-1-yl)benzo[c]isothiazol-3-yl)azetidin-3-yl)(methyl)carbamate (131.1 mg, 0.248 mmol) in three steps following the procedure reported in Method 1, Step 8: $^1$H NMR (400 MHz, DMSO-$d_6$) δ 9.89-10.10 (m, 1H), 7.79 (d, J=8.4 Hz, 1H), 7.73 (s, 1H), 7.43 (ddd, J=8.2, 5.1, 2.9 Hz, 1H), 7.20-7.30 (m, 3H), 7.05 (d, J=2.2 Hz, 1H), 6.81 (dd, J=16.7, 10.5 Hz, 1H), 6.10-6.23 (m, 1H), 5.69-5.81 (m, 1H), 5.37-5.59 (m, 1H), 4.63-4.74 (m, 3H), 4.53-4.61 (m, 1H), 3.14-3.23 (m, 3H). $^{19}$F NMR (376 MHz, DMSO-$d_6$) δ−124.10 (s, 1F), m/z (ESI, +ve) 468.0 (M+H)⁺.

TABLE 5

Compounds 5-2 to 5-9 were prepared following the procedure described in Method 5, Steps 1-6, above as follows:

| Ex. # | Chemical Structure | Name | Reagent |
|---|---|---|---|
| 5-2 | 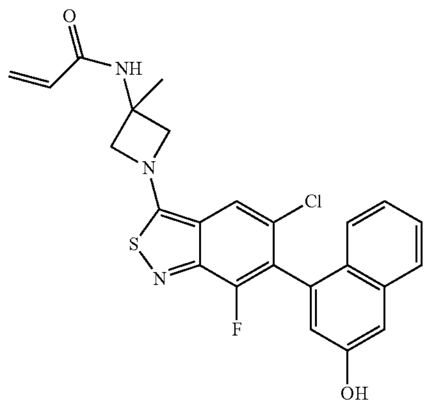 [SMILES: C=CC(=O)NC1(C)CN(c2snc3c(F)c(-c4cc(O)cc5ccccc45)c(Cl)cc23)C1] | N-(1-(5-chloro-7-fluoro-6-(3-hydroxy-1-naphthalenyl)-2,1-benzothiazol-3-yl)-3-methyl-3-azetidinyl)-2-propenamide | Step 5: 3-(Boc-amino)-3-methylazetidine hydrochloride (Advanced ChemBlocks, Inc., Burlingame, CA, USA) |
| 5-3 | 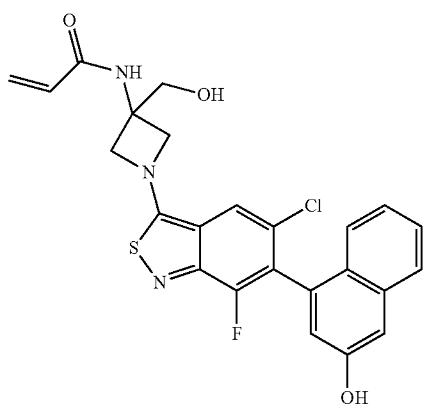 [SMILES: C=CC(=O)NC1(CO)CN(c2snc3c(F)c(-c4cc(O)cc5ccccc45)c(Cl)cc23)C1] | N-(1-(5-chloro-7-fluoro-6-(3-hydroxy-1-naphthalenyl)-2,1-benzothiazol-3-yl)-3-(hydroxymethyl)-3-azetidinyl)-2-propenamide | Step 5: tert-butyl 3-(hydroxymethyl)azetidin-3-ylcarbamate (Oakwood Products, Inc. Estill, Sc, USA) |
| 5-4 | 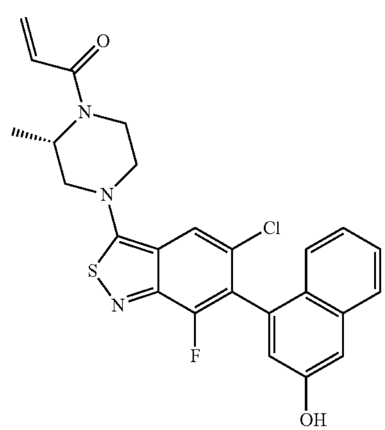 [SMILES: C=CC(=O)N1CCN(c2snc3c(F)c(-c4cc(O)cc5ccccc45)c(Cl)cc23)C[C@@H]1C] | 1-((2S)-4-(5-chloro-7-fluoro-6-(3-hydroxy-1-naphthalenyl)-2,1-benzothiazol-3-yl)-2-methyl-1-piperazinyl)-2-propen-1-one | Step 5: (S)-1-N-boc-2-methylpiperazine (Combi-blocks Inc., San Diego, CA, USA) |

TABLE 5-continued

Compounds 5-2 to 5-9 were prepared following the procedure described in Method 5, Steps 1-6, above as follows:

| Ex. # | Chemical Structure | Name | Reagent |
|---|---|---|---|
| 5-5 | 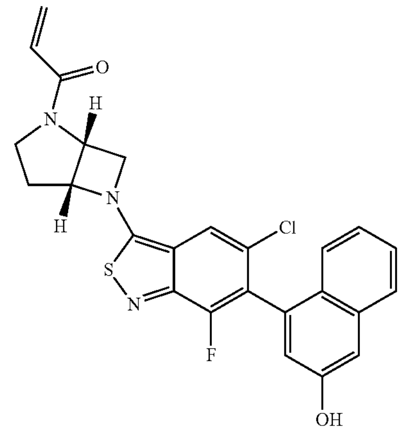 [SMILES: C=CC(=O)N1CC[C@@H]2[C@H]1CN2c1snc2c(F)c(-c3cc(O)cc4ccccc34)c(Cl)cc12] | 1-((1R,5R)-6-(5-chloro-7-fluoro-6-(3-hydroxy-1-naphthalenyl)-2,1-benzothiazol-3-yl)-2,6-diazabicyclo[3.2.0]heptan-2-yl)-2-propen-1-one | Step 5: tert-butyl 2,6-diazabicyclo[3.2.0]heptane-2-carboxylate (eNovation Chemicals LLC, Bridgewater, NJ, USA) |
| 5-6 | 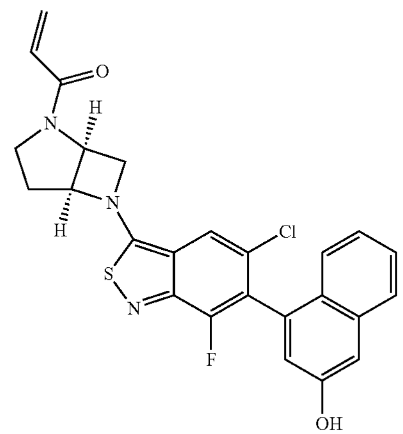 [SMILES: C=CC(=O)N1CC[C@H]2[C@@H]1CN2c1snc2c(F)c(-c3cc(O)cc4ccccc34)c(Cl)cc12] | 1-((1S,5S)-6-(5-chloro-7-fluoro-6-(3-hydroxy-1-naphthalenyl)-2,1-benzothiazol-3-yl)-2,6-diazabicyclo[3.2.0]heptan-2-yl)-2-propen-1-one | Step 5: tert-butyl 2,6-diazabicyclo[3.2.0]heptane-2-carboxylate (eNovation Chemicals LLC, Bridgewater, NJ, USA) |
| 5-7 | 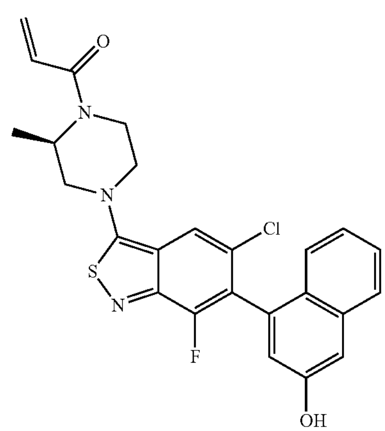 [SMILES: C=CC(=O)N1CCN(c2snc3c(F)c(-c4cc(O)cc5ccccc45)c(Cl)cc23)C[C@H]1C] | 1-((2R)-4-(5-chloro-7-fluoro-6-(3-hydroxy-1-naphthalenyl)-2,1-benzothiazol-3-yl)-2-methyl-1-piperazinyl)-2-propen-1-one | Step 5: (R)-1-boc-2-methyl-piperazine (J & W Pharmlab, LLC, Levittown, PA, USA) |

TABLE 5-continued

Compounds 5-2 to 5-9 were prepared following the procedure described in Method 5, Steps 1-6, above as follows:

| Ex. # | Chemical Structure | Name | Reagent |
|---|---|---|---|
| 5-8 | | 1-(cis-2-(5-chloro-7-fluoro-6-(3-hydroxy-1-naphthalenyl)-2,1-benzothiazol-3-yl)-2,6-diazabicyclo[3.2.0]heptan-6-yl)-2-propen-1-one | Step 5: 1-(2,6-diazabicyclo[3.2.0]heptan-6-yl)prop-2-en-1-one (eNovation Chemicals LLC, Bridgewater, NJ, USA) |
| 5-9 | 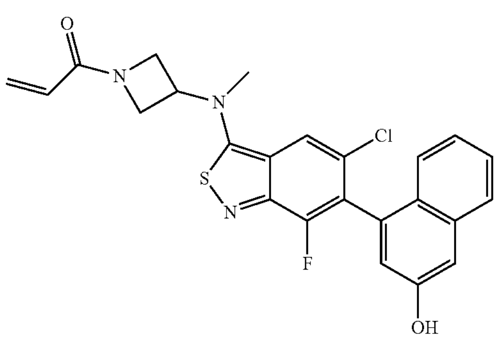 [SMILES: C=CC(=O)N1CC(N(C)c2snc3c(F)c(-c4cc(O)cc5ccccc45)c(Cl)cc23)C1] | 1-(3-((5-chloro-7-fluoro-6-(3-hydroxynaphthalen-1-yl)benzo[c]isothiazol-3-yl)(methyl)amino)azetidin-1-yl)prop-2-en-1-one | Step 5: 1-azetidinecarboxylic acid, 3-(methylamino)-, 1,1-dimethylethyl ester |

Method 6

Example 6-1: 1-(4-(6-(6-Amino-3-chloro-2-pyridinyl)-5-chloro-7-fluoro-2,1-benzothiazol-3-yl)-1-piperazinyl)-2-propen-1-one

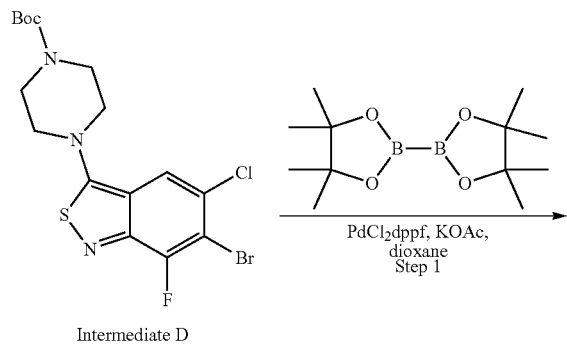

Intermediate D

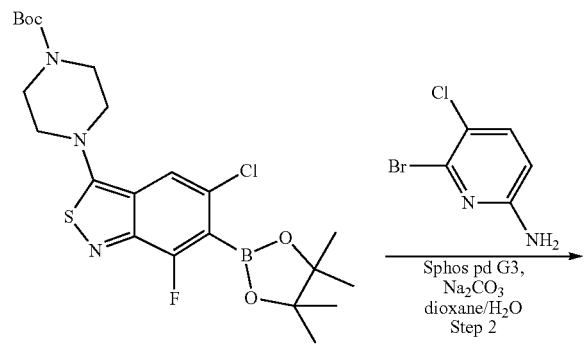

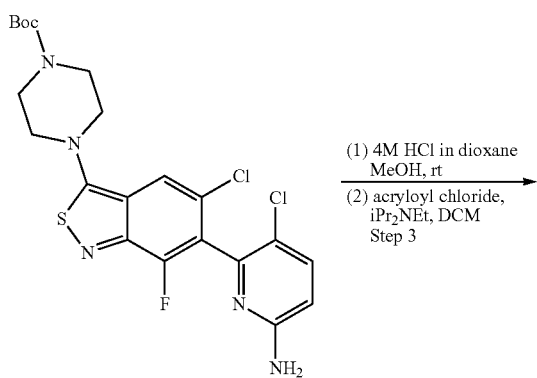

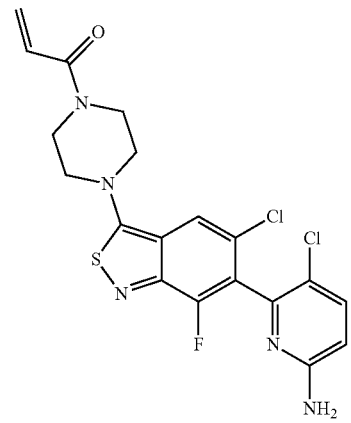

Step 1: tert-Butyl 4-(5-chloro-7-fluoro-6-(4,4,5,5-tetramethyl-1,3,2-dioxaborolan-2-yl)benzo[c]isothiazol-3-yl)piperazine-1-carboxylate. A mixture of tert-butyl 4-(6-bromo-5-chloro-7-fluorobenzo[c]isothiazol-3-yl)piperazine-1-carboxylate (Intermediate D, 1.10 g, 2.45 mmol), bis(pinacolato)diboron (1.86 g, 7.34 mmol), potassium acetate (0.61 mL, 9.8 mmol), and Pd(dppf)Cl$_2$·DCM (0.537 g, 0.734 mmol) in 1,4-dioxane (12 mL) was heated at 100° C. for 40 h. The reaction mixture was then concentrated in vacuo and chromatographically purified (silica gel, 0% to 100% (3:1) EtOAc-EtOH in heptane) to provide tert-butyl 4-(5-chloro-7-fluoro-6-(4,4,5,5-tetramethyl-1,3,2-dioxaborolan-2-yl)benzo[c]isothiazol-3-yl)piperazine-1-carboxylate: $^1$H NMR (400 MHz, DMSO-d$_6$) δ 7.85 (s, 1H), 3.59 (br d, J=4.7 Hz, 4H), 3.44-3.54 (m, 4H), 1.43 (s, 9H), 1.35 (s, 5H), 1.15 (s, 7H). $^{19}$F NMR (376 MHz, DMSO-d$_6$) δ−125.11 (s, 1F), m/z (ESI, +ve) 498.0 (M+H)$^+$.

Step 2: tert-Butyl 4-(6-(6-amino-3-chloropyridin-2-yl)-5-chloro-7-fluorobenzo[c]isothiazol-3-yl)piperazine-1-carboxylate. A mixture of tert-butyl 4-(5-chloro-7-fluoro-6-(4,4,5,5-tetramethyl-1,3,2-dioxaborolan-2-yl)benzo[c]isothiazol-3-yl)piperazine-1-carboxylate (99.5 mg, 0.200 mmol), SPhos Pd G3 (17.3 mg, 0.020 mmol), 6-bromo-5-chloropyridin-2-amine (Combi-blocks Inc., San Diego, CA, USA, 124 mg, 0.6 mmol), sodium carbonate (85 mg, 0.80 mmol) in water (0.25 mL), and 1,2-DCE (0.75 mL) was heated at 50° C. for 2 h. The reaction mixture was concentrated in vacuo and chromatographically purified (silica gel, 0% to 100% (3:1) EtOAc-EtOH in heptane) to give tert-butyl 4-(6-(6-amino-3-chloropyridin-2-yl)-5-chloro-7-fluorobenzo[c]isothiazol-3-yl)piperazine-1-carboxylate: m/z (ESI, +ve) 498.0 (M+H)$^+$.

Step 3: 1-(4-(6-(6-Amino-3-chloro-2-pyridinyl)-5-chloro-7-fluoro-2,1-benzothiazol-3-yl)-1-piperazinyl)-2-propen-1-one. The title compound was prepared from tert-butyl 4-(6-(6-amino-3-chloropyridin-2-yl)-5-chloro-7-fluorobenzo[c]isothiazol-3-yl)piperazine-1-carboxylate (31.6 mg, 0.063 mmol) in two steps following the procedure reported in Method 1, Step 8: $^1$H NMR (400 MHz, DMSO-d$_6$) δ 7.97-8.10 (m, 1H), 7.60 (d, J=8.9 Hz, 1H), 6.86 (dd, J=16.6, 10.6 Hz, 1H), 6.57 (d, J=8.9 Hz, 1H), 6.38 (s, 2H), 6.19 (dd, J=16.8, 2.3 Hz, 1H), 5.71-5.84 (m, 1H), 3.86 (br d, J=19.9 Hz, 4H), 3.63 (br d, J=1.0 Hz, 4H). $^{19}$F NMR (376 MHz, DMSO-d$_6$) δ −126.04 (s, 1F), m/z (ESI, +ve) 452.0 (M+H)$^+$.

TABLE 6

Compound 6-2 was prepared following the procedure described in Method 6, Steps 1-3, above as follows:

| Ex. # | Chemical Structure | Name | Reagent |
|---|---|---|---|
| 6-2 | 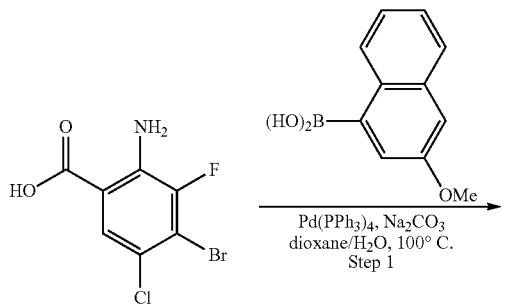 | 1-(4-(5-chloro-6-(3-chloro-2-pyridinyl)-7-fluoro-2,1-benzothiazol-3-yl)-1-piperazinyl)-2-propen-1-one | Step 2: 2-bromo-3-chloropyridine |

Method 7

Example 7-1: 1-((3R)-4-(5-Chloro-7-fluoro-6-(3-hydroxy-1-naphthalenyl)-2,1-benzothiazol-3-yl)-3-(difluoromethyl)-1-piperazinyl)-2-propen-1-one|1-((3A)-4-(5-chloro-7-fluoro-6-(3-hydroxy-1-naphthalenyl)-2,1-benzothiazol-3-yl)-3-(difluoromethyl)-1-piperazinyl)-2-propen-1-one

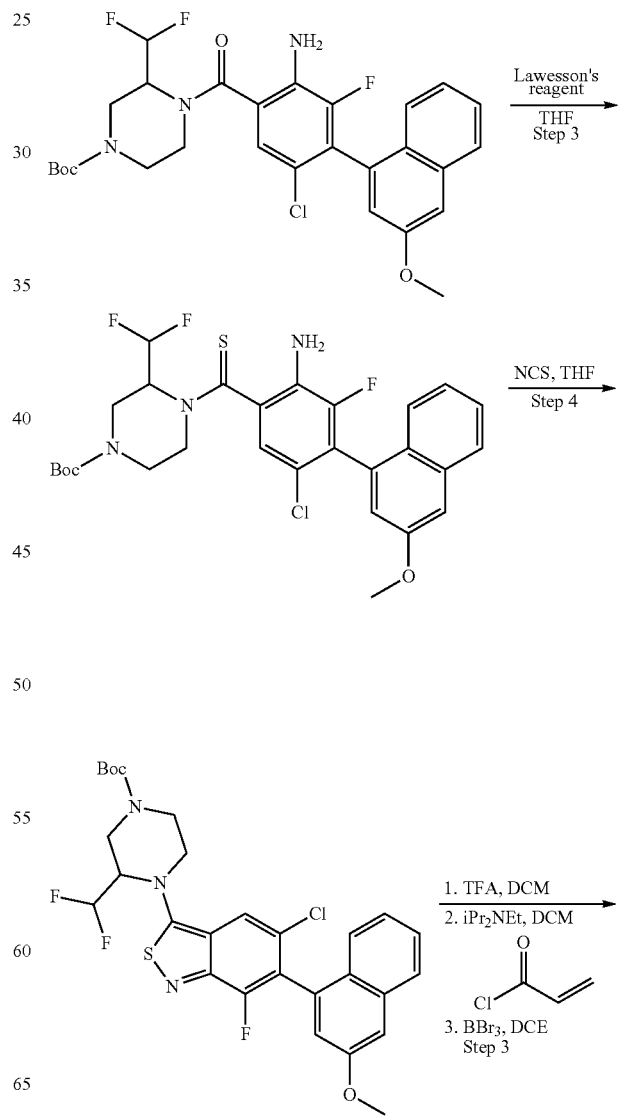

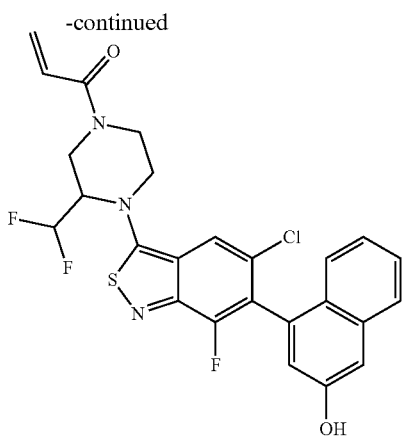

Step 1: 2-Amino-5-chloro-3-fluoro-4-(3-methoxynaphthalen-1-yl)benzoic acid. Prepared from Intermediate A using a procedure analogous to that described in Method 1, Step 7: m/z (ESI, +ve) 346.0 (M+H)$^+$.

Step 2: tert-Butyl 4-(2-amino-5-chloro-3-fluoro-4-(3-methoxynaphthalen-1-yl)benzoyl)-3-(difluoromethyl)piperazine-1-carboxylate. A mixture of 2-amino-5-chloro-3-fluoro-4-(3-methoxynaphthalen-1-yl)benzoic acid (0.150 g, 0.434 mmol), TBTU (0.188 g, 0.586 mmol), tert-butyl 3-(difluoromethyl)piperazine-1-carboxylate (0.123 g, 0.521 mmol), and DIPEA (0.23 mL, 1.302 mmol) in DMF (4 mL) was stirred at ambient temperature for 3 h. The reaction mixture was then washed with saturated aqueous NaHCO$_3$, and the aqueous wash was extracted with EtOAc. The combined organic layers were dried over Na$_2$SO$_4$, filtered, and concentrated in vacuo. Chromatographic purification of the residue (silica gel, 0-40% EtOAc/heptane) provided tert-butyl 4-(2-amino-5-chloro-3-fluoro-4-(3-methoxynaphthalen-1-yl)benzoyl)-3-(difluoromethyl)piperazine-1-carboxylate: m/z (ESI, +ve) 586 (M+Na)$^+$.

Step 3: tert-Butyl 4-(2-amino-5-chloro-3-fluoro-4-(3-methoxynaphthalen-1-yl)phenylcarbonothioyl)-3-(difluoromethyl)piperazine-1-carboxylate. Lawesson's reagent (0.041 mL, 0.10 mmol) was added to a solution of tert-butyl 4-(2-amino-5-chloro-3-fluoro-4-(3-methoxynaphthalen-1-yl)benzoyl)-3-(difluoromethyl)piperazine-1-carboxylate (0.095 g, 0.168 mmol) in THF (4 mL), and the resulting mixture was stirred at 50° C. for 18 h. The reaction mixture was then concentrated in vacuo and purified by column chromatography (silica gel, 0-30% EtOAc/heptane) to give tert-butyl 4-(2-amino-5-chloro-3-fluoro-4-(3-methoxynaphthalen-1-yl)phenylcarbonothioyl)-3-(difluoromethyl)piperazine-1-carboxylate: m/z (ESI, +ve) 602.2 (M+Na)$^+$.

Step 4: tert-Butyl 4-(5-chloro-7-fluoro-6-(3-methoxynaphthalen-1-yl)benzo[c]isothiazol-3-yl)-3-(difluoromethyl)piperazine-1-carboxylate. NBS (0.022 g, 0.17 mmol) was added to a solution of tert-butyl 4-(2-amino-5-chloro-3-fluoro-4-(3-methoxynaphthalen-1-yl)phenylcarbonothioyl)-3-(difluoromethyl)piperazine-1-carboxylate in THF (7 mL), and the resulting mixture was stirred at ambient temperature for 15 min. The reaction mixture was diluted with water and washed with 10% sodium thiosulfate. The aqueous wash was extracted with EtOAc, and the combined organic layers were then concentrated in vacuo to give tert-butyl 4-(5-chloro-7-fluoro-6-(3-methoxynaphthalen-1-yl)benzo[c]isothiazol-3-yl)-3-(difluoromethyl)piperazine-1-carboxylate: m/z (ESI, +ve) 578.2 (M+H)$^+$.

Step 5: 1-((3R)-4-(5-Chloro-7-fluoro-6-(3-hydroxy-1-naphthalenyl)-2,1-benzothiazol-3-yl)-3-(difluoromethyl)-1-piperazinyl)-2-propen-1-one|1-((3A)-4-(5-chloro-7-fluoro-6-(3-hydroxy-1-naphthalenyl)-2,1-benzothiazol-3-yl)-3-(difluoromethyl)-1-piperazinyl)-2-propen-1-one. Prepared using a procedure analogous to that described in Method 1, Step 8: $^1$H NMR (400 MHz, DMSO-d$_6$) δ 10.13 (br. s., 1H) 8.12 (d, J=2.2 Hz, 1H) 7.80 (d, J=8.2 Hz, 1H) 7.43 (br t, J=7.0 Hz, 1H) 7.20-7.30 (m, 3H) 7.08 (dd, J=5.8, 2.2 Hz, 1H) 6.78-6.91 (m, 1H) 6.27-6.70 (m, 1H) 6.20 (dd, j=16.6, 2.0 Hz, 1H) 5.76-5.84 (m, 1H) 4.73-4.87 (m, 1H) 4.19-4.72 (m, 2H) 3.55-3.90 (m, 3H) 3.36-3.47 (m, 1H). m/z (ESI, +ve) 518.0 (M+H)$^+$.

TABLE 7

Compounds 7-2 and 7-3 were prepared following the procedure described in Method 7, Steps 1-5, above as follows:

| Ex.# | Chemical Structure | Name | Reagent |
|---|---|---|---|
| 7-2 | 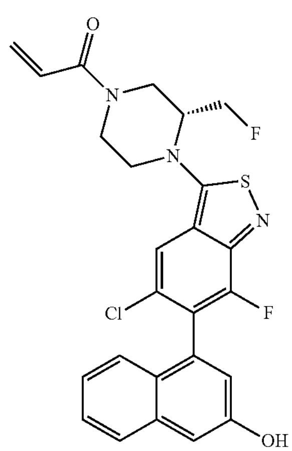 [SMILES: C=CC(=O)N1CCN(c2snc3c(F)c(-c4cc(O)cc5ccccc45)c(Cl)cc23)[C@@H](CF)C1] | 1-(4-(5-chloro-7-fluoro-6-(3-hydroxy-1-naphthalenyl)-2,1-benzothiazol-3-yl)-3-(fluoromethyl)-1-piperazinyl)-2-propen-1-one | Step 2: 3-fluoromethyl-piperazine-1-carboxylic acid tert-butyl ester (eNovation Chemicals LLC, Bridgewater, NJ, USA) |

TABLE 7-continued
Compounds 7-2 and 7-3 were prepared following the procedure described in Method 7, Steps 1-5, above as follows:
| Ex.# | Chemical Structure | Name | Reagent |
|---|---|---|---|
| | 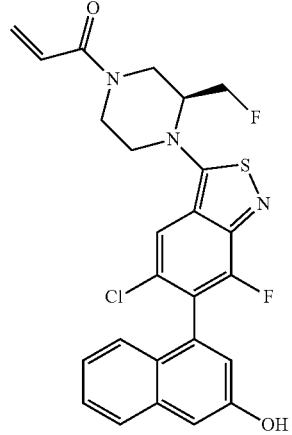 | | |
| 7-3 | 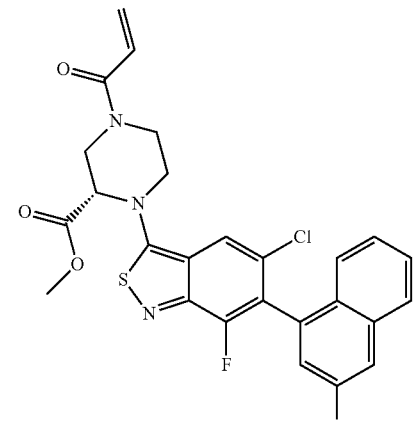<br><br>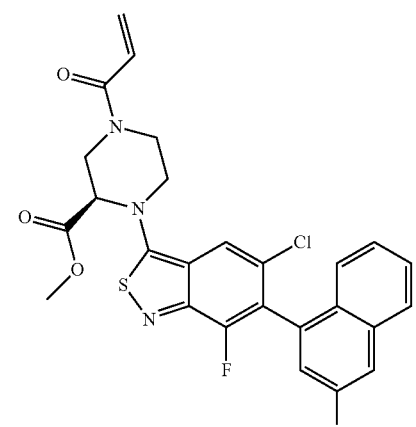 | methyl 1-(5-chloro-7-fluoro-6-(3-hydroxy-1-naphthalenyl)-2,1-benzothiazol-3-yl)-4-(2-propenoyl)-2-piperazinecarboxylate | Step 2: 4-boc-piperazine-2-carboxylic acid methyl ester (Combi-blocks Inc., San Diego, CA, USA) |

Method 8

Example 8-1: 6-Chloro-7-(2-fluoro-6-hydroxyphenyl)-1-(2-(2-propanyl)phenyl)-4-(4-(2-propenoyl)-1-piperazinyl)-2(1H)-quinazolinone

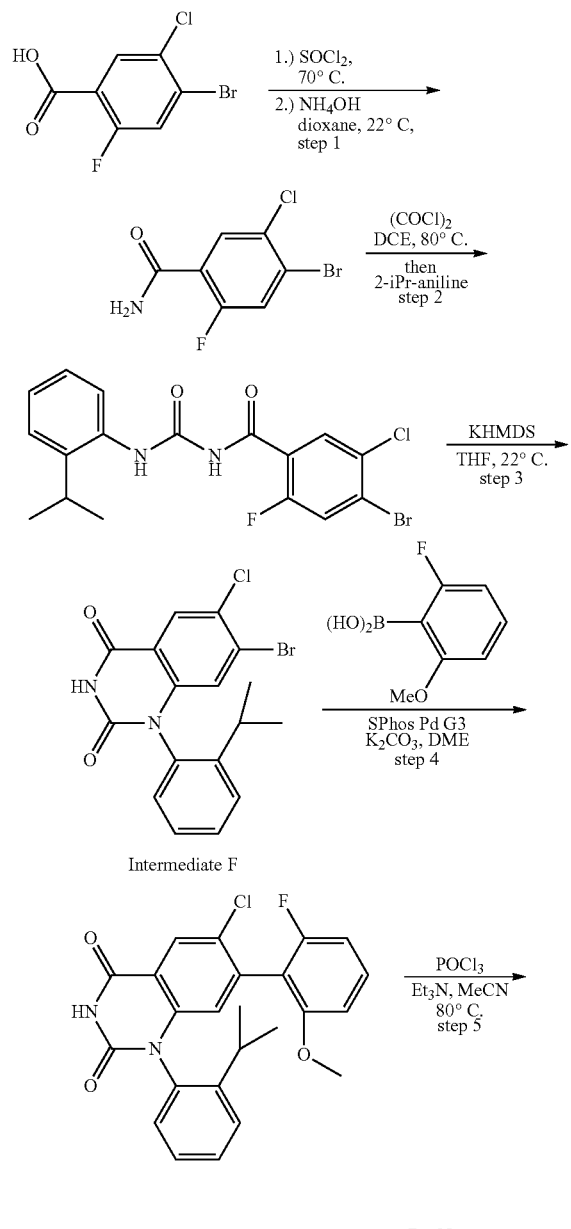

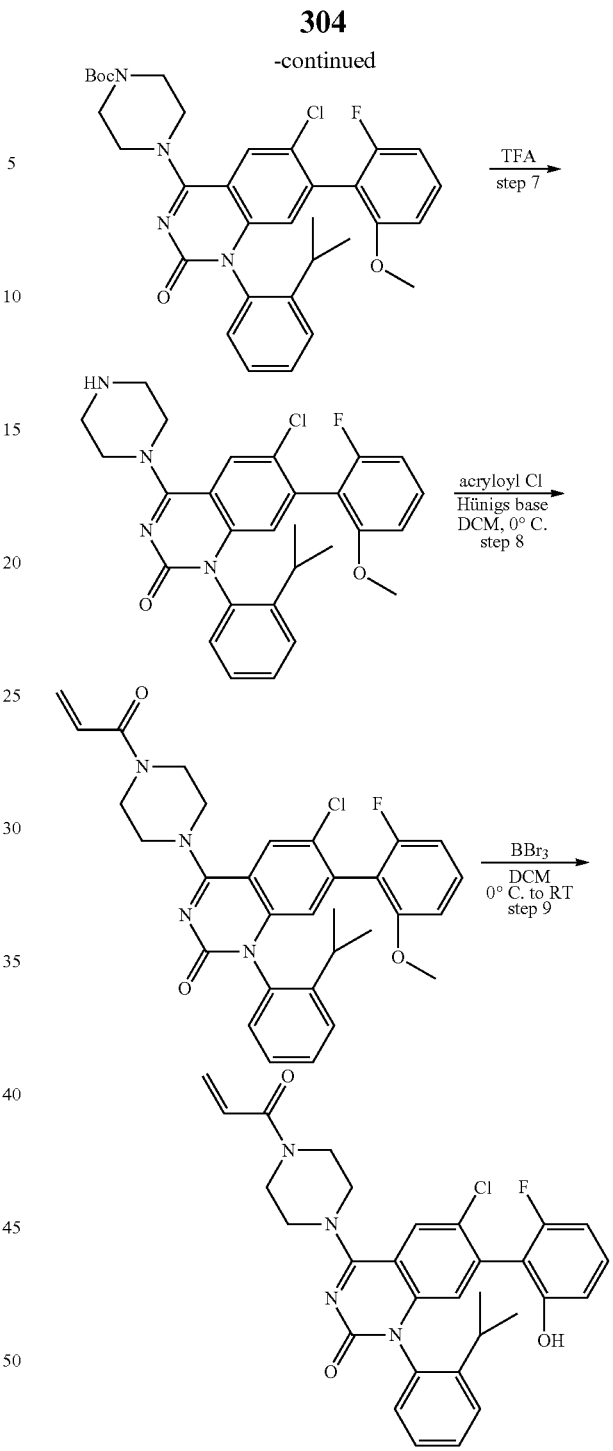

Step 1: 4-Bromo-5-chloro-2-fluorobenzamide. A mixture of 4-bromo-5-chloro-2-fluorobenzoic acid (23.3 g, 92 mmol) in thionyl chloride (67 mL, 0.92 mol) was stirred at 70° C. under a reflux condenser for 1 h. The reaction mixture was then concentrated in vacuo, and the residue was taken up in 1,4-dioxane (200 mL), treated with ammonium hydroxide (30% aqueous, 82 mL, 0.64 mol), and stirred at rt for 15 min. The reaction mixture was concentrated in vacuo to give 4-bromo-5-chloro-2-fluorobenzamide: m/z (ESI, +ve) 251.8 (M+H)+.

Step 2: 4-Bromo-5-chloro-2-fluoro-N-((2-isopropylphenyl)carbamoyl)benzamide. A mixture of 4-bromo-5-chloro- 2-fluorobenzamide (5.90 g, 23.4 mmol) and oxalyl chloride (1 M in DCM; 12.9 mL, 25.7 mmol) in DCE (100 mL) was stirred under a reflux condenser at 80° C. for 1 h. The reaction mixture was then cooled to rt and 2-isopropylaniline (6.62 mL, 46.7 mmol) was added. The resulting mixture was stirred at rt for 15 min, then cooled to 0° C. The precipitated solid was removed by filtration, and the collected filtrate was concentrated in vacuo to give 4-bromo-5-chloro-2-fluoro-N-((2-isopropylphenyl)carbamoyl)benzamide: $^1$H NMR (400 MHz, DMSO-d$_6$) δ 11.06 (br. s., 1H) 10.31 (s, 1H) 7.97-8.05 (m, 2H) 7.82 (d, J=7.2 Hz, 1H) 7.32-7.38 (m, 1H) 7.14-7.25 (m, 2H) 3.11 (spt, J=6.8 Hz, 1H) 1.24 (d, J=6.8 Hz, 6H). $^{19}$F NMR (376 MHz, DMSO-de) 5-113.6 (s, 1F). m/z (ESI, +ve) 412.7 and 414.6 (M+H)$^+$.

Step 3: 7-Bromo-6-chloro-1-(2-isopropylphenyl)quinazoline-2,4(1H,3H)-dione (Intermediate F). KHMDS (1 M in THF, 8.30 mL, 8.30 mmol) was added to a mixture of 4-bromo-5-chloro-2-fluoro-N-((2-isopropylphenyl)carbamoyl)benzamide (1.56 g, 3.77 mmol) in THF (19 mL) at −20° C., and the resulting mixture was allowed to warm to rt over 1 h. The reaction mixture was then diluted with EtOAc (150 mL) and washed with saturated aqueous ammonium chloride (2×100 mL). The organic layer was dried over Na$_2$SO$_4$, filtered, and concentrated in vacuo. The residue was suspended in DCM (5 mL), sonicated, collected by filtration, and dried in vacuo to give 7-bromo-6-chloro-1-(2-isopropylphenyl)quinazoline-2,4(1H,3H)-dione: $^1$H NMR (400 MHz, CDCl$_6$) δ 9.43 (br. s., 1H) 8.29 (s, 1H) 7.55-7.59 (m, 2H) 7.39-7.44 (m, 1H) 7.16 (d, J=7.8 Hz, 1H) 6.75 (s, 1H) 2.59-2.77 (m, 1H) 1.17-1.24 (m, 3H) 1.11 (d, J=6.8 Hz, 3H). m/z (ESI, +ve) 392.9 and 395.0 (M+H)$^+$.

Step 4: 6-Chloro-7-(2-fluoro-6-methoxyphenyl)-1-(2-isopropylphenyl)quinazoline-2,4(1H,3H)-dione. A mixture of 7-bromo-6-chloro-1-(2-isopropylphenyl)quinazoline-2,4(1H,3H)-dione (Intermediate F, 1.17 g, 2.96 mmol), (2-fluoro-6-methoxyphenyl)boronic acid (2.02 g, 11.9 mmol), SPhos Pd G3 (0.128 g, 0.148 mmol), and potassium carbonate (2 M in water, 4.45 mL, 8.90 mmol) in DME (30 mL) was stirred at 85° C. for 16 h. The reaction mixture was then diluted with EtOAc (150 mL) and washed with saturated aqueous NaHCO$_3$ (3×100 mL). The organic layer was dried over Na$_2$SO$_4$, filtered, and concentrated in vacuo. Chromatographic purification of the residue (silica gel, 0-50% EtOAc in heptane) gave 6-chloro-7-(2-fluoro-6-methoxyphenyl)-1-(2-isopropylphenyl)quinazoline-2,4(1H,3H)-dione: $^1$H NMR (400 MHz, DMSO-d$_6$) δ 11.90 (d, J=1.2 Hz, 1H) 8.11 (d, J=3.3 Hz, 1H) 7.53-7.59 (m, 1H) 7.48 (tt, 0.7=7.0, 2.2 Hz, 1H) 7.38-7.44 (m, 1H) 7.32-7.37 (m, 2H) 6.93 (dd, J=8.4, 4.3 Hz, 1H) 6.86 (t, J=8.7 Hz, 1H) 6.15 (s, 1H) 3.66 (d, J=30 Hz, 3H) 2.73 (dq, J=14.2, 7.0 Hz, 1H) 1.11 (t, 0.7=7.1 Hz, 3H) 1.03 (dd, J=12.7, 6.8 Hz, 3H). $^{19}$F NMR (376 MHz, DMSO-d$_6$) δ−113.8 (s, 1F) −115.2 (s, 1F), m/z (ESI, +ve) 439.1 (M+H)$^+$.

Step 5: 4,6-Dichloro-7-(2-fluoro-6-methoxyphenyl)-1-(2-isopropylphenyl)quinazolin-2(1H)-one. To a solution of 6-chloro-7-(2-fluoro-6-methoxyphenyl)-1-(2-isopropylphenyl)quinazoline-2,4(1H,3H)-dione (0.395 g, 0.900 mmol) and Et$_3$N (0.753 mL, 5.40 mmol) in acetonitrile (9 mL) was added phosphorus oxychloride (0.503 mL, 5.40 mmol), and the resulting solution was stirred at 80° C. for 1.5 h. The reaction mixture was concentrated in vacuo to give 4,6-dichloro-7-(2-fluoro-6-methoxyphenyl)-1-(2-isopropylphenyl)quinazolin-2(1H)-one: m/z (ESI, +ve) 457.1 (M+H)$^+$.

Alternative procedure for Step 5 (used as noted in the table below): To a stirred mixture of the product from Step 4 (1.0 equiv.), triethylamine (18.0 equiv.), and 1H-benzo[d][1,2,3]triazole (12 equiv.) in acetonitrile (0.07 M) was added phosphorus oxychloride (6.0 equiv.), and the resulting reaction mixture was stirred at 80° C. for 3.5 h. The reaction mixture was then poured slowly into rapidly stirred water (100 mL) at 10° C. The aqueous suspension was stirred for 15 min before being extracted with EtOAc (100 mL). The organic layer was washed with brine (100 mL), dried over MgSO$_4$, filtered, and concentrated in vacuo to give a benzotriazole adduct intermediate that was used directly in Step 6.

Step 6: tert-Butyl 4-(6-chloro-7-(2-fluoro-6-methoxyphenyl)-1-(2-isopropylphenyl)-2-oxo-1,2-dihydroquinazolin-4-yl)piperazine-1-carboxylate. A solution of 4,6-dichloro-7-(2-fluoro-6-methoxyphenyl)-1-(2-isopropylphenyl)quinazolin-2(1H)-one (obtained from Method 8, Step 5), tert-butyl piperazine-1-carboxylate (0.335 g, 1.80 mmol), and Et$_3$N (0.753 mL, 5.40 mmol) in DCE (9 mL) was stirred at 60° C. for 20 min. The reaction mixture was diluted with EtOAc (100 mL) and washed with saturated aqueous NaHCO$_3$ (3×75 mL). The organic layer was dried over Na$_2$SO$_4$ and concentrated in vacuo. Chromatographic purification of the residue (silica gel, 0-60% (3:1) EtOAc-EtOH in heptane) provided tert-butyl 4-(6-chloro-7-(2-fluoro-6-methoxyphenyl)-1-(2-isopropylphenyl)-2-oxo-1,2-dihydroquinazolin-4-yl)piperazine-1-carboxylate: m/z (ESI, +ve) 607.3 (M+H)$^+$.

Note: When (5)-1-(3-methylpiperazin-1-yl)prop-2-en-1-one 2,2,2-trifluoroacetate was used, it was synthesized as follows:

(S)-1-(3-Methylpiperazin-1-yl)prop-2-en-1-one 2,2, 2-trifluoroacetate

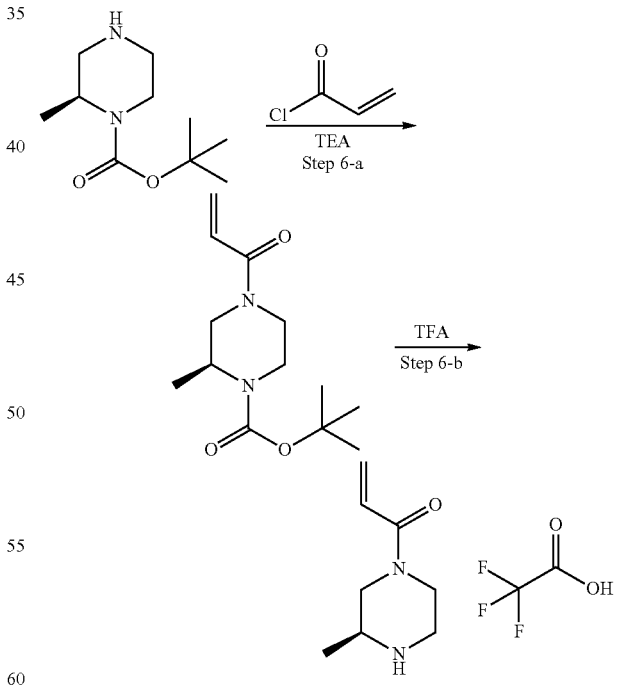

Step 6-a: (A)-tert-Butyl 4-acryloyl-2-methylpiperazine-1-carboxylate. Acryloyl chloride (1.34 mL, 16.5 mmol) was added to a solution of (S)-1-boc-2-methy 1-piperazine (3.00 g, 15.0 mmol, Boc Sciences, Shirley, NY) in THF (30.0 mL) at −10° C., and the resulting mixture was stirred at −10° C. for 5 min. Triethylamine (6.26 mL, 44.9 mmol) was then slowly added, and the resulting mixture was stirred at −10° C. for 15 min, then allowed to warm to rt. The reaction mixture was partitioned between EtOAc and saturated aqueous NaHCO₃. The aqueous layer was extracted with EtOAc (3/), and the organic layers were then combined, dried over MgSO₄, filtered, and concentrated in vacuo. Chromatographic purification of the residue (silica gel, 0-100% EtOAc in heptane) furnished (S)-tert-butyl 4-acryloyl-2-methylpiperazine-1-carboxylate: ¹H NMR (400 MHz, DMSO-d₆) δ 6.72-6.85 (m, 1H) 6.10-6.18 (m, 1H) 5.68-5.76 (m, 1H) 4.08-4.32 (m, 2H) 3.68-4.03 (m, 2H) 2.86-3.14 (m, 2H) 2.66-2.80 (m, 1H) 1.38-1.43 (s, 9H) 0.96-1.04 (m, 3H). m/z (ESI, +ve) 2113 (M+Na)⁺.

Step 6-b: (A)-1-(3-Methylpiperazin-1-yl)prop-2-en-1-one 2,2,2-trifluoroacetate. A mixture of (S)-tert-butyl 4-acryloyl-2-methylpiperazine-1-carboxylate (3.21 g, 12.62 mmol) and TEA (4.7 mL, 63.1 mmol) in DCM (16 mL) was stirred at rt for 24 h. The reaction mixture was then concentrated in vacuo to give (S)-1-(3-methylpiperazin-1-yl)prop-2-en-1-one 2,2,2-trifluoroacetate: ¹H NMR (400 MHz, DMSO-d₆) δ 8.70-8.99 (m, 1H) 6.74-6.91 (m, 1H) 6.12-6.26 (m, 1H) 5.70-5.84 (m, 1H) 4.25-4.44 (m, 1H) 4.07-4.25 (m, 1H) 3.49-3.53 (m, 1H) 3.22-3.32 (m, 2H) 2.92-3.08 (m, 2H) 1.14-1.29 (m, 3H). m/z (ESI, +ve) 155.1 (M+H)⁺.

Step 7: 6-Chloro-7-(2-fluoro-6-methoxyphenyl)-1-(2-isopropylphenyl)-4-(piperazin-1-yl)quinazolin-2(1H)-one. A solution of tert-butyl 4-(6-chloro-7-(2-fluoro-6-methoxyphenyl)-1-(2-isopropylphenyl)-2-oxo-1,2-dihydroquinazolin-4-yl)piperazine-1-carboxylate (0.594 g, 0.978 mmol) in TEA (4 mL) was stirred at ambient temperature for 30 min. The reaction mixture was concentrated in vacuo to give 6-chloro-7-(2-fluoro-6-methoxyphenyl)-1-(2-isopropylphenyl)-4-(piperazin-1-yl)quinazolin-2(1H)-one: m/z (ESI, +ve) 507.2 (M+H)⁺.

Step 8: 4-(4-Acryloylpiperazin-1-yl)-6-chloro-7-(2-fluoro-6-methoxyphenyl)-1-(2-isopropylphenyl)quinazolin-2(1H)-one. To an ice-cooled solution of 6-chloro-7-(2-fluoro-6-methoxyphenyl)-1-(2-isopropylphenyl)-4-(piperazin-1-yl)quinazolin-2(1H)-one and DIPEA (0.85 mL, 4.9 mmol) in DCM (10 mL) at 0° C. was added acryloyl chloride (0.079 mL, 0.98 mmol), and the resulting mixture was stirred at 0° C. for 30 min. The reaction mixture was then diluted with EtOAc (100 mL) and washed with saturated aqueous NaHCO₃ (3×75 mL). The organic layer was dried over Na₂SO₄, decanted, and concentrated in vacuo. Chromatographic purification of the residue (silica gel, 0-100% (3:1)EtOAc-EtOH in heptane) gave 4-(4-acryloylpiperazin-1-yl)-6-chloro-7-(2-fluoro-6-methoxy phenyl)-1-(2-isopropylphenyl)quinazolin-2(1H)-one: ¹H NMR (400 MHz, CDCl₃) δ 7.86 (d, J=1.2 Hz, 1H) 7.41-7.54 (m, 2H) 7.29-7.37 (m, 2H) 7.14 (dt, j=7.8, 1.7 Hz, 1H) 6.70-6.79 (m, 2H) 6.58-6.68 (m, 1H) 6.50 (d, j=7.4 Hz, 1H) 6.39 (dd, j=16.8, 1.8 Hz, 1H) 5.75-5.84 (m, 1H) 3.79-4.06 (m, 8H) 3.75 (s, 2H) 3.66 (s, 1H) 2.69 (tt, j=13.4, 6.8 Hz, 1H) 1.20-1.24 (m, 3H) 1.07 (dd, J=6.8, 3.9 Hz, 3H). ¹⁹F NMR (377 MHz, CDCl₃) δ−113.05 (s, 1F) −113.55 (s, 1F). m/z (ESI, +ve) 561.2 (M+H)⁺.

Step 9: 6-Chloro-7-(2-fluoro-6-hydroxyphenyl)-1-(2-(2-propanyl)phenyl)-4-(4-(2-propenoyl)-1-piperazinyl)-2(1H)-quinazolinone. BBn (1 M in DCE, 3.3 mL, 3.3 mmol) was added to an ice-cooled solution of 4-(4-acryloylpiperazin-1-yl)-6-chloro-7-(2-fluoro-6-methoxyphenyl)-1-(2-isopropylphenyl)quinazolin-2(1H)-one (0.372 g, 0.663 mmol) in DCE (1.7 mL), and the resulting mixture was stirred at 0° C. for 20 min, then allowed to warm to rt and stir at rt for 2 h. Saturated aqueous NaHCO₃ was added to the reaction mixture, followed by EtOAc (150 mL). The organic layer was separated and washed with saturated aqueous NaHCO₃ (3×100 mL). The organic layer was then dried over Na₂SO₄, filtered, and concentrated in vacuo. Chromatographic purification of the residue (silica gel, 0-100% (3:1) EtOAc-EtOH in heptane) provided 6-chloro-7-(2-fluoro-6-hydroxyphenyl)-1-(2-(2-propanyl)phenyl)-4-(4-(2-propenoyl)-1-piperazinyl)-2(1H)-quinazolinone: ¹H NMR (400 MHz, DMSO-d₆) δ 10.06 (hr. d, J=15.1 Hz, 1H) 8.03 (d, J=1.2 Hz, 1H) 7.51-7.56 (m, 1H) 7.45 (t, J=7.6 Hz, 1H) 7.33 (tdd, J=7.5, 7.5, 3.8, 1.4 Hz, 1H) 7.14-7.25 (m, 2H) 6.84 (dd, J=16.8, 10.4 Hz, 1H) 6.62-6.74 (m, 2H) 6.14-6.26 (m, 2H) 5.71-5.78 (m, 1H) 3.71-3.99 (m, 8H) 2.52-2.59 (m, 1H) 1.02-1.12 (m, 6H). ¹⁹F NMR (377 MHz, DMSO-d₆) δ−113.6 (s, 1F) −114.8 (s, 1F), m/z (ESI, +ve) 547.1 (M+H)⁺.

TABLE 8

Compounds 8-2 to 8-6 were prepared following the procedure described in Method 8, Steps 1-9, above as follows:

| Ex. # | Chemical Structure | Name | Method changes | Starting material | Reagents |
|---|---|---|---|---|---|
| 8-2 | [structure] | 6-chloro-7-(2-fluoro-6-hydroxyphenyl)-1-(2-(2-propanyl)phenyl)-4-(4-(2-propenoyl)-1-piperazinyl)pyrido[2,3-d]pyrimidin-2(1H)-one | Omit steps 7 and 8 | 2,5,6-trichloronicotinic acid | Step 4: sodium carbonate Step 6: 1-(piperazin-1-yl)prop-2-en-1-one (eNovation Chemicals LLC, Bridgewater, NJ, USA) |

TABLE 8-continued

Compounds 8-2 to 8-6 were prepared following the procedure described in Method 8, Steps 1-9, above as follows:

| Ex. # | Chemical Structure | Name | Method changes | Starting material | Reagents |
|---|---|---|---|---|---|
| 8-3 | 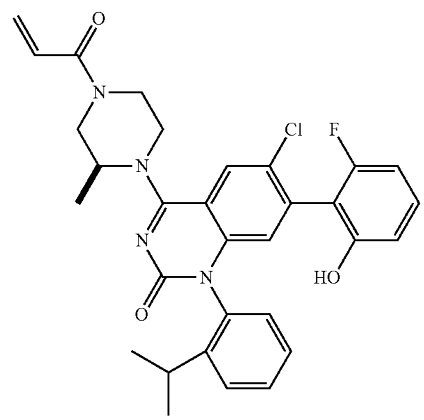 [SMILES: C=CC(=O)N1CCN(c2nc(=O)n(-c3ccccc3C(C)C)c3cc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(2-(2-propanyl)phenyl)-2(1H)-quinazolinone | — | 4-bromo-5-chloro-2-fluorobenzoic acid | Step 6: (S)-tert-butyl 3-methylpiperazine-1-carboxylate (CNH Technologies, Inc., Woburn, MA) |
| 8-4 | 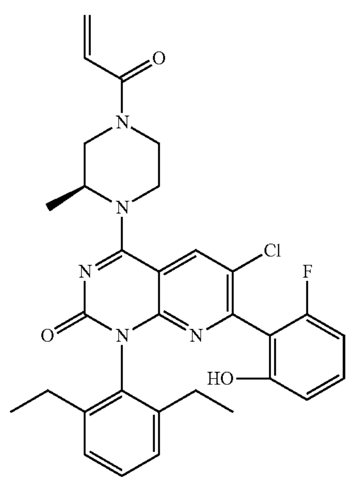 [SMILES: C=CC(=O)N1CCN(c2nc(=O)n(-c3c(CC)cccc3CC)c3nc(-c4c(O)cccc4F)c(Cl)cc23)[C@@H](C)C1] | 6-chloro-1-(2,6-diethylphenyl)-7-(2-fluoro-6-hydroxyphenyl)-4-((2S)-2-methyl-4-(2-propenoyl)-1-piperazinyl) pyrido[2,3-d]pyrimidin-2(1H)-one | Omit steps 7 and 8 | 2,5,6-trichloronicotinic acid | Step 2: 2,6-diethylaniline, Step 5: benzotriazole, Step 6: (S)-1-(3-methylpiperazin-1-yl)prop-2-en-1-one 2,2,2-trifluoroacetate (See Step 6 note for synthesis) |
| 8-5 | 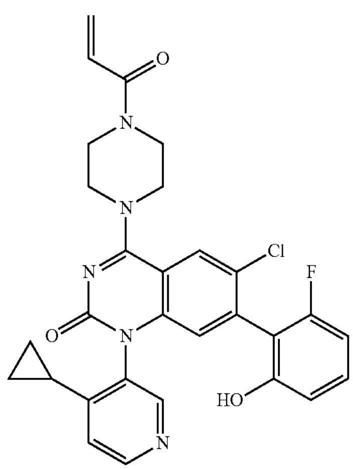 [SMILES: C=CC(=O)N1CCN(c2nc(=O)n(-c3cnccc3C3CC3)c3cc(-c4c(O)cccc4F)c(Cl)cc23)CC1] | 6-chloro-1-(4-cyclopropyl-3-pyridinyl)-7-(2-fluoro-6-hydroxyphenyl)-4-(4-(2-propenoyl)-1-piperazinyl)-2(1H)-quinazolinone | — | 4-bromo-5-chloro-2-fluorobenzoic acid | Step 2: 4-cyclopropylpyridin-3-amine (Combi-Phos Catalysts Inc. Trenton, NJ, USA), 1,4-dioxane/water, 100° C. |

TABLE 8-continued

Compounds 8-2 to 8-6 were prepared following the procedure described in Method 8, Steps 1-9, above as follows:

| Ex. # | Chemical Structure | Name | Method changes | Starting material | Reagents |
|---|---|---|---|---|---|
| 8-6 | 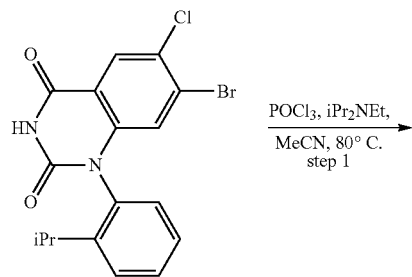 | 6-chloro-7-(2-fluoro-6-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | Omit steps 7 and 8 | 2,5,6-trichloronicotinic acid | Step 4: sodium carbonate Step 6: (S)-1-(3-methylpiperazin-1-yl)prop-2-en-1-one 2,2,2-trifluoroacetate (See Step 6 note for synthesis) |

Method 9

Example 9-1: 6-Chloro-7-(2,3-dichloro-5-hydroxyphenyl)-4-((2S)-2-methyl-4-(2-propenoyl)-1-piperazinyl)-1-(2-(2-propanyl)phenyl)-2(1H)-quinazolinone

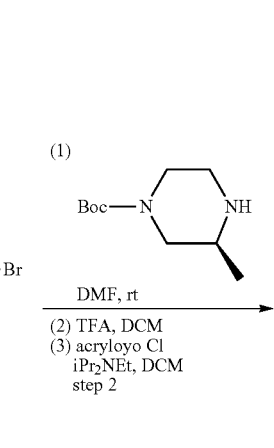

Intermediate F

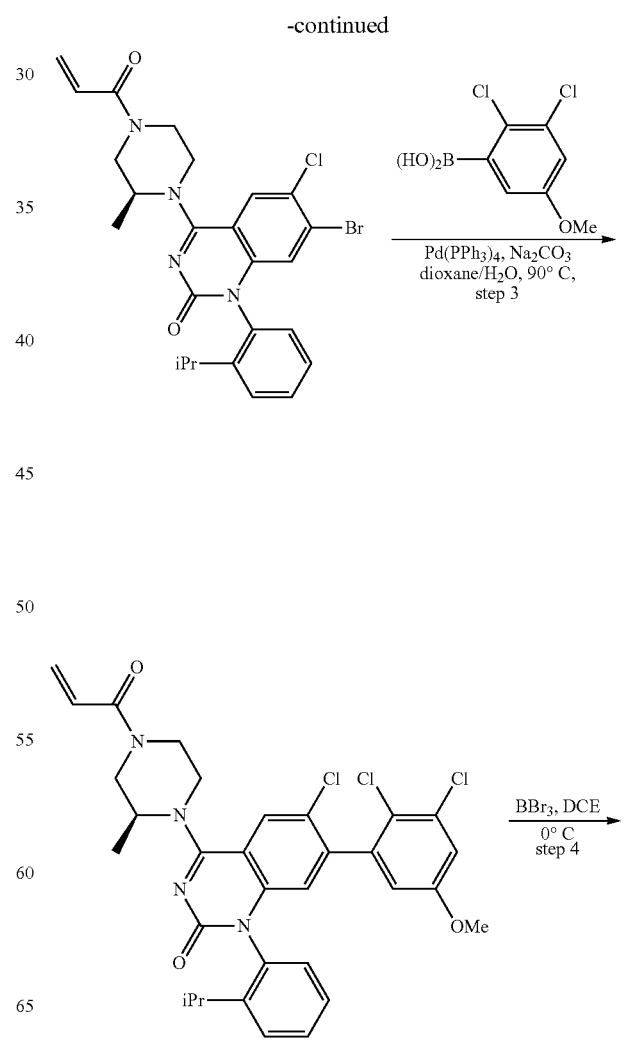

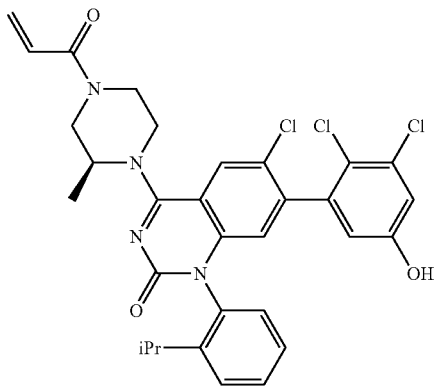

Step 1: 7-Bromo-4,6-dichloro-1-(2-isopropylphenyl)quinazolin-2(1H)-one. To a mixture of 7-bromo-6-chloro-1-(2-isopropylphenyl)quinazoline-2,4(1H,3H)-dione (Intermediate F, 470 mg, 1.194 mmol) and DIPEA (0.623 mL, 3.58 mmol) in acetonitrile (11.4 mL) was added phosphorus oxychloride (0.915 mL, 5.97 mmol). The resulting mixture was heated at 80° C. for 2 h, then cooled to ambient temperature and concentrated in vacuo to give 7-bromo-4,6-dichloro-1-(2-isopropylphenyl)quinazolin-2(1H)-one: m/z (ESI, +ve) 413.0 (M+H)$^+$.

Step 2: (A)-4-(4-Acryloyl-2-methylpiperazin-1-yl)-7-bromo-6-chloro-1-(2-isopropylphenyl)quinazolin-2(1H)-one. A mixture of 7-bromo-4,6-dichloro-1-(2-isopropylphenyl)quinazolin-2(1H)-one (492 mg, 1.19 mmol), (S)-4-iV-boc-2-methyl piperazine (478 mg, 2.39 mmol), and DIPEA (0.623 mL, 3.58 mmol) in DMF (2.3 mL) was stirred at rt for 10 min. Ice water (10 mL) was then added, and the resulting mixture stirred for 15 min. The precipitated solid was collected by filtration, washed with water, and dried in vacuo to give (S)-tert-butyl 4-(7-bromo-6-chloro-1-(2-isopropylphenyl)-2-oxo-1,2-dihydroquinazolin-4-yl)-3-methylpiperazine-1-carboxylate: m/z (ESI, +ve) 577.1 (M+H)$^+$.

TFA (2.0 mL, 26.8 mmol) was added to a solution of (5)-tert-butyl 4-(7-bromo-6-chloro-1-(2-isopropylphenyl)-2-oxo-1,2-dihydroquinazolin-4-yl)-3-methylpiperazine-1-carboxylate (297 mg, 0.516 mmol) in DCM (2.0 mL), and the resulting mixture was stirred at rt for 15 min. Concentration of the resulting mixture in vacuo provided (5)-7-bromo-6-chloro-1-(2-isopropylphenyl)-4-(2-methylpiperazin-1-yl)quinazolin-2(1H)-one: m/z (ESI, +ve) 477.0 (M+H)$^+$.

Acryloyl chloride (0.258 M in DCM, 4.0 mL, 1.031 mmol) was added to an ice-cooled mixture of (5)-7-bromo-6-chloro-1-(2-isopropylphenyl)-4-(2-methylpiperazin-1-yl)quinazolin-2(1H)-one and DIPEA (0.269 mL, 1.547 mmol) in DCM (2.0 mL), and the resulting mixture was stirred at 0° C. for 20 min. Concentration in vacuo followed by chromatographic purification of the residue (silica gel, 0-100% (3:1) EtOAc-EtOH in heptane) gave (S)-4-(4-acryloyl-2-methylpiperazin-1-yl)-7-bromo-6-chloro-1-(2-isopropylphenyl)quinazolin-2(1H)-one: $^1$H NMR (400 MHz, DMSO-d$_6$) δ 7.91-8.08 (m, 1H), 7.49-7.67 (m, 2H), 7.41 (br d, J=5.8 Hz, 1H), 7.21 (hr s, 1H), 6.76-6.98 (m, 1H), 6.52-6.67 (m, 1H), 6.09-6.29 (m, 1H), 5.75 (hr s, 1H), 4.61-4.96 (m, 1H), 4.23-4.48 (m, 1H), 3.93-4.21 (m, 2H), 3.50-3.77 (m, 1H), 3.33-3.49 (m, 1H), 3.23-3.28 (m, 1H), 2.94-3.24 (m, 1H), 1.27 (br d, J=9.3 Hz, 6H), 1.09 (hr s, 3H). m/z (ESI, +ve) 531.1 (M+H)$^+$.

Step 3: (A)-4-(4-Acryloyl-2-methylpiperazin-1-yl)-6-chloro-7-(2,3-dichloro-5-methoxyphenyl)-1-(2-isopropylphenyl)quinazolin-2(1H)-one. A mixture of (S)-4-(4-acryloyl-2-methylpiperazin-1-yl)-7-bromo-6-chloro-1-(2-isopropylphenyl)quinazolin-2(1H)-one (120 mg, 0.226 mmol), 2-(2,3-dichloro-5-methoxyphenyl)-4,4,5,5-tetramethyl-1,3,2-dioxaborolane (82 mg, 0.272 mmol), Na$_2$CO$_3$ (96 mg, 0.906 mmol), and Pd(PPh$_3$)$_4$ (26.2 mg, 0.023 mmol) in 1,4-dioxane (1.6 mL) and water (0.4 mL) was heated at 90° C. for 17 h. The reaction mixture was then concentrated in vacuo and chromatographically purified (silica gel, 0-100% (3:1) EtOAc-EtOH in heptane) to provide (5)-4-(4-acryloyl-2-methylpiperazin-1-yl)-6-chloro-7-(2,3-dichloro-5-methoxyphenyl)-1-(2-isopropylphenyl)quinazolin-2(1H)-one: m/z (ESI, +ve) 627.0 (M+H)$^+$.

Step 4: 6-Chloro-7-(2,3-dichloro-5-hydroxyphenyl)-4-((2A)-2-methyl-4-(2-propenoyl)-1-piperazinyl)-1-(2-(2-propanyl)phenyl)-2(1H)-quinazolinone. BBr$_3$ (1 M in hexanes, 0.32 mL, 0.320 mmol) was added to an ice-cooled mixture of (S)-4-(4-acryloyl-2-methylpiperazin-1-yl)-6-chloro-7-(2,3-dichloro-5-methoxyphenyl)-1-(2-isopropylphenyl)quinazolin-2(1H)-one (40 mg, 0.064 mmol) and DCE (1.0 mL), and the resulting mixture was stirred at 0° C. for 30 min. Saturated aqueous NaHCO$_3$ (2.0 mL) was added, and the resulting mixture was extracted with (2:1) DCM/MeOH (5 mL). The organic extract was dried over Na$_2$SO$_4$, filtered, and concentrated in vacuo. Chromatographic purification of the residue (silica gel, 0-10% MeOH in DCM) gave 6-chloro-7-(2,3-dichloro-5-hydroxyphenyl)-4-((25)-2-methyl-4-(2-propenoyl)-1-piperazinyl)-1-(2-(2-propanyl)phenyl)-2(1H)-quinazolinone: $^1$H NMR (400 MHz, DMSO-d$_6$) δ 10.42 (br d, 0.1=17.0 Hz, 1H), 7.86-8.11 (m, 1H), 7.50-7.63 (m, 1H), 7.47 (br t, J=6.0 Hz, 1H), 7.36 (t, J=7.5 Hz, 1H), 7.15-7.26 (m, 1H), 7.05 (d, 0.7=2.3 Hz, 1H), 6.78-6.96 (m, 1H), 6.44-6.58 (m, 1H), 6.11-6.29 (m, 2H), 5.71-5.82 (m, 1H), 4.68-4.98 (m, 1H), 3.96-4.52 (m, 3H), 3.52-3.85 (m, 2H), 3.34-3.51 (m, 1H), 2.95-3.26 (m, 1H), 1.27-1.41 (m, 3H), 0.95-1.13 (m, 6H). m/z (ESI, +ve) 611.0 (M+H)$^+$.

TABLE 9

Compounds 9-2 to 9-14 were prepared following the procedure described in Method 9, Steps 1-4, above as follows:

| Ex. # | Chemical Structure | Name | Method changes | Starting material | Reagent |
|---|---|---|---|---|---|
| 9-2 | 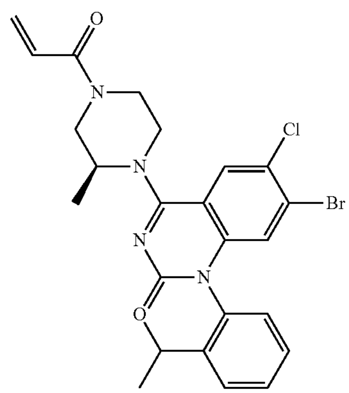 | 7-bromo-6-chloro-4-((2S)-2-methyl-4-(2-propenoyl)-1-piperazinyl)-1-(2-(2-propanyl)phenyl)-2(1H)-quinazolinone | Omit Steps 3 and 4 | 7-bromo-6-chloro-1-(2-isopropylphenyl)quinazoline-2,4(1H,3H)-dione | — |
| 9-3 | 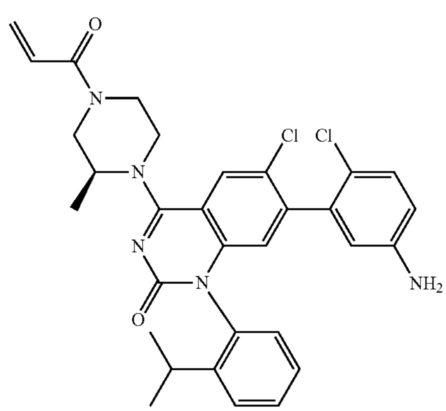 [SMILES: C=CC(=O)N1CCN(c2nc(=O)n(-c3ccccc3C(C)C)c3cc(-c4cc(N)ccc4Cl)c(Cl)cc23)[C@@H](C)C1] | 7-(5-amino-2-chlorophenyl)-6-chloro-4-((2S)-2-methyl-4-(2-propenoyl)-1-piperazinyl)-1-(2-(2-propanyl)phenyl)-2(1H)-quinazolinone | Omit Step 4 | 7-bromo-6-chloro-1-(2-isopropylphenyl)quinazoline-2,4(1H,3H)-dione | Step 3: (5-amino-2-chlorophenyl)boronic acid hydrochloride (Combi-blocks Inc., San Diego, CA, USA) |

TABLE 9-continued

Compounds 9-2 to 9-14 were prepared following the procedure described in
Method 9, Steps 1-4, above as follows:

| Ex. # | Chemical Structure | Name | Method changes | Starting material | Reagent |
|---|---|---|---|---|---|
| 9-4 | 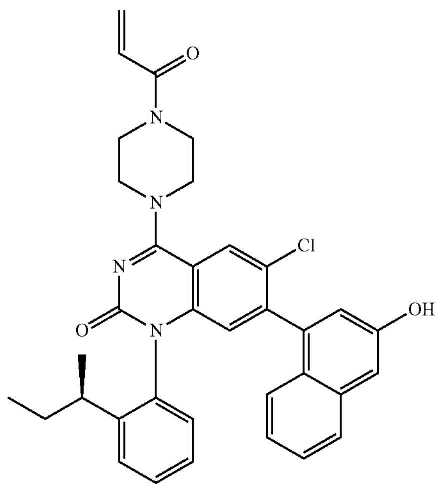 [SMILES: C=CC(=O)N1CCN(c2nc(=O)n(-c3ccccc3[C@H](C)CC)c3cc(-c4cc(O)cc5ccccc45)c(Cl)cc23)CC1] | 1-(2-(2-butanyl)phenyl)-6-chloro-7-(3-hydroxy-1-naphthalenyl)-4-(4-(2-propenoyl)-1-piperazinyl)-2(1H)-quinazolinone | SM prepared according to Method 8, steps 1-3 | 7-bromo-1-(2-(sec-butyl)phenyl)-6-chloroquinazoline-2,4(1H,3H)-dione | Method 8, Step 2: (2-sec-butylphenyl)amine (Key Organics Inc., Bedford, MA, USA), Step 2: 1-boc-piperazine, Step 3: (3-methoxynaphthalen-1-yl)boronic acid (Ark Pharm Inc. Arlington Heights, IL, USA), SPhos Pd G3, $K_2CO_3$, 1,4-dioxane/water, 100° C. |
| 9-5 | 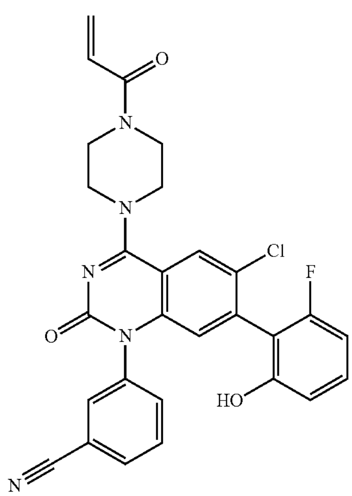 [SMILES: C=CC(=O)N1CCN(c2nc(=O)n(-c3cccc(C#N)c3)c3cc(-c4c(O)cccc4F)c(Cl)cc23)CC1] | 3-(6-chloro-7-(2-fluoro-6-hydroxyphenyl)-2-oxo-4-(4-(2-propenoyl)-1-piperazinyl)-1(2H)-quinazolinyl)benzonitrile | SM prepared according to Method 8, steps 1-3 | 3-(7-bromo-6-chloro-2,4-dioxo-3,4-dihydroquinazolin-1(2H)-yl)benzonitrile | Method 8, Step 2: 3-aminobenzonitrile (Frontier Scientific Services, Inc., Newark, DE, USA), Step 2: 1-boc-piperazine, Step 3: 2-fluoro-6-hydroxyphenylboronic acid (Combi-blocks Inc., San Diego, CA, USA), SPhos Pd G3, $K_2CO_3$, 1,4-dioxane/water, 100° C. |

TABLE 9-continued

Compounds 9-2 to 9-14 were prepared following the procedure described in
Method 9, Steps 1-4, above as follows:

| Ex. # | Chemical Structure | Name | Method changes | Starting material | Reagent |
|---|---|---|---|---|---|
| 9-6 | 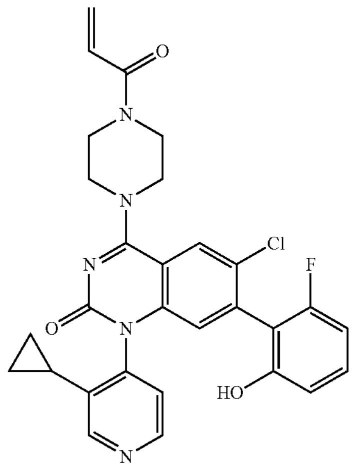 [SMILES: C=CC(=O)N1CCN(c2nc(=O)n(-c3ccncc3C3CC3)c3cc(-c4c(O)cccc4F)c(Cl)cc23)CC1] | 6-chloro-1-(3-cyclopropyl-4-pyridinyl)-7-(2-fluoro-6-hydroxyphenyl)-4-(4-(2-propenoyl)-1-piperazinyl)-2(1H)-quinazolinone | SM prepared according to Method 8, steps 1-3 | 7-bromo-6-chloro-1-(3-cyclopropyl pyridin-4-yl)quinazoline-2,4(1H,3H)-dione | Method 8, Step 2: 3-cyclopropylpyridin-4-amine (Combi-Phos Catalysts Inc. Trenton, NJ, USA), Step 2:1-boc-piperazine, Step 3: 2-fluoro-6-hydroxyphenylboronic acid (Combi-blocks Inc., San Diego, CA, USA), SPhos Pd G3, $K_2CO_3$, 1,4-dioxane/water, 100° C. |
| 9-7-2 | 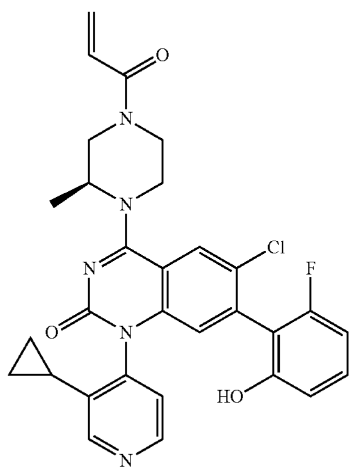 [SMILES: C=CC(=O)N1CCN(c2nc(=O)n(-c3ccncc3C3CC3)c3cc(-c4c(O)cccc4F)c(Cl)cc23)[C@@H](C)C1] | 6-chloro-1-(3-cyclopropyl-4-pyridinyl)-7-(2-fluoro-6-hydroxyphenyl)-4-((2S)-2-methyl-4-(2-propenoyl)-1-piperazinyl)-2(1H)-quinazolinone [2$^{nd}$ eluting isomer] | SM prepared according to Method 8, steps 1-3 | 7-bromo-6-chloro-1-(3-cyclopropylpyridin-4-yl)quinazoline-2,4(1H,3H)-dione | Method 8, Step 2: 3-cyclopropylpyridin-4-amine (Combi-Phos Catalysts Inc. Trenton, NJ, USA), Step 3: 2-fluoro-6-hydroxyphenylboronic acid (Combi-blocks Inc., San Diego, CA, USA), SPhos Pd G3, $K_2CO_3$, 1,4-dioxane/water, 100° C. |
| 9-7-1 | 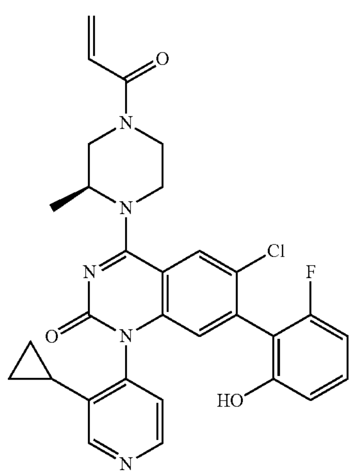 [SMILES: C=CC(=O)N1CCN(c2nc(=O)n(-c3ccncc3C3CC3)c3cc(-c4c(O)cccc4F)c(Cl)cc23)[C@@H](C)C1] | 6-chloro-1-(3-cyclopropyl-4-pyridinyl)-7-(2-fluoro-6-hydroxyphenyl)-4-((2S)-2-methyl-4-(2-propenoyl)-1-piperazinyl)-2(1H)-quinazolinone [1$^{st}$ eluting isomer] | SM prepared according to Method 8, steps 1-3 | 7-bromo-6-chloro-1-(3-cyclopropylpyridin-4-yl)quinazoline-2,4(1H,3H)-dione | Method 8, Step 2: 3-cyclopropylpyridin-4-amine (Combi-Phos Catalysts Inc. Trenton, NJ, USA), Step 3: 2-fluoro-6-hydroxyphenylboronic acid (Combi-blocks Inc., San Diego, CA, USA), SPhos Pd G3, $K_2CO_3$, 1,4-dioxane/water, 100° C. |

TABLE 9-continued

Compounds 9-2 to 9-14 were prepared following the procedure described in Method 9, Steps 1-4, above as follows:

| Ex. # | Chemical Structure | Name | Method changes | Starting material | Reagent |
|---|---|---|---|---|---|
| 9-9 | 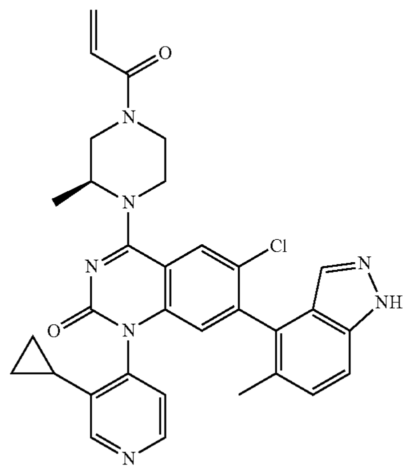 [SMILES: C=CC(=O)N1CCN(c2nc(=O)n(-c3ccncc3C3CC3)c3cc(-c4c(C)ccc5[nH]ncc45)c(Cl)cc23)[C@@H](C)C1] | 6-chloro-1-(3-cyclopropyl-4-pyridinyl)-7-(5-methyl-1H-indazol-4-yl)-4-((2S)-2-methyl-4-(2-propenoyl)-1-piperazinyl)-2(1H)-quinazolinone | SM prepared according to Method 8, steps 1-3, omit step 4 | 7-bromo-6-chloro-1-(3-cyclopropylpyridin-4-yl)quinazoline-2,4(1H,3H)-dione | Method 8, Step 2: 3-cyclopropylpyridin-4-amine, (Combi-Phos Catalysts Inc. Trenton, NJ, USA), Step 3: 4-borono-5-methyl-1h-indazole (Ark-Pharm Inc.), SPhos Pd G3, K₂CO₃, 1,4-dioxane/water, 100° C. |
| 9-10 | 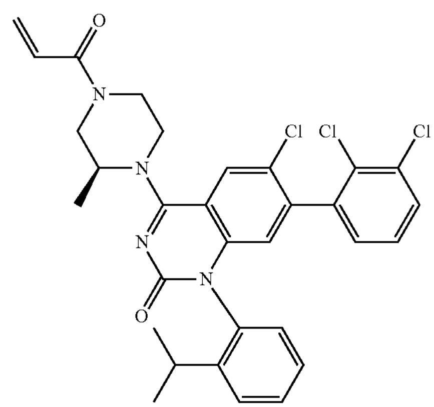 [SMILES: C=CC(=O)N1CCN(c2nc(=O)n(-c3ccccc3C(C)C)c3cc(-c4cccc(Cl)c4Cl)c(Cl)cc23)[C@@H](C)C1] | 6-chloro-7-(2,3-dichlorophenyl)-4-((2S)-2-methyl-4-(2-propenoyl)-1-piperazinyl)-1-(2-(2-propanyl)phenyl)-2(1H)-quinazolinone | Omit Step 4 | 7-bromo-6-chloro-1-(2-isopropylphenyl)quinazoline-2,4(1H,3H)-dione | Step 3: 2,3-dichlorobenzeneboronic acid (Alfa Aesar, Haver Hill, MA, USA) |
| 9-11 | 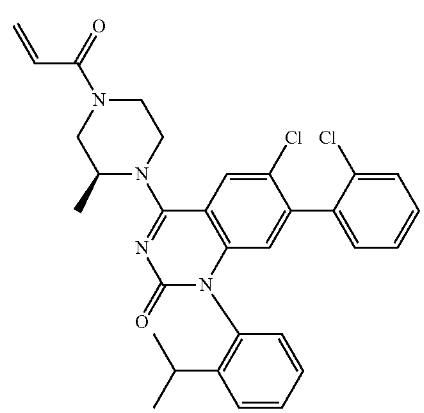 [SMILES: C=CC(=O)N1CCN(c2nc(=O)n(-c3ccccc3C(C)C)c3cc(-c4ccccc4Cl)c(Cl)cc23)[C@@H](C)C1] | 6-chloro-7-(2-chlorophenyl)-4-((2S)-2-methyl-4-(2-propenoyl)-1-piperazinyl)-1-(2-(2-propanyl)phenyl)-2(1H)-quinazolinone | Omit Step 4 | 7-bromo-6-chloro-1-(2-isopropylphenyl)quinazoline-2,4(1H,3H)-dione | Step 3: 2-chlorobenzeneboronic acid (Alfa Aesar, Haver Hill, MA, USA) |

TABLE 9-continued

Compounds 9-2 to 9-14 were prepared following the procedure described in
Method 9, Steps 1-4, above as follows:

| Ex. # | Chemical Structure | Name | Method changes | Starting material | Reagent |
|---|---|---|---|---|---|
| 9-12 | 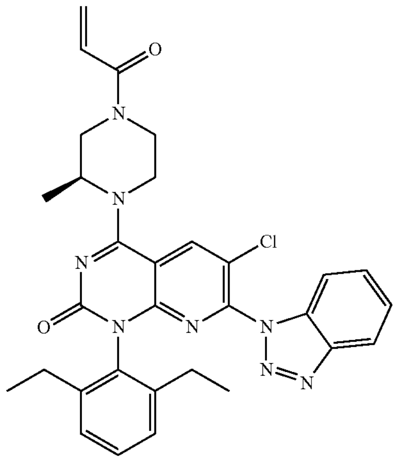 [SMILES: C=CC(=O)N1CCN(c2nc(=O)n(-c3c(CC)cccc3CC)c3nc(-n4nnc5ccccc54)c(Cl)cc23)[C@@H](C)C1] | 7-(1H-benzotriazol-1-yl)-6-chloro-1-(2,6-diethylphenyl)-4-((2S)-2-methyl-4-(2-propenoyl)-1-piperazinyl)pyrido[2,3-d]pyrimidin-2(1H)-one | SM prepared according to Method 8, steps 1-3. Omit steps 2-2 and 2-3; compound isolated in step 2-1 | 2,5,6-trichloronicotinic acid | Method 8 Step 2: 2,6-diethylaniline. Step 1: benzotriazole (see Method 8, step 5 alternate conditions), Step 2-1: (S)-1-(3-methylpiperazin-1-yl)prop-2-en-1-one 2,2,2-trifluoroacetate (See Method 8 Step 6 note for synthesis) |
| 9-13 | 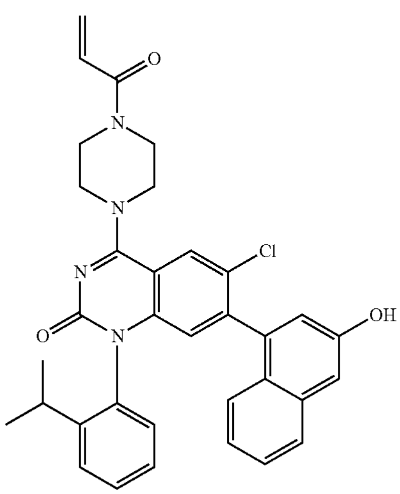 [SMILES: C=CC(=O)N1CCN(c2nc(=O)n(-c3ccccc3C(C)C)c3cc(-c4cc(O)cc5ccccc45)c(Cl)cc23)CC1] | 6-chloro-7-(3-hydroxy-1-naphthalenyl)-1-(2-(2-propanyl)phenyl)-4-(4-(2-propenoyl)-1-piperazinyl)-2(1H)-quinazolinone | — | 7-bromo-6-chloro-1-(2-isopropylphenyl)quinazoline-2,4(1H,3H)-dione | Step 1: benzotriazole (see Method 8, step 5 alternate conditions), Step 2-1: tert-butyl piperazine-1-carboxylate Step 2-3: NEt$_3$ Step 3: SPhos Pd G3, (3-methoxynaphthalen-1-yl)boronic acid, DME |

TABLE 9-continued

Compounds 9-2 to 9-14 were prepared following the procedure described in
Method 9, Steps 1-4, above as follows:

| Ex. # | Chemical Structure | Name | Method changes | Starting material | Reagent |
|---|---|---|---|---|---|
| 9-14 | 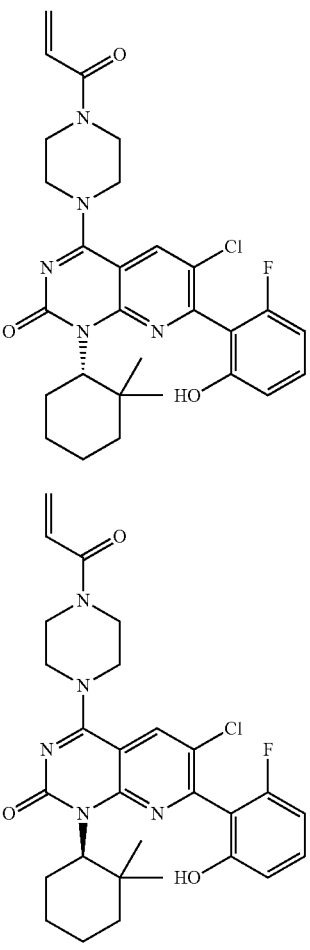 | 6-chloro-1-((1R)-2,2-dimethylcyclohexyl)-7-(2-fluoro-6-hydroxyphenyl)-4-(4-(2-propenoyl)-1-piperazinyl)pyrido[2,3-d]pyrimidin-2(1H)-one | 6-chloro-1-((1S)-2,2-dimethylcyclohexyl)-7-(2-fluoro-6-hydroxyphenyl)-4-(4-(2-propenoyl)-1-piperazinyl)pyrido[2,3-d]pyrimidin-2(1H)-one | SM prepared according to Method 8, steps 1-3 Omit steps 2-2, 2-3, and 4 | 2,5,6-trichloronicotinic acid | Method 8 Step 2: 2,2-dimethylcyclohexan-1-amine Step 2(1): 1-(piperazin-1-yl)prop-2-en-1-one (eNovation Chemicals LLC, Bridgewater, NJ, USA) Step 3: SPhos Pd G3, 2-fluoro-6-hydroxyphenylboronic acid Combi-blocks Inc., San Diego, CA, USA), DME |

Method 10

Example 10-1: 1-(4-(7-Chloro-6-(2-fluoro-6-hydroxyphenyl)-4-(2-methylphenyl)-1-phthalazinyl)-1-piperazinyl)-2-propen-1-one

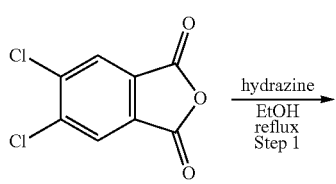

hydrazine
EtOH
reflux
Step 1

-continued

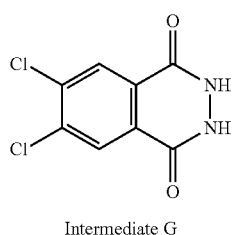

Intermediate G

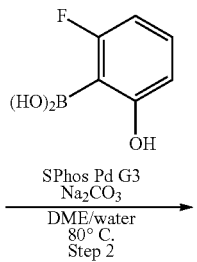

SPhos Pd G3
Na$_2$CO$_3$
DME/water
80° C.
Step 2

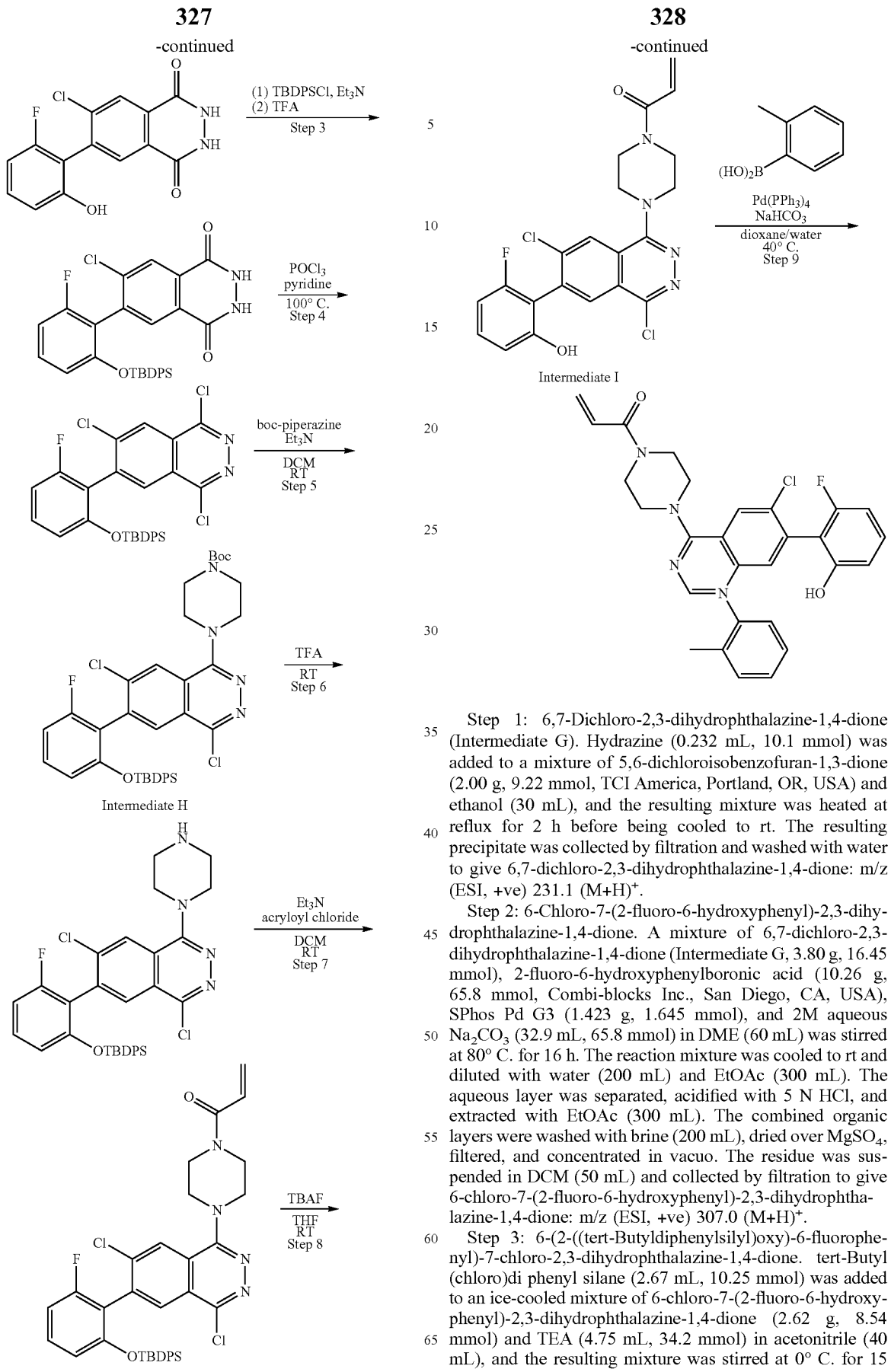

Step 1: 6,7-Dichloro-2,3-dihydrophthalazine-1,4-dione (Intermediate G). Hydrazine (0.232 mL, 10.1 mmol) was added to a mixture of 5,6-dichloroisobenzofuran-1,3-dione (2.00 g, 9.22 mmol, TCI America, Portland, OR, USA) and ethanol (30 mL), and the resulting mixture was heated at reflux for 2 h before being cooled to rt. The resulting precipitate was collected by filtration and washed with water to give 6,7-dichloro-2,3-dihydrophthalazine-1,4-dione: m/z (ESI, +ve) 231.1 (M+H)$^+$.

Step 2: 6-Chloro-7-(2-fluoro-6-hydroxyphenyl)-2,3-dihydrophthalazine-1,4-dione. A mixture of 6,7-dichloro-2,3-dihydrophthalazine-1,4-dione (Intermediate G, 3.80 g, 16.45 mmol), 2-fluoro-6-hydroxyphenylboronic acid (10.26 g, 65.8 mmol, Combi-blocks Inc., San Diego, CA, USA), SPhos Pd G3 (1.423 g, 1.645 mmol), and 2M aqueous Na$_2$CO$_3$ (32.9 mL, 65.8 mmol) in DME (60 mL) was stirred at 80° C. for 16 h. The reaction mixture was cooled to rt and diluted with water (200 mL) and EtOAc (300 mL). The aqueous layer was separated, acidified with 5 N HCl, and extracted with EtOAc (300 mL). The combined organic layers were washed with brine (200 mL), dried over MgSO$_4$, filtered, and concentrated in vacuo. The residue was suspended in DCM (50 mL) and collected by filtration to give 6-chloro-7-(2-fluoro-6-hydroxyphenyl)-2,3-dihydrophthalazine-1,4-dione: m/z (ESI, +ve) 307.0 (M+H)$^+$.

Step 3: 6-(2-(((tert-Butyldiphenylsilyl)oxy)-6-fluorophenyl)-7-chloro-2,3-dihydrophthalazine-1,4-dione. tert-Butyl(chloro)diphenyl silane (2.67 mL, 10.25 mmol) was added to an ice-cooled mixture of 6-chloro-7-(2-fluoro-6-hydroxyphenyl)-2,3-dihydrophthalazine-1,4-dione (2.62 g, 8.54 mmol) and TEA (4.75 mL, 34.2 mmol) in acetonitrile (40 mL), and the resulting mixture was stirred at 0° C. for 15 min, then warmed to rt and stirred for 1.5 h. Additional tert-butyl(chloro)diphenylsilane (2.67 mL, 10.25 mmol) was added, and the resulting mixture was stirred at rt for 16 h. The reaction mixture was subsequently diluted with water (300 mL), acidified with 5 N HCl, and extracted with EtOAc (300 mL). The organic layer was separated and sequentially washed with brine (250 mL), dried over MgSO$_4$, filtered, and concentrated in vacuo. The residue was taken up in DCM (200 mL), TFA (20 mL) was added, and the resulting mixture was stirred at rt for 45 min. The reaction mixture was then diluted with saturated aqueous NaHCO$_3$ (200 mL) and extracted with DCM (2×250 mL). The combined organic extracts were dried over MgSO$_4$, filtered, and concentrated in vacuo to give 6-(2-((tert-butyldiphenylsilyl)oxy)-6-fluorophenyl)-7-chloro-2,3-dihydrophthalazine-1,4-dione: m/z (ESI, +ve) 545.2 (M+H)$^+$.

Step 4: 6-(2-((tert-Butyldiphenylsilyl)oxy)-6-fluorophenyl)-1,4,7-trichlorophthalazine. Pyridine (1.45 mL, 17.1 mmol) was added to a mixture of 6-(2-((tert-butyldiphenylsilyl)oxy)-6-fluorophenyl)-7-chloro-2,3-dihydrophthalazine-1,4-dione (4.66 g, 8.55 mmol) and phosphorus oxychloride (6.39 mL, 68.4 mmol), and the resulting mixture was heated at 100° C. for 1.5 h. The reaction mixture was then cooled to rt and slowly poured into stirred water (300 mL) while maintaining an internal temperature of <10° C. After stirring for 15 min, the resulting mixture was extracted with EtOAc (400 mL), and the organic extract was sequentially washed with brine (250 mL), dried over MgSO$_4$, filtered, and concentrated in vacuo. Chromatographic purification of the residue (silica gel, 0-25% EtOAc in heptane) provided 6-(2-((tert-butyldiphenylsilyl)oxy)-6-fluorophenyl)-1,4,7-trichlorophthalazine: in z (ESI, +ve) 581.1 (M+H)$^+$.

Step 5: tert-Butyl 4-(6-(2-((tert-butyldiphenylsilyl)oxy)-6-fluorophenyl)-4,7-dichlorophthalazin-1-yl)piperazine-1-carboxylate (Intermediate H). 1-Boc-piperazine (5.00 g, 26.9 mmol) was added to a mixture of 6-(2-((tert-butyldiphenylsilyl)oxy)-6-fluorophenyl)-1,4,7-trichlorophthalazine (5.21 g, 8.95 mmol) and triethylamine (3.77 mL, 26.9 mmol) in DCM (35 mL), and the resulting mixture was stirred at rt for 19 h. The reaction mixture was then partitioned between DCM (300 mL) and saturated aqueous NaHCO$_3$ (200 mL). The organic layer was separated, dried over MgSO$_4$, filtered, and concentrated in vacuo. Chromatographic purification of the residue (silica gel, 0-50% EtOAc in heptane) gave a mixture of tert-butyl 4-(6-(2-((tert-butyldiphenylsilyl)oxy)-6-fluorophenyl)-4,7-dichlorophthalazin-1-yl)piperazine-1-carboxylate and tert-butyl 4-(7-(2-((tert-butyldiphenylsilyl)oxy)-6-fluorophenyl)-4,6-dichlorophthalazin-1-yl)piperazine-1-carboxylate. The individual regioisomers were isolated by chiral SFC purification (OJ-H column (30×250 mm, 5 μm), 15% (20 mM NH$_3$ in MeOH) in supercritical CO$_2$), providing tert-butyl 4-(6-(2-((tert-butyldiphenylsilyl)oxy)-6-fluorophenyl)-4,7-dichlorophthalazin-1-yl)piperazine-1-carboxylate as the second-eluting isomer: $^1$H NMR (400 MHz, CDCl$_3$) δ 8.27 (s, 1H) 8.17 (s, 1H) 7.56-7.61 (m, 4H) 7.40-7.46 (m, 2H) 7.31-7.37 (m, 4H) 6.99-7.07 (m, 1H) 6.77 (t, J=8.61 Hz, 1H) 6.42 (d, J=8.22 Hz, 1H) 3.72-3.77 (m, 4H) 3.53-3.59 (m, 4H) 1.51 (s, 9H) 0.66 (s, 9H). m/z (ESI, +ve) 731.2 (M+H)$^+$.

Step 6: 6-(2-((tert-Butyldiphenylsilyl)oxy)-6-fluorophenyl)-4,7-dichloro-1-(piperazin-1-yl)phthalazine. Trifluoroacetic acid (2 mL, 26.8 mmol) was added to a stirred solution of tert-butyl 4-(6-(2-((tert-butyldiphenylsilyl)oxy)-6-fluorophenyl)-4,7-dichlorophthalazin-1-yl)piperazine-1-carboxylate (Intermediate H, 1.21 g, 1.654 mmol) in DCM (10 mL), and the resulting mixture was stirred at rt for 1.5 h. The reaction mixture was then diluted with saturated aqueous NaHCO$_3$ (75 mL) and extracted with DCM (2×100 mL). The combined organic extracts were dried over MgSO$_4$, filtered, and concentrated in vacuo to give 6-(2-((tert-butyldiphenylsilyl)oxy)-6-fluorophenyl)-4,7-dichloro-1-(piperazin-1-yl)phthalazine: m/z (ESI, +ve) 631.3 (M+H)$^+$.

Step 7: 1-(4-(6-(2-((tert-Butyldiphenylsilyl)oxy)-6-fluorophenyl)-4,7-dichlorophthalazin-1-yl)piperazin-1-yl)prop-2-en-1-one. Acryloyl chloride (0.148 mL, 1.81 mmol) was added to a mixture of 6-(2-((tert-butyldiphenylsilyl)oxy)-6-fluorophenyl)-4,7-dichloro-1-(piperazin-1-yl)phthalazine (1.04 g, 1.647 mmol) and triethylamine (0.694 mL, 4.94 mmol) in DCM (10 mL), and the resulting mixture was stirred at rt for 45 min. Saturated aqueous NaHCO$_3$ (75 mL) was added, and the resulting mixture was extracted with DCM (3×100 mL). The combined organic extracts were dried over MgSO$_4$, filtered, and concentrated in vacuo to give 1-(4-(6-(2-((tert-butyldiphenylsilyl)oxy)-6-fluorophenyl)-4,7-dichlorophthalazin-1-yl)piperazin-1-yl)prop-2-en-1-one: m/z (ESI, +ve) 685.1 (M+H)$^+$.

Step 8: 1-(4-(4,7-Dichloro-6-(2-fluoro-6-hydroxyphenyl)phthalazin-1-yl)piperazin-1-yl)prop-2-en-1-one (Intermediate I). TBAF (1 M in THF, 3.3 mL, 3.30 mmol) was added to a solution of 1-(4-(6-(2-((tert-butyldiphenylsilyl)oxy)-6-fluorophenyl)-4,7-dichlorophthalazin-1-yl)piperazin-1-yl)prop-2-en-1-one (1.13 g, 1.648 mmol) in THF (10 mL), and the resulting mixture was stirred at rt for 15 min. The reaction mixture was concentrated in vacuo, and the residue was purified by column chromatography (silica gel, 0-100% EtOAc in heptane) to give 1-(4-(4,7-dichloro-6-(2-fluoro-6-hydroxyphenyl)phthalazin-1-yl)piperazin-1-yl)prop-2-en-1-one: $^1$H NMR (400 MHz, DMSO-d$_6$) δ 10.26 (br s, 1H) 8.31 (s, 1H) 8.14 (s, 1H) 7.31-7.40 (m, 1H) 6.78-6.92 (m, 3H) 6.17 (dd, J=16.63, 2.35 Hz, 1H) 5.74 (dd, J=10.37, 2.35 Hz, 1H) 3.79-3.92 (m, 4H) 3.46-3.55 (m, 4H). m/z (ESI, +ve) 447.0 (M+H)$^+$.

Step 9: 1-(4-(7-Chloro-6-(2-fluoro-6-hydroxyphenyl)-4-(o-tolyl)phthalazin-1-yl)piperazin-1-yl)prop-2-en-1-one. A mixture of 1-(4-(4,7-dichloro-6-(2-fluoro-6-hydroxyphenyl)phthalazin-1-yl)piperazin-1-yl)prop-2-en-1-one (Intermediate 1.25 mg, 0.056 mmol), 2-tolylboronic acid (30.4 mg, 0.224 mmol, Frontier Scientific Inc., Logan UT, USA), Pd(PPh$_3$)$_4$ (6.46 mg, 5.59 μmol, Strem Chemicals Inc., NewburyPort, MA, USA), and 2M aqueous Na$_2$CO$_3$ (0.084 mL, 0.168 mmol) in 1,4-dioxane (0.3 mL) was stirred at 40° C. for 18 h. The reaction mixture was then diluted with EtOAc (20 mL) and washed with water (15 mL). The organic layer was separated and sequentially washed with brine (15 mL), dried over MgSO$_4$, filtered, and concentrated in vacuo. Chromatographic purification of the residue (silica gel, 0-100% EtOAc in heptane) furnished 1-(4-(7-chloro-6-(2-fluoro-6-hydroxyphenyl)-4-(o-tolyl)phthalazin-1-yl)piperazin-1-yl)prop-2-en-1-one: $^1$H NMR (400 MHz, DMSO-d$_6$) δ 10.15 (br s, 1H) 8.33 (s, 1H) 7.36-7.45 (m, 2H) 7.24-7.36 (m, 4H) 6.90 (dd, J=16.63, 10.37 Hz, 1H) 6.70-6.80 (m, 2H) 6.18 (dd, J=16.73, 2.25 Hz, 1H) 5.75 (dd, J=10.56, 2.15 Hz, 1H) 3.83-3.97 (m, 4H) 3.47-3.62 (m, 4H) 1.98-2.06 (m, 3H). m/z (ESI, +ve) 503.1 (M+H)$^+$.

TABLE 10

Compounds 10-2 to 10-13 were prepared following the procedure described in Method 10, Steps 1-9, above as follows:

| Ex. # | Chemical Structure | Name | Method changes | Reagent |
|---|---|---|---|---|
| 10-2 | 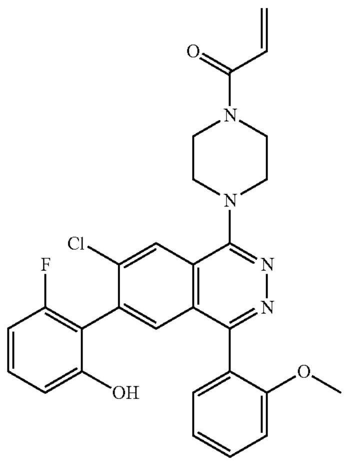 [SMILES: C=CC(=O)N1CCN(c2nnc(-c3ccccc3OC)c3cc(-c4c(O)cccc4F)c(Cl)cc23)CC1] | 1-(4-(7-chloro-6-(2-fluoro-6-hydroxyphenyl)-4-(2-methoxyphenyl)phthalazin-1-yl)-piperazin-1-yl)prop-2-en-1-one | — | Step 9: 2-methoxybenzeneboronic acid |
| 10-3 | 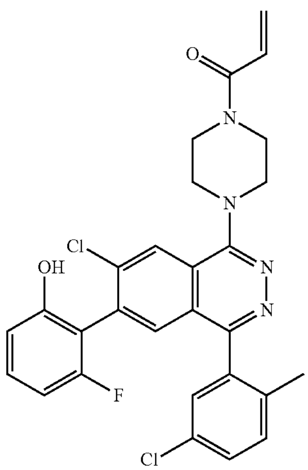 [SMILES: C=CC(=O)N1CCN(c2nnc(-c3cc(Cl)ccc3C)c3cc(-c4c(O)cccc4F)c(Cl)cc23)CC1] | 1-(4-(7-chloro-4-(5-chloro-2-methylphenyl)-6-(2-fluoro-6-hydroxyphenyl)-1-phthalazinyl)-1-piperazinyl)-2-propen-1-one | — | Step 9: (5-chloro-2-methylphenyl)boronic acid (Combi-blocks Inc., San Diego, CA, USA) |
| 10-4 | 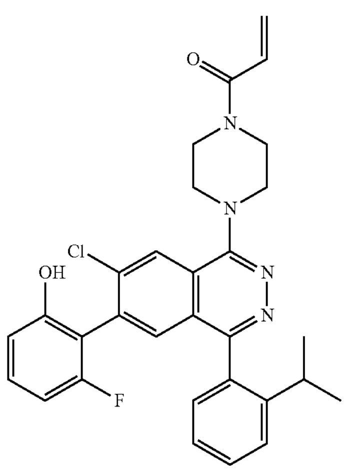 [SMILES: C=CC(=O)N1CCN(c2nnc(-c3ccccc3C(C)C)c3cc(-c4c(O)cccc4F)c(Cl)cc23)CC1] | 1-(4-(7-chloro-6-(2-fluoro-6-hydroxyphenyl)-4-(2-(2-propanyl)-phenyl)-1-phthalazinyl)-1-piperazinyl)-2-propen-1-one | — | Step 9: 2-isopropylphenylboronic acid (Alfa Aesar, Haver Hill, MA, USA) |

TABLE 10-continued

Compounds 10-2 to 10-13 were prepared following the procedure described in Method 10, Steps 1-9, above as follows:

| Ex. # | Chemical Structure | Name | Method changes | Reagent |
|---|---|---|---|---|
| 10-5 | 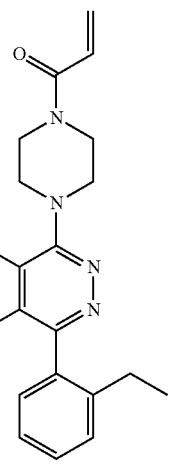 | 1-(4-(7-chloro-4-(2-ethylphenyl)-6-(2-fluoro-6-hydroxyphenyl)-1-phthalazinyl)-1-piperazinyl)-2-propen-1-one | — | Step 9: 2-ethyl-benzeneboronic acid (Alfa Aesar, Haver Hill, MA, USA) |
| 10-6 | 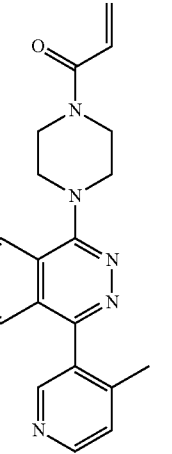 | 1-(4-(7-chloro-6-(2-fluoro-6-hydroxyphenyl)-4-(4-methyl-3-pyridinyl)-1-phthalazinyl)-1-piperazinyl)-2-propen-1-one | — | Step 9: 4-methyl-pyridine-3-boronic acid pinacol ester (run at 60° C.) |
| 10-7 | 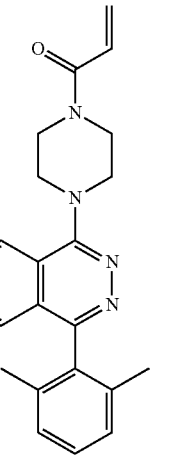 | 1-(4-(7-chloro-4-(2,6-dimethyl-phenyl)-6-(2-fluoro-6-hydroxy-phenyl)-1-phthalazinyl)-1-piperazinyl)-2-propen-1-one | — | Step 9: 2,6-dimethyl-phenylboronic acid (run at 80° C.) |

TABLE 10-continued

Compounds 10-2 to 10-13 were prepared following the procedure described in Method 10, Steps 1-9, above as follows:

| Ex. # | Chemical Structure | Name | Method changes | Reagent |
|---|---|---|---|---|
| 10-8 | 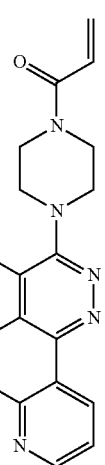 | 1-(4-(7-chloro-6-(2-fluoro-6-hydroxyphenyl)-4-(2-methyl-3-pyridinyl)-1-phthalazinyl)-1-piperazinyl)-2-propen-1-one | — | Step 9: 2-methyl-pyridine-3-boronic acid pinacol ester (Frontier Scientific, Inc. Logan, UT, USA) |
| 10-9 | 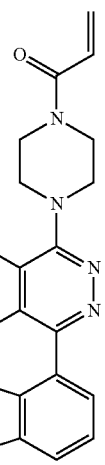 | 1-(4-(7-chloro-6-(2-fluoro-6-hydroxyphenyl)-4-(1H-indol-4-yl)-1-phthalazinyl)-1-piperazinyl)-2-propen-1-one | — | Step 9: 1H-indol-4-yl-4-boronic acid |
| 10-10 | 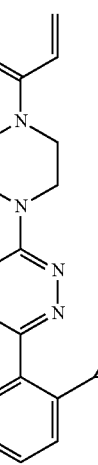 | 1-(4-(7-chloro-4-(2-cyclopropyl-phenyl)-6-(2-fluoro-6-hydroxy-phenyl)-1-phthalazinyl)-1-piperazinyl)-2-propen-1-one | — | Step 9: 2-cyclopropyl-benzeneboronic acid (Combi-Phos Catalysts, Inc., Trenton, NJ, USA) |

TABLE 10-continued

Compounds 10-2 to 10-13 were prepared following the procedure described in Method 10, Steps 1-9, above as follows:

| Ex. # | Chemical Structure | Name | Method changes | Reagent |
|---|---|---|---|---|
| 10-11 | 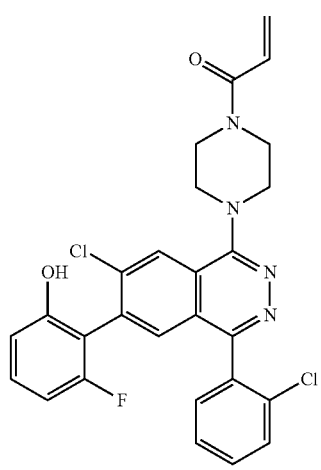 [SMILES: C=CC(=O)N1CCN(c2nnc(-c3ccccc3Cl)c3cc(-c4c(O)cccc4F)c(Cl)cc23)CC1] | 1-(4-(7-chloro-4-(2-chlorophenyl)-6-(2-fluoro-6-hydroxyphenyl)-1-phthalazinyl)-1-piperazinyl)-2-propen-1-one | — | Step 9: 2-chlorophenylboronic acid (Matrix Scientific, Columbia, SC, USA) |
| 10-12 | 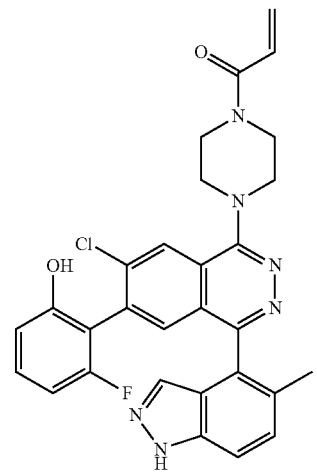 [SMILES: C=CC(=O)N1CCN(c2nnc(-c3c(C)ccc4[nH]ncc34)c3cc(-c4c(O)cccc4F)c(Cl)cc23)CC1] | 1-(4-(7-chloro-6-(2-fluoro-6-hydroxyphenyl)-4-(5-methyl-1H-indazol-4-yl)-1-phthalazinyl)-1-piperazinyl)-2-propen-1-one | — | Step 9: (5-methyl-1H-indazol-4-yl)boronic acid (Combi-Blocks, Inc., San Diego, CA, USA) |
| 10-13 | 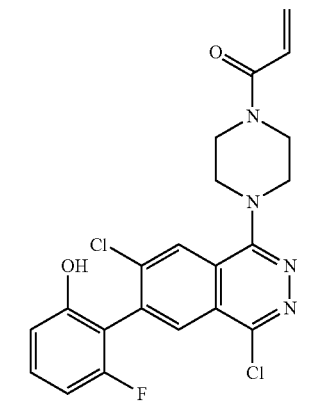 [SMILES: C=CC(=O)N1CCN(c2nnc(Cl)c3cc(-c4c(O)cccc4F)c(Cl)cc23)CC1] | 1-(4-(4,7-dichloro-6-(2-fluoro-6-hydroxyphenyl)-1-phthalazinyl)-1-piperazinyl)-2-propen-1-one | Omit Step 9 | — |

Method 11
Example 11-1: 6-chloro-7-(5-methyl-1H-indazol-4-yl)-1-(2-(2-propanyl)phenyl)-4-(4-(2-propenoyl)-1-piperazinyl)-2(1H)-quinazolinone
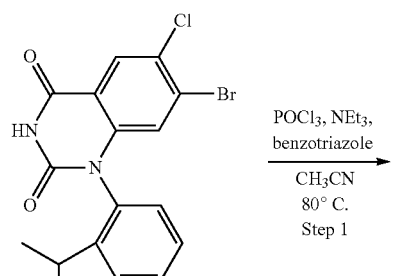
Intermediate F
POCl₃, NEt₃, benzotriazole
CH₃CN
80° C.
Step 1
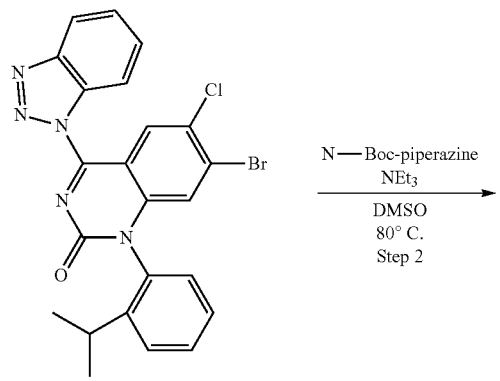
N—Boc-piperazine
NEt₃
DMSO
80° C.
Step 2
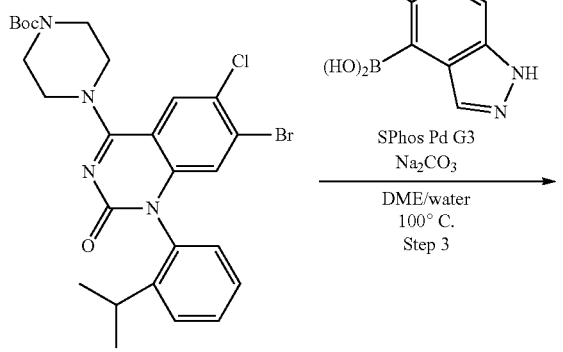
SPhos Pd G3
Na₂CO₃
DME/water
100° C.
Step 3
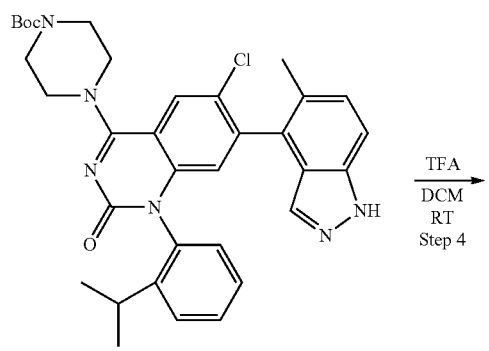
TFA
DCM
RT
Step 4
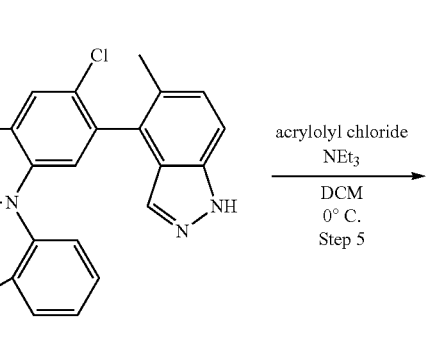
acrylolyl chloride
NEt₃
DCM
0° C.
Step 5
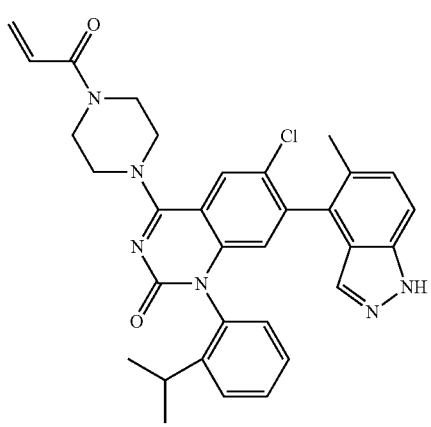
Example 11-1-1
1st eluting isomeric mixture

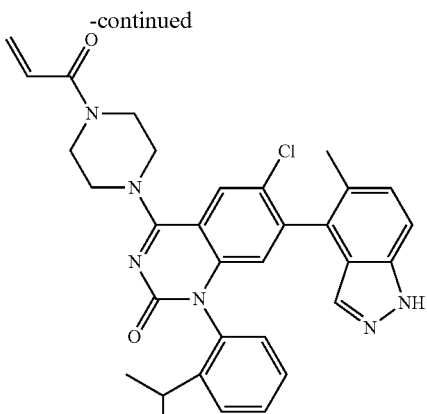

Example 11-1-2
2nd eluting isomeric mixture

Step 1: 4-(1H-benzo[d][1,2,3]triazol-1-yl)-7-bromo-6-chloro-1-(2-isopropylphenyl)quinazolin-2(1H)-one. Phosphorus oxychloride (1.204 mL, 7.85 mmol) was added to a stirred mixture of 7-bromo-6-chloro-1-(2-isopropylphenyl)quinazoline-2,4(1H,3H)-dione (Intermediate F, 515 mg, 1.308 mmol), triethylamine (3.31 mL, 23.55 mmol), and 1H-benzo[d][1,2,3]triazole (2.01 g, 16.87 mmol) in acetonitrile (15 mL). The reaction mixture was heated to 80° C. and stirred for 1 h. The reaction mixture was cooled to rt and filtered. The filtrate was then poured slowly into rapidly stirred water (150 mL) at 10° C. The aqueous suspension was stirred for 15 min before being extracted two times with EtOAc (150 mL). The organic layers were combined, washed with brine (150 mL), dried over MgSO$_4$, filtered, and concentrated in vacuo to give crude 4-(1H-benzo[d][1,2,3]triazol-1-yl)-7-bromo-6-chloro-1-(2-isopropylphenyl)quinazolin-2(1H)-one. m/z (ESI) M+H: 494.0.

Step 2: tert-butyl 4-(7-bromo-6-chloro-1-(2-isopropylphenyl)-2-oxo-1,2-dihydroquinazolin-4-yl)piperazine-1-carboxylate. tert-Butyl piperazine-1-carboxylate (268 mg, 1.438 mmol) was added to a stirred mixture of crude 4-(1H-benzo[d][1,2,3]triazol-1-yl)-7-bromo-6-chloro-1-(2-isopropylphenyl)quinazolin-2(1H)-one (647 mg, 1.308 mmol) and triethylamine (3.68 mL, 26.2 mmol) in dimethyl sulfoxide (6 mL). The reaction mixture was stirred at 80° C. for 30 min. The reaction mixture was diluted with EtOAc (100 mL) and washed with water (75 mL). The organic layer was separated, washed with brine (75 mL), dried over MgSO$_4$, filtered, and concentrated in vacuo. Chromatographic purification of the residue (silica gel, 0 to 100% EtOAc in heptane) gave tert-butyl 4-(7-bromo-6-chloro-1-(2-isopropylphenyl)-2-oxo-1,2-dihydroquinazolin-4-yl)piperazine-1-carboxylate. $^1$H NMR (400 MHz, CHLOROFORM-d) δ 7.79 (1H, s) 7.49-7.59 (2H, m) 7.36-7.42 (1H, m) 7.11 (1H, d, J=7.63 Hz) 6.80 (1H, s) 3.79-3.92 (4H, m) 3.62-3.73 (4H, m) 2.60 (1H, spt, J=6.80 Hz) 1.49-1.54 (9H, m) 1.22 (3H, d, J=6.85 Hz) 1.08 (3H, d, J=6.85 Hz), m/z (ESI) M+H: 561.0.

Step 3: tert-butyl 4-(6-chloro-1-(2-isopropylphenyl)-7-(5-methyl-1H-indazol-4-yl)-2-oxo-1,2-dihydroquinazolin-4-yl)piperazine-1-carboxylate. tert-Butyl 4-(7-bromo-6-chloro-1-(2-isopropylphenyl)-2-oxo-1,2-dihydroquinazolin-4-yl)piperazine-1-carboxylate (115 mg, 0.205 mmol), 4-borono-5-methyl-1h-indazole (0.144 mL, 0.819 mmol, Ark Pharm Inc., Arlington Heights, IL, USA), Sphos Pd G3 (0.016 mL, 0.020 mmol), and sodium carbonate (2 M aqueous, 0.409 mL, 0.819 mmol) were mixed in 1,2-dimethoxyethane (1 mL) under an argon atmosphere in a sealed vial. The reaction mixture was stirred at 100° C. for 24 h. The reaction mixture was cooled to rt and diluted with EtOAc (50 mL) and water (40 mL). The organic layer was separated, washed with brine (40 mL), dried over MgSO$_4$, filtered, and concentrated in vacuo. Chromatographic purification of the residue (silica gel, 0 to 50% (3:1 EtOAc/EtOH) in heptane) gave tert-butyl 4-(6-chloro-1-(2-isopropylphenyl)-7-(5-methyl-1H-indazol-4-yl)-2-oxo-1,2-dihydroquinazolin-4-yl)piperazine-1-carboxylate. m/z (ESI) M+H: 613.2.

Step 4: 6-chloro-1-(2-isopropylphenyl)-7-(5-methyl-1H-indazol-4-yl)-4-(piperazin-1-yl)quinazolin-2(1H)-one. Trifluoroacetic acid (0.5 mL, 6.71 mmol) was added to a stirred mixture of tert-butyl 4-(6-chloro-1-(2-isopropylphenyl)-7-(5-methyl-1H-indazol-4-yl)-2-oxo-1,2-dihydroquinazolin-4-yl)piperazine-1-carboxylate (78 mg, 0.127 mmol) in dichloromethane (1 mL). The reaction mixture was stirred at rt for 1 h. The reaction mixture was concentrated in vacuo to give crude 6-chloro-1-(2-isopropylphenyl)-7-(5-methyl-1H-indazol-4-yl)-4-(piperazin-1-yl)quinazolin-2(1H)-one. m/z (ESI) M+H: 513.2.

Step 5: 6-chloro-7-(5-methyl-1H-indazol-4-yl)-1-(2-(2-propanyl)phenyl)-4-(4-(2-propenoyl)-1-piperazinyl)-2(1H)-quinazolinone. Acryloyl chloride (10.33 μl, 0.127 mmol) was added to a stirred mixture of 6-chloro-1-(2-isopropylphenyl)-7-(5-methyl-1H-indazol-4-yl)-4-(piperazin-1-yl)quinazolin-2(1H)-one (65 mg, 0.127 mmol) and triethylamine (0.178 mL, 1.267 mmol) in dichloromethane (2 mL) at 0° C. The reaction mixture was stirred at 0° C. for 20 min. Additional acryloyl chloride (5.17 μl, 0.064 mmol) was added, and the reaction mixture was stirred at 0° C. for another 20 min. The reaction mixture was diluted with DCM (25 mL) and quenched with saturated aqueous sodium bicarbonate (20 mL). The organic layer was separated, dried over MgSO$_4$, filtered, and concentrated in vacuo. Chromatographic purification of the residue (silica gel, 0 to 80% (3:1 EtOAc/EtOH) in heptane) gave impure product. Further chromatographic purification of the impure product (silica gel, 0 to 100% acetone in heptane) gave the separated diastereomers. 6-chloro-7-(5-methyl-1H-indazol-4-yl)-1-(2-(2-propanyl)phenyl)-4-(4-(2-propenoyl)-1-piperazinyl)-2(1H)-quinazolinone (Example 11-1-1), was the first diastereomer to elute. $^1$H NMR (400 MHz, CHLOROFORM-d) δ 10.28 (1H, hr s) 7.94 (1H, s) 7.35-7.49 (4H, m) 7.25-7.31 (2H, m) 7.11 (1H, d, J=7.67 Hz) 6.64 (1H, dd, J=16.79, 10.57 Hz) 6.54 (1H, s) 6.41 (1H, dd, J=16.79, 1.87 Hz) 5.81 (1H, dd, j=10.57, 1.66 Hz) 3.83-4.07 (8H, m) 2.74 (1H, spt, j=6.84 Hz) 2.13 (3H, s) 1.23 (3H, d, J=6.84 Hz) 1.04 (3H, d, J=6.84 Hz), m/z (ESI) M+H: 567.2. The second diastereomer to elute was further purified by column chromatography (silica gel, 0 to 80% (3:1 EtOAc/EtOH) in heptane) to give 6-chloro-7-(5-methyl-1H-indazol-4-yl)-1-(2-(2-propanyl)phenyl)-4-(4-(2-propenoyl)-1-piperazinyl)-2(1H)-quinazolinone (Example 11-1-2). $^1$H NMR (400 MHz, CHLOROFORM-d) δ 10.37 (1H, hr s) 7.94 (1H, s) 7.34-7.50 (4H, m) 7.21-7.31 (2H, m) 7.13 (1H, d, J=7.67 Hz) 6.64 (1H, dd, J=16.90, 10.68 Hz) 6.55 (1H, s) 6.41 (1H, dd, J=16.79, 1.66 Hz) 5.81 (1H, dd, J=10.47, 1.55 Hz) 3.83-4.08 (8H, m) 2.70 (1H, spt, J=6.84 Hz) 2.13 (3H, s) 1.22 (3H, d, J=6.84 Hz) 1.03 (3H, d, J=6.84 Hz), m/z (ESI) M+H: 567.2.

Method 11, Steps 1-5, above as follows:

| Ex.# | Chemical Structure | Name | Reagent | Isomer |
|---|---|---|---|---|
| 11-2-1 | 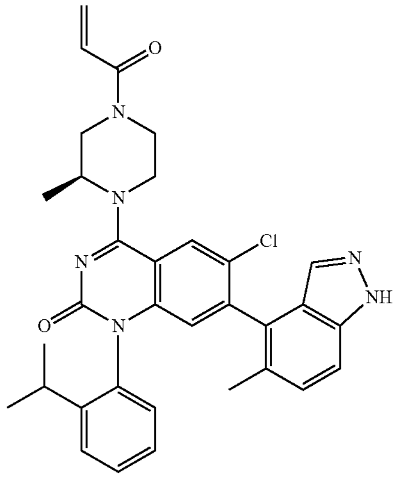 [SMILES: C=CC(=O)N1CCN(c2nc(=O)n(-c3ccccc3C(C)C)c3cc(-c4c(C)ccc5[nH]ncc45)c(Cl)cc23)[C@@H](C)C1] | 6-chloro-7-(5-methyl-1H-indazol-4-yl)-4-((2S)-2-methyl-4-(2-propenoyl)-1-piperazinyl)-1-(2-(2-propanyl)-phenyl)-2(1H)-quinazolinone | Step 2: (S)-4-n-boc-2-methyl piperazine (CNH Technologies, Inc., Woburn, MA, USA), run at room temp overnight. | 1st eluting isomeric mixture |
| 11-2-2 | 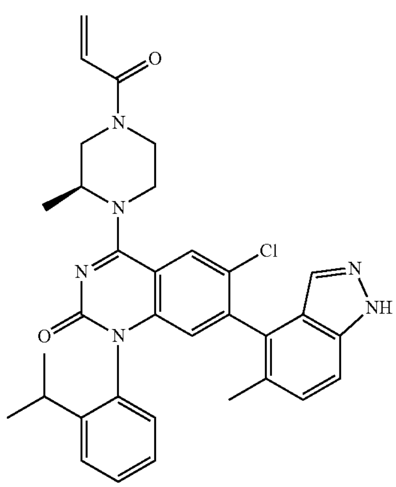 [SMILES: C=CC(=O)N1CCN(c2nc(=O)n(-c3ccccc3C(C)C)c3cc(-c4c(C)ccc5[nH]ncc45)c(Cl)cc23)[C@@H](C)C1] | 6-chloro-7-(5-methyl-1H-indazol-4-yl)-4-((2S)-2-methyl-4-(2-propenoyl)-1-piperazinyl)-1-(2-(2-propanyl)-phenyl)-2(1H)-quinazolinone | Step 2: (S)-4-n-boc-2-methyl piperazine (CNH Technologies, Inc., Woburn, MA, USA), run at room temp overnight. | 2nd eluting isomeric mixture |

Section 2—Individual Examples

Example 12

1-(4-(7-Chloro-4-cyclopropyl-6-(2-fluoro-6-hydroxyphenyl)-1-phthalazinyl)-1-piperazinyl)-2-propen-1-one

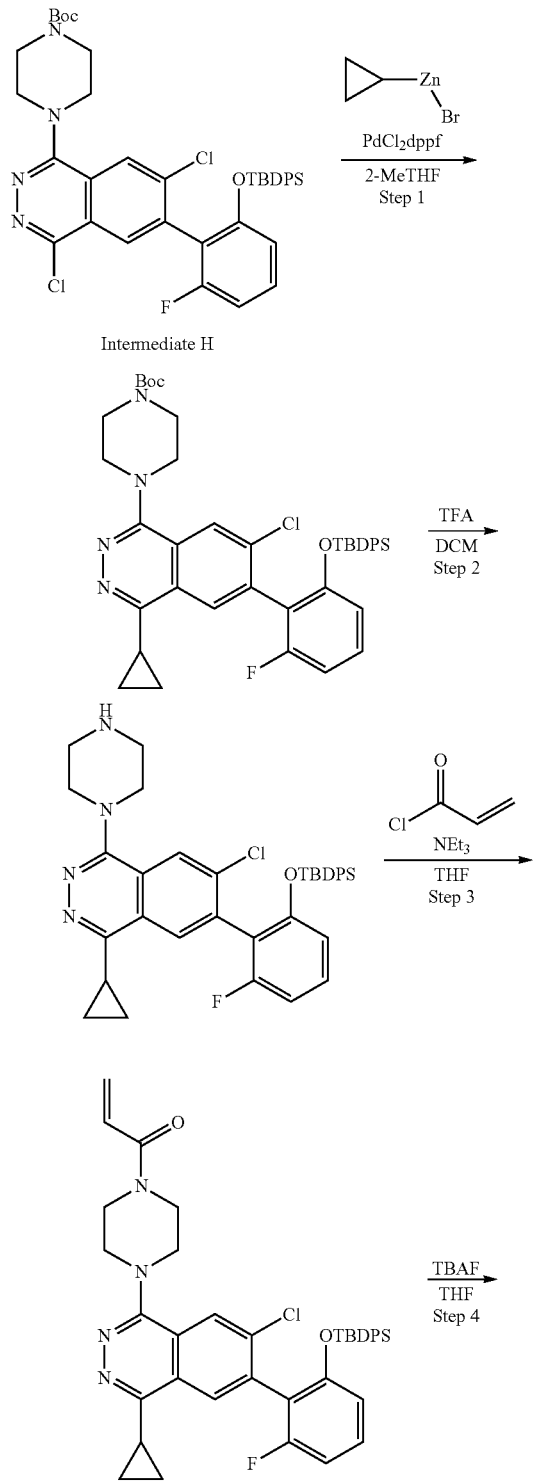

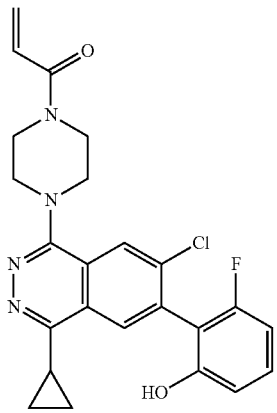

Step 1: tert-Butyl 4-(6-(2-((tert-butyldiphenylsilyl)oxy)-6-fluorophenyl)-7-chloro-4-cyclopropylphthalazin-1-yl)piperazine-1-carboxylate. To a 20 mL vial charged with tert-butyl 4-(6-(2-((tert-butyldiphenylsilyl)oxy)-6-fluorophenyl)-4,7-dichlorophthalazin-1-yl)piperazine-1-carboxylate (Intermediate H, 0.060 g, 0.082 mmol) was added [1,1'-bis(diphenylphosphino)ferrocene]dichloropalladium (II), complex with dichloromethane (0.033 g, 0.041 mmol) and 2-methyltetrahydrofuran (2.0 mL). The resulting mixture was capped and stirred at rt for 10 min before cyclopropylzinc bromide (0.5 M in THF, 0.820 mL, 0.410 mmol; Rieke Metals, Lincoln, NE, USA) was added via syringe. The reaction mixture was heated at 80° C. for 3 h before being cooled to rt and partitioned between EtOAc (30 mL) and water (10 mL). The aqueous layer was extracted once more with EtOAc (20 mL). The combined organic layers were dried over MgSO$_4$, filtered, and concentrated in vacuo. The crude product was purified by column chromatography (24 g of silica gel, 0 to 30% acetone in heptane) to obtain tert-butyl 4-(6-(2-((tert-butyldiphenylsilyl)oxy)-6-fluorophenyl)-7-chloro-4-cyclopropylphthalazin-1-yl)piperazine-1-carboxylate. $^1$H NMR (CHLOROFORM-d) δ: 8.31-8.38 (m, 1H), 8.15-8.23 (m, 1H), 7.55-7.64 (m, 4H), 7.39-7.47 (m, 2H), 7.29-7.38 (m, 4H), 6.99-7.09 (m, 1H), 6.74-6.85 (m, 1H), 6.36-6.47 (m, 1H), 3.68-3.79 (m, 4H), 3.37-3.51 (m, 4H), 2.37-2.48 (m, 1H), 1.48-1.54 (m, 9H), 1.37-1.45 (m, 1H), 1.30-1.33 (m, 1H), 1.00-1.15 (m, 2H), 0.61-0.71 (m, 9H). m/z (ESI) M+H: 737.4.

Step 2: 6-(2-((tert-Butyldiphenylsilyl)oxy)-6-fluorophenyl)-7-chloro-4-cyclopropyl-1-(piperazin-1-yl)phthalazine. Trifluoroacetic acid (0.316 mL, 4.10 mmol) was added to a solution of tert-butyl 4-(6-(2-((tert-butyldiphenylsilyl)oxy)-6-fluorophenyl)-7-chloro-4-cyclopropylphthalazin-1-yl)piperazine-1-carboxylate in DCM (0.7 mL). The resulting mixture was capped and stirred at rt for 30 min. The reaction mixture was diluted with DCM (10 mL) and basified using saturated aqueous NaHCO$_3$ (5 mL). The aqueous layer was extracted once more with DCM (10 mL). The combined organic layers were dried over MgSO$_4$, filtered, and concentrated in vacuo to obtain 6-(2-((tert-butyldiphenylsilyl)oxy)-6-fluorophenyl)-7-chloro-4-cyclopropyl-1-(piperazin-1-yl)phthalazine. $^1$H NMR (CHLOROFORM-d) δ: 8.30-8.36 (m, 1H), 8.18-8.24 (m, 1H), 7.55-7.64 (m, 4H), 7.40-7.46 (m, 2H), 7.33 (q, J=7.1 Hz, 4H), 6.97-7.09 (m, 1H), 6.74-6.83 (m, 1H), 6.36-6.46 (m, 1H), 3.45-3.55 (m, 4H), 3.16-3.26 (m, 4H), 2.35-2.49 (m, 1H), 1.37-1.46 (m, 1H), 1.30-1.33 (m, 1H), 1.06-1.12 (m, 2H), 0.61-0.70 (m, 9H). m/z (ESI) M+H: 637.2.

Step 3: 1-(4-(6-(2-((tert-Butyldiphenylsilyl)oxy)-6-fluorophenyl)-7-chloro-4-cyclopropylphthalazin-1-yl)piperazin-1-yl)prop-2-en-1-one. To a 20 mL vial charged with 6-(2-((tert-butyldiphenylsilyl)oxy)-6-fluorophenyl)-7-chloro-4-cyclopropyl-1-(piperazin-1-yl)phthalazine (0.023 g, 0.036 mmol) was added triethylamine (16 μl, 0.114 mmol) and dichloromethane (1.0 mL). The resulting mixture was capped and stirred at rt for 10 min before acryloyl chloride (4.0 μl, 0.049 mmol) was added via syringe. The reaction mixture was capped and continued to stir at rt for 20 min. The reaction was quenched with saturated aqueous NaHCO₃ (3 mL) and diluted with DCM (10 mL). The aqueous layer was extracted once more with DCM (5 mL). The combined organic layers were dried over MgSO₄, filtered, and concentrated in vacuo to obtain 1-(4-(6-(2-((tert-butyldiphenylsilyl)oxy)-6-fluorophenyl)-7-chloro-4-cyclopropylphthalazin-1-yl)piperazin-1-yl)prop-2-en-1-one. $^1$H NMR (CHLOROFORM-d) δ: 8.32-8.38 (m, 1H), 8.16-8.24 (m, 1H), 7.55-7.65 (m, 4H), 7.40-7.48 (m, 2H), 7.31-7.38 (m, 4H), 6.98-7.10 (m, 1H), 6.75-6.84 (m, 1H), 6.60-6.72 (m, 1H), 6.41-6.47 (m, 1H), 6.31-6.40 (m, 1H), 5.72-5.82 (m, 1H), 3.79-4.08 (m, 4H), 3.44-3.62 (m, 4H), 2.38-2.49 (m, 1H), 1.40-1.45 (m, 1H), 1.33-1.37 (m, 1H), 1.04-1.13 (m, 2H), 0.62-0.68 (m, 9H). m/z (ESI) M+H: 691.2.

Step 4: 1-(4-(7-Chloro-4-cyclopropyl-6-(2-fluoro-6-hydroxyphenyl)-1-phthalazinyl)-1-piperazinyl)-2-propen-1-one. To a 20 mL vial charged with 1-(4-(6-(2-((tert-butyldiphenylsilyl)oxy)-6-fluorophenyl)-7-chloro-4-cyclopropylphthalazin-1-yl)piperazin-1-yl)prop-2-en-1-one (0.022 g, 0.032 mmol) was added tetrahydrofuran (2.0 mL) followed by tetrabutylammonium fluoride (1.0 M solution in THF, 0.070 mL, 0.070 mmol). The vial was capped and stirred at rt for 30 min. The reaction mixture was concentrated in vacuo. The crude product was purified by column chromatography (24 g of silica, 0 to 5% MeOH in DCM) to obtain 1-(4-(7-chloro-4-cyclopropyl-6-(2-fluoro-6-hydroxyphenyl)-1-phthalazinyl)-1-piperazinyl)-2-propen-1-one. $^1$H NMR (CHLOROFORM-d) δ: 8.30-8.37 (m, 1H), 8.11-8.18 (m, 1H), 7.29-7.38 (m, 1H), 6.96-7.18 (m, 1H), 6.88-6.94 (m, 1H), 6.76-6.85 (m, 1H), 6.59-6.72 (m, 1H), 6.31-6.42 (m, 1H), 5.73-5.84 (m, 1H), 3.73-4.05 (m, 4H), 3.35-3.62 (m, 4H), 2.40-2.52 (m, 1H), 1.35-1.42 (m, 1H), 1.29-1.34 (m, 1H), 1.03-1.14 (m, 2H). m/z (ESI) M+H: 453.2.

Example 13

1-(4-(4-Anilino-7-chloro-6-(2-fluoro-6-hydroxyphenyl)-1-phthalazinyl)-1-piperazinyl)-2-propen-1-one

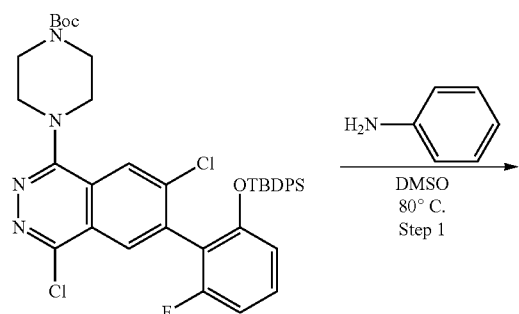

Intermediate H

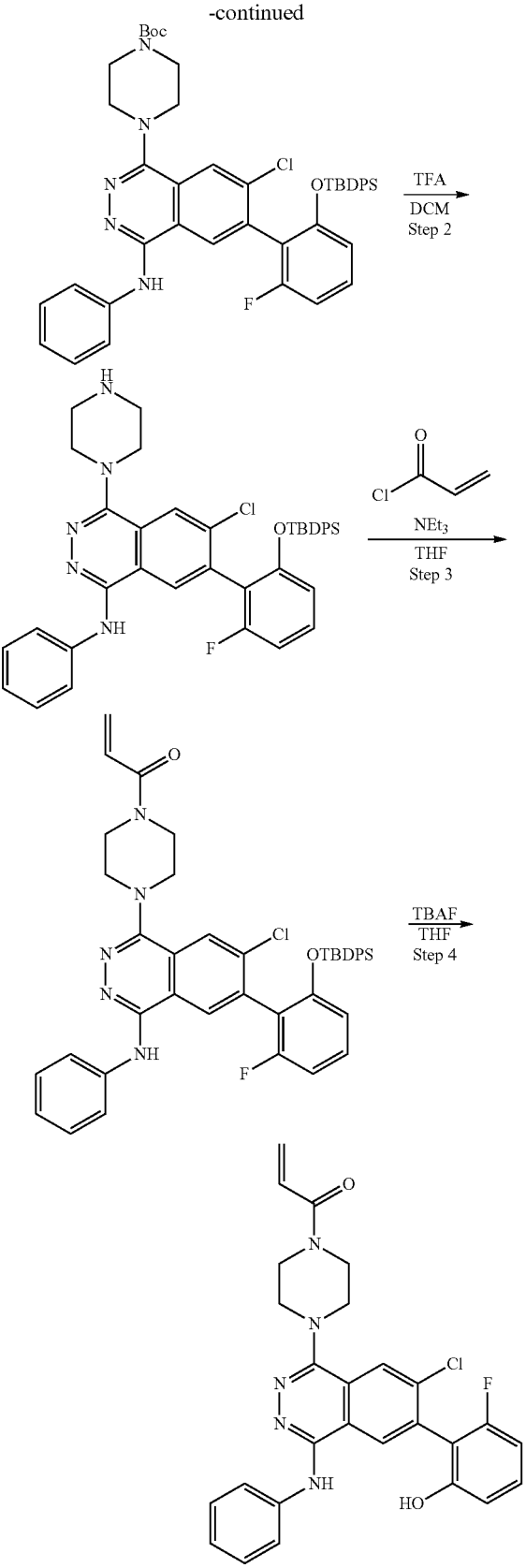

Step 1: tert-Butyl 4-(6-(2-((tert-butyldiphenylsilyl)oxy)-6-fluorophenyl)-7-chloro-4-(phenylamino)phthalazin-1-yl)

piperazine-1-carboxylate. To a 20 mL vial charged with tert-butyl 4-(6-(2-((tert-butyldiphenylsilyl)oxy)-6-fluorophenyl)-4,7-dichlorophthalazin-1-yl)piperazine-1-carboxylate (0.060 g, 0.082 mmol) was added dimethyl sulfoxide (2.0 mL) followed by aniline (0.075 mL, 0.820 mmol). The vial was capped and refluxed at 80° C. for 3 h. The reaction was cooled to rt and partitioned between EtOAc (30 mL) and water (10 mL). The organic layer was separated and washed with water (2×10 mL). The organic layer was dried over MgSO₄, filtered, and concentrated in vacuo. The crude product was purified by column chromatography (40 g of silica, 0 to 30% EtOAc in heptane) to obtain tert-butyl 4-(6-(2-((tert-butyldiphenylsilyl)oxy)-6-fluorophenyl)-7-chloro-4-(phenylamino)phthalazin-1-yl)piperazine-1-carboxylate. $^1$H NMR (CHLOROFORM-d) δ: 8.17-8.25 (m, 1H), 7.76-7.81 (m, 1H), 7.60-7.69 (m, 5H), 7.50-7.55 (m, 2H), 7.40-7.46 (m, 2H), 7.31-7.37 (m, 5H), 7.06-7.11 (m, 2H), 6.76-6.83 (m, 1H), 6.57-6.66 (m, 1H), 6.39-6.50 (m, 1H), 3.66-3.81 (m, 4H), 3.32-3.43 (m, 4H), 1.51-1.53 (m, 9H), 0.69-0.75 (m, 9H). m/z (ESI) M+H: 788.2.

Step 2: 7-(2-((tert-Butyldiphenylsilyl)oxy)-6-fluorophenyl)-6-chloro-1N-phenyl-4-(piperazin-1-yl)phthalazin-1-amine. Analogous to Example 12, step 2, the reaction of tert-butyl 4-(6-(2-((tert-butyldiphenylsilyl)oxy)-6-fluorophenyl)-7-chloro-4-(phenylamino)phthalazin-1-yl)piperazine-1-carboxy late delivered 7-(2-((tert-butyldiphenylsilyl)oxy)-6-fluorophenyl)-6-chloro-N-phenyl-4-(piperazin-1-yl)phthalazin-1-amine. $^1$H NMR (CHLOROFORM-d) δ: 8.19-8.26 (m, 1H), 7.75-7.80 (m, 1H), 7.60-7.68 (m, 5H), 7.49-7.55 (m, 2H), 7.39-7.46 (m, 3H), 7.32-7.37 (m, 5H), 7.02-7.11 (m, 2H), 6.75-6.84 (m, 1H), 6.59-6.67 (m, 1H), 6.43-6.53 (m, 1H), 3.35-3.47 (m, 4H), 3.16-3.27 (m, 4H), 0.70-0.76 (m, 9H). m/z (ESI) M+H: 688.2.

Step 3: 1-(4-(6-(2-((tert-Butyldiphenylsilyl)oxy)-6-fluorophenyl)-7-chloro-4-(phenylamino)phthalazin-1-yl)piperazin-1-yl)prop-2-en-1-one. Analogous to Example 12, step 3, the reaction of 7-(2-((tert-butyldiphenylsilyl)oxy)-6-fluorophenyl)-6-chloro-N-phenyl-4-(piperazin-1-yl)phthalazin-1-amine delivered 1-(4-(6-(2-((tert-butyldiphenylsilyl)oxy)-6-fluorophenyl)-7-chloro-4-(phenylamino)phthalazin-1-yl)piperazin-1-yl)prop-2-en-1-one. $^1$H NMR (CHLOROFORM-d) δ: 8.16-8.24 (m, 1H), 7.77-7.84 (m, 1H), 7.62-7.67 (m, 4H), 7.52-7.55 (m, 1H), 7.41-7.46 (m, 3H), 7.32-7.38 (m, 6H), 7.02-7.11 (m, 2H), 6.77-6.84 (m, 1H), 6.65-6.71 (m, 1H), 6.46-6.51 (m, 1H), 6.30-6.39 (m, 2H), 5.73-5.81 (m, 1H), 3.86-4.05 (m, 4H), 3.37-3.53 (m, 4H), 0.69-0.75 (m, 9H). m/z (ESI) M+H: 742.3.

Step 4: 1-(4-(4-Anilino-7-chloro-6-(2-fluoro-6-hydroxyphenyl)-1-phthalazinyl)-1-piperazinyl)-2-propen-1-one. Analogous to Example 12, step 4, the reaction of 1-(4-(6-(2-((tert-butyldiphenylsilyl)oxy)-6-fluorophenyl)-7-chloro-4-(phenylamino)phthalazin-1-yl)piperazin-1-yl)prop-2-en-1-one delivered 1-(4-(4-anilino-7-chloro-6-(2-fluoro-6-hydroxyphenyl)-1-phthalazinyl)-1-piperazinyl)-2-propen-1-one. $^1$H NMR (CHLOROFORM-d) δ: 7.96-8.09 (m, 2H), 7.46-7.57 (m, 2H), 7.37-7.44 (m, 1H), 7.29-7.33 (m, 1H), 7.20-7.26 (m, 1H), 6.96-7.07 (m, 1H), 6.81-6.87 (m, 1H), 6.70-6.77 (m, 1H), 6.54-6.67 (m, 1H), 6.29-6.41 (m, 1H), 5.68-5.82 (m, 1H), 3.74-3.96 (m, 4H), 3.12-3.43 (m, 4H). m/z (ESI) M+H: 504.2.

Example 14

1-(4-(7-Chloro-4-cyclopentyl-6-(2-fluoro-6-hydroxyphenyl)-1-phthalazinyl)-1-piperazinyl)-2-propen-1-one

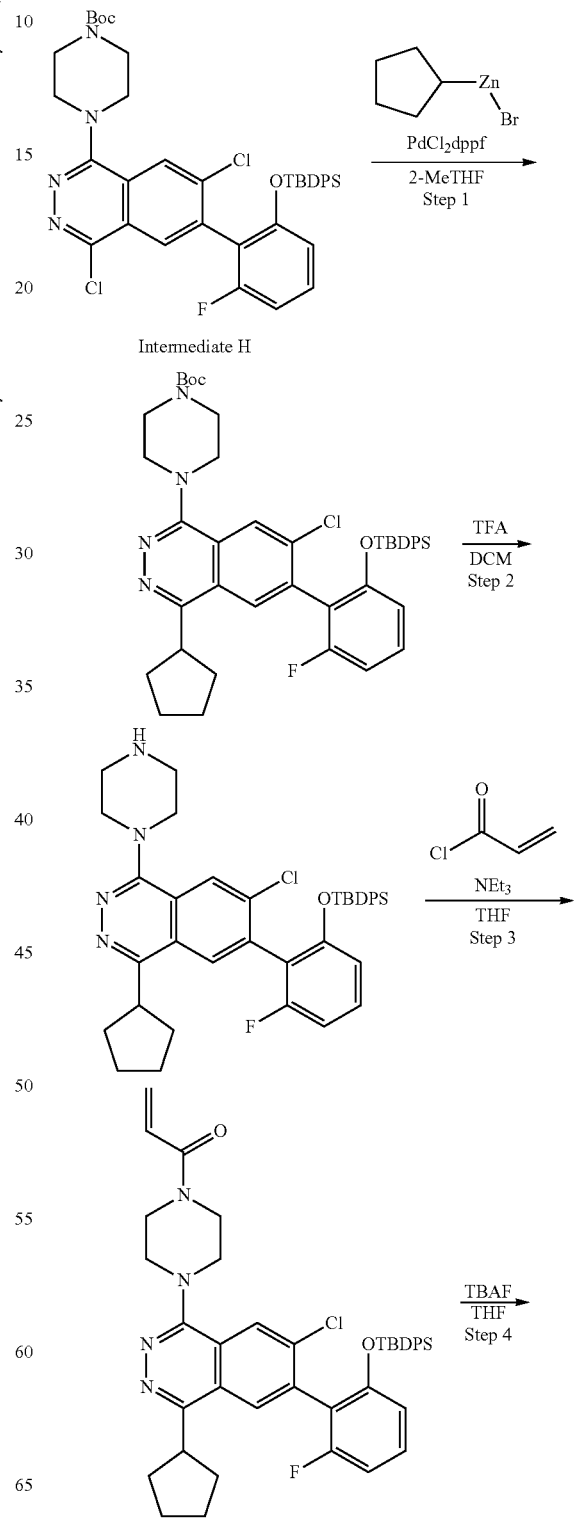

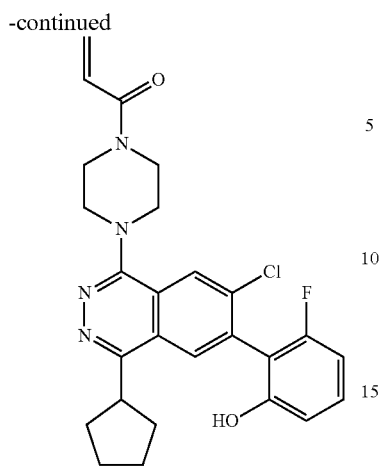

Step 1: tert-Butyl 4-(6-(2-((tert-butyldiphenylsilyl)oxy)-6-fluorophenyl)-7-chloro-4-cyclopentylphthalazin-1-yl)piperazine-1-carboxylate. Analogous to Example 12, step 1, the reaction of tert-butyl 4-(6-(2-((tert-butyldiphenylsilyl)oxy)-6-fluorophenyl)-4,7-dichlorophthalazin-1-yl)piperazine-1-carboxylate (Intermediate H) and cyclopentylzinc bromide (0.5 M in THF, Rieke Metals, Lincoln, NE) delivered tert-butyl 4-(6-(2-((tert-butyldiphenylsilyl)oxy)-6-fluorophenyl)-7-chloro-4-cyclopentylphthalazin-1-yl)piperazine-1-carboxylate. $^1$H NMR (CHLOROFORM-d) δ: 8.18-8.22 (m, 1H), 8.12-8.16 (m, 1H), 7.60-7.66 (m, 2H), 7.50-7.56 (m, 2H), 7.39-7.47 (m, 2H), 7.34-7.38 (m, 2H), 7.28-7.33 (m, 2H), 7.09 (br d, J=1.2 Hz, 1H), 6.75-6.82 (m, 1H), 6.37-6.44 (m, 1H), 3.72-3.78 (m, 4H), 3.44-3.51 (m, 4H), 2.03-2.23 (m, 4H), 1.87-1.96 (m, 2H), 1.67-1.79 (m, 3H), 1.51-1.54 (m, 9H), 0.62-0.67 (m, 9H). m/z (ESI) M+H: 765.2.

Step 2: 6-(2-((tert-Butyldiphenylsilyl)oxy)-6-fluorophenyl)-7-chloro-4-cyclopentyl-1-(piperazin-1-yl)phthalazine. Analogous to Example 12, step 2, the reaction of tert-butyl 4-(6-(2-((tert-butyldiphenylsilyl)oxy)-6-fluorophenyl)-7-chloro-4-cyclopentylphthalazin-1-yl)piperazine-1-carboxylate delivered 6-(2-((tert-butyldiphenylsilyl)oxy)-6-fluorophenyl)-7-chloro-4-cyclopentyl-1-(piperazin-1-yl)phthalazine. $^1$H NMR (CHLOROFORM-d) δ: 8.17-8.21 (m, 1H), 8.12-8.16 (m, 1H), 7.61-7.66 (m, 2H), 7.51-7.56 (m, 2H), 7.40-7.46 (m, 2H), 7.34-7.38 (m, 2H), 7.29-7.33 (m, 2H), 6.99-7.08 (m, 1H), 6.74-6.82 (m, 1H), 6.37-6.45 (m, 1H), 3.58-3.67 (m, 4H), 3.27-3.36 (m, 4H), 2.18-2.22 (m, 1H), 2.08-2.12 (m, 2H), 1.86-1.91 (m, 3H), 1.69-1.77 (m, 3H), 0.59-0.67 (m, 9H). m/z (ESI) M+H: 665.2.

Step 3: 1-(4-(6-(2-((tert-Butyldiphenylsilyl)oxy)-6-fluorophenyl)-7-chloro-4-cyclopentylphthalazin-1-yl)piperazin-1-yl)prop-2-en-1-one. Analogous to Example 12, step 3, the reaction of 6-(2-((tert-butyldiphenylsilyl)oxy)-6-fluorophenyl)-7-chloro-4-cyclopentyl-1-(piperazin-1-yl)phthalazine delivered 1-(4-(6-(2-((tert-butyldiphenylsilyl)oxy)-6-fluorophenyl)-7-chloro-4-cyclopentylphthalazin-1-yl)piperazin-1-yl)prop-2-en-1-one. $^1$H NMR (CHLOROFORM-d) δ: 8.18-8.25 (m, 1H), 8.13-8.17 (m, 1H), 7.61-7.67 (m, 2H), 7.50-7.57 (m, 2H), 7.39-7.48 (m, 2H), 7.28-7.37 (m, 4H), 6.99-7.10 (m, 1H), 6.75-6.83 (m, 1H), 6.62-6.71 (m, 1H), 6.33-6.43 (m, 2H), 5.73-5.81 (m, 1H), 3.84-4.07 (m, 4H), 3.71-3.82 (m, 1H), 3.49-3.65 (m, 4H), 1.80-1.96 (m, 4H), 1.67-1.77 (m, 4H), 0.62-0.67 (m, 9H). m/z (ESI) M+H: 719.2.

Step 4: 1-(4-(7-Chloro-4-cyclopentyl-6-(2-fluoro-6-hydroxyphenyl)-1-phthalazinyl)-1-piperazinyl)-2-propen-1-one. Analogous to Example 12, step 4, the reaction of 1-(4-(6-(2-((tert-butyldiphenylsilyl)oxy)-6-fluorophenyl)-7-chloro-4-cyclopentylphthalazin-1-yl)piperazin-1-yl)prop-2-en-1-one delivered 1-(4-(7-chloro-4-cyclopentyl-6-(2-fluoro-6-hydroxyphenyl)-1-phthalazinyl)-1-piperazinyl)-2-propen-1-one. $^1$H NMR (CHLOROFORM-d) δ: 8.10-8.22 (m, 2H), 7.29-7.38 (m, 1H), 6.86-6.93 (m, 1H), 6.77-6.85 (m, 1H), 6.61-6.72 (m, 1H), 6.33-6.44 (m, 1H), 5.74-5.85 (m, 1H), 3.82-4.05 (m, 4H), 3.75-3.82 (m, 1H), 3.40-3.63 (m, 4H), 2.06-2.24 (m, 4H), 1.81-1.96 (m, 2H), 1.67-1.79 (m, 2H). m/z (ESI) M+H: 481.2.

Example 15

1-(4-(7-Chloro-6-(2-fluoro-6-hydroxyphenyl)-4-(1-piperidinyl)-1-phthalazinyl)-1-piperazinyl)-2-propen-1-one

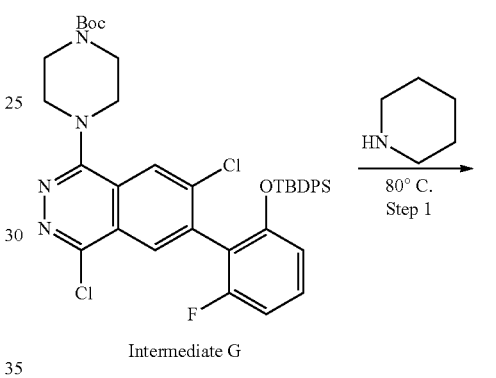

Intermediate G

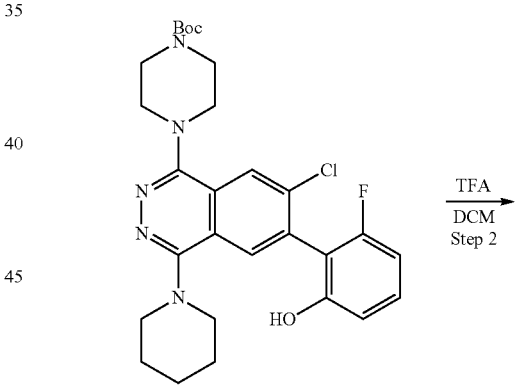

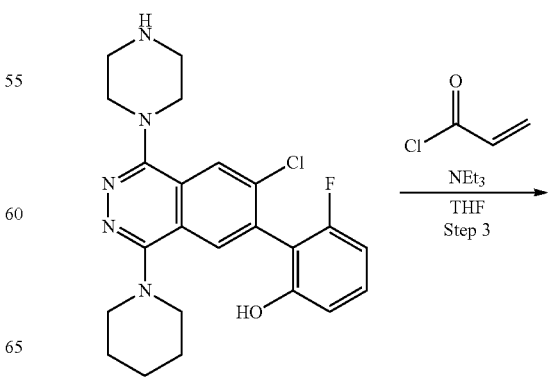

-continued

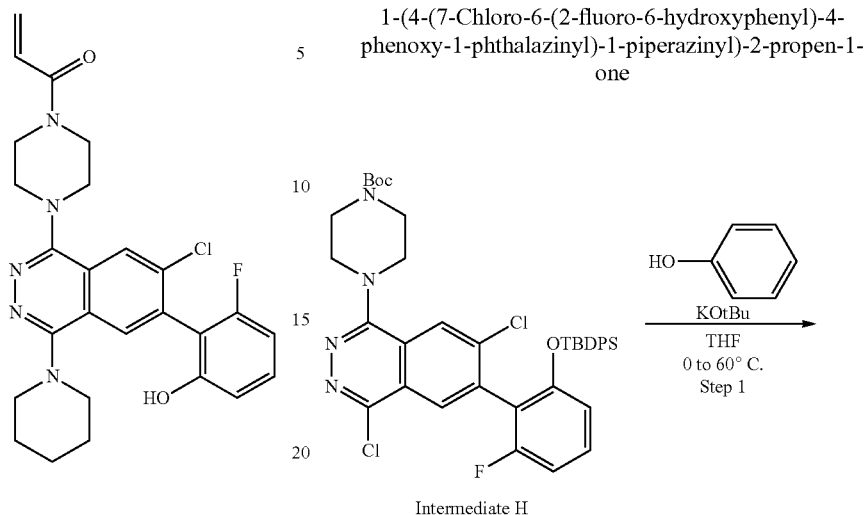

Example 16

1-(4-(7-Chloro-6-(2-fluoro-6-hydroxyphenyl)-4-phenoxy-1-phthalazinyl)-1-piperazinyl)-2-propen-1-one

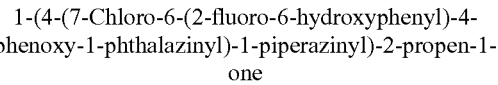

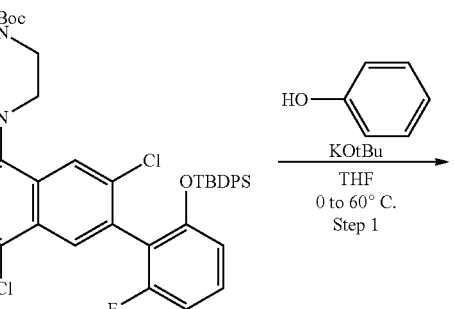

Intermediate H

Step 1: tert-Butyl 4-(7-chloro-6-(2-fluoro-6-hydroxyphenyl)-4-(piperidin-1-yl)phthalazin-1-yl)piperazine-1-carboxylate. To a 20 mL vial charged with tert-butyl 4-(6-(2-(((tert-butyldiphenylsilyl)oxy)-6-fluorophenyl)-4,7-dichlorophthalazin-1-yl)piperazine-1-carboxylate (Intermediate H, 0.060 g, 0.082 mmol) was added piperidine (1.0 mL, 10.10 mmol). The vial was capped and heated at 80° C. for 2 h. The reaction was cooled to rt and partitioned between EtOAc (30 mL) and water (10 mL). The organic layer was separated and washed with water (2×10 mL). The combined organic layers were dried over MgSO$_4$, filtered, and concentrated in vacuo to obtain tert-butyl 4-(7-chloro-6-(2-fluoro-6-hydroxyphenyl)-4-(piperidin-1-yl)phthalazin-1-yl)piperazine-1-carboxylate. $^1$H NMR (CHLOROFORM-d) δ: 8.09-8.14 (m, 1H), 7.97-8.03 (m, 1H), 7.28-7.35 (m, 1H), 6.75-6.88 (m, 2H), 3.65-3.76 (m, 4H), 3.30-3.44 (m, 8H), 1.72-1.81 (m, 4H), 1.61-1.71 (m, 3H), 1.48-1.53 (m, 9H). m/z (ESI) M+H: 542.2.

Step 2: 2-(7-Chloro-1-(piperazin-1-yl)-4-(piperidin-1-yl)phthalazin-6-yl)-3-fluorophenol. Analogous to Example 12, step 2, the reaction of tert-butyl 4-(7-chloro-6-(2-fluoro-6-hydroxyphenyl)-4-(piperidin-1-yl)phthalazin-1-yl)piperazine-1-carboxylate delivered 2-(7-chloro-1-(piperazin-1-yl)-4-(piperidin-1-yl)phthalazin-6-yl)-3-fluorophenol. $^1$H NMR (CHLOROFORM-d) δ: 8.09-8.13 (m, 1H), 7.95-8.03 (m, 1H), 7.28-7.38 (m, 1H), 6.83-6.89 (m, 1H), 6.75-6.82 (m, 1H), 3.39-3.48 (m, 4H), 3.31-3.38 (m, 4H), 3.12-3.21 (m, 4H), 1.75-1.80 (m, 4H), 1.64-1.69 (m, 2H). m/z (ESI) M+H: 442.2.

Step 3: 1-(4-(7-Chloro-6-(2-fluoro-6-hydroxyphenyl)-4-(1-piperidinyl)-1-phthalazinyl)-1-piperazinyl)-2-propen-1-one. Analogous to Example 12, step 3, the reaction of 2-(7-chloro-1-(piperazin-1-yl)-4-(piperidin-1-yl)phthalazin-6-yl)-3-fluorophenol delivered 1-(4-(7-Chloro-6-(2-fluoro-6-hydroxyphenyl)-4-(1-piperidinyl)-1-phthalazinyl)-1-piperazinyl)-2-propen-1-one. $^1$H NMR (CHLOROFORM-d) δ: 8.08-8.15 (m, 1H), 7.98-8.05 (m, 1H), 7.29-7.39 (m, 1H), 6.86-6.94 (m, 1H), 6.76-6.85 (m, 1H), 6.59-6.70 (m, 1H), 6.30-6.43 (m, 1H), 5.72-5.84 (m, 1H), 3.77-4.05 (m, 4H), 3.40-3.56 (m, 4H), 3.32-3.38 (m, 4H), 1.73-1.85 (m, 4H), 1.64-1.70 (m, 2H). m/z (ESI) M+H: 496.2.

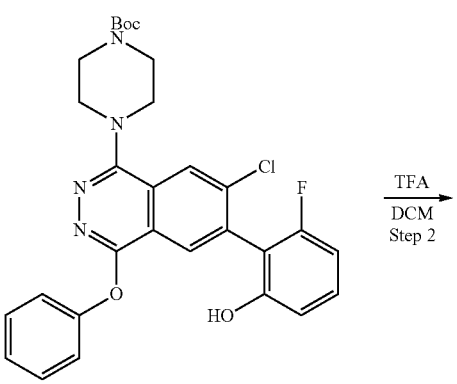

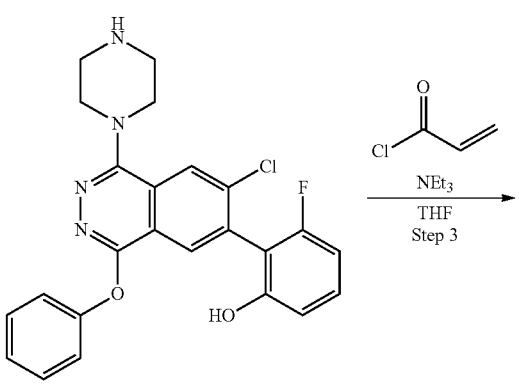

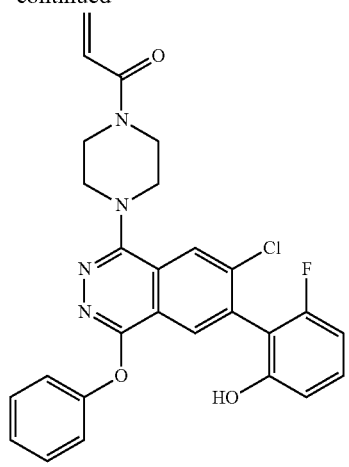

Step 1: tert-Butyl 4-(7-chloro-6-(2-fluoro-6-hydroxyphenyl)-4-phenoxyphthalazin-1-yl)piperazine-1-carboxylate. A dry 50 mL rbf was charged with phenol (0.130 g, 1.381 mmol) and tetrahydrofuran (3.0 mL). The mixture was cooled to 0° C. before potassium t-butoxide (0.153 g, 1.367 mmol) was added. The mixture was stirred at 0° C. for 10 min before being warmed to rt and stirred for 30 min. tert-Butyl 4-(6-(2-((tert-butyldiphenylsilyl)oxy)-6-fluorophenyl)-4,7-dichlorophthalazin-1-yl)piperazine-1-carboxylate (Intermediate H, 0.100 g, 0.137 mmol) was added, and the resulting mixture was heated at 60° C. for 2 h. The reaction was cooled to rt and quenched with water. The resulting mixture was partitioned between EtOAc (30 mL) and water (15 mL). The aqueous layer was extracted once more with EtOAc (20 mL). The combined organic layers were dried over $MgSO_4$, filtered, and concentrated in vacuo. The crude product was purified by column chromatography (40 g of silica, 10 to 50% acetone) to obtain tert-butyl 4-(7-chloro-6-(2-fluoro-6-hydroxyphenyl)-4-phenoxyphthalazin-1-yl)piperazine-1-carboxylate: m/z (ESI) M+H: 551.2.

Step 2: 2-(7-chloro-4-phenoxy-1-(piperazin-1-yl)phthalazin-6-yl)-3-fluorophenol. Analogous to Example 12, step 2, the reaction of 4-(7-chloro-6-(2-fluoro-6-hydroxyphenyl)-4-phenoxyphthalazin-1-yl)piperazine-1-carboxylate delivered. 2-(7-chloro-4-phenoxy-1-(piperazin-1-yl)phthalazin-6-yl)-3-fluorophenol. $^1$H NMR (CHLOROFORM-d) δ: 8.37-8.42 (m, 1H), 8.14-8.19 (m, 1H), 7.37-7.45 (m, 2H), 7.29-7.34 (m, 1H), 7.19-7.25 (m, 2H), 6.89-6.98 (m, 1H), 6.76-6.87 (m, 4H), 3.36-3.45 (m, 4H), 3.13-3.22 (m, 4H). m/z (ESI) M+H: 451.2.

Step 3: 1-(4-(7-Chloro-6-(2-fluoro-6-hydroxyphenyl)-4-phenoxy-1-phthalazinyl)-1-piperazinyl)-2-propen-1-one. Analogous to Example 12, step 3, the reaction of 2-(7-chloro-4-phenoxy-1-(piperazin-1-yl)phthalazin-6-yl)-3-fluorophenol delivered 1-(4-(7-chloro-6-(2-fluoro-6-hydroxyphenyl)-4-phenoxy-1-phthalazinyl)-1-piperazinyl)-2-propen-1-one. $^1$H NMR (CHLOROFORM-d) δ: 8.41-8.45 (m, 1H), 8.17-8.20 (m, 1H), 7.40-7.45 (m, 2H), 7.28-7.37 (m, 2H), 7.20-7.26 (m, 1H), 6.78-6.87 (m, 2H), 6.59-6.70 (m, 1H), 6.31-6.41 (m, 1H), 5.97-6.06 (m, 1H), 5.74-5.81 (m, 1H), 3.76-4.03 (m, 4H), 3.38-3.53 (m, 4H). m/z (ESI) M+H: 505.2.

Examples 17-1 and 17-2

(2E)-1-(4-(5-Chloro-7-fluoro-6-(3-methoxy-1-naphthalenyl)-2,1-benzothiazol-3-yl)-1-piperazinyl)-4-(dimethylamino)-2-buten-1-one (Example 17-1) and (2E)-1-(4-(5-chloro-7-fluoro-6-(3-hydroxy-1-naphthalenyl)-2,1-benzothiazol-3-yl)-1-piperazinyl)-4-(dimethylamino)-2-buten-1-one (Example 17-2)

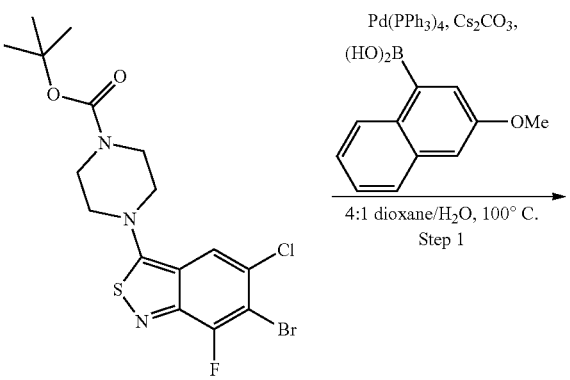

Intermediate D

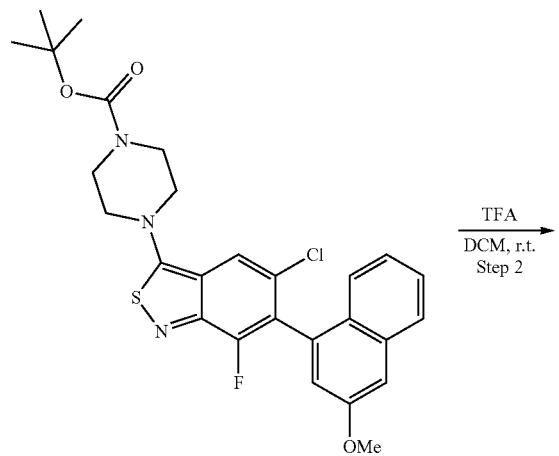

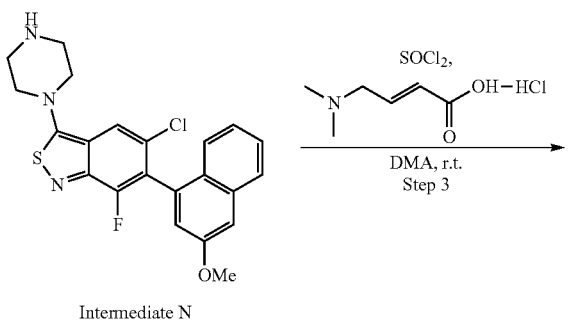

Intermediate N

-continued

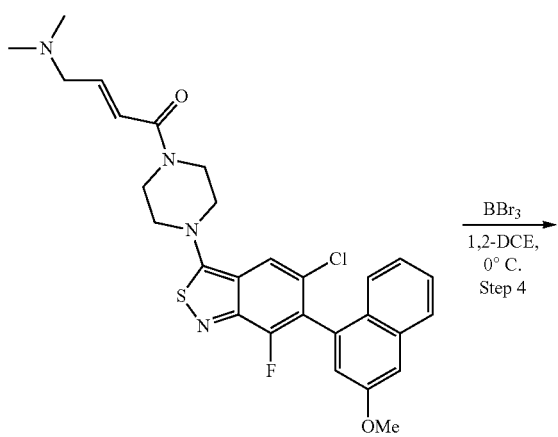

Example 17-1

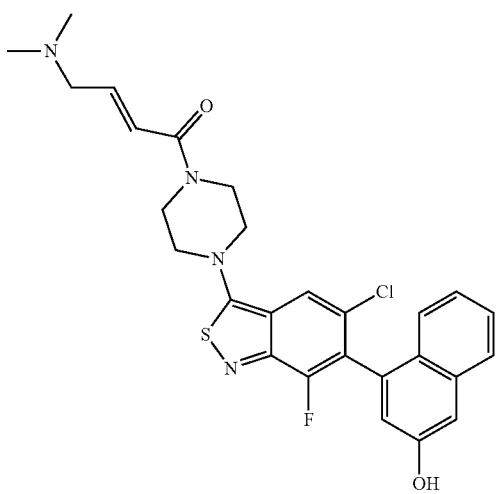

Example 17-2

Step 1: tert-Butyl 4-(5-chloro-6-(3-methoxynaphthalen-1-yl)benzo[c]isothiazol-3-yl)piperazine-1-carboxylate. A slurry of tert-butyl 4-(6-bromo-5-chloro-7-fluorobenzo[c]isothiazol-3-yl)piperazine-1-carboxylate (Intermediate D, 459 mg, 1.02 mmol), (3-methoxynaphthalen-1-yl)boronic acid (823 mg, 4.07 mmol) and cesium carbonate (1.33 g, 4.07 mmol) in a mixture of 1,4-dioxane (8 mL) and water (2 mL) was degassed with an argon stream. Tetrakis(triphenylphosphine)palladium (118 mg, 0.10 mmol) was added, and the mixture was again degassed with an Argon stream. The reaction mixture was sealed and heated at 100° C. for 23 h. The reaction was allowed to cool to rt, diluted with brine (60 mL), and extracted two times with EtOAc. The combined organic layers were dried over anhydrous sodium sulfate and concentrated. The residue was purified by silica gel chromatography (eluent: 0-2% MeOH in DCM) to provide tert-butyl 4-(5-chloro-6-(3-methoxynaphthalen-1-yl)benzo[c]isothiazol-3-yl)piperazine-1-carboxylate. m/z (ESI) M+H: 528.0.

Step 2: 5-Chloro-6-(3-methoxynaphthalen-1-yl)-3-(piperazin-1-yl)benzo[c]isothiazole. To a solution of tert-butyl 4-(5-chloro-6-(3-methoxynaphthalen-1-yl)benzo[c]isothiazol-3-yl)piperazine-1-carboxylate (327 mg, 0.56 mmol) in DCM (6 mL) was added trifluoroacetic acid (1.04 mL, 13.9 mmol) via syringe. The resulting yellow solution was stirred at rt for 4 h and then was concentrated. The residue was purified by silica gel chromatography (eluent: 0-25% MeOH in DCM) to provide the mono-TFA salt of 5-chloro-6-(3-methoxynaphthalen-1-yl)-3-(piperazin-1-yl)benzo[c]isothiazole . . . m/z (ESI) M+H: 428.0.

Step 3: (2E)-1-(4-(5-Chloro-7-fluoro-6-(3-methoxy-1-naphthalenyl)-2,1-benzothiazol-3-yl)-1-piperazinyl)-4-(dimethylamino)-2-buten-1-one. To a solution of 5-chloro-6-(3-methoxynaphthalen-1-yl)-3-(piperazin-1-yl)benzo[c]isothiazole (74 mg of the mono-TFA salt, 0.14 mmol) and trans-4-dimethylaminocrotonoic acid hydrochloride (38 mg, 0.23 mmol) in DMA (2 mL) was added thionyl chloride (41 µL, 0.69 mmol) via syringe. The resulting brown solution was stirred at rt for 2.5 h. The reaction mixture was quenched with water (50 mL) and extracted with 8:1 DCM/MeOH. The organic layer was dried over anhydrous sodium sulfate and concentrated. The residue was purified by silica gel chromatography (eluent: 0-15% MeOH in DCM) to provide (2E)-1-(4-(5-chloro-7-fluoro-6-(3-methoxy-1-naphthalenyl)-2,1-benzothiazol-3-yl)-1-piperazinyl)-4-(dimethylamino)-2-buten-1-one. $^1$H NMR (400 MHz, DMSO-d$_6$) δ 8.10 (s, 1H), 7.94 (d, J=8.4 Hz, 1H), 7.46-7.55 (m, 2H), 7.27-7.35 (m, 2H), 7.19 (d, J=2.5 Hz, 1H), 6.61-6.72 (m, 2H), 3.94 (s, 3H), 3.80-3.93 (m, 4H), 3.62-3.68 (m, 4H), 3.07 (d, J=4.3 Hz, 2H), 2.18 (s, 6H). m/z (ESI) M+H: 539.2.

Step 4: (2E)-1-(4-(5-Chloro-7-fluoro-6-(3-hydroxy-1-naphthalenyl)-2,1-benzothiazol-3-yl)-1-piperazinyl)-4-(dimethylamino)-2-buten-1-one. To a solution of (2E)-1-(4-(5-chloro-7-fluoro-6-(3-methoxy-1-naphthalenyl)-2,1-benzothiazol-3-yl)-1-piperazinyl)-4-(dimethylamino)-2-buten-1-one (23.5 mg, 0.044 mmol) in 1,2-dichloroethane (4 mL) at 0° C. was added boron tribromide (1.0 M in hexanes, 218 µL, 0.22 mmol) dropwise via syringe. The resulting yellow slurry was stirred at 0° C. for 2.75 h and then quenched with saturated aqueous NaHCO$_3$ (4 mL). The mixture was extracted two times with a 4:1 mixture of DCM/MeOH. The combined organic layers were dried over anhydrous sodium sulfate and concentrated. The residue was purified by silica gel chromatography (eluent: 0-18% MeOH in DCM) to provide (2E)-1-(4-(5-chloro-7-fluoro-6-(3-hydroxy-1-naphthalenyl)-2,1-benzothiazol-3-yl)-1-piperazinyl)-4-(dimethylamino)-2-buten-1-one. $^1$H NMR (400 MHz, DMSO-d$_6$) δ 9.97 (s, 1H), 8.10 (s, 1H), 7.80 (d, J=8.4 Hz, 1H), 7.40-7.46 (m, 1H), 7.19-7.30 (m, 3H), 7.07 (d, J=2.4 Hz, 1H), 6.62-6.71 (m, 2H), 3.80-3.93 (m, 4H), 3.62-3.69 (m, 4H), 3.07 (d, J=4.1 Hz, 2H), 2.17 (s, 6H). m/z (ESI) M+H: 525.0.

Examples 18-1 to 18-3

1-(4-(5-chloro-7-fluoro-6-(3-methoxy-1-naphthalenyl)-2,1-benzothiazol-3-yl)-1-piperazinyl)-2-(hydroxymethyl)-2-propen-1-one. (Example 18-1) and 2-(bromomethyl)-1-(4-(5-chloro-7-fluoro-6-(3-hydroxy-1-naphthalenyl)-2,1-benzothiazol-3-yl)-1-piperazinyl)-2-propen-1-one (Example 18-2) and 1-(4-(5-chloro-7-fluoro-6-(3-hydroxy-1-naphthalenyl)-2,1-benzothiazol-3-yl)-1-piperazinyl)-2-(hydroxymethyl)-2-propen-1-one (Example 18-3)

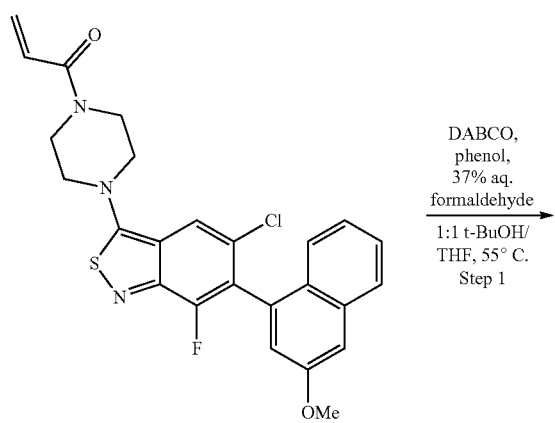

Intermediate O

DABCO, phenol, 37% aq. formaldehyde
1:1 t-BuOH/THF, 55° C.
Step 1

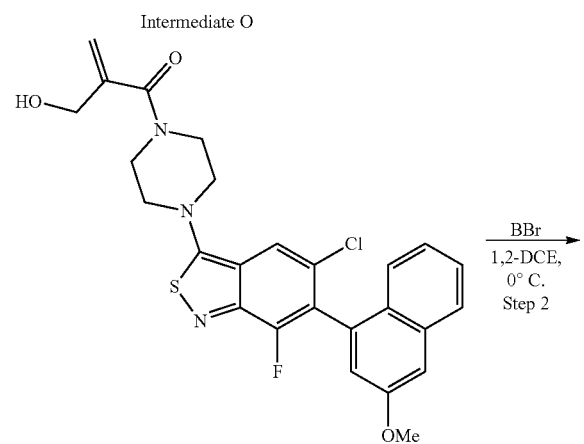

Example 18-1

BBr
1,2-DCE, 0° C.
Step 2

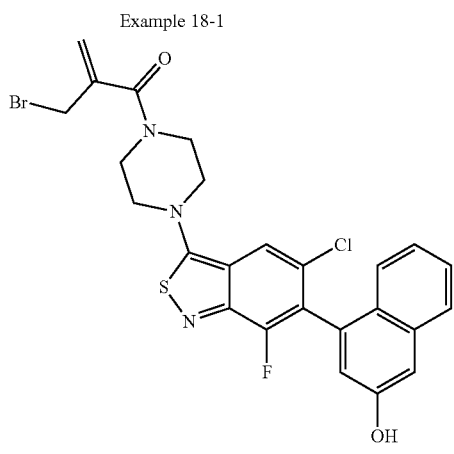

Example 18-2

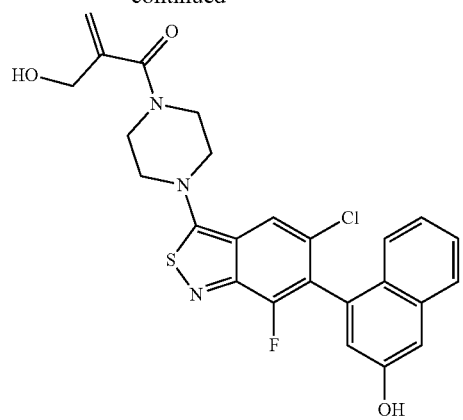

Example 18-3

Step 1: 1-(4-(5-Chloro-7-fluoro-6-(3-methoxy-1-naphthalenyl)-2,1-benzothiazol-3-yl)-1-piperazinyl)-2-(hydroxymethyl)-2-propen-1-one. A vial was charged with a solution of 1-(4-(5-chloro-7-fluoro-6-(3-methoxynaphthalen-1-yl)benzo[c]isothiazol-3-yl)piperazin-1-yl)prop-2-en-1-one (Intermediate O, 29 mg, 0.06 mmol) in tert-butanol (0.4 mL) and water (0.4 mL). Phenol (5.7 mg, 0.06 mmol), DABCO (20.3 mg, 0.18 mmol) and formaldehyde (37% aqueous solution, 24 µL, 0.24 mmol) were added sequentially. The resulting solution was sealed and heated at 55° C. for 29 h. The reaction was cooled to rt and partitioned between water (6 mL) and 10:1 DCM/MeOH. The organic layer was separated, and the aqueous layer was extracted two more times with 10:1 DCM/MeOH. The combined organic layers were dried over anhydrous sodium sulfate and concentrated. The residue was purified by silica gel chromatography (eluent: 0-3.5% MeOH in DCM) to provide 1-(4-(5-chloro-7-fluoro-6-(3-methoxy-1-naphthalenyl)-2,1-benzothiazol-3-yl)-1-piperazinyl)-2-(hydroxymethyl)-2-propen-1-one. $^1$H NMR (400 MHz, DMSO-$d_6$) δ 8.12 (s, 1H), 7.94 (d, J=8.2 Hz, 1H), 7.47-7.55 (m, 2H), 7.25-7.34 (m, 2H), 7.19 (d, J=2.5 Hz, 1H), 5.43 (br. s, 1H), 5.20 (br. s, 1H), 5.14 (t, J=5.8 Hz, 1H), 4.12 (d, J=5.7 Hz, 2H), 3.94 (s, 3H), 3.78-3.85 (m, 4H), 3.54-3.66 (m, 4H). m/z (ESI) M+H: 512.0.

Step 2: 2-(Bromomethyl)-1-(4-(5-chloro-7-fluoro-6-(3-hydroxy-1-naphthalenyl)-2,1-benzothiazol-3-yl)-1-piperazinyl)-2-propen-1-one and 1-(4-(5-chloro-7-fluoro-6-(3-hydroxy-1-naphthalenyl)-2,1-benzothiazol-3-yl)-1-piperazinyl)-2-(hydroxymethyl)-2-propen-1-one. To a solution of 1-(4-(5-chloro-7-fluoro-6-(3-methoxy-1-naphthalenyl)-2,1-benzothiazol-3-yl)-1-piperazinyl)-2-(hydroxymethyl)-2-propen-1-one (17.1 mg, 0.033 mmol) in 1,2-dichloroethane (4 mL) at 0° C. was added boron tribromide solution (1.0 M in hexanes, 167 µL, 0.17 mmol) dropwise via syringe. The resulting slurry was stirred at 0° C. for 40 min before being quenched with saturated aqueous NaHCO$_3$ (5 mL). The mixture was extracted twice with a 4:1 mixture of DCM/MeOH. The combined organic layers were dried over anhydrous sodium sulfate and concentrated. The residue was purified by silica gel chromatography (eluent: 0-7% MeOH in DCM) to give two products.

First-eluting peak: 2-(bromomethyl)-1-(4-(5-chloro-7-fluoro-6-(3-hydroxynaphthalen-1-yl)benzo[c]isothiazol-3-yl)piperazin-1-yl)prop-2-en-1-one. ¹H NMR (400 MHz, DMSO-d₆) δ 9.96 (hr. s, 1H), 8.13 (s, 1H), 7.80 (d, J=8.2 Hz, 1H), 7.40-7.47 (m, 1H), 7.19-7.29 (m, 3H), 7.07 (d, J=2.4 Hz, 1H), 5.78 (s, 1H), 5.41 (s, 1H), 4.38 (s, 2H), 3.84-3.93 (m, 4H), 3.62-3.72 (m, 4H). m/z (ESI) M+H: 560.0

Second-eluting peak: 1-(4-(5-chloro-7-fluoro-6-(3-hydroxynaphthalen-1-yl)benzo[c]isothiazol-3-yl)piperazin-1-yl)-2-(hydroxymethyl)prop-2-en-1-one. ¹H NMR (400 MHz, DMSO-d₆) δ 9.98 (hr. s, 1H), 8.11 (s, 1H), 7.79 (d, J=8.2 Hz, 1H), 7.37-7.48 (m, 1H), 7.17-7.28 (m, 3H), 7.07 (d, J=2.4 Hz, 1H), 5.43 (hr. s, 1H), 5.20 (hr. s, 1H), 5.07-5.14 (m, 1H), 4.12 (hr. s, 2H), 3.78-3.86 (m, 4H), 3.57-3.66 (m, 4H). m/z (ESI) M+H: 498.0

Examples 19-1 to 19-3

1-(4-(5-chloro-7-fluoro-6-(5-methoxy-1-methyl-1H-indazol-7-yl)-2,1-benzothiazol-3-yl)-1-piperazinyl)-2-propen-1-one (Example 19-1) and 1-(4-(5-chloro-7-fluoro-6-(5-hydroxy-1-methyl-1H-indazol-7-yl)-2,1-benzothiazol-3-yl)-1-piperazinyl)-2-propen-1-one (Example 19-2) and 1-(4-(5-chloro-7-fluoro-6-(5-hydroxy-2-methyl-2H-indazol-7-yl)-2,1-benzothiazol-3-yl)-1-piperazinyl)-2-propen-1-one (Example 19-3)

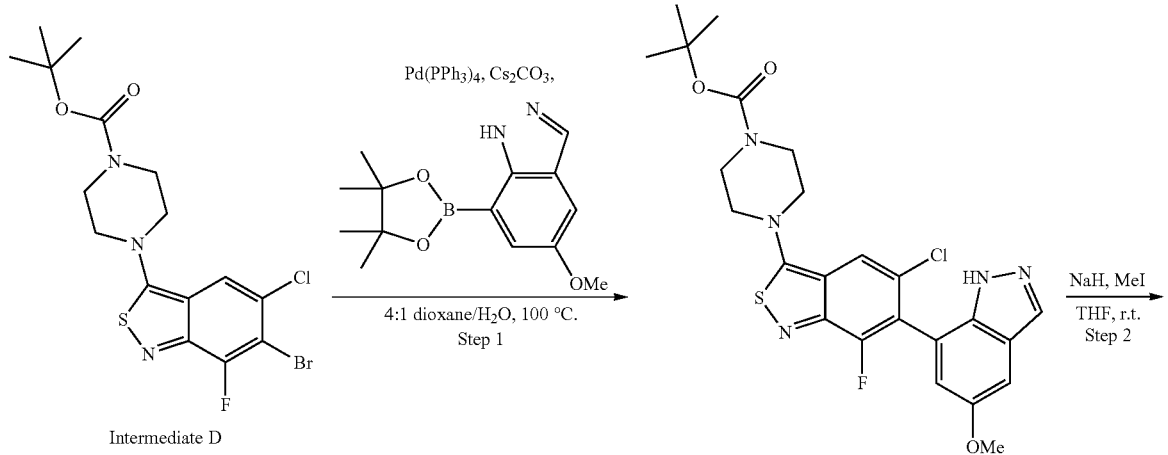

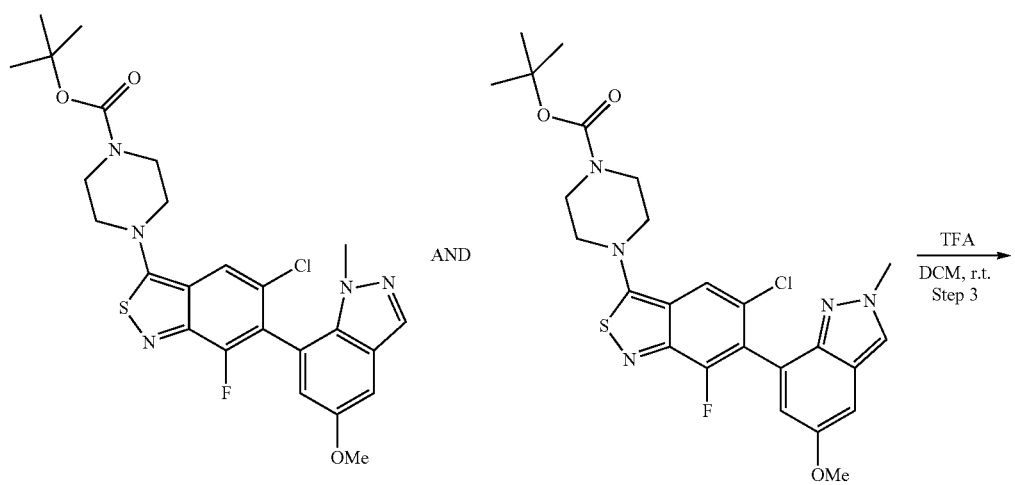

-continued
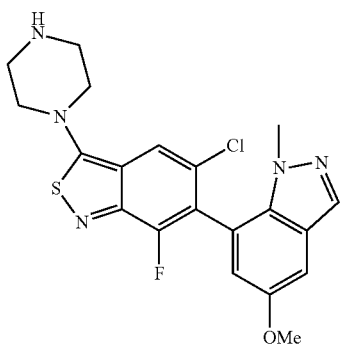
Intermediate J
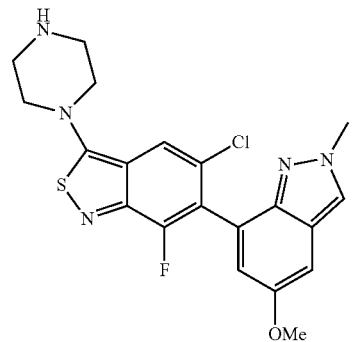
Intermediate K
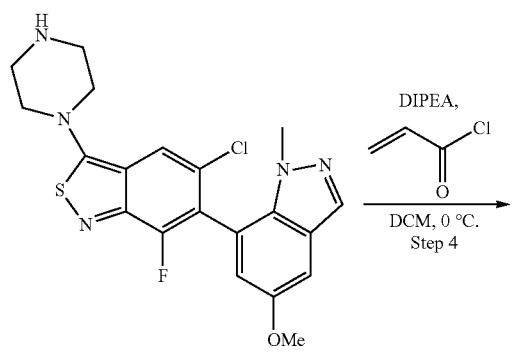
Intermediate J
DIPEA, 
acryloyl chloride
DCM, 0 °C.
Step 4
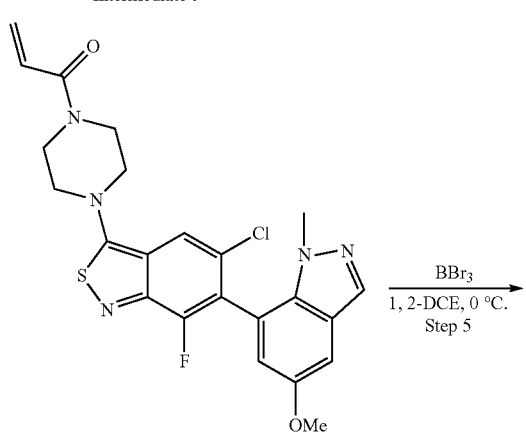
Example 19-1
BBr₃
1,2-DCE, 0 °C.
Step 5
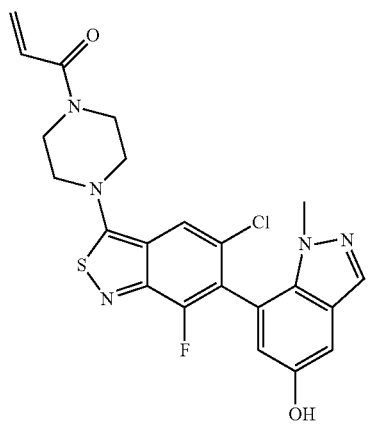
Example 19-2

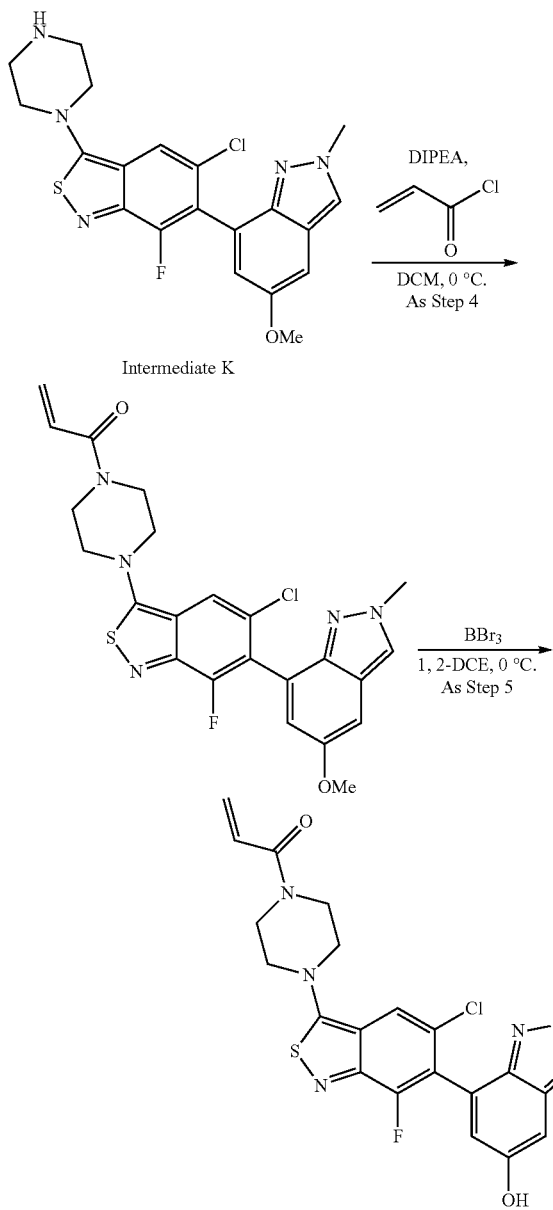

Example 19-3

Step 1: tert-butyl 4-(5-chloro-7-fluoro-6-(5-methoxy-1H-indazol-7-yl)benzo[c]isothiazol-3-yl)piperazine-1-carboxylate. A slurry of Intermediate D (232 mg, 0.51 mmol), 5-methoxy-7-(4,4,5,5-tetramethyl-1,3,2-dioxaborolan-2-yl)-1H-indazole (535 mg, 1.95 mmol, see synthesis below) and cesium carbonate (636 mg, 1.95 mmol) in a mixture of 1,4-dioxane (8 mL) and water (2 mL) was degassed with an Argon stream. Tetrakis(triphenylphosphine)palladium (59 mg, 0.05 mmol) was added and the mixture was again degassed with an Argon stream. The reaction mixture was sealed and heated at 100° C. for 18 h. The reaction was allowed to cool to rt and partitioned between brine (40 mL) and EtOAc. The aqueous later was twice extracted with EtOAc and the combined organic layers were dried over anhydrous sodium sulfate and concentrated. The residue was purified by silica gel chromatography (eluent: 0-4.5% DCM/MeOH) to provide tert-butyl 4-(5-chloro-7-fluoro-6-(5-methoxy-1H-indazol-7-yl)benzo[c]isothiazol-3-yl)piperazine-1-carboxylate. LCMS-ESI (POS.) m/z: 518.2 (M+H)$^+$. $^1$H NMR (400 MHz, DMSO-A) δ 12.90 (hr. s, 1H), 8.06 (s, 1H), 8.03 (s, 1H), 7.31 (d, J=1.4 Hz, 1H), 6.99 (d, J=2.2 Hz, 1H), 3.83 (s, 3H), 3.61-3.69 (m, 4H), 3.54-3.60 (m, 4H), 1.45 (s, 9H).

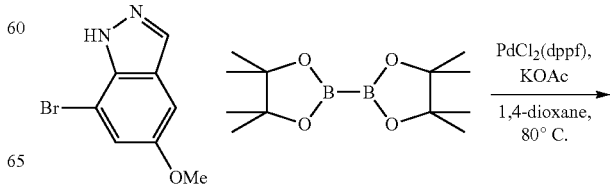

-continued

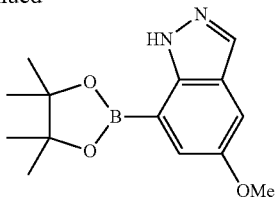

5-methoxy-7-(4,4,5,5-tetramethyl-1,3,2-dioxaborolan-2-yl)-1H-indazole. A suspension of 7-bromo-5-methoxy-1H-indazole (1.00 g, 4.40 mmol, Ark Pharm Inc. Arlington Heights, IL, USA), potassium acetate (1.30 g, 13.2 mmol) and bis(pinocolato)diboron (1.23 g, 4.84 mmol) in 1,4-dioxane (18 mL) was degassed with an Argon stream. Added [1,1'-bis(diphenylphosphino)ferrocene]dichloropalladium (ii) complex with dichloromethane (108 mg, 0.13 mmol) and again degassed with an Argon stream. The reaction mixture was sealed and heated at 80° C. for 2 d. The reaction was allowed to cool to rt and partitioned between water (50 mL) and EtOAc. The aqueous layer was twice extracted with EtOAc and the combined organic layers were dried over anhydrous sodium sulfate and concentrated. The residue was purified by silica gel chromatography (eluent: 2-65% EtOAc/heptane) to provide 5-methoxy-7-(4,4,5,5-tetramethyl-1,3,2-dioxaborolan-2-yl)-1H-indazole. LCMS-ESI (POS.) m/z: 275.1 (M+H)$^+$.

Step 2: tert-butyl 4-(5-chloro-7-fluoro-6-(5-methoxy-1-methyl-1H-indazol-7-yl)benzo[c]isothiazol-3-yl)piperazine-1-carboxylate and tert-butyl 4-(5-chloro-7-fluoro-6-(5-methoxy-2-methyl-2H-indazol-7-yl)benzo[c]isothiazol-3-yl)piperazine-1-carboxylate. To a solution of tert-butyl 4-(5-chloro-7-fluoro-6-(5-methoxy-1H-indazol-7-yl)benzo[c]isothiazol-3-yl)piperazine-1-carboxylate (115 mg, 0.22 mmol) in THF (5 mL) was added sodium hydride (60% dispersion in mineral oil, 44.5 mg, 1.1 mmol). After 10 min, iodomethane (69 μL, 1.1 mmol) was added and the reaction stirred at rt for an additional 15 min before being partitioned between saturated aqueous ammonium chloride (10 mL) and DCM. The aqueous layer was extracted twice with DCM and the combined organic layers were dried over anhydrous sodium sulfate and concentrated to afford a mixture of tert-butyl 4-(5-chloro-7-fluoro-6-(5-methoxy-1-methyl-1H-indazol-7-yl)benzo[c]isothiazol-3-yl)piperazine-1-carboxylate and tert-butyl 4-(5-chloro-7-fluoro-6-(5-methoxy-2-methyl-2H-indazol-7-yl)benzo[c]isothiazol-3-yl)piperazine-1-carboxylate. The crude mixture was used in the subsequent step without purification. LCMS-ESI (POS.) m/z: 532.0 (M+H)$^+$.

Step 3: 5-chloro-7-fluoro-6-(5-methoxy-1-methyl-1H-indazol-7-yl)-3-(piperazin-1-yl)benzo[c]isothiazole (Intermediate J) and 5-chloro-7-fluoro-6-(5-methoxy-2-methyl-2H-indazol-7-yl)-3-(piperazin-1-yl)benzo[c]isothiazole (Intermediate K). To a solution of the crude mixture of mixture of tert-butyl 4-(5-chloro-7-fluoro-6-(5-methoxy-1-methyl-1H-indazol-7-yl)benzo[c]isothiazol-3-yl)piperazine-1-carboxylate and tert-butyl 4-(5-chloro-7-fluoro-6-(5-methoxy-2-methyl-2H-indazol-7-yl)benzo[c]isothiazol-3-yl)piperazine-1-carboxylate (143 mg) in DCM (6 mL) was added trifluoroacetic acid (484 μL, 6.5 mmol) via syringe. The resulting solution was stirred at rt for 25 min and then was concentrated. The residue was purified by silica gel chromatography (eluent: 0-25% DCM/MeOH).

First-eluting peak: The mono-TFA salt of 5-chloro-7-fluoro-6-(5-methoxy-1-methyl-1H-indazol-7-yl)-3-(piperazin-1-yl)benzo[c]isothiazole (Intermediate J). LCMS-ESI (POS.) m/z: 432.0 (M+H)$^+$. $^1$H NMR (400 MHz, DMSO-d$^6$) δ 8.16 (s, 1H), 8.03 (s, 1H), 7.35 (d, J=2.4 Hz, 1H), 6.99 (d, J=2.4 Hz, 1H), 3.84 (s, 3H), 3.67-3.76 (m, 4H), 3.56 (s, 3H), 3.36-3.42 (m, 4H).

Second-eluting peak: The mono-TFA salt of 5-chloro-7-fluoro-6-(5-methoxy-2-methyl-2H-indazol-7-yl)-3-(piperazin-1-yl)benzo[c]isothiazole (Intermediate K). LCMS-ESI (POS.) m/z: 432.0 (M+H)$^+$.

Step 4: 1-(4-(5-chloro-7-fluoro-6-(5-methoxy-1-methyl-1H-indazol-7-yl)-2,1-benzothiazol-3-yl)-1-piperazinyl)-2-propen-1-one. To an ice-cooled slurry of the mono-TFA salt of Intermediate J (108 mg, 0.20 mmol) in DCM (5 mL) was added DIPEA (104 μL, 0.60 mmol) followed by acryloyl chloride (24 μL, 0.30 mmol) dropwise via syringe. The resulting solution was stirred at 0° C. for 3 h and was then quenched with saturated aqueous NaHCO$_3$ solution (15 mL) and extracted twice with DCM. The combined organic layers were dried over anhydrous sodium sulfate and concentrated. The residue was purified by silica gel chromatography (eluent: 0-7% DCM/MeOH) to provide 1-(4-(5-chloro-7-fluoro-6-(5-methoxy-1-methyl-1H-indazol-7-yl)-2,1-benzothiazol-3-yl)-1-piperazinyl)-2-propen-1-one. LCMS-ESI (POS.) m/z: 486.0 (M+H)$^+$. $^1$H NMR (400 MHz, DMSO-d$_6$) δ 8.13 (s, 1H), 8.02 (s, 1H), 7.33 (d, J=2.2 Hz, 1H), 6.99 (d, J=2.4 Hz, 1H), 6.85 (dd, J=16.6, 10.6 Hz, 1H), 6.18 (dd, J=16.7, 2.3 Hz, 1H), 5.76 (dd, J=10.5, 2.3 Hz, 1H), 3.85-3.95 (m, 4H), 3.84 (s, 3H), 3.62-3.72 (m, 4H), 3.56 (s, 3H).

Step 5: 1-(4-(5-chloro-7-fluoro-6-(5-hydroxy-1-methyl-1H-indazol-7-yl)-2,1-benzothiazol-3-yl)-1-piperazinyl)-2-propen-1-one. To an ice-cooled solution of 1-(4-(5-chloro-7-fluoro-6-(5-methoxy-1-methyl-1H-indazol-7-yl)benzo[c]isothiazol-3-yl)piperazin-1-yl)prop-2-en-1-one (72.5 mg, 0.15 mmol) in 1,2-dichloroethane (5 mL) was added boron tribromide solution (1.0 M in hexanes, 746 μL, 0.75 mmol) dropwise via syringe. The resulting slurry was stirred at 0° C. for 3.75 h and was then quenched with saturated aqueous NaHCO$_3$ solution (5 mL) and extracted twice with a 4:1 mixture of DCM/MeOH. The combined organic layers were dried over anhydrous sodium sulfate and concentrated. The residue was purified by silica gel chromatography (eluent: 0-6% DCM/MeOH) to provide 1-(4-(5-chloro-7-fluoro-6-(5-hydroxy-1-methyl-1H-indazol-7-yl)benzo[c]isothiazol-3-yl)piperazin-1-yl)prop-2-en-1-one. LCMS-ESI (POS.) m/z: 472.0 (M+H)$^+$. $^1$H NMR (400 MHz, DMSO-d$_6$) δ 9.40 (s, 1H), 8.12 (s, 1H), 7.92 (s, 1H), 7.12 (d, J=2.2 Hz, 1H), 6.81-6.91 (m, 2H), 6.18 (dd, J=16.7, 2.5 Hz, 1H), 5.76 (dd, J=10.4, 2.4 Hz, 1H), 3.81-3.94 (m, 4H), 3.62-3.70 (m, 4H), 3.52 (s, 3H).

For the synthesis of 1-(4-(5-chloro-7-fluoro-6-(5-hydroxy-2-methyl-2H-indazol-7-yl)-2,1-benzothiazol-3-yl)-1-piperazinyl)-2-propen-1-one.

Using Intermediate K from Step 3, Steps 4 and 5 were performed as above to deliver 1-(4-(5-chloro-7-fluoro-6-(5-hydroxy-2-methyl-2h-indazol-7-yl)-2,1-benzothiazol-3-yl)-1-piperazinyl)-2-propen-1-one. LCMS-ESI (POS.) m/z: 472.0 (M+H)$^+$. $^1$H NMR (400 MHz, DMSO-d$_6$) δ 9.28 (s, 1H), 8.11 (s, 1H), 8.01 (s, 1H), 6.95 (d, J=2.0 Hz, 1H), 6.77-6.90 (m, 2H), 6.18 (dd, J=16.7, 2.5 Hz, 1H), 5.76 (dd, J=10.4, 2.2 Hz, 1H), 4.03 (s, 3H), 3.80-3.94 (m, 4H), 3.58-3.66 (m, 4H).

Example 20

1-(4-(5-chloro-7-fluoro-6-(3-hydroxy-1-naphthalenyl)-2,1-benzothiazol-3-yl)-1-piperazinyl)-4-hydroxy-2-methylidene-1-butanone

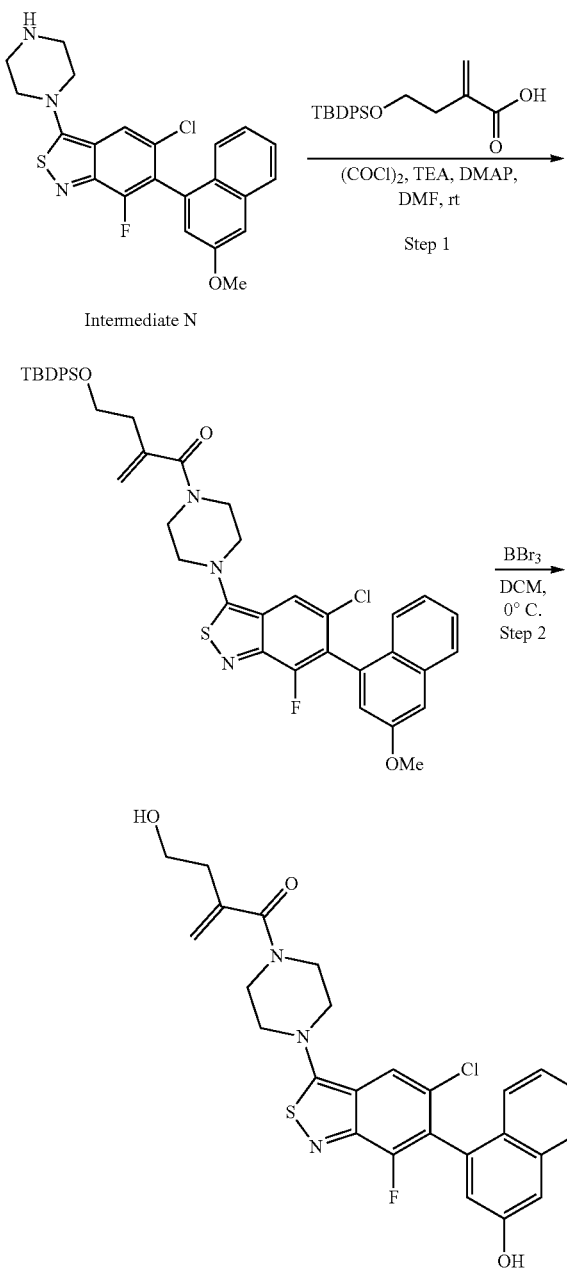

Step 1: 4-((tert-butyldiphenylsilyl)oxy)-1-(4-(5-chloro-7-fluoro-6-(3-methoxynaphthalen-1-yl)benzo[c]isothiazol-3-yl)piperazin-1-yl)-2-methylenebutan-1-one. To a solution of 4-((tert-butyldiphenylsilyl)oxy)-2-methylenebutanoic acid (101 mg, 0.29 mmol, prepared according to Pihko, P. M., *J. Org. Chem.*, 2006, 71, 2538-2541 and Greaney, M. F., *Org. Lett.*, 2007, 9, 1931-1934) in DCM (2 mL) was added a 2M solution of oxalyl chloride (0.21 mL, 0.43 mmol) at 0° C. followed by a catalytic amount of DMF (5 μL). The reaction mixture was allowed to warm to rt and stirred for 2 h. The reaction mixture was concentrated in vacuo then diluted with DCM (1 mL) and added to a solution of 5-chloro-7-fluoro-6-(3-methoxynaphthalen-1-yl)-3-(piperazin-1-yl)benzo[c]isothiazole (Intermediate N, 122 mg, 0.29 mmol), triethylamine (0.20 mL, 1.43 mmol), and DCM (2 mL). The reaction mixture was allowed to warm to rt and DMAP (2 mg, 0.016 mmol) was added. The reaction mixture was stirred at rt for 15 h then concentrated in vacuo and purified by silica gel column chromatography (eluent: 0-50% EtOAc:heptanes) to give 4-((tert-butyldiphenylsilyl)oxy)-1-(4-(5-chloro-7-fluoro-6-(3-methoxynaphthalen-1-yl)benzo[c]isothiazol-3-yl)piperazin-1-yl)-2-methylenebutan-1-one. $^1$H NMR (400 MHz, DMSO-$d_6$) δ 8.06 (s, 1H), 7.94 (d, J=8.0 Hz, 1H), 7.63-7.61 (m, 4H), 7.52-7.49 (m, 2H), 7.47-7.40 (m, 6H), 7.33-7.28 (m, 2H), 7.20-7.19 (m, 1H), 5.37 (s, 1H), 5.24 (s, 1H), 3.94 (s, 3H), 3.83-3.76 (m, 6H), 3.53 (br s, 2H), 3.31 (s, 4H), 1.01 (s, 9H). m/z (ESI) M+H: 764.

Step 2: 1-(4-(5-chloro-7-fluoro-6-(3-hydroxy-1-naphthalenyl)-2,1-benzothiazol-3-yl)-1-piperazinyl)-4-hydroxy-2-methylidene-1-butanone. To a solution of 4-((tert-butyldiphenylsilyl)oxy)-1-(4-(5-chloro-7-fluoro-6-(3-methoxynaphthalen-1-yl)benzo[c]isothiazol-3-yl)piperazin-1-yl)-2-methylenebutan-1-one (85 mg, 0.11 mmol) and DCM (2 mL) was added a 2M solution of BBr$_3$ (0.28 mL, 0.56 mmol) in DCM at 0° C. The reaction mixture was quenched with water, concentrated in vacuo and purified by silica gel column chromatography (elution with 0-50% heptane/3:1 EtOAc:EtOH) to afford 1-(4-(5-chloro-7-fluoro-6-(3-hydroxy-1-naphthalenyl)-2,1-benzothiazol-3-yl)-1-piperazinyl)-4-hydroxy-2-methylidene-1-butanone. $^1$H NMR (400 MHz, DMSO-d6) δ 9.93 (br s, 1H), 8.11 (s, 1H), 7.80 (d, J=12 Hz, 1H), 7.43 (m, 1H), 7.26-7.20 (m, 3H), 7.07 (s, 1H), 5.32 (s, 1H), 5.16 (s, 1H), 3.83 (br s, 4H), 3.63 (br s, 4H), 3.53 (t, J=8.0 Hz, 2H), 2.42 (t, J=8.0 Hz, 2H). $^{19}$FNMR (377 MHz, DMSO-$d_6$) δ−123.8 (s, 1F), m/z (ESI) M+H: 512.

Example 21

1-(4-(5-chloro-7-fluoro-6-(7-hydroxy-5-quinolinyl)-2,1-benzothiazol-3-yl)-1-piperazinyl)-2-propen-1-one

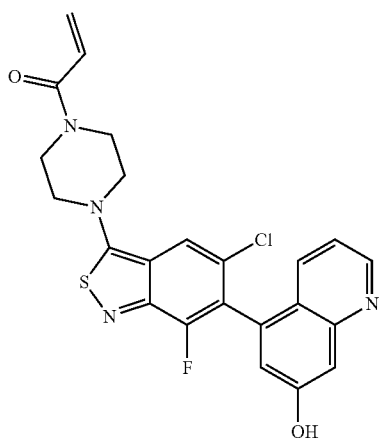 [SMILES: C=CC(=O)N1CCN(c2snc3c(F)c(-c4cc(O)cc5ncccc45)c(Cl)cc23)CC1]

1-(4-(5-chloro-7-fluoro-6-(7-hydroxy-5-quinolinyl)-2,1-benzothiazol-3-yl)-1-piperazinyl)-2-propen-1-one was made from Intermediate D by Method 1 using 7-methoxy-5-(4,4,5,5-tetramethyl-1,3,2-dioxaborolan-2-yl)quinoline (synthesis below) with the following changes: in Step 7, S-Phos Pd G3, aqueous potassium carbonate, and DME were used; in Step 8-1, TFA/DCM was used; in Step 8-2, DCE was used as solvent; and in Step 8-3, boron tribromide solution (1.0 M in DCE) was used to give 1-(4-(5-chloro-7-fluoro-6-(7-hydroxy-5-quinolinyl)-2,1-benzothiazol-3-yl)-1-piperazinyl)-2-propen-1-one. $^1$H NMR (400 MHz, CDCl$_3$) δ 8.81 (dd, J=4.2, 1.3 Hz, 1H) 7.72-7.78 (m, 2H) 7.64 (s, 1H) 7.28 (d, J=2.2 Hz, 1H) 7.16 (dd, J=8.4, 4.3 Hz, 1H) 6.56-6.66 (m, 1H) 6.40 (dd, J=16.8, 1.6 Hz, 1H) 5.78-5.87 (m, 1H) 4.01 (br. s., 2H) 3.89 (br. s., 2H) 3.50-3.60 (m, 4H). $^{19}$F NMR (376 MHz, CDCl$_3$) δ−121.33 (s, 1F). MS (ESI, +ve) m/z: 469.1 (M+1)+.

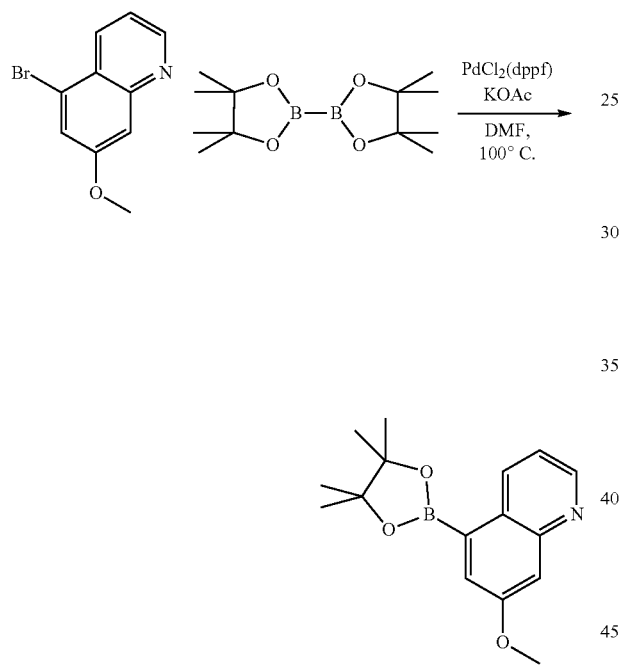

7-methoxy-5-(4,4,5,5-tetramethyl-1,3,2-dioxaborolan-2-yl)quinoline. A solution of 5-bromo-7-methoxyquinoline (0.407 g, 1.71 mmol, OxChem, Wood Dale, IL, USA), 4,4,4',4',5,5,5',5'-octamethyl-2,2'-bi(1,3,2-dioxaborolane) (0.912 g, 3.59 mmol), PdCl$_2$(dppf) (0.051 g, 0.070 mmol), and potassium acetate (0.503 g, 5.13 mmol) in DMF (9 mL) was stirred at 90° C. for 1 h then at 100° C. for 45 min. The reaction mixture was diluted with EtOAc (100 mL), and washed with saturated, aqueous sodium bicarbonate (2×75 mL). The organic layer was separated, dried over anhydrous Na$_2$SO$_4$, and concentrated in vacuo. The crude product was adsorbed onto silica and purified via column chromatography (silica gel, 0-80% heptane/EtOAc) to give 7-methoxy-5-(4,4,5,5-tetramethyl-1,3,2-dioxaborolan-2-yl)quinoline. MS (ESI, +ve) m/z: 286.1 (M+1)+.

Example 22

1-(5-chloro-7-fluoro-6-(3-hydroxy-1-naphthalenyl)-2,1-benzothiazol-3-yl)-4-(2-propenoyl-2-piperazinecarboxylic acid

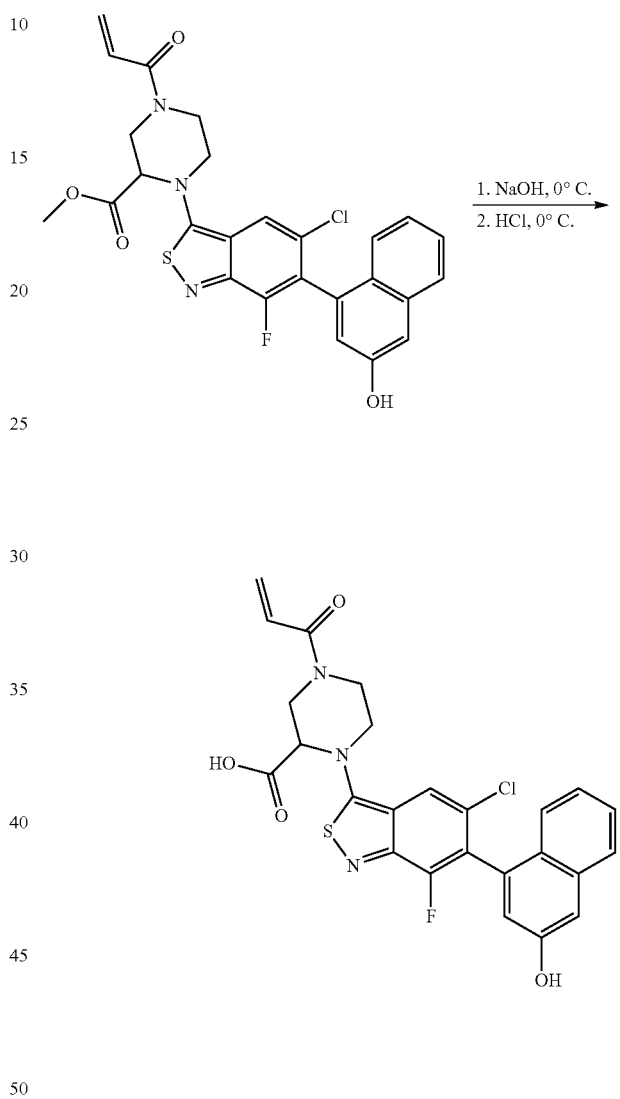

To a solution of methyl 4-acryloyl-1-(5-chloro-7-fluoro-6-(3-hydroxynaphthalen-1-yl)benzo[c]isothiazol-3-yl)piperazine-2-carboxylate (Example 7-3, 0.022 g, 0.042 mmol) in THF/EtOH (1:1; 6 mL) at 0° C. was added NaOH (5 N aq.; 1.0 mL, 5.0 mmol), and the resulting mixture was stirred at 0° C. for 5 min. The reaction was acidified with 5 N HCl at 0° C., extracted with EtOAc, and purified by HPLC to afford 1-(5-chloro-7-fluoro-6-(3-hydroxy-1-naphthalenyl)-2,1-benzothiazol-3-yl)-4-(2-propenoyl)-2-piperazinecarboxylic acid, m/z (ESI, +ve) 512.0 (M+H)$^+$. $^1$H NMR (400 MHz, DMSO-d$_6$) δ 3.14-3.28 (m, 1H) 3.52-3.87 (m, 3H) 4.15-5.03 (m, 2H) 5.15-5.23 (m, 1H) 5.77-5.83 (m, 1H) 6.13-6.24 (m, 1H) 6.86 (br. s., 1H) 7.06-7.12 (m, 1H) 7.20-7.30 (m, 3H) 7.38-7.49 (m, 1H) 7.76-7.84 (m, 1H) 8.07-8.13 (m, 1H) 9.98 (br. s., 1H) 13.42 (br. s., 1H).

Example 23

1-(4-(5-chloro-6-(5-cyclopropyl-1H-indazol-4-yl)-7-fluoro-2,1-benzothiazol-3-yl)-1-piperazinyl)-2-propen-1-one

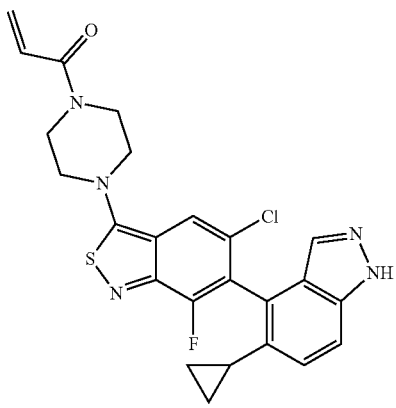 [SMILES: C=CC(=O)N1CCN(c2snc3c(F)c(-c4c(C5CC5)ccc5[nH]ncc45)c(Cl)cc23)CC1]

Example 23 was made as described in Method 1 using (5-cyclopropyl-1H-indazol-4-yl)boronic acid (see synthesis below) in Step 7, and omitting Step 8-3 . . . m/z (ESI, +ve) 482.0 (M+H)+. ¹H NMR (400 MHz, DMSO-d₆) δ 12.92-13.19 (1H, m), 8.02-8.21 (1H, m), 7.47-7.60 (2H, m), 7.02-7.09 (1H, m), 6.80-6.93 (1H, m), 6.15-6.25 (1H, m), 5.71-5.82 (1H, m), 3.80-3.96 (4H, m), 3.60-3.72 (4H, m), 1.55-1.74 (1H, m), 0.72-0.79 (2H, m), 0.58-0.71 (2H, m).

(5-cyclopropyl-1H-indazol-4-yl)boronic acid

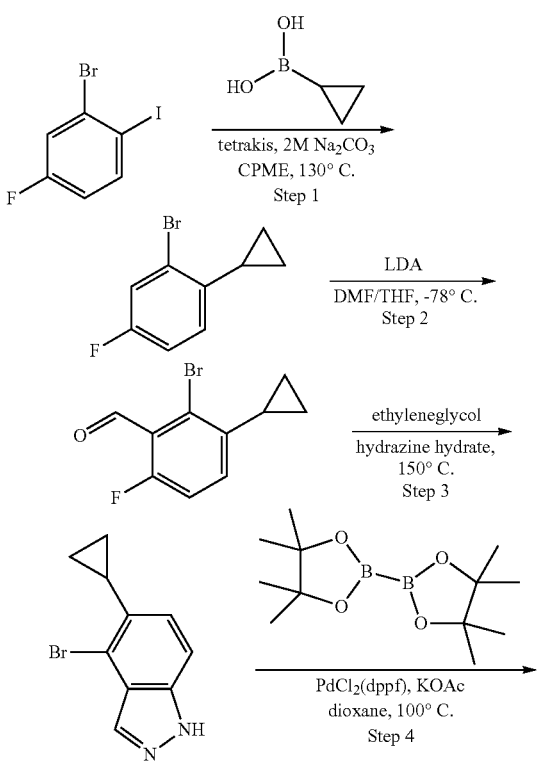

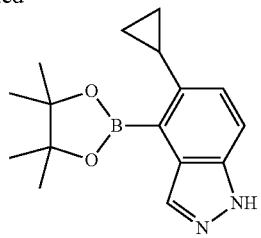

Step 1: 2-bromo-1-cyclopropyl-4-fluorobenzene. To a 2-L round bottom flask at ambient temperature was added 2-bromo-4-fluoro-1-iodobenzene (22 g, 73.1 mmol) and cyclopropylboronic acid (12.6 g, 146 mmol) in cyclopentyl methyl ether (1.1 L). Na₂CO₃ (2 M aq.; 183 mL) was added, and the reaction was degassed with N₂-gas for 20 minutes. Tetrakis (8.45 g, 7.31 mmol) was added, and the reaction was degassed again with N₂-gas for 20 minutes. The reaction mixture was then transferred to a 5-L autoclave under N₂-atm and heated to 130° C. for 40 h. The reaction mixture was cooled to ambient temperature, filtered through a Celite pad, and washed with diethyl ether (200 mL). To the filtrate was added water (500 mL), and the organic layer was separated. The aqueous layer was extracted with diethyl ether (2×300 mL), and the combined organic layers were dried over anhydrous sodium sulfate and evaporated under reduced pressure. The crude material was adsorbed onto a plug of silica gel and chromatographically purified (silica gel, 100% petroleum ether) to provide 2-bromo-1-cyclopropyl-4-fluorobenzene. GC-MS m/z: 214/216 ¹H NMR (400 MHz, CDCl₃) δ 7.36-7.23 (m, 1H), 6.95 (dt, J=7.0, 1.5 Hz, 2H), 2.09 (ddd, J=13.8, 8.5, 5.4 Hz, 1H), 1.12-0.88 (m, 2H), 0.76-0.50 (m, 2H).

Step 2: 2-bromo-3-cyclopropyl-6-fluorobenzaldehyde. To a 500-mL round-bottom flask was added 2-bromo-1-cyclopropyl-4-fluorobenzene (6.5 g, 30.2 mmol) in tetrahydrofuran (130 mL) under N₂-atm. LDA (18.1 mL, 36.3 mmol, 2 M in THF, 1.2 equiv) was added dropwise at −78° C. (internal temperature maintained between −65° C. to −70° C.), and the reaction mixture was stirred for 1 h. DMF (6 mL) was then added dropwise to the reaction mixture (internal temperature maintained between −65° C. to −70° C.), and the reaction was stirred for a further 3 h at −78° C. The reaction was quenched with saturated aqueous ammonium chloride solution (100 mL) and slowly warmed to ambient temperature. The mixture was diluted with diethyl ether (200 mL), and the organic layer separated and washed with a brine solution (2×50 mL). The combined organic layers were dried over anhydrous Na₂SO₄ and evaporated under reduced pressure. The crude material was adsorbed onto a plug of silica gel and chromatographically purified (silica gel, 0-2% EtOAc/hexane) to provide 2-bromo-3-cyclopropyl-6-fluorobenzaldehyde. GC-MS m/z: 242 ¹H NMR (400 MHz, CDCl₃) δ 10.43 (d, J=1.5 Hz, 1H), 7.26-7.12 (m, 1H), 7.06 (t, J=9.3 Hz, 1H), 2.15 (td, J=8.4, 4.3 Hz, 1H), 1.17-0.94 (m, 2H), 0.78-0.52 (m, 2H).

Step 3: 4-bromo-5-cyclopropyl-1H-indazole. To a 100-mL sealed tube was added 2-bromo-3-cyclopropyl-6-fluorobenzaldehyde (4 g, 16.5 mmol) and hydrazine hydrate (4.0 mL, 82 mmol) in ethylene glycol (40 mL). The reaction was stirred for 2 h at 90° C. and then heated to 150° C. for 16 h. The reaction mixture was cooled to ambient temperature, and ice cold water (40 mL) and EtOAc (50 mL) were added. The organic layer was separated and the aqueous layer was extracted with EtOAc (2×40 mL). The combined organic layers were washed with water (2×40 mL) and brine solution (40 mL), dried over anhydrous aqueous sodium sulfate, and concentrated in vacuo. The crude material was adsorbed onto a plug of silica gel and chromatographically purified (silica gel, 0-20% EtOAc/hexane) to provide 4-bromo-5-cyclopropyl-1H-indazole. The compound was purified by reverse phase preparative liquid chromatography (YMC: $C_{18}$, 150×20 mm, 5 μm; mobile phase: 0.1% TFA in water and acetonitrile; flow rate: 15 mL/min) to afford pure compound. MS (ESI positive ion) m/z: 237/239.0 (M+1). $^1$H NMR (400 MHz, DMSO-$d_6$) δ 13.31 (s, 1H), 7.97 (s, 1H), 7.46 (d, J=8.6 Hz, 1H), 6.97 (d, J=8.6 Hz, 1H), 2.21 (tt, J=8.5, 5.3 Hz, 1H), 1.24-0.87 (m, 2H), 0.93-0.33 (m, 2H).

Step 4: 5-cyclopropyl-1H-indazol-4-yl)boronic acid. To a 100-mL round-bottomed flask was added 4-bromo-5-cyclopropyl-1H-indazole (0.62 g, 2.6 mmol) and bis(pinacolato)diboron (0.996 g, 3.92 mmol) in 1,4-dioxane (25 mL); potassium acetate (0.77 g, 7.84 mmol) was added, and the reaction mixture was degassed with $N_2$-gas for 10 minutes. $PdCl_2$(dppf) DCM adduct (0.213 g, 0.261 mmol) was added to the reaction mixture; the reaction mixture was again degassed with $N_2$-gas for 10 minutes then heated to 100° C. for 16 h. The reaction mixture was cooled to ambient temperature, filtered through a Celite pad, and washed with EtOAc (50 mL). The filtrate was concentrated in vacuo, and the crude material was adsorbed onto a plug of silica gel and chromatographically purified (silica gel, 0-50% EtOAc/hexane). The compound was further purified by reverse phase preparative liquid chromatography (Grace column; 0-70% MeCN/water) to provide 5-cyclopropyl-1H-indazol-4-yl)boronic acid. MS (ESI positive ion) m/z: 285.2 (M+1). $^1$H NMR (400 MHz, DMSO-$d_6$) δ 12.88 (s, 1H), 8.13 (q, J=1.3 Hz, 1H), 7.50 (d, J=8.7 Hz, 1H), 6.83 (dd, J=8.8, 1.4 Hz, 1H), 2.78-2.60 (m, 1H), 1.38 (d, J=1.4 Hz, 12H), 1.07-0.85 (m, 2H), 0.75-0.48 (m, 2H).

Example 24

1-(4-(5-Chloro-7-fluoro-6-(3-(methylamino)-1-isoquinolinyl)-2,1-benzothiazol-3-yl)-1-piperazinyl)-2-propen-1-one

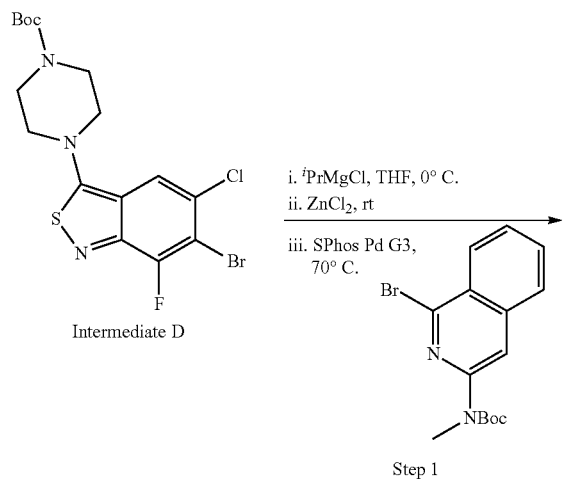

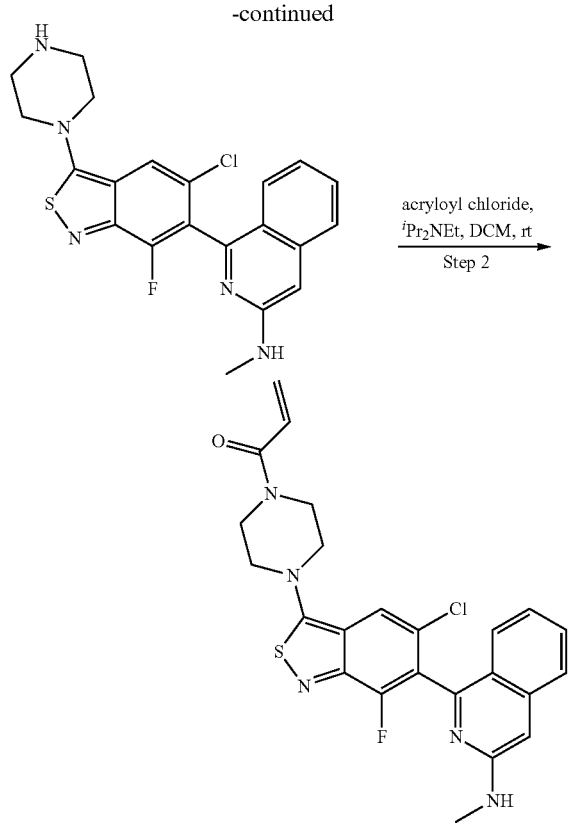

Step 1: 1-(5-Chloro-7-fluoro-3-(piperazin-1-yl)benzo[c]isothiazol-6-yl)-N-methylisoquinolin-3-amine. To a solution of tert-butyl 4-(6-bromo-5-chloro-7-fluorobenzo[c]isothiazol-3-yl)piperazine-1-carboxylate (Intermediate D, 30 mg, 0.067 mmol) in tetrahydrofuran (0.6 mL) at 0° C. was added a solution of isopropylmagnesium chloride (2.0 M solution in tetrahyrdofuran, 0.050 mL, 0.100 mmol). The mixture was stirred for 5 min before zinc chloride (1.9 M solution in 2-methyltetrahydrofuran, 0.053 mL, 0.100 mmol) was added, and the reaction mixture was warmed to rt and stirred for 40 min. The reaction mixture was then transferred to a vial containing Sphos Pd G3 (5.76 mg, 6.66 μmol) and tert-butyl (1-bromoisoquinolin-3-yl)(methyl)carbamate (24.7 mg, 0.073 mmol, see synthesis below) and heated to 70° C. overnight. The crude reaction was diluted with sat. aq. $NH_4Cl$ (50 mL) and EtOAc (50 mL). The organic layer was separated, dried over $Na_2SO_4$, filtered, and concentrated. Purification by silica gel column chromatography eluting with 6-20% MeOH in DCM afforded 1-(5-chloro-7-fluoro-3-(piperazin-1-yl)benzo[c]isothiazol-6-yl)-N-methylisoquinolin-3-amine, in z (ESI, +ve) 428.1 (M+H)$^+$.

Synthesis of tert-butyl (1-bromoisoquinolin-3-yl)(methyl)carbamate: To a solution of 1-bromoisoquinolin-3-amine (200 mg, 0.897 mmol, Maybridge Chemical Co., Altrincham, UK) in tetrahydrofuran (5 mL) at rt was added sodium bis(trimethylsilyl)amide (1M solution in tetrahydrofuran, 1.79 mL, 1.79 mmol). The mixture was stirred for 10 min before a solution of Boc-anhydride (0.208 mL, 0.897 mmol) in THF (1 mL) was added. The reaction mixture was stirred for 5 min before being diluted with sat. aq. $NH_4Cl$ (50 mL) and EtOAc (50 mL). The organic layer was separated, dried over $Na_2SO_4$, filtered, and concentrated. Purification by silica gel column chromatography eluting with 0-20%

EtOAc in heptane afforded tert-butyl (1-bromoisoquinolin-3-yl)carbamate. m/z (ESI, +ve) 345.0 (M+Na)⁺.

To a solution of tert-butyl (1-bromoisoquinolin-3-yl)carbamate (140 mg, 0.433 mmol) in tetrahydrofuran (3 mL) at rt was added sodium hydride (60% dispersion in mineral oil, 22.52 mg, 0.563 mmol). The mixture was stirred for 15 min before methyl iodide (0.033 mL, 0.520 mmol) was added. After stirring overnight the reaction was diluted with sat. aq. NH₄Cl (50 mL) and EtOAc (50 mL). The organic layer was separated, dried over Na₂SO₄, filtered, and concentrated. Purification by silica gel column chromatography eluting with 0-10% EtOAc in heptane afforded tert-butyl (1-bromoisoquinolin-3-yl)(methyl)carbamate. ¹H NMR (400 MHz, METHANOL-d₄) δ 8.25 (d, J=8.61 Hz, 1H), 7.88-7.95 (m, 2H), 7.79 (t, J=7.5 Hz, 1H), 7.70 (t, J=7.6 Hz, 1H), 3.42 (s, 3H), 1.54 (s, 9H). m/z (ESI, +ve) 359.1 (M+H)⁺.

Step 2: 1-(4-(5-Chloro-7-fluoro-6-(3-(methylamino)-1-isoquinolinyl)-2,1-benzothiazol-3-yl)-1-piperazinyl)-2-propen-1-one. Procedure analogous to Method 1, Step 8-2. Purified by silica gel column chromatography eluting with 0-14% MeOH in DCM over 15 min. ¹H NMR (400 MHz, METHANOL-d₄) δ 7.90 (s, 1H), 7.63 (d, J=8.5 Hz, 1H), 7.43 (t, J=7.4 Hz, 1H), 7.24 (d, J=8.5 Hz, 1H), 7.05 (t, J=7.4 Hz, 1H), 6.72-6.84 (m, 1H), 6.67 (s, 1H), 6.15-6.28 (m, 1H), 5.68-5.81 (m, 1H), 3.87-3.97 (m, 4H), 3.63 (m, 4H), 2.90 (s, 3H). m/z (ESI, +ve) 482.0 (M+H)⁺.

Example 25

1-(4-(6-(3-Amino-1-isoquinolinyl)-5-chloro-7-fluoro-2,1-benzothiazol-3-yl)-1-piperazinyl)-2-propen-1-one

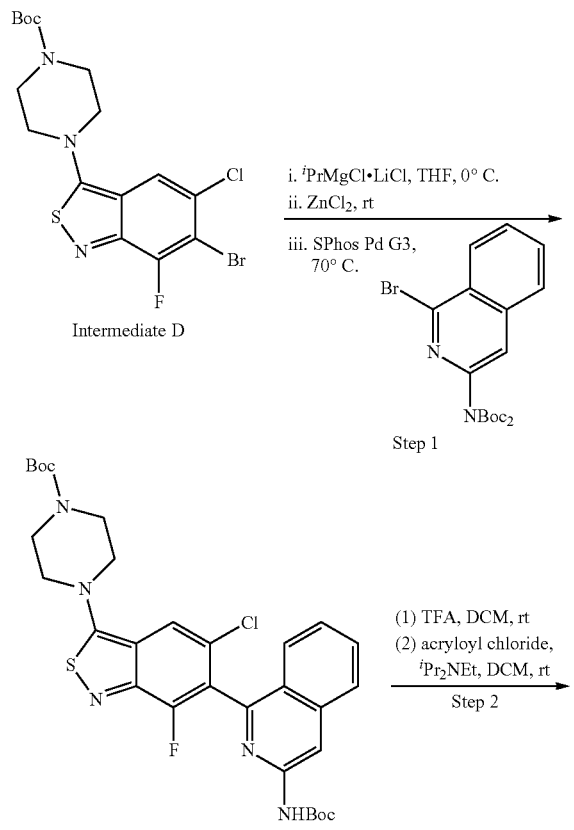

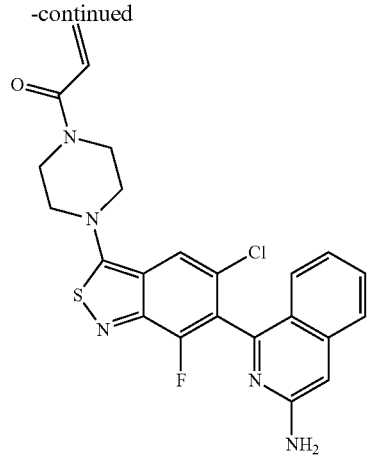

Step 1: tert-Butyl 4-(6-(3-((tert)-butoxycarbonyl)amino)isoquinolin-1-yl)-5-chloro-7-fluorobenzo[c]isothiazol-3-yl)piperazine-1-carboxylate. Procedure analogous to Example 25, Step 1, using a solution of 1.3 M isopropylmagnesium lithium chloride in THF in place of isopropylmagnesium chloride solution and bis(2-methyl-2-propanyl) (1-bromo-3-isoquinolinyl)-2-imidodicarbonate (synthesis below) in place of tert-butyl (1-bromoisoquinolin-3-yl)(methyl)carbamate. m/z (ESI, +ve) 614.2 (M+H)⁺.

Synthesis of bis(2-methyl-2-propanyl) (1-bromo-3-isoquinolinyl)-2-imidodicarbonate: To a solution of 1-bromoisoquinolin-3-amine (1.0 g, 4.48 mmol, Maybridge Chemical Co., Altrincham, UK) in DCM (50 mL) at 0° C. was added Boc-anhydride (3.12 mL, 13.45 mmol) and DMAP (0.055 g, 0.448 mmol). The reaction was warmed to rt and stirred overnight. The reaction mixture was then diluted with sat. aq. NH₄Cl (100 mL) and DCM (50 mL). The organic layer was separated, dried over Na₂SO₄, filtered, and concentrated. Purification by silica gel column chromatography eluting with 0-10% EtOAc in heptane over 15 min afforded bis(2-methyl-2-propanyl) (1-bromo-3-isoquinolinyl)-2-imidodicarbonate. ¹H NMR (400 MHz, METHANOL-d₄) δ 8.36 (d, J=8.5 Hz, 1H), 8.03 (d, J=8.1 Hz, 1H), 7.77-7.92 (m, 3H), 1.44 (s, 18H). m/z (ESI, +ve) 267.0 (M+H)⁺.

Step 2: 1-(4-(6-(3-Amino-1-isoquinolinyl)-5-chloro-7-fluoro-2,1-benzothiazol-3-yl)-1-piperazinyl)-2-propen-1-one. Procedure analogous to Method 1, Steps 8-1 and 8-2 with the use of TEA in DCM in place of 4M HCl in dioxane/MeOH in Step 8-1. Purified by silica gel column chromatography eluting with 0-12% MeOH in DCM. This material was then subjected to SFC purification: diol column (21.2×250 mm, 5 μm) using 17% (20 mM NH₃ in MeOH) in supercritical CO₂ (total flow rate was 7 g/min) to afford 1-(4-(6-(3-amino-1-isoquinolinyl)-5-chloro-7-fluoro-2,1-benzothiazol-3-yl)-1-piperazinyl)-2-propen-1-one. ¹H NMR (400 MHz, METHANOL-d₄) δ 7.85 (s, 1H), 7.53 (d, J=8.5 Hz, 1H), 7.39 (t, J=1F Hz, 1H), 7.23 (d, J=8.5 Hz, 1H), 7.03 (t, J=7.8 Hz, 1H), 6.82 (s, 1H), 6.71 (dd, J=10.8, 16.8 Hz, 1H), 6.2 (dd, J=1.5, 16.8 Hz, 1H), 5.70 (dd, J=1.5, 10.8 Hz, 1H), 3.82-3.93 (m, 4H), 3.50-3.66 (m, 4H). m/z (ESI, +ve) 468.0 (M+H)⁺.

Example 26

1-(4-(6-(2-Amino-4-quinolinyl)-5-chloro-7-fluoro-2,1-benzothiazol-3-yl)-1-piperazinyl)-2-propen-1-one

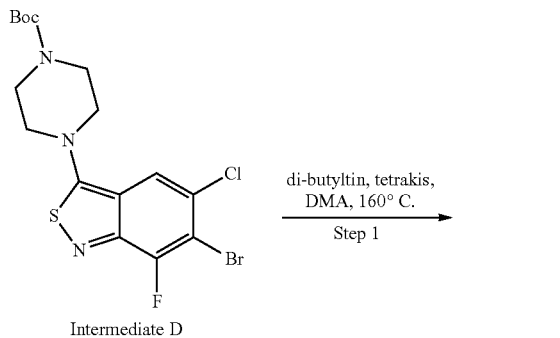

Intermediate D

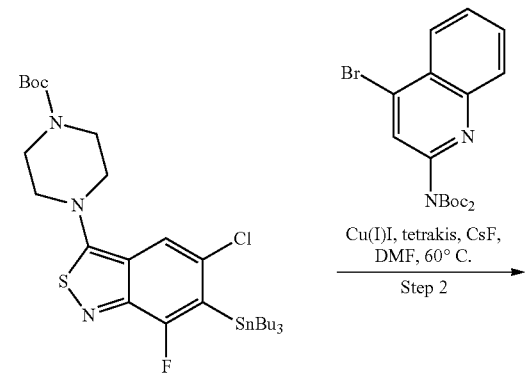

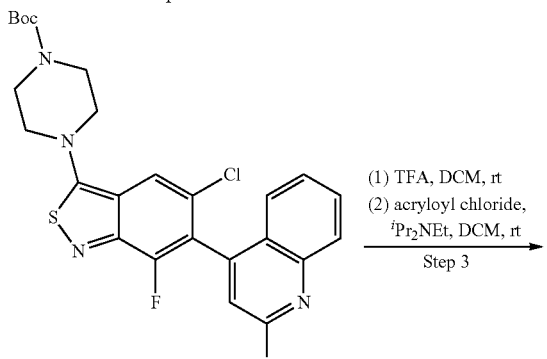

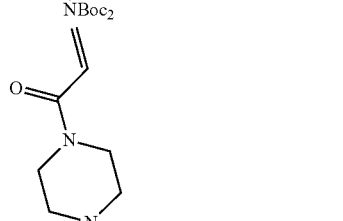

Step 1: tert-Butyl 4-(5-chloro-7-fluoro-6-(tributylstannyl)benzo[c]isothiazol-3-yl)piperazine-1-carboxylate. A solution of tert-butyl 4-(6-bromo-5-chloro-7-fluorobenzo[c]isothiazol-3-yl)piperazine-1-carboxylate (Intermediate D, 320 mg, 0.710 mmol), 1,1,1,2,2,2-hexabutyldistannane (824 mg, 1.420 mmol), and tetrakis(triphenylphosphine)palladium(0) (82 mg, 0.071 mmol, Strem Chemicals Inc., Newbury Port, MA, USA) in N,N-dimethylacetamide (5 mL) was heated in a sealed vial in the microwave at 160° C. for 40 min. The reaction mixture was diluted with sat. aq. NaHCO$_3$ (50 mL), brine (50 mL) and EtOAc (100 mL). The organic layer separated, dried over Na$_2$SO$_4$, filtered, and concentrated. Purification by silica gel column chromatography eluting with 0-30% EtOAc in heptane afforded tert-butyl 4-(5-chloro-7-fluoro-6-(tributylstannyl)benzo[c]isothiazol-3-yl)piperazine-1-carboxylate. m/z (ESI, +ve) 662.2 (M+H)$^+$.

Step 2: 2-Methyl-2-propanyl 4-(6-(2-(bis(((2-methyl-2-propanyl)oxy)carbonyl)amino)-4-quinolinyl)-5-chloro-7-fluoro-2,1-benzothiazol-3-yl)-1-piperazinecarboxylate. A solution of di-tert-butyl (4-bromoquinolin-2-yl)-2-imidodicarbonate (19.2 mg, 0.045 mmol, prepared in analogous fashion to bis(2-methyl-2-propanyl) (1-bromo-3-isoquinolinyl)-2-imidodicarbonate in Example 26 using 4-bromoquinolin-2-amine (Ark Pharm Inc. Arlington Heights, IL, USA) as starting material, tert-butyl 4-(5-chloro-7-fluoro-6-(tributylstannyl)benzo[c]isothiazol-3-yl)piperazine-1-carboxylate (20 mg, 0.030 mmol), tetrakis(triphenylphosphine)palladium(0) (6.99 mg, 6.05 µmol, Strem Chemicals Inc., Newbury Port, MA, USA), copper(I) iodide (1.153 mg, 6.05 µmol) and cesium fluoride (13.79 mg, 0.091 mmol) in DMF (0.5 mL) was heated in a sealed vial at 60° C. for 30 min. The crude reaction was diluted with sat. aq. NaHCO$_3$ (50 mL) and EtOAc (100 mL). The organic layer was separated, dried over Na$_2$SO$_4$, filtered, and concentrated. Purification by silica gel column chromatography eluting with 0-50% EtOAc in heptane afforded 2-methyl-2-propanyl 4-(6-(2-(bis(((2-methyl-2-propanyl)oxy)carbonyl)amino)-4-quinolinyl)-5-chloro-7-fluoro-2,1-benzothiazol-3-yl)-1-piperazinecarboxylate. m/z (ESI, +ve) 714.2 (M+H)$^+$.

Step 3: 1-(4-(6-(2-amino-4-quinolinyl)-5-chloro-7-fluoro-2,1-benzothiazol-3-yl)-1-piperazinyl)-2-propen-1-one. Procedure analogous to Method 1, Steps 8-1 and 8-2 with the use of TEA in DCM in place of 4 M HCl in dioxane/MeOH in Step 8-1. $^1$H NMR (400 MHz, METHANOL-d$_4$) δ 7.90 (s, 1H), 7.53 (d, J=8.2 Hz, 1H), 7.42-7.49 (m, 1H), 7.10 (d, J=8.0 Hz, 1H), 7.03-7.08 (m, J=7.6 Hz, 1H), 6.67-6.81 (m, 2H), 6.19 (dd, J=1.8, 16.6 Hz, 1H), 5.72 (dd, J=1.8, 10.6 Hz, 1H), 3.87-3.93 (m, 4H), 3.56-3.66 (m, 4H). m/z (ESI, +ve) 468.0 (M+H)$^+$.

Example 27

1-(4-(3-(2-Fluoro-6-hydroxyphenyl)-2-methyl-5-(2-(2-propanyl)phenyl)pyrido[2,3-d]pyridazin-8-yl)-1-piperazinyl)-2-propen-1-one

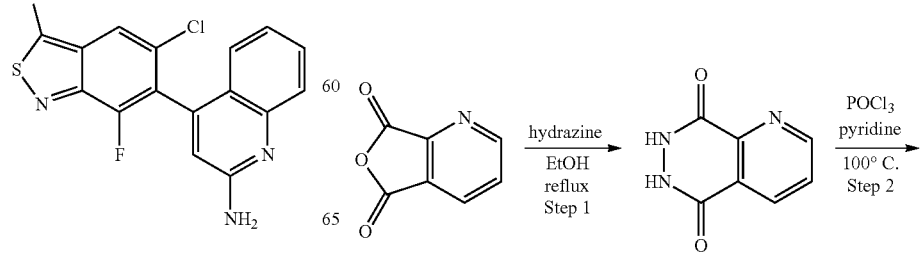

381
-continued
382
-continued
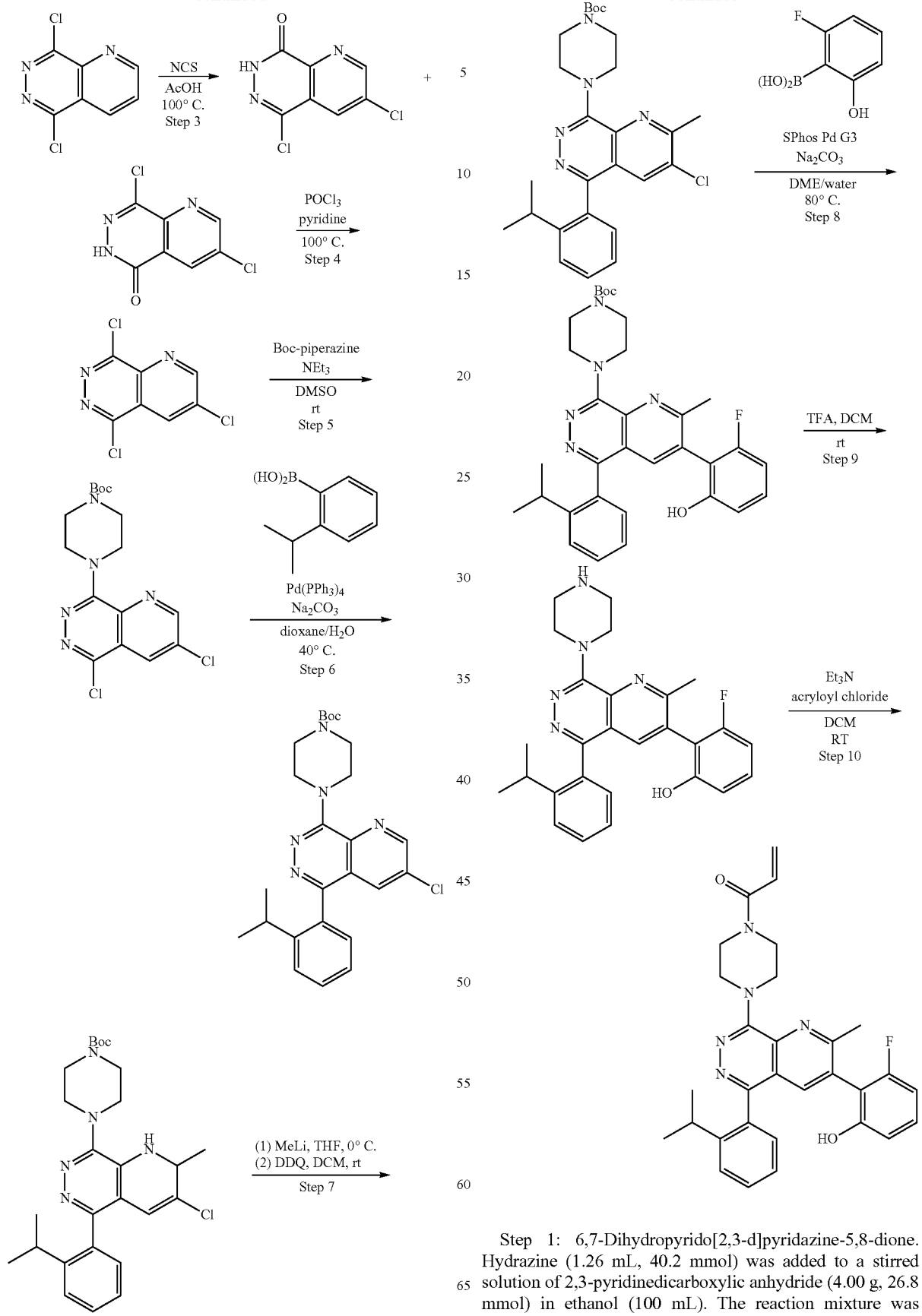
Step 1: 6,7-Dihydropyrido[2,3-d]pyridazine-5,8-dione. Hydrazine (1.26 mL, 40.2 mmol) was added to a stirred solution of 2,3-pyridinedicarboxylic anhydride (4.00 g, 26.8 mmol) in ethanol (100 mL). The reaction mixture was refluxed for 16 h before being cooled to rt and concentrated in vacuo to give crude 6,7-dihydropyrido[2,3-d]pyridazine-5,8-dione that was used directly in the next step, m/z (ESI) M+H: 164.1.

Step 2: 5,8-Dichloropyrido[2,3-d]pyridazine. Pyridine (4.57 mL, 53.7 mmol) was added to a mixture of crude 6,7-dihydropyrido[2,3-d]pyridazine-5,8-dione (4.38 g, 26.8 mmol) in phosphorus(v) oxychloride (20.1 mL, 215 mmol). The reaction mixture was stirred at 100° C. for 2 h. The reaction mixture was cooled and poured slowly into rapidly stirred water (250 mL) at 10° C. The aqueous suspension was stirred for 15 min before being extracted with EtOAc (250 mL). The organic layer was separated, washed with brine (200 mL), dried over MgSO$_4$, filtered, and concentrated in vacuo. Chromatographic purification of the residue (silica gel, 0 to 100% EtOAc in heptane) gave 5,8-dichloropyrido[2,3-d]pyridazine. $^1$H NMR (400 MHz, CHLOROFORM-d) δ 9.41 (1H, dd, J=4.30, 1.56 Hz) 8.65 (1H, dd, J=8.41, 1.56 Hz) 8.02 (1H, dd, J=8.41, 4.30 Hz), m/z (ESI) M+H: 200.0.

Step 3: 3,5-Dichloropyrido[2,3-d]pyridazin-8(7H)-one and 3,8-dichloropyrido[2,3-d]pyridazin-5(6H)-one. A-Chlorosuccinimide (1268 mg, 9.50 mmol, TCI America, Portland, OR, USA) was added to a stirred solution of 5,8-dichloropyrido[2,3-d]pyridazine (950 mg, 4.75 mmol) in acetic acid (20 mL) and the reaction mixture was heated to 100° C. for 16 h. Additional A-chlorosuccinimide (1268 mg, 9.50 mmol, TCI America, Portland, OR, USA) was added, and the reaction mixture was stirred at 100° C. for another 4 h. Additional/V-chlorosuccinimide (634 mg, 4.75 mmol, TCI America, Portland, OR, USA) was added, and the reaction mixture was stirred for another 4 h. The reaction mixture was then diluted with water (75 mL) and extracted three times with EtOAc (100 mL). The combined organic layers were washed with brine (150 mL), dried over MgSO$_4$, filtered, and concentrated in vacuo. Chromatographic purification of the residue (silica gel, 0 to 75% EtOAc in heptane) gave a regioisomeric mixture of 3,5-dichloropyrido[2,3-d]pyridazin-8(7H)-one compound and 3,8-dichloropyrido[2,3-d]pyridazin-5(6H)-one. m/z (ESI) M+H: 215.9.

Step 4: 3,5,8-Trichloropyrido[2,3-d]pyridazine. Pyridine (2.024 mL, 23.79 mmol) was added to the regioisomeric mixture of 3,5-dichloropyrido[2,3-d]pyridazin-8(7H)-one and 3,8-dichloropyrido[2,3-d]pyridazin-5(6H)-one (2.57 g, 11.90 mmol) in phosphorus oxychloride (8.90 mL, 95 mmol). The reaction mixture was stirred at 100° C. for 1.5 h. The reaction mixture was cooled and poured slowly into rapidly stirred water (150 mL) at 10° C. The aqueous suspension was stirred for 15 min before being extracted with EtOAc (200 mL). The organic layer was separated, washed with brine (150 mL), dried over MgSO$_4$, filtered, and concentrated in vacuo. Chromatographic purification of the residue (silica gel, 0 to 50% EtOAc in heptane) gave 3,5,8-trichloropyrido[2,3-d]pyridazine. $^1$H NMR (400 MHz, CHLOROFORM-d) δ 9.27 (1H, d, J=2.35 Hz) 8.58 (1H, d, J=2.35 Hz), m/z (ESI) M+H: 233.9.

Step 5: tert-Butyl 4-(3,5-dichloropyrido[2,3-d]pyridazin-8-yl)piperazine-1-carboxylate. 1-Boc-piperazine (278 mg, 1.494 mmol) was added to a stirred mixture of 3,5,8-trichloropyrido[2,3-d]pyridazine (292 mg, 1.245 mmol) and triethylamine (0.350 mL, 2.491 mmol) in dimethyl sulfoxide (5 mL). The reaction mixture was stirred at rt for 3 h before being diluted with EtOAc (75 mL), and washed with saturated aqueous sodium bicarbonate (75 mL). The organic layer was separated, washed with brine (50 mL), dried over MgSO$_4$, filtered, and concentrated in vacuo. Chromatographic purification of the residue (silica gel, 0 to 25% acetone in heptane) gave tert-butyl 4-(3,5-dichloropyrido[2,3-d]pyridazin-8-yl)piperazine-1-carboxylate, the first of two regioisomers to elute. $^1$H NMR (400 MHz, CHLOROFORM-d) δ 9.01 (1H, d, J=2.54 Hz) 8.43 (1H, d, J=2.54 Hz) 4.04-4.15 (4H, m) 3.64-3.70 (4H, m) 1.50 (9H, s). m/z (ESI) M+H: 384.0.

Step 6: tert-Butyl 4-(3-chloro-5-(2-isopropylphenyl)pyrido[2,3-d]pyridazin-8-yl)piperazine-1-carboxylate. tert-Butyl 4-(3,5-dichloropyrido[2,3-d]pyridazin-8-yl)piperazine-1-carboxylate (199 mg, 0.518 mmol), 2-isopropylphenylboronic acid (93 mg, 0.570 mmol, Alfa Aesar, Haver Hill, MA, USA), tetrakis(triphenylphosphine) palladium (59.8 mg, 0.052 mmol, Strem Chemicals Inc., Newbury Port, MA, USA), and sodium carbonate (2 M aqueous, 1.036 mL, 2.072 mmol) were mixed in 1,4-dioxane (4 mL) under an argon atmosphere. The reaction mixture was stirred at 40° C. for 16 h. The reaction mixture was cooled to rt, diluted with EtOAc (50 mL), and washed with water (40 mL). The organic layer was separated, washed with brine (50 mL), dried over MgSO$_4$, filtered, and concentrated in vacuo. Chromatographic purification of the residue (silica gel, 0 to 50% EtOAc in heptane) gave a mixture of starting material and desired product. The mixture was re-subjected to the original reaction conditions using less 2-isopropylphenylboronic acid (56 mg, 0.342 mmol, Alfa Aesar, Haver Hill, MA, USA). The mixture was stirred at 40° C. for 16 h. Additional 2-isopropylphenylboronic acid (28 mg, 0.171 mmol, Alfa Aesar, Haver Hill, MA, USA) was added, and the reaction mixture was stirred for another 6 h. The reaction mixture was cooled to rt, diluted with EtOAc (50 mL), and washed with water (40 mL). The organic layer was separated, washed with brine (50 mL), dried over MgSO$_4$, filtered, and concentrated in vacuo. Chromatographic purification of the residue (silica gel, 0 to 50% EtOAc in heptane) gave tert-butyl 4-(3-chloro-5-(2-isopropylphenyl)pyrido[2,3-d]pyridazin-8-yl)piperazine-1-carboxylate. $^1$H NMR (400 MHz, CHLOROFORM-d) δ 8.95 (1H, d, J=2.35 Hz) 7.72 (1H, d, J=2.54 Hz) 7.45-7.53 (2H, m) 7.26-7.33 (1H, m) 7.16-7.21 (1H, m) 4.04-4.23 (4H, m) 3.66-3.73 (4H, m) 2.67 (1H, spt, J=6.75 Hz) 1.48 (9H, s) 1.16 (3H, d, J=6.85 Hz) 1.03 (3H, d, J=6.85 Hz), m/z (ESI) M+H: 468.2.

Step 7: tert-Butyl 4-(3-chloro-5-(2-isopropylphenyl)-2-methylpyrido[2,3-d]pyridazin-8-yl)piperazine-1-carboxylate. Methyllithium (1.6 M solution in diethyl ether, 0.137 mL, 0.219 mmol) was added to a stirred solution of tert-butyl 4-(3-chloro-5-(2-isopropylphenyl)pyrido[2,3-d]pyridazin-8-yl)piperazine-1-carboxylate (93 mg, 0.199 mmol) in tetrahydrofuran (1 mL) at −78° C. The reaction mixture was stirred at −78° C. for 5 min before being allowed to warm to 0° C. and stirred for 30 min. The reaction mixture was cooled back down to −78° C. and additional methyllithium (1.6 M solution in diethyl ether, 0.068 mL, 0.109 mmol) was added. The reaction mixture was stirred at −78° C. for 5 min before being allowed to warm to 0° C. and stirred for another 15 min. The reaction mixture was quenched with water (20 mL) and extracted with EtOAc (30 mL). The organic layer was separated, washed with brine (20 mL), dried over MgSO$_4$, filtered, and concentrated in vacuo to give crude tert-butyl 4-(3-chloro-5-(2-isopropylphenyl)-2-methyl-1,2-dihydropyrido[2,3-d]pyridazin-8-yl)piperazine-1-carboxylate, m/z (ESI) M+H: 484.3.

4,5-Dichloro-3,6-dioxo-1,4-cyclohexadiene-1,2-dicarbonitrile (45.0 mg, 0.198 mmol) was added to a stirred mixture of crude tert-butyl 4-(3-chloro-5-(2-isopropylphenyl)-2-methyl-1,2-dihydropyrido[2,3-d]pyridazin-8-yl)piperazine-1-carboxylate (96 mg, 0.198 mmol) in dichloromethane (2 mL). The reaction mixture was stirred at rt for 10 min. The reaction mixture was diluted with DCM (30 mL) and washed with water (20 mL). The organic layer was separated, dried over MgSO$_4$, filtered, and concentrated in vacuo. Chromatographic purification of the residue (silica gel, 0 to 50% EtOAc in heptane) gave tert-butyl 4-(3-chloro-5-(2-isopropylphenyl)-2-methylpyrido[2,3-d]pyridazin-8-yl)piperazine-1-carboxylate. $^1$H NMR (400 MHz, CHLOROFORM-tit) δ 7.72 (1H, s) 7.51-7.55 (2H, m) 7.32-7.37 (1H, m) 7.22-7.27 (1H, m) 4.08-4.25 (4H, m) 3.71-3.79 (4H, m) 2.87 (3H, s) 2.73 (1H, spt, J=6.68 Hz) 1.54 (9H, s) 1.21 (3H, d, J=6.85 Hz) 1.07 (3H, d, J=6.85 Hz), m/z (ESI) M+H: 482.1.

Step 8: tert-Butyl 4-(3-(2-fluoro-6-hydroxyphenyl)-5-(2-isopropylphenyl)-2-methylpyrido[2,3-d]pyridazin-8-yl)piperazine-1-carboxylate. tert-Butyl 4-(3-chloro-5-(2-isopropylphenyl)-2-methylpyrido[2,3-d]pyridazin-8-yl)piperazine-1-carboxylate (78 mg, 0.162 mmol), (2-fluoro-6-hydroxyphenyl)boronic acid (101 mg, 0.647 mmol, Combi-Blocks), Sphos Pd G3 (14.00 mg, 0.016 mmol) and sodium carbonate (2 M aqueous, 0.324 mL, 0.647 mmol) were mixed in 1,2-dimethoxy ethane (1 mL) under an argon atmosphere and then heated at 80° C. for 2.5 h. The reaction mixture was cooled, diluted with EtOAc (30 mL), and washed with water (25 mL). The organic layer was separated, washed with brine (25 mL), dried over MgSO$_4$, filtered, and concentrated in vacuo. Chromatographic purification of the residue (silica gel, 0 to 50% EtOAc in heptane) gave tert-butyl 4-(3-(2-fluoro-6-hydroxyphenyl)-5-(2-isopropylphenyl)-2-methylpyrido[2,3-d]pyridazin-8-yl)piperazine-1-carboxylate (66 mg, 0.118 mmol, 73.1% yield), m/z (ESI) M+H: 558.2.

Step 9: 3-Fluoro-2-(5-(2-isopropylphenyl)-2-methyl-8-(piperazin-1-yl)pyrido[2,3-d]pyridazin-3-yl)phenol. Trifluoroacetic acid (0.2 mL, 2.68 mmol) was added to a stirred solution of tert-butyl 4-(3-(2-fluoro-6-hydroxyphenyl)-5-(2-isopropylphenyl)-2-methylpyrido[2,3-d]pyridazin-8-yl)piperazine-1-carboxylate (64 mg, 0.115 mmol) in dichloromethane (0.5 mL). The reaction mixture was stirred at rt for 30 min. The reaction mixture was diluted with DCM (30 mL) and quenched with saturated aqueous sodium bicarbonate (20 mL). The organic layer was separated, dried over MgSO$_4$, filtered, and concentrated in vacuo to give crude 3-fluoro-2-(5-(2-isopropylphenyl)-2-methyl-8-(piperazin-1-yl)pyrido[2,3-d]pyridazin-3-yl)phenol. m/z (ESI) M+H: 458.1.

Step 10: 1-(4-(3-(2-Fluoro-6-hydroxyphenyl)-5-(2-isopropylphenyl)-2-methylpyrido[2,3-d]pyridazin-8-yl)piperazin-1-yl)prop-2-en-1-one. Acryloyl chloride (9.45 μl, 0.116 mmol) was added to a stirred mixture of 3-fluoro-2-(5-(2-isopropylphenyl)-2-methyl-8-(piperazin-1-yl)pyrido[2,3-d]pyridazin-3-yl)phenol (53 mg, 0.116 mmol) and triethylamine (0.049 mL, 0.348 mmol) in dichloromethane (1 mL) at 0° C. The reaction mixture was stirred at 0° C. for 10 min. The reaction mixture was diluted with DCM (25 mL) and quenched with saturated aqueous sodium bicarbonate (20 mL). The organic layer was separated, dried over MgSO$_4$, filtered, and concentrated in vacuo. Chromatographic purification of the residue (silica gel, 0 to 100% EtOAc in heptane) gave 1-(4-(3-(2-fluoro-6-hydroxyphenyl)-2-methyl-5-(2-(2-propanyl)phenyl)pyrido[2,3-d]pyridazin-8-yl)-1-piperazinyl)-2-propen-1-one. $^1$H NMR (400 MHz, CHLOROFORM-d) δ 9.51 (0.6H, br s) 8.98 (0.4H, br s) 7.63 (0.4H, s) 7.58 (0.6H, s) 7.35-7.43 (2H, m) 7.10-7.26 (3H, m) 6.78 (1H, dd, J=16.63, 8.22 Hz) 6.59-6.71 (2H, m) 6.36 (1H, dd, J=16.82, 1.57 Hz) 5.78 (1H, dd, J=10.56, 1.37 Hz) 4.10-4.38 (4H, m) 3.80-4.03 (4H, m) 2.60-2.72 (1H, m) 2.61 (1.2H, s) 2.59 (1.8H, s) 0.91-1.08 (6H, m). m/z (ESI) M+H: 512.3.

Example 28

1-(4-(7-Chloro-6-(2-fluoro-6-hydroxyphenyl)-4-((1R)-1-phenylethyl)-1-phthalazinyl)-1-piperazinyl)-2-propen-1-one and 1-(4-(7-chloro-6-(2-fluoro-6-hydroxyphenyl)-4-((1S)-1-phenylethyl)-1-phthalazinyl)-1-piperazinyl)-2-propen-1-one

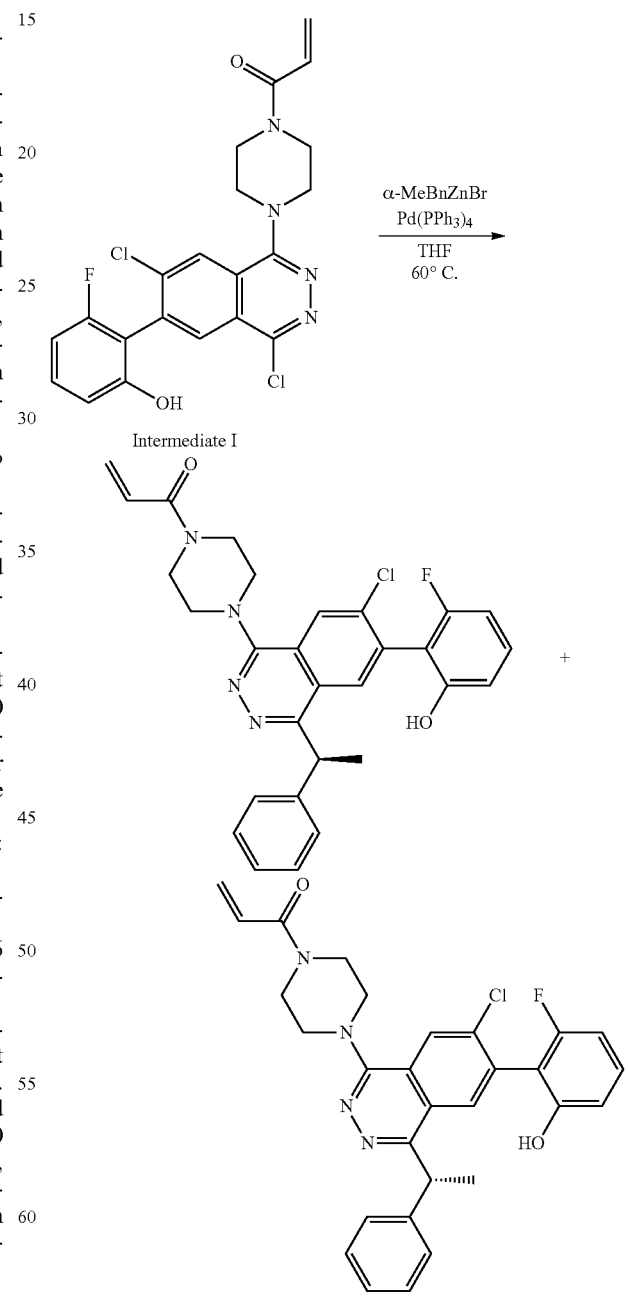

A mixture of α-methylbenzylzinc bromide (0.5 M in THF, 492 μl, 0.246 mmol), tetrakis(triphenylphosphine)palladium (5.68 mg, 4.92 μmol, Strem Chemicals Inc., NewburyPort, MA, USA), and 1-(4-(4,7-dichloro-6-(2-fluoro-6-hydroxyphenyl)phthalazin-1-yl)piperazin-1-yl)prop-2-en-1-one (Intermediate I, 22 mg, 0.049 mmol) was stirred at 60° C. in a sealed vial for 16 h. The reaction mixture was concentrated and chromatographic purification of the residue (silica gel, 0 to 100% EtOAc in heptane) gave a mixture of 1-(4-(7-chloro-6-(2-fluoro-6-hydroxyphenyl)-4-((1R)-1-phenylethyl)-1-phthalazinyl)-1-piperazinyl)-2-propen-1-one and 1-(4-(7-chloro-6-(2-fluoro-6-hydroxyphenyl)-4-((1S)-1-phenylethyl)-1-phthalazinyl)-1-piperazinyl)-2-propen-1-one. $^1$H NMR (400 MHz, METHANOL-$d_4$) δ 8.27 (1H, s) 8.15 (0.33H, s) 8.10 (0.67H, s) 7.19-7.31 (5H, m) 7.10-7.16 (1H, m) 6.86 (1H, dd, J=16.73, 10.66 Hz) 6.62-6.78 (2H, m) 6.27 (1H, dd, J=16.82, 1.96 Hz) 5.80 (1H, dd, J=10.66, 1.86 Hz) 4.94-5.01 (1H, m) 3.93-4.03 (4H, m) 3.49-3.60 (4H, m) 1.81 (3H, d, J=7.04 Hz), m/z (ESI) M+H: 517.1.

Example 29

1-(4-(7-Chloro-4-(4-fluorobenzyl)-6-(2-fluoro-6-hydroxyphenyl)-1-phthalazinyl)-1-piperazinyl)-2-propen-1-one

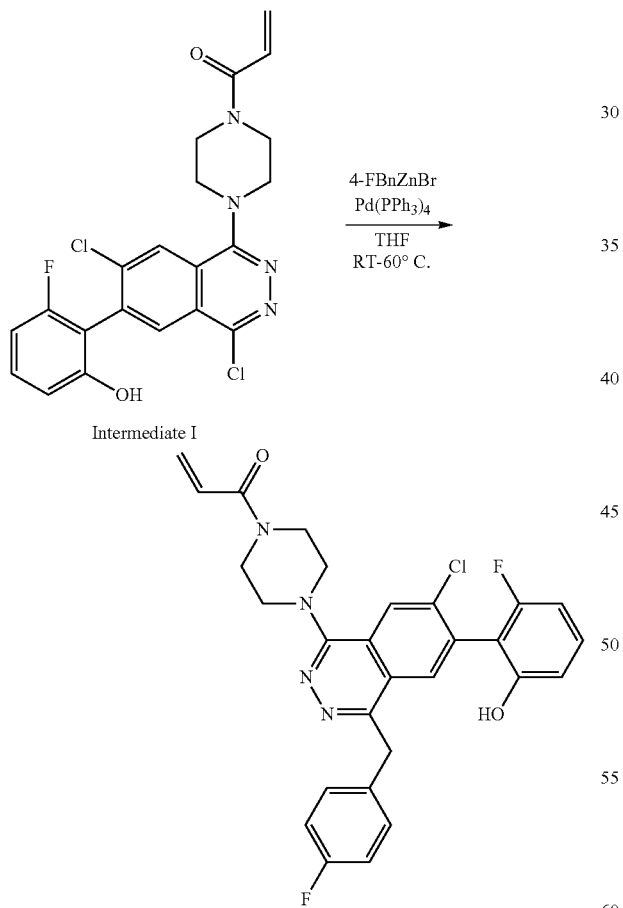

4-Fluorobenzylzinc chloride (0.5 M in THF, 0.089 mL, 0.044 mmol) was added to a stirred mixture of 1-(4-(4,7-dichloro-6-(2-fluoro-6-hydroxyphenyl)phthalazin-1-yl)piperazin-1-yl)prop-2-en-1-one (Intermediate I, 18 mg, 0.040 mmol) and tetrakis(triphenylphosphine)palladium (4.65 mg, 4.02 µmol, Strem Chemicals Inc., NewburyPort, MA, USA) in tetrahydrofuran (0.1 mL) in a sealed vial under an argon atmosphere. The reaction mixture was stirred at rt for 2 h before being heated to 40° C. for 3 h. Additional 4-fluorobenzylzinc chloride (0.089 mL, 0.044 mmol) was added, and the reaction mixture was stirred at 40° C. for another 16 h. Additional 4-fluorobenzylzinc chloride (0.089 mL, 0.044 mmol) was added, and the reaction mixture was heated to 60° C. and stirred for 6 h. The reaction mixture was concentrated in vacuo. Chromatographic purification of the residue (silica gel, 0 to 100% EtOAc in heptane) gave 1-(4-(7-chloro-4-(4-fluorobenzyl)-6-(2-fluoro-6-hydroxyphenyl)-1-phthalazinyl)-1-piperazinyl)-2-propen-1-one. $^1$H NMR (400 MHz, METHANOL-$d_4$) δ 8.32 (1H, s) 8.19 (1H, s) 7.26-7.34 (3H, m) 6.98 (2H, t, J=8.71 Hz) 6.69-6.91 (3H, m) 6.28 (1H, dd, J=16.92, 1.86 Hz) 5.82 (1H, dd, J=10.56, 1.76 Hz) 4.54-4.65 (2H, m) 3.99 (4H, m) 3.58 (4H, m). m/z (ESI) M+H: 521.2.

Examples 30 and 31

2-(1-(4-Acryloyl-1-piperazinyl)-7-chloro-4-phenyl-6-phthalazinyl)-3-fluorophenol (Example 30) and 2-(4-(4-acryloyl-1-piperazinyl)-7-chloro-1-phenyl-6-phthalazinyl)-3-fluorophenol (Example 31)

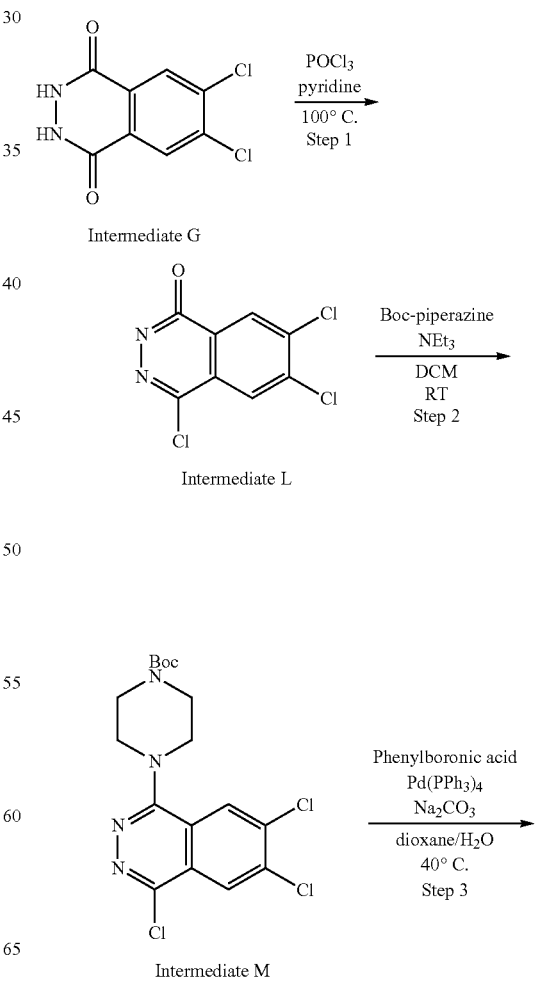

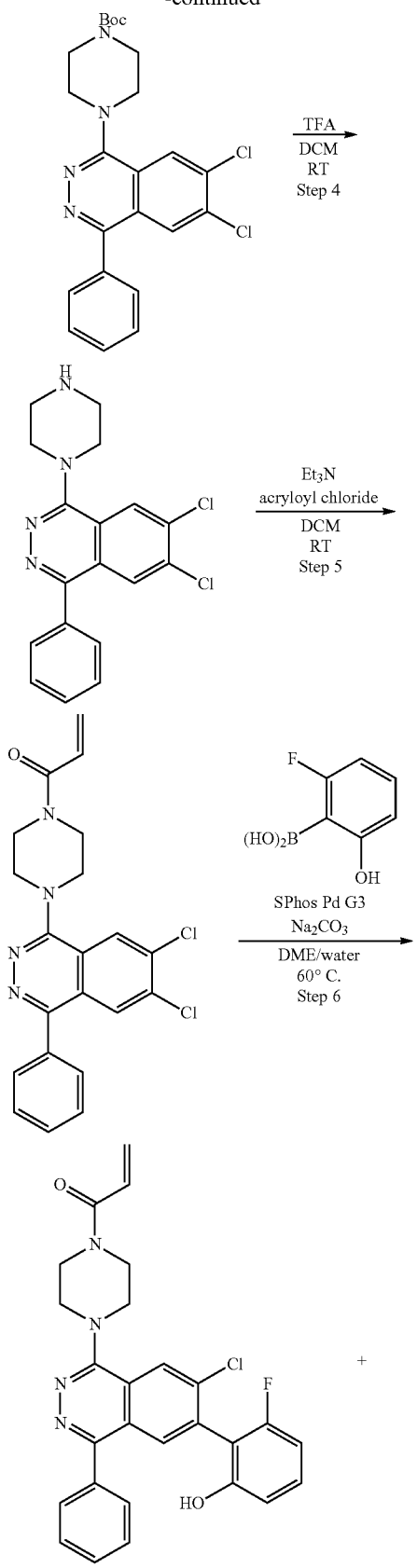

Example 30

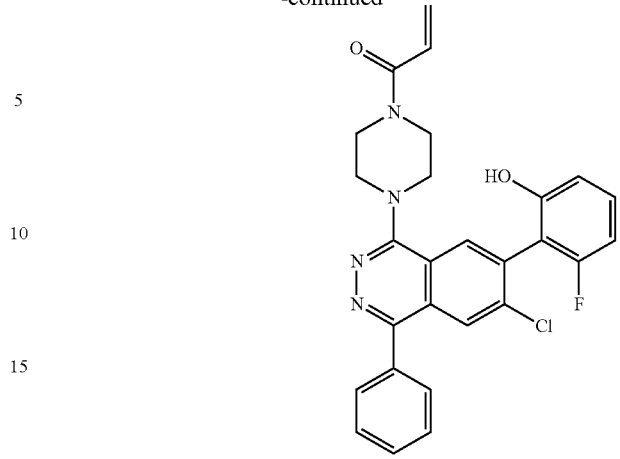

Example 31

Step 1: 1,4,6,7-Tetrachlorophthalazine (Intermediate L). Pyridine (431 μl, 5.28 mmol) was added to a stirred mixture of 6,7-dichloro-2,3-dihydrophthalazine-1,4-dione (Intermediate G, 610 mg, 2.64 mmol) in phosphorus oxychloride (2.4 mL, 26.4 mmol). The reaction mixture was heated to 100° C. for 2 h then cooled and poured slowly into rapidly stirred water (75 mL) at 10° C. The resulting suspension was filtered, and the solid was washed with water to give 1,4,6,7-tetrachlorophthalazine. $^1$H NMR (400 MHz, CHLOROFORM-d) δ 8.43 (2H, s). m/z (ESI) M+H: 266.9.

Step 2: tert-Butyl 4-(4,6,7-trichlorophthalazin-1-yl)piperazine-1-carboxylate (Intermediate M). 1-Boc-piperazine (340 mg, 1.824 mmol) was added to a stirred mixture of 1,4,6,7-tetrachlorophthalazine (Intermediate L, 543 mg, 2.027 mmol) and triethylamine (0.846 mL, 6.08 mmol) in dichloromethane (8 mL). The reaction mixture was stirred at rt for 2 days. Additional 1-boc-piperazine (340 mg, 1.824 mmol) was added, and the reaction mixture was stirred at rt for another 23 h. The reaction mixture was quenched with saturated aqueous sodium bicarbonate (20 mL) and extracted with DCM (30 mL). The organic layer was separated, washed with brine (20 mL), dried over MgSO$_4$, filtered, and concentrated in vacuo. Chromatographic purification of the residue (silica gel, 0 to 50% EtOAc in heptane) gave tert-butyl 4-(4,6,7-trichlorophthalazin-1-yl)piperazine-1-carboxylate. $^1$H NMR (400 MHz, Chloroform-d) δ 8.35 (1H, s) 8.12 (1H, s) 3.68-3.75 (4H, m) 3.45-3.52 (4H, m) 1.51 (9H, s). m/z (ESI) M+H: 417.0.

Step 3: tert-Butyl 4-(6,7-dichloro-4-phenylphthalazin-1-yl)piperazine-1-carboxylate. tert-Butyl 4-(4,6,7-trichlorophthalazin-1-yl)piperazine-1-carboxylate (Intermediate M, 95 mg, 0.227 mmol), tetrakis(triphenylphosphine)palladium (26.3 mg, 0.023 mmol, Strem Chemicals Inc., NewburyPort, MA, USA), phenylboronic acid (27.7 mg, 0.227 mmol), and sodium carbonate (2 M aqueous, 0.341 mL, 0.682 mmol) were mixed in 1,4-dioxane (1 mL) in a sealed vial under an argon atmosphere. The reaction mixture was stirred at 40° C. for 24 h. Additional tetrakis(triphenylphosphine)palladium (26.3 mg, 0.023 mmol) and phenylboronic acid (13.5 mg, 0.113 mmol) were added, and the reaction mixture was stirred at 40° C. for another 24 h. The reaction mixture was quenched with saturated aqueous sodium bicarbonate (20 mL) and extracted with EtOAc (25 mL). The organic layer was separated, washed with brine (20 mL), dried over MgSO$_4$, filtered, and concentrated in vacuo. Chromatographic purification of the residue (silica gel, 0 to 100% EtOAc in heptane) gave tert-butyl 4-(6,7-dichloro-4-phenylphthalazin-1-yl)piperazine-1-carboxylate. ¹H NMR (400 MHz, Chloroform-d) δ 8.13 (1H, s) 8.07 (1H, s) 7.62-7.67 (2H, m) 7.50-7.55 (3H, m) 3.65-3.74 (4H, m) 3.44-3.53 (4H, m) 1.47 (9H, s). m/z (ESI) M+H: 459.1.

Step 4: 6,7-Dichloro-1-phenyl-4-(piperazin-1-yl)phthalazine. tert-Butyl 4-(6,7-dichloro-4-phenylphthalazin-1-yl)piperazine-1-carboxylate (68 mg, 0.148 mmol) was stirred in trifluoroacetic acid (1 mL, 13.46 mmol) at rt for 20 min. The reaction mixture was quenched with saturated aqueous sodium bicarbonate (20 mL) and extracted two times with DCM (25 mL). The organic layer was separated, dried over MgSO₄, filtered, and concentrated in vacuo to give crude 6,7-dichloro-1-phenyl-4-(piperazin-1-yl)phthalazine that was used directly in the next step, m/z (ESI) M+H: 359.0.

Step 5: 1-(4-(6,7-Dichloro-4-phenylphthalazin-1-yl)piperazin-1-yl)prop-2-en-1-one. Acryloyl chloride (0.013 mL, 0.162 mmol) was added to a stirred mixture of 6,7-dichloro-1-phenyl-4-(piperazin-1-yl)phthalazine (53 mg, 0.148 mmol) and triethylamine (0.062 mL, 0.443 mmol) in dichloromethane (1 mL). The reaction mixture was stirred at rt for 30 min. The reaction mixture was quenched with saturated aqueous sodium bicarbonate (15 mL) and extracted with DCM (20 mL). The organic layer was separated, dried over MgSO₄, filtered, and concentrated in vacuo. Chromatographic purification of the residue (silica gel, 0 to 100% EtOAc in heptane) gave 1-(4-(6,7-dichloro-4-phenylphthalazin-1-yl)piperazin-1-yl)prop-2-en-1-one. ¹H NMR (400 MHz, Cloroform-d) δ 8.20 (1H, s) 8.14 (1H, s) 7.66-7.75 (2H, m) 7.54-7.62 (3H, m) 6.66 (1H, dd, J=16.63, 10.37 Hz) 6.37 (1H, dd, J=16.82, 1.96 Hz) 5.78 (1H, dd, J=10.56, 1.96 Hz) 3.85-4.04 (1H, m) 3.53-3.72 (1H, m). m/z (ESI) M+H: 431.2.

Step 6: 2-(1-(4-Acryloyl-1-piperazinyl)-7-chloro-4-phenyl-6-phthalazinyl)-3-fluorophenol and 2-(4-(4-acryloyl-1-piperazinyl)-7-chloro-1-phenyl-6-phthalazinyl)-3-fluorophenol. 1-(4-(6,7-Dichloro-4-phenylphthalazin-1-yl)piperazin-1-yl)prop-2-en-1-one (43 mg, 0.104 mmol), 2-fluoro-6-hydroxyphenylboronic acid (17.84 mg, 0.114 mmol, Combi-Blocks Inc., San Diego, CA, USA), Sphos Pd G3 (9.00 mg, 10.40 μmol), and sodium carbonate (2 M aqueous, 0.156 mL, 0.312 mmol) were mixed in 1,2-dimethoxyethane (0.5 mL) in a sealed vial under an argon atmosphere. The reaction mixture was stirred at 60° C. for 3 h. Additional 2-fluoro-6-hydroxyphenylboronic acid (8.92 mg, 0.057 mmol, Combi-Blocks Inc., San Diego, CA, USA) and SPhos Pd G3 (9.00 mg, 10.40 μmol) were added, and the reaction mixture was stirred at 60° C. for another 2 h. The reaction mixture was quenched with saturated aqueous sodium bicarbonate (15 mL) and extracted with EtOAc (20 mL). The organic layer was separated, washed with brine (10 mL), dried over MgSO₄, filtered, and concentrated in vacuo. Chromatographic purification of the residue (silica gel, 0 to 100% EtOAc in heptane) gave a mixture of the two regioisomeric products. Reverse phase preparative chromatography (XBridge Prep C18 5 μm OBD, 150×30 mm; 35 to 55% (0.1% TEA in water) in (0.1% TEA in acetonitrile); flow rate=30 mL/min) gave the separated regioisomeric products. The fractions containing the individual regioisomers were neutralized with saturated aqueous sodium bicarbonate and extracted with DCM, and the organic extracts were concentrated in vacuo. The separated regioisomers were further individually purified by column chromatography (silica gel, 0 to 100% EtOAc in heptane). 2-(1-(4-acryloyl-1-piperazinyl)-7-chloro-4-phenyl-6-phthalazinyl)-3-fluorophenol (Example 30), was the first regioisomer to elute from the reverse phase preparative chromatography. ¹H NMR (400 MHz, CHLOROFORM-d) δ 8.21 (1H, s) 8.06 (1H, s) 7.62-7.69 (2H, m) 7.45-7.51 (3H, m) 7.24-7.32 (1H, m) 6.81-6.90 (1H, m) 6.75 (1H, t, J=8.41 Hz) 6.65 (1H, dd, J=16.82, 10.56 Hz) 6.38 (1H, dd, J=16.82, 1.76 Hz) 5.79 (1H, dd, J=10.56, 1.76 Hz) 3.86-4.02 (4H, m) 3.57-3.76 (4H, m). m/z (ESI) M+H: 489.0. 2-(4-(4-acryloyl-1-piperazinyl)-7-chloro-1-phenyl-6-phthalazinyl)-3-fluorophenol (Example 31), was the second regioisomer to elute from the reverse phase column. ¹H NMR (400 MHz, CHLOROFORM-d) δ 8.15 (1H, s) 8.12 (1H, s) 7.68-7.73 (2H, m) 7.53-7.58 (3H, m) 7.30 (1H, hr td, J=8.22, 6.65 Hz) 6.88 (1H, d, J=8.22 Hz) 6.78 (1H, t, J=8.61 Hz) 6.57 (1H, dd, J=16.82, 10.56 Hz) 6.28 (1H, dd, J=16.73, 1.66 Hz) 5.71 (1H, dd, J=10.56, 1.56 Hz) 3.78-3.89 (4H, m) 3.51-3.73 (4H, m). m/z (ESI) M+H: 489.1.

Examples 32 and 33

2-(1-(4-Acryloyl-1-piperazinyl)-7-chloro-4-methoxy-6-phthalazinyl)-3-fluorophenol (Example 32) and 2-(4-(4-acryloyl-1-piperazinyl)-7-chloro-1-methoxy-6-phthalazinyl)-3-fluorophenol (Example 33)

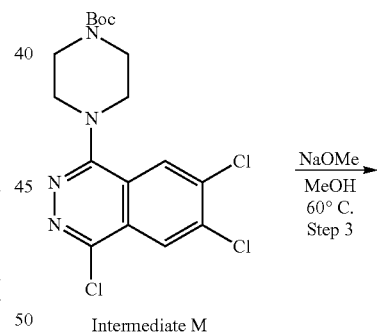

Intermediate M

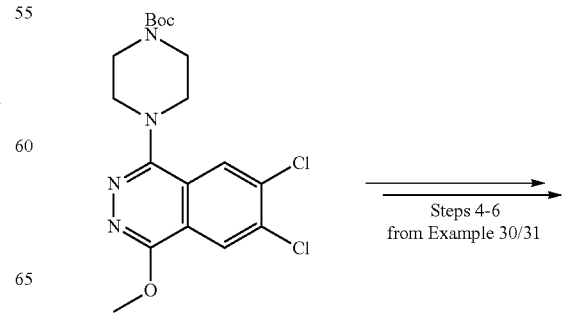

Steps 4-6 from Example 30/31

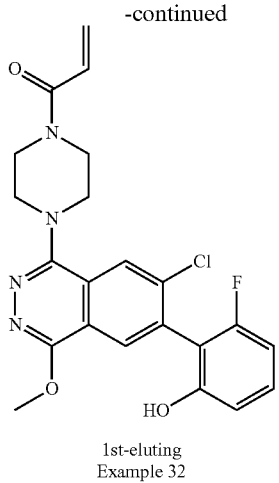

1st-eluting
Example 32

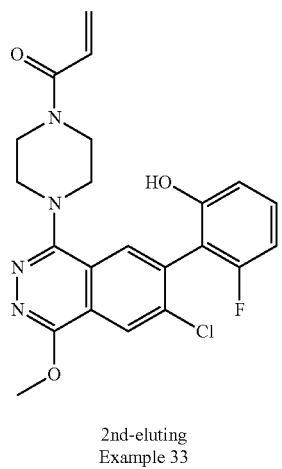

2nd-eluting
Example 33

Examples 32 and 33 were prepared in an analogous method to Examples 30 and 31 with the exception of Step 3, which was changed as follows:

Step 3: tert-Butyl 4-(6,7-dichloro-4-methoxyphthalazin-1-yl)piperazine-1-carboxylate. tert-Butyl 4-(4,6,7-trichlorophthalazin-1-yl)piperazine-1-carboxylate (Intermediate M, 198 mg, 0.474 mmol) and sodium methoxide (25% solution in methanol, 2 mL, 8.75 mmol) were mixed in a sealed vial. The reaction mixture was stirred at 60° C. for 2 h. The reaction mixture was quenched with saturated aqueous sodium bicarbonate (25 mL) and extracted with EtOAc (25 mL). The organic layer was separated, washed with brine (20 mL), dried over MgSO$_4$, filtered, and concentrated in vacuo. Chromatographic purification of the residue (silica gel, 0 to 50% EtOAc in heptane) gave tert-butyl 4-(6,7-dichloro-4-methoxyphthalazin-1-yl)piperazine-1-carboxylate. $^1$H NMR (400 MHz, CHLOROFORM-d) δ 8.29 (1H, s) 8.08 (1H, s) 4.22 (3H, s) 3.68-3.73 (4H, m) 3.33-3.38 (4H, m) 1.51 (9H, s). m/z (ESI) M+H: 413.1.

From step 6: First eluting regioisomer: 2-(1-(4-acryloyl-1-piperazinyl)-7-chloro-4-methoxy-6-phthalazinyl)-3-fluorophenol (Example 32) $^1$H NMR (400 MHz, CHLOROFORM-d) δ 8.23 (1H, s) 8.11 (1H, s) 7.32 (1H, td, j=8.31, 6.46 Hz) 6.88 (1H, d, J=8.22 Hz) 6.77-6.83 (1H, m) 6.65 (1H, dd, J=16.82, 10.56 Hz) 6.37 (1H, dd, J=16.82, 1.86 Hz) 5.79 (1H, dd, J=10.47, 1.86 Hz) 4.18 (3H, s) 3.79-4.05 (4H, m) 3.34-3.54 (4H, m). m/z (ESI) M+H: 443.1.

Second eluting regioisomer: 2-(4-(4-acryloyl-1-piperazinyl)-7-chloro-1-methoxy-6-phthalazinyl)-3-fluorophenol (Example 33) $^1$H NMR (400 MHz, CHLOROFORM-d) δ 8.32 (1H, s) 8.01 (1H, s) 7.32 (1H, td, J=8.27, 6.55 Hz) 6.89 (1H, d, J=8.22 Hz) 6.77-6.83 (1H, m) 6.60 (1H, dd, J=17.02, 10.56 Hz) 6.30 (1H, dd, J=16.82, 1.76 Hz) 5.75 (1H, dd, J=10.56, 1.76 Hz) 4.22 (3H, s) 3.67-3.98 (4H, m) 3.25-3.55 (4H, m). m/z (ESI) M+H: 443.1.

Example 34

1-(4-Acryloyl-1-piperazinyl)-4-benzyl-6,7-dichlorophthalazine

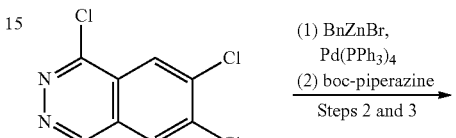

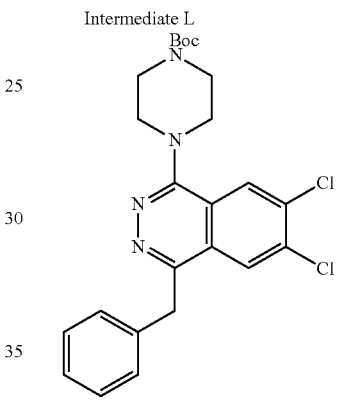

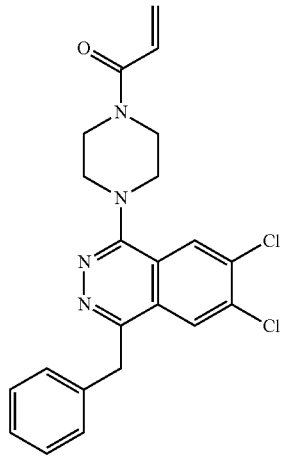

Example 34 was prepared in an analogous method to Examples 30 and 31 with the exception of step 6, which was omitted, and Steps 2 and 3, which were changed as follows:

Steps 2 and 3: tert-Butyl 4-(4-benzyl-6,7-dichlorophthalazin-1-yl)piperazine-1-carboxylate. Benzylzinc bromide (0.5 M in THF, 1.926 mL, 0.963 mmol) was added to a sealed vial containing 1,4,6,7-tetrachlorophthalazine (Intermediate L, 258 mg, 0.963 mmol) and tetrakis(triphenylphosphine)palladium (111 mg, 0.096 mmol, Strem Chemicals Inc., NewburyPort, MA, USA) under an argon atmosphere. The reaction mixture was stirred at rt for 16 h. 1-Boc-piperazine (1.79 g, 9.63 mmol) was added, and the reaction mixture was stirred at 60° C. for 5 h. The reaction mixture was quenched with saturated aqueous sodium bicarbonate (40 mL) and extracted with EtOAc (50 mL). The organic layer was separated, washed with brine (40 mL), dried over MgSO₄, filtered, and concentrated in vacuo. Chromatographic purification of the residue (silica gel, 0 to 50% EtOAc in heptane) gave tot-butyl 4-(4-benzyl-6,7-dichlorophthalazin-1-yl)piperazine-1-carboxylate. ¹H NMR (400 MHz, CHLOROFORM-d) δ 8.11 (1H, s) 8.10 (1H, s) 7.27-7.35 (4H, m) 7.20-7.25 (1H, m) 4.59 (2H, s) 3.69-3.74 (4H, m) 3.44-3.49 (4H, m) 1.52 (9H, s). m/z (ESI) M+H: 473.1. m/z (ESI) M+H: 473.1.

From step 5: 1-(4-acryloyl-1-piperazinyl)-4-benzyl-6,7-dichlorophthalazine. ¹H NMR (400 MHz, CHLOROFORM-d) δ ppm 8.13 (1H, s) 8.12 (1H, s) 7.28-7.36 (4H, m) 7.20-7.26 (1H, m) 6.65 (1H, dd, 0.7=16.82, 10.56 Hz) 6.37 (1H, dd, 0.7=16.82, 1.57 Hz) 5.78 (1H, dd, 0.7=10.56, 1.56 Hz) 4.61 (2H, s) 3.83-4.01 (4H, m) 3.48-3.62 (4H, m). m/z (ESI) M+H: 427.1.

Example 35 and 36

2-(1-(4-Acryloyl-1-piperazinyl)-4-benzyl-7-chloro-6-phthalazinyl)-3-fluorophenol (Example 35) and 2-(4-(4-acryloyl-1-piperazinyl)-1-benzyl-7-chloro-6-phthalazinyl)-3-fluorophenol (Example 36)

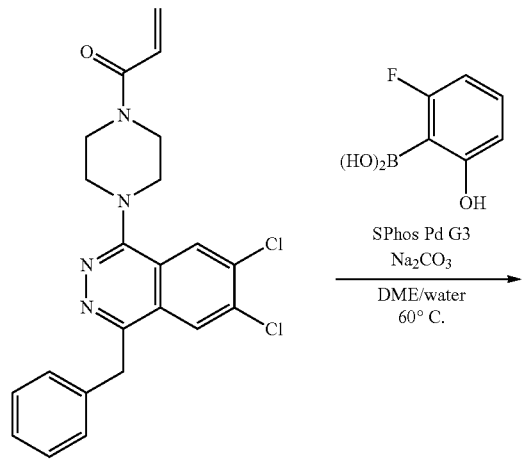

Example 34

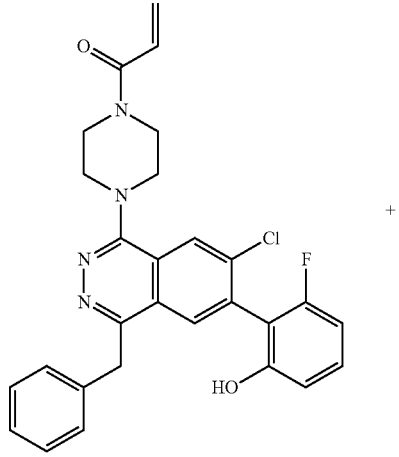

Example 35

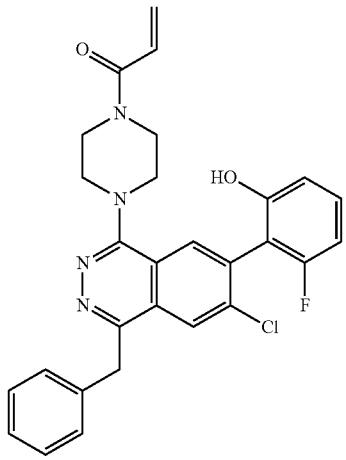

Example 36

1-(4-(4-Benzyl-6,7-dichlorophthalazin-1-yl)piperazin-1-yl)prop-2-en-1-one. (Example 34, 35 mg, 0.082 mmol), 2-fluoro-6-hydroxyphenylboronic acid (12.77 mg, 0.082 mmol, Combi-Blocks Inc., San Diego, CA, USA), SPhos Pd G3 (7.09 mg, 8.19 μmol), and sodium carbonate (2 M aqueous, 0.123 mL, 0.246 mmol) were mixed in 1,2-dimethoxyethane (0.3 mL) in a sealed vial under an argon atmosphere. The reaction mixture was stirred at 60° C. for 1 h. The reaction mixture was quenched with saturated aqueous sodium bicarbonate (15 mL) and extracted with EtOAc (20 mL). The organic layer was separated, washed with brine (10 mL), dried over MgSO₄, filtered, and concentrated in vacuo. Chromatographic purification of the residue (silica gel, 0 to 100% EtOAc in heptane) gave a mixture of the two regioisomeric products. Reverse phase preparative chromatography (XBridge Prep C18 5 μm OBD, 150×30 mm; 20 to 90% (0.1% TFA in water) in (0.1% TFA in acetonitrile); flow rate=30 mL/min) gave the partially separated regioisomeric products. The fractions containing the regioisomers were neutralized with saturated aqueous sodium bicarbonate and extracted with DCM, and the organic extracts were concentrated in vacuo. 2-(1-(4-acryloyl-1-piperazinyl)-4-benzyl-7-chloro-6-phthalazinyl)-3-fluorophenol (Example 35), was the first regioisomer to elute during reverse phase preparative chromatography, and contained approximately 36% of the second regioisomer to elute. ¹H NMR (400 MHz, CHLOROFORM-d) δ 8.13 (1H, s) 8.11 (1H, s) 7.12-7.37 (6H, m) 6.91 (1H, d, J=8.22 Hz) 6.77 (1H, t, J=8.61 Hz) 6.64 (1H, dd, J=16.82, 10.56 Hz) 6.37 (1H, dd, J=16.82, 1.76 Hz) 5.79 (1H, dd, J=10.56, 1.96 Hz) 4.55 (2H, s) 3.34-4.01 (8H, m). m/z (ESI) M+H: 503.1. 2-(4-(4-acryloyl-1-piperazinyl)-1-benzyl-7-chloro-6-phthalazinyl)-3-fluorophenol (Example 36), was the second regioisomer to elute. ¹H NMR (400 MHz, CHLOROFORM-d) δ 8.12 (1H, s) 8.05 (1H, s) 7.26-7.36 (5H, m) 7.19-7.24 (1H, m) 6.93 (1H, d, J=8.41 Hz) 6.76 (1H, t, J=8.31 Hz) 6.58 (1H, dd, J=16.82, 10.76 Hz) 6.28 (1H, dd, J=16.82, 1.76 Hz) 5.75 (1H, dd, J=10.56, 1.76 Hz) 4.54 (2H, s) 3.32-3.93 (8H, m). m/z (ESI) M+H: 503.1.

Example 37

1-(4-acryloyl-1-piperazinyl)-4-benzyl-6-chloro-7-(5-methyl-1H-indazol-4-yl)phthalazine and 1-(4-acryloyl-1-piperazinyl)-4-benzyl-7-chloro-6-(5-methyl-1H-indazol-4-yl)phthalazine

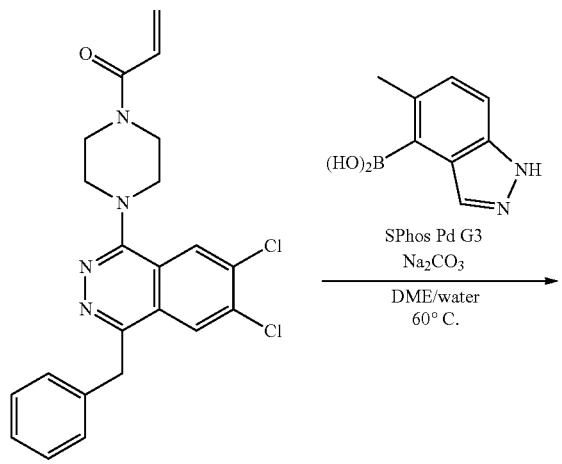

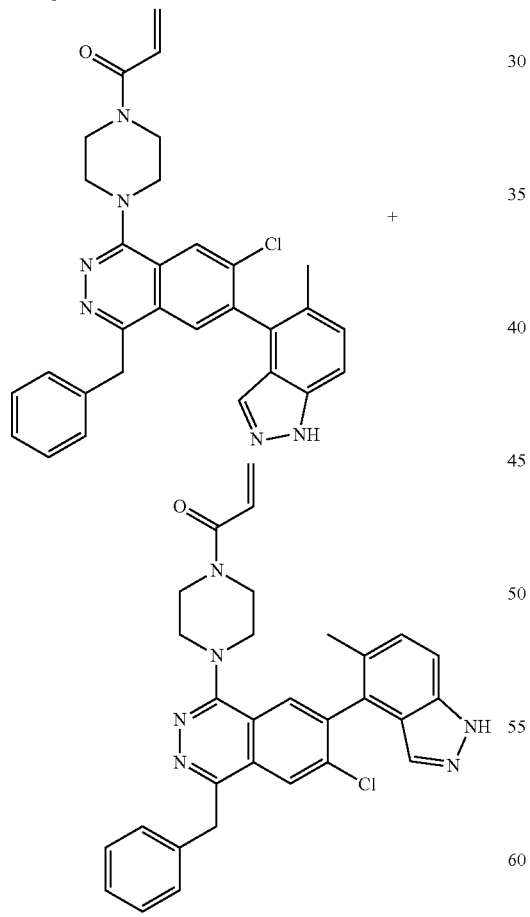

Example 37 was prepared in an analogous method to Examples 35 and 36 with 5-methyl-1h-indazol-4-yl boronic acid (Combi-Blocks Inc., San Diego, CA, USA) in place of 2-fluoro-6-hydroxyphenylboronic acid. In this embodiment the two regioisomeric products were not separated. $^1$H NMR (400 MHz, CHLOROFORM-d) δ 8.23 (0.6H, s) 8.22 (0.4H, s) 8.02 (0.4H, s) 8.00 (0.6H, s) 7.19-7.57 (8H, m) 6.68 (0.4H, dd, J=16.82, 10.56 Hz) 6.60 (0.6H, dd, J=16.82, 10.56 Hz) 6.38 (0.4H, dd, J=16.63, 1.76 Hz) 6.32 (0.6H, dd, J=16.82, 1.76 Hz) 5.79 (0.4H, dd, J=10.56, 1.76 Hz) 5.73 (0.6H, dd, J=10.56, 1.76 Hz) 4.67 (1.2H, s) 4.60 (0.8H, s) 3.74-4.06 (4H, m) 3.46-3.70 (4H, m) 2.21 (1.8H, s) 2.06 (1.2H, s). m/z (ESI) M+H: 523.

Example 38

6-chloro-1-(cyclopropylmethyl)-7-(2-fluoro-6-hydroxyphenyl)-4-(4-(2-propenoyl)-1-piperazinyl)pyrido[2,3-d]pyrimidin-2(1H)-one

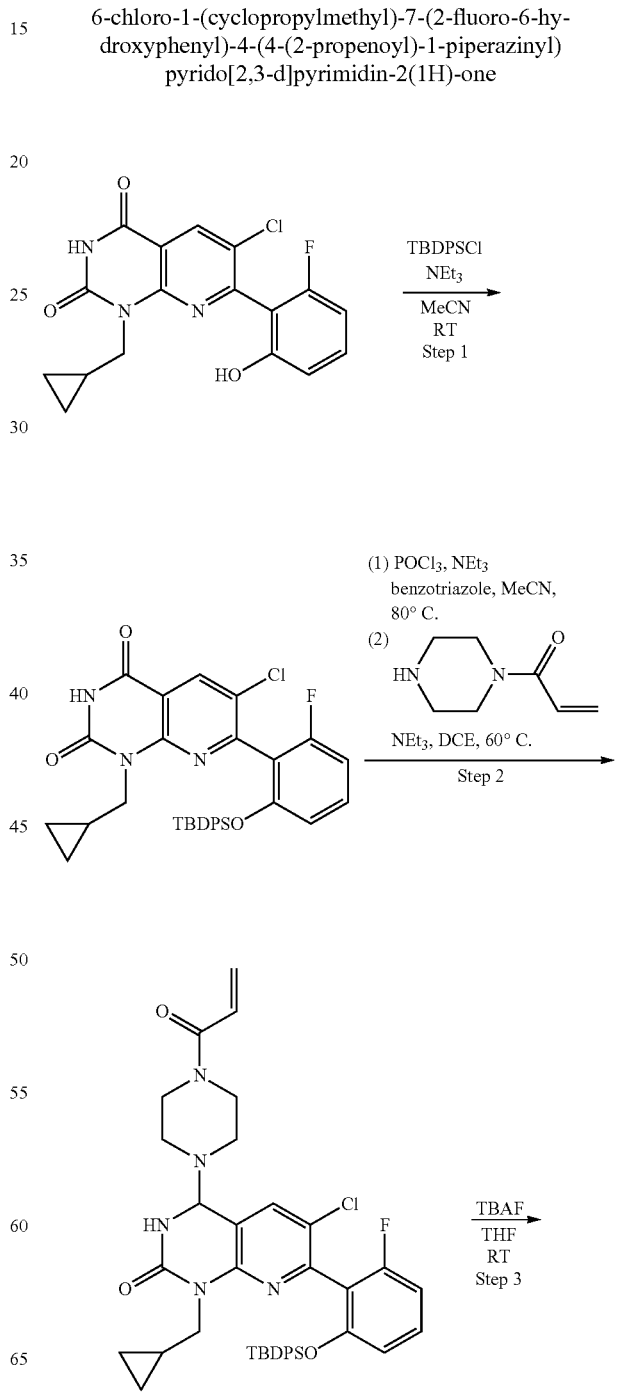

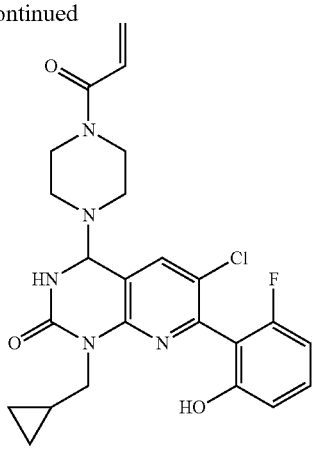

The starting material for Example 38 was prepared using Method 8 Steps 1-4 with reagents 2,5,6-trichloronicotinic acid (Step 1), aminomethylcyclopropane (Step 2), 2-fluoro-6-hydroxyphenylboronic acid (Step 4, Combi-Blocks Inc., San Diego, CA, USA), and sodium carbonate (Step 4).

Step 1: 7-(2-((tert-butyldiphenylsilyl)oxy)-6-fluorophenyl)-6-chloro-1-(cyclopropylmethyl)pyrido[2,3-d]pyrimidine-2,4(1H,3H)-dione. tert-Butylchlorodiphenylsilane (0.036 mL, 0.139 mmol) was added to a stirred mixture of 6-chloro-1-(cyclopropylmethyl)-7-(2-fluoro-6-hydroxyphenyl)pyrido[2,3-d]pyrimidine-2,4(1H,3H)-dione (42 mg, 0.116 mmol) and triethylamine (0.065 mL, 0.464 mmol) in acetonitrile (0.5 mL). The reaction mixture was stirred at rt for 1 h. The reaction mixture was quenched with saturated aqueous NH₄Cl (25 mL) and extracted with EtOAc (30 mL). The organic layer was separated, washed with brine (25 mL), dried over MgSO₄, filtered, and concentrated in vacuo to give crude 7-(2-((tert-butyldiphenylsilyl)oxy)-6-fluorophenyl)-6-chloro-1-(cyclopropylmethyl)pyrido[2,3-d]pyrimidine-2,4(1H,3H)-dione that was used directly in the next step, m/z (ESI) M+H: 599.8.

Step 2: 4-(4-acryloylpiperazin-1-yl)-7-(2-((tert-butyldiphenylsilyl)oxy)-6-fluorophenyl)-6-chloro-1-(cyclopropylmethyl)pyrido[2,3-d]pyrimidin-2(1H)-one. Phosphorus oxychloride (0.087 mL, 0.933 mmol) was added to a stirred mixture of crude 7-(2-((tert-butyldiphenylsilyl)oxy)-6-fluorophenyl)-6-chloro-1-(cyclopropylmethyl)pyrido[2,3-d]pyrimidine-2,4(1H,3H)-dione (70 mg, 0.117 mmol), triethylamine (0.295 mL, 2.099 mmol), and 1H-benzo[d][1,2,3]triazole (167 mg, 1.400 mmol) in acetonitrile (2 mL). The reaction mixture was stirred at 80° C. for 4 h. The reaction mixture was concentrated in vacuo. The resulting residue was taken up in 1,2-dichloroethane (2 mL), and triethylamine (0.295 mL, 2.099 mmol) and 1-(piperazin-1-yl)prop-2-en-1-one (32.7 mg, 0.233 mmol, eNovation Chemicals LLC, Bridgewater, NJ, USA) were added. The reaction mixture was stirred at rt for 16 h. Additional triethylamine (0.148 mL, 1.050 mmol) and 1-(piperazin-1-yl)prop-2-en-1-one (32.7 mg, 0.233 mmol, eNovation Chemicals LLC, Bridgewater, NJ, USA) were added, and the reaction mixture was stirred at rt for 1 h before being heated to 60° C. and stirred for 4 h. The reaction mixture was diluted with saturated aqueous NaHCO₃ (40 mL) and extracted with DCM (50 mL). The organic layer was separated, dried over MgSO₄, filtered, and concentrated in vacuo. The resulting residue was again taken up in 1,2-dichloroethane (2 mL), and triethylamine (0.295 mL, 2.099 mmol) and 1-(piperazin-1-yl)prop-2-en-1-one (32.7 mg, 0.233 mmol, eNovation Chemicals LLC, Bridgewater, NJ, USA) were added. The reaction mixture was stirred at 60° C. for 6 h. The reaction mixture was diluted with saturated aqueous NaHCO₃ (40 mL) and extracted with DCM (50 mL). The organic layer was separated, dried over MgSO₄, filtered, and concentrated in vacuo. Chromatographic purification of the residue (silica gel, 0 to 100% (3:1 EtOAc/EtOH) in heptane) gave 4-(4-acryloylpiperazin-1-yl)-7-(2-((tert-butyldiphenylsilyl)oxy)-6-fluorophenyl)-6-chloro-1-(cyclopropylmethyl)pyrido[2,3-d]pyrimidin-2(1H)-one that was taken on in the next step without further purification, m/z (ESI) M+H: 721.8.

Step 3: 4-(4-acryloylpiperazin-1-yl)-6-chloro-1-(cyclopropylmethyl)-7-(2-fluoro-6-hydroxyphenyl)pyrido[2,3-d]pyrimidin-2(1H)-one. Tetrabutylammonium fluoride (1.0 M solution in tetrahydrofuran, 0.025 mL, 0.025 mmol) was added to a stirred mixture of 4-(4-acryloylpiperazin-1-yl)-7-(2-((tert-butyldiphenylsilyl)oxy)-6-fluorophenyl)-6-chloro-1-(cyclopropylmethyl)pyrido[2,3-d]pyrimidin-2(1H)-one (6 mg, 8.31 μmol) in tetrahydrofuran (0.2 mL). The reaction mixture was stirred at rt for 20 min before being concentrated in vacuo. Chromatographic purification of the residue (silica gel, 0 to 100% (3:1 EtOAc/EtOH) in heptane) gave 6-chloro-1-(cyclopropylmethyl)-7-(2-fluoro-6-hydroxyphenyl)-4-(4-(2-propenoyl)-1-piperazinyl)pyrido[2,3-d]pyrimidin-2(1H)-one. ¹H NMR (400 MHz, CHLOROFORM-d) δ 8.04 (1H, s) 7.26-7.33 (1H, m) 6.82 (1H, d, J=8.29 Hz) 6.71 (1H, t, J=8.91 Hz) 6.51 (1H, dd, J=16.79, 10.57 Hz) 6.30 (1H, dd, J=16.79, 1.45 Hz) 5.72 (1H, dd, J=10.47, 1.55 Hz) 4.15 (2H, br d, J=6.43 Hz) 3.69-3.90 (8H, m) 1.14-1.27 (4H, m) 0.73-0.88 (1H, m). m/z (ESI) M+H: 483.8.

Example 39

6-Chloro-7-(2-fluoro-6-hydroxyphenyl)-1-(2-methyl-6-(2-propanyl)phenyl)-4-((2S)-2-methyl-4-(2-propenoyl)-1-piperazinyl)pyrido[2,3-d]pyrimidin-2(1H)-one

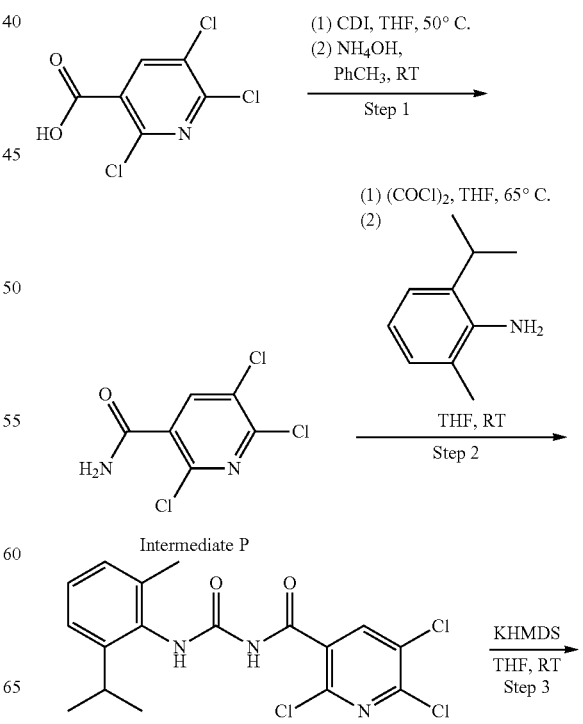

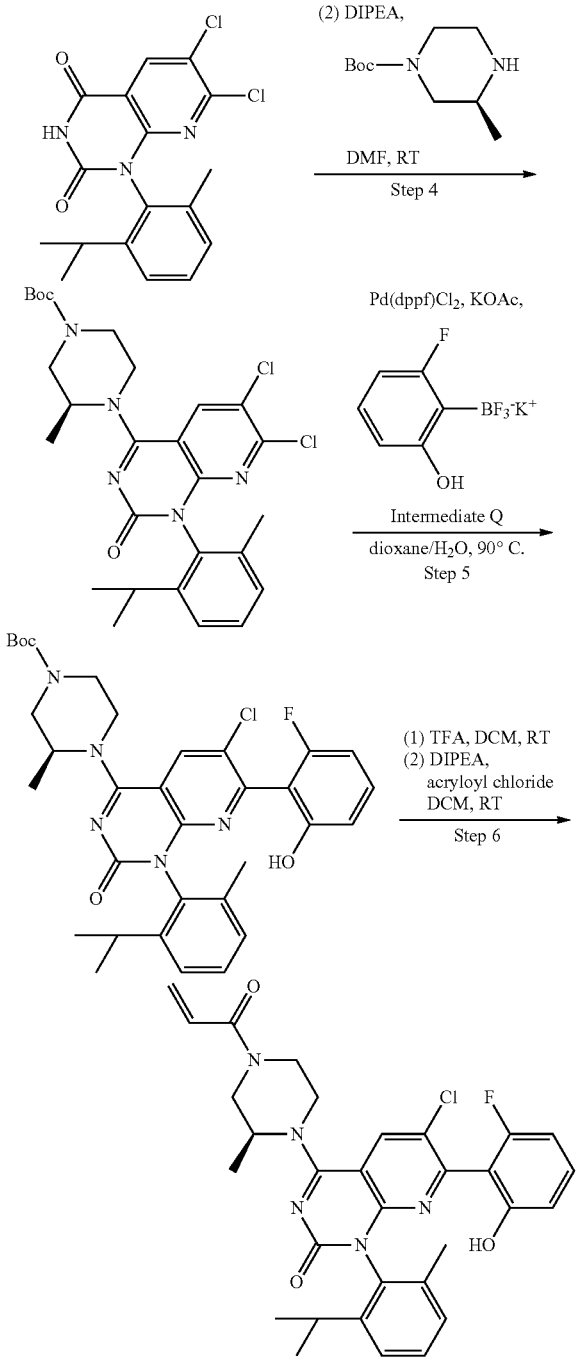

Step 1: 2,5,6-trichloronicotinamide (Intermediate P). 1,1'-Carbonyldiimidazole (40 g, 247 mmol) was added in portions to 2,5,6-trichloronicotinic acid (50.7 g, 224 mmol, Combi-Blocks, San Diego, CA, USA) in THF (400 mL), allowing gas evolution to cease between additions. The resulting mixture was stirred for 5 min and then was degassed with house vacuum and flushed with nitrogen (×2). The resulting mixture was heated to 50° C. for 60 min, then diluted with toluene (100 mL) and concentrated to half volume. The resulting mixture was cooled to 0° C. and ammonium hydroxide (60 mL, 437 mmol) was added slowly via syringe. The reaction was stirred for 10 min at room temperature, diluted with EtOAc (200 mL) and washed with water (3×100 mL). The organic layer was dried over anhydrous sodium sulfate and concentrated. The residue was suspended in 9:1 heptane/EtOAc (300 mL) and filtered. The filtered solids were collected and the remaining mother liquor was partially evaporated to half volume, cooled to 0° C., and filtered. The two crops of filtered solids were combined to provide 2,5,6-trichloronicotinamide.

Step 2: 2,5,6-trichloro-N-((2-isopropyl-6-methylphenyl)carbamoyl)nicotinamide. To a mixture of 2,5,6-trichloronicotinamide (Intermediate P, 1.13 g, 5.0 mmol) in THF (30 mL) was added oxalyl chloride (2M solution in DCM, 2.7 mL, 5.4 mmol). The resulting slurry was heated at 65° C. for 40 min, then heating was stopped and the reaction was allowed to cool to room temperature. 2-Isopropyl-6-methylaniline (0.80 mL, 5.36 mmol, Enamine, Monmouth Junction, NJ, USA) was added and the reaction was stirred at room temperature for 14 h. The reaction was concentrated and the residue was partitioned between EtOAc (50 mL) and saturated aqueous sodium bicarbonate solution (10 mL). The organic layer was washed with brine (10 mL), dried over anhydrous sodium sulfate and concentrated. The residue was suspended in 5:1 heptane/EtOAc (10 mL) and filtered. The filtered solids were collected to provide 2,5,6-trichloro-N-((2-isopropyl-6-methylphenyl)carbamoyl)nicotinamide. $^1$H NMR (400 MHz, CHLOROFORM-d) δ ppm 9.63 (s, 1H), 9.35 (hr s, 1H), 8.25 (s, 1H), 7.19-7.26 (m, 2H), 7.13 (d, J=7.3 Hz, 1H), 3.14 (quin, J=6.9 Hz, 1H), 2.29 (s, 3H), 1.23 (d, J=6.8 Hz, 6H). m/z (ESI, +ve ion): 400.0 (M+H)$^+$.

Step 3: 6,7-dichloro-1-(2-isopropyl-6-methylphenyl)pyrido[2,3-d]pyrimidine-2,4(1H,3H)-dione. To a mixture of 2,5,6-trichloro-N-((2-isopropyl-6-methylphenyl)carbamoyl)nicotinamide (1.45 g, 3.6 mmol) in THF (20 mL) was added KHMDS (1 M solution in THF, 7.5 mL, 7.5 mmol). After stirring for 30 min at room temperature, the reaction was concentrated to ⅓ volume and quenched with saturated aqueous ammonium chloride solution (10 mL). The mixture was extracted with EtOAc (40 mL). The organic layer was washed with brine (10 mL), dried over anhydrous sodium sulfate and concentrated to provide 6,7-dichloro-1-(2-isopropyl-6-methylphenyl)pyrido[2,3-d]pyrimidine-2,4(1H,3H)-dione. This material was used without further purification in the following step. m/z (ESI, +ve ion): 364.0 (M+H)$^+$.

Step 4: (S)-tert-butyl 4-(6,7-dichloro-1-(2-isopropyl-6-methylphenyl)-2-oxo-1,2-dihydropyrido[2,3-d]pyrimidin-4-yl)-3-methylpiperazine-1-carboxylate. To a mixture of crude 6,7-dichloro-1-(2-isopropyl-6-methylphenyl)pyrido[2,3-d]pyrimidine-2,4(1H,3H)-dione (3.6 mmol) in acetonitrile (10 mL) was added DIPEA (1.50 mL, 8.6 mmol) followed by phosphorus oxychloride (0.50 mL, 5.3 mmol). The resulting mixture was heated at 80° C. for 1 h, then was cooled to room temperature and concentrated. The residue was dissolved in DMF (15 mL) and treated with DIPEA (1.50 mL, 8.6 mmol), followed by (S)-4-N-Boc-2-methyl piperazine (900 mg, 4.5 mmol, ArkPharm Inc., Arlington Heights, IL, USA). The resulting solution was stirred at room temperature for 14 h and then was diluted with EtOAc (30 mL). The mixture was washed with water (10 mL) and brine (10 mL), and the organic layer was dried over anhydrous magnesium sulfate and concentrated. The residue was purified by silica gel chromatography (eluent: 10-50% 3:1 EtOAc-EtOH/heptane) to provide (S)-tert-butyl 4-(6,7-dichloro-1-(2-isopropyl-6-methylphenyl)-2-oxo-1,2-dihydropyrido[2,3-d]pyrimidin-4-yl)-3-methylpiperazine-1-carboxylate. $^1$H NMR (400 MHz, MeOH-d$_4$) δ ppm 8.45 (s, 1H), 7.34-7.43 (m, 2H), 7.23 (d, J=7.3 Hz, 1H), 4.97 (br s, 1H), 4.34 (br d, J=13.3 Hz, 1H), 4.15 (br d, J=12.0 Hz, 1H), 4.01 (br d, J=13.7 Hz, 1H), 3.80 (br s, 1H), 3.09-3.32 (m, 2H), 2.49-2.59 (m, 1H), 1.99 (d, J=3.7 Hz, 3H), 1.55 (s, 9H), 1.50 (dd, J=1.7, 6.6 Hz, 3H), 1.18 (dd, J=6.7, 1.8 Hz, 3H), 1.09 (dd, j=6.8, 2.3 Hz, 3H). m/z (ESI, +ve ion): 546.1 (M+H)$^+$.

Step 5: (5S)-tert-butyl 4-(6-chloro-7-(2-fluoro-6-hydroxyphenyl)-1-(2-isopropyl-6-methylphenyl)-2-oxo-1,2-dihydropyrido[2,3-d]pyrimidin-4-yl)-3-methylpiperazine-1-carboxylate. A round-bottomed flask was charged (S)-tert-butyl 4-(6,7-dichloro-1-(2-isopropyl-6-methylphenyl)-2-oxo-1,2-dihydropyrido[2,3-d]pyrimidin-4-yl)-3-methylpiperazine-1-carboxylate (8.3 g, 15.19 mmol), potassium acetate (7.50 g, 76 mmol) and [1,1'-bis(diphenylphosphino)ferrocene]-dichloropalladium (II), complex with dichloromethane (0.495 g, 0.606 mmol). 1,4-Dioxane (40 mL) and water (8 mL) were added and the mixture was heated to 90° C. (2-Fluoro-6-hydroxyphenyl)potassium trifluoroborate (Intermediate Q, 7.45 g, 34.2 mmol) and additional[1,1'-bis(diphenylphosphino)ferrocene]-dichloropalladium (II), complex with dichloromethane (0.176 g) were added. The resulting mixture was stirred at room temperature for 2.5 h, then was cooled to room temperature, diluted with EtOAc (200 mL) and washed with water (1×) and brine (1×). The organic layer was dried over anhydrous sodium sulfate and concentrated. The residue was purified by silica gel chromatography (eluent: 5-40% 3:1 EtOAc-EtOH/heptane) to provide (3S)-tert-butyl 4-(6-chloro-7-(2-fluoro-6-hydroxyphenyl)-1-(2-isopropyl-6-methylphenyl)-2-oxo-1,2-dihydropyrido[2,3-d]pyrimidin-4-yl)-3-methylpiperazine-1-carboxylate. $^1$H NMR (400 MHz, CHLOROFORM-d) δ ppm 8.68 (br s, 1H), 8.14 (br s, 1H), 7.33-7.45 (m, 2H), 7.25 (d, j=6.3 Hz, 2H), 6.64-6.73 (m, 2H), 3.91-5.15 (m, 4H), 3.67 (br s, 1H), 3.32 (br s, 2H), 2.49-2.76 (m, 1H), 1.95-2.08 (m, 3H), 1.53 (s, 12H), 1.14-1.29 (m, 3H), 0.95-1.07 (m, 3H). $^{19}$F NMR (377 MHz, CHLOROFORM-d) δ ppm −104.56 (br s, 1F). m/z (ESI, +ve ion): 622.1 (M+H)$^+$.

Step 6: 6-Chloro-7-(2-fluoro-6-hydroxyphenyl)-1-(2-methyl-6-(2-propanyl)phenyl)-4-((2A)-2-methyl-4-(2-propenoyl)-1-piperazinyl)pyrido[2,3-d]pyrimidin-2(1H)-one. To a solution of (3S)-tert-butyl 4-(6-chloro-7-(2-fluoro-6-hydroxyphenyl)-1-(2-isopropyl-6-methylphenyl)-2-oxo-1,2-dihydropyrido[2,3-d]pyrimidin-4-yl)-3-methylpiperazine-1-carboxylate (680 mg, 1.1 mmol) in DCM (10 mL) was added trifluoroacetic acid (1.5 mL, 19.6 mmol). The reaction was stirred for 1.5 h at room temperature, and then was concentrated. The residue was partitioned between EtOAc (40 mL) and saturated aqueous sodium bicarbonate (2×15 mL). The organic layer was washed with brine (5 mL), dried over anhydrous sodium sulfate and concentrated. The residue was dissolved in DCM (10 mL) and treated with DIPEA (0.5 mL, 2.9 mmol) followed by acryloyl chloride (0.09 mL, 1.1 mmol). The reaction was stirred for 10 min at room temperature, then was diluted with EtOAc (30 mL) and washed with saturated aqueous sodium bicarbonate solution (10 mL) and brine (5 mL). The organic layer was dried over anhydrous sodium sulfate and concentrated. The residue was purified by silica gel chromatography (eluent: 10-60% 3:1 EtOAc-EtOH/heptane) to provide 6-chloro-7-(2-fluoro-6-hydroxyphenyl)-1-(2-methyl-6-(2-propanyl)phenyl)-4-((2S)-2-methyl-4-(2-propenoyl)-1-piperazinyl)pyrido[2,3-d]pyrimidin-2(1H)-one. $^1$H NMR (400 MHz, DMSO-4) δ ppm 10.07 (s, 1H), 8.40 (br s, 1H), 7.17-7.25 (m, 3H), 7.06-7.13 (m, 1H), 6.79-6.91 (m, 2H), 6.69 (d, J=8.0 Hz, 1H), 6.65 (t, J=8.8 Hz, 1H), 6.20 (br d, J=16.8 Hz, 1H), 5.73-5.78 (m, 1H), 4.91 (br s, 1H), 4.21-4.46 (m, 2H), 3.95-4.20 (m, 1H), 3.42-3.80 (m, 2H), 3.03-3.27 (m, 1H), 2.53-2.63 (m, 1H), 1.85 (br s, 3H), 1.32 (br t, J=5.9 Hz, 3H), 1.05 (d, J=6.8 Hz, 3H), 0.91 (br d, j=6.6 Hz, 3H). $^{19}$F NMR (377 MHz, DMSO-d$_6$) δ ppm −115.71−−115.50 (m, 1F), −116.16 (br s, 1F). m/z (ESI, +ve ion): 576.0 (M+H)$^+$.

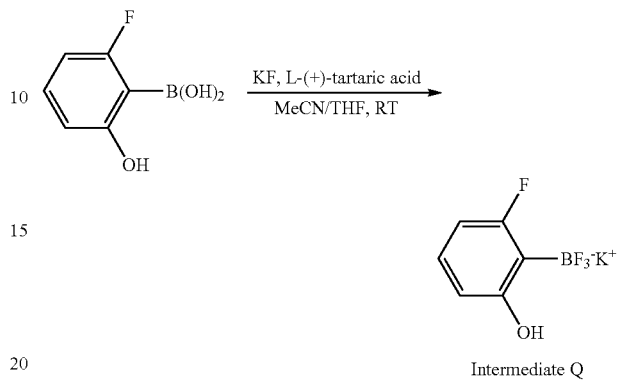

Intermediate Q (2-Fluoro-6-hydroxyphenyl)potassium trifluoroborate (Intermediate Q). A solution of potassium fluoride (44.7 g, 770 mmol) in water (75 mL) was added to a suspension of (2-fluoro-6-hydroxyphenyl)boronic acid (30 g, 192 mmol, Combi-Blocks, San Diego, CA, USA) in acetonitrile (750 mL). The mixture was stirred for 2 min and then a solution of L-(+)-tartaric acid (72.2 g, 481 mmol) in THF (375 mL) was added over a 10 min period via addition funnel. The mixture was stirred vigorously with a mechanical stirrer for 1 h, and then the resulting suspension was filtered, and the filtered solids were washed with a small amount of THF. The solids were discarded and the filtrate was partially concentrated until solids started to precipitate out of solution. The mixture was then cooled to −20° C. and stirred for 16 h. The reaction was slowly warmed and 2-propanol (20 mL) was added. The resulting suspension was filtered and the filtered solids were washed with 2-propanol. The filtrate was again partially concentrated until a suspension formed and then was cooled to −20° C. and stirred for an additional 20 min. The resulting suspension was diluted with 2-propanol and filtered, and the filtered solids were washed with 2-propanol. The two batches of solids were combined to provide 2-fluoro-6-hydroxyphenyl)potassium trifluoroborate (Intermediate Q). $^1$H NMR (400 MHz, DMSO-d$_6$) δ ppm 8.07 (q, J=14.7 Hz, 1H) 6.93 (q, J=7.5 Hz, 1H) 6.30-6.38 (m, 2H).

Example 40

6-Chloro-7-(2-fluorophenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one

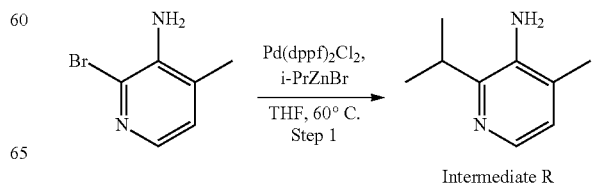

Intermediate R

-continued

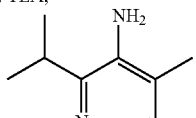

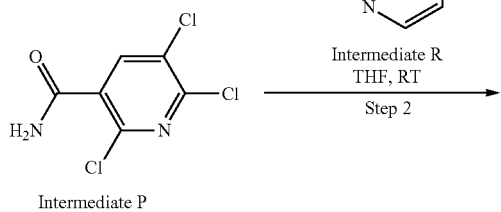

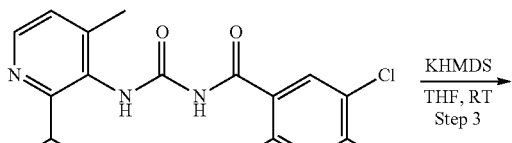

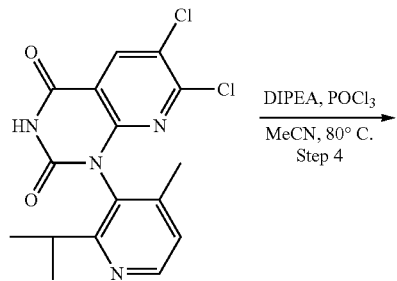

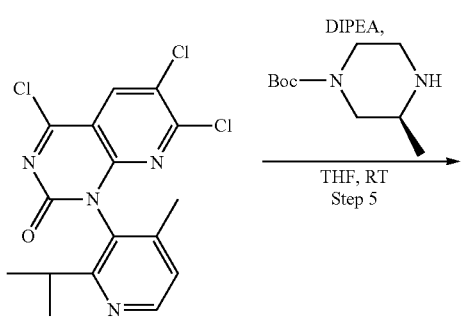

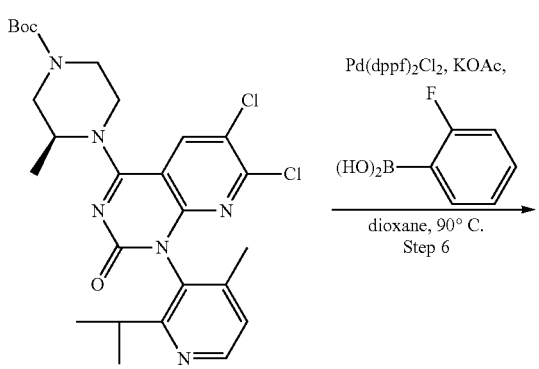

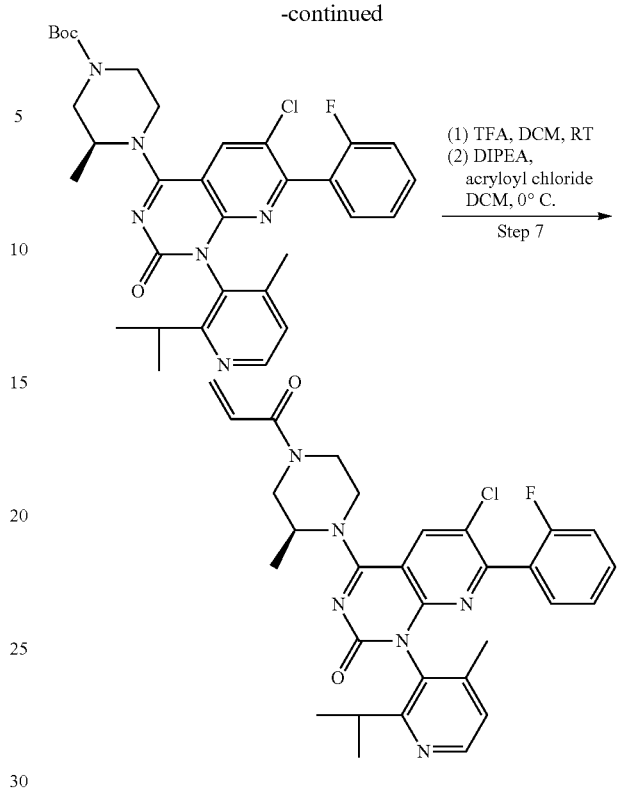

Step 1: 2-Isopropyl-4-methylpyridin-3-amine (Intermediate R). To a slurry of 3-amino-2-bromo-4-picoline (360 mg, 1.9 mmol, Combi-Blocks, San Diego, CA, USA) in THF (4 mL) was added [1,1'-bis(diphenylphosphino)ferrocene]dichloropalladium(II), complex with dichloromethane (79 mg, 0.10 mmol). The resulting slurry was deoxygenated with argon for 2 min and then 2-propylzinc bromide (0.5 M solution in THF, 5.40 mL, 2.7 mmol, Sigma-Aldrich, St. Louis, MO) was added. The resulting solution was heated at 60° C. for 17 h, then the heating was stopped and the reaction was allowed to cool to room temperature. The reaction mixture was quenched with water (10 mL) and 1 N NaOH solution (20 mL) and then was extracted with EtOAc (2×). The combined organic layers were dried over anhydrous sodium sulfate and concentrated. The residue was purified by silica gel chromatography (eluent: 0-15% MeOH/DCM) to provide 2-isopropyl-4-methylpyridin-3-amine. $^1$H NMR (400 MHz, DMSO-$d_6$) δ ppm 7.66 (d, J=4.6 Hz, 1H), 6.78 (d, J=4.8 Hz, 1H), 4.72 (hr s, 2H), 3.14-3.25 (m, 1H), 2.08 (s, 3H), 1.14 (d, J=6.8 Hz, 6H). m/z (ESI, +ve ion): 151.1 (M+H)$^+$.

Step 2: 2,5,6-Trichloro-N-((2-isopropyl-4-methylpyridin-3-yl)carbamoyl)nicotinamide. To a −78° C. slurry of 2,5,6-trichloronicotinamide (Intermediate P, 3.10 g, 13.8 mmol) in THF (46 mL) was added oxalyl chloride (2 M solution in DCM, 7.4 mL, 14.7 mmol) slowly via syringe. The resulting slurry was heated at 60° C. for 3.5 h, then heating was stopped and the reaction was cooled to −78° C. Triethylamine (6.0 mL, 42.6 mmol) was added followed by a solution of 2-isopropyl-4-methylpyridin-3-amine (Intermediate R, 2.12 g, 14.1 mmol) via cannula. The resulting slurry was warmed to room temperature and stirred for 1 h, then was partitioned between water (120 mL) and EtOAc (175 mL). The organic layer was dried over anhydrous sodium sulfate and concentrated. The residue was suspended in 9:1 heptane/EtOAc and filtered. The filtered solids were collected to provide 2,5,6-trichloro-N-((2-isopropyl-4-methylpyridin-3-yl)carbamoyl)nicotinamide. $^1$H NMR (400 MHz, DMSO-d$_6$) δ ppm 11.31 (s, 1H), 9.54 (s, 1H), 8.66 (s, 1H), 8.34 (d, J=4.8 Hz, 1H), 7.16 (d, J=5.0 Hz, 1H), 3.24-3.33 (m, 1H), 2.22 (s, 3H), 1.17 (d, J=6.6 Hz, 6H). m/z (ESI, +ve ion): 400.9 (M+H)$^+$.

Step 3: 6,7-Dichloro-1-(2-isopropyl-4-methylpyridin-3-yl)pyrido[2,3-d]yrimidine-2,4(1H,3H)-dione. To an ice-cooled solution of 2,5,6-trichloro-N-((2-isopropyl-4-methylpyridin-3-yl)carbamoyl)nicotinamide (4.71 g, 11.7 mmol) in THE (55 mL) was added KHMDS (1 M solution in THE, 23.5 mL, 23.5 mmol) slowly via syringe. After 10 min the ice bath was removed and the resulting solution was stirred for an additional 30 min at room temperature. The reaction was quenched with saturated aqueous ammonium chloride (125 mL) and extracted with EtOAc (250 mL). The organic layer was washed with brine (1×), dried over anhydrous sodium sulfate, and concentrated. The residue was purified by silica gel chromatography (eluent: 0-11% MeOH/DCM) to provide 6,7-dichloro-1-(2-isopropyl-4-methylpyridin-3-yl)pyrido[2,3-d]pyrimidine-2,4(1H,3H)-dione. $^1$H NMR (400 MHz, DMSO-d$_6$) δ ppm 12.27 (hr s, 1H), 8.59 (s, 1H), 8.52 (d, J=5.0 Hz, 1H), 7.28 (d, J=5.0 Hz, 1H), 2.82-2.92 (m, 1H), 2.04 (s, 3H), 1.08 (d, J=6.6 Hz, 3H), 1.01 (d, J=6.8 Hz, 3H). m/z (ESI, +ve ion): 365.0 (M+H)$^+$.

Step 4: 4,6,7-Trichloro-1-(2-isopropyl-4-methylpyridin-3-yl)pyrido[2,3-d]yrimidin-2(1H)-one. To a slurry of 6,7-dichloro-1-(2-isopropyl-4-methylpyridin-3-yl)pyrido[2,3-d]pyrimidine-2,4(1H,3H)-dione (2.52 g, 6.9 mmol) in acetonitrile (45 mL) was added DIPEA (1.80 mL, 10.3 mmol) followed by phosphorus oxychloride (1.58 mol, 10.3 mmol), slowly via syringe. The resulting mixture was heated at 80° C. for 1.75 h, and then was cooled to room temperature and concentrated to provide 4,6,7-trichloro-1-(2-isopropyl-4-methylpyridin-3-yl)pyrido[2,3-d]pyrimidin-2(1H)-one. This material was used without further purification in the following step.

Step 5: (A)-tert-Butyl-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate. To a solution of 4,6,7-trichloro-1-(2-isopropyl-4-methylpyridin-3-yl)pyrido[2,3-d]pyrimidin-2(1H)-one (2.64 g, 6.9 mmol) in THE (40 mL) was added DIPEA (3.61 mL, 20.7 mmol), followed by (5)-4-N-Boc-2-methyl piperazine (2.07 g, 10.3 mmol, Combi-Blocks, Inc., San Diego, CA, USA). The resulting solution was stirred at room temperature for 1.5 h, and then ice water (60 mL) was added. The mixture was stirred for an additional 5 min, then was extracted with EtOAc (3×). The combined organic layers were dried over anhydrous sodium sulfate and concentrated. The residue was purified by silica gel chromatography (eluent: 0-11% MeOH/DCM) to provide (S)-tert-butyl 4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 8.46 (dd, J=11.6, 5.2 Hz, 2H), 7.25 (d, J=4.8 Hz, 1H), 4.79-4.93 (m, 1H), 4.10-4.24 (m, 1H), 3.87-4.05 (m, 1H), 3.77-3.87 (m, 1H), 3.62-3.76 (m, 1H), 2.99-3.25 (m, 2H), 2.55-2.69 (m, 1H), 1.94 (d, J=2.5 Hz, 3H), 1.45 (s, 9H), 1.32 (hr t, J=5.7 Hz, 3H), 1.06 (d, J=6.8 Hz, 3H), 1.00 (d, J=6.6 Hz, 3H). m/z (ESI, +ve ion): 547.2 (M+H)$^+$.

Step 6: (A)-tert-Butyl-4-(6-chloro-7-(2-fluorophenyl)-1-(2-isopropyl-4-methylpyridin-3-yl)-2-oxo-1,2-dihydro-pyrido[2,3-d]pyrimidin-4-yl)-3-methylpiperazine-1-carboxylate. To a solution of (S)-tert-butyl 4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (1.02 g, 1.8 mmol) in 1,4-dioxane (17 mL) was added potassium acetate (914 mg, 9.3 mmol) and (2-fluorophenyl)boronic acid (313 mg, 2.2 mmol, Sigma-Aldrich, St. Louis, MO, USA). The mixture was sparged with argon and then [1,1'-bis(diphenylphosphino)ferrocene]dichloropalladium(II), complex with dichloromethane (76 mg, 0.093 mmol) was added. The mixture was again sparged with argon and heated at 90° C. After 30 seconds three drops of water were added to the reaction mixture. Heating was continued at 90° C. for 40 min, and then the reaction was allowed to cool to room temperature. Water (50 mL) and brine (4 mL) were added and the resulting mixture was extracted with EtOAc (2×). The combined organic layers were washed with brine (1×), dried over anhydrous sodium sulfate and concentrated. The residue was purified by silica gel chromatography (eluent: 0-9% MeOH/DCM) to provide (S)-tert-butyl 4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 8.43 (d, J=2.5 Hz, 1H), 8.39 (d, J=4.8 Hz, 1H), 7.47-7.55 (m, 1H), 7.16-7.33 (m, 4H), 4.86-4.97 (m, 1H), 4.21-4.30 (m, 1H), 3.90-4.06 (m, 2H), 3.80-3.89 (m, 1H), 3.67-3.78 (m, 1H), 3.04-3.16 (m, 1H), 2.65-2.75 (m, 1H), 1.93 (s, 3H), 1.48 (s, 9H), 1.36 (br d, J=6.6 Hz, 3H), 1.06 (d, J=6.6 Hz, 3H), 0.94 (dd, 0.7=6.6, 2.1 Hz, 3H). m/z (ESI, +ve ion): 607.0 (M+H)$^+$.

Step 7: 6-Chloro-7-(2-fluorophenyl)-1-(4-methyl-2-(2-propanyl)-3-pyridinyl)-4-((2A)-2-methyl-4-(2-propenoyl)-1-piperazinyl)pyrido[2,3-d]pyrimidin-2(1H)-one. Trifluoroacetic acid (4.0 mL, 53.9 mmol) was added to a solution of (S)-tert-butyl 4-(6-chloro-7-(2-fluorophenyl)-1-(2-isopropyl-4-methylpyridin-3-yl)-2-oxo-1,2-dihydropyrido[2,3-<7]pyrimidin-4-yl)-3-methylpiperazine-1-carboxylate (935 mg, 1.54 mmol) in DCM (20 mL). The resulting solution was stirred at room temperature for 1.5 h and then was concentrated. The residue was dissolved in DCM (12 mL), cooled to 0° C., and treated with DIPEA (0.807 mL, 4.62 mmol) followed by acryloyl chloride (0.131 mL, 1.62 mmol; added dropwise via syringe). The resulting solution was stirred at 0° C. for 35 min, then was quenched with saturated aqueous sodium bicarbonate (35 mL) and extracted with DCM (2×). The combined organic layers were dried over anhydrous sodium sulfate and concentrated. The residue was purified by silica gel chromatography (eluent: 0-11% MeOH/DCM) to provide 6-chloro-7-(2-fluorophenyl)-1-(4-methyl-2-(2-propanyl)-3-py ridinyl)-4-((25)-2-methyl-4-(2-propenoyl)-1-piperazinyl)pyrido[2,3-d]pyrimidin-2(1H)-one. $^1$H NMR (400 MHz, DMSO-d$_6$) δ ppm 8.46 (br d, J=4.6 Hz, 1H), 8.39 (d, j=4.8 Hz, 1H), 7.47-7.55 (m, 1H), 7.16-7.34 (m, 4H), 6.78-6.94 (m, 1H), 6.15-6.26 (m, 1H), 5.73-5.80 (m, 1H), 4.95 (hr s, 1H), 4.36-4.45 (m, 0.5H), 4.24-4.36 (m, 1.5H), 4.11-4.21 (m, 0.5H), 3.98-4.08 (m, 0.5H), 3.71-3.85 (m, 1H), 3.60-3.69 (m, 0.5H), 3.41-3.53 (m, 0.5H), 3.06-3.27 (m, 1H), 2.65-2.75 (m, 1H), 1.94 (d, J=1.7 Hz, 3H), 1.34 (d, J=6.2 Hz, 3H), 1.07 (d, j=6.6 Hz, 3H), 0.94 (dd, j=6.5, 0.9 Hz, 3H). m/z (ESI, +ve ion): 560.9 (M+H)$^+$.

Example 41

6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one

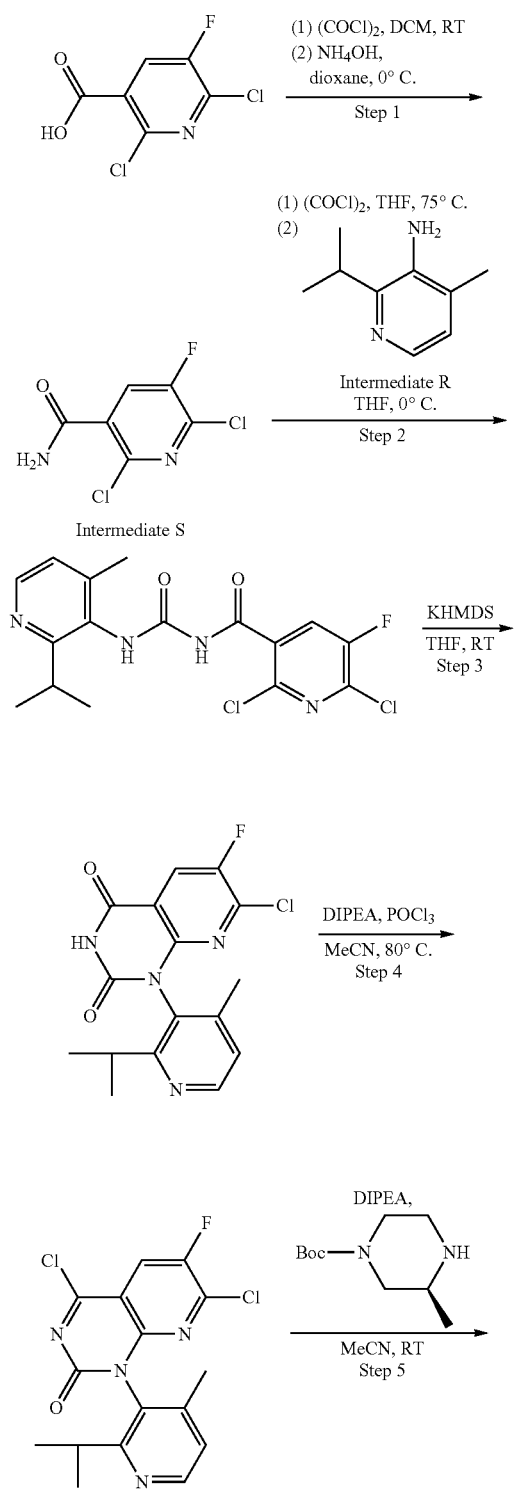

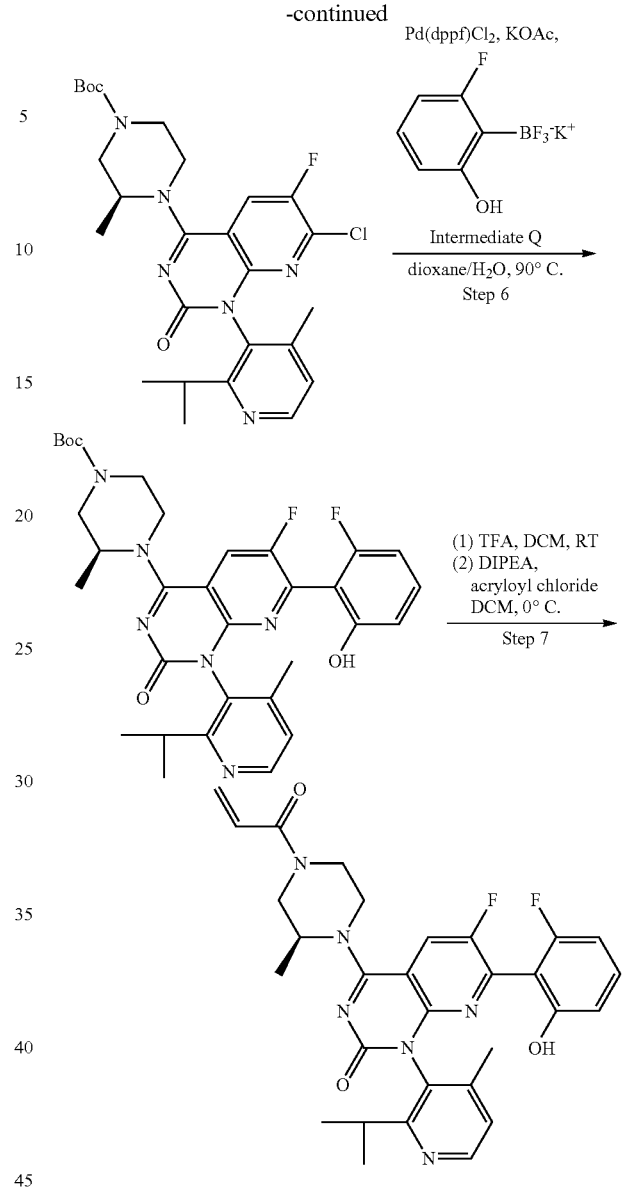

Step 1: 2,6-Dichloro-5-fluoronicotinamide (Intermediate S). To a mixture of 2,6-dichloro-5-fluoro-nicotinic acid (4.0 g, 19.1 mmol, AstaTech Inc., Bristol, PA) in dichloromethane (48 mL) was added oxalyl chloride (2M solution in DCM, 11.9 mL, 23.8 mmol), followed by a catalytic amount of DMF (0.05 mL). The reaction was stirred at room temperature overnight and then was concentrated. The residue was dissolved in 1,4-dioxane (48 mL) and cooled to 0° C. Ammonium hydroxide solution (28.0-30% $NH_3$ basis, 3.6 mL, 28.6 mmol) was added slowly via syringe. The resulting mixture was stirred at 0° C. for 30 min and then was concentrated. The residue was diluted with a 1:1 mixture of EtOAc/Heptane and agitated for 5 min, then was filtered. The filtered solids were discarded, and the remaining mother liquor was partially concentrated to half volume and filtered. The filtered solids were washed with heptane and dried in a reduced-pressure oven (45° C.) overnight to provide 2,6-dichloro-5-fluoronicotinamide. $^1$H NMR (400 MHz, DMSO-$d_6$) δ ppm 8.23 (d, J=7.9 Hz, 1H) 8.09 (hr s, 1H) 7.93 (hr s, 1H). m/z (ESI, +ve ion): 210.9 (M+H)$^+$.

Step 2: 2,6-Dichloro-5-fluoro-N-((2-isopropyl-4-methylpyridin-3-yl)carbamoyl)nicotinamide. To an ice-cooled slurry of 2,6-dichloro-5-fluoronicotinamide (Intermediate S, 5.0 g, 23.9 mmol) in THF (20 mL) was added oxalyl chloride (2 M solution in DCM, 14.4 mL, 28.8 mmol) slowly via syringe. The resulting mixture was heated at 75° C. for 1 h, then heating was stopped, and the reaction was concentrated to half volume. After cooling to 0° C., THF (20 mL) was added, followed by a solution of 2-isopropyl-4-methylpyridin-3-amine (Intermediate R, 3.59 g, 23.92 mmol) in THF (10 mL), dropwise via cannula. The resulting mixture was stirred at 0° C. for 1 h and then was quenched with a 1:1 mixture of brine and saturated aqueous ammonium chloride. The mixture was extracted with EtOAc (3×) and the combined organic layers were dried over anhydrous sodium sulfate and concentrated to provide 2,6-dichloro-5-fluoro-N-((2-isopropyl-4-methylpyridin-3-yl)carbamoyl)nicotinamide. This material was used without further purification in the following step, m/z (ESI, +ve ion): 385.1 $(M+H)^+$.

Step 3: 7-Chloro-6-fluoro-1-(2-isopropyl-4-methylpyridin-3-yl)pyrido[2,3-d]pyrimidine-2,4(1H,3H)-dione. To an ice-cooled solution of 2,6-dichloro-5-fluoro-N-((2-isopropyl-4-methylpyridin-3-yl)carbamoyl)nicotinamide (9.2 g, 24.0 mmol) in THF (40 mL) was added KHMDS (1 M solution in THF, 50.2 mL, 50.2 mmol) slowly via syringe. The ice bath was removed and the resulting mixture was stirred for 40 min at room temperature. The reaction was quenched with saturated aqueous ammonium chloride and extracted with EtOAc (3×). The combined organic layers were dried over anhydrous sodium sulfate and concentrated. The residue was purified by silica gel chromatography (eluent: 0-50% 3:1 EtOAc-EtOH/heptane) to provide 7-chloro-6-fluoro-1-(2-isopropyl-4-methylpyridin-3-yl)pyrido[2,3-d]pyrimidine-2,4(1H,3H)-dione. $^1$H NMR (400 MHz, DMSO-$d_6$) δ ppm 12.27 (hr s, 1H), 8.48-8.55 (m, 2H), 7.29 (d, J=4.8 Hz, 1H), 2.87 (quin, J=6.6 Hz, 1H), 1.99-2.06 (m, 3H), 1.09 (d, J=6.6 Hz, 3H), 1.01 (d, J=6.6 Hz, 3H). $^{19}$F NMR (376 MHz, DMSO-$d_6$) δ: −126.90 (s, 1° F.). m/z (ESI, +ve ion): 349.1 $(M+H)^+$.

Step 4: 4,7-Dichloro-6-fluoro-1-(2-isopropyl-4-methylpyridin-3-yl)pyrido[2,3-d]pyrimidin-2(1H)-one. To a solution of 7-chloro-6-fluoro-1-(2-isopropyl-4-methylpyridin-3-yl)pyrido[2,3-d]pyrimidine-2,4(1H,3H)-dione (4.7 g, 13.5 mmol) and DIPEA (3.5 mL, 20.2 mmol) in acetonitrile (20 mL) was added phosphorus oxychloride (1.63 mL, 17.5 mmol), dropwise via syringe. The resulting mixture was heated at 80° C. for 1 h, and then was cooled to room temperature and concentrated to provide 4,7-dichloro-6-fluoro-1-(2-isopropyl-4-methylpyridin-3-yl)pyrido[2,3-d]pyrimidin-2(1H)-one. This material was used without further purification in the following step, m/z (ESI, +ve ion): 367.1 $(M+H)^+$.

Step 5: (A)-tert-Butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate. To an ice-cooled solution of 4,7-dichloro-6-fluoro-1-(2-isopropyl-4-methylpyridin-3-yl)pyrido[2,3-d]pyrimidin-2(1H)-one (13.5 mmol) in acetonitrile (20 mL) was added DIPEA (7.1 mL, 40.3 mmol), followed by (<5)-4-N-Boc-2-methyl piperazine (3.23 g, 16.1 mmol, Combi-Blocks, Inc., San Diego, CA, USA). The resulting mixture was warmed to room temperature and stirred for 1 h, then was diluted with cold saturated aqueous sodium bicarbonate solution (200 mL) and EtOAc (300 mL). The mixture was stirred for an additional 5 min, the layers were separated, and the aqueous layer was extracted with more EtOAc (1×). The combined organic layers were dried over anhydrous sodium sulfate and concentrated. The residue was purified by silica gel chromatography (eluent: 0-50% EtOAc/heptane) to provide (S)-tert-butyl 4-(7-chloro-6-fluoro-1-(2-isopropyl-4-methylpyridin-3-yl)-2-fluoro-1,2-dihydropyrido[2,3-d]pyrimidin-4-yl)-3-methylpiperazine-1-carboxylate. m/z (ESI, +ve ion): 531.2 $(M+H)^+$.

Step 6: (3A)-tert-Butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate. A mixture of (S)-tert-butyl 4-(7-chloro-6-fluoro-1-(2-isopropyl-4-methylpyridin-3-yl)-2-fluoro-1,2-dihydropyrido[2,3-d]pyrimidin-4-yl)-3-methylpiperazine-1-carboxylate (4.3 g, 8.1 mmol), potassium trifluoro(2-fluoro-6-hydroxyphenyl)borate (Intermediate Q, 2.9 g, 10.5 mmol), potassium acetate (3.2 g, 32.4 mmol) and [1,1'-bis(diphenylphosphino)ferrocene]dichloropalladium(II), complex with dichloromethane (661 mg, 0.81 mmol) in 1,4-dioxane (80 mL) was degassed with nitrogen for 1 min. De-oxygenated water (14 mL) was added, and the resulting mixture was heated at 90° C. for 1 h. The reaction was allowed to cool to room temperature, quenched with half-saturated aqueous sodium bicarbonate, and extracted with EtOAc (2×) and DCM (1×). The combined organic layers were dried over anhydrous sodium sulfate and concentrated. The residue was purified by silica gel chromatography (eluent: 0-60% 3:1 EtOAc-EtOH/heptane) to provide (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 10.19 (hr s, 1H), 8.38 (d, J=5.0 Hz, 1H), 8.26 (dd, J=12.5, 9.2 Hz, 1H), 7.23-7.28 (m, 1H), 7.18 (d, J=5.0 Hz, 1H), 6.72 (d, J=8.0 Hz, 1H), 6.68 (t, J=8.9 Hz, 1H), 4.77-4.98 (m, 1H), 4.24 (hr t, J=14.2 Hz, 1H), 3.93-4.08 (m, 1H), 3.84 (br d, 0.7=12.9 Hz, 1H), 3.52-3.75 (m, 1H), 3.07-3.28 (m, 1H), 2.62-2.74 (m, 1H), 1.86-1.93 (m, 3H), 1.43-1.48 (m, 9H), 1.35 (dd, J=10.8, 6.8 Hz, 3H), 1.26-1.32 (m, 1H), 1.07 (dd, J=6.6, 1.7 Hz, 3H), 0.93 (dd, J=6.6, 2.1 Hz, 3H). $^{19}$F NMR (376 MHz, DMSO-$d_6$) δ: −115.65 (s, 1F), −128.62 (s, 1F). m/z (ESI, +ve ion): 607.3 $(M+H)^+$.

Step 7: 6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one. Trifluoroacetic acid (25 mL, 324 mmol) was added to a solution of (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (6.3 g, 10.4 mmol) in DCM (30 mL). The resulting mixture was stirred at room temperature for 1 h and then was concentrated. The residue was dissolved in DCM (30 mL), cooled to 0° C., and sequentially treated with DIPEA (7.3 mL, 41.7 mmol) and a solution of acryloyl chloride (0.849 mL, 10.4 mmol) in DCM (3 mL; added dropwise via syringe). The reaction was stirred at 0° C. for 10 min, then was quenched with half-saturated aqueous sodium bicarbonate and extracted with DCM (2×). The combined organic layers were dried over anhydrous sodium sulfate and concentrated. The residue was purified by silica gel chromatography (eluent: 0-100% 3:1 EtOAc-EtOH/heptane) to provide 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one. $^1$H NMR (400 MHz, DMSO-$d_6$) δ ppm 10.20 (s, 1H), 8.39 (d, J=4.8 Hz, 1H), 8.24-8.34 (m, 1H), 7.23-7.32 (m, 1H), 7.19 (d, J=5.0 Hz, 1H), 6.87 (td, J=16.3, 11.0 Hz, 1H), 6.74 (d, 0.7=8.6 Hz, 1H), 6.69 (t, j=8.9 Hz, 1H), 6.21 (br d, 0.7=16.2 Hz, 1H), 5.74-5.80 (m, 1H), 4.91 (br s, 1H), 4.23-4.45 (m, 2H), 3.97-4.21 (m, 1H), 3.44-3.79 (m, 2H), 3.11-3.31 (m, 1H), 2.67-2.77 (m, 1H), 1.91 (s, 3H), 1.35 (d, 0.7=6.8 Hz, 3H), 1.08 (d, J=6.6 Hz, 3H), 0.94 (d, 0.7=6.8 Hz, 3H). $^{19}$F NMR (376 MHz, DMSO-$d_6$) δ ppm −115.64 (s, 1° F.), −128.63 (s, 1F). m/z (ESI, +ve ion): 561.2 (M+H)$^+$.

Example 42

1-(2-Cyclopropyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one

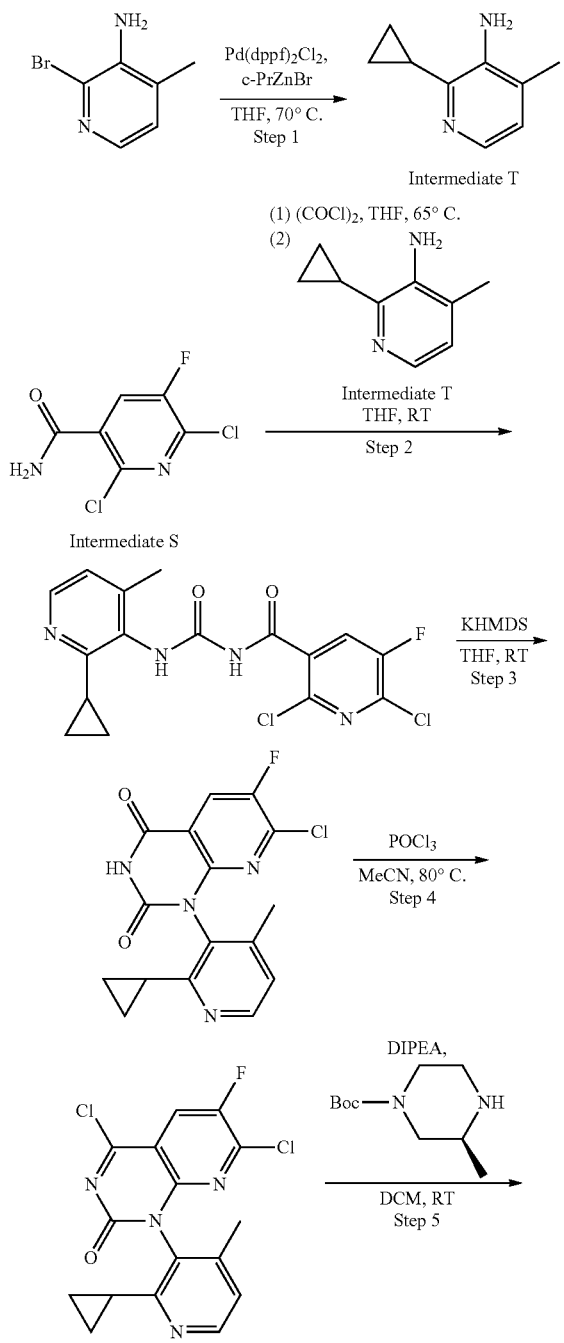

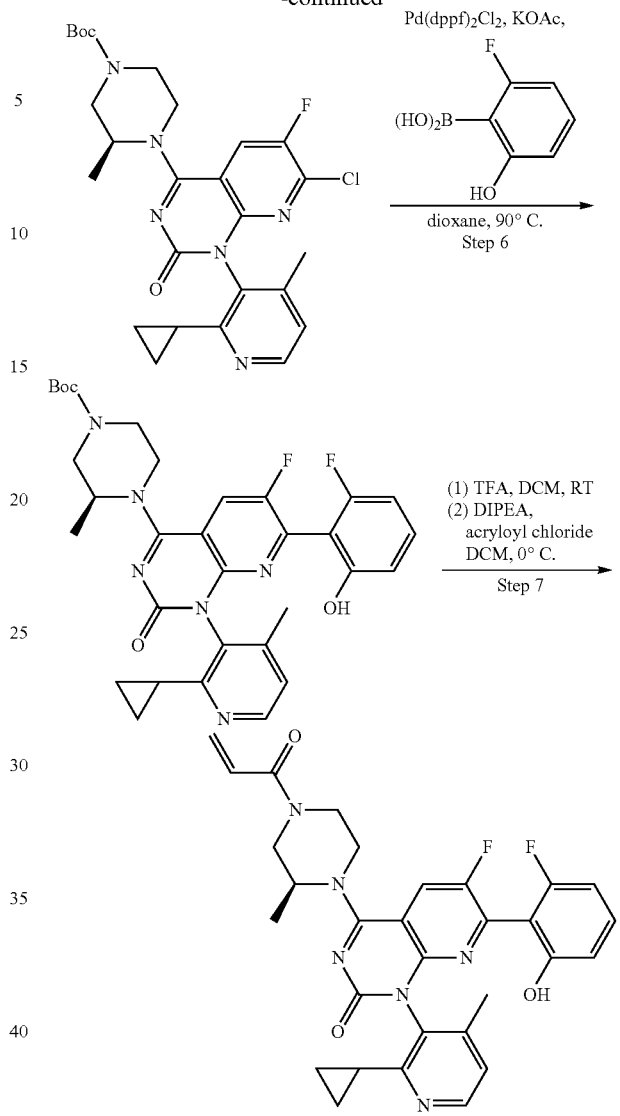

Step 1: 2-Cyclopropyl-4-methylpyridin-3-amine (Intermediate T). To a slurry of 3-amino-2-bromo-4-picoline (4.0 g, 21.4 mmol, Combi-Blocks, San Diego, CA, USA) and dichloro[1,1′-bis(diphenylphosphino)ferrocene]dichloride palladium(ii) dichloromethane adduct (1.78 g, 2.1 mmol) in THF (100 mL) was added cyclopropylzinc bromide (0.5 M solution in THF, 68.4 mL, 34.2 mmol, Sigma-Aldrich, St. Louis, MO) slowly via an addition funnel. The resulting mixture was heated at 70° C. for 6 h, then the heating was stopped and the reaction was allowed to cool to room temperature. The reaction mixture was quenched with 5 N NaOH solution and extracted with EtOAc (1×). The organic layer was dried over anhydrous magnesium sulfate and concentrated. The residue was purified by silica gel chromatography (eluent: 0-50% 3:1 EtOAc-EtOH/heptane) to provide 2-cyclopropyl-4-methylpyridin-3-amine. $^1$H NMR (400 MHz, CHLOROFORM-d) δ ppm 7.84 (d, J=4.8 Hz, 1H), 6.82 (d, J=4.8 Hz, 1H), 3.82 (br s, 2H), 2.17 (s, 3H), 1.85 (quin, J=6.7 Hz, 1H), 0.92-0.99 (m, 4H). m/z (ESI, +ve ion): 149.1 (M+H)$^+$.

Step 2: 2,6-Dichloro-N-((2-cyclopropyl-4-methylpyridin-3-yl)carbamoyl)-5-fluoronicotinamide. To a solution of 2,6- dichloro-5-fluoronicotinamide (Intermediate S, 3.0 g, 14.4 mmol) in THF (30 mL) was added oxalyl chloride (2 M solution in DCM, 10.7 mL, 21.5 mmol) slowly via syringe. The resulting mixture was heated at 65° C. for 2 h, then heating was stopped and the reaction was concentrated. The residue was dissolved in THF (30 mL) and added via cannula to a solution of 2-cyclopropyl-4-methylpyridin-3-amine (Intermediate T, 2.1 g, 14.4 mmol) in THF (105 mL). The resulting mixture was stirred at room temperature for 3 h, then was quenched with water and extracted with EtOAc (3×). The combined organic layers were dried over anhydrous sodium sulfate and concentrated. The residue was purified by silica gel chromatography (eluent: 0-50% EtOAc/heptane) to provide 2,6-dichloro-N-((2-cyclopropyl-4-methylpyridin-3-yl)carbamoyl)-5-fluoronicotinamide. $^1$H NMR (400 MHz, CHLOROFORM-d) δ ppm 9.85 (s, 1H), 9.68 (s, 1H), 8.29 (d, J=4.8 Hz, 1H), 7.97 (d, J=7.0 Hz, 1H), 6.99 (d, J=4.8 Hz, 1H), 2.29 (s, 3H), 2.08-2.16 (m, 1H), 1.08-1.13 (m, 2H), 0.95-1.02 (m, 2H). m/z (ESI, +ve ion): 383.0 (M+H)$^+$.

Step 3: 7-Chloro-1-(2-cyclopropyl-4-methylpyridin-3-yl)-6-fluoropyrido[2,3-</]pyrimidine-2,4(1H,3H)-dione. To an ice-cooled solution of 2,6-dichloro-N-((2-cyclopropyl-4-methylpyridin-3-yl)carbamoyl)-5-fluoronicotinamide (3.35 g, 8.7 mmol) in THF (30 mL) was added KHMDS (1 M solution in THF, 17.5 mL, 17.5 mmol) slowly via syringe. The ice bath was removed and the resulting mixture was stirred for 14 h at room temperature. The reaction was quenched with saturated aqueous ammonium chloride and extracted with EtOAc (3×). The combined organic layers were dried over anhydrous sodium sulfate and concentrated to provide 7-chloro-1-(2-cyclopropyl-4-methylpyridin-3-yl)-6-fluoropyrido[2,3-d]pyrimidine-2,4(1H,3H)-dione. This material was used without further purification in the following step, m/z (ESI, +ve ion): 347.0 (M+H)$^+$.

Step 4: 4,7-Dichloro-1-(2-cyclopropyl-4-methylpyridin-3-yl)-6-fluoropyrido[2,3-d]pyrimidin-2(1H)-one. To a solution of 7-chloro-1-(2-cyclopropyl-4-methylpyridin-3-yl)-6-fluoropyrido[2,3-d]pyrimidine-2,4(1H,3H)-dione (8.7 mmol) and DIPEA (2.32 mL, 13.1 mmol) in acetonitrile (25 mL) was added phosphorus oxychloride (1.22 mL, 13.1 mmol), dropwise via syringe. The resulting mixture was heated at 80° C. for 3 h, and then was cooled to room temperature and concentrated to provide 4,7-dichloro-1-(2-cyclopropyl-4-methylpyridin-3-yl)-6-fluoropyrido[2,3-d]pyrimidin-2(1H)-one. This material was used without further purification in the following step, in z (ESI, +ve ion): 365.0 (M+H)$^+$.

Step 5: (A)-tert-Butyl 4-(7-chloro-1-(2-cyclopropyl-4-methylpyridin-3-yl)-6-fluoro-2-oxo-1,2-dihydropyrido[2,3-d]pyrimidin-4-yl)-3-methylpiperazine-1-carboxylate. To an ice-cooled solution of 4,7-dichloro-1-(2-cyclopropyl-4-methylpyridin-3-yl)-6-fluoropyrido[2,3-d]pyrimidin-2(1H)-one (8.7 mmol) in DCM (25 mL) was added DIPEA (7.74 mL, 43.7 mmol), followed by (5)-4-N-Boc-2-methyl piperazine (1.75 g, 8.7 mmol, Combi-Blocks, Inc., San Diego, CA, USA). The resulting mixture was stirred at 0° C. for 2 h, then was quenched with water and extracted with EtOAc (3×). The combined organic layers were dried over anhydrous sodium sulfate and concentrated. The residue was purified by silica gel chromatography (eluent: 0-60% EtOAc/heptane) to provide (S)-tert-butyl 4-(7-chloro-1-(2-cyclopropyl-4-methylpyridin-3-yl)-6-fluoro-2-oxo-1,2-dihydropyrido[2,3-d]pyrimidin-4-yl)-3-methylpiperazine-1-carboxylate. $^1$H NMR (400 MHz, DMSO-d$_6$) δ ppm 8.31-8.39 (m, 2H), 7.18 (d, 0.7=4.8 Hz, 1H), 4.82 (hr s, 1H), 4.10-4.21 (m, 1H), 3.96 (hr s, 1H), 3.82 (br d, J=13.3 Hz, 1H), 3.62-3.72 (m, 1H), 3.19-3.52 (m, 2H), 1.94 (s, 3H), 1.62 (dq, J=8.2, 4.0 Hz, 1H), 1.45 (s, 9H), 1.32 (dd, j=6.5, 3.6 Hz, 3H), 0.87-0.98 (m, 1H), 0.69-0.84 (m, 2H), 0.57-0.68 (m, 1H). m/z (ESI, +ve ion): 529.0 (M+H)$^+$.

Step 6: (3A)-tert-Butyl 4-(1-(2-cyclopropyl-4-methylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate. A mixture of (S)-tert-butyl 4-(7-chloro-1-(2-cyclopropyl-4-methylpyridin-3-yl)-6-fluoro-2-oxo-1,2-dihydropyrido[2,3-d]pyrimidin-4-yl)-3-methylpiperazine-1-carboxylate (987 mg, 1.87 mmol), (2-fluoro-6-hydroxyphenyl)boronic acid (524 mg, 3.36 mmol, Combi-Blocks, San Diego, CA, USA), potassium acetate (916 mg, 9.33 mmol) and [1,1'-bis(diphenylphosphino)ferrocene]dichloropalladium(II), complex with dichloromethane (152 mg, 0.19 mmol) in 1,4-dioxane (10 mL) was sparged with argon and heated at 80° C. After 2 min three drops of water were added to the reaction mixture and the temperature was raised to 90° C. Heating was continued at 90° C. for 1 h, and then the reaction was allowed to cool to room temperature. Water was added and the resulting mixture was extracted with EtOAc (3×). The combined organic layers were washed with brine (1×), dried over anhydrous sodium sulfate and concentrated. The residue was purified by silica gel chromatography (eluent: 0-65% EtOAc/heptane) to provide (3S)-tert-butyl 4-(1-(2-cyclopropyl-4-methylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 10.22 (s, 1H), 8.19-8.31 (m, 2H), 7.23-7.32 (m, 1H), 7.10 (d, J=5.0 Hz, 1H), 6.74 (d, J=8.3 Hz, 1H), 6.69 (t, J=8.8 Hz, 1H), 4.76-4.98 (m, 1H), 4.15-4.31 (m, 1H), 3.99 (br s, 1H), 3.78-3.89 (m, 1H), 3.55-3.77 (m, 1H), 2.99-3.29 (m, 2H), 1.91 (d, J=2.7 Hz, 3H), 1.68 (td, J=8.0, 4.5 Hz, 1H), 1.45 (s, 9H), 1.35 (dd, J=18.7, 6.6 Hz, 3H), 0.82-0.89 (m, 1H), 0.71-0.82 (m, 2H), 0.57-0.66 (m, 1H). m/z (ESI, +ve ion): 605.0 (M+H)$^+$.

Step 7: 1-(2-Cyclopropyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one. Trifluoroacetic acid (2.17 mL, 28.1 mmol) was added to a solution of (3S)-tert-butyl 4-(1-(2-cyclopropyl-4-methylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate (850 mg, 1.41 mmol) in DCM (10 mL). The resulting mixture was stirred at room temperature for 3 h and then was concentrated. The residue was dissolved in DCM (10 mL), cooled to 0° C., and treated with DIPEA (1.23 mL, 7.03 mmol), followed by acryloyl chloride (0.103 mL, 1.27 mmol), dropwise via syringe. The reaction was stirred at 0° C. for 2 h, then was quenched with water and extracted with DCM (3×). The combined organic layers were dried over anhydrous sodium sulfate and concentrated. The residue was purified by silica gel chromatography (eluent: 0-80% 3:1 EtOAc-EtOH/heptane) to provide 1-(2-cyclopropyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one. $^1$H NMR (400 MHz, DMSO-d$_6$) δ ppm 8.32 (br t, J=10.1 Hz, 1H), 8.28 (d, j=5.0 Hz, 1H), 7.51-7.60 (m, 1H), 7.27-7.38 (m, 3H), 7.14 (d, j=4.8 Hz, 1H), 6.80-6.92 (m, 1H), 6.20 (br d, J=16.6 Hz, 1H), 5.69-5.80 (m, 1H), 4.92 (br d, J=1.5 Hz, 1H), 4.24-4.46 (m, 2H), 3.97-4.19 (m, 1H), 3.71 (br s, 1H), 3.42-3.66 (m, 1H), 3.05-3.30 (m, 1H), 1.97 (s, 3H), 1.65 (br s, 1H), 1.33 (d, j=6.6 Hz, 3H), 0.90 (td, J=5.4, 2.6 Hz, 1H), 0.80-0.87 (m, 1H), 0.70-0.79 (m, 1H), 0.60-0.70 (m, 1H). m/z (ESI, +ve ion): 559.0 (M+H)$^+$.

Example 43

6-Chloro-1-(4,6-di(2-propanyl)-5-pyrimidinyl)-7-(2-fluorophenyl)-4-((2S)-2-methyl-4-(2-propenoyl)-1-piperazinyl)pyrido[2,3-d]pyrimidin-2(1H)-one

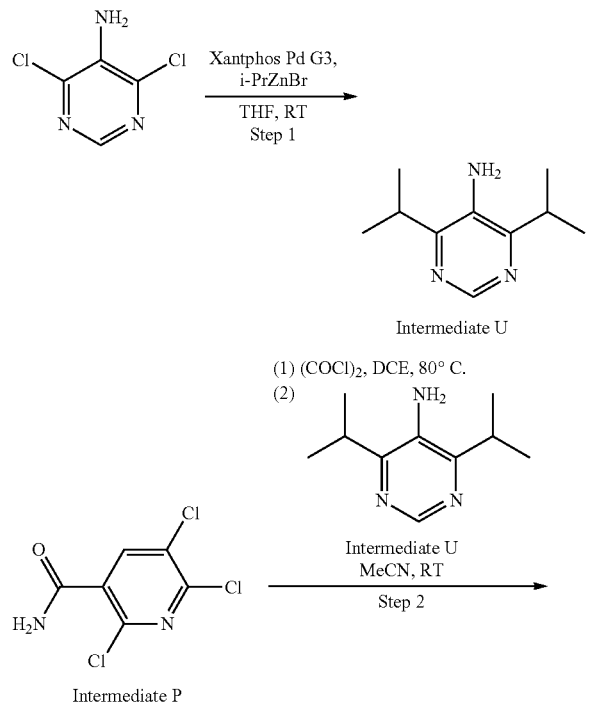

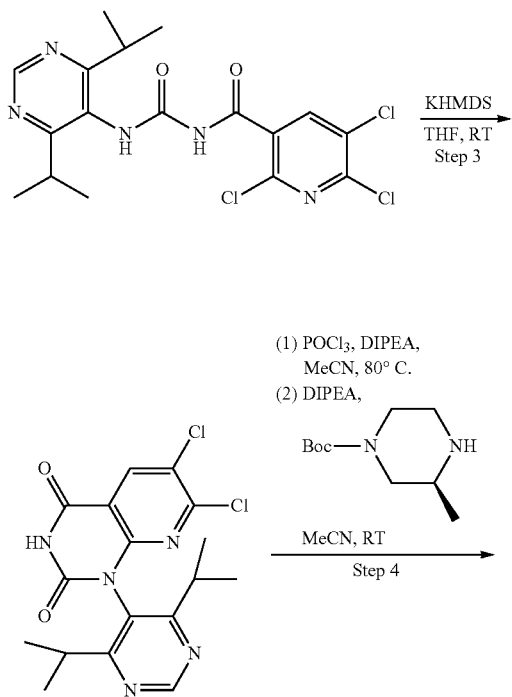

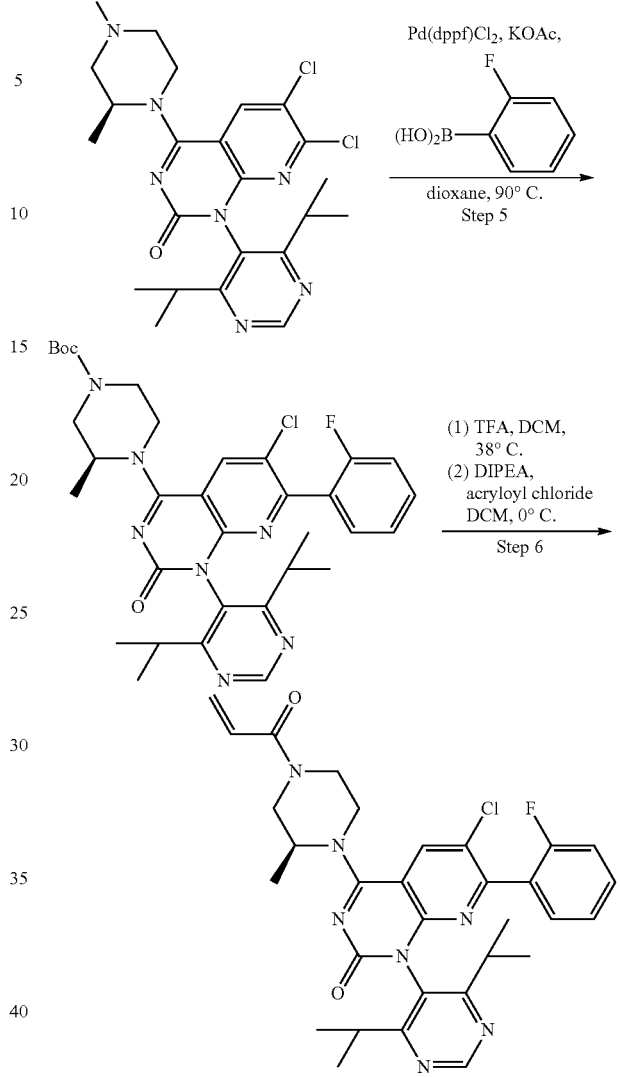

Step 1: 4,6-Diisopropylpyrimidin-5-amine (Intermediate U). A solution of 4,6-dichloro-5-aminopyrimidine (3.00 g, 18.29 mmol, Combi-Blocks Inc., San Diego, CA, USA) in THF (18 mL) was deoxygenated by bubbling argon into the mixture for 5 min. 2-Propylzinc bromide (0.5 M solution in THF, 91.0 mL, 45.5 mmol, Sigma-Aldrich, St. Louis, MO) was added via syringe followed by XantPhos Pd G3 (434 mg, 0.46 mmol, Sigma-Aldrich, St. Louis, MO, USA). The resulting mixture was stirred at room temperature for 16 h and then was filtered through a pad of Celite. The filter cake was rinsed with EtOAc, and the filtrate was collected and concentrated to afford 4,6-diisopropylpyrimidin-5-amine (3.45 g). This material was used without further purification in the following step, in z (ESI, +ve ion): 180.2 (M+H)$^+$.

Step 2: 2,5,6-Trichloro-N-((4,6-diisopropylpyrimidin-5-yl)carbamoyl)nicotinamide. A solution of 2,5,6-trichloronicotinamide (Intermediate P, 3.30 g, 14.6 mmol) in 1,2-dichloroethane (49 mL) was treated with oxalyl chloride (2 M solution in DCM, 11.0 mL, 22.0 mmol). The mixture was heated at 80° C. for 45 min, then the heating was stopped and the reaction was concentrated. The residue was dissolved in acetonitrile (49 mL), cooled to −10° C., and a solution of 4,6-diisopropylpyrimidin-5-amine (Intermediate U, 3.15 g, 17.6 mmol) in acetonitrile (5 mL) was added via cannula. The resulting mixture was stirred at room temperature overnight and then was concentrated. The residue was suspended in warm 10:1 heptane/EtOAc (110 mL) and filtered. The filtrate was concentrated and the residue was purified by silica gel chromatography (eluent: 0-40% EtOAc/heptane) to provide 2,5,6-trichloro-N-((4,6-diisopropylpyrimidin-5-yl)carbamoyl)nicotinamide. $^1$H NMR (400 MHz, DMSO-$d_6$) δ ppm 11.30-11.46 (m, 1H), 9.66 (hr s, 1H), 8.95-9.01 (m, 1H), 8.65-8.72 (m, 1H), 3.26 (s, 2H), 1.17 (d, J=6.6 Hz, 12H). m/z (ESI, +ve ion): 432.0 (M+H)$^+$.

Step 3: 6,7-Dichloro-1-(4,6-diisopropylpyrimidin-5-yl)pyrido[2,3-d]pyrimidine-2,4(1H,3H)-dione. To a −20° C. solution of 2,5,6-trichloro-N-((4,6-diisopropylpyrimidin-5-yl)carbamoyl)nicotinamide (2.10 g, 4.9 mmol) in THF (49 mL) was added KHMDS (1 M solution in THF, 12.2 mL, 12.2 mmol). The cooling bath was removed and the resulting mixture was stirred for 2 h at room temperature. The reaction mixture was quenched with saturated aqueous ammonium chloride (50 mL), diluted with brine, and extracted with 3:1 EtOAc/MeOH (1×). The layers were separated and the aqueous layer was extracted with additional EtOAc (1×). The combined organic layers were dried over anhydrous magnesium sulfate and concentrated. The residue was suspended in heptane/EtOAc and filtered. The filtrate was concentrated to provide 6,7-dichloro-1-(4,6-diisopropylpyrimidin-5-yl)pyrido[2,3-d]pyrimidine-2,4(1H,3H)-dione. $^1$H NMR (400 MHz, DMSO-$d_6$) δ ppm 12.33 (s, 1H), 9.18 (s, 1H), 8.61 (s, 1H), 2.90-3.02 (m, 2H), 1.10 (d, J=6.6 Hz, 6H), 0.99 (d, J=6.6 Hz, 6H). m/z (ESI, +ve ion): 394.0 (M+H)$^+$.

Step 4: (A)-tert-Butyl 4-(6,7-dichloro-1-(4,6-diisopropylpyrimidin-5-yl)-2-oxo-1,2-dihydropyrido[2,3-d]pyrimidin-4-yl)-3-methylpiperazine-1-carboxylate. To a solution of 6,7-dichloro-1-(4,6-diisopropylpyrimidin-5-yl)pyrido[2,3-d]pyrimidine-2,4(1H,3H)-dione (900 mg, 2.28 mmol) and DIPEA (0.518 mL, 2.97 mmol) in acetonitrile (15 mL) was added phosphorous oxychloride (0.255 mL, 2.74 mmol) slowly via syringe. The resulting mixture was heated at 80° C. for 45 min, and then was cooled to −10° C. DIPEA (1.2 mL, 6.88 mmol) was added, followed by a solution of (5)-4-N-Boc-2-methyl piperazine (1.37 g, 6.85 mmol, Combi-Blocks, Inc., San Diego, CA, USA) in acetonitrile (5 mL) via cannula. The resulting mixture was warmed to room temperature and stirred for 10 min, and then additional DIPEA (1.2 mL, 6.88 mmol) was added. The reaction mixture was poured into ice water and extracted with EtOAc (2×). The combined organic layers were washed with brine (1×), dried over anhydrous magnesium sulfate and concentrated. The residue was purified by silica gel chromatography (eluent: 0-80% EtOAc/heptane) to provide (S)-tert-butyl 4-(6,7-dichloro-1-(4,6-diisopropylpyrimidin-5-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 9.15 (s, 1H), 8.48 (s, 1H), 5.75 (s, 1H), 4.90 (hr s, 1H), 4.21 (br d, 0.7=14.1 Hz, 1H), 3.91-4.06 (m, 1H), 3.83 (br d, J=13.3 Hz, 1H), 3.73 (br t, J=10.6 Hz, 1H), 3.03-3.19 (m, 1H), 2.69 (dq, J=13.4, 6.7 Hz, 2H), 1.45 (s, 9H), 1.31-1.36 (m, 3H), 1.09 (d, J=6.6 Hz, 6H), 1.00 (d, J=6.6 Hz, 6H). m/z (ESI, +ve ion): 576.2 (M+H)$^+$.

Step 5: (A)-tert-Butyl 4-(6-chloro-1-(4,6-diisopropylpyrimidin-5-yl)-7-(2-fluorophenyl)-2-oxo-1,2-dihydropyrido[2,3-d]pyrimidin-4-yl)-3-methylpiperazine-1-carboxylate. A mixture of (5)-tert-butyl 4-(6,7-dichloro-1-(4,6-diisopropylpyrimidin-5-yl)-2-oxo-1,2-dihydropyrido[2,3-d]pyrimidin-4-yl)-3-methylpiperazine-1-carboxylate (500 mg, 0.87 mmol) and potassium acetate (426 mg, 4.34 mmol) in 1,4-dioxane (4.3 mL) was deoxygenated by bubbling argon into the mixture for 5 min. [1,1'-Bis(diphenylphosphino)ferrocene]dichloropalladium(II), complex with dichloromethane (63 mg, 0.087 mmol) was added and the mixture was heated at 90° C. for 10 min. A solution of 2-fluorophenylboronic acid (243 mg, 1.735 mmol, Combi-Blocks, Inc., San Diego, CA, USA) in 1,4-dioxane (2 mL) was added slowly followed by 6 drops of water. The resulting mixture was heated at 90° C. for 1 h. The reaction mixture was absorbed onto a plug of silica gel and purified by silica gel chromatography (eluent: 0-8% MeOH/DCM) to provide (S)-tert-butyl-4-(6-chloro-1-(4,6-diisopropylpyrimidin-5-yl)-7-(2-fluorophenyl)-2-oxo-1,2-dihydropyrido[2,3-<7]pyrimidin-4-yl)-3-methylpiperazine-1-carboxylate. $^1$H NMR (400 MHz, DMSO-$d_6$) δ ppm 9.05 (s, 1H), 8.46 (s, 1H), 8.15 (s, 1H), 7.49-7.54 (m, 1H), 7.27-7.32 (m, 1H), 7.12-7.16 (m, 1H), 4.93 (br s, 1H), 4.29 (br d, J=13.9 Hz, 1H), 4.07 (br d, j=4.6 Hz, 1H), 3.85 (br d, J=13.7 Hz, 1H), 3.75 (br t, J=11.0 Hz, 1H), 3.56 (s, 2H), 3.08-3.22 (m, 3H), 2.67-2.78 (m, 2H), 1.45 (s, 9H), 1.08 (d, J=6.6 Hz, 6H), 0.92 (d, J=6.6 Hz, 6H). m/z (ESI, +ve ion): 636.2 (M+H)$^+$.

Step 6. 6-Chloro-1-(4,6-di(2-propanyl)-5-pyrimidinyl)-7-(2-fluorophenyl)-4-((2A)-2-methyl-4-(2-propenoyl)-1-piperazinyl)pyrido[2,3-d]pyrimidin-2(1H)-one. Trifluoroacetic acid (0.176 mL, 2.36 mmol) was added to a solution of (S)-tert-butyl 4-(6-chloro-1-(4,6-diisopropylpyrimidin-5-yl)-7-(2-fluorophenyl)-2-oxo-1,2-dihydropyrido[2,3-<7]pyrimidin-4-yl)-3-methylpiperazine-1-carboxylate (150 mg, 0.24 mmol) in DCM (2.4 mL). The resulting mixture was heated at 38° C. for 2 h and then was concentrated. The residue was dissolved in DCM (2.4 mL), cooled to 0° C., and treated with DIPEA (0.494 mL, 2.83 mmol). After 2 min, acryloyl chloride (0.019 mL, 0.24 mmol) was added dropwise via syringe, and the reaction was stirred at 0° C. for an additional 10 min. The reaction mixture was concentrated and the residue was partitioned between saturated aqueous sodium bicarbonate and EtOAc (2×). The combined organic layers were dried over anhydrous magnesium sulfate and concentrated. The residue was purified by silica gel chromatography (eluent: 0-100% EtOAc/heptane followed by 0-8% MeOH/DCM) to provide 6-chloro-1-(4,6-di(2-propanyl)-5-pyrimidinyl)-7-(2-fluorophenyl)-4-((25)-2-methyl-4-(2-propenoyl)-1-piperazinyl)pyrido[2,3-<7]pyrimidin-2(1H)-one. $^1$H NMR (400 MHz, DMSO-$d_6$) δ ppm 9.06 (s, 1H), 8.46-8.52 (m, 1H), 7.48-7.55 (m, 1H), 7.26-7.34 (m, 2H), 7.17 (td, J=7.4, 1.6 Hz, 1H), 6.82-6.93 (m, 1H), 6.22 (br d, J=16.6 Hz, 1H), 5.75-5.80 (m, 1H), 5.00 (br s, 1H), 4.31-4.43 (m, 2H), 4.02-4.21 (m, 1H), 3.81 (br d, J=8.9 Hz, 1H), 3.45-3.70 (m, 1H), 3.10-3.30 (m, 1H), 2.73 (br d, J=6.4 Hz, 2H), 1.36 (d, J=6.6 Hz, 3H), 1.09 (d, J=6.6 Hz, 6H), 0.93 (d, J=6.4 Hz, 6H). m/z (ESI, +ve ion): 590.2 (M+H)$^+$.

Example 44

6-Chloro-1-(2-cyclopropyl-4-methyl-3-pyridinyl)-7-(2-fluoro-6-hydroxyphenyl)-4-((2A)-2-methyl-4-(2-propenoyl)-1-piperazinyl)pyrido[2,3-d]pyrimidin-2(1H)-one

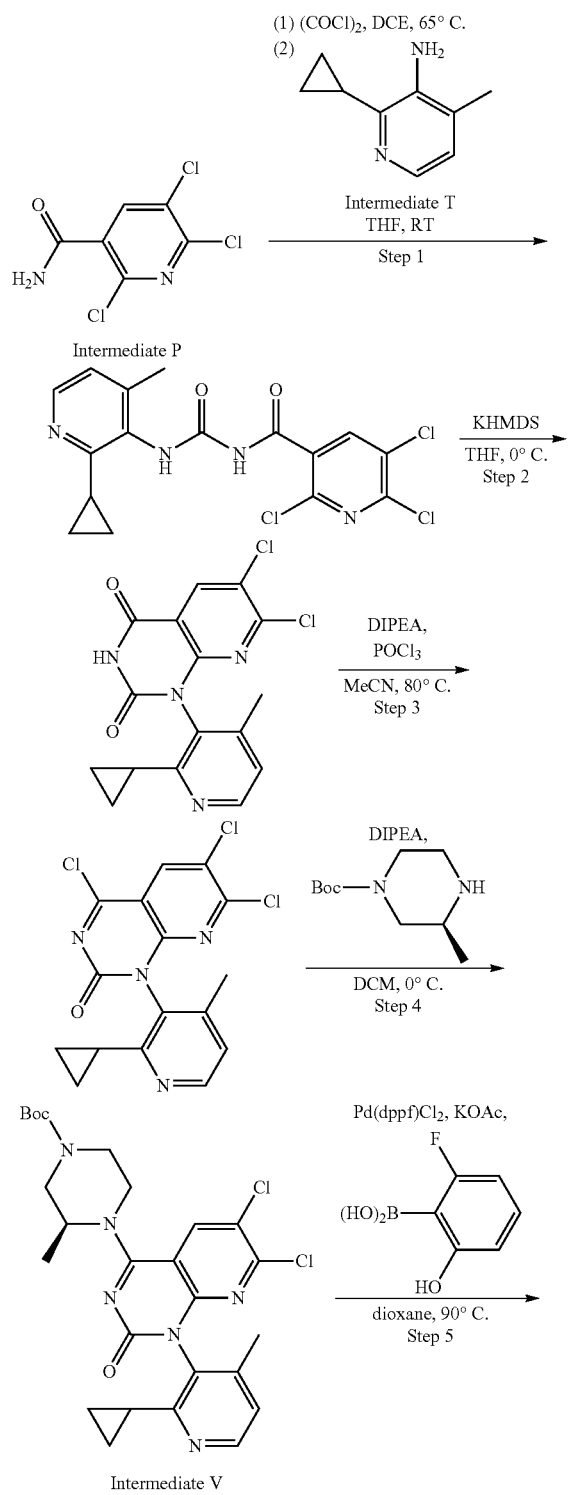

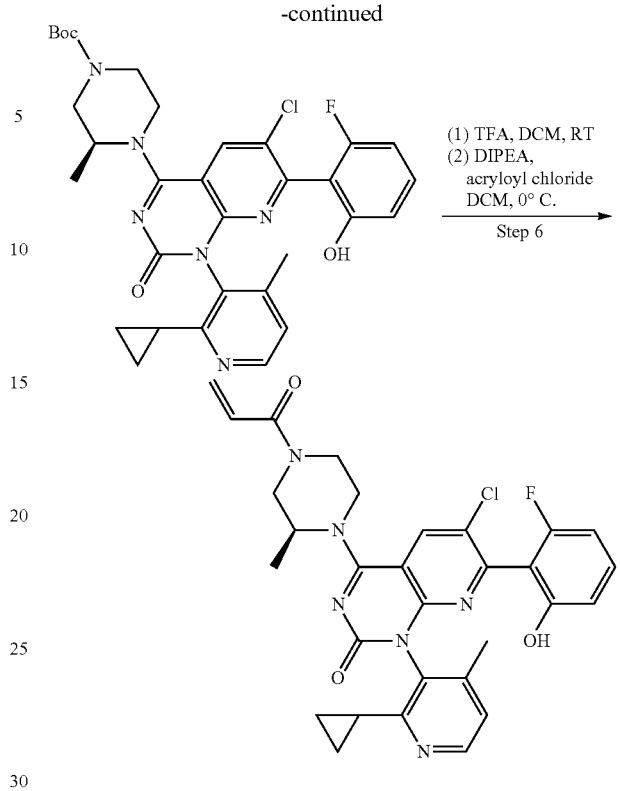

Step 1: 2,5,6-Trichloro-N-((2-cyclopropyl-4-methylpyridin-3-yl)carbamoyl)nicotinamide. To a solution of 2,5,6-trichloronicotinamide (Intermediate P, 3.5 g, 15.5 mmol) in THF (30 mL) was added oxalyl chloride (2 M solution in DCM, 11.6 mL, 23.3 mmol) slowly via syringe. The resulting mixture was heated at 65° C. for 2 h, then heating was stopped and the reaction was concentrated. The residue was dissolved in THF (30 mL) and treated with a solution of 2-cyclopropyl-4-methylpyridin-3-amine (Intermediate T, 2.5 g, 17.1 mmol) in THF (15 mL) via cannula. The resulting mixture was stirred at room temperature for 2 h, then was quenched with water and extracted with EtOAc (3×). The combined organic layers were dried over anhydrous sodium sulfate and concentrated to provide 2,5,6-trichloro-N-((2-cyclopropyl-4-methylpyridin-3-yl)carbamoyl)nicotinamide. This material was used without further purification in the following step. $^1$H NMR (400 MHz, DMSO-$d_6$) δ ppm 11.30 (hr s, 1H), 9.44-9.73 (m, 1H), 8.64 (s, 1H), 8.21 (d, J=5.0 Hz, 1H), 7.07 (d, J=5.0 Hz, 1H), 2.22 (s, 3H), 0.92 (s, 2H), 0.91 (d, J=3.5 Hz, 2H). m/z (ESI, +ve ion): 400.9 (M+H)$^+$.

Step 2: 6,7-Dichloro-1-(2-cyclopropyl-4-methylpyridin-3-yl)pyrido[2,3-d]pyrimidine-2,4(1H,3H)-dione. To an ice-cooled solution of 2,5,6-trichloro-N-((2-cyclopropyl-4-methylpyridin-3-yl)carbamoyl)nicotinamide (460 mg, 1.15 mmol) in THF (5 mL) was added KHMDS (1 M solution in THF, 2.30 mL, 2.30 mmol) slowly via syringe. The resulting mixture was stirred at 0° C. for 2 h, then was quenched with saturated aqueous ammonium chloride and extracted with EtOAc (3×). The combined organic layers were dried over anhydrous sodium sulfate and concentrated. The residue was purified by silica gel chromatography (eluent: 0-40% 3:1 EtOAc-EtOH/heptane) to provide 6,7-dichloro-1-(2-cyclopropyl-4-methylpyridin-3-yl)pyrido[2,3-d]pyrimidine-2,4 (1H,3H)-dione. $^1$H NMR (400 MHz, DMSO-$d_6$) δ ppm 12.26 (hr s, 1H), 8.59 (s, 1H), 8.36 (d, J=5.0 Hz, 1H), 7.19 (d, J=5.0 Hz, 1H), 2.05 (s, 3H), 1.86-1.96 (m, 1H), 0.88-0.95

(m, 1H), 0.79-0.87 (m, 1H), 0.73-0.79 (m, 1H), 0.62-0.70 (m, 1H). m/z (ESI, +ve ion): 362.9 (M+H)⁺.

Step 3: 4,6,7-Trichloro-1-(2-cyclopropyl-4-methylpyridin-3-yl)pyrido[2,3-d]pyrimidin-2(1H)-one. To a solution of 6,7-dichloro-1-(2-cyclopropyl-4-methylpyridin-3-yl) pyrido[2,3-d]pyrimidine-2,4(1H,3H)-dione (4.60 g, 12.7 mmol) and DIPEA (3.32 mL, 19.0 mmol) in acetonitrile (25 mL) was added phosphorus oxychloride (1.77 mL, 19.0 mmol). The resulting mixture was heated at 80° C. for 3 h, and then was cooled to room temperature and concentrated to provide 4,6,7-trichloro-1-(2-cyclopropyl-4-methylpyridin-3-yl)pyrido[2,3-d]pyrimidin-2(1H)-one. This material was used without further purification in the following step, m/z (ESI, +ve ion): 380.9 (M+H)⁺.

Step 4: (A)-tert-Butyl 4-(6,7-dichloro-1-(2-cyclopropyl-4-methylpyridin-3-yl)-2-oxo-1,2-dihydropyrido[2,3-d]pyrimidin-4-yl)-3-methylpiperazine-1-carboxylate (Intermediate V). To an ice-cooled solution of 4,6,7-trichloro-1-(2-cyclopropyl-4-methylpyridin-3-yl)pyrido[2,3-d]pyrimidin-2(1H)-one (12.7 mmol) in DCM (40 mL) was added DIPEA (11.1 mL, 63.3 mmol), followed by (S)-4-N-Boc-2-methyl piperazine (2.54 g, 12.7 mmol, Combi-Blocks, Inc., San Diego, CA, USA). The resulting mixture was stirred at 0° C. for 1 h, then was quenched with water and extracted with DCM (3×). The combined organic layers were dried over anhydrous sodium sulfate and concentrated. The residue was purified by silica gel chromatography (eluent: 0-50% 3:1 EtOAc-EtOH/heptane) to provide (S)-tert-butyl 4-(6,7-dichloro-1-(2-cyclopropyl-4-methylpyridin-3-yl)-2-oxo-1,2-dihydropyrido[2,3-d]pyrimidin-4-yl)-3-methylpiperazine-1-carboxylate. ¹H NMR (400 MHz, DMSO-d₆) δ ppm 8.44 (d, J=7.0 Hz, 1H), 8.33 (d, J=5.0 Hz, 1H), 7.17 (d, J=5.2 Hz, 1H), 4.85 (br s, 1H), 4.16 (br d, J=11.0 Hz, 1H), 3.96 (br dd, 0.7=3.4, 2.2 Hz, 1H), 3.82 (br d, J=13.3 Hz, 1H), 3.69 (q, J=12.0 Hz, 1H), 3.19-3.29 (m, 1H), 3.03-3.19 (m, 1H), 1.95 (d, J=3.9 Hz, 3H), 1.58-1.68 (m, 1H), 1.45 (s, 9H), 1.32 (dd, j=6.6, 2.5 Hz, 3H), 0.88-0.97 (m, 1H), 0.77-0.86 (m, 1H), 0.70-0.77 (m, 1H), 0.59-0.69 (m, 1H). m/z (ESI, +ve ion): 544.9 (M+H)⁺.

Step 5: (3A)-tert-Butyl 4-(6-chloro-1-(2-cyclopropyl-4-methylpyridin-3-yl)-7-(2-fluoro-6-hydroxyphenyl)-2-oxo-1,2-dihydropyrido[2,3-d]pyrimidin-4-yl)-3-methylpiperazine-1-carboxylate. A mixture of (S)-tert-butyl 4-(6,7-dichloro-1-(2-cyclopropyl-4-methylpyridin-3-yl)-2-oxo-1, 2-dihydropyrido[2,3-d]pyrimidin-4-yl)-3-methylpiperazine-1-carboxylate (Intermediate V, 992 mg, 1.82 mmol), (2-fluoro-6-hydroxyphenyl)boronic acid (510 mg, 3.27 mmol, Combi-Blocks, San Diego, CA, USA), potassium acetate (892 mg, 9.09 mmol) and [1,1'-bis(diphenylphosphino)ferrocene]dichloropalladium(II), complex with dichloromethane (119 mg, 0.15 mmol) in 1,4-dioxane (16 mL) was degassed with argon and heated at 80° C. After 2 min two drops of water were added to the reaction mixture and the temperature was raised to 90° C. Heating was continued at 90° C. for 1 h, and then the reaction was allowed to cool to room temperature. Water was added and the resulting mixture was extracted with EtOAc (3×). The combined organic layers were dried over anhydrous magnesium sulfate and concentrated. The residue was purified by silica gel chromatography (eluent: 0-50% 3:1 EtOAc-EtOH/heptane) to provide (3S)-tert-butyl 4-(6-chloro-1-(2-cyclopropyl-4-methylpyridin-3-yl)-7-(2-fluoro-6-hydroxyphenyl)-2-oxo-1,2-dihydropyrido[2,3-d]pyrimidin-4-yl)-3-methylpiperazine-1-carboxylate. ¹H NMR (400 MHz, DMSO-d₆) δ ppm 10.04-10.22 (m, 1H), 8.31-8.45 (m, 1H), 8.23 (d, j=5.0 Hz, 1H), 7.19-7.31 (m, 1H), 7.09 (br s, 1H), 6.60-6.76 (m, 2H), 4.75-5.02 (m, 1H), 4.10-4.36 (m, 1H), 3.92-4.06 (m, 1H), 3.56-3.89 (m, 2H), 2.91-3.30 (m, 2H), 1.90 (br d, J=19.3 Hz, 3H), 1.61-1.77 (m, 1H), 1.45 (s, 9H), 1.30-1.40 (m, 3H), 0.59-0.90 (m, 4H). m/z (ESI, +ve ion): 620.9 (M+H)⁺.

Step 6: 1-(2-Cyclopropyl-4-methyl-3-pyridinyl)-6-chloro-7-(2-fluoro-6-hydroxyphenyl)-4-((2A)-2-methyl-4-(2-propenoyl)-1-piperazinyl)pyrido[2,3-d]pyrimidin-2(1H)-one. Trifluoroacetic acid (2.47 mL, 33.2 mmol) was added to a solution of (3S)-tert-butyl 4-(6-chloro-1-(2-cyclopropyl-4-methylpyridin-3-yl)-7-(2-fluoro-6-hydroxyphenyl)-2-oxo-1,2-dihydropyrido[2,3-d]pyrimidin-4-yl)-3-methylpiperazine-1-carboxylate (1.03 g, 1.66 mmol) in DCM (10 mL). The resulting mixture was stirred at room temperature for 3 h and then was concentrated. The residue was dissolved in DCM (10 mL), cooled to 0° C., and treated with DIPEA (1.45 mL, 8.29 mmol) followed by acryloyl chloride (0.120 mL, 1.49 mmol), dropwise via syringe. The reaction was stirred at 0° C. for 2 h, then was quenched with water and extracted with DCM (3×). The combined organic layers were dried over anhydrous sodium sulfate and concentrated. The residue was purified by silica gel chromatography (eluent: 0-50% 3:1 EtOAc-EtOH/heptane) to provide 6-chloro-1-(2-cyclopropyl-4-methyl-3-pyridinyl)-7-(2-fluoro-6-hydroxyphenyl)-4-((2S)-2-methyl-4-(2-propenoyl)-1-piperazinyl)pyrido[2,3-d]pyrimidin-2(1H)-one. ¹H NMR (400 MHz, DMSO-d₆) δ ppm 10.06-10.26 (m, 1H), 8.33-8.49 (m, 1H), 8.23 (d, J=4.8 Hz, 1H), 7.20-7.34 (m, 1H), 7.09 (br d, J=2.1 Hz, 1H), 6.79-6.92 (m, 1H), 6.63-6.78 (m, 2H), 6.16-6.29 (m, 1H), 5.76 (dd, J=10.4, 2.3 Hz, 1H), 4.77-5.08 (m, 1H), 4.21-4.47 (m, 2H), 3.98-4.20 (m, 1H), 3.39-3.92 (m, 2H), 2.92-3.28 (m, 1H), 1.85-1.99 (m, 3H), 1.62-1.79 (m, 1H), 1.34 (br d, J=19.5 Hz, 3H), 0.74-0.88 (m, 3H), 0.56-0.68 (m, 1H). m/z (ESI, +ve ion): 574.9 (M+H)⁺.

Example 45

6-Chloro-1-(2-cyclopropyl-4-methyl-3-pyridinyl)-7-(2-fluorophenyl)-4-((2A)-2-methyl-4-(2-propenoyl)-1-piperazinyl)pyrido[2,3-d]pyrimidin-2(1H)-one

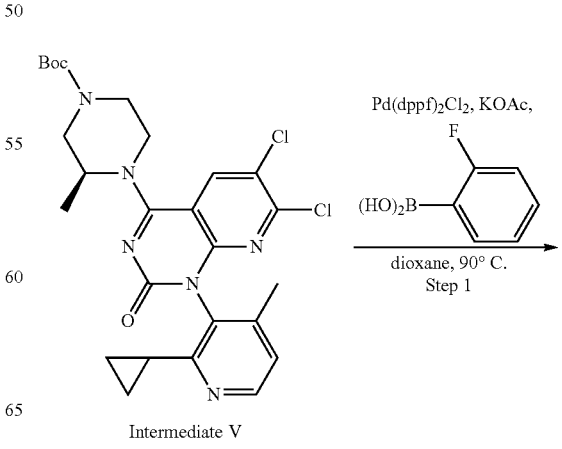

Intermediate V

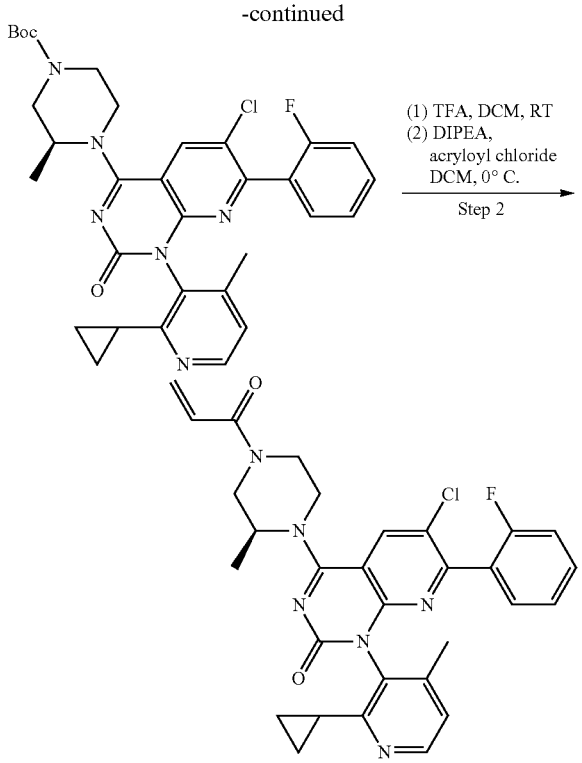

Step 1: (A)-tert-Butyl 4-(6-chloro-1-(2-cyclopropyl-4-methylpyridin-3-yl)-7-(2-fluorophenyl)-2-oxo-1,2-dihydropyrido[2,3-d]pyrimidin-4-yl)-3-methylpiperazine-1-carboxylate. A mixture of (5)-tert-butyl 4-(6,7-dichloro-1-(2-cyclopropyl-4-methylpyridin-3-yl)-2-oxo-1,2-dihydropyrido[2,3-d]pyrimidin-4-yl)-3-methylpiperazine-1-carboxylate (Intermediate V, 500 mg, 0.92 mmol), (2-fluorophenyl)boronic acid (269 mg, 1.92 mmol, Combi-Blocks, San Diego, CA, USA), potassium acetate (450 mg, 4.58 mmol) and [1,1'-bis(diphenylphosphino)ferrocene]dichloropalladium(II), complex with dichloromethane (75 mg, 0.09 mmol) in 1,4-dioxane (7 mL) was degassed with argon and heated at 80° C. After 2 min three drops of water were added to the reaction mixture and the temperature was raised to 90° C. Heating was continued at 90° C. for 1 h, and then the reaction was allowed to cool to room temperature. Water was added and the resulting mixture was extracted with EtOAc (3×). The combined organic layers were dried over anhydrous magnesium sulfate and concentrated. The residue was purified by silica gel chromatography (eluent: 0-40% 3:1 EtOAc-EtOH/heptane) to provide (S)-tert-butyl 4-(6-chloro-1-(2-cyclopropyl-4-methylpyridin-3-yl)-7-(2-fluorophenyl)-2-oxo-1,2-dihydropyrido[2,3-d]pyrimidin-4-yl)-3-methylpiperazine-1-carboxylate. ¹H NMR (400 MHz, DMSO-d₆) δ ppm 8.41 (d, J=2.5 Hz, 1H), 8.25 (d, J=5.0 Hz, 1H), 7.49-7.56 (m, 1H), 7.25-7.35 (m, 3H), 7.11 (d, J=4.8 Hz, 1H), 4.90 (br d, J=1.5 Hz, 1H), 4.24 (br d, J=13.7 Hz, 1H), 3.93-4.07 (m, 1H), 3.85 (br d, 0.7=13.9 Hz, 1H), 3.65-3.79 (m, 1H), 3.21-3.30 (m, 1H), 3.09-3.20 (m, 1H), 1.96 (s, 3H), 1.60-1.70 (m, 1H), 1.45 (s, 9H), 1.36 (d, J=6.6 Hz, 3H), 0.86-0.93 (m, 1H), 0.72-0.83 (m, 2H), 0.61-0.71 (m, 1H). m/z (ESI, +ve ion): 605.0 (M+H)⁺.

Step 2: 6-Chloro-1-(2-cyclopropyl-4-methyl-3-pyridinyl)-7-(2-fluorophenyl)-4-((2A)-2-methyl-4-(2-propenoyl)-1-piperazinyl)pyrido[2,3-d]pyrimidin-2(1H)-one. Trifluoroacetic acid (1.28 mL, 17.2 mmol) was added to a solution of (S)-tert-butyl 4-(6-chloro-1-(2-cyclopropyl-4-methylpyridin-3-yl)-7-(2-fluorophenyl)-2-oxo-1,2-dihydropyrido[2,3-d]pyrimidin-4-yl)-3-methylpiperazine-1-carboxylate (521 mg, 0.86 mmol) in DCM (10 mL). The resulting mixture was stirred at room temperature for 3 h and then was concentrated. The residue was dissolved in DCM (10 mL), cooled to 0° C., and treated with DIPEA (0.762 mL, 4.31 mmol), followed by acryloyl chloride (0.440 mL, 0.86 mmol), dropwise via syringe. The reaction was stirred at 0° C. for 2 h, then was quenched with water and extracted with DCM (1×). The organic layer was dried over anhydrous sodium sulfate and concentrated. The residue was purified by silica gel chromatography (eluent: 0-50% 3:1 EtOAc-EtOH/heptane) to provide 6-chloro-1-(2-cyclopropyl-4-methyl-3-pyridinyl)-7-(2-fluorophenyl)-4-((2S)-2-methyl-4-(2-propenoyl)-1-piperazinyl)pyrido[2,3-7]pyrimidin-2(1H)-one. ¹H NMR (400 MHz, DMSO-d₆) δ ppm 8.44 (br s, 1H), 8.25 (d, J=5.0 Hz, 1H), 7.48-7.56 (m, 1H), 7.24-7.35 (m, 3H), 7.11 (d, 0.7=5.0 Hz, 1H), 6.78-6.92 (m, 1H), 6.20 (br d, J=16.2 Hz, 1H), 5.72-5.79 (m, 1H), 4.94 (br s, 1H), 4.25-4.44 (m, 2H), 3.99-4.20 (m, 1H), 3.43-3.69 (m, 2H), 3.02-3.15 (m, 1H), 1.96 (d, J=3.3 Hz, 3H), 1.60-1.71 (m, 1H), 1.34 (d, J=6.8 Hz, 3H), 0.89 (br dd, j=8.3, 4.6 Hz, 1H), 0.72-0.84 (m, 2H), 0.61-0.71 (m, 1H). m/z (ESI, +ve ion): 559.0 (M+H)⁺.

Example 46

6-Chloro-1-(2-ethyl-4-methyl-3-pyridinyl)-7-(2-fluorophenyl)-4-((2S)-2-methyl-4-(2-propenoyl)-1-piperazinyl)pyrido[2,3-d]pyrimidin-2(1H)-one

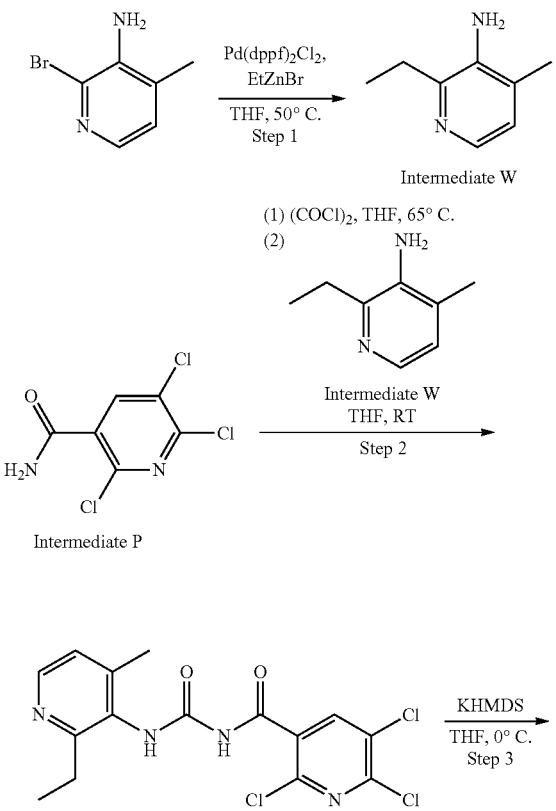

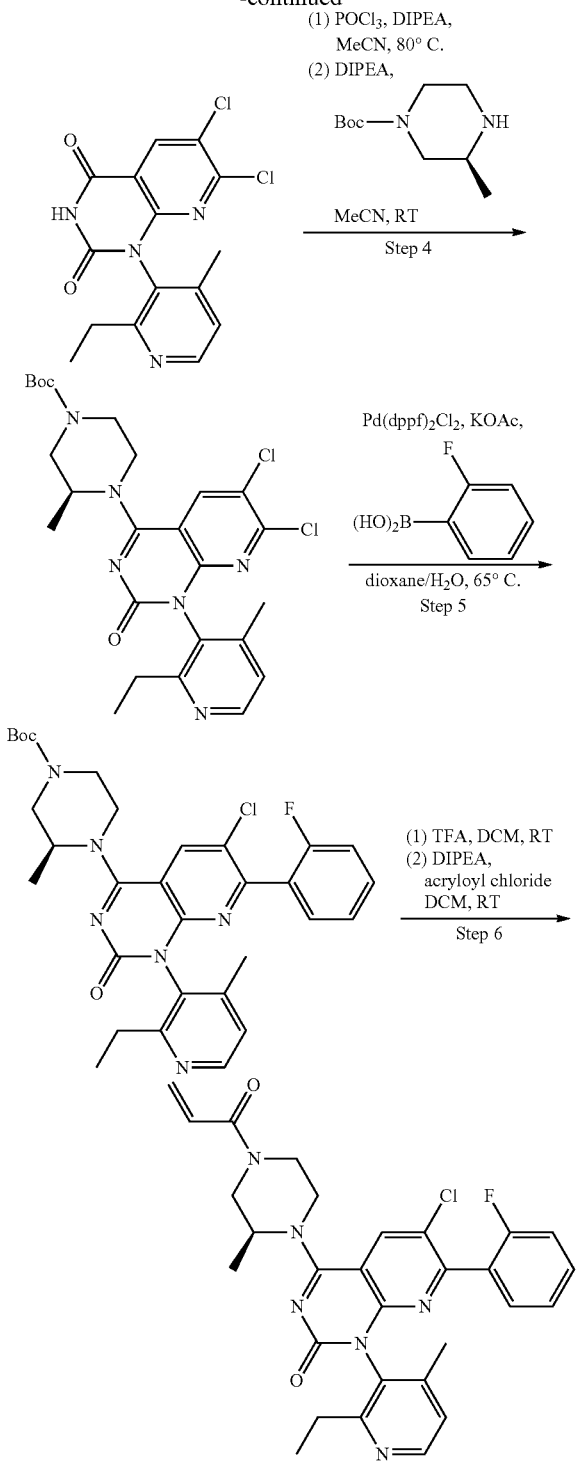

Step 1: 2-Ethyl-4-methylpyridin-3-amine (Intermediate W). Ethylmagnesium bromide (3 M solution in diethyl ether, 3.5 mL, 10.5 mmol) was added to a solution of zinc chloride (0.5 M in THF, 18 mL, 9.0 mmol) slowly via syringe. The addition was exothermic. The solution was stirred at room temperature for 10 min, and then 3-amino-2-bromo-4-picoline (1.5 g, 8.0 mmol, Combi-Blocks, San Diego, CA, USA) and dichloro[1,1'-bis(diphenylphosphino)ferrocene] dichloride palladium(ii) dichloromethane adduct (120 mg, 0.16 mmol) were added. The resulting mixture was heated at 50° C. for 20 min, then the heating was stopped and the reaction was allowed to cool to room temperature. The reaction mixture was quenched with 10% ammonium hydroxide solution (30 mL) and extracted with EtOAc (80 mL, 2×40 mL). The combined organic layers were dried over anhydrous sodium sulfate and concentrated. The residue was purified by silica gel chromatography (eluent: 1-5% MeOH/DCM) to provide 2-ethyl-4-methylpyridin-3-amine. $^1$H NMR (400 MHz, CHLOROFORM-d) δ ppm 7.92 (d, J=5.0 Hz, 1H), 6.87 (d, J=4.8 Hz, 1H), 3.59 (hr s, 2H), 2.74 (q, 0.7=7.6 Hz, 2H), 2.19 (s, 3H), 1.33 (t, 7=7.6 Hz, 3H). m/z (ESI, +ve ion): 137.1 (M+H)$^+$.

Step 2: 2,5,6-Trichloro-N-((2-ethyl-4-methylpyridin-3-yl)carbamoyl)nicotinamide. To a solution of 2,5,6-trichloronicotinamide (Intermediate P, 2.5 g, 11.1 mmol) in THF (20 mL) was added oxalyl chloride (2 M solution in DCM, 5.4 mL, 10.8 mmol) slowly via syringe. The resulting mixture was heated at 65° C. for 1.5 h, then heating was stopped and the reaction was allowed to cool to room temperature. A solution of 2-ethyl-4-methylpyridin-3-amine (Intermediate W, 1.5 g, 10.7 mmol) in THF (15 mL) was added via cannula. The resulting mixture was stirred at room temperature for 1 h, and then was partially concentrated to remove most of the THF. The residue was partitioned between saturated aqueous sodium bicarbonate (30 mL) and EtOAc (50 mL). The organic layer was washed with brine (1×), dried over anhydrous sodium sulfate and concentrated. The residue was suspended in 10:1 heptane/EtOAc (60 mL) and filtered to provide 2,5,6-trichloro-N-((2-ethyl-4-methylpyridin-3-yl)carbamoyl)nicotinamide. The product was carried on directly into the next step.

Step 3: 6,7-Dichloro-1-(2-ethyl-4-methylpyridin-3-yl)pyrido[2,3-d]pyrimidine-2,4(1H,3H)-dione. To an ice-cooled solution of 2,5,6-trichloro-N-((2-ethyl-4-methylpyridin-3-yl)carbamoyl)nicotinamide (10.7 mmol) in THF (60 mL) was added KHMDS (1 M solution in THF, 16.0 mL, 16.0 mmol) slowly via syringe. The resulting solution was stirred at 0° C. for 10 min, then was quenched with saturated aqueous ammonium chloride (20 mL) and extracted with EtOAc (60 mL). The organic layer was washed with brine (1×), dried over anhydrous sodium sulfate and concentrated. The residue was suspended in 9:1 heptane/EtOAc (60 mL) and filtered to provide 6,7-dichloro-1-(2-ethyl-4-methylpyridin-3-yl)pyrido[2,3-d]pyrimidine-2,4(1H,3H)-dione. $^1$H NMR (400 MHz, DMSO-d$_6$) δ ppm 12.14-12.39 (m, 1H), 8.54 (s, 1H), 8.47 (d, J=5.0 Hz, 1H), 7.28 (d, J=5.0 Hz, 1H), 2.41-2.49 (m, 2H), 2.03 (s, 3H), 1.07 (t, J=7.5 Hz, 3H). m/z (ESI, +ve ion): 350.9 (M+H)$^+$.

Step 4: (A)-tert-Butyl 4-(6,7-dichloro-1-(2-ethyl-4-methylpyridin-3-yl)-2-oxo-1,2-dihydropyrido[2,3-d]pyrimidin-4-yl)-3-methylpiperazine-1-carboxylate. To a solution of 6,7-dichloro-1-(2-ethyl-4-methylpyridin-3-yl)pyrido[2,3-d]pyrimidine-2,4(1H,3H)-dione (1.0 g, 2.9 mmol) and DIPEA (1.5 mL, 8.6 mmol) in acetonitrile (8 mL) was added phosphorous oxychloride (0.40 mL, 4.3 mmol). The resulting solution was heated at 80° C. for 30 min, and then was cooled to 0° C. DIPEA (1.5 mL, 8.6 mmol) was added, followed by (S)-4-N-Boc-2-methyl piperazine (800 mg, 4.0 mmol, Combi-Blocks, Inc., San Diego, CA, USA). The resulting mixture was warmed to room temperature and stirred for 30 min, then was diluted with EtOAc (30 mL) and washed with saturated aqueous sodium bicarbonate (10 mL) and brine (10 mL). The organic layer was dried over anhydrous magnesium sulfate and concentrated. The residue was purified by silica gel chromatography (eluent: 10-50% 3:1 EtOAc-EtOH/heptane) to provide (S)-tert-butyl 4-(6,7-dichloro-1-(2-ethyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 8.46 (d, J=5.0 Hz, 1H), 8.44 (s, 1H), 7.27 (d, J=5.0 Hz, 1H), 4.85 (br s, 1H), 4.12-4.21 (m, 1H), 3.95 (br s, 1H), 3.82 (br d, J=12.9 Hz, 1H), 3.69 (br d, J=11.4 Hz, 1H), 2.94-3.27 (m, 2H), 2.25-2.43 (m, 2H), 1.94 (d, J=1.7 Hz, 3H), 1.45 (s, 9H), 1.32 (t, J=6.2 Hz, 3H), 1.05 (t, J=7.6 Hz, 3H). m/z (ESI, +ve ion): 533.0 (M+H)$^+$.

Step 5: (A)-tert-Butyl 4-(6-chloro-1-(2-ethyl-4-methylpyridin-3-yl)-7-(2-fluorophenyl)-2-oxo-1,2-dihydropyrido[2,3-d]pyrimidin-4-yl)-3-methylpiperazine-1-carboxylate. A mixture of (S)-tert-butyl 4-(6,7-dichloro-1-(2-ethyl-4-methylpyridin-3-yl)-2-oxo-1,2-dihydropyrido[2,3-d]pyrimidin-4-yl)-3-methylpiperazine-1-carboxylate (450 mg, 0.84 mmol), (2-fluorophenyl)boronic acid (199 mg, 1.43 mmol, Combi-Blocks, San Diego, CA, USA), potassium acetate (250 mg, 2.55 mmol) and [1,1'-bis(diphenylphosphino)ferrocene]dichloropalladium(II), complex with dichloromethane (33 mg, 0.04 mmol) in 1,4-dioxane (5 mL) and water (1 mL) was degassed with nitrogen and heated at 65° C. for 1.5 h. The reaction was allowed to cool to room temperature, then was diluted with EtOAc (40 mL) and washed with saturated aqueous sodium bicarbonate (10 mL) and brine (10 mL). The organic layer was dried over anhydrous magnesium sulfate and concentrated. The residue was purified by silica gel chromatography (eluent: 10-50% 3:1 EtOAc-EtOH/heptane) to provide (S)-tert-butyl 4-(6-chloro-1-(2-ethyl-4-methylpyridin-3-yl)-7-(2-fluorophenyl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 8.43 (s, 1H), 8.36 (d, J=5.0 Hz, 1H), 7.47-7.55 (m, 1H), 7.20-7.33 (m, 4H), 4.90 (hr s, 1H), 4.24 (hr s, 1H), 3.99 (hr s, 1H), 3.85 (br d, J=13.3 Hz, 1H), 3.72 (br d, J=11.6 Hz, 1H), 3.33-3.47 (m, 1H), 3.03-3.21 (m, 1H), 2.30-2.43 (m, 2H), 1.95 (s, 3H), 1.46 (s, 9H), 1.36 (t, J=6.1 Hz, 3H), 1.04 (dt, J=7.5, 2.3 Hz, 3H). $^{19}$F NMR (377 MHz, CHLOROFORM-d) δ ppm −113.84−−113.85 (2s, 1F). m/z (ESI, +ve ion): 592.9 (M+H)$^+$.

Step 6: 6-Chloro-1-(2-ethyl-4-methyl-3-pyridinyl)-7-(2-fluorophenyl)-4-((2S)-2-methyl-4-(2-propenoyl)-1-piperazinyl)pyrido[2,3-d]pyrimidin-2(1H)-one. Trifluoroacetic acid (3.0 mL, 40.3 mmol) was added to a solution of (S)-tert-butyl 4-(6-chloro-1-(2-ethyl-4-methylpyridin-3-yl)-7-(2-fluorophenyl)-2-oxo-1,2-dihydropyrido[2,3-d]pyrimidin-4-yl)-3-methylpiperazine-1-carboxylate (500 mg, 0.84 mmol) in DCM (10 mL). The resulting mixture was stirred at room temperature for 30 min and then was concentrated. The residue was dissolved in DCM (10 mL) and treated with DIPEA (0.500 mL, 2.86 mmol), followed by a solution of acryloyl chloride (0.100 mL, 1.23 mmol) in DCM (2 mL). The reaction was stirred at room temperature for 30 min, and then was quenched with saturated aqueous sodium bicarbonate (10 mL) and brine (5 mL). The mixture was extracted with EtOAc (2×15 mL) and the combined organic layers were dried over anhydrous sodium sulfate and concentrated. The residue was purified by silica gel chromatography (eluent: 10-60% 3:1 EtOAc-EtOH/heptane) to provide 6-chloro-1-(2-ethyl-4-methyl-3-pyridinyl)-7-(2-fluorophenyl)-4-((2S)-2-methyl-4-(2-propenoyl)-1-piperazinyl) pyrido[2,3-d]pyrimidin-2(1H)-one. $^1$H NMR (400 MHz, CHLOROFORM-d) δ ppm 8.45 (d, J=5.0 Hz, 1H), 8.10 (s, 1H), 7.38-7.46 (m, 1H), 7.08-7.20 (m, 4H), 6.62 (br s, 1H), 6.42 (dd, J=16.7, 1.6 Hz, 1H), 5.82 (dd, J=10.5, 1.8 Hz, 1H), 4.24-5.21 (m, 3H), 3.60-4.15 (m, 3H), 3.00-3.36 (m, 1H), 2.41-2.60 (m, 2H), 2.00-2.12 (m, 3H), 1.45-1.61 (m, 3H), 1.15-1.22 (m, 3H). $^{19}$F NMR (377 MHz, CHLOROFORM-d) δ ppm −111.94−−113.08 (m, 1F). m/z (ESI, +ve ion): 547.2 (M+H)$^+$.

Example 47

6-Chloro-1-(4,6-diethyl-5-pyrimidinyl)-7-(2-fluorophenyl)-4-((2S)-2-methyl-4-(2-propenoyl)-1-piperazinyl)pyrido[2,3-d]pyrimidin-2(1H)-one

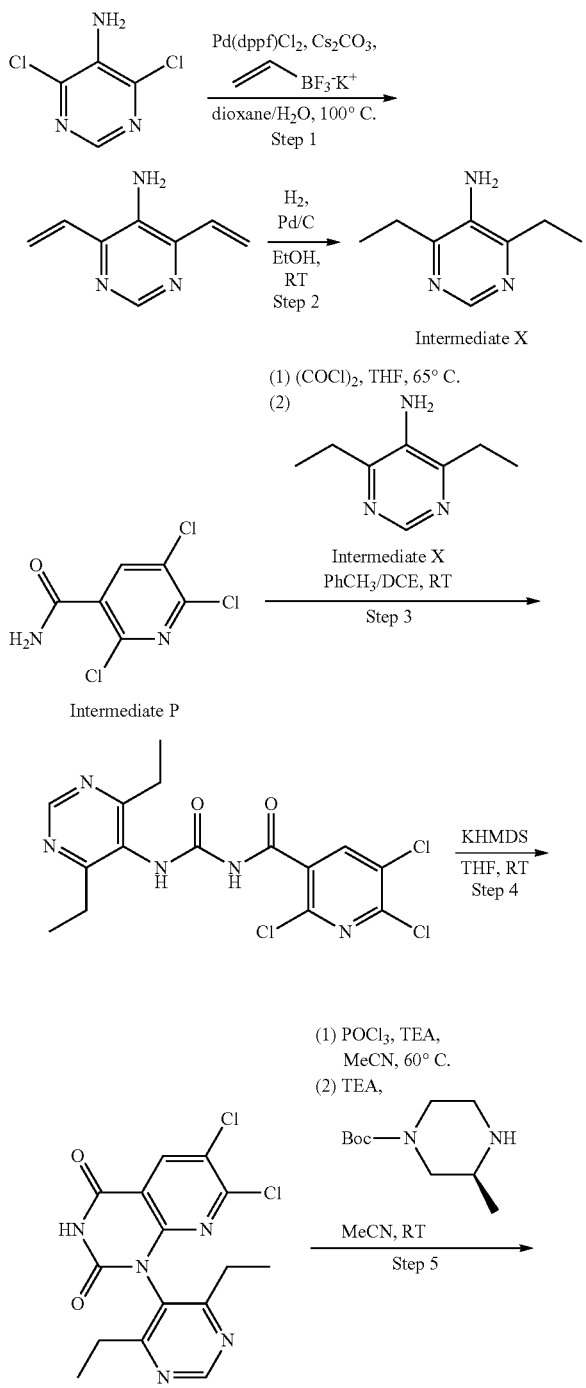

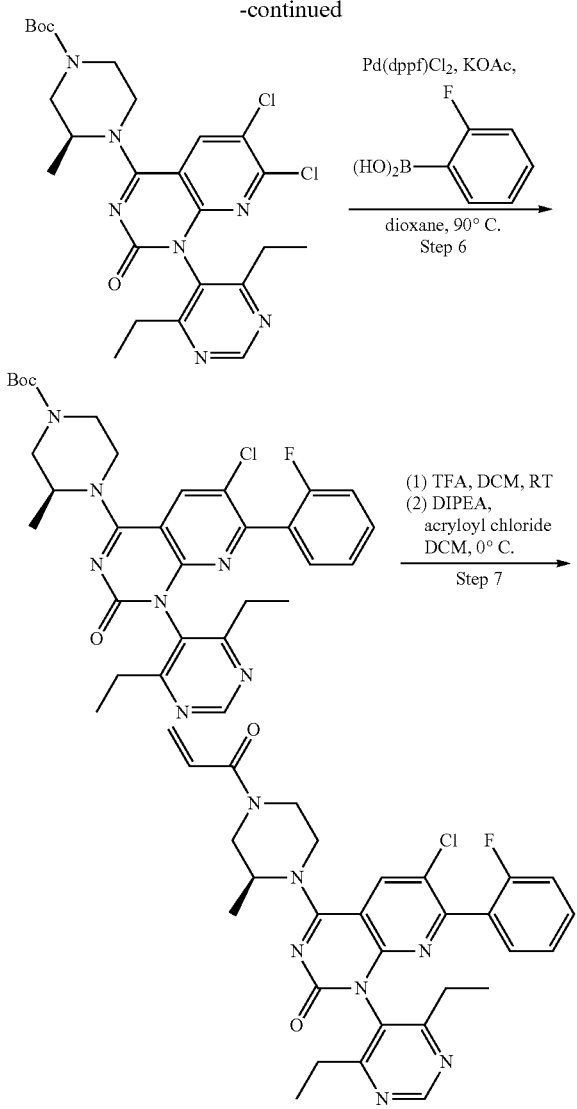

Step 1: 4,6-Divinylpyrimidin-5-amine. A mixture of 4,6-dichloro-5-aminopyrimidine (5.0 g, 30.5 mmol, Sigma Aldrich, St. Louis, MO), potassium vinyltrifluoroborate (16.3 g, 122 mmol, Sigma Aldrich, St. Louis, MO), Pd(dppf)Cl$_2$ (1.12 g, 1.52 mmol) and cesium carbonate (49.7 g, 152 mmol) in 1,4-dioxane (130 mL) and water (13 mL) was degassed with nitrogen and heated at 100° C. for 4 h. The reaction was allowed to cool to room temperature and was then diluted with water and sequentially extracted with EtOAc (3×100 mL) and DCM (5×100 mL). The combined organic layers were dried over anhydrous magnesium sulfate and concentrated. The residue was purified by silica gel chromatography (eluent: 0-20% 4:1 DCM-MeOH/DCM) to provide 4,6-divinylpyrimidin-5-amine. $^1$H NMR (400 MHz, CHLOROFORM-d) δ ppm 8.62 (s, 1H), 6.80-6.89 (m, 2H), 6.46 (dd, J=17.0, 1.7 Hz, 2H), 5.71 (dd, J=10.9, 1.8 Hz, 2H), 3.86 (br s, 2H). m/z (ESI, +ve ion): 148.1 (M+H)$^+$.

Step 2: 4,6-Diethylpyrimidin-5-amine (Intermediate X). A solution of 4,6-divinylpyrimidin-5-amine (3.1 g, 21.1 mmol) in ethanol (50 mL) was treated with palladium (10 wt. % on activated carbon, 1.12 g, 1.05 mmol). The mixture was purged with 20 psi hydrogen (4×) and stirred under 20 psi of hydrogen at room temperature for 4 h. The reaction mixture was filtered through a pad of Celite and concentrated to afford 4,6-diethylpyrimidin-5-amine. $^1$H NMR (400 MHz, CHLOROFORM-d) δ ppm 8.59 (s, 1H), 3.62 (br s, 2H), 2.70 (q, J=7.6 Hz, 4H), 1.34 (t, J=7.6 Hz, 6H). m/z (ESI, +ve ion): 152.2 (M+H)$^+$.

Step 3: 2,5,6-Trichloro-N-((4,6-diethylpyrimidin-5-yl)carbamoyl)nicotinamide. To a suspension of 2,5,6-trichloronicotinamide (Intermediate P, 4.67 g, 20.7 mmol) in THF (100 mL) was added oxalyl chloride (2 M solution in DCM, 15.5 mL, 31.0 mmol). The resulting mixture was heated at 65° C. for 1 h, then heating was stopped and the reaction was concentrated to one-third volume. Toluene (100 mL) was added and the mixture was cooled to 0° C. A solution of 4,6-diethylpyrimidin-5-amine (Intermediate X, 3.13 g, 20.7 mmol) in 1,2-dichloroethane (20 mL) was added dropwise via cannula. The resulting mixture was warmed to room temperature and stirred for 15 min, and then was concentrated. The residue was suspended in MTBE (50 mL) and filtered. The filtered solids were dried briefly in a vacuum oven at 50° C. to provide 2,5,6-trichloro-N-((4,6-diethylpyrimidin-5-yl)carbamoyl)nicotinamide. m/z (ESI, +ve ion): 402.1 (M+H)$^+$.

Step 4: 6,7-Dichloro-1-(4,6-diethylpyrimidin-5-yl)pyrido[2,3-d]pyrimidine-2,4(1H,3H)-dione. To an ice-cooled solution of 2,5,6-trichloro-N-((4,6-diethyl pyrimidino-yl)carbamoyl)nicotinamide (7.28 g, 18.1 mmol) in THF (100 mL) was added KHMDS (1 M solution in THF, 36.2 mL, 36.2 mmol) slowly via syringe. The resulting mixture was warmed to room temperature and stirred for 5 min, then was quenched with saturated aqueous ammonium chloride and extracted with EtOAc (5×100 mL). The combined organic layers were dried over anhydrous magnesium sulfate and concentrated. The residue was dried overnight in a vacuum oven at 45° C. to provide 6,7-dichloro-1-(4,6-diethylpyrimidin-5-yl)pyrido[2,3-d]pyrimidine-2,4(1H,3H)-dione. This material was used without further purification in the following step. m/z (ESI, +ve ion): 366.0 (M+H)$^+$.

Step 5: (S)-tert-Butyl 4-(6,7-dichloro-1-(4,6-diethylpyrimidin-5-yl)-2-oxo-1,2-dihydropyrido[2,3-d]pyrimidin-4-yl)-3-methylpiperazine-1-carboxylate.

A solution of 6,7-dichloro-1-(4,6-diethylpyrimidin-5-yl)pyrido[2,3-d]pyrimidine-2,4(1H,3H)-dione (3.87 g, 10.6 mmol) in acetonitrile (30 mL) was treated with triethylamine (3.71 mL, 26.4 mmol) followed by phosphorus oxychloride (1.26 mL, 12.7 mmol). The resulting mixture was heated at 60° C. for 30 min, and then was cooled to 0° C. Triethylamine (1.50 mL, 10.7 mmol) was added, followed by (S)-4-N-Boc-2-methyl piperazine (2.22 g, 11.1 mmol, Combi-Blocks, Inc., San Diego, CA, USA). The reaction mixture was warmed to room temperature and stirred for 30 min, then was partitioned between EtOAc (100 mL) and brine (40 mL). The organic layer was washed with water (30 mL) and brine (50 mL), dried over anhydrous magnesium sulfate and concentrated. The residue was purified by silica gel chromatography (eluent: 0-100% EtOAc/heptane) to provide (S)-tert-butyl 4-(6,7-dichloro-1-(4,6-diethylpyrimidin-5-yl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 9.09 (s, 1H), 8.48 (s, 1H), 4.88 (hr s, 1H), 4.19 (br d, 0.7=13.7 Hz, 1H), 3.90-4.00 (m, 1H), 3.83 (br d, J=13.7 Hz, 1H), 3.66-3.78 (m, 1H), 3.05-3.35 (m, 2H), 2.35-2.46 (m, 4H), 1.45 (s, 9H), 1.33 (d, J=6.6 Hz, 3H), 1.08 (t, J=7.5 Hz, 6H). m/z (ESI, +ve ion): 548.2 (M+H)$^+$.

Step 6: (A)-tert-Butyl 4-(6-chloro-1-(4,6-diethylpyrimidin-5-yl)-7-(2-fluorophenyl)-2-oxo-1,2-dihydropyrido[2,3-d]pyrimidin-4-yl)-3-methylpiperazine-1-carboxylate. A mixture of (S)-tert-butyl 4-(6,7-dichloro-1-(4,6-diethylpyrimidin-5-yl)-2-oxo-1,2-dihydropyrido[2,3-d]pyrimidin-4-yl)-3-methylpiperazine-1-carboxylate (354 mg, 0.65 mmol), (2-fluorophenyl)boronic acid (108 mg, 0.78 mmol, Combi-Blocks, San Diego, CA, USA), potassium acetate (317 mg, 3.23 mmol) and [1,1'-bis(diphenylphosphino)ferrocene]dichloropalladium(II), complex with dichloromethane (23 mg, 0.03 mmol) in 1,4-dioxane (6.5 mL) was degassed with argon for 5 min. Four drops of water were added and the mixture was heated at 90° C. for 30 min. The reaction was allowed to cool to room temperature, and then was partitioned between water (10 mL) and EtOAc (20 mL). The aqueous layer was extracted with DCM (20 mL). The combined organic layers were washed with brine (20 mL), dried over anhydrous magnesium sulfate and concentrated. The residue was purified by silica gel chromatography (eluent: 0-30% 4:1 DCM-MeOH/DCM) to provide (S)-tert-butyl 4-(6-chloro-1-(4,6-diethylpyrimidin-5-yl)-7-(2-fluorophenyl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 9.01 (s, 1H), 8.45 (s, 1H), 7.49-7.57 (m, 1H), 7.26-7.34 (m, 2H), 7.20-7.26 (m, 1H), 4.88-4.98 (m, 1H), 4.27 (br d, J=13.7 Hz, 1H), 3.93-4.03 (m, 1H), 3.85 (br d, J=13.5 Hz, 1H), 3.70-3.81 (m, 1H), 3.05-3.35 (m, 2H), 2.35-2.46 (m, 4H), 1.46 (s, 9H), 1.37 (d, J=6.6 Hz, 3H), 1.06 (td, J=7.5, 1.6 Hz, 6H). $^{19}$F NMR (377 MHz, DMSO-$d_6$) δ ppm −114.01 (s, 1F). m/z (ESI, +ve ion): 608.2 (M+H)$^+$.

Step 7: 6-Chloro-1-(4,6-diethyl-5-pyrimidinyl)-7-(2-fluorophenyl)-4-((2S)-2-methyl-4-(2-propenoyl)-1-piperazinyl)pyrido[2,3-d]pyrimidin-2(1H)-one. Trifluoroacetic acid (3.0 mL, 38.9 mmol) was added to a solution of (S)-tert-butyl 4-(6-chloro-1-(4,6-diethylpyrimidin-5-yl)-7-(2-fluorophenyl)-2-oxo-1,2-dihydropyrido[2,3-d]pyrimidin-4-yl)-3-methylpiperazine-1-carboxylate (327 mg, 0.54 mmol) in DCM (5 mL). The resulting mixture was stirred at room temperature for 15 min and then was concentrated. The residue was dissolved in DCM (10 mL), cooled to 0° C., and treated with DIPEA (0.470 mL, 2.69 mmol), followed by acryloyl chloride (0.048 mL, 0.59 mmol). The reaction was stirred at 0° C. for 10 min, and then additional DIPEA (0.300 mL, 1.71 mmol) was added, followed by additional acryloyl chloride (0.020 mL, 0.25 mmol). After an additional 20 min at 0° C., the reaction was quenched with saturated aqueous sodium bicarbonate (10 mL) and extracted with DCM (2×30 mL). The combined organic layers were dried over anhydrous magnesium sulfate and concentrated. The residue was purified by silica gel chromatography (eluent: 0-60% 4:1 DCM-MeOH/DCM) to provide 6-chloro-1-(4,6-diethyl-5-pyrimidinyl)-7-(2-fluorophenyl)-4-((2S)-2-methyl-4-(2-propenoyl)-1-piperazinyl)pyrido[2,3-d]pyrimidin-2(1H)-one.
$^1$H NMR (400 MHz, DMSO-$d_6$) δ ppm 9.01 (s, 1H), 8.48 (br d, J=5.0 Hz, 1H), 7.50-7.57 (m, 1H), 7.27-7.35 (m, 3H), 7.20-7.27 (m, 1H), 6.79-6.93 (m, 1H), 6.17-6.26 (m, 1H), 5.65-5.80 (m, 1H), 4.92-5.02 (m, 1H), 4.23-4.44 (m, 2H), 3.99-4.20 (m, 1H), 3.72-3.88 (m, 1H), 3.40-3.71 (m, 1H), 2.35-2.48 (m, 4H), 1.36 (d, j=6.6 Hz, 3H), 1.06 (t, j=7.5 Hz, 6H). $^{19}$F NMR (377 MHz, DMSO-$d_6$) δ ppm −114.01 (s, 1F). m/z (ESI, +ve ion): 562.1 (M+H)$^+$.

Example 48

6-Chloro-7-(2-fluoro-6-hydroxyphenyl)-4-((2S)-2-methyl-4-(2-propenoyl)-1-piperazinyl)-1-(4-(2-propanyl)-1,3-thiazol-5-yl)pyrido[2,3-d]pyrimidin-2(1H)-one

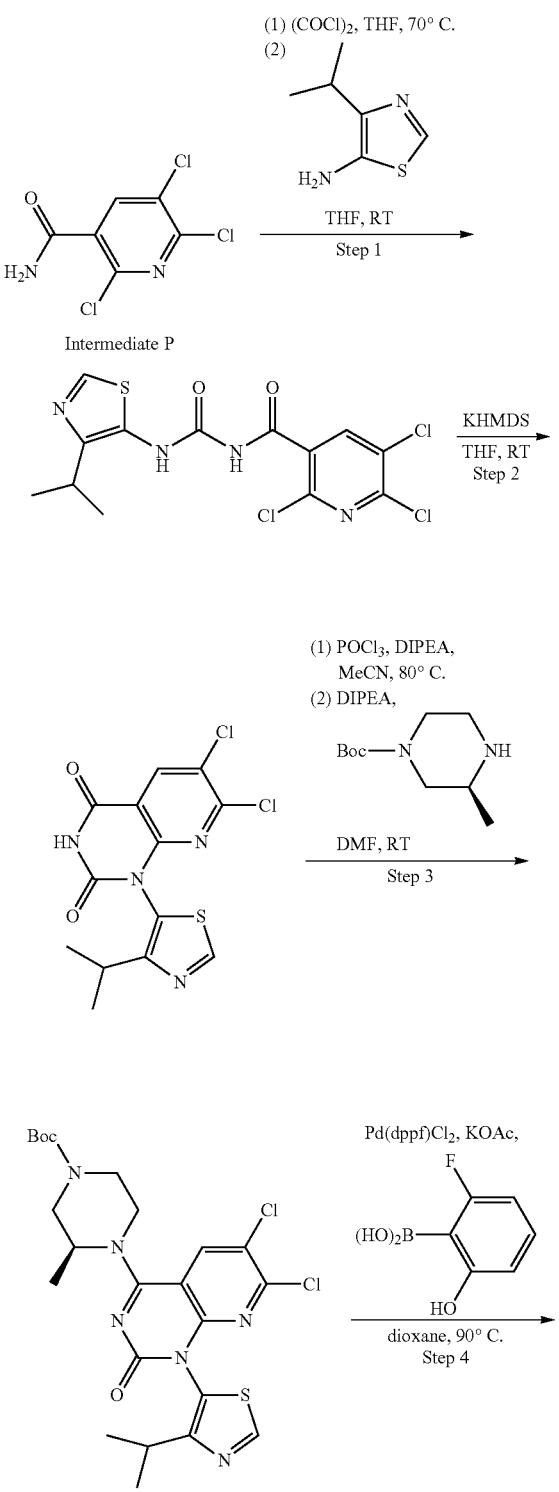

-continued

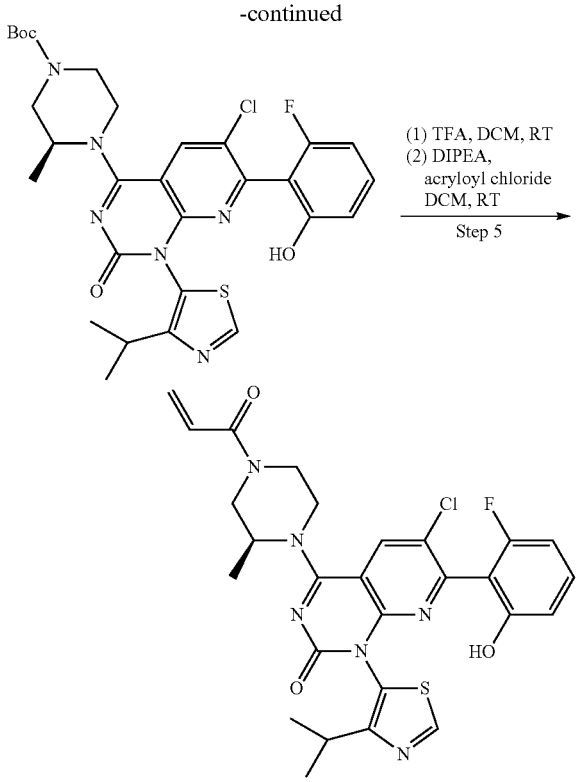

Step 1: 2,5,6-Trichloro-N-((4-isopropylthiazol-5-yl)carbamoyl)nicotinamide. To a mixture of 2,5,6-trichloronicotinamide (Intermediate P, 1.00 g, 4.5 mmol) in THF (20 mL) was added oxalyl chloride (2 M solution in DCM, 2.4 mL, 4.9 mmol). The resulting mixture was heated at 70° C. for 30 min, then heating was stopped and the reaction was allowed to cool to room temperature. 4-(Propan-2-yl)-1,3-thiazol-5-amine (715 mg, 5.0 mmol, Enamine, Monmouth Junction, NJ, USA) was added. The reaction mixture was stirred at room temperature for 10 min and then was concentrated. The residue was suspended in MeOH and filtered. The filtered solids were discarded and the filtrate was concentrated to provide 2,5,6-trichloro-N-((4-isopropylthiazol-5-yl)carbamoyl)nicotinamide. $^1$H NMR (400 MHz, DMSO-d$_6$) δ ppm 11.69 (hr s, 1H), 10.64 (hr s, 1H), 8.71 (s, 1H), 8.58 (s, 1H), 3.13 (br d, J=6.4 Hz, 1H), 1.25 (d, J=6.8 Hz, 6H). m/z (ESI, +ve ion): 393.0 (M+H)$^+$.

Step 2: 6,7-Dichloro-1-(4-isopropylthiazol-5-yl)pyrido[2,3-d]pyrimidine-2,4(1H,3H)-dione. To an ice-cooled solution of 2,5,6-trichloro-N-((4-isopropylthiazol-5-yl)carbamoyl)nicotinamide (1.75 g, 4.5 mmol) in THF (20 mL) was added KHMDS (1 M solution in THF, 9.3 mL, 9.3 mmol). The resulting mixture was warmed to room temperature and stirred for 30 min, then was re-cooled to 0° C. and treated with KHMDS (1 M solution in THF, 1.0 mL, 1.0 mmol). The reaction was warmed to room temperature and stirred for 15 min, then was quenched with half-saturated aqueous ammonium chloride (60 mL) and extracted with EtOAc (2×50 mL). The combined organic layers were washed with water (60 mL), dried by elution through a Chem Elut extraction cartridge (Agilent Technologies, Santa Clara, CA) and concentrated. The residue was purified by silica gel chromatography (eluent: 5-70% EtOAc/heptane) to provide 6,7-dichloro-1-(4-isopropylthiazol-5-yl)pyrido[2,3-d]pyrimidine-2,4(1H,3H)-dione. $^1$H NMR (400 MHz, DMSO-d$_6$) δ ppm 12.20 (s, 1H), 9.14 (s, 1H), 8.54 (s, 1H), 2.86 (quin, J=6.8 Hz, 1H), 1.11 (t, J=7.4 Hz, 6H). m/z (ESI, +ve ion): 357.0 (M+H)$^+$.

Step 3: (S)-tert-butyl 4-(6,7-dichloro-1-(4-isopropylthiazol-5-yl)-2-oxo-1,2-dihydropyrido[2,3-d]pyrimidin-4-yl)-3-methylpiperazine-1-carboxylate. To a mixture of 6,7-dichloro-1-(4-isopropylthiazol-5-yl)pyrido[2,3-d]pyrimidine-2,4(1H,3H)-dione (3.01 g, 8.4 mmol) in acetonitrile (40 mL) was added DIPEA (4.40 mL, 25.3 mmol), followed by phosphorus oxychloride (1.57 mL, 16.8 mmol). The resulting mixture was heated at 80° C. for 15 min, then was cooled to room temperature and concentrated. The residue was dissolved in DMF (30 mL) and treated with DIPEA (7.34 mL, 42.2 mmol), followed by (S)-4-N-Boc-2-methyl piperazine (1.89 g, 9.5 mmol, Sigma-Aldrich, St. Louis, MO, USA). The resulting solution was stirred at room temperature for 5 min, then ice water (100 mL) was added and the mixture was stirred for an additional 15 min. The mixture was filtered and the filtered solids were dissolved with DCM, dried by passing through a Chem Elut extraction cartridge (Agilent Technologies, Santa Clara, CA) and concentrated. The residue was purified by silica gel chromatography (eluent: 40-100% EtOAc/heptane) to provide (S)-tert-butyl 4-(6,7-dichloro-1-(4-isopropylthiazol-5-yl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 9.10 (s, 1H), 8.40 (d, J=1.7 Hz, 1H), 4.85 (hr s, 1H), 4.07-4.18 (m, 1H), 3.88-4.00 (m, 1H), 3.81 (br d, j=13.9 Hz, 1H), 3.64-3.77 (m, 1H), 3.28 (s, 1H), 3.01-3.19 (m, 1H), 2.65 (t, 0.7=13.3, 6.6 Hz, 1H), 1.44 (s, 9H), 1.31 (dd, 0.7=6.4, 3.3 Hz, 3H), 1.09-1.13 (m, 6H). m/z (ESI, +ve ion): 539.2 (M+H)$^+$.

Step 4: (3A)-tert-butyl 4-(6-chloro-7-(2-fluoro-6-hydroxyphenyl)-1-(4-isopropylthiazol-5-yl)-2-oxo-1,2-dihydropyrido[2,3-d]pyrimidin-4-yl)-3-methylpiperazine-1-carboxylate. A mixture of (5)-tert-butyl 4-(6,7-dichloro-1-(4-isopropylthiazol-5-yl)-2-oxo-1,2-dihydropyrido[2,3-d]pyrimidin-4-yl)-3-methylpiperazine-1-carboxylate (2.03 g, 3.76 mmol), potassium acetate (1.86 g, 18.9 mmol), (2-fluoro-6-hydroxyphenyl)boronic acid (911 mg, 5.84 mmol, Combi-Blocks, San Diego, CA, USA) and [1,1'-bis(diphenylphosphino)ferrocene]-dichloropalladium (II), complex with dichloromethane (282 mg, 0.39 mmol) in 1,4-dioxane (36 mL) was degassed with argon for 5 min. A drop of water was added and the resulting mixture was heated to 90° C. for 1.5 h. The reaction was allowed to cool to room temperature, and then was partitioned between water (50 mL) and EtOAc (2×50 mL). The combined organic extracts were washed with water (60 mL), dried by elution through a Chem Elut extraction cartridge (Agilent Technologies, Santa Clara, CA) and concentrated. The residue was purified by silica gel chromatography (eluent: 50-100% EtOAc/heptane) to provide (3S)-tert-butyl 4-(6-chloro-7-(2-fluoro-6-hydroxyphenyl)-1-(4-isopropylthiazol-5-yl)-2-oxo-1,2-dihydropyrido[2,3-d]pyrimidin-4-yl)-3-methylpiperazine-1-carboxylate. $^1$H NMR (400 MHz, DMSO-4) δ ppm 10.10 (s, 1H), 9.00 (s, 1H), 8.31-8.39 (m, 1H), 7.21-7.32 (m, 1H), 6.65-6.77 (m, 2H), 4.88 (hr s, 1H), 4.11-4.33 (m, 1H), 3.91-3.98 (m, 1H), 3.83 (br d, J=13.9 Hz, 1H), 3.64-3.78 (m, 1H), 3.28 (hr s, 1H), 3.03-3.21 (m, 1H), 2.63 (hr s, 1H), 1.45 (s, 9H), 1.36 (hr s, 3H), 1.09 (br d, J=6.8 Hz, 3H), 1.01 (d, 0.7=6.8 Hz, 3H). $^{19}$F NMR (376 MHz, DMSO-d$_6$) δ ppm −115.41 (hr s, 1F). m/z (ESI, +ve ion): 615.2 (M+H)$^+$.

Step 5: 6-Chloro-7-(2-fluoro-6-hydroxyphenyl)-4-((2A)-2-methyl-4-(2-propenoyl)-1-piperazinyl)-1-(4-(2-propanyl)-1,3-thiazol-5-yl)pyrido[2,3-d]pyrimidin-2(1H)-one.

Trifluoroacetic acid (10 mL, 130 mmol) was added to a solution of (3S)-tert-butyl 4-(6-chloro-7-(2-fluoro-6-hydroxyphenyl)-1-(4-isopropylthiazol-5-yl)-2-oxo-1,2-dihydropyrido[2,3-d]pyrimidin-4-yl)-3-methylpiperazine-1-carboxylate (2.15 g, 3.50 mmol) in DCM (20 mL). The reaction was stirred for 30 min at room temperature and then was concentrated. The residue was dissolved in DCM (20 mL), cooled to 0° C., and treated with DIPEA (3.05 mL, 17.5 mmol), followed by acryloyl chloride solution (0.258 M in DCM, 10.84 mL, 2.8 mmol). The reaction mixture was warmed to room temperature and stirred for 15 min, then was re-cooled to 0° C. and treated with acryloyl chloride solution (0.258 M in DCM, 2.0 mL, 0.52 mmol). After warming to room temperature and stirring for an additional 10 min, the reaction was concentrated. The residue was purified by silica gel chromatography (eluent: 40-100% 3:1 EtOAc-EtOH/heptane) to provide 6-chloro-7-(2-fluoro-6-hydroxyphenyl)-4-((2S)-2-methyl-4-(2-propenoyl)-1-piperazinyl)-1-(4-(2-propanyl)-1,3-thiazol-5-yl)pyrido[2,3-<7]pyrimidin-2(1H)-one. $^1$H NMR (400 MHz, DMSO-$d_6$) δ ppm 10.10 (s, 1H), 9.01 (s, 1H), 8.37 (hr s, 1H), 7.22-7.32 (m, 1H), 6.80-6.93 (m, 1H), 6.66-6.77 (m, 2H), 6.20 (br d, J=16.6 Hz, 1H), 5.71-5.81 (m, 1H), 4.83-5.04 (m, 1H), 3.98-4.45 (m, 3H), 3.56-3.87 (m, 2H), 3.07 (hr dd, J=4.1, 2.9 Hz, 1H), 2.59-2.70 (m, 1H), 1.33 (br d, J=5.8 Hz, 3H), 1.07-1.14 (m, 3H), 1.01 (br d, J=6.6 Hz, 3H). $^{19}$F NMR (376 MHz, DMSO-$d_6$) δ ppm −115.41 (hr s, 1F). m/z (ESI, +ve ion): 569.2 (M+H)$^+$.

Example 49

6-Chloro-7-(2-fluoro-6-hydroxyphenyl)-1-(2-(2-methyl-2-propanyl)phenyl)-4-((2S)-2-methyl-4-(2-propenoyl)-1-piperazinyl)pyrido[2,3-d]pyrimidin-2(1H)-one

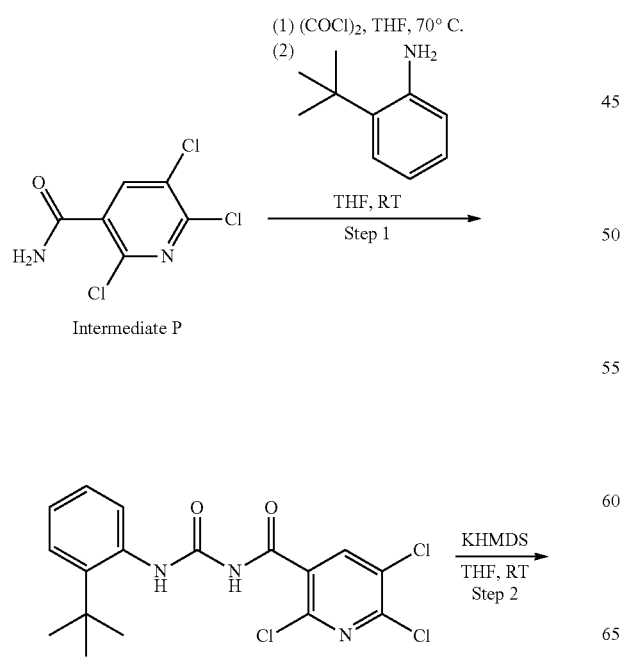

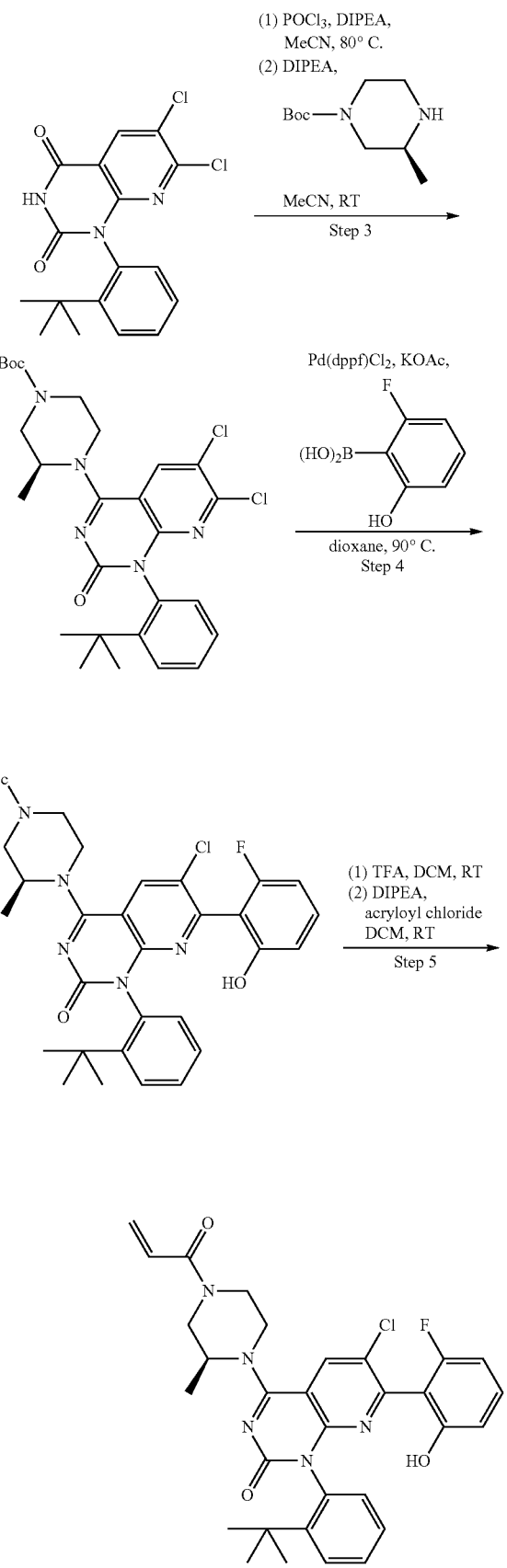

Step 1: N-((2-(tert-Butyl)phenyl)carbamoyl)-2,5,6-trichloronicotinamide. To a mixture of 2,5,6-trichloronicotinamide (Intermediate P, 1.02 g, 4.5 mmol) in THF (20 mL) was added oxalyl chloride (2 M solution in DCM, 2.5 mL, 5.0 mmol). The resulting mixture was heated at 70° C. for 40 min, then heating was stopped and the reaction was allowed to cool to room temperature. 2-tert-butylaniline (0.708 mL, 4.5 mmol, Ark Pharm, Arlington Heights, IL, USA) was added. The reaction mixture was stirred at room temperature for 10 min and then was concentrated. The residue was suspended in MeOH and filtered. The filtered solids were collected to provide N-((2-(tert-butyl)phenyl)carbamoyl)-2,5,6-trichloronicotinamide. $^1$H NMR (400 MHz, DMSO-d$_6$) δ ppm 11.43 (hr s, 1H), 9.79-10.16 (m, 1H), 8.65 (s, 1H), 7.49 (hr dd, J=7.5, 1.7 Hz, 1H), 7.43 (br d, J=7.7 Hz, 1H), 7.18-7.28 (m, 2H), 1.40 (s, 9H). m/z (ESI, +ve ion): 422.0 (M+Na)$^+$.

Step 2: 1-(2-(tert-Butyl)phenyl)-6,7-dichloropyrido[2,3-d]pyrimidine-2,4(1H,3H)-dione. To an ice-cooled mixture of N-((2-(tert-butyl)phenyl)carbamoyl)-2,5,6-trichloronicotinamide (1.26 g, 3.1 mmol) in THF (20 mL) was added KHMDS (1 M solution in THF, 6.6 mL, 6.6 mmol). The resulting mixture was warmed to room temperature and stirred for 10 min, then was quenched by addition of half-saturated aqueous ammonium chloride (60 mL) and extracted with EtOAc (2×50 mL). The combined organic layers were washed with water (60 mL), dried by elution through a Chem Elut extraction cartridge (Agilent Technologies, Santa Clara, CA) and concentrated. The residue was suspended in MeOH and filtered. The filtered solids were collected to provide 1-(2-(tert-butyl)phenyl)-6,7-dichloropyrido[2,3-d]pyrimidine-2,4(1H,3H)-dione. $^1$H NMR (400 MHz, DMSO-d$_6$) δ ppm 12.19 (s, 1H), 8.56 (s, 1H), 7.65 (dd, J=8.2, 1.3 Hz, 1H), 7.41-7.46 (m, 1H), 7.33 (td, J=7.5, 1.2 Hz, 1H), 7.21 (dd, J=7.8, 1.3 Hz, 1H), 1.17 (s, 9H). m/z (ESI, +ve ion): 364.0 (M+H)$^+$.

Step 3: (A)-tert-Butyl 4-(1-(2-(tert-butyl)phenyl)-6,7-dichloro-2-oxo-1,2-dihydropyrido[2,3-d]pyrimidin-4-yl)-3-methylpiperazine-1-carboxylate. To a mixture of 1-(2-(tert-butyl)phenyl)-6,7-dichloropyrido[2,3-d]pyrimidine-2,4(1H, 3H)-dione (925 mg, 2.54 mmol) in acetonitrile (20 mL) was added DIPEA (0.574 mL, 3.30 mmol), followed by phosphorus oxychloride (0.284 mL, 3.05 mmol). The resulting mixture was heated at 80° C. for 45 min, then was cooled to 0° C. DIPEA (1.33 mL, 7.62 mmol) was added, followed by (S)-4-N-Boc-2-methyl piperazine (0.522 g, 2.61 mmol, Sigma-Aldrich, St. Louis, MO, USA). The resulting solution was allowed to gradually warm up to room temperature over a 40 min period, then was poured into cold saturated aqueous sodium bicarbonate solution (50 mL) and stirred for an additional 10 min. The mixture was extracted with EtOAc (2×30 mL) and the combined organic extracts were dried by elution through a Chem Elut extraction cartridge (Agilent Technologies, Santa Clara, CA) and concentrated. The residue was purified by silica gel chromatography (eluent: 30-80% EtOAc/heptane) to provide (S)-tert-butyl 4-(1-(2-(tert-butyl)phenyl)-6,7-dichloro-2-oxo-1,2-dihydropyrido[2,3-d]pyrimidin-4-yl)-3-methylpiperazine-1-carboxylate. $^1$H NMR (400 MHz, DMSO-d$_6$) δ ppm 8.33-8.48 (m, 1H), 7.61 (d, J=7.9 Hz, 1H), 7.36-7.42 (m, 1H), 7.29 (td, J=7.5, 1.2 Hz, 1H), 7.00 (dd, J=7.7, 1.0 Hz, 1H), 4.68-4.89 (m, 1H), 3.88-4.25 (m, 2H), 3.77-3.86 (m, 1H), 3.52-3.71 (m, 1H), 3.09-3.26 (m, 1H), 2.84-3.07 (m, 1H), 1.44 (s, 9H), 1.24 (s, 3H), 1.13 (d, J=2.3 Hz, 9H). m/z (ESI, +ve ion): 546.2 (M+H)$^+$.

Step 4: (3A)-tert-Butyl 4-(1-(2-(tert-butyl)phenyl)-6-chloro-7-(2-fluoro-6-hydroxyphenyl)-2-oxo-1,2-dihydropyrido[2,3-d]pyrimidin-4-yl)-3-methylpiperazine-1-carboxylate. A mixture of (5)-tert-butyl 4-(1-(2-(tert-butyl)phenyl)-6,7-dichloro-2-oxo-1,2-dihydropyrido[2,3-d]pyrimidin-4-yl)-3-methylpiperazine-1-carboxylate (1.00 g, 1.83 mmol), potassium acetate (905 mg, 9.22 mmol), (2-fluoro-6-hydroxyphenyl)boronic acid (347 mg, 2.22 mmol, Combi-Blocks, San Diego, CA, USA) and [1,1'-bis(diphenylphosphino)ferrocene]-dichloropalladium (II), complex with dichloromethane (137 mg, 0.19 mmol) in 1,4-dioxane (20 mL) was degassed with argon for 5 min. A drop of water was added and the resulting mixture was heated to 90° C. for 1.5 h. The reaction was allowed to cool to room temperature, and then was partitioned between water (40 mL) and EtOAc (2×40 mL). The combined organic extracts were washed with water (40 mL), dried by elution through a Chem Elut extraction cartridge (Agilent Technologies, Santa Clara, CA) and concentrated. The residue was purified by silica gel chromatography (eluent: 40-100% EtOAc/heptane) to provide (35)-tert-butyl 4-(1-(2-(tert-butyl)phenyl)-6-chloro-7-(2-fluoro-6-hydroxyphenyl)-2-oxo-1,2-dihydropyrido[2,3-d]pyrimidin-4-yl)-3-methylpiperazine-1-carboxylate. $^1$H NMR (400 MHz, DMSO-fife) δ ppm 10.03-10.09 (m, 1H), 8.31-8.39 (m, 1H), 7.53 (d, J=8.1 Hz, 1H), 7.25-7.32 (m, 1H), 7.18-7.24 (m, 2H), 6.94 (br d, J=6.6 Hz, 1H), 6.61-6.73 (m, 2H), 4.80 (br d, J=1.2 Hz, 1H), 4.09-4.25 (m, 1H), 3.92-4.01 (m, 1H), 3.84 (br d, J=12.9 Hz, 1H), 3.63 (hr d, J=9.1 Hz, 1H), 2.99-3.26 (m, 2H), 1.45 (s, 9H), 1.29-1.37 (m, 3H), 1.11 (s, 9H). $^{19}$F NMR (376 MHz, DMSO-d$_6$) δ ppm −115.35-−115.44 (m, 1F). m/z (ESI, +ve ion): 622.2 (M+H)$^+$.

Step 5: 6-Chloro-7-(2-fluoro-6-hydroxyphenyl)-1-(2-(2-methyl-2-propanyl)phenyl)-4-((25)-2-methyl-4-(2-propenoyl)-1-piperazinyl)pyrido[2,3-d]pyrimidin-2(1H)-one. Trifluoroacetic acid (5.0 mL, 64.9 mmol) was added to a solution of (35)-tert-butyl 4-(1-(2-(tert-butyl)phenyl)-6-chloro-7-(2-fluoro-6-hydroxy phenyl)-2-oxo-1,2-dihydropyrido[2,3-d]pyrimidin-4-yl)-3-methylpiperazine-1-carboxylate (984 mg, 1.58 mmol) in DCM (10 mL). The resulting mixture was stirred at room temperature for 30 min and then was concentrated. The residue was dissolved in DCM (10 mL), cooled to 0° C., and treated with DIPEA (1.38 mL, 7.91 mmol), followed by acryloyl chloride solution (0.258 M in DCM, 4.90 mL, 1.27 mmol). The reaction mixture was warmed to room temperature and stirred for 30 min, then was re-cooled to 0° C. and treated with acryloyl chloride solution (0.258 M in DCM, 1.0 mL, 0.26 mmol). After warming to room temperature and stirring for an additional 5 min, the reaction was concentrated. The residue was purified by silica gel chromatography (eluent: 40-100% 3:1 EtOAc-EtOH/heptane) to provide 6-chloro-7-(2-fluoro-6-hydroxyphenyl)-1-(2-(2-methyl-2-propanyl)phenyl)-4-((25)-2-methyl-4-(2-propenoyl)-1-piperazinyl)pyrido[2,3-<7]pyrimidin-2(1H)-one. $^1$H NMR (400 MHz, DMSO-d$_6$) δ ppm 10.06 (br d, J=5.4 Hz, 1H), 8.38 (br d, J=12.2 Hz, 1H), 7.54 (d, J=7.7 Hz, 1H), 7.17-7.32 (m, 3H), 6.91-7.02 (m, 1H), 6.83 (hr dd, J=10.2, 16.4 Hz, 1H), 6.61-6.74 (m, 2H), 6.20 (br d, J=16.6 Hz, 1H), 5.72-5.80 (m, 1H), 4.85 (br d, J=2.1 Hz, 1H), 4.07-4.51 (m, 3H), 3.59-3.81 (m, 3H), 1.24-1.37 (m, 3H), 1.06-1.13 (m, 9H). $^{19}$F NMR (376 MHz, DMSO-d$_6$) δ ppm −115.42 (m, 1F). m/z (ESI, +ve ion): 576.2 (M+H)$^+$.

Example 50

6-Chloro-7-(2-fluorophenyl)-4-((2S)-2-methyl-4-(2-propenoyl)-1-piperazinyl)-1-(2-(2-propanyl)phenyl)-2(1H)-pteridinone

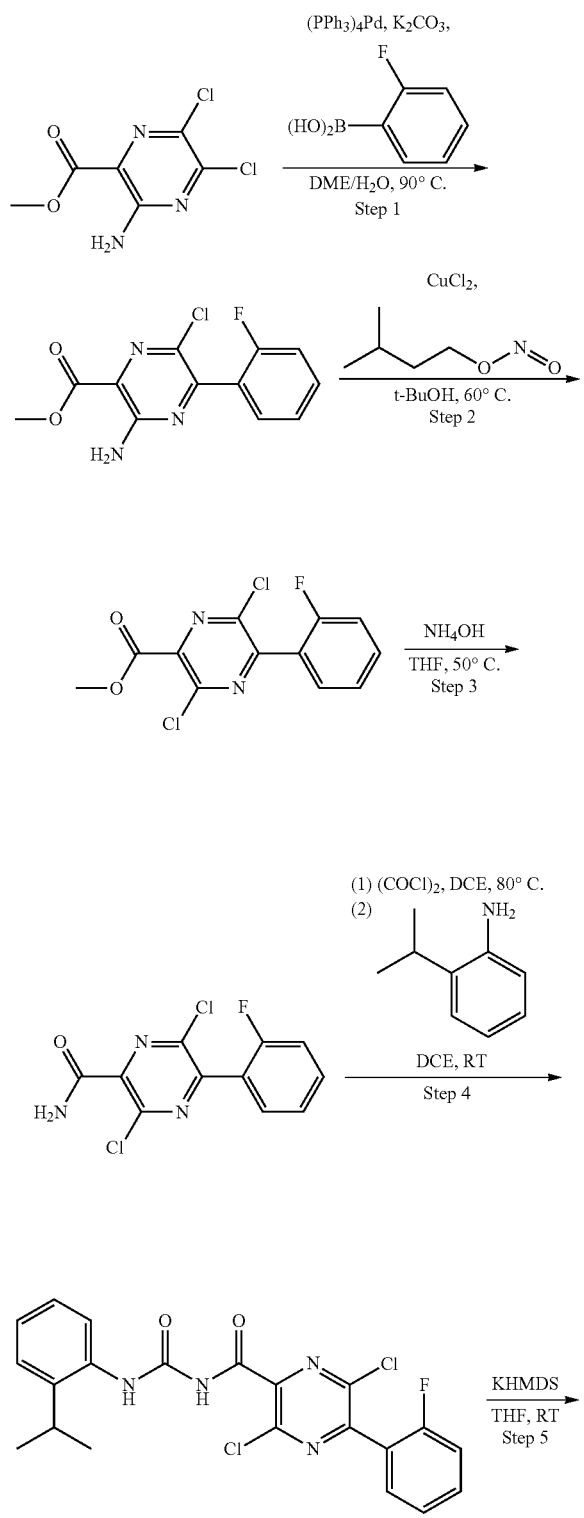

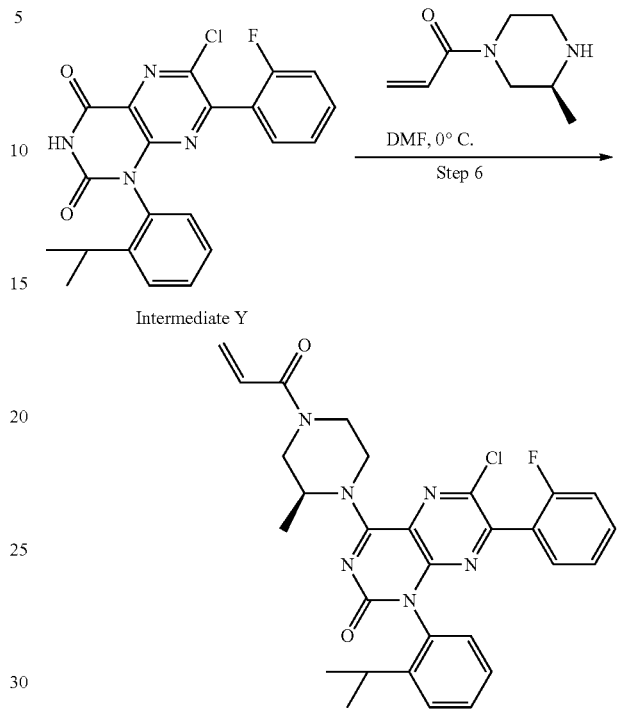

Intermediate Y

Step 1: Methyl 3-amino-6-chloro-5-(2-fluorophenyl)pyrazine-2-carboxylate. A mixture of methyl 3-amino-5,6-dichloropyrazine-2-carboxylate (10.0 g, 45 mmol, Ark Pharm, Inc., Arlington Heights, IL), (2-fluorophenyl)boronic acid (6.93 g, 49.5 mmol, Combi-Blocks, San Diego, CA, USA) and potassium carbonate (13.1 g, 95 mmol) in a 10:1 mixture of DME/water (220 mL) was degassed with nitrogen for 5 min and then tetrakis(triphenylphosphine)palladium(0) (1.04 g, 0.90 mmol) was added. The reaction mixture was stirred at 90° C. for 16 h, then was allowed to cool to room temperature and partitioned between EtOAc (200 mL) and 1 N HCl (200 mL). The organic layer was dried over anhydrous sodium sulfate and concentrated to provide methyl 3-amino-6-chloro-5-(2-fluorophenyl)pyrazine-2-carboxylate. m/z (ESI, +ve): 282.1 (M+H)$^+$.

Step 2: Methyl 3,6-dichloro-5-(2-fluorophenyl)pyrazine-2-carboxylate. To a solution of methyl 3-amino-6-chloro-5-(2-fluorophenyl)pyrazine-2-carboxylate (22.0 g, 78 mmol) in Z-BuOH (220 mL) was added isoamyl nitrite (15.8 mL, 117 mmol) and copper chloride (12.6 g, 94 mmol). The resulting mixture was stirred at 60° C. for 16 h and then was partitioned between water (1 L) and EtOAc (2 L). The organic layer was dried over anhydrous sodium sulfate and concentrated. The residue was purified by silica gel chromatography (eluent: 0-5% EtOAc/hexane) to provide methyl 3,6-dichloro-5-(2-fluorophenyl)pyrazine-2-carboxylate. m/z (ESI, +ve ion): 300.9 (M+H)$^+$.

Step 3:3,6-Dichloro-5-(2-fluorophenyl)pyrazine-2-carboxamide. To a solution of methyl 3,6-dichloro-5-(2-fluorophenyl)pyrazine-2-carboxylate (13.5 g, 44.8 mmol) in THF (150 mL) was added ammonium hydroxide solution (30%, 150 mL, 44.8 mmol). The resulting mixture was heated at 50° C. for 4 h, then was allowed to cool to room temperature and partitioned between water and EtOAc (500 mL). The organic layer was dried over anhydrous sodium sulfate and concentrated. The residue was purified by silica gel chromatography (eluent: 0-30% EtOAc/hexanes) to provide 3,6-dichloro-5-(2-fluorophenyl)pyrazine-2-carboxamide. $^1$H NMR (400 MHz, DMSO-d$_6$) δ ppm 8.32 (hr s, 1H), 8.16 (hr s, 1H), 7.64-7.77 (m, 2H), 7.41-7.47 (m, 2H). m/z (ESI, +ve): 286.0 (M+H)$^+$.

Step 4: 3,6-Dichloro-5-(2-fluorophenyl)-N-((2-isopropylphenyl)carbamoyl)pyrazine-2-carboxamide. A mixture of 3,6-dichloro-5-(2-fluorophenyl)pyrazine-2-carboxamide (704 mg, 2.46 mmol) and oxalyl chloride solution (2 M in DCM, 1.35 mL, 2.71 mmol) in DCE (15 mL) was heated at 80° C. for 1 h. The reaction was cooled to room temperature and 2-isopropylaniline (0.35 mL, 2.46 mmol) was added. The resulting mixture was stirred at room temperature for 3 h and then was concentrated. The residue was treated with EtOAc, sonicated and filtered. The filtered solids were collected to provide 3,6-dichloro-5-(2-fluorophenyl)-N-((2-isopropylphenyl)carbamoyl)pyrazine-2-carboxamide, m/z (ESI, +ve): 446.8 (M+H)$^+$.

Step 5: 6-Chloro-7-(2-fluorophenyl)-1-(2-isopropylphenyl)pteridine-2,4(1H,3H)-dione (Intermediate Y). KHMDS (1 M solution in THF, 0.93 mL, 0.93 mmol) was added to an ice-cooled mixture of 3,6-dichloro-5-(2-fluorophenyl)-N-((2-isopropylphenyl)carbamoyl)pyrazine-2-carboxamide (208 mg, 0.46 mmol) in THF (4 mL). The resulting mixture was allowed to warm to room temperature and stirred 2 h. The reaction was partitioned between EtOAc (10 mL) and saturated aqueous ammonium chloride (2×5 mL). The organic layer was dried over anhydrous sodium sulfate and concentrated. The residue was purified by silica gel chromatography (eluent: 0-50% EtOAc/heptane) to provide 6-chloro-7-(2-fluorophenyl)-1-(2-isopropylphenyl)pteridine-2,4(1H,3H)-dione. $^1$H NMR (400 MHz, CHLOROFORM-d) δ ppm 8.50 (hr s, 1H), 7.40-7.47 (m, 3H), 7.31 (dt, J=8.3, 4.2 Hz, 1H), 7.17-7.24 (m, 2H), 7.09-7.16 (m, 2H), 2.69 (quin, J=6.8 Hz, 1H), 1.22 (d, J=6.8 Hz, 3H), 1.06 (d, J=6.8 Hz, 3H). m/z (ESI, +ve): 410.9 (M+H)$^+$.

Step 6: 6-Chloro-7-(2-fluorophenyl)-4-((2S)-2-methyl-4-(2-propenoyl)-1-piperazinyl)-1-(2-(2-propanyl)phenyl)-2(1H)-pteridinone. To a solution of 6-chloro-7-(2-fluorophenyl)-1-(2-isopropylphenyl)pteridine-2,4(1H,3H)-dione (373 mg, 0.91 mmol) in acetonitrile (5 mL) was added DIPEA (0.269 mL, 1.54 mmol), followed by phosphorus oxychloride (0.127 mL, 1.36 mmol). The resulting solution was stirred at 80° C. for 30 min and then was concentrated. The residue was dissolved in DMF (5 mL), cooled to 0° C., and treated with DIPEA (0.54 mL, 3.08 mmol), followed by a solution of (S)-1-(3-methylpiperazin-1-yl)prop-2-en-1-one 2,2,2-trifluoroacetate (582 mg, 1.00 mmol) in DMF (0.5 mL). The resulting solution was stirred at 0° C. for 30 min and then was allowed to gradually warm up to room temperature. The reaction was partitioned between EtOAc (10 mL) and water (2×10 mL). The organic layer was dried over anhydrous sodium sulfate and concentrated. The residue was purified by silica gel chromatography (eluent: 0-3% MeOH/DCM) to provide 6-chloro-7-(2-fluorophenyl)-4-((2S)-2-methyl-4-(2-propenoyl)-1-piperazinyl)-1-(2-(2-propanyl)phenyl)-2(1H)-pteridinone. $^1$H NMR (400 MHz, DMSO-d$_6$) δ ppm 7.51-7.61 (m, 1H), 7.44 (dt, J=7.9, 1.9 Hz, 1H), 7.33-7.38 (m, 2H), 7.27-7.32 (m, 2H), 7.24 (br t, J=7.7 Hz, 1H), 7.13 (hr dt, J=7.9, 1.7 Hz, 1H), 6.89 (br dd, J=16.4, 10.4 Hz, 1H), 6.22 (br d, J=16.4 Hz, 1H), 5.76 (dd, J=10.2, 1.2 Hz, 1H), 4.68-5.54 (m, 1H), 4.21-4.44 (m, 6H), 2.69-2.83 (m, 1H), 1.21-1.31 (m, 3H), 1.10 (t, J=6.3 Hz, 3H), 0.99 (dd, J=6.7, 3.4 Hz, 3H). m/z (ESI, +ve): 546.8 (M+H)$^+$.

Example 51

7-(2-Fluorophenyl)-6-methyl-4-((2A)-2-methyl-4-(2-propenoyl)-1-piperazinyl)-1-(2-(2-propanyl)phenyl)-2(1H)-pteridinone

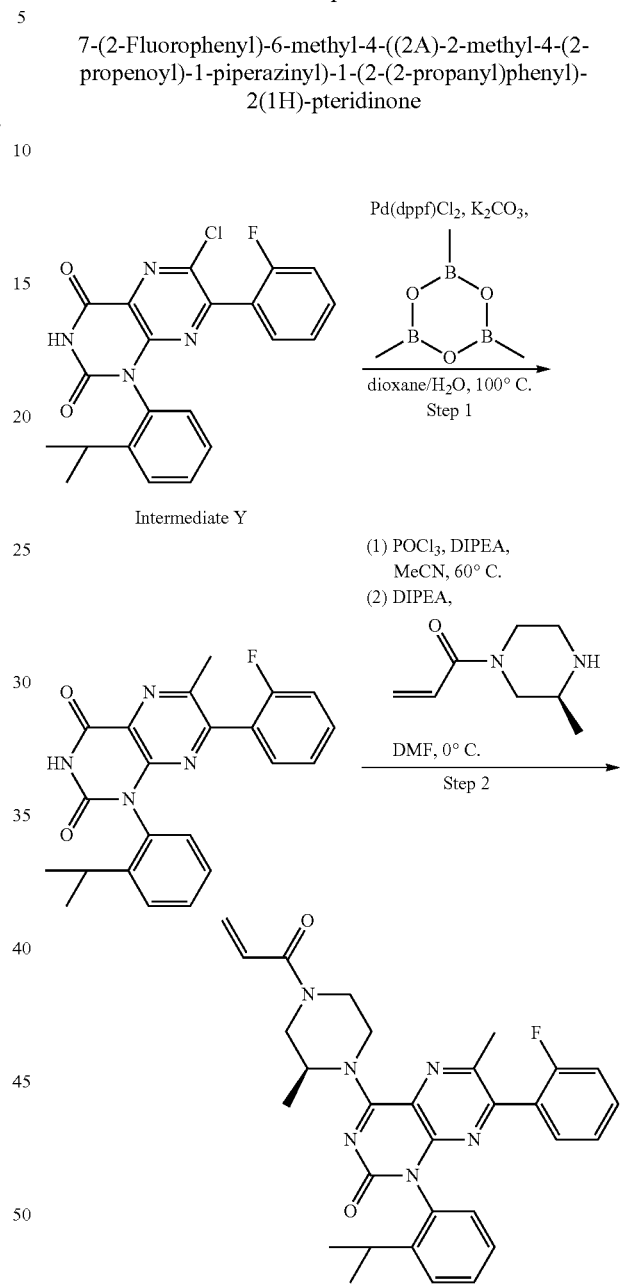

Step 1: 7-(2-Fluorophenyl)-1-(2-isopropylphenyl)-6-methylpteridine-2,4(1H,3H)-dione. A glass microwave reaction vessel was charged with a mixture of 6-chloro-7-(2-fluorophenyl)-1-(2-isopropylphenyl)pteridine-2,4(1H,3H)-dione (Intermediate Y, 930 mg, 2.27 mmol), [1,1'-bis(diphenylphosphino)ferrocene]-dichloropalladium (II), complex with dichloromethane (166 mg, 0.28 mmol), trimethylboroxine (0.64 mL, 4.54 mmol, Sigma-Aldrich, St. Louis, MO, USA) and potassium carbonate (0.63 g, 4.54 mmol) in 10:1 dioxane/water (11 mL). The reaction was degassed with nitrogen for 5 min and heated in a Emrys Optimizer microwave reactor (Biotage, Uppsala, Sweden) at 100° C. for 1.5 h. The reaction was allowed to cool to room temperature, and then was partitioned between water (10 mL) and EtOAc (10 mL). The organic layer was dried over anhydrous sodium sulfate and concentrated. The residue was purified by silica gel chromatography (eluent: 0-40% EtOAc/heptane) to provide 7-(2-fluorophenyl)-1-(2-isopropylphenyl)-6-methylpteridine-2,4(1H,3H)-dione. $^1$H NMR (400 MHz, CHLOROFORM-<7) δ ppm 8.53 (hr s, 1H), 7.38-7.48 (m, 3H), 7.30 (dt, J=8.3, 4.2 Hz, 1H), 7.08-7.20 (m, 4H), 2.71 (quin, J=6.8 Hz, 1H), 2.61 (d, j=2.3 Hz, 3H), 1.21 (d, J=6.8 Hz, 3H), 1.05 (d, J=6.8 Hz, 3H). m/z (ESI, +ve): 391.0 (M+H)$^+$.

Step 2: 7-(2-Fluorophenyl)-6-methyl-4-((2A)-2-methyl-4-(2-propenoyl)-1-piperazinyl)-1-(2-(2-propanyl)phenyl)-2(1H)-pteridinone. To a solution of 7-(2-fluorophenyl)-1-(2-isopropylphenyl)-6-methylpteridine-2,4(1H,3H)-dione (330 mg, 0.85 mmol) in acetonitrile (5 mL) was added DIPEA (0.252 mL, 1.44 mmol) followed by phosphorus oxychloride (0.119 mL, 1.27 mmol). The resulting solution was stirred at 60° C. for 1 h and then was concentrated. The residue was dissolved in DMF (5 mL), cooled to 0° C. and treated with DIPEA (0.51 mL, 2.88 mmol), followed by a solution of (5)-1-(3-methylpiperazin-1-yl)prop-2-en-1-one 2,2,2-trifluoroacetate (544 mg, 0.93 mmol) in DMF (0.5 mL) via cannula. The resulting mixture was stirred at 0° C. for 30 min and then was allowed to gradually warm up to room temperature. The reaction was partitioned between EtOAc (10 mL) and water (2×10 mL). The organic layer was dried over anhydrous sodium sulfate and concentrated. The residue was purified by silica gel chromatography (eluent: 0-3% MeOH/DCM) to provide 7-(2-fluorophenyl)-6-methyl-4-((25)-2-methyl-4-(2-propenoyl)-1-piperazinyl)-1-(2-(2-propanyl)phenyl)-2(1H)-pteridinone. $^1$H NMR (400 MHz, DMSO-d$_6$) δ ppm 7.48-7.57 (m, 1H), 7.42 (dt, 0.7=7.7, 1.9 Hz, 1H), 7.32-7.37 (m, 2H), 7.20-7.31 (m, 3H), 7.10 (br dt, 0.7=7.1, 1.0 Hz, 1H), 6.80-6.95 (m, 1H), 6.20 (br d, 0.7=16.6 Hz, 1H), 5.75 (dd, J=10.3, 2.0 Hz, 1H), 4.66-5.57 (m, 1H), 4.13-4.46 (m, 3H), 3.44-3.73 (m, 3H), 2.56-2.70 (m, 1H), 2.42 (s, 3H), 1.25 (br s, 3H), 1.09 (t, J=6.1 Hz, 3H), 0.97 (dd, j=6.6, 1.7 Hz, 3H). m/z (ESI, +ve): 527.0 (M+H)$^+$.

Example 52

7-(2-fluoro-6-hydroxyphenyl)-6-methyl-4-((2S)-2-methyl-4-(2-propenoyl)-1-piperazinyl)-1-(2-(2-propanyl)phenyl)pyrido[2,3-d]pyrimidin-2(1H)-one

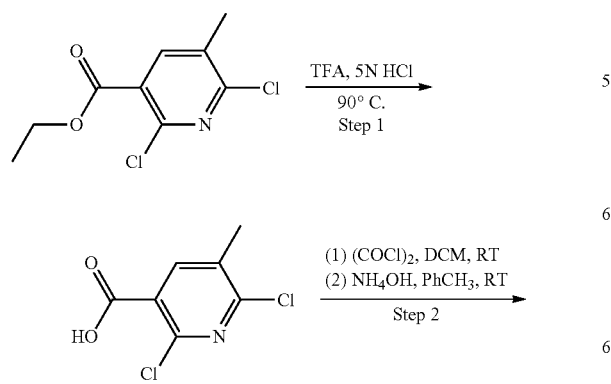

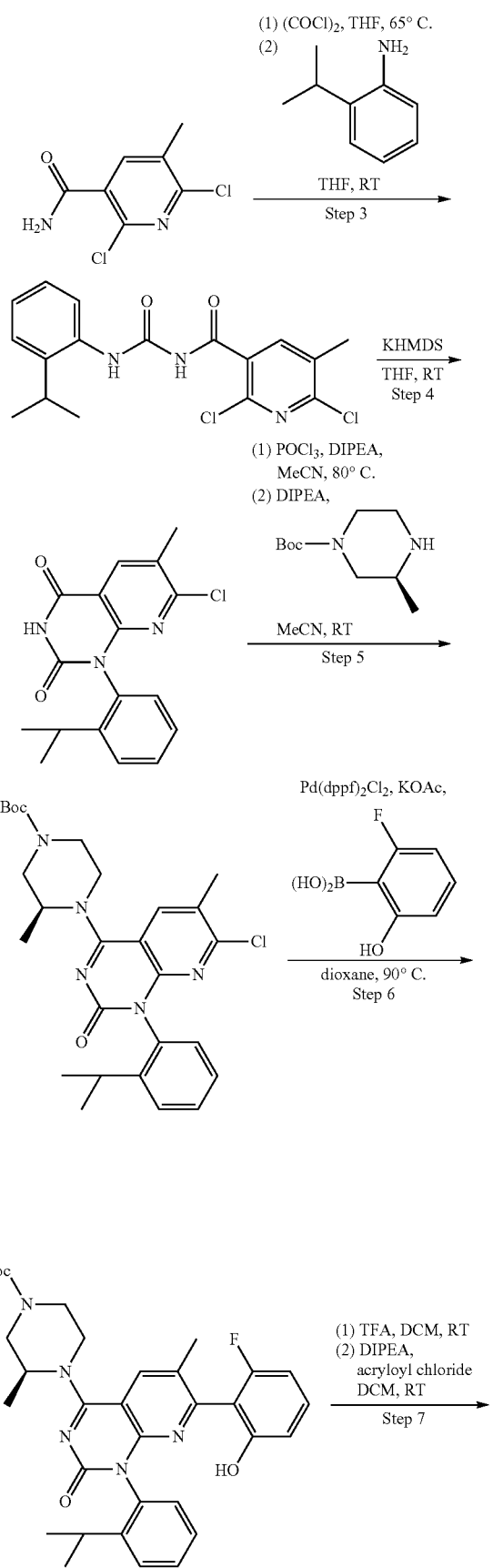

-continued

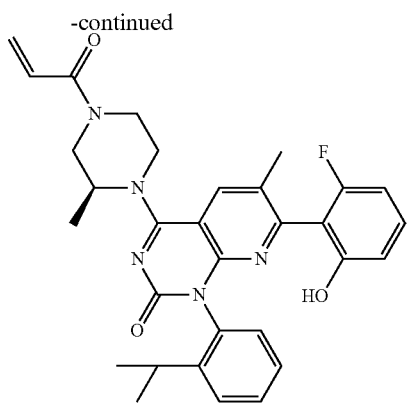

Step 1: 2,6-Dichloro-5-methylnicotinic acid. A mixture of ethyl 2,6-dichloro-5-methylnicotinate (6.49 g, 27.7 mmol, Pharmablock Inc., Sunnyvale, CA, USA) in TFA (30 mL) and 5 N HCl (24 mL) was heated at 90° C. for 16 h. The reaction was allowed to cool to room temperature and then was partially concentrated. Water was added and the mixture was filtered. The filtered solids were collected and dried under vacuum to provide 2,6-dichloro-5-methylnicotinic acid, m/z (ESI, +ve): 205.9 (M+H)$^+$.

Step 2: 2,6-Dichloro-5-methylnicotinamide. To an ice-cooled mixture of 2,6-dichloro-5-methylnicotinic acid (4.55 g, 22.1 mmol) in DCM (30 mL) was added oxalyl chloride (2 M solution in DCM, 16.6 mL, 33.1 mmol), followed by several drops of DMF. The reaction mixture was allowed to gradually warm to room temperature and stirred for 1 h and then was concentrated. The residue was suspended in toluene (15 mL), cooled to 0° C., and treated with ammonium hydroxide (30%, 9.1 mL, 62 mmol). The reaction was stirred at room temperature for 30 min and then was filtered. The filtered solids were washed with water and dried under vacuum to provide 2,6-dichloro-5-methylnicotinamide. m/z (ESI, +ve): 204.9 (M+H)$^+$.

Step 3: 2,6-Dichloro-N-((2-isopropylphenyl)carbamoyl)-5-methylnicotinamide. A mixture of 2,6-dichloro-5-methylnicotinamide (513 mg, 2.50 mmol) and oxalyl chloride (2 M solution in DCM, 1.38 mL, 2.63 mmol) in THF (10 mL) was heated at 65° C. for 1 h. The reaction was cooled to room temperature and 2-isopropylaniline (0.36 mL, 2.63 mmol) was added. The resulting mixture was stirred at room temperature for 1 h and then was concentrated. The residue was partitioned between EtOAc (50 mL) and saturated aqueous sodium bicarbonate (15 mL). The organic layer was dried over anhydrous sodium sulfate and concentrated. The residue was suspended in 5:1 heptane/EtOAc and filtered. The filtered solids were collected to provide 2,6-dichloro-N-((2-isopropylphenyl)carbamoyl)-5-methylnicotinamide. m/z (ESI, +ve): 365.8 (M+H)$^+$.

Step 4: 7-Chloro-1-(2-isopropylphenyl)-6-methylpyrido [2,3-d]pyrimidine-2,4(1H,3H)-dione. KHMDS (1 M solution in THF, 4.54 mL, 4.54 mmol) was added via syringe to an ice-cooled mixture of 2,6-dichloro-N-((2-isopropylphenyl)carbamoyl)-5-methylnicotinamide (831 mg, 2.27 mmol) in THF (10 mL). The resulting mixture was allowed to warm to room temperature and stirred 2 h. The reaction was partitioned between EtOAc (20 mL) and saturated aqueous ammonium chloride (2×10 mL). The organic layer was dried over anhydrous sodium sulfate and concentrated. The residue was suspended in 5:1 heptane/EtOAc and filtered. The filtered solids were collected to provide 7-chloro-1-(2-isopropylphenyl)-6-methylpyrido[2,3-d]pyrimidine-2,4(1H, 3H)-dione. $^1$H NMR (400 MHz, DMSO-d$_6$) δ ppm 8.36 (s, 1H), 7.49 (dd, J=8.5, 1.4 Hz, 1H), 7.44 (td, j=6.8, 1.2 Hz, 1H), 7.26-7.33 (m, 1H), 7.23 (dd, 0.7=7.9, 1.7 Hz, 1H), 2.68 (quin, j=6.8 Hz, 1H), 2.34 (s, 3H), 1.08 (d, 0.7=6.8 Hz, 3H), 1.02 (d, J=6.6 Hz, 3H). m/z (ESI, +ve): 329.9 (M+H)$^+$.

Step 5: tert-Butyl (S)-4-(7-chloro-1-(2-isopropylphenyl)-6-methyl-2-oxo-1,2-dihydropyrido[2,3-d]pyrimidin-4-yl)-3-methylpiperazine-1-carboxylate. To a solution of 7-chloro-1-(2-isopropylphenyl)-6-methylpyrido[2,3-d]pyrimidine-2,4(1H,3H)-dione (444 mg, 1.35 mmol) in acetonitrile (5 mL) was added DIPEA (0.70 mL, 4.04 mmol), followed by phosphorus oxychloride (0.125 mL, 1.35 mmol). The resulting solution was stirred at 80° C. for 2 h and then was concentrated. The residue was dissolved in acetonitrile (5 mL), cooled to 0° C., and treated with DIPEA (0.70 mL, 4.04 mmol), followed by (S)-4-N-Boc-2-methyl piperazine (297 mg, 1.48 mmol, Combi-Blocks, Inc., San Diego, CA, USA). The resulting mixture was stirred at 0° C. for 30 min and then was allowed to gradually warm up to room temperature. The reaction was partitioned between EtOAc (10 mL) and water (2×10 mL). The organic layer was dried over anhydrous sodium sulfate and concentrated. The residue was purified by silica gel chromatography (eluent: 0-30% 3:1 EtOAc-EtOH/heptane) to provide tert-butyl (S)-4-(7-chloro-1-(2-isopropylphenyl)-6-methyl-2-oxo-1,2-dihydropyrido[2,3-d]pyrimidin-4-yl)-3-methylpiperazine-1-carboxylate. $^1$H NMR (400 MHz, DMSO-d$_6$) δ ppm 8.16 (d, J=16.2 Hz, 1H), 7.47 (dd, J=6.8, 1.2 Hz, 1H), 7.41 (br t, J=7.3 Hz, 1H), 7.28 (dt, J=7.7, 1.2 Hz, 1H), 7.09 (dt, J=7.8, 1.6 Hz, 1H), 4.70-4.90 (m, 1H), 3.89-4.20 (m, 2H), 3.97-4.09 (m, 2H), 3.76-3.88 (m, 1H), 3.53-3.72 (m, 1H), 2.44 (td, J=6.8, 4.9 Hz, 1H), 2.35 (d, J=0.8 Hz, 3H), 1.45 (s, 9H), 1.25 (br s, 3H), 1.06 (d, J=6.8 Hz, 3H), 1.02 (dd, 0.7=6.8, 1.7 Hz, 3H). m/z (ESI, +ve): 511.9 (M+H)$^+$.

Step 6: tert-Butyl (3S)-4-(7-(2-fluoro-6-hydroxyphenyl)-1-(2-isopropylphenyl)-6-methyl-2-oxo-1,2-dihydropyrido [2,3-d]pyrimidin-4-yl)-3-methylpiperazine-1-carboxylate. A mixture of tert-butyl (S)-4-(7-chloro-1-(2-isopropylphenyl)-6-methyl-2-oxo-1,2-dihydropyrido[2,3-d]pyrimidin-4-yl)-3-methylpiperazine-1-carboxylate (458 mg, 0.89 mmol), potassium acetate (439 mg, 4.47 mmol), (2-fluoro-6-hydroxyphenyl)boronic acid (418 mg, 2.68 mmol, Combi-Blocks, San Diego, CA, USA) and [1,1'-bis(diphenylphosphino)ferrocene]-dichloropalladium (II), complex with dichloromethane (65 mg, 0.09 mmol) in 1,4-dioxane (7 mL) and water (0.05 was heated at 90° C. for 2 h. The reaction was allowed to cool to room temperature, and then was partitioned between saturated aqueous sodium bicarbonate (15 mL) and EtOAc (20 mL). The organic layer was washed with brine (10 mL), dried over anhydrous sodium sulfate and concentrated. The residue was purified by silica gel chromatography (eluent: 0-30% 3:1 EtOAc-EtOH/heptane) to provide tert-butyl (3S)-4-(7-(2-fluoro-6-hydroxyphenyl)-1-(2-isopropylphenyl)-6-methyl-2-oxo-1,2-dihydropyrido[2, 3-d]pyrimidin-4-yl)-3-methylpiperazine-1-carboxylate. m/z (ESI, +ve): 587.9 (M+H)$^+$.

Step 7: 7-(2-Fluoro-6-hydroxyphenyl)-6-methyl-4-((2S)-2-methyl-4-(2-propenoyl)-1-piperazinyl)-1-(2-(2-propanyl) phenyl)pyrido[2,3-d]pyrimidin-2(1H)-one. Trifluoroacetic acid (1.7 mL, 14.7 mmol) was added to a solution of tert-butyl (3S)-4-(7-(2-fluoro-6-hydroxyphenyl)-1-(2-isopropylphenyl)-6-methyl-2-oxo-1,2-dihydropyrido[2,3-d]pyrimidin-4-yl)-3-methylpiperazine-1-carboxylate (288 mg, 0.49 mmol) in DCM (5 mL). The resulting mixture was stirred at room temperature for 30 min and then was concentrated. The residue was dissolved in DCM (3 mL), cooled to 0° C., and treated with DIPEA (0.34 mL, 1.96 mmol), followed by a solution of acryloyl chloride (0.042 mL, 0.51 mmol) in DCM (0.5 mL). The reaction mixture was warmed to room temperature and stirred for 30 min, then was quenched with saturated aqueous sodium bicarbonate (5 mL) and extracted with EtOAc (10 mL). The organic layer was washed with brine (5 mL), dried over anhydrous sodium sulfate and concentrated. The residue was purified by silica gel chromatography (eluent: 0-50% 3:1 EtOAc-EtOH/heptane) to provide 7-(2-fluoro-6-hydroxyphenyl)-6-methyl-1-(2-methyl-6-(2-propanyl)phenyl)-4-((2S)-2-methyl-4-(2-propenoyl)-1-piperazinyl)pyrido[2,3-d]pyrimidin-2(1H)-one. $^1$H NMR (400 MHz, DMSO-d$_6$) δ ppm 9.94 (s, 1H), 8.10-8.19 (m, 1H), 7.38 (dd, J=7.5, 1.0 Hz, 1H), 7.31 (td, j=7.1, 0.8 Hz, 1H), 7.16-7.24 (m, 2H), 7.06 (br dt, J=7.9, 1.9 Hz, 1H), 6.75-6.97 (m, 1H), 6.71 (d, J=8.1 Hz, 1H), 6.64 (t, J=8.8 Hz, 1H), 6.21 (br dd, J=16.9, 5.7 Hz, 1H), 5.76 (dd, J=10.2, 2.5 Hz, 1H), 4.76-4.98 (m, 1H), 4.10-4.51 (m, 2H), 3.24-3.81 (m, 4H), 2.43-2.49 (m, 1H), 2.12 (d, j=2.9 Hz, 3H), 1.22-1.33 (m, 3H), 1.05 (d, j=6.8 Hz, 3H), 0.96 (d, j=6.8 Hz, 3H). m/z (ESI, +ve): 541.8 (M+H)$^+$.

Example 53

6-Chloro-7-(2-fluorophenyl)-1-(4-methyl-1-(2-propanyl)-1H-pyrazol-5-yl)-4-((2S)-2-methyl-4-(2-propenoyl)-1-piperazinyl)pyrido[2,3-d]pyrimidin-2(1H)-one

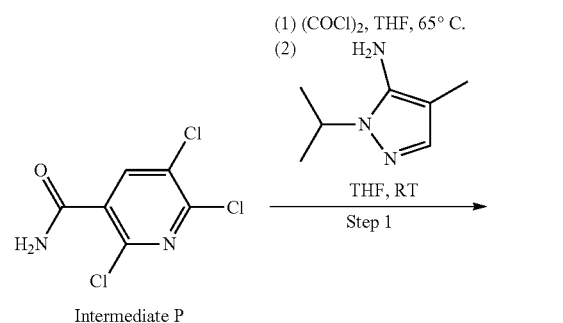

Intermediate P

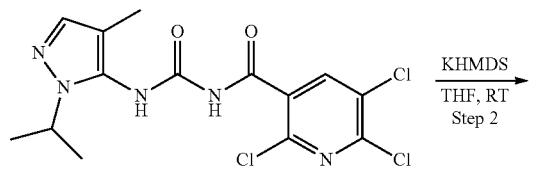

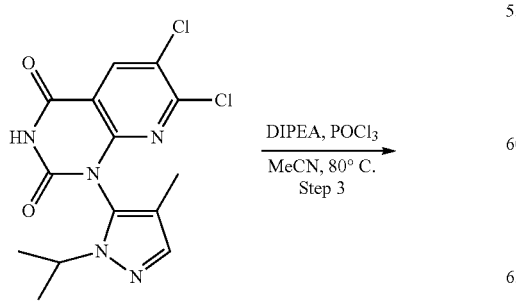

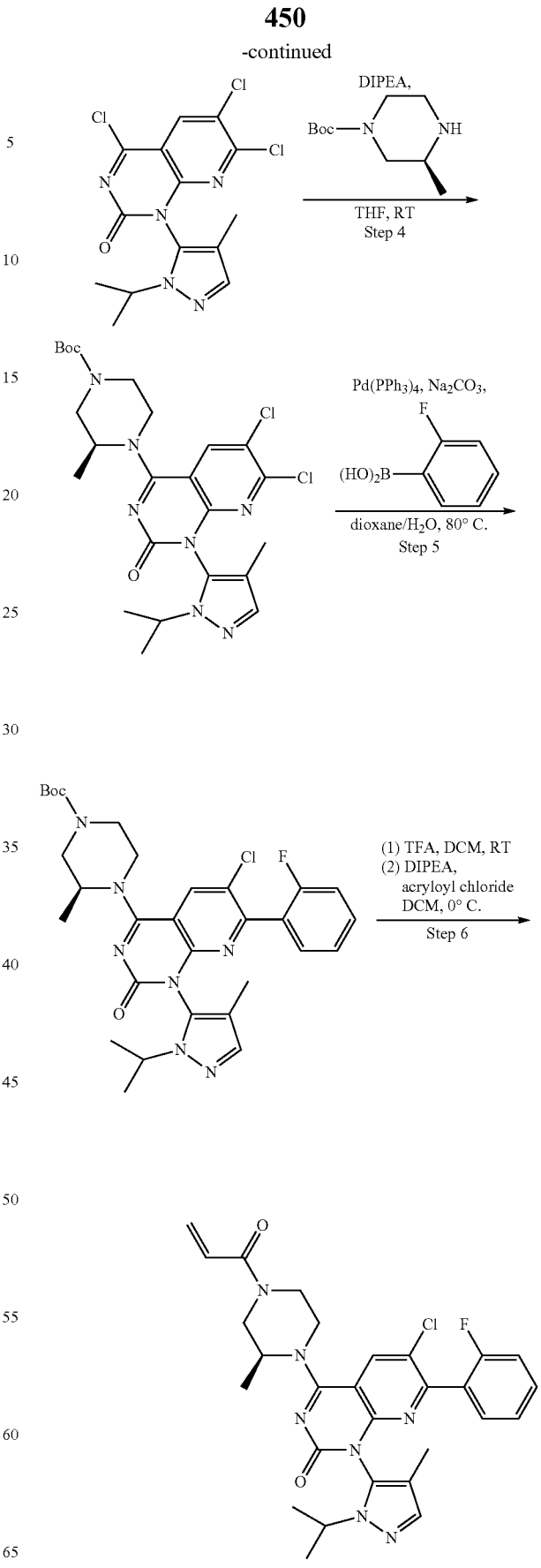

Step 1: 2,5,6-Trichloro-N-((1-isopropyl-4-methyl-1H-pyrazol-5-yl)carbamoyl)nicotinamide. To a mixture of 2,5,6-trichloronicotinamide (Intermediate P, 2.43 g, 10.8 mmol) in THF (21.5 mL) was added oxalyl chloride solution (2 M in DCM, 5.70 mL, 11.4 mmol) at room temperature. The resulting mixture was heated at 65° C. for 3 h, then heating was stopped and the reaction was allowed cooled to 0° C. A solution of 1-isopropyl-4-methyl-1H-pyrazol-5-amine (1.50 g, 10.8 mmol, ChemBridge, San Diego, CA, USA) in THF (15 mL) was added via cannula. The resulting mixture was stirred at 0° C. for 30 min and then was warmed to room temperature and stirred for an additional 16 h. The reaction mixture was filtered, and the filtered solids were collected and washed with acetonitrile (20 mL) to provide 2,5,6-trichloro-N-((1-isopropyl-4-methyl-1H-pyrazol-5-yl)carbamoyl)nicotinamide. $^1$H NMR (400 MHz, DMSO-$d_6$) δ ppm 11.39 (hr s, 1H), 9.51 (hr s, 1H), 8.62 (s, 1H), 7.29 (s, 1H), 4.33-4.44 (m, 1H), 1.87 (s, 3H), 1.33 (d, J=6.6 Hz, 6H). m/z (ESI, +ve ion): 389.9 (M+H)$^+$.

Step 2: 6,7-Dichloro-1-(1-isopropyl-4-methyl-1H-pyrazol-5-yl)pyrido[2,3-d]pyrimidine-2,4(1H,3H)-dione. KHMDS (1 M solution in THF, 18.0 mL, 18.0 mmol) was added slowly via syringe to an ice-cooled mixture of 2,5,6-trichloro-N-((1-isopropyl-4-methyl-1H-pyrazol-5-yl)carbamoyl)nicotinamide (3.52 g, 9.0 mmol) in THF (30 mL). After 10 min the resulting mixture was allowed to warm to room temperature and stirred 18 h. The resulting slurry was quenched with saturated aqueous ammonium chloride (50 mL) and brine (50 mL), and then was extracted with EtOAc (2×50 mL). The combined organic layers were washed with brine (50 mL), dried over anhydrous sodium sulfate and concentrated to provide 6,7-dichloro-1-(1-isopropyl-4-methyl-1H-pyrazol-5-yl)pyrido[2,3-d]pyrimidine-2,4(1H,3H)-dione. This material was used without further purification in the following step. $^1$H NMR (400 MHz, DMSO-$d_6$) δ ppm 12.22 (hr s, 1H), 8.55 (s, 1H), 7.45 (s, 1H), 4.22-4.34 (m, 1H), 1.78 (s, 3H), 1.25 (t, J=6.6 Hz, 6H). m/z (ESI, +ve ion): 353.9 (M+H)$^+$.

Step 3: 4,6,7-Trichloro-1-(1-isopropyl-4-methyl-1H-pyrazol-5-yl)pyrido[2,3-d]pyrimidin-2(1H)-one. To a solution of 6,7-dichloro-1-(1-isopropyl-4-methyl-1H-pyrazol-5-yl)pyrido[2,3-d]pyrimidine-2,4(1H,3H)-dione (3.19 g, 9.0 mmol) and DIPEA (4.71 mL, 27.0 mmol) in acetonitrile (60 mL) was added phosphorus oxychloride (1.68 mL, 18.0 mmol). The resulting mixture was heated at 80° C. for 30 min, and then was cooled to room temperature and concentrated to provide 4,6,7-trichloro-1-(1-isopropyl-4-methyl-1H-pyrazol-5-yl)pyrido[2,3-d]pyrimidin-2(1H)-one. This material was used without further purification in the following step.

Step 4: (A)-tert-Butyl 4-(6,7-dichloro-1-(1-isopropyl-4-methyl-1H-pyrazol-5-yl)-2-oxo-1,2-dihydropyrido[2,3-d]pyrimidin-4-yl)-3-methylpiperazine-1-carboxylate. To a solution of 4,6,7-trichloro-1-(1-isopropyl-4-methyl-1H-pyrazol-5-yl)pyrido[2,3-d]pyrimidin-2(1H)-one (3.36 g, 9.0 mmol) in THF (45 mL) was added DIPEA (4.71 mL, 27.1 mmol), followed by (5)-4-N-Boc-2-methyl piperazine (2.71 g, 13.6 mmol, Combi-Blocks, Inc., San Diego, CA, USA). The resulting mixture was stirred at room temperature for 1 h, then was quenched with ice-cold saturated aqueous sodium bicarbonate (100 mL) and extracted with EtOAc (100 mL, 2×50 mL). The combined organic layers were dried over anhydrous sodium sulfate and concentrated. The residue was purified by silica gel chromatography (eluent: 0-50% 3:1 EtOAc-EtOH/heptane) to provide (S)-tert-butyl 4-(6,7-dichloro-1-(1-isopropyl-4-methyl-1H-pyrazol-5-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 8.43 (d, J=19.1 Hz, 1H), 7.42 (s, 1H), 4.77-4.98 (m, 1H), 4.15 (br dd, J=26.7, 13.5 Hz, 1H), 3.61-4.07 (m, 4H), 2.94-3.28 (m, 2H), 1.72 (d, J=5.2 Hz, 3H), 1.44 (s, 9H), 1.32 (br dd, J=13.0, 6.7 Hz, 3H), 1.21-1.28 (m, 6H). m/z (ESI, +ve ion): 536.0 (M+H)$^+$.

Step 5: tert-Butyl (A)-4-(6-chloro-7-(2-fluorophenyl)-1-(1-isopropyl-4-methyl-1H-pyrazol-5-yl)-2-oxo-1,2-dihydropyrido[2,3-d]pyrimidin-4-yl)-3-methylpiperazine-1-carboxylate. A mixture of tert-butyl (S)-4-(6,7-dichloro-1-(1-isopropyl-4-methyl-1H-pyrazol-5-yl)-2-oxo-1,2-dihydropyrido[2,3-d]pyrimidin-4-yl)-3-methylpiperazine-1-carboxylate (703 mg, 1.31 mmol), (2-fluorophenyl)boronic acid (330 mg, 2.36 mmol, Combi-Blocks, San Diego, CA, USA), anhydrous sodium carbonate (416 mg, 3.93 mmol) and tetrakis(triphenylphosphine)palladium(0) (151 mg, 0.13 mmol) in 1,4-dioxane (3.5 mL) and water (0.87 mL) was heated at 80° C. for 2 h. The reaction was concentrated and the residue was purified by silica gel chromatography (eluent: 0-100% EtOAc/heptane) to provide tert-butyl (S)-4-(6-chloro-7-(2-fluorophenyl)-1-(1-isopropyl-4-methyl-1H-pyrazol-5-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 8.41 (d, J=8.9 Hz, 1H), 7.50-7.66 (m, 1H), 7.24-7.37 (m, 4H), 4.92 (br s, 1H), 4.24 (br t, J=12.4 Hz, 1H), 3.95-4.12 (m, 2H), 3.67-3.89 (m, 2H), 3.00-3.29 (m, 2H), 1.70 (s, 3H), 1.45 (s, 9H), 1.36 (t, J=6.6 Hz, 3H), 1.14-1.28 (m, 6H). $^{19}$F NMR (376 MHz, DMSO-$d_6$) δ ppm −113.95 (d, J=6.9 Hz, 1F). m/z (ESI, +ve ion): 596.0 (M+H)$^+$.

Step 6: 6-Chloro-7-(2-fluorophenyl)-1-(4-methyl-1-(2-propanyl)-1H-pyrazol-5-yl)-4-((2A)-2-methyl-4-(2-propenoyl)-1-piperazinyl)pyrido[2,3-d]pyrimidin-2(1H)-one. Trifluoroacetic acid (7.4 mL, 63.6 mmol) was added to a solution of tert-butyl (5)-4-(6-chloro-7-(2-fluorophenyl)-1-(1-isopropyl-4-methyl-1H-pyrazol-5-yl)-2-oxo-1,2-dihydropyrido[2,3-d]pyrimidin-4-yl)-3-methylpiperazine-1-carboxylate (532 mg, 0.74 mmol) in DCM (7.4 mL). The resulting mixture was stirred at room temperature for 1 h and then was concentrated. The residue was dissolved in DCM (7.4 mL), cooled to 0° C., and treated with DIPEA (1.28 mL, 7.35 mmol), followed by acryloyl chloride (0.2 M solution in DCM, 3.67 mL, 0.74 mmol). The resulting mixture was stirred at 0° C. for 20 min, then was quenched with saturated aqueous sodium bicarbonate (50 mL) and extracted with DCM (2×50 mL). The combined organic layers were dried over anhydrous sodium sulfate and concentrated. The residue was purified by silica gel chromatography (eluent: 0-50% EtOAc/heptane followed by 0-50% 4:1 DCM-MeOH/DCM) to provide 6-chloro-7-(2-fluorophenyl)-1-(4-methyl-1-(2-propanyl)-1H-pyrazol-5-yl)-4-((2S)-2-methyl-4-(2-propenoyl)-1-piperazinyl)pyrido[2,3-d]pyrimidin-2(1H)-one. $^1$H NMR (400 MHz, DMSO-$d_6$) δ ppm 8.44 (br d, J=1.5 Hz, 1H), 7.50-7.59 (m, 1H), 7.23-7.41 (m, 4H), 6.77-6.93 (m, 1H), 6.21 (br d, J=16.4 Hz, 1H), 5.71-5.81 (m, 1H), 4.96 (br s, 1H), 4.22-4.46 (m, 2H), 3.96-4.21 (m, 2H), 3.37-3.89 (m, 2H), 3.00-3.28 (m, 1H), 1.71 (d, J=2.5 Hz, 3H), 1.34 (t, j=6.8 Hz, 3H), 1.12-1.29 (m, 6H). $^{19}$F NMR (376 MHz, DMSO-$d_6$) δ ppm −113.96 (d, J=9.5 Hz, 1F). m/z (ESI, +ve ion): 550.2 (M+H)$^+$.

TABLE 12

Separated Compound Examples Including Stereoisomers, some of which are Atropisomers

| Ex.# | Chemical Structure | Name | Racemic SM/ separation conditions |
|---|---|---|---|
| 2-5-1 | 1st-eluting isomer | 1-((3S)-4-(5-chloro-6-(3-hydroxy-1-naphthalenyl)-[1,2]thiazolo-[3,4-b]-pyridin-3-yl)-3-methyl-1-piperazinyl)-2-propen-1-one or 1-((3R)-4-(5-chloro-6-(3-hydroxy-1-naphthalenyl)-[1,2]thiazolo-[3,4-b]pyridin-3-yl)-3-methyl-1-piperazinyl)-2-propen-1-one | 2-5/SFC (Chiralpak AD-H, 20 × 150 mm, 5 μm, 55% MeOH/CO$_2$, 80 mL/min, 100 bar). |
| 2-5-2 | 2nd-eluting isomer | 1-((3R)-4-(5-chloro-6-(3-hydroxy-1-naphthalenyl)-[1,2]thiazolo-[3,4-b]pyridin-3-yl)-3-methyl-1-piperazinyl)-2-propen-1-one or 1-((3S)-4-(5-chloro-6-(3-hydroxy-1-naphthalenyl)-[1,2]thiazolo-[3,4-b]pyridin-3-yl)-3-methyl-1-piperazinyl)-2-propen-1-one | 2-5/SFC (Chiralpak AD-H, 20 × 150 mm, 5 μm, 55% MeOH/CO$_2$, 80 mL/min, 100 bar). |
| 2-6-1 | 1st-eluting isomer | 1-((3S)-4-(5-chloro-6-(5-methyl-1H-indazol-4-yl)-[1,2]thiazolo-[3,4-b]pyridin-3-yl)-3-methyl-1-piperazinyl)-2-propen-1-one or 1-((3R)-4-(5-chloro-6-(5-methyl-1H-indazol-4-yl)-[1,2]thiazolo-[3,4-b]pyridin-3-yl)-3-methyl-1-piperazinyl)-2-propen-1-one | 2-6/SFC (Phenomenex (S,S)-Whelk-O1, 250 × 20 mm, 3 μm, 50% MeOH/CO$_2$ containing 20 mM NH$_3$, 60 g/min, 102 bar) |

TABLE 12-continued

Separated Compound Examples Including Stereoisomers, some of which are Atropisomers

| Ex.# | Chemical Structure | Name | Racemic SM/ separation conditions |
|---|---|---|---|
| 2-6-2 | 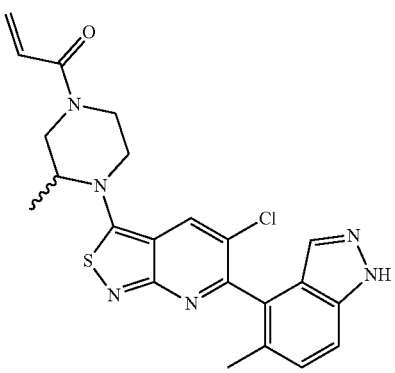<br>2nd-eluting isomer | 1-((3R)-4-(5-chloro-6-(5-methyl-1H-indazol-4-yl)-[1,2]thiazolo-[3,4-b]pyridin-3-yl)-3-methyl-1-piperazinyl)-2-propen-1-one or 1-((3S)-4-(5-chloro-6-(5-methyl-1H-indazol-4-yl)-[1,2]thiazolo-[3,4-b]pyridin-3-yl)-3-methyl-1-piperazinyl)-2-propen-1-one | 2-6/SFC (Phenomenex (S,S)-Whelk-O1, 250 × 20 mm, 3 μm, 50% MeOH/CO$_2$ containing 20 mM NH$_3$, 60 g/min, 102 bar) |
| 1-19-1 | 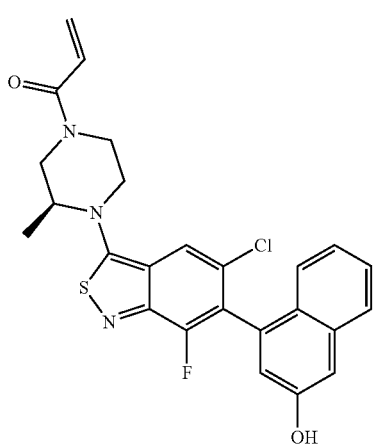<br>1st-eluting isomer | 1-((3S)-4-(5-chloro-7-fluoro-6-(3-hydroxy-1-naphthalenyl)-2,1-benzothiazol-3-yl)-3-methyl-1-piperazinyl)-2-propen-1-one | 1-19/SFC (IC 250 × 30 mm, 5 μm, 50% MeOH/CO$_2$ (w/20 mM NH$_3$), 100 g/min, 100 bar). |
| 1-19-2 | 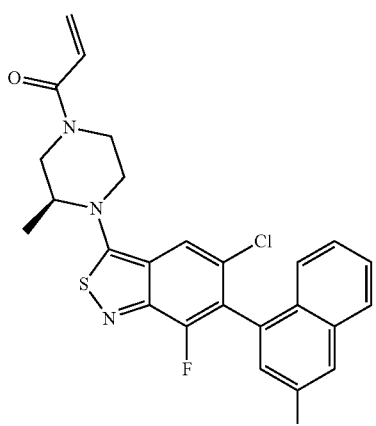<br>2nd-eluting isomer | 1-((3S)-4-(5-chloro-7-fluoro-6-(3-hydroxy-1-naphthalenyl)-2,1-benzothiazol-3-yl)-3-methyl-1-piperazinyl)-2-propen-1-one | 1-19/SFC (IC 250 × 30 mm, 5 μm, 50% MeOH/CO$_2$ (w/20 mM NH$_3$), 100 g/min, 100 bar). |

TABLE 12-continued

Separated Compound Examples Including Stereoisomers, some of which are Atropisomers

| Ex.# | Chemical Structure | Name | Racemic SM/ separation conditions |
|---|---|---|---|
| 3-1-1 | 1st-eluting isomer | 1-(4-(5-chloro-7-fluoro-6-(3-hydroxy-1-naphthalenyl)-2,1-benzothiazol-3-yl)-1-piperazinyl)-2-propen-1-one | 3-1/SFC(OD-H 250 × 21 mm, 5 μm 40% MeOH/$CO_2$ (w/20 mM $NH_3$), 60 mL/min, 100 bar). |
| 3-1-2 | 2nd-eluting isomer | 1-(4-(5-chloro-7-fluoro-6-(3-hydroxy-1-naphthalenyl)-2,1-benzothiazol-3-yl)-1-piperazinyl)-2-propen-1-one | 3-1/SFC (OD-H 250 × 21 mm, 5 μm 40% MeOH/$CO_2$ (w/20 mM $NH_3$), 60 mL/min, 100 bar). |
| 8-6-1 | 1st-eluting isomer | 6-chloro-7-(2-fluoro-6-hydroxy-phenyl)-4-((2S)-2-methyl-4-(2-propenoyl)-1-piperazinyl)-1-(2-(2-propanyl)-phenyl)pyrido-[2,3-d]pyrimidin-2(1H)-one | 8-6/SFC (Chiralpak IC, 150 × 30 mm, 5 μm, 30% MeOH/$CO_2$ (w/20 mM $NH_3$), 120 g/min, 102 bar). |

TABLE 12-continued

Separated Compound Examples Including Stereoisomers, some of which are Atropisomers

| Ex.# | Chemical Structure | Name | Racemic SM/ separation conditions |
|---|---|---|---|
| 8-6-2 | 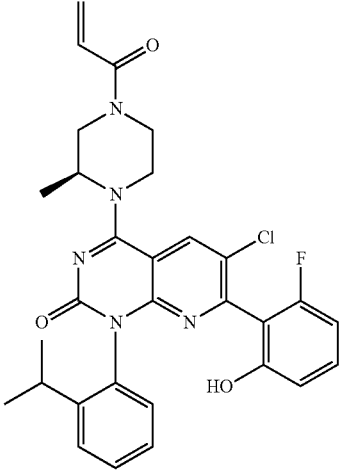<br>2nd-eluting isomer | 6-chloro-7-(2-fluoro-6-hydroxy-phenyl)-4-((2S)-2-methyl-4-(2-propenoyl)-1-piperazinyl)-1-(2-(2-propanyl)-phenyl)pyrido-[2,3-d]pyrimidin-2(1H)-one | 8-6/SFC (Chiralpak IC, 150 × 30 mm, 5 μm, 30% MeOH/CO$_2$ (w/20 mM NH$_3$), 120 g/min, 102 bar). |
| 8-1-1 | 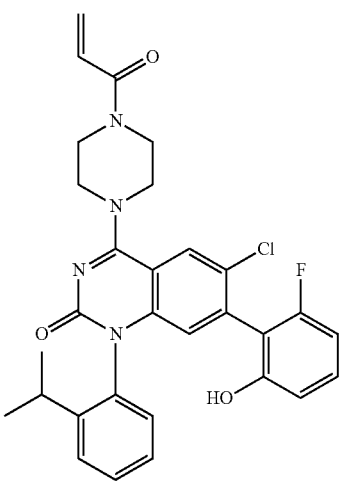<br>1st-eluting isomer | 6-chloro-7-(2-fluoro-6-hydroxy-phenyl)-1-(2-(2-propanyl)phenyl)-4-(4-(2-propenoyl)-1-piperazinyl)-2(1H)-quinazolinone | 8-1/SFC (Chiralpak IC, 300 × 15 mm, 5 μm, 40% MeOH/CO$_2$ (w/20 mM NH$_3$), 135 g/min, 188 bar). |
| 8-1-2 | 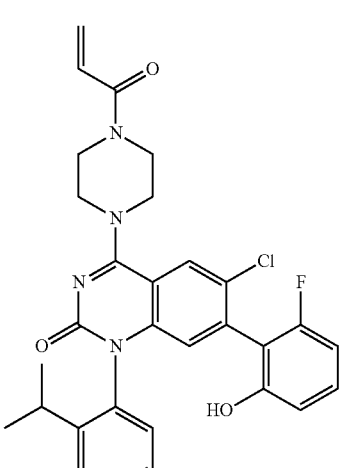<br>2nd-eluting isomer | 6-chloro-7-(2-fluoro-6-hydroxy-phenyl)-1-(2-(2-propanyl)phenyl)-4-(4-(2-propenoyl)-1-piperazinyl)-2(1H)-quinazolinone | 8-1/SFC (Chiralpak IC, 300 × 15 mm, 5 μm, 40% MeOH/CO$_2$ (w/20 mM NH$_3$), 135 g/min, 188 bar). |

TABLE 12-continued

Separated Compound Examples Including Stereoisomers, some of which are Atropisomers

| Ex.# | Chemical Structure | Name | Racemic SM/ separation conditions |
|---|---|---|---|
| 8-3-1 | 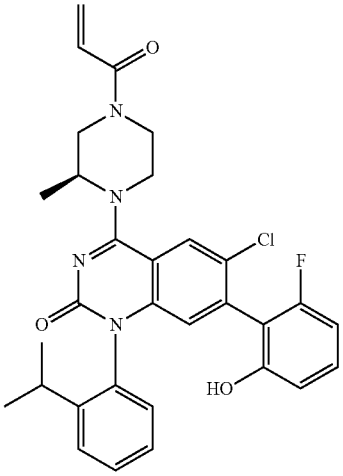<br>1st-eluting isomer | 6-chloro-7-(2-fluoro-6-hydroxy-phenyl)-4-((2S)-2-methyl-4-(2-propenoyl)-1-piperazinyl)-1-(2-(2-propanyl)-phenyl)-2(1H)-quinazolinone | 8-3/SFC (Whelk-01 (S,S), 250 × 21 mm, 5 μm, 30% EtOH/CO$_2$ (w/20 mM NH$_3$), 70 g/min, 187 bar). |
| 8-3-2 | 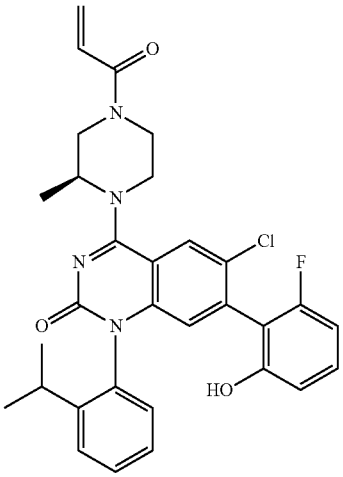<br>2nd-eluting isomer | 6-chloro-7-(2-fluoro-6-hydoxy-phenyl)-4-((2S)-2-methyl-4-(2-propenoyl)-1-piperazinyl)-1-(2-(2-propanyl)-phenyl)-2(1H)-quinazolinone | 8-3/SFC (Whelk-01 (S,S), 250 × 21 mm, 5 μm, 30% EtOH/CO$_2$ (w/20 mM NH$_3$), 70 g/min, 187 bar). |

TABLE 12 (b)

Separated Compound Examples Including Atropisomers

| Ex. # | Chemical Structure | Name | Racemic SM/ separation conditions |
|---|---|---|---|
| 39-1 | 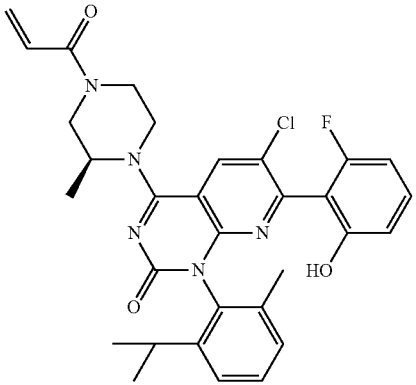<br>1st-eluting isomer | 6-chloro-7-(2-fluoro-6-hydroxyphenyl)-1-(2-methyl-6-(2-propanyl)phenyl)-4-((2S)-2-methyl-4-(2-propenoyl)-1-piperazinyl)pyrido-[2,3-d]pyrimidin-2(1H)-one | 39/SFC (Chiralpak OD-H, 21 × 250 mm, 5 μm, 30% MeOH/CO$_2$, 50 mL/min, 100 bar). |
| 39-2 | 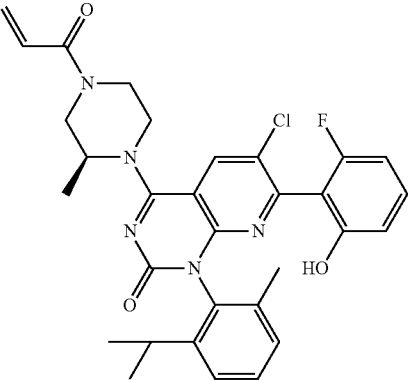<br>2nd-eluting isomer | 6-chloro-7-(2-fluoro-6-hydroxyphenyl)-1-(2-methyl-6-(2-propanyl)phenyl)-4-((2S)-2-methyl-4-(2-propenoyl)-1-piperazinyl)pyrido-[2,3-d]pyrimidin-2(1H)-one | 39/SFC (Chiralpak OD-H, 21 × 250 mm, 5 μm, 30% MeOH/CO$_2$, 50 mL/min, 100 bar). |
| 40-1 | 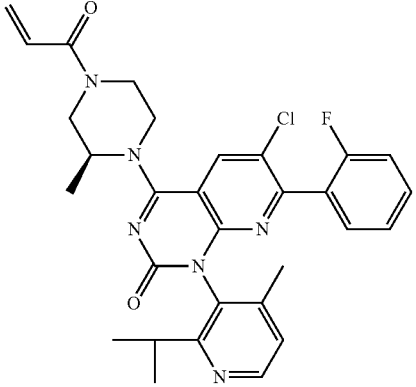<br>1st-eluting isomer | 6-chloro-7-(2-fluorophenyl)-1-(4-methyl-2-(2-propanyl)-3-pyridinyl)-4-((2S)-2-methyl-4-(2-propenoyl)-1-piperazinyl)pyrido-[2,3-d]pyrimidin-2(1H)-one | 40/SFC (Chiralpak IC, 21 × 150 mm, 5 μm, 60% MeOH/CO$_2$, 50 mL/min, 100 bar). |

TABLE 12 (b)-continued

Separated Compound Examples Including Atropisomers

| Ex. # | Chemical Structure | Name | Racemic SM/ separation conditions |
|---|---|---|---|
| 40-2 | 2nd-eluting isomer | 6-chloro-7-(2-fluoro-phenyl)-1-(4-methyl-2-(2-propanyl)-3-pyridinyl)-4-((2S)-2-methyl-4-(2-propenoyl)-1-piperazinyl)pyrido-[2,3-d]pyrimidin-2(1H)-one | 40/SFC (Chiralpak IC, 21 × 150 mm, 5 μm, 60% MeOH/CO$_2$, 50 mL/min, 100 bar). |
| 41-1 | 1st-eluting isomer | 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido-[2,3-d]pyrimidin-2(1H)-one | 41/SFC (Chiralpak IC, 30 × 250 mm, 5 μm, 55% MeOH/CO$_2$, 120 g/min, 103 bar). |
| 41-2 | 2nd-eluting isomer | 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido-[2,3-d]pyrimidin-2(1H)-one | 41/SFC (Chiralpak IC, 30 × 250 mm, 5 μm, 55% MeOH/CO$_2$, 120 g/min, 103 bar). |

TABLE 12 (b)-continued

Separated Compound Examples Including Atropisomers

| Ex. # | Chemical Structure | Name | Racemic SM/ separation conditions |
|---|---|---|---|
| 42-1 | 1st-eluting isomer | 1-(2-cyclopropyl-4-methyl-3-pyridinyl)-6-fluoro-7-(2-fluoro-6-hydroxyphenyl)-4-((2S)-2-methyl-4-(2-propenoyl)-1-piperazinyl)pyrido-[2,3-d]pyrimidin-2(1H)-one | 42/SFC (Chiralpak OD-H, 21 × 250 mm, 5 μm, 20% EtOH/CO$_2$, 80 mL/min, 100 bar). |
| 42-2 | 2nd-eluting isomer | 1-(2-cyclopropyl-4-methyl-3-pyridinyl)-6-fluoro-7-(2-fluoro-6-hydroxyphenyl)-4-((2S)-2-methyl-4-(2-propenoyl)-1-piperazinyl)pyrido-[2,3-d]pyrimidin-2(1H)-one | 42/SFC (Chiralpak OD-H, 21 × 250 mm, 5 μm, 20% EtOH/CO$_2$, 80 mL/min, 100 bar). |
| 44-1 | 1st-eluting isomer | 1-(2-cyclopropyl-4-methyl-3-pyridinyl)-6-fluoro-7-(2-fluoro-6-hydroxyphenyl)-4-((2S)-2-methyl-4-(2-propenoyl)-1-piperazinyl)pyrido-[2,3-d]pyrimidin-2(1H)-one | 44/SFC (Chiralpak OD-H, 21 × 250 mm, 5 μm, 20% EtOH/CO$_2$, 80 mL/min, 100 bar). |

TABLE 12 (b)-continued

Separated Compound Examples Including Atropisomers

| Ex. # | Chemical Structure | Name | Racemic SM/ separation conditions |
|---|---|---|---|
| 44-2 | 2nd-eluting isomer | 1-(2-cyclopropyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | 44/SFC (Chiralpak OD-H, 21 × 250 mm, 5 μm, 20% EtOH/CO$_2$, 80 mL/min, 100 bar). |
| 45-1 | 1st-eluting isomer | 6-chloro-1-(2-cyclopropyl-4-methyl-3-pyridinyl)-7-(2-fluorophenyl)-4-((2S)-2-methyl-4-(2-propenoyl)-1-piperazinyl)pyrido[2,3-d]pyrimidin-2(1H)-one | 45/SFC (Chiralpak OD-H, 21 × 250 mm, 5 μm, 20% EtOH/CO$_2$, 80 mL/min, 100 bar). |
| 45-2 | 2nd-eluting isomer | 6-chloro-1-(2-cyclopropyl-4-methyl-3-pyridinyl)-7-(2-fluorophenyl)-4-((2S)-2-methyl-4-(2-propenoyl)-1-piperazinyl)pyrido[2,3-d]pyrimidin-2(1H)-one | 45/SFC (Chiralpak OD-H, 21 × 250 mm, 5 μm, 20% EtOH/CO$_2$, 80 mL/min, 100 bar). |

TABLE 12 (b)-continued

Separated Compound Examples Including Atropisomers

| Ex. # | Chemical Structure | Name | Racemic SM/ separation conditions |
|---|---|---|---|
| 46-1 | 1st-eluting isomer | 6-chloro-1-(2-ethyl-4-methyl-3-pyridinyl)-7-(2-fluorophenyl)-4-((2S)-2-methyl-4-(2-propenoyl)-1-piperazinyl)pyrido-[2,3-d]pyrimidin-2(1H)-one | 46/SFC (Chiralpak AD-H, 20 × 250 mm, 5 μm, 30% i-PrOH/CO$_2$, 50 mL/min, 100 bar). |
| 46-2 | 2nd-eluting isomer | 6-chloro-1-(2-ethyl-4-methyl-3-pyridinyl)-7-(2-fluorophenyl)-4-((2S)-2-methyl-4-(2-propenoyl)-1-piperazinyl)pyrido-[2,3-d]pyrimidin-2(1H)-one | 46/SFC (Chiralpak AD-H, 20 × 250 mm, 5 μm, 30% i-PrOH/CO$_2$, 50 mL/min, 100 bar). |
| 49-1 | 1st-eluting isomer | 6-chloro-7-(2-fluoro-6-hydroxyphenyl)-1-(2-(2-methyl-2-propanyl)phenyl)-4-((2S)-2-methyl-4-(2-propenoyl)-1-piperazinyl)pyrido-[2,3-d]pyrimidin-2(1H)-one | 49/SFC (Chiralpak IF, 21 × 250 mm, 5 μm, 50% MeOH/CO$_2$, 65 mL/min, 102 bar). |

TABLE 12 (b)-continued

Separated Compound Examples Including Atropisomers

| Ex. # | Chemical Structure | Name | Racemic SM/ separation conditions |
|---|---|---|---|
| 49-2 | 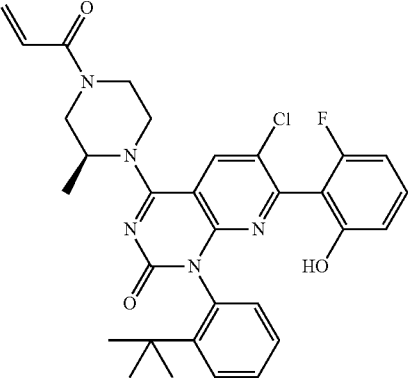<br>2nd-eluting isomer | 6-chloro-7-(2-fluoro-6-hydroxyphenyl)-1-(2-(2-methyl-2-propanyl)phenyl)-4-((2S)-2-methyl-4-(2-propenoyl)-1-piperazinyl)pyrido-[2,3-d]pyrimidin-2(1H)-one | 49/SFC (Chiralpak IF, 21 × 250 mm, 5 μm, 50% MeOH/CO$_2$, 65 mL/min, 102 bar). |
| 50-1 | 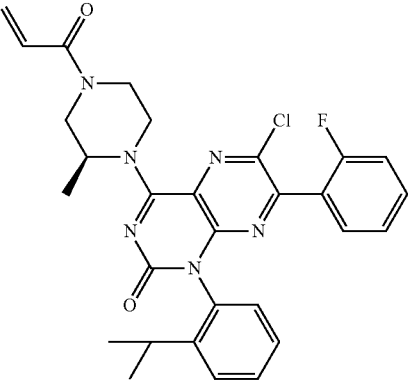<br>1st-eluting isomer | 6-chloro-7-(2-fluorophenyl)-4-((2S)-2-methyl-4-(2-propenoyl)-1-piperazinyl)-1-(2-(2-propanyl)phenyl)-2(1H)-pteridinone, | 50/SFC (Chiralpak OD, 21 × 250 mm, 5 μm, 17% MeOH/CO$_2$, 80 g/min, 102 bar). |
| 50-2 | 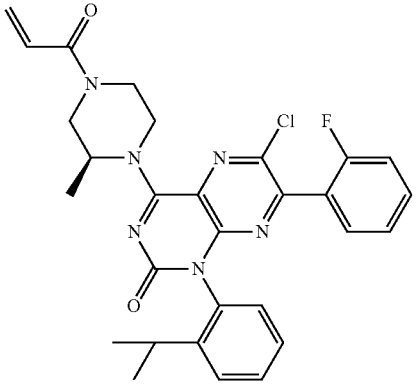<br>2nd-eluting isomer | 6-chloro-7-(2-fluorophenyl)-4-((2S)-2-methyl-4-(2-propenoyl)-1-piperazinyl)-1-(2-(2-propanyl)phenyl)-2(1H)-pteridinone | 50/SFC (Chiralpak OD, 21 × 250 mm, 5 μm, 17% MeOH/CO$_2$, 80 g/min, 102 bar). |

TABLE 12 (b)-continued

Separated Compound Examples Including Atropisomers

| Ex. # | Chemical Structure | Name | Racemic SM/ separation conditions |
|---|---|---|---|
| 51-1 | 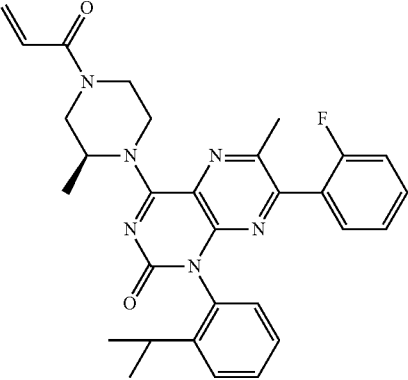<br>1st-eluting isomer | 7-(2-fluorophenyl)- 6-methyl-4-((2S)- 2-methyl-4-(2- propenoyl)-1- piperazinyl)-1-(2- (2-propanyl)phenyl)- 2(1H)-pteridinone | 51/SFC ((S,S) Whelk- 01, 21 × 250 mm, 5 μm, 60% MeOH/CO$_2$, 60 g/min, 110 bar). |
| 51-2 | 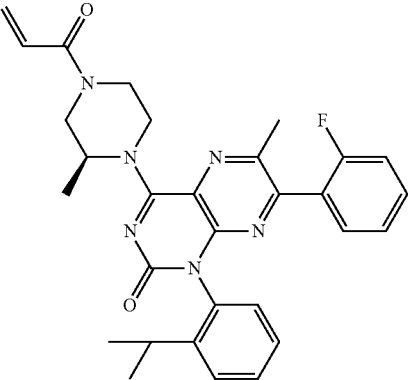<br>2nd-eluting isomer | 7-(2-fluorophenyl)- 6-methyl-4-((2S)- 2-methyl-4-(2- propenoyl)-1- piperazinyl)-1-(2- (2-propanyl)phenyl)- 2(1H)-pteridinone | 51/SFC ((S,S) Whelk- 01, 21 × 250 mm, 5 μm, 60% MeOH/CO$_2$, 60 g/min, 110 bar). |
| 52-1 | 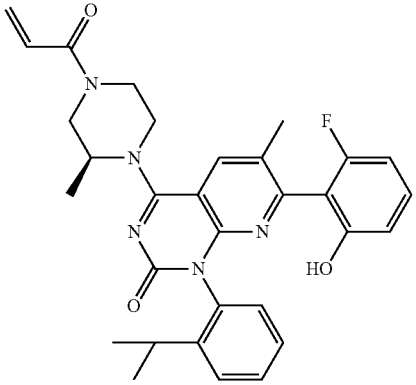<br>1st-eluting isomer | 7-(2-fluoro-6- hydroxyphenyl)- 6-methyl-4-((2S)- 2-methyl-4-(2- propenoyl)-1- piperazinyl)-1-(2- (2-propanyl)phenyl)- pyrido[2,3-d]- pyrimidin-2(1H)-one | 52/SFC (Chiralpak AS-H, 21 × 250 mm, 5 μm, 25% MeOH/CO$_2$, 50 g/min, 125 bar). |

TABLE 12 (b)-continued

Separated Compound Examples Including Atropisomers

| Ex. # | Chemical Structure | Name | Racemic SM/ separation conditions |
|---|---|---|---|
| 52-2 | 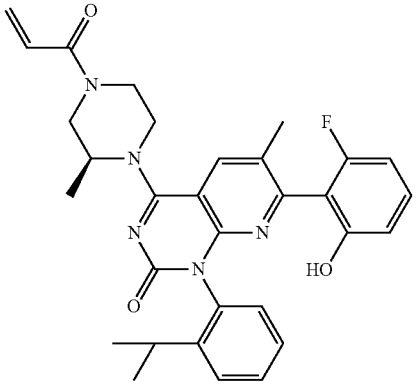 2nd-eluting isomer | 7-(2-fluoro-6-hydroxyphenyl)-6-methyl-4-((2S)-2-methyl-4-(2-propenoyl)-1-piperazinyl)-1-(2-(2-propanyl)-phenyl)pyrido-[2,3-d]pyrimidin-2(1H)-one | 52/SFC (Chiralpak AS-H, 21 × 250 mm, 5 μm, 25% MeOH/CO$_2$, 50 g/min, 125 bar). |
| 53-1 | 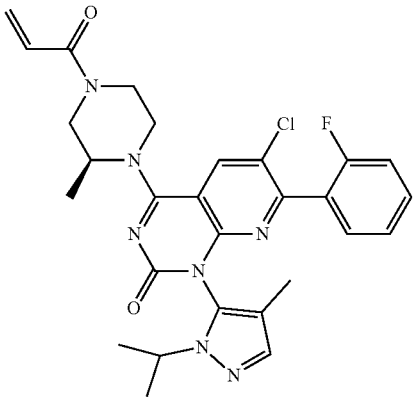 1st-eluting isomer | 6-chloro-7-(2-fluoro-phenyl)-1-(4-methyl-1-(2-propanyl)-1H-pyrazol-5-yl)-4-((2S)-2-methyl-4-(2-propenoyl)-1-piperazinyl)pyrido-[2,3-d]pyrimidin-2(1H)-one | 53/SFC ((S,S) Whelk-01, 21 × 250 mm, 5 μm, 25% MeOH/CO$_2$, 90 g/min, 102 bar). |
| 53-2 | 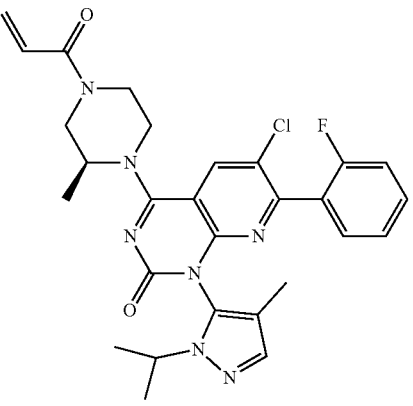 2nd-eluting isomer | 6-chloro-7-(2-fluoro-phenyl)-1-(4-methyl-1-(2-propanyl)-1H-pyrazol-5-yl)-4-((2S)-2-methyl-4-(2-propenoyl)-1-piperazinyl)pyrido-[2,3-d]pyrimidin-2(1H)-one | 53/SFC ((S,S) Whelk-01, 21 × 250 mm, 5 μm, 25% MeOH/CO$_2$, 90 g/min, 102 bar). |

TABLE 13

Analytical Data for General Procedures

| Ex. # | LRMS: (ESI, +ve ion) m/z | NMR |
|---|---|---|
| 1-1 | 498.0 | ¹H NMR (400 MHz, DMSO-d₆) δ 9.99 (br s, 1H), 8.04 (s, 1 H), 7.55 (d, J = 8.7 Hz, 1 H), 6.81-6.94 (m, 2 H), 6.79 (d, J = 2.9 Hz, 1 H), 6.19 (dd, J = 16.7, 2.2 Hz, 1 H), 5.77 (dd, J = 10.5, 2.2 Hz, 1 H), 3.87 (br d, J = 19.5 Hz, 4 H), 3.63 (br t, J = 5.1 Hz, 4 H). 19F NMR (376 MHz, DMSO-d₆) δ −123.78 (s, 1 F). |
| 1-2 | 441.1 | ¹H NMR (400 MHz, DMSO-d₆) δ 8.19 (s, 1H), 7.91 (d, J = 8.4 Hz, 1H), 7.45-7.53 (m, 2H), 7.43 (d, J = 2.4 Hz, 1H), 7.26-7.35 (m, 2H), 7.10 (d, J = 2.5 Hz, 1H), 6.87 (dd, J = 16.7, 10.5 Hz, 1H), 6.18 (dd, J = 16.7, 2.3 Hz, 1H), 5.76 (d, J = 10.3, 2.4 Hz, 1H), 3.93 (s, 3H), 3.81-3.93 (m, 4H), 3.58-3.64 (m, 4H). |
| 1-3 | 450.0 | ¹H NMR (400 MHz, DMSO-d₆) δ 9.91 (br. s, 1H), 8.18 (s, 1H), 7.76 (d, J = 8.2 Hz, 1H), 7.47 (s, 1H), 7.37-7.43 (m, 1H), 7.24-7.29 (m, 1H), 7.17-7.23 (m, 2H), 7.01 (d, J = 2.4 Hz, 1H), 6.87 (dd, J = 16.7, 10.5 Hz, 1H), 6.19 (dd, J = 16.7, 2.3 Hz, 1H), 5.73-5.79 (m, 1H), 3.82-3.95 (m, 4H), 3.58-3.64 (m, 4H). |
| 1-4 | 464.0 | ¹H NMR (400 MHz, DMSO-d₆) δ 8.19 (s, 1H), 7.91 (d, J = 8.4 Hz, 1H), 7.46-7.52 (m, 2H), 7.43 (d, J = 2.4 Hz, 1H), 7.25-7.36 (m, 2H), 7.10 (d, J = 2.5 Hz, 1H), 6.87 (dd, J = 16.7, 10.5 Hz, 1H), 6.31 (dd, J = 1.9, 16.8 Hz, 1H), 5.74-5.80 (m, 1H), 3.93 (s, 3H), 3.82-3.93 (m, 4H), 3.56-3.63 (m, 4H). |
| 1-5 | 432.0 | ¹H NMR (400 MHz, DMSO-d₆) δ 8.12 (s, 1H), 7.41-7.49 (m, 1H), 7.41 (s, 1H), 7.00 (d, J = 8.4 Hz, 1H), 6.80-6.92 (m, 2H), 6.18 (dd, J = 16.8, 2.4 Hz, 1H), 5.75 (dd, J = 10.5, 2.3 Hz, 1H), 3.79-3.93 (m, 4H), 3.75 (s, 3H), 3.53-3.62 (m, 4H). |
| 1-6 | 418.0 | ¹H NMR (400 MHz, DMSO-d₆) δ 9.98 (br s., 1H), 8.10 (s, 1H), 7.39 (s, 1H), 7.20-7.29 (m, 1H), 6.68-6.90 (m, 3H), 6.17 (dd, J = 16.6, 2.4 Hz, 1H), 5.75 (dd, J = 10.4, 2.4 Hz, 1H), 3.78-3.93 (m, 4H), 3.53-3.58 (m, 4H). |
| 1-7 | 498 | ¹H NMR (400 MHz, DMSO-d₆) δ 9.79-10.10 (1 H, m), 8.05-8.12 (1 H, m), 7.77-7.83 (1 H, m), 7.39-7.48 (1 H, m), 7.21-7.29 (3 H, m), 7.04-7.09 (1 H, m), 6.76-6.91 (1 H, m), 6.14-6.24 (1 H, m), 5.74-5.81 (1 H, m), 5.02-5.30 (1 H, m), 4.08-4.53 (3 H, m), 3.54-3.81 (6 H, m). |
| 1-8 | 496 | ¹H NMR (400 MHz, DMSO-d₆) δ 9.83-10.10 (1 H, m), 8.01-8.07 (1 H, m), 7.77-7.84 (1 H, m), 7.39-7.47 (1 H, m), 7.19-7.31 (3 H, m), 7.04-7.10 (1 H, m), 6.80-6.94 (1 H, m), 6.15-6.28 (1 H, m), 5.75-5.83 (1 H, m), 4.38-4.58 (1 H, m), 4.06-4.27 (2 H, m), 3.51-3.89 (3 H, m), 3.19-3.29 (1 H, m), 1.58-1.74 (2 H, m), 0.90-0.99 (3 H, m). |
| 1-9 | 467.8 | ¹H NMR (400 MHz, DMSO-d₆) δ 9.85-10.08 (1 H, m), 8.73-8.90 (1 H, m), 7.77-7.83 (1 H, m), 7.72-7.76 (1 H, m), 7.41-7.47 (1 H, m), 7.21-7.28 (3 H, m), 7.04-7.09 (1 H, m), 6.15-6.23 (2 H, m), 5.67-5.72 (1 H, m), 4.90-5.01 (1 H, m), 4.36-4.58 (2 H, m), 4.16-4.31 (1 H, m), 1.54-1.62 (3 H, m). |
| 1-10 | 470 | ¹H NMR (400 MHz, DMSO-d₆) δ 13.03-13.21 (1 H, m), 8.05-8.11 (1 H, m), 7.53-7.63 (2 H, m), 7.35-7.41 (1 H, m), 6.80-6.99 (1 H, m), 6.15-6.28 (1 H, m), 5.74-5.83 (1 H, m), 4.28-4.55 (2 H, m), 4.15-4.28 (1 H, m), 3.48-3.83 (4 H, m), 2.16-2.22 (3 H, m), 1.17-1.28 (3 H, m). |
| 1-11 | 512 | ¹H NMR (400 MHz, DMSO-d₆) δ 9.83-10.06 (1 H, m), 8.19-8.25 (1 H, m), 7.76-7.85 (1 H, m), 7.38-7.48 (1 H, m), 7.19-7.30 (3 H, m), 7.03-7.10 (1 H, m), 6.81-6.95 (1 H, m), 6.15-6.27 (1 H, m), 5.74-5.81 (1 H, m), 4.73-4.88 (1 H, m), 4.36-4.59 (2 H, m), 4.13-4.26 (1 H, m), 4.07-4.14 (1 H, m), 3.49-3.80 (5 H, m), 1.72-1.89 (2 H, m). |
| 1-12 | 511 | ¹H NMR (400 MHz, DMSO-d₆) δ 8.26-8.34 (1 H, m), 8.00-8.09 (2 H, m), 7.70-7.77 (2 H, m), 7.53-7.61 (2 H, m), 7.41-7.49 (2 H, m), 7.32-7.41 (2 H, m), 7.18-7.25 (1 H, m), 5.15-5.27 (1 H, m), 4.31-4.56 (2 H, m), 3.63-3.91 (2 H, m), 3.42-3.60 (2 H, m). |
| 1-13 | 482.0 | ¹H NMR (400 MHz, DMSO-d₆) δ 8.13 (d, J = 9.1 Hz, 1H), 8.09 (s, 1H), 7.97 (d, J = 6.8 Hz, 1H), 7.62 (d, J = 9.0 Hz, 1H), 7.38-7.44 (m, 2H), 7.22 (d, J = 8.8 Hz, 1H), 6.87 (dd, J = 16.8, 10.6 Hz, 1H), 6.19 (dd, J = 16.8, 2.4 Hz, 1H), 5.77 (dd, J = 10.5, 2.3 Hz, 1H), 3.82-3.94 (m, 4H), 3.87 (s, 3H), 3.63-3.69 (m, 4H). |
| 1-14 | 468.0 | ¹H NMR (400 MHz, DMSO-d₆) δ 9.91 (br. s., 1H), 8.07 (s, 1H), 7.90 (d, J = 9.0 Hz, 1H), 7.87 (d, J = 7.8 Hz, 1H), 7.27-7.38 (m, 3H), 7.15 (d, J = 8.2 Hz, 1H), 6.87 (dd, J = 16.6, 10.6 Hz, 1H), 6.19 (dd, J = 16.7, 2.3 Hz, 1H), 5.76 (dd, J = 10.5, 2.3 Hz, 1H), 3.80-3.95 (m, 4H), 3.60-3.67 (m, 4H). |
| 1-15 | 497.8 | ¹H NMR (400 MHz, DMSO-d₆) δ 8.03-8.12 (1 H, m), 7.68-7.79 (1 H, m), 7.32-7.44 (1 H, m), 7.11-7.26 (3 H, m), 6.98-7.06 (1 H, m), 6.77-6.91 (1 H, m), 6.13-6.26 (1 H, m), 5.73-5.83 (1 H, m), 4.08-4.54 (3 H, m), 3.54-3.80 (7 H, m). |
| 1-16 | 498.0 | ¹H NMR (400 MHz, DMSO-d₆) δ 9.88-10.15 (1 H, m), 8.08-8.16 (1 H, m), 7.77-7.83 (1 H, m), 7.40-7.48 (1 H, m), 7.18-7.30 (3 H, m), 7.05-7.10 (1 H, m), 6.80-6.92 (1 H, m), 6.15-6.24 (1 H, m), 5.73-5.80 (1 H, m), 4.58-4.71 (1 H, m), 4.26-4.43 (1 H, m), 3.99-4.24 (2 H, m), 3.39-4.00 (6 H, m). |
| 1-17 | 494.0 | ¹H NMR (400 MHz, DMSO-d₆) δ 9.81-10.05 (1 H, m), 8.06-8.12 (1 H, m), 7.77-7.84 (1 H, m), 7.40-7.47 (1 H, m), 7.19-7.29 (3 H, m), 7.03-7.08 (1 H, m), 6.77-6.88 (1 H, m), 6.19-6.30 (1 H, m), 5.73-5.82 (1 H, m), 4.73-4.86 (2 H, m), 3.82-3.96 (2 H, m), 3.44-3.52 (2 H, m), 1.88-2.14 (4 H, m). |
| 1-18 | 498.0 | ¹H NMR (400 MHz, DMSO-d₆) δ 9.85-10.08 (1 H, m), 8.07-8.13 (1 H, m), 7.77-7.83 (1 H, m), 7.40-7.48 (1 H, m), 7.22-7.30 (3 H, m), 7.04-7.09 (1 H, m), 6.76-6.92 (1 H, m), 6.15-6.25 (1 H, m), 5.74-5.81 (1 H, m), 5.04-5.29 (1 H, m), 4.10-4.52 (3 H, m), 3.53-3.78 (5 H, m). |
| 1-19 | 482.0 | ¹H NMR (400 MHz, DMSO-d₆) δ ppm 9.90-10.04 (1 H, m), 8.02-8.08 (1 H, m), 7.76-7.82 (1 H, m), 7.38-7.46 (1 H, m), 7.20-7.30 (3 H, m), 7.04-7.08 (1 H, m), 6.79-6.95 (1 H, m), 6.14-6.27 (1 H, m), 5.73-5.81 (1 H, m), 4.38-4.55 (3 H, |

TABLE 13-continued

Analytical Data for General Procedures

| Ex. # | LRMS: (ESI, +ve ion) m/z | NMR |
|---|---|---|
| | | m), 4.28-4.37 (1 H, m), 4.12-4.26 (1 H, m), 3.46-3.83 (2 H, m), 1.15-1.21 (3 H, m) |
| 1-19-1 | 482.0 | $^1$H NMR (400 MHz, DMSO-$d_6$) δ ppm 9.83-10.08 (1 H, m), 8.04-8.11 (1 H, m), 7.77-7.84 (1 H, m), 7.38-7.48 (1 H, m), 7.19-7.31 (3 H, m), 7.05-7.10 (1 H, m), 6.81-6.98 (1 H, m), 6.16-6.28 (1 H, m), 5.75-5.83 (1 H, m), 4.40-4.59 (1 H, m), 4.16-4.40 (1 H, m), 3.96-4.07 (1 H, m), 3.48-3.83 (3 H, m), 3.16-3.29 (1 H, m), 1.10-1.31 (3 H, m). |
| 1-19-2 | 482.0 | $^1$H NMR (400 MHz, DMSO-$d_6$) δ ppm 9.83-10.10 (1 H, m), 8.03-8.10 (1 H, m), 7.77-7.83 (1 H, m), 7.38-7.48 (1 H, m), 7.19-7.31 (3 H, m), 7.05-7.10 (1 H, m), 6.81-6.98 (1 H, m), 6.15-6.28 (1 H, m), 5.73-5.83 (1 H, m), 4.39-4.56 (2 H, m), 4.15-4.38 (1 H, m), 3.97-4.10 (1 H, m), 3.48-3.84 (3 H, m), 1.13-1.27 (3 H, m). |
| 1-20 | 454.0 | $^1$H NMR (400 MHz, DMSO-$d_6$) δ 9.83-10.05 (1 H, m), 9.11-9.35 (1 H, m), 8.02-8.07 (1 H, m), 7.76-7.83 (1 H, m), 7.40-7.47 (1 H, m), 7.20-7.28 (3 H, m), 7.02-7.09 (1 H, m), 6.33-6.46 (1 H, m), 6.11-6.22 (1 H, m), 5.69-5.78 (1 H, m), 4.69-4.80 (1 H, m), 4.40-4.49 (1 H, m), 4.31-4.41 (1 H, m), 4.21-4.30 (1 H, m), 3.99-4.09 (1 H, m). |
| 1-21 | 482.0 | $^1$H NMR (400 MHz, DMSO-$d_6$) δ 9.85-10.10 (1 H, m), 8.04-8.09 (1 H, m), 7.77-7.83 (1 H, m), 7.40-7.47 (1 H, m), 7.19-7.30 (3 H, m), 7.05-7.09 (1 H, m), 6.74-6.99 (1 H, m), 6.09-6.36 (1 H, m), 5.66-5.88 (1 H, m), 4.39-4.57 (2 H, m), 4.17-4.39 (1 H, m), 3.96-4.07 (1 H, m), 3.48-3.83 (3 H, m), 1.10-1.29 (3 H, m). |
| 1-22 | 468.0 | $^1$H NMR (400 MHz, DMSO-$d_6$) δ 9.87-10.03 (1 H, m), 8.45-8.66 (1 H, m), 7.94-8.01 (1 H, m), 7.76-7.83 (1 H, m), 7.39-7.47 (1 H, m), 7.21-7.29 (3 H, m), 7.01-7.10 (1 H, m), 6.10-6.25 (2 H, m), 5.59-5.70 (1 H, m), 4.56-4.68 (1 H, m), 3.99-4.13 (1 H, m), 3.75-3.87 (2 H, m), 3.55-3.66 (1 H, m), 2.35-2.48 (1 H, m), 2.06-2.21 (1 H, m). |
| 1-23 | 482.0 | $^1$H NMR (400 MHz, DMSO-$d_6$) δ 9.85-10.06 (1 H, m), 8.27-8.35 (1 H, m), 7.95-8.00 (1 H, m), 7.76-7.84 (1 H, m), 7.39-7.48 (1 H, m), 7.20-7.29 (3 H, m), 7.01-7.10 (1 H, m), 6.23-6.37 (1 H, m), 6.10-6.20 (1 H, m), 5.58-5.68 (1 H, m), 4.00-4.11 (1 H, m), 3.89-3.99 (1 H, m), 3.67-3.77 (1 H, m), 3.35-3.49 (2 H, m), 1.94-2.07 (2 H, m), 1.77-1.90 (1 H, m), 1.62-1.72 (1 H, m). |
| 2-7 | 496.2 | $^1$H NMR (DMSO-$d_6$) δ: 9.83-10.11 (m, 1H), 7.90-7.95 (m, 1H), 7.76-7.84 (m, 1H), 7.37-7.49 (m, 1H), 7.19-7.31 (m, 3H), 7.06-7.10 (m, 1H), 6.86-7.00 (m, 1H), 6.22-6.31 (m, 1H), 5.78-5.86 (m, 1H), 4.59-4.86 (m, 1H), 4.07-4.22 (m, 3H), 3.89-4.01 (m, 1H), 3.71-3.84 (m, 1H), 3.40-3.52 (m, 1H), 1.22-1.34 (m, 6H) |
| 2-8 | 506.0 | $^1$H NMR (DMSO-$d_6$) δ 13.04-13.25 (m, 1H), 8.09-8.15 (m, 1H), 7.55-7.62 (m, 2H), 7.35-7.41 (m, 1H), 6.76-6.94 (m, 1H), 6.36-6.62 (m, 1H), 6.16-6.24 (m, 1H), 5.75-5.83 (m, 1H), 4.59-4.86 (m, 1H), 4.19-4.58 (m, 1H), 3.52-3.92 (m, 3H), 3.40-3.50 (m, 1H), 3.13-3.27 (m, 1H), 2.13-2.21 (m, 3H) |
| 2-9 | 486.0 | $^1$H NMR (DMSO-$d_6$) δ: 10.08-10.30 (m, 1H), 7.98-8.07 (m, 1H), 7.29-7.39 (m, 1H), 6.72-6.91 (m, 3H), 6.23-6.63 (m, 1H), 6.13-6.24 (m, 1H), 5.74-5.81 (m, 1H), 4.58-4.82 (m, 1H), 4.42-4.57 (m, 1H), 4.17-4.38 (m, 1H), 3.52-3.89 (m, 4H) |
| 2-10 | 510.0 | $^1$H NMR (DMSO-$d_6$) δ: 9.83-10.06 (m, 1H), 7.93-8.06 (m, 1H), 7.75-7.85 (m, 1H), 7.39-7.51 (m, 1H), 7.17-7.32 (m, 3H), 7.00-7.15 (m, 1H), 6.76-6.96 (m, 1H), 6.12-6.30 (m, 1H), 5.68-5.86 (m, 1H), 4.59-4.71 (m, 1H), 4.35-4.47 (m, 1H), 4.06-4.28 (m, 1H), 3.60-4.06 (m, 3H), 3.43-3.58 (m, 1H), 2.08-2.25 (m, 1H), 1.00-1.11 (m, 3H), 0.86-0.97 (m, 3H) |
| 1-28 | 436.0 | $^1$H NMR (400 MHz, DMSO-$d_6$) δ 9.63 (s, 1 H) 8.04 (s, 1 H) 7.09-7.24 (m, 1 H) 6.72-6.95 (m, 3 H), 6.12-6.24 (m, 1 H) 5.74-5.77 (m, 1 H) 3.83-3.88 (d, 4 H) 3.52-3.72 (m, 4 H) |
| 2-1 | 451.0 | $^1$H NMR (400 MHz, DMSO-$d_6$) δ 9.97 (br. s, 1H), 8.72 (s, 1H), 7.79 (d, J = 8.6 Hz, 1H), 7.42 (t, J = 7.1 Hz, 1H), 7.17-7.28 (m, 3H), 7.09 (d, J = 2.1 Hz, 1H), 6.86 (dd, J = 16.7, 10.5 Hz, 1H), 6.19 (dd, J = 16.7, 2.3 Hz, 1H), 5.74-5.79 (m, 1H), 3.81-3.95 (m, 4H), 3.68-3.76 (m, 4H) |
| 2-2 | 447.0 | $^1$H NMR (400 MHz, DMSO-$d_6$) δ 8.58 (d, J = 3.7 Hz, 1H), 7.47-7.55 (m, 1H), 7.03 (d, J = 8.4 Hz, 1H), 6.96 (t, J = 8.7 Hz, 1H), 6.79-6.93 (m, 1H), 6.13-6.24 (m, 1H), 5.77 (dd, J = 10.5, 2.1 Hz, 1H), 4.26-4.54 (m, 2H), 3.96-4.25 (m, 1H), 3.65-3.84 (m, 2H), 3.76 (d, J = 2.4 Hz, 3H), 3.47-3.64 (m, 2H), 1.19 (s, 3H). |
| 2-3 | 433.0 | $^1$H NMR (400 MHz, METHANOL-$d_4$) δ 8.51 (2, 1H), 7.25-7.34 (m, 1H), 6.74-6.93 (m, 1H), 6.65-6.76 (m, 2H), 6.31 (d, J = 16.4 Hz, 1H), 5.84 (dd, J = 10.6, 1.5 Hz, 1H), 4.41-4.53 (m, 2H), 4.03-4.15 (m, 1H), 3.54-3.88 (m, 4H), 1.30 (d, J = 6.6 Hz, 3H). |
| 2-4 | 479.0 | $^1$H NMR (400 MHz, DMSO-$d_6$) δ 8.67 (s, 1H), 7.93 (d, J = 8.2 Hz, 1H), 7.45-7.53 (m, 2H), 7.26-7.37 (m, 2H), 7.19 (d, J = 2.5 Hz, 1H), 6.81-6.95 (m, 1H), 6.15-6.22 (m, 1H), 5.78 (dd, J = 10.4, 2.2 Hz, 1H), 4.39-4.58 (m, 2H), 4.16-4.26 (m, 1H), 3.94 (s, 3H), 3.68-3.84 (m, 2H), 3.48-3.64 (m, 2H), 1.22 (br.s, 3H). |
| 2-5 | 465.0 | $^1$H NMR (400 MHz, DMSO-$d_6$) δ 9.96 (s, 1H), 8.66 (s, 1H), 7.79 (d, J = 8.4 Hz, 1H), 7.42 (t, J = 7.0 Hz, 1H), 7.17-7.30 (m, 3H), 7.09 (d, J = 2.4 Hz, 1H), 6.80-6.94 (m, 1H), 6.14-6.27 (m, 1H), 5.78 (dd, J = 10.6, 2.2 Hz, 1H), 3.97-4.57 (m, 3H), 3.48-3.83 (m, 4H), 1.22 (br. s, 3H). |
| 2-6 | 453.0 | $^1$H NMR (400 MHz, DMSO-$d_6$) δ 13.11 (br. s., 1H), 8.66 (d, J = 2.3 Hz, 1H), 7.55 (d, J = 8.5 Hz, 2H), 7.33 (d, J = 8.5 Hz, 1H), 6.80-6.93 (m, 1H), 6.16-6.24 (m, 1H), 5.78 (dd, J = 10.5, 2.3 Hz, 1H), 3.97-4.56 (m, 4H), 3.48-3.85 (m, 3H), 2.19 (s, 3H), 1.22 (br s., 3H). |
| 3-1 | 468.0 | $^1$H NMR (400 MHz, DMSO-$d_6$) δ 9.90-10.04 (1H, m), 8.10 (1H, s), 7.80 (1H, d, J = 8.41 Hz), 7.43 (1H, ddd, J = 1.96, 6.11, 8.17 Hz), 7.16-7.31 (3H, m), 7.07 (1H, d, J = 2.35 Hz), 6.87 (1H, dd, J = 10.47, 16.73 Hz), 6.19 (1H, dd, J = 2.25, 16.73 Hz), 5.77 (1H, dd, J = 2.25, 10.47 |

TABLE 13-continued

Analytical Data for General Procedures

| Ex. # | LRMS: (ESI, +ve ion) m/z | NMR |
|---|---|---|
| | | Hz), 3.88 (4H, br d, J = 19.56 Hz), 3.61-3.72 (4H, m). $^{19}$F NMR (376 MHz, DMSO-d$_6$) δ −123.78 (s, 1F). |
| 3-2 | 469 | $^1$H NMR (400 MHz, CDCl$_3$) δ 9.43 (br. s., 1 H) 8.12 (d, J = 15.1 Hz, 1 H), 7.77 (d, J = 9.6 Hz, 1 H) 7.66 (d, J = 7.6 Hz, 1 H) 7.59 (d, J = 8.0 Hz, 1 H), 7.45 (s, 1 H) 7.21-7.26 (m, 1 H) 7.03 (br d, J = 10.4 Hz, 1 H), 6.95 (d, J = 15.1 Hz, 1 H), 6.71 (d, J = 9.6 Hz, 1 H) 3.93-4.14 (m, 4 H) 3.52-3.59 (m, 4H). $^{19}$F NMR (376 MHz, CDCl$_3$) δ −123.91 (s, 1 F). |
| 3-3 | 453.0 | $^1$H NMR (400 MHz, DMSO-d$_6$) δ 8.82-8.88 (1 H, m), 8.52-8.63 (1 H, m), 8.09-8.22 (2 H, m), 7.89-8.02 (2 H, m), 7.67-7.74 (1 H, m), 6.80-6.96 (1 H, m), 6.13-6.25 (1 H, m), 5.72-5.84 (1 H, m), 3.77-4.03 (4 H, m), 3.56-3.74 (4 H, m). |
| 3-4 | 469.0 | H NMR (400 MHz, DMSO-d$_6$) δ 11.81-12.11 (1 H, m), 8.05-8.15 (1 H, m), 7.58-7.67 (1 H, m), 7.42-7.49 (1 H, m), 7.35-7.42 (1 H, m), 7.14-7.20 (1 H, m), 6.80-6.93 (1 H, m), 6.44-6.53 (1 H, m), 6.14-6.24 (1 H, m), 5.72-5.82 (1 H, m), 3.80-3.95 (4 H, m), 3.61-3.69 (4 H, m). |
| 3-5 | 456.0 | $^1$H NMR (400 MHz, DMSO-d$_6$) δ 12.99-13.26 (1 H, m), 8.10-8.14 (1 H, m), 7.54-7.60 (1 H, m), 7.33-7.40 (1 H, m), 6.81-6.94 (1 H, m), 6.14-6.25 (1 H, m), 5.74-5.80 (1 H, m), 3.81-3.95 (4 H, m), 3.62-3.71 (4 H, m), 2.12-2.20 (3 H, m). |
| 3-6 | 436.0 | $^1$H NMR (400 MHz, METHANOL-d$_4$) δ 7.84 (d, J = 1.17 Hz, 1H), 7.26 (dt, J = 6.75, 8.27 Hz, 1H), 6.71-6.90 (m, 2H), 6.62-6.71 (m, 1H), 6.25 (dd, J = 1.96, 16.82 Hz, 1H), 5.79 (dd, J = 1.86, 10.66 Hz, 1H), 3.91-4.03 (m, 4H), 3.57-3.71 (m, 4H), 3.33 (s, 1H). $^{19}$F NMR (377 MHz, METHANOL-d$_4$) δ −116.77 (1 F, s), −125.66 (1 F, d, J = 2.6 Hz) |
| 3-7 | 438.0 | $^1$H NMR (400 MHz, DMSO-d$_6$) δ 8.08 (s, 1 H), 7.53-7.62 (m, 1 H), 7.47 (td, J = 9.7, 2.5 Hz, 1 H), 7.28 (td, J = 8.5, 2.2 Hz, 1 H), 6.85 (dd, J = 16.7, 10.5 Hz, 1 H), 6.18 (dd, J = 16.7, 2.2 Hz, 1 H), 5.71-5.79 (m, 1 H), 3.86 (br d, J = 19.6 Hz, 4 H), 3.63 (t, J = 5.2 Hz, 4 H) |
| 3-8 | 432.2 | $^1$H NMR (400 MHz, DMSO-d$_6$) δ 9.38 (s, 1 H), 8.02 (s, 1 H), 7.15 (d, J = 8.4 Hz, 1 H), 6.85 (dd, J = 16.7, 10.5 Hz, 1 H), 6.77 (dd, J = 8.2, 2.5 Hz, 1 H), 6.58 (d, J = 2.5 Hz, 1 H), 6.18 (dd, J = 16.6, 2.3 Hz, 1 H), 5.72-5.80 (m, 1 H), 3.77-3.93 (m, 4 H), 3.62 (t, J = 5.1 Hz, 4 H), 1.94 (s, 3 H). $^{19}$F NMR (376 MHz, DMSO-d$_6$) δ −124.66 (s, 1 F) |
| 3-9 | 467.8 | $^1$H NMR (400 MHz, DMSO-d$_6$) δ 8.05 (s, 1 H) 7.54 (d, J = 8.8 Hz, 1 H) 7.10 (dd, J = 8.8, 3.1 Hz, 1 H) 7.02-7.07 (m, 1 H) 6.85 (dd, J = 16.7, 10.5 Hz, 1 H) 6.18 (dd, J = 16.7, 2.2 Hz, 1 H) 5.72-5.79 (m, 1 H) 3.86 (br d, J = 19.4 Hz, 4 H) 3.79 (s, 3 H) 3.62 (t, J = 5.1 Hz, 4 H). $^{19}$F NMR (376 MHz, DMSO-d$_6$) δ −123.83 (s, 1 F) |
| 3-10 | 454.0 | $^1$H NMR (400 MHz, DMSO-d$_6$) δ 10.09 (s, 1 H), 8.05 (s, 1 H), 7.39 (dd, J = 11.0, 9.6 Hz, 1 H), 6.97 (dd, J = 9.5, 7.1 Hz, 1 H), 6.85 (dd, J = 16.6, 10.4 Hz, 1 H), 6.17 (dd, J = 16.6, 2.2 Hz, 1 H), 5.75 (dd, J = 10.5, 2.2 Hz, 1 H), 3.76-3.95 (m, 4 H), 3.62 (br t, J = 5.1 Hz, 4 H). $^{19}$F NMR (376 MHz, DMSO-d$_6$) δ −122.67 (br s, 1 F), −123.60 (d, J = 4.3 Hz, 1 F), −130.52 (d, J = 2.6 Hz, 1 F) |
| 3-11 | 453.8 | $^1$H NMR (400 MHz, DMSO-d$_6$) δ 9.83-10.02 (1 H, m), 8.04 (1 H, s), 7.40 (1 H, br d, J = 8.6 Hz), 6.76-7.03 (3 H, m), 6.12-6.22 (1 H, m), 5.69-5.82 (1 H, m), 3.86 (4 H, br d, J = 18.6 Hz), 3.63 (4 H, br d, J = 4.7 Hz). $^{19}$F NMR (376 MHz, DMSO-d$_6$) δ −124.09 (s, 1 F) |
| 3-12 | 431.0 | $^1$H NMR (400 MHz, DMSO-d$_6$) δ 8.00 (s, 1 H), 6.99 (d, J = 8.2 Hz, 1 H), 6.85 (dd, J = 16.6, 10.4 Hz, 1 H), 6.57 (dd, J = 8.0, 2.0 Hz, 1 H), 6.39 (d, J = 1.8 Hz, 1 H), 6.18 (dd, J = 16.7, 2.2 Hz, 1 H), 5.69-5.85 (m, 1 H), 4.99 (s, 2 H), 3.86 (br d, J = 19.6 Hz, 4 H), 3.56-3.70 (m, 4 H), 1.88 (s, 3H). $^{19}$F NMR (376 MHz, DMSO-d$_6$) δ −124.75 (1 F, s) |
| 3-13 | 473.0 | $^1$H NMR (400 MHz, DMSO-d$_6$) δ 9.98 (s, 1 H), 8.05 (s, 1 H), 7.54 (br d, J = 8.4 Hz, 1 H), 7.49 (s, 1 H), 7.29 (d, J = 8.4 Hz, 1 H), 6.85 (dd, J = 16.5, 10.5 Hz, 1 H), 6.18 (dd, J = 16.6, 2.0 Hz, 1 H), 5.76 (dd, J = 10.5, 2.1 Hz, 1 H), 3.86 (br d, J = 19.8 Hz, 4 H), 3.63 (br t, J = 4.9 Hz, 4 H), 2.03 (s, 3 H), 2.01 (s, 3 H). $^{19}$F NMR (376 MHz, DMSO-d$_6$) δ −124.58 (s, 1 F) |
| 3-14 | 435.0 | $^1$H NMR (400 MHz, DMSO-d$_6$) δ 8.03 (s, 1 H), 7.01 (t, J = 9.2 Hz, 1 H), 6.85 (dd, J = 16.7, 10.5 Hz, 1 H), 6.62-6.71 (m, 1 H), 6.52 (dd, J = 6.1, 2.7 Hz, 1 H), 6.18 (dd, J = 16.7, 2.2 Hz, 1 H), 5.70-5.81 (m, 1 H), 5.11 (s, 2 H), 3.86 (br d, J = 19.6 Hz, 4 H), 3.52-3.69 (m, 4 H). $^{19}$F NMR (376 MHz, DMSO-d$_6$) δ −123.91 (s, 1 F), −131.17 (s, 1 F) |
| 3-15 | 453.0 | $^1$H NMR (400 MHz, DMSO-d$_6$) δ 8.06 (s, 1 H), 6.85 (dd, J = 16.7, 10.5 Hz, 1 H), 6.63 (ddd, J = 13.0, 6.6, 2.5 Hz, 1 H), 6.33 (br d, J = 2.0 Hz, 1 H), 6.18 (dd, J = 16.6, 2.3 Hz, 1 H), 5.71-5.82 (m, 1 H), 5.44 (s, 2 H), 3.76-3.96 (m, 4 H), 3.56-3.71 (m, 4 H) |
| 3-16 | 453.9 | $^1$H NMR (400 MHz, DMSO-d$_6$) δ 10.12 (s, 1 H), 8.08 (s, 1 H), 6.92 (ddd, J = 12.3, 6.5, 2.9 Hz, 1 H), 6.85 (dd, J = 16.6, 10.4 Hz, 1 H), 6.58-6.65 (m, 1 H), 6.18 (dd, J = 16.7, 2.2 Hz, 1 H), 5.72-5.79 (m, 1 H), 3.78-3.92 (m, 4 H), 3.63 (t, J = 5.2 Hz, 4 H) |
| 3-17 | 486.0 | $^1$H NMR (400 MHz, DMSO-d$_6$) δ 10.86 (br s, 1 H), 8.05 (s, 1 H), 7.68 (s, 1 H), 6.96 (s, 1 H), 6.85 (dd, J = 16.6, 10.4 Hz, 1 H), 6.18 (dd, J = 16.6, 2.3 Hz, 1 H), 5.76 (dd, J = 10.5, 2.2 Hz, 1 H), 3.78-3.93 (m, 4 H), 3.56-3.68 (m, 4 H). $^{19}$F NMR (376 MHz, DMSO-d$_6$) δ −123.87 (s, 1 F) |
| 3-18 | 469.9 | $^1$H NMR (400 MHz, DMSO-d$_6$) δ 10.36-10.69 (m, 1 H), 8.04 (s, 1 H), 7.55 (d, J = 11.0 Hz, 1 H), 6.98 (d, J = 9.0 Hz, 1 H), 6.85 (dd, J = 16.7, 10.5 Hz, 1 H), 6.18 (dd, J = 16.7, 2.2 Hz, 1 H), 5.70-5.80 (m, 1 H), 3.86 (br d, J = 19.8 Hz, 4 H), 3.62 (br t, J = 5.1 Hz, 4 H). $^{19}$F NMR (376 MHz, DMSO-d$_6$) δ −123.82 (s, 1 F), −132.61 (br s, 1 F) |
| 3-19 | 451.0 | $^1$H NMR (400 MHz, DMSO-d$_6$) δ 8.01 (s, 1 H), 7.20 (d, J = 8.6 Hz, 1 H), 6.85 (dd, J = 16.7, 10.5 Hz, 1 H), 6.66 (dd, J = 8.6, 2.7 Hz, 1 H), 6.54 (d, J = 2.5 Hz, 1 H), 6.17 (dd, J = 16.7, 2.2 Hz, 1 H), 5.67-5.82 (m, 1 H), 5.40 (s, 2 H), 3.85 (br d, J = 19.4 Hz, 4 H), 3.54-3.73 (m, 4 H). $^{19}$F NMR (376 MHz, DMSO-d$_6$) δ −124.25 (1 F, s) |

TABLE 13-continued

Analytical Data for General Procedures

| Ex. # | LRMS: (ESI, +ve ion) m/z | NMR |
|---|---|---|
| 3-20 | 485.0 | $^1$H NMR (400 MHz, DMSO-$d_6$) δ 8.04 (s, 1 H), 7.50 (s, 1 H), 6.85 (dd, J = 16.7, 10.5 Hz, 1 H), 6.79 (s, 1 H), 6.18 (dd, J = 16.7, 1.9 Hz, 1 H), 5.76 (dd, J = 10.6, 1.8 Hz, 1 H), 5.70 (s, 2 H), 3.86 (br d, J = 19.8 Hz, 4 H), 3.63 (br d, J = 4.9 Hz, 4 H). $^{19}$F NMR (376 MHz, DMSO-$d_6$) δ −124.05 (br s, 1 F) |
| 3-21 | 445.2 | $^1$H NMR (400 MHz, DMSO-$d_6$) δ 8.54 (d, J = 5.4 Hz, 1 H), 8.29 (s, 1 H), 8.02 (s, 1 H), 7.47 (d, J = 5.2 Hz, 1 H), 6.78 (dd, J = 16.7, 10.5 Hz, 1 H), 6.10 (dd, J = 16.7, 2.2 Hz, 1 H), 5.62-5.75 (m, 1 H), 3.71-3.88 (m, 4 H), 3.56 (br t, J = 5.3 Hz, 4 H), 2.4-2.64 (m, 1 H), 1.10 (d, J = 6.8 Hz, 3 H), 1.01 (d, J = 6.8 Hz, 3 H). $^{19}$F NMR (376 MHz, DMSO-$d_6$) δ −123.04 (1 F, s) |
| 3-22 | 486.0 | $^1$H NMR (400 MHz, DMSO-$d_6$) δ 10.52 (br s, 1 H), 8.07 (s, 1 H), 7.14 (d, J = 2.7 Hz, 1 H), 6.78-6.93 (m, 2 H), 6.19 (dd, J = 16.7, 2.2 Hz, 1 H), 5.70-5.82 (m, 1 H), 3.79-3.92 (m, 4 H), 3.63 (br t, J = 5.0 Hz, 4 H). $^{19}$F NMR (376 MHz, DMSO-$d_6$) δ −124.13 (s, 1 F) |
| 3-23 | 452.1 | $^1$H NMR (400 MHz, DMSO-$d_6$) δ 8.03-8.14 (m, 3 H) 7.41-7.69 (m, 5 H) 6.84-6.91 (m, 1 H) 6.17-6.22 (m, 1 H) 5.76-5.79 (m, 1 H) 3.86-3.91 (m, 4 H) 3.65-3.67 (m, 4 H) |
| 3-24 | 453 | $^1$H NMR (400 MHz, DMSO-$d_6$) δ 8.78-8.87 (m, 1 H) 8.43-8.54 (m, 1 H) 8.04-8.40 (m, 2 H) 7.45-7.79 (m, 2 H) 7.53-7.65 (m, 1 H) 6.74-6.98 (m, 1 H) 6.09-6.26 (m, 1 H) 5.79-5.81 (m, 1 H) 3.83-3.93 (m, 4 H) 3.52-3.66 (m, 4 H) |
| 3-25 | 442 | $^1$H NMR (400 MHz, DMSO-$d_6$) δ 8.03 (s, 1 H) 6.81-6.98 (m, 4 H) 6.15-6.20 (m, 1 H) 5.72-5.86 (m, 3 H) 3.83-3.88 (m, 4 H) 3.6-3.62 (m, 4 H) |
| 4-1 | 480.0 | $^1$H NMR (400 MHz, DMSO-$d_6$) δ 9.82-10.04 (1 H, m), 7.79 (1 H, d, J = 8.2 Hz), 7.66 (1 H, s), 7.43 (1 H, dt, J = 8.3, 4.0 Hz), 7.26 (1 H, d, J = 2.3 Hz), 7.22 (2 H, d, J = 3.7 Hz), 7.05 (1 H, d, J = 2.3 Hz), 6.26-6.38 (1 H, m), 6.12 (1 H, dd, J = 16.8, 2.2 Hz), 5.66-5.72 (1 H, m), 4.58-4.67 (4 H, m), 4.50 (2 H, s), 4.22 (2 H, s). $^{19}$F NMR (376 MHz, DMSO-$d_6$) δ −123.98 (1 F, s) |
| 4-2 | 418.0 | $^1$H NMR (400 MHz, DMSO-$d_6$) δ 7.65 (1 H, d, J = 1.4 Hz), 6.25-6.36 (1 H, m), 6.10 (1 H, dd, J = 17.0, 2.3 Hz), 5.64-5.72 (1 H, m), 4.58 (4 H, s), 4.47 (2 H, s), 4.18 (2 H, s). $^{19}$F NMR (376 MHz, DMSO-$d_6$) δ −113.54 (1 F, s) |
| 4-3 | 494.0 | $^1$H NMR (400 MHz, DMSO-$d_6$) δ 7.93 (1 H, d, J = 8.4 Hz), 7.67 (1 H, s), 7.45-7.57 (2 H, m), 7.23-7.36 (2 H, m), 7.16 (1 H, d, J = 2.5 Hz), 6.27-6.39 (1 H, m), 6.11 (1 H, dd, J = 17.0, 2.2 Hz), 5.65-5.76 (1 H, m), 4.58-4.67 (4 H, m), 4.50 (2 H, s), 4.22 (2 H, s), 3.93 (3 H, s). $^{19}$F NMR (376 MHz, DMSO-$d_6$) δ −123.88 (1 F, s) |
| 4-4 | 391.8 | $^1$H NMR (400 MHz, DMSO-$d_6$) δ 8.93 (1 H, br s), 7.63-7.77 (1 H, m), 6.04-6.33 (2 H, m), 5.60-5.77 (1 H, m), 4.89 (1 H, br d, J = 3.3 Hz), 4.72 (2 H, br dd, J = 8.1, 3.6 Hz), 4.28 (2 H, br dd, J = 8.0, 3.9 Hz). $^{19}$F NMR (377 MHz, DMSO-$d_6$) δ −113.24 (1 F, s) |
| 4-5 | 468.0 | $^1$H NMR (400 MHz, DMSO-$d_6$) δ 8.92-9.00 (1 H, m), 7.93 (1 H, d, J = 8.2 Hz), 7.72 (1 H, s), 7.45-7.60 (2 H, m), 7.25-7.36 (2 H, m), 7.17 (1 H, d, J = 2.3 Hz), 6.08-6.36 (2 H, m), 5.69 (1 H, dd, J = 9.8, 2.2 Hz), 4.87-5.01 (1 H, m), 4.69-4.84 (2 H, m), 4.33 (2 H, br d, J = 3.3 Hz), 3.94 (3 H, s). $^{19}$F NMR (376 MHz, DMSO-$d_6$) δ −123.93 (1 F, s) |
| 4-6 | 454.0 | $^1$H NMR (400 MHz, DMSO-$d_6$) δ 9.95 (1 H, s), 8.97 (1 H, d, J = 7.0 Hz), 7.80 (1 H, d, J = 8.2 Hz), 7.72 (1 H, s), 7.39-7.49 (1 H, m), 7.16-7.32 (3 H, m), 7.05 1 H, d, J = 2.2 Hz), 6.08-6.36 (2 H, m), 5.65-5.73 (1 H, m), 4.87-5.05 (1 H, m), 4.77 (2 H, td, J = 8.2, 2.6 Hz), 4.33 (2 H, br t, J = 6.2 Hz). $^{19}$F NMR (376 MHz, DMSO-$d_6$) δ −124.03 (1 F, s) |
| 4-7 | 391.8 | $^1$H NMR (400 MHz, DMSO-$d_6$) δ 9.23-9.42 (1 H, m), 8.04 (1 H, d, J = 1.0 Hz), 6.37 (1 H, dd, J = 17.0, 10.2 Hz), 6.15 (1 H, dd, J = 17.0, 2.0 Hz), 5.65-5.86 (1 H, m), 4.70 (1 H, br t, J = 8.0 Hz), 4.35-4.48 (1 H, m), 4.25-4.33 (1 H, m), 4.22 (1 H, br dd, J = 9.0, 4.3 Hz), 3.99 (1 H, br dd, J = 10.3, 4.4 Hz). $^{19}$F NMR (376 MHz, DMSO-$d_6$) δ −113.81 (1 F, s) |
| 4-8 | 420.0 | $^1$H NMR (400 MHz, DMSO-$d_6$) δ 8.64 (1 H, br s), 8.15 (1 H, br d, J = 8.8 Hz), 6.58-6.97 (1 H, m), 5.97-6.27 (1 H, m), 5.58-5.74 (1 H, m), 4.50 (1 H, br d, J = 11.5 Hz), 3.91 (1 H, br d, J = 13.5 Hz), 3.14-3.28 (2 H, m), 2.85-2.97 (1 H, m), 2.08-2.23 (1 H, m), 1.79-1.91 (1 H, m), 1.64-1.78 (1 H, m), 1.45-1.60 (1 H, m). $^{19}$F NMR (376 MHz, DMSO-$d_6$) δ −114.17 (1 F, br s) |
| 4-9 | 482.0 | $^1$H NMR (400 MHz, DMSO-$d_6$) δ 9.87-10.07 (1 H, m), 8.50-8.70 (1 H, m), 8.06-8.23 (1 H, m), 7.70-7.88 (1 H, m), 7.39-7.48 (1 H, m), 7.19-7.28 (3 H, m), 7.02-7.08 (1 H, m), 6.68-6.93 (1 H, m), 6.05-6.23 (1 H, m), 5.64-5.78 (1 H, m), 4.51-4.63 (1 H, m), 4.06-4.17 (1 H, m), 3.91-4.04 (1 H, m), 3.14-3.30 (1 H, m), 2.91-3.01 (1 H, m), 2.14-2.29 (1 H, m), 1.83-1.96 (1 H, m), 1.68-1.82 (1 H, m), 1.49-1.65 (1 H, m). |
| 5-1 | 468.0 | $^1$H NMR (400 MHz, DMSO-$d_6$) δ 9.89-10.10 (m, 1 H), 7.79 (d, J = 8.4 Hz, 1 H), 7.73 (s, 1H), 7.43 (ddd, J = 8.2, 5.1, 2.9 Hz, 1 H), 7.20-7.30 (m, 3 H), 7.05 (d, J = 2.2 Hz, 1 H), 6.81 (dd, J = 16.7, 10.5 Hz, 1 H), 6.10-6.23 (m, 1 H), 5.69-5.81 (m, 1 H), 5.37-5.59 (m, 1 H), 4.63-4.74 (m, 3 H), 4.53-4.61 (m, 1 H), 3.14-3.23 (m, 2 H). $^{19}$F NMR (376 MHz, DMSO-$d_6$) δ −124.10 (1 F, s) |
| 5-2 | 468.2 | $^1$H NMR (400 MHz, DMSO-$d_6$) δ 9.89-10.09 (m, 1 H), 8.70 (s, 1 H), 7.79 (d, J = 8.2 Hz, 1 H), 7.69 (s, 1 H), 7.39-7.46 (m, 1 H), 7.16-7.31 (m, 3 H), 7.05 (d, J = 2.2 Hz, 1 H), 6.20-6.32 (m, 1 H), 6.08-6.18 (m, 1 H), 5.65 (dd, J = 10.1, 1.9 Hz, 1 H), 4.57 (dd, J = 8.1, 1.9 Hz, 2 H), 4.40 (br d, J = 8.4 Hz, 2 H), 1.67 (s, 3 H). $^{19}$F NMR (376 MHz, DMSO-$d_6$) δ −124.13 (1 F, s) |
| 5-3 | 484.0 | $^1$H NMR (400 MHz, DMSO-$d_6$) δ 9.95 (s, 1 H), 8.74 (s, 1 H), 7.79 (d, J = 8.4 Hz, 1 H), 7.70 (s, 1 H), 7.42 (br t, J = 6.6 Hz, 1 H), 7.16-7.28 (m, 3 H), 7.05 (d, J = 2.2 Hz, 1 H), 6.23-6.41 (m, 1 H), 6.07-6.19 (m, 1 H), 5.66 (dd, J = 10.1, 1.7 |

TABLE 13-continued

Analytical Data for General Procedures

| Ex. # | LRMS: (ESI, +ve ion) m/z | NMR |
|---|---|---|
| | | Hz, 1 H), 5.36 (br t, J = 5.8 Hz, 1 H), 4.49 (s, 4 H), 3.74 (br d, J = 5.5 Hz, 2 H). $^{19}$F NMR (376 MHz, DMSO-d$_6$) δ −124.12 (1 F, s) |
| 5-4 | 482.1 | $^1$H NMR (400 MHz, DMSO-d$_6$) δ 9.99 (s, 1 H), 8.02 (s, 1 H), 7.80 (d, J = 8.1 Hz, 1 H), 7.38-7.52 (m, 1 H), 7.16-7.34 (m, 3 H), 7.07 (s, 1 H), 6.75-6.96 (m, 1 H), 6.11-6.35 (m, 1 H), 5.66-5.90 (m, 1 H), 4.43-4.91 (m, 1 H), 4.07-4.39 (m, 1 H), 3.90-4.05 (m, 1 H), 3.71-3.87 (m, 1 H), 3.61 (br d, J = 9.7 Hz, 1 H), 3.33-3.51 (m, 2 H), 1.36 (br s, 3 H). $^{19}$F NMR (376 MHz, DMSO-d$_6$) δ −124.10 (1 F, s) |
| 5-5 | 480.1 | $^1$H NMR (400 MHz, DMSO-d$_6$) δ 9.97 (s, 1 H), 7.80 (d, J = 8.3 Hz, 1 H), 7.69 (d, J = 4.4 Hz, 1 H), 7.38-7.49 (m, 1 H), 7.16-7.29 (m, 3 H), 7.05 (d, J = 1.0 Hz, 1 H), 6.54-6.86 (m, 1 H), 6.14-6.31 (m, 1 H), 5.74-5.80 (m, 1 H), 5.21-5.40 (m, 1 H), 4.96-5.17 (m, 1 H), 4.61-4.73 (m, 1 H), 4.15-4.42 (m, 2 H), 3.55-3.92 (m, 1 H, 2.25-2.47 (m, 1 H), 1.93-2.20 (m, 1 H) |
| 5-6 | 480.1 | $^1$H NMR (400 MHz, DMSO-d$_6$) δ 9.97 (s, 1 H), 7.80 (d, J = 8.1 Hz, 1 H), 7.69 (d, J = 4.1 Hz, 1 H), 7.43 (dt, J = 8.1, 4.1 Hz, 1 H), 7.26 (d, J = 2.3 Hz, 1 H), 7.19-7.25 (m, 2 H), 7.05 (d, J = 2.1 Hz, 1 H), 6.55-6.83 (m, 1 H), 6.23 (ddd, J = 16.5, 7.5, 2.2 Hz, 1 H), 5.79 (br d, J = 2.1 Hz, 1 H), 5.22-5.40 (m, 1 H), 4.96-5.18 (m, 1 H), 4.61-4.72 (m, 1 H), 4.18-4.44 (m, 2 H), 3.57-3.94 (m, 1 H), 2.27-2.45 (m, 1 H), 1.92-2.24 (m, 1 H) |
| 5-7 | 482.1 | $^1$H NMR (400 MHz, DMSO-d$_6$) δ 9.97 (1 H, br s), 8.02 (1 H, s), 7.80 (1 H, d, J = 8.5 Hz), 7.35-7.53 (1 H, m), 7.17-7.33 (3 H, m), 7.07 (1 H, d, J = 2.3 Hz), 6.84 (1 H, dd, J = 16.7, 10.5 Hz), 6.19 (1 H, dd, J = 16.8, 1.7 Hz), 5.68-5.83 (1 H, m), 4.43-4.93 (1 H, m), 4.08-4.39 (1 H, m), 3.93-4.05 (1 H, m), 3.79 (1 H, br d, J = 11.6 Hz), 3.54-3.66 (1 H, m), 3.37-3.50 (2 H, m), 1.35 (3 H, br s). $^{19}$F NMR (376 MHz, DMSO-d$_6$) δ −123.81 (1 F, d, J = 16.5 Hz) |
| 5-8 | 480.0 | $^1$H NMR (400 MHz, DMSO-d$_6$) δ 9.98 (s, 1 H), 7.86 (br d, J = 8.7 Hz, 1 H), 7.80 (d, J = 8.1 Hz, 1 H), 7.37-7.53 (m, 1 H), 7.19-7.31 (m, 3 H), 7.06 (br s, 1 H), 6.25-6.55 (m, 1 H), 6.11-6.24 (m, 1 H), 5.64-5.82 (m, 1 H), 5.14-5.44 (m, 1 H), 5.03-5.12 (m, 1 H), 4.24-4.59 (m, 1 H), 3.63-4.20 (m, 3 H), 2.22-2.48 (m, 2 H). $^{19}$F NMR (376 MHz, DMSO-d$_6$) δ −124.17-−123.93 (m, 1 F) |
| 5-9 | 468.0 | $^1$H NMR (400 MHz, DMSO-d$_6$) δ 9.98 (s, 1 H), 8.04 (s, 1 H), 7.80 (d, J = 8.5 Hz, 1 H), 7.38-7.52 (m, 1 H), 7.15-7.35 (m, 3 H), 7.07 (d, J = 2.3 Hz, 1 H), 6.39 (dd, J = 17.0, 10.4 Hz, 1 H), 6.16 (dd, J = 17.0, 2.1 Hz, 1 H), 5.66-5.81 (m, 1 H), 4.94-5.06 (m, 1 H), 4.67 (br t, J = 8.7 Hz, 1 H), 4.49 (br dd, J = 9.4, 5.3 Hz, 1 H), 4.31-4.43 (m, 1 H), 4.21 (br dd, J = 10.6, 5.2 Hz, 1 H), 3.43 (s, 3 H). $^{19}$F NMR (376 MHz, DMSO-d$_6$) δ −124.00 (s, 1 F) |
| 6-1 | 452.0 | $^1$H NMR (400 MHz, DMSO-d$_6$) δ 7.97-8.10 (m, 1 H), 7.60 (d, J = 8.9 Hz, 1 H), 6.86 (dd, J = 16.6, 10.6 Hz, 1 H), 6.57 (d, J = 8.9 Hz, 1 H), 6.38 (s, 2 H), 6.19 (dd, J = 16.8, 2.3 Hz, 1 H), 5.71-5.84 (m, 1 H), 3.86 (br d, J = 19.9 Hz, 4 H), 3.63 (br d, J = 1.0 Hz, 4 H). $^{19}$F NMR (376 MHz, DMSO-d$_6$) δ −126.04 (1 F, s) |
| 6-2 | 437.0 | $^1$H NMR (400 MHz, DMSO-d$_6$) δ 8.67-8.79 (1 H, m), 8.18 (1 H, dd, J = 8.3, 1.0 Hz), 8.10 (1 H, s), 7.61 (1 H, dd, J = 8.2, 4.7 Hz), 6.86 (1 H, dd, J = 16.6, 10.4 Hz), 6.19 (1 H, dd, J = 16.8, 2.3 Hz), 5.77 (1 H, dd, J = 10.4, 2.3 Hz), 3.79-3.97 (4 H, m), 3.58-3.73 (4 H, m). $^{19}$F NMR (376 MHz, DMSO-d$_6$) δ −125.75 (1 F, s) |
| 7-1 | 518.0 | $^1$H NMR (400 MHz, DMSO-d$_6$) δ 10.13 (br. s., 1 H) 8.12 (d, J = 2.2 Hz, 1 H) 7.80 (d, J = 8.2 Hz, 1 H) 7.43 (br t, J = 7.0 Hz, 1 H) 7.20-7.30 (m, 3 H) 7.08 (dd, J = 5.8, 2.2 Hz, 1 H) 6.78-6.91 (m, 1 H) 6.27-6.70 (m, 1 H) 6.20 (dd, J = 16.6, 2.0 Hz, 1 H) 5.76-5.84 (m, 1 H) 4.73-4.87 (m, 1 H) 4.19-4.72 (m, 2 H) 3.55-3.90 (m, 3 H) 3.36-3.47 (m, 1 H) |
| 7-2 | 500.0 | $^1$H NMR (DMSO-d$_6$) δ: 9.73-10.17 (m, 1H), 8.04-8.12 (m, 1H), 7.77-7.84 (m, 1H), 7.39-7.48 (m, 1H), 7.20-7.30 (m, 3H), 7.06-7.10 (m, 1H), 6.77-6.93 (m, 1H), 6.15-6.24 (m, 1H), 5.74-5.83 (m, 1H), 4.57-4.92 (m, 3H), 4.14-4.54 (m 2H), 3.55-3.87 (m, 3H), 3.21-3.29 (m, 1H) |
| 7-3 | 526.0 | $^1$H NMR (DMSO-d$_6$) δ: 9.76-10.22 (m, 1H), 8.09-8.14 (m, 1H), 7.77-7.84 (m, 1H), 7.39-7.48 (m, 1H), 7.20-7.29 (m, 3H), 7.04-7.11 (m, 1H), 6.82 (br. s., 1H), 6.14-6.22 (m, 1H), 5.77-5.83 (m, 1H), 3.68-5.36 (m, 4H), 3.60-3.67 (m, 3H) |
| 8-1 | 547 | $^1$H NMR (400 MHz, DMSO-d$_6$) δ 10.06 (br. d., J = 15.1 Hz, 1 H) 8.03 (d, J = 1.2 Hz, 1 H) 7.51-7.56 (m, 1 H) 7.45 (t, J = 7.6 Hz, 1 H) 7.33 (tdd, J = 7.5, 7.5, 3.8, 1.4 Hz, 1 H) 7.14-7.25 (m, 2 H) 6.84 (dd, J = 16.8, 10.4 Hz, 1 H) 6.62-6.74 (m, 2 H) 6.14-6.26 (m, 2 H) 5.71-5.78 (m, 1 H) 3.71-3.99 (m, 8 H) 2.52-2.59 (m, 1 H) 1.02-1.12 (m, 6 H). $^{19}$F NMR (377 MHz, DMSO-d$_6$) δ −113.6 (s, 1 F) −114.8 (s, 1 F). |
| 8-2 | 548.2 | $^1$H NMR (400 MHz, CDCl$_3$) δ 8.61 (1 H, br s) 8.17 (1 H, s) 7.49-7.55 (2 H, m) 7.35-7.43 (1 H, m) 7.23-7.30 (1 H, m) 7.09 (1 H, d, J = 7.88 Hz) 6.58-6.72 (3 H, m) 6.41 (1 H, dd, J = 16.79, 1.66 Hz) 5.82 (1 H, dd, J = 10.47, 1.55 Hz) 3.80-4.15 (8 H, m) 2.71 (1 H, spt, J = 6.84 Hz) 1.23 (3 H, d, J = 6.84 Hz) 1.03 (4 H, d, J = 6.84 Hz) |
| 8-3 | 561 | $^1$H NMR (400 MHz, CDCl$_3$) δ 7.81 (s, 1 H) 7.35-7.49 (m, 2 H) 7.18-7.32 (m, 1 H) 7.01-7.17 (m, 2 H) 6.67-6.74 (m, 1 H) 6.48-6.65 (m, 3 H) 6.32-6.44 (m, 1 H) 5.77-5.83 (m, 1 H) 4.19-5.14 (m, 3 H) 3.75-3.98 (m, 1 H) 3.41-3.68 (m, 2 H) 2.85-3.28 (m, 1 H) 2.49-2.71 (m, 1 H) 1.34-1.54 (m, 3 H) 1.13-1.21 (m, 3 H) 1.00-1.07 (m, 3H). $^{19}$F NMR (377 MHz, CDCl$_3$) δ −113.43-−113.3 (m, 1 F)−114.3-−113.9 (m, 1 F). |
| 8-3-1 | 561-2 | $^1$H NMR (400 MHz, CDCl$_3$) δ 7.82 (s, 1 H) 7.37-7.51 (m, 2 H) 7.21-7.34 (m, 1 H) 7.05-7.20 (m, 2 H) 6.70 (br d, J = 8.1 Hz, 1 H) 6.52-6.67 (m, 3 H) 6.39 (dd, J = 16.8, 1.7 Hz, 1 H) 5.80 (dd, J = 10.5, 1.6 Hz, 1 H) 4.26-5.00 (m, 3 H) 3.40-4.00 (m, 3 H) 3.06-3.24 (m, 1 H) 2.52-2.69 (m, 1 H) 1.20 (d, J = 6.2 Hz, 6 H) 1.04 (br d, J = 6.4 Hz, 3 H). $^{19}$F NMR |

TABLE 13-continued

Analytical Data for General Procedures

| Ex. # | LRMS: (ESI, +ve ion) m/z | NMR |
|---|---|---|
| | | (377 MHz, CDCl$_3$) δ −113.31 (br d, J = 63.3 Hz, 1 F) −113.99 (br d, J = 33.8 Hz, 1 F). |
| 8-3-2 | 561.2 | $^1$H NMR (400 MHz, CDCl$_3$) δ 7.79 (br s, 1 H) 7.35-7.48 (m, 2 H) 7.21-7.32 (m, 1 H) 7.04-7.17 (m, 2 H) 6.68 (d, J = 8.3 Hz, 1 H) 6.49-6.66 (m, 3 H) 6.36 (br d, J = 16.6 Hz, 1 H) 5.78 (dd, J = 10.4, 1.9 Hz, 1 H) 4.29-5.11 (m, 2 H) 3.46-4.02 (m, 3 H) 2.93-3.29 (m, 2 H) 2.49-2.68 (m, 1 H) 1.48 (dd, J = 14.5, 2.1 Hz, 6 H) 1.03 (br d, J = 6.0 Hz, 3 H). $^{19}$F NMR (377 MHz, CDCl$_3$) δ −113.32 (br d, J = 9.5 Hz, 1 F) −114.02-−113.78 (m, 1 F). |
| 8-4 | 576 | $^1$H NMR (400 MHz, CDCl$_3$) δ 8.58 (s, 1 H), 8.13 (s, 1 H) 7.41-7.50 (m, 1 H) 7.32 (s, 1 H) 7.30 (s, 1 H) 7.22-7.30 (m, 1 H) 6.53-6.75 (m, 3 H) 6.42 (dd, J = 16.8, 1.7 Hz, 1 H) 5.77-5.86 (m, 1 H) 3.53-5.25 (m, 6 H) 2.98-3.34 (m, 1 H) 2.16-2.49 (m, 4 H) 1.52 (br d, J = 19.5 Hz, 3 H) 1.07-1.17 (m, 6 H). $^{19}$F NMR (377 MHz, CDCl$_3$) δ −104.8 (br. s., 1 F) −104.9 (br. s., 1 F). |
| 8-5 | 546.2 | $^1$H NMR (400 MHz, DMSO-d$_6$) δ 10.08-10.10 (m, 1 H) 8.47-8.48 (m, 1 H) 8.37 (s, 1H), 8.05 (s, 1H), 7.16-7.26 (m, 1H) 7.04-7.25 (m, 1 H) 6.82-6.90 (m, 1 H) 6.63-6.77 (m, 2 H) 6.30-6.31 (m, 1 H) 6.16-6.21 (m, 1 H) 5.72-5.79 (m, 1 H) 3.84-4.02 (m, 6 H) 3.76-3.81 (m, 2 H), 1.54-1.55 (m, 1 H) 1.23 (s, 2H) 0.74-0.85 (m, 1 H), 0.52-0.69 (m, 1 H) |
| 8-6 | 562.1 | $^1$H NMR (400 MHz, CDCl$_3$) δ 8.62 (1 H, br s) 8.10-8.13 (1 H, m) 7.49-7.56 (2 H, m) 7.35-7.43 (1 H, m) 7.22-7.30 (1 H, m) 7.10 (1 H, br s) 6.54-6.73 (3 H, m) 6.38-6.45 (1 H, m) 5.82 (1 H, dd, J = 10.57, 1.45 Hz) 2.60-5.27 (8 H, m) 1.42-1.54 (3 H, m) 1.23 (3 H, d, J = 6.84 Hz) 1.03 (3 H, d, J = 6.84 Hz) |
| 9-1 | 611.0 | $^1$H NMR (400 MHz, DMSO-d$_6$) δ 10.42 (br d, J = 17.0 Hz, 1 H), 7.86-8.11 (m, 1 H), 7.50-7.63 (m, 1 H), 7.47 (br t, J = 6.0 Hz, 1 H), 7.36 (t, J = 7.5 Hz, 1 H), 7.15-7.26 (m, 1 H), 7.05 (d, J = 2.3 Hz, 1 H), 6.78-6.96 (m, 1 H), 6.44-6.58 (m, 1 H), 6.11-6.29 (m, 2 H), 5.71-5.82 (m, 1 H), 4.68-4.98 (m, 1 H), 3.96-4.52 (m, 3 H), 3.52-3.85 (m, 2 H), 3.34-3.51 (m, 1 H), 2.95-3.26 (m, 1 H), 1.27-1.41 (m, 3 H), 0.95-1.13 (m, 6 H) |
| 9-2 | 531.0 | $^1$H NMR (400 MHz, DMSO-d$_6$) δ 7.91-8.08 (m, 1 H), 7.49-7.67 (m, 2 H), 7.41 (br d, J = 5.8 Hz, 1 H), 7.21 (br s, 1 H), 6.76-6.98 (m, 1 H), 6.52-6.67 (m, 1 H), 6.09-6.29 (m, 1 H), 5.75 (br s, 1 H), 4.61-4.96 (m, 1 H), 4.23-4.48 (m, 1 H), 3.93-4.21 (m, 2 H), 3.50-3.77 (m, 1H), 3.33-3.49 (m, 1 H), 3.23-3.28 (m, 1 H), 2.94-3.24 (m, 1 H), 1.27 (br d, J = 9.3 Hz, 6 H), 1.09 (br s, 3 H) |
| 9-3 | 576.2 | $^1$H NMR (400 MHz, DMSO-d$_6$) δ 7.88-8.01 (m, 1 H), 7.49-7.61 (m, 1 H), 7.46 (br t, J = 7.6 Hz, 1 H), 7.36 (t, J = 7.3 Hz, 1 H), 7.15-7.25 (m, 1 H), 7.08 (d, J = 8.7 Hz, 1 H), 6.76-6.95 (m, 1 H), 6.57 (dd, J = 8.7, 2.5 Hz, 1 H), 6.17-6.32 (m, 2 H), 6.11-6.16 (m, 1 H), 5.72-5.81 (m, 1 H), 5.40 (br d, J = 10.8 Hz, 2 H), 4.66-4.99 (m, 1 H), 4.21-4.52 (m, 2 H), 3.94-4.20 (m, 2 H), 3.53-3.82 (m, 2 H), 3.36-3.51 (m, 1 H), 1.27-1.40 (m, 3 H), 0.95-1.12 (m, 6 H) |
| 9-4 | 593.2 | $^1$H NMR (400 MHz, DMSO-d$_6$) δ 9.94 (br. s., 1H), 8.10 (s, 1H), 7.72 (d, J = 8.1 Hz, 1H), 7.43-7.51 (m, 1H), 7.31-7.42 (m, 3H), 7.11-7.27 (m, 4H), 6.68-6.93 (m, 2H), 6.14-6.36 (m, 2H), 5.70-5.83 (m, 1H), 3.72-4.12 (m, 8H), 2.23-2.40 (m, 1H), 1.32-1.65 (m, 2H), 0.95-1.16 (m, 3H), 0.36-0.75 (m, 3H). |
| 9-5 | 530.2 | $^1$H NMR (400 MHz, DMSO-d$_6$) δ 7.97 (s, 1 H), 7.85-7.90 (m, 2 H) 7.64-7.72 (m, 2 H) 7.10-7.18 (m, 1 H) 6.73-6.78 (m, 1 H) 6.57-6.67 (m, 2 H) 6.33 (s, 1 H) 6.10-6.14 (m, 1 H) 5.66-5.72 (m, 1 H) 3.85-3.96 (m, 4 H) 3.48-3.79 (m, 2 H) 3.68-3.75 (m, 2 H) |
| 9-6 | 546.2 | $^1$H NMR (400 MHz, DMSO-d$_6$) δ 9.92-10.25 (m, 1 H) 8.44-8.82 (m, 1 H) 8.27-8.40 (m, 1 H) 7.99 (s, 1 H) 7.27-7.28 (m, 1 H) 7.11-7.21 (m, 1 H) 6.72-6.91 (m, 1 H) 6.48-6.71 (m, 2 H) 6.03-6.31 (m, 2 H) 5.48-5.79 (m, 1 H) 3.57 4.16 (m, 8 H) 1.36-1.70 (m, 1 H) 0.21-0.92 (m, 4 H) |
| 9-7 | 561.2 | $^1$H NMR (400 MHz, METHANOL-d$_4$) δ 8.44-8.56 (m, 1 H) 8.41-8.44 (m, 1 H) 8.00-8.03 (m, 1 H) 7.35-7.37 (m, 1 H) 7.14-7.23 (m, 1 H) 6.75-6.83 (m, 1 H), 6.56-6.66 (m, 2 H) 6.40-6.46 (m, 1 H) 6.25-6.31 (m, 1 H) 5.75-5.82 (m, 1 H) 4.42-4.67 (m, 2 H) 3.59-3.89 (m, 2 H) 1.57-1.70 (m, 1 H) 1.45-1.52 (m, 3 H) 1.27 (s, 4H) 0.80-0.88 (m, 3 H) |
| 9-8 | 561.2 | $^1$H NMR (400 MHz, METHANOL-d$_4$) δ 8.43-8.50 (m, 1 H) 8.30-8.36 (m, 1 H) 7.91-7.97 (m, 1 H) 7.25-7.32 (m, 1 H) 7.07-7.14 (m, 1 H) 6.70-6.78 (m, 1 H) 6.47-6.60 (m, 2 H) 6.33-6.41 (m, 1 H) 6.16-6.26 (m, 1 H) 5.68-5.77 (m, 1 H) 4.32-4.52 (m, 2 H) 3.50-3.81 (m, 2 H) 1.51-1.62 (m, 1 H) 1.36-1.41 (m, 3 H) 1.19 (s, 4 H) 0.74-0.85 (m, 3 H) |
| 9-9 | 581.2 | $^1$H NMR (400 MHz, METHANOL-d$_4$) δ 8.48-8.57 (m, 1 H) 8.31-8.41 (m, 1 H) 8.13-8.18 (m, 1 H) 7.38-7.54 (m, 3 H) 7.28-7.40 (m, 1 H) 6.82-6.95 (m, 1 H) 6.45-6.50 (m, 1 H) 6.28-6.38 (m, 1 H) 5.81-5.90 (m, 1 H) 4.47-4.63 (m, 2 H) 4.07-4.25 (m, 1 H) 3.63-3.94 (m, 2 H) 2.13-2.21 (m, 3 H) 1.62-1.75 (m, 1 H) 1.51-1.57 (m, 3 H) 1.27-1.37 (m, 3 H) 0.86-0.95 (m, 3 H) |
| 9-10 | 597.2 | $^1$H NMR (400 MHz, DMSO-d$_6$) δ 8.01 (br d, J = 18.0 Hz, 1 H), 7.71 (d, J = 8.1 Hz, 1 H), 7.50-7.58 (m, 1 H), 7.39-7.49 (m, 2 H), 7.35 (t, J = 7.4 Hz, 1 H), 7.09-(7.27 (m, 2 H), 6.78-6.97 (m, 1 H), 6.14-6.29 (m, 2 H), 5.71-5.82 (m, 1 H), 4.70-4.98 (m, 1 H), 3.98-4.54 (m, 3 H), 3.39-3.85 (m, 2 H), 2.91-3.29 (m, 1 H), 1.27-1.41 (m, 3 H), 1.10 (br t, J = 6.2 Hz, 3 H), 0.94-1.07 (m, 3 H) |
| 9-11 | 561.2 | $^1$H NMR (400 MHz, DMSO-d$_6$) δ 7.99 (br d, J = 16.6 Hz, 1 H), 7.49-7.68 (m, 2 H), 7.29-7.48 (m, 4 H), 7.10-7.26 (m, 2 H), 6.76-6.96 (m, 1 H), 6.12-6.31 (m, 2 H), 5.71-5.82 (m, 1 H), 4.68-4.97 (m, 1 H), 3.95-4.51 (m, 3 H), 3.44-3.85 (m, 2 |

TABLE 13-continued

Analytical Data for General Procedures

| Ex. # | LRMS: (ESI, +ve ion) m/z | NMR |
|---|---|---|
| | | H), 2.92-3.26 (m, 2 H), 1.27-1.41 (m, 3 H), 1.06-1.17 (m, 3 H), 0.92-1.06 (m, 3 H) |
| 9-12 | 583 | $^1$H NMR (400 MHz, CDCl$_3$) δ 8.35 (s, 1 H) 8.08 (d, J = 8.3 Hz, 1 H) 7.51-7.59 (m, 1 H) 7.34-7.44 (m, 3 H) 7.21 (td, J = 7.7, 0.8 Hz, 1 H) 6.85 (d, J = 8.5 Hz, 1 H) 6.56-6.75 (m, 1 H) 6.45 (dd, J = 16.8, 1.7 Hz, 1 H) 5.81-5.90 (m, 1 H) 4.33-5.25 (m, 3 H) 3.82-4.01 (m, 1 H) 3.05-3.71 (m, 3 H) 2.40-2.58 (m, 2 H) 2.20-2.37 (m, 2 H) 1.57 (br d, J = 18.0 Hz, 3 H) 1.10 (td, J = 7.6, 0.8 Hz, 6 H). |
| 9-13 | 579.2 | $^1$H NMR (400 MHz, CDCl$_3$) δ 7.93 (0.5 H, s) 7.92 (0.5 H, s) 7.69-7.74 (1 H, m) 7.18-7.51 (7 H, m) 7.11-7.16 (1 H, m) 6.88 (1 H, dd, J = 25.82, 2.54 Hz) 6.59-6.68 (2 H, m) 6.42 (1 H, dd, J = 16.82, 1.76 Hz) 5.82 (1 H, dd, J = 10.56, 1.56 Hz) 3.81-4.11 (8 H, m) 2.65-2.74 (1 H, m) 1.25 (1.5 H, d, J = 6.85 Hz) 1.22 (1.5 H, d, J = 6.85 Hz) 1.13 (1.5 H, d, J = 6.85 Hz) 0.98 (1.5 H, d, J = 6.85 Hz) |
| 9-14 | 540.2 | $^1$H NMR (400 MHz, DMSO-d$_6$) δ 10.21 (0.6 H, br s) 10.12 (0.4 H, br s) 8.29-8.35 (1 H, m) 7.28-7.38 (1 H, m) 6.73-6.85 (3 H, m) 6.17 (1 H, dd, J = 16.59, 2.28 Hz) 5.74 (1 H, dd, J = 10.37, 2.28 Hz) 5.30-5.38 (0.6 H, m) 5.00-5.06 (0.4 H, m) 3.61-3.96 (8 H, m) 2.90-3.06 (1 H, m) 1.69-1.83 (1 H, m) 1.15-1.52 (6 H, m) 0.69-1.04 (6 H, m) |
| 10-1 | 503.1 | $^1$H NMR (400 MHz, DMSO-d$_6$) δ 10.15 (1 H, br s) 8.33 (1 H, s) 7.36-7.45 (2 H, m) 7.24-7.36 (4 H, m) 6.90 (1 H, dd, J = 16.63, 10.37 Hz) 6.70-6.80 (2 H, m) 6.18 (1 H, dd, J = 16.73, 2.25 Hz) 5.75 (1 H, dd, J = 10.56, 2.15 Hz) 3.83-3.97 (4 H, m) 3.47-3.62 (4 H, m) 1.98-2.06 (3 H, m) |
| 10-2 | 519.2 | $^1$H NMR (CDCl$_3$) δ: 8.16-8.24 (m, 1H), 7.61-7.67 (m, 1H), 7.43-7.52 (m, 2H), 7.15-7.23 (m, 1H), 7.05-7.13 (m, 1H), 6.92-7.02 (m, 1H), 6.70-6.82 (m, 2H), 6.57-6.69 (m, 1H), 6.30-6.40 (m, 1H), 5.68-5.81 (m, 1H), 3.81-4.03 (m, 4H), 3.49-3.71 (m, 7H), 2.52-2.66 (m, 1H). |
| 10-3 | 537.0 | $^1$H NMR (400 MHz, METHANOL-d$_4$) δ 8.35 (1 H, s) 7.38-7.42 (1 H, m) 7.37 (1 H, s) 7.31-7.36 (2 H, m) 7.21 (1 H, td, J = 8.31, 6.85 Hz) 6.83 (1 H, dd, J = 16.73, 10.66 Hz) 6.69 (1 H, d, J = 8.41 Hz) 6.63 (1 H, br t, J = 8.80 Hz) 6.24 (1 H, dd, J = 16.82, 1.96 Hz) 5.77 (1 H, dd, J = 10.66, 1.86 Hz) 3.94-4.01 (4 H, m) 3.58-3.66 (4 H, m) 1.99-2.04 (3 H, m) |
| 10-4 | 531.2 | $^1$H NMR (400 MHz, METHANOL-d$_4$) δ 8.34 (1 H, s) 7.44-7.51 (2 H, m) 7.34 (1 H, d, J = 4.30 Hz) 7.27-7.32 (1 H, m) 7.15-7.25 (2 H, m) 6.83 (1 H, dd, J = 16.82, 10.56 Hz) 6.66 (1 H, d, J = 8.22 Hz) 6.57-6.64 (1 H, m) 6.21-6.27 (1 H, m) 5.77 (1 H, dd, J = 10.66, 1.86 Hz) 3.93-4.02 (4 H, m) 3.56-3.65 (4 H, m) 2.46-2.56 (2 H, m) 0.98-1.13 (6 H, m) |
| 10-5 | 517.1 | $^1$H NMR (400 MHz, METHANOL-d$_4$) δ 8.44 (1 H, s) 7.46-7.57 (3 H, m) 7.26-7.44 (3 H, m) 6.94 (1 H, dd, J = 16.73, 10.66 Hz) 6.77 (1 H, d, J = 8.22 Hz) 6.68-6.75 (1 H, m) 6.35 (1 H, dd, J = 16.73, 1.86 Hz) 5.88 (1 H, dd, J = 10.76, 1.96 Hz) 4.04-4.12 (4 H, m) 3.67-3.76 (4 H, m) 2.36-2.60 (2 H, m) 1.06 (3 H, q, J = 7.63 Hz) |
| 10-6 | 504.1 | $^1$H NMR (400 MHz, METHANOL-d$_4$) δ 8.56 (1 H, br d, J = 5.09 Hz) 8.51 (1 H, s) 8.42 (1 H, s) 7.49 (1 H, br d, J = 5.09 Hz) 7.43 (1 H, s) 7.22-7.29 (1 H, m) 6.87 (1 H, dd, J = 16.73, 10.66 Hz) 6.72 (1 H, br d, J = 8.41 Hz) 6.67 (1 H, br t, J = 8.71 Hz) 6.28 (1 H, dd, J = 16.73, 1.27 Hz) 5.79-5.84 (1 H, m) 3.98-4.06 (4 H, m) 3.64-3.73 (4 H, m) 2.19 (3 H, s) |
| 10-7 | 517.2 | $^1$H NMR (400 MHz, METHANOL-d$_4$) δ 8.46 (1 H, s) 7.24-7.41 (5 H, m) 6.93 (1 H, dd, J = 16.82, 10.56 Hz) 6.76 (1 H, d, J = 8.41 Hz) 6.68-6.74 (1 H, m) 6.34 (1 H, dd, J = 16.82, 1.96 Hz) 5.87 (1 H, dd, J = 10.56, 1.96 Hz) 4.05-4.11 (4 H, m) 3.68-3.76 (4 H, m) 2.02 (3 H, s) 2.00 (3 H, s) |
| 10-8 | 504.2 | $^1$H NMR (400 MHz, METHANOL-d$_4$) δ 8.62 (1 H, dd, J = 4.89, 1.56 Hz) 8.43 (1 H, s) 7.87 (1 H, dd, J = 7.73, 1.47 Hz) 7.48 (1 H, dd, J = 7.63, 5.09 Hz) 7.43 (1 H, s) 7.27 (1 H, td, J = 8.31, 6.85 Hz) 6.89 (1 H, dd, J = 16.82, 10.56 Hz) 6.74 (1 H, d, J = 8.22 Hz) 6.68 (1 H, t, J = 8.80 Hz) 6.30 (1 H, dd, J = 16.73, 1.86 Hz) 5.83 (1 H, dd, J = 10.66, 1.86 Hz) 3.99-4.07 (4 H, m) 3.65-3.74 (4 H, m) 2.34 (3 H, s) |
| 10-9 | 528.2 | $^1$H NMR (400 MHz, METHANOL-d$_4$) δ 8.33 (1 H, s) 7.75 (1 H, s) 7.52-7.56 (1 H, m) 7.12-7.28 (4 H, m) 6.82 (1 H, dd, J = 16.73, 10.66 Hz) 6.64 (1 H, d, J = 8.41 Hz) 6.55-6.61 (1 H, m) 6.24 (1 H, dd, J = 16.82, 1.96 Hz) 6.14 (1 H, dd, J = 3.33, 0.78 Hz) 5.77 (1 H, dd, J = 10.56, 1.96 Hz) 3.91-4.01 (4 H, m) 3.55-3.63 (4 H, m) |
| 10-10 | 529.1 | $^1$H NMR (400 MHz, METHANOL-d$_4$) δ 8.52 (1 H, s) 7.55-7.63 (2 H, m) 7.44-7.51 (2 H, m) 7.35-7.43 (1 H, m) 7.24 (1 H, t, J = 7.04 Hz) 7.02 (1 H, dd, J = 16.73, 10.66 Hz) 6.83-6.90 (1 H, m) 6.76-6.83 (1 H, m) 6.43 (1 H, dd, J = 16.73, 1.66 Hz) 5.97 (1 H, dd, J = 10.66, 1.66 Hz) 4.13-4.19 (4 H, m) 3.76-3.82 (4 H, m) 1.56-1.70 (1 H, m) 0.70-0.92 (3 H, m) 0.55-0.68 (1 H, m) |
| 10-11 | 523.1 | $^1$H NMR (400 MHz, METHANOL-d$_4$) δ 8.40 (1 H, s) 7.50-7.70 (4 H, m) 7.42 (1 H, s) 7.22-7.30 (1 H, m) 6.89 (1 H, dd, J = 16.73, 10.66 Hz) 6.63-6.76 (2 H, m) 6.30 (1 H, dd, J = 16.73, 1.86 Hz) 5.83 (1 H, dd, J = 10.56, 1.96 Hz) 3.98-4.10 (4 H, m) 3.62-3.76 (4 H, m) |
| 10-12 | 543.1 | $^1$H NMR (400 MHz, METHANOL-d$_4$) δ 8.45 (1 H, s) 7.63-7.67 (1 H, m) 7.51-7.54 (1 H, m) 7.44-7.48 (1 H, m) 7.34-7.37 (1 H, m) 7.21 (1 H, td, J = 8.22, 6.85 Hz) 6.90 (1 H, dd, J = 16.73, 10.66 Hz) 6.58-6.72 (2 H, m) 6.31 (1 H, dd, J = 16.82, 1.96 Hz) 5.84 (1 H, dd, J = 10.56, 1.96 Hz) 4.03-4.08 (4 H, m) 3.69-3.75 (4 H, m) 2.22 (1.25 H, s) 2.20 (1.75 H, s) |
| 10-13 | 447.0 | $^1$H NMR (400 MHz, DMSO-d$_6$) δ 10.26 (1 H, br s) 8.31 (1 H, s) 8.14 (1 H, s) 7.31-7.40 (1 H, m) 6.78-6.92 (3 H, m) 6.17 (1 H, dd, J = 16.63, 2.35 Hz) 5.74 (1 H, dd, J = 10.37, 2.35 Hz) 3.79-3.92 (4 H, m) 3.46-3.55 (4 H, m) |
| 11-1-1 | 567.2 | $^1$H NMR (400 MHz, CDCl$_3$) δ 10.28 (1 H, br s) 7.94 (1 H, s) 7.35-7.49 (4 H, m) 7.25-7.31 (2 H, m) 7.11 (1 H, d, J = 7.67 Hz) 6.64 (1 H, dd, J = 16.79, 10.57 Hz) 6.54 (1 H, s) 6.41 (1 H, dd, J = |

TABLE 13-continued

Analytical Data for General Procedures

| Ex. # | LRMS: (ESI, +ve ion) m/z | NMR |
|---|---|---|
| | | 16.79, 1.87 Hz) 5.81 (1 H, dd, J = 10.57, 1.66 Hz) 3.83-4.07 (8 H, m) 2.74 (1 H, spt, J = 6.84 Hz) 2.13 (3 H, s) 1.23 (3 H, d, J = 6.84 Hz) 1.04 (3 H, d, J = 6.84 Hz) |
| 11-1-2 | 567.2 | $^1$H NMR (400 MHz, CDCl$_3$) δ 10.37 (1 H, br s) 7.94 (1 H, s) 7.34-7.50 (4 H, m) 7.21-7.31 (2 H, m) 7.13 (1 H, d, J = 7.67 Hz) 6.64 (1 H, dd, J = 16.90, 10.68 Hz) 6.55 (1 H, s) 6.41 (1 H, dd, J = 16.79, 1.66 Hz) 5.81 (1 H, dd, J = 10.47, 1.55 Hz) 3.83-4.08 (8 H, m) 2.70 (1 H, spt, J = 6.84 Hz) 2.13 (3 H, s) 1.22 (3 H, d, J = 6.84 Hz) 1.03 (3 H, d, J = 6.84 Hz). MS (ESI, +ve) m/z: 567.2 [M + H]$^+$. |
| 11-2-1 | 581.3 | $^1$H NMR (400 MHz, METHANOL-d$_4$) δ 8.12-8.21 (m, 1H), 7.30-7.56 (m, 6H), 7.21 (d, J = 7.7 Hz, 1H), 6.80-6.97 (m, 1H), 6.46 (s, 1H), 6.30-6.41 (m, 1H), 5.79-5.94 (m, 1H), 5.02-5.14 (m, 1H), 4.39-4.69 (m, 2H), 4.07-4.30 (m, 1H), 3.67 (s, 2H), 3.21-3.51 (m, 1H), 2.68-2.84 (m, 1H), 2.13 (s, 3H), 1.54 (br d, J = 6.0 Hz, 3H), 1.23 (d, J = 7.1 Hz, 3H), 1.05 (d, J = 6.8 Hz, 3H) |
| 11-2-2 | 581.2 | $^1$H NMR (400 MHz, METHANOL-d$_4$) δ 8.15 (s, 1H), 7.42-7.58 (m, 4H), 7.30-7.39 (m, 2H), 7.25 (d, J = 7.7 Hz, 1H), 6.81-6.98 (M, 1H), 6.48 (s, 1H), 6.29-6.41 (m, 1H), 5.87 (dd, J = 1.35, 10.68 Hz, 1H), 5.02-5.12 (m, 1H), 4.42-4.69 (m, 2H), 4.05-4.29 (m, 1H), 3.65-3.93 (m, 2H), 3.21-3.47 (m, 1H), 2.64-2.79 (m, 1H), 2.15 (s, 3H), 1.53 (br d, J = 6.6 Hz, 3H), 1.23 (br d, J = 6.8 Hz, 3H), 1.06 (d, J = 6.8 Hz, 3H) |

TABLE 14

Analytical Data for Individual Examples

| Ex. # | LRMS: (ESI, +ve ion) m/z | NMR |
|---|---|---|
| 12 | 453.2 | $^1$H NMR (CDCl$_3$) δ: 8.30-8.37 (m, 1H), 8.11-8.18 (m, 1H), 7.29-7.38 (m, 1H), 6.96-7.18 (m, 1H), 6.88-6.94 (m, 1H), 6.76-6.85 (m, 1H) 6.59-6.72 (m, 1H), 6.31-6.42 (m, 1H), 5.73-5.84 (m, 1H), 3.73-4.05 (m, 4H), 3.35-3.62 (m, 4H), 2.40-2.52 (m, 1H), 1.35-1.42 (m, 1H), 1.29-1.34 (m, 1H), 1.03-1.14 (m, 2H). m/z (ESI) M + H: 453.2. |
| 13 | 504.2 | $^1$H NMR (CDCl$_3$) δ: 7.96-8.09 (m, 2H), 7.46-7.57 (m, 2H), 7.37-7.44 (m, 1H), 7.29-7.33 (m, 1H), 7.20-7.26 (m, 1H), 6.96-7.07 (m, 1H), 6.81-6.87 (m, 1H), 6.70-6.77 (m, 1H), 6.54-6.67 (m, 1H), 6.29-6.41 (m, 1H), 5.68-5.82 (m, 1H), 3.74-3.96 (m, 4H), 3.12-3.43 (m, 4H). |
| 14 | 481.2. | $^1$H NMR (CDCl$_3$) δ: 8.10-8.22 (m, 2H), 7.29-7.38 (m, 1H), 6.86-6.93 (m, 1H), 6.77-6.85 (m, 1H), 6.61-6.72 (m, 1H), 6.33-6.44 (m, 1H), 5.74-5.85 (m, 1H), 3.82-4.05 (m, 4H), 3.75-3.82 (m, 1H), 3.40-3.63 (m, 4H), 2.06-2.24 (m, 4H), 1.81-1.96 (m, 1H), 1.67-1.79 (m, 2H). |
| 15 | 496.2 | $^1$H NMR (CDCl$_3$) δ: 8.08-8.15 (m, 1H), 7.98-8.05 (m, 1H), 7.29-7.39 (m, 1H), 6.86-6.94 (m, 1H), 6.76-6.85 (m, 1H), 6.59-6.70 (m, 1H), 6.30-6.43 (m, 1H), 5.72-5.84 (m, 1H), 3.77-4.05 (m, 4H), 3.40-3.56 (m, 4H), 3.32-3.38 (m, 4H), 1.73-1.85 (m, 4H), 1.64-1.70 (m, 2H) |
| 16 | 505.2 | $^1$H NMR (CDCl$_3$) δ: 8.41-8.45 (m, 1H), 8.17-8.20 (m, 1H), 7.40-7.45 (m, 2H), 7.28-7.37 (m, 2H), 7.20-7.26 (m, 1H), 6.78-6.87 (m, 2H), 6.59-6.70 (m, 1H), 6.31-6.41 (m, 1H), 5.97-6.06 (m, 1H), 5.74-5.81 (m, 1H), 3.76-4.03 (m, 4H), 3.38-3.53 (m, 4H). |
| 17-1 | 539.2 | $^1$H NMR (400 MHz, DMSO-d$_6$) δ 9.97 (s, 1H), 8.10 (s, 1H), 7.80 (d, J = 8.4 Hz, 1H), 7.40-7.46 (m, 1H), 7.19-7.30 (m, 3H), 7.97 (d, J = 2.4 Hz, 1H), 6.62-6.71 (m, 2H), 3.80-3.93 (m, 4H), 3.62-3.69 (m, 4H), 3.07 (d, J = 4.1 Hz, 2H), 2.17 (s, 6H). |
| 17-2 | 525.0 | $^1$H NMR (400 MHz, DMSO-d$_6$) δ 9.97 (s, 1H), 8.10 (s, 1H), 7.80 (d, J = 8.4 Hz, 1H), 7.40-7.46 (m, 1H), 7.19-7.30 (m, 3H), 7.97 (d, J = 2.4 Hz, 1H), 6.62-6.71 (m, 2H), 3.80-3.93 (m, 4H), 3.62-3.69 (m, 4H), 3.07 (d, J = 4.1 Hz, 2H), 2.17 (s, 6H). |
| 18-1 | 512.0 | $^1$H NMR (400 MHz, DMSO-d$_6$) δ 8.12 (s, 1H), 7.94 (d, J = 8.2 Hz, 1H), 7.47-7.55 (m, 2H), 7.25-7.34 (m, 2H), 7.19 (d, J = 2.5 Hz, 1H), 5.43 (br. s, 1H), 5.20 (br. s, 1H), 5.14 (t, J = 5.8 Hz, 1H), 4.12 (d, J = 5.7 Hz, 2H), 3.94 (s, 3H), 3.78-3.85 (m, 4H), 3.54-3.66 (m, 4H). |
| 18-2 | 560.0 | $^1$H NMR (400 MHz, DMSO-d$_6$) δ 9.96 (br. s, 1H), 8.13 (s, 1H), 7.80 (d, J = 8.2 Hz, 1H), 7.40-7.47 (m, 1H), 7.19-7.29 (m, 3H), 7.07 (d, J = 2.4 Hz, 1H), 5.41 (s, 1H), 4.38 (s, 1H), 4.38 (s, 2H), 3.84-3.93 (m, 4H), 3.62-3.72 (m, 4H). |
| 18-3 | 498.0 | $^1$H NMR (400 MHz, DMSO-d$_6$) δ 9.98 (br. s, 1H), 8.11 (s, 1H), 7.79 (d, J = 8.2 Hz, 1H), 7.37-7.48 (m, 1H), 7.17-7.28 (m, 3H), 7.07 (d, J = 2.4 Hz, 1H), 5.43 (br. s, 1H), 5.20 (br. s, 1H), 5.07-5.14 (m, 1H), 4.12 (br. s, 2H), 3.78-3.86 (m, 4H), 3.57-3.66 (m, 4H). |
| 19-1 | 486.0 | $^1$H NMR (400 MHz, DMSO-d$_6$) δ 8.13 (s, 1H), 8.02 (s, 1H), 7.33 (d, J = 2.2 Hz, 1H), 6.99 (d, J = 2.4 Hz, 1H), 6.85 (dd, J = 16.6, 10.6 Hz, 1H), 6.18 (dd, J = 16.7, 2.3 Hz, 1H), 5.76 (dd, J = 10.5, 2.3 Hz, 1H), 3.85-3.95 (m, 4H), 3.84 (s, 3H), 3.62-3.72 (m, 4H), 3.56 (s, 3H). |
| 19-2 | 472.0 | $^1$H NMR (400 MHz, DMSO-d$_6$) δ 9.40 (s, 1H), 8.12 (s, 1H), 7.92 (s, 1H), 7.12 (d, J = 2.2 Hz, 1H), 6.81-6.91 (m, 2H), 6.18 (dd, J = 16.7, 2.5 Hz, 1H), 5.76 (dd, J = 10.4, 2.4 Hz, 1H), 3.81-3.94 (m, 4H), 3.62-3.70 (m, 4H), 3.52 (s, 3H). |
| 19-3 | 472.0 | $^1$H NMR (400 MHz, DMSO-d$_6$) δ 9.28 (s, 1H), 8.11 (s, 1H), 8.01 (s, 1H), 6.95 (d, J = 2.0 Hz, 1H), 6.77-6.90 (m, 2H), 6.18 (dd, J = 16.7, 2.5 Hz, 1H), 5.76 (dd, J = 10.4, 2.2 Hz, 1H), 4.03 (s, 3H), 3.80-3.94 (m, 4H), 3.58-3.66 (m, 4H). |
| 20 | 512 | $^1$H NMR (400 MHz, DMSO-d$_6$) δ 9.93 (br s, 1H), 8.11 (s, 1H), 7.80 (d, J = 12 Hz, 1H), 7.43 (m, 1H), 7.26-7.20 (m, 3H), 7.07 (s, 1H), 5.32 (s, 1H), 5.16 (s, 1H), 3.83 (br s, 4H), 3.63 (br s, 4H), 3.53 (t, J = 8.0 Hz, 2H), 2.42 (t, J = 8.0 Hz, 2H). $^{19}$FNMR (377 MHz, DMSO-d$_6$) δ -123.8 (s, 1F). |
| 21 | 469 | $^1$H NMR (400 MHz, CDCl$_3$) δ 8.81 (dd, J = 4.2, 1.3 Hz, 1 H) 7.72-7.78 (m, 2 H) 7.64 (s, 1 H) 7.28 (d, J = 2.2 Hz, 1 H) |

TABLE 14-continued

Analytical Data for Individual Examples

| Ex. # | LRMS: (ESI, +ve ion) m/z | NMR |
|---|---|---|
| | | 7.16 (dd, J = 8.4, 4.3 Hz, 1 H) 6.56-6.66 (m, 1 H) 6.40 (dd, J = 16.8, 1.6 Hz, 1 H) 5.78-5.87 (m, 1 H) 4.01 (br. s, 2 H) 3.89 (br. s, 2 H) 3.50-3.60 (m, 4 H). $^{19}$F NMR (376 MHz, CDCl$_3$) δ -121.33 (s, 1 F). |
| 22 | 512.0 | $^1$H NMR (400 MHz, DMSO-d$_6$) δ 3.14-3.28 (m, 1 H) 3.52-3.87 (m, 3 H) 4.15-5.03 (m, 2 H) 5.15-5.23 (m, 1 H) 5.77-5.83 (m, 1 H) 6.13-6.24 (m, 1 H) 6.86 (br. s, 1 H) 7.06-7.12 (m, 1 H) 7.20-7.30 (m, 3 H) 7.38-7.49 (m, 1 H) 7.76-7.84 (m, 1 H) 8.07-8.13 (m, 1 H) 9.98 (br. s, 1 H) 13.42 (br. s, 1 H). |
| 23 | 482.0 | $^1$H NMR (400 MHz, DMSO-d$_6$) δ 12.92-13.19 (1 H, m), 8.02-8.21 (1 H, m), 7.47-7.60 (2 H, m), 7.02-7.09 (1 H, m), 6.80-6.93 (1 H, m), 6.15-6.25 (1 H, m), 5.71-5.82 (1 H, m), 3.80-3.96 (4 H, m), 3.60-3.72 (4 H, m), 1.55-1.74 (1 H, m), 0.72-0.79 (2 H, m), 0.58-0.71 (2 H, m). |
| 24 | 482.0 | $^1$H NMR (400 MHz, METHANOL-d$_4$) δ 7.90 (s, 1H), 7.63 (d, J = 8.5 Hz, 1H), 7.43 (t, J = 7.4 Hz, 1H), 7.24 (d, J = 8.5 Hz, 1H), 7.05 (t, J = 7.4 Hz, 1H), 6.72-6.84 (m, 1H), 6.67 (s, 1H), 6.15-6.28 (m, 1H), 5.68-5.81 (m, 1H), 3.87-3.97 (m, 4H), 3.63 (m, 4H), 2.90 (s, 3H). |
| 25 | 468.0 | $^1$H NMR (400 MHz, METHANOL-d$_4$) δ 7.85 (s, 1H), 7.53 (d, J = 8.5 Hz, 1H), 7.39 (t, J = 7.6 Hz, 1H), 7.23 (d, J = 8.5 Hz, 1H), 7.03 (t, J = 7.8 Hz, 1H), 6.82 (s, 1H), 6.71 (dd, J = 10.8, 16.8 Hz, 1H), 6.2 (dd, J = 1.5, 16.8 Hz, 1H), 5.70 (dd, J = 1.5, 10.8 Hz, 1H), 3.82-3.93 (m, 4H), 3.50-3.66 (m, 4H) |
| 26 | 468.0 | $^1$H NMR (400 MHz, METHANOL-d$_4$) δ 7.90 (s, 1H), 7.53 (d, J = 8.2 Hz, 1H), 7.42-7.49 (m, 1H), 7.10 (d, J = 8.0 Hz, 1H), 7.03-7.08 (m, J = 7.6 Hz, 1H), 6.67-6.81 (m, 2H), 6.19 (dd, J = 1.8, 16.6 Hz, 1H), 5.72 (dd, J = 1.8, 10.6 Hz, 1H), 3.87-3.93 (m, 4H), 3.56-3.66 (m, 4H). |
| 27 | 512.3 | $^1$H NMR (400 MHz, CDCl$_3$) δ 9.51 (0.6 H, br s) 8.98 (0.4 H, br s) 7.63 (0.4 H, s) 7.58 (0.6 H, s) 7.35-7.43 (2 H, m) 7.10-7.26 (3 H, m) 6.78 (1 H, dd, J = 16.63, 8.22 Hz) 6.59-6.71 (2 H, m) 6.36 (1 H, dd, J = 16.82, 1.57 Hz) 5.78 (1 H, dd, J = 10.56, 1.37 Hz) 4.10-4.38 (4 H, m) 3.80-4.03 (4 H, m) 2.60-2.72 (1 H, m) 2.61 (1.2 H, s) 2.59 (1.8 H, s) 0.91-1.08 (6 H, m) |
| 28 | 517.1 | $^1$H NMR (400 MHz, METHANOL-d$_4$) δ 8.27 (1 H, s) 8.15 (0.33 H, s) 8.10 (0.67 H, s) 7.19-7.31 (5 H, m) 7.10-7.16 (1 H, m) 6.86 (1 H, dd, J = 16.73, 10.66 Hz) 6.62-6.78 (2 H, m) 6.27 (1 H, dd, J = 16.82, 1.96 Hz) 5.80 (1 H, dd, J = 10.66, 1.86 Hz) 4.94-5.01 (1 H, m) 3.93-4.03 (4 H, m) 3.49-3.60 (4 H, m) 1.81 (3 H, d, J = 7.04 Hz) |
| 29 | 521.1 | $^1$H NMR (400 MHz, METHANOL-d$_4$) δ 8.32 (1 H, s) 8.19 (1 H, s) 7.26-7.34 (3 H, m) 6.98 (2 H, t, J = 8.71 Hz) 6.69-6.91 (3 H, m) 6.28 (1 H, dd, J = 16.92, 1.86 Hz) 5.82 (1 H, dd, J = 10.56, 1.76 Hz) 4.54-4.65 (2 H, m) 3.99 (4 H, m) 3.58 (4 H, m) |
| 30 | 489.0 | $^1$H NMR (400 MHz, CHLOROFORM-d) δ 8.21 (1 H, s) 8.06 (1 H, s) 7.62-7.69 (2 H, m) 7.45-7.51 (3 H, m) 7.24-7.32 (1 H, m) 6.81-6.90 (1 H, m) 6.75 (1 H, t, J = 8.41 Hz) 6.65 (1 H, dd, J = 16.82, 10.56 Hz) 6.38 (1 H, dd, J = 16.82, 1.76 Hz) 5.79 (1 H, dd, J = 10.56, 1.76 Hz) 3.86-4.02 (4 H, m) 3.57-3.76 (4 H, m) |
| 31 | 489.1 | $^1$H NMR (400 MHz, CDCl$_3$) δ 8.15 (1 H, s) 8.12 (1 H, s) 7.68-7.73 (2 H, m) 7.53-7.58 (3 H, m) 7.30 (1 H, br td, J = 8.22, 6.65 Hz) 6.88 (1 H, d, J = 8.22 Hz) 6.78 (1 H, t, J = 8.61 Hz) 6.57 (1 H, dd, J = 16.82, 10.56 Hz) 6.28 (1 H, dd, J = 16.73, 1.66 Hz) 5.71 (1 H, dd, J = 10.56, 1.56 Hz) 3.78-3.89 (4 H, m) 3.51-3.73 (4 H, m) |
| 32 | 443.1 | $^1$H NMR (400 MHz, CDCl$_3$) δ 8.23 (1 H, s) 8.11 (1 H, s) 7.32 (1 H, td, J = 8.31, 6.46 Hz) 6.88 (1 H, d, J = 8.22 Hz) 6.77-6.83 (1 H, m) 6.65 (1 H, dd, J = 16.82, 10.56 Hz) 6.37 (1 H, dd, J = 16.82, 1.76 Hz) 5.79 (1 H, dd, J = 10.47, 1.86 Hz) 4.18 (3 H, s) 3.79-4.05 (4 H, m) 3.34-3.54 (4 H, m) |
| 33 | 443.1 | $^1$H NMR (400 MHz, CDCl$_3$) δ 8.32 (1 H, s) 8.01 (1 H, s) 7.32 (1 H, td, J = 8.27, 6.55 Hz) 6.89 (1 H, d, J = 8.22 Hz) 6.77-6.83 (1 H, m) 6.60 (1 H, dd, J = 17.02, 10.56 Hz) 6.30 (1 H, dd, J = 16.82, 1.76 Hz) 5.75 (1 H, dd, J = 10.56, 1.76 Hz) 4.22 (3 H, s) 3.67-3.98 (4 H, m) 3.25-3.55 (4 H, m) |
| 34 | 427.1 | $^1$H NMR (400 MHz, CDCl$_3$) δ ppm 8.13 (1 H, s) 8.12 (1 H, s) 7.28-7.36 (4 H, m) 7.20-7.26 (1 H, m) 6.65 (1 H, dd, J = 16.82, 10.56 Hz) 6.37 (1 H, dd, J = 16.82, 1.57 Hz) 5.78 (1 H, dd, J = 10.56, 1.56 Hz) 4.61 (2 H, s) 3.83-4.01 (4 H, m) 3.48-3.62 (4 H, m). |
| 35 | 503.1 | $^1$H NMR (400 MHz, CDCl$_3$) δ 8.13 (1 H, s) 8.11(1 H, s) 7.12-7.37 (6H, m) 6.91 (1 H, d, J = 8.22 Hz) 6.77 (1 H, t, J = 8.61 Hz) 6.64 (1 H, dd, J = 16.82, 10.56 Hz) 6.37 (1 H, dd, J = 16.82, 1.76 Hz) 5.79 (1 H, dd, J = 10.56, 1.96 Hz) 4.55 (2 H, s) 3.34-4.01 (8 H, m) |
| 36 | 503.1 | $^1$H NMR (400 MHz, CDCl$_3$) δ 8.12 (1 H, s) 8.05 (1 H, s) 7.26 - 7.36 (5 H, m) 7.19-7.24 (1 H, m) 6.93 (1 H, d, J = 8.41 Hz) 6.76 (1 H, t, J = 8.31 Hz) 6.58 (1 H, dd, J = 16.82, 10.76 Hz) 6.28 (1 H, dd, J = 16.82, 1.76 Hz) 5.75 (1 H, dd, J = 10.56, 1.76 Hz) 4.54 (2 H, s) 3.32 - 3.93 (8 H, m) |
| 37 | 523 | $^1$H NMR (400 MHz, CDCl$_3$) δ 8.23 (0.6 H, s) 8.22 (0.4 H, s) 8.02 (0.4 H, s) 8.00 (0.6 H, s) 7.19-7.57 (8 H, m) 6.68 (0.4 H, dd, J = 16.82, 10.56 Hz) 6.60 (0.6 H, dd, J = 16.82, 10.56 Hz) 6.38 (0.4 H, dd, J = 16.63, 1.76 Hz) 6.32 (0.6 H, dd, J = 16.82, 1.76 Hz) 5.79 (0.4 H, dd, J = 10.56, 1.76 Hz) 5.73 (0.6 H, dd, J = 10.56, 1.76 Hz) 4.67 (1.2 H, s) 4.60 (0.8 H, s) 3.74-4.06 (4 H, m) 3.46-3.70 (4 H, m) 2.21 (1.8 H, s) 2.06 (1.2 H, s) |
| 38 | 483.3 | $^1$H NMR (400 MHz, CDCl$_3$) δ 8.04 (1 H, s) 7.26-7.33 (1 H, m) 6.82 (1 H, d, J = 8.29 Hz) 6.71 (1 H, t, J = 8.91 Hz) 6.51 (1 H, dd, J = 16.79, 10.57 Hz) 6.30 (1 H, dd, J = 16.79, 1.45 Hz) 5.72 (1 H, dd, J = 10.47, 1.55 Hz) 4.15 (2 H, br d, J = 6.43 Hz) 3.69-3.90 (8 H, m) 1.14-1.27 (4 H, m) 0.73-0.88 (1 H, m) |

TABLE 14(b)

Analytical Data for Individual Examples

| Ex. # | LRMS: (ESI, +ve ion) m/z | NMR |
|---|---|---|
| 39-1 | 576.0 | $^1$H NMR (400 MHz, DMSO-d$_6$) δ ppm 10.07 (s, 1 H), 9.96-10.13 (m, 1 H), 8.39 (br s, 1H), 7.17-7.26 (m, 3 H), 7.09 (br d, J = 5.9 Hz, 1 H), 6.84 (br s, 1 H), 6.60-6.71 (m, 2 H), 6.20 (br d, J = 17.2 Hz, 1 H), 5.74-5.78 (m, 1 H), 4.77-4.99 (m, 1 H), 4.26 (br s, 3 H), 3.58-3.86 (m, 1 H), 3.57 (s, 1 H), 3.13 (br d, J = 1.7 Hz, 1 H), 1.85 (br s, 3 H), 1.34 (br d, J = 6.4 Hz, 3 H), 1.05 (d, J = 6.6 Hz, 3 H), 0.92 (d, J = 6.6 Hz, 3 H). $^{19}$F NMR (376 MHz, CHLOROFORM-d) δ ppm −104.54 (br d, J = 10.4 Hz, 1F). |
| 39-2 | 576.0 | $^1$H NMR (400 MHz, DMSO-d$_6$) δ ppm 10.07 (s, 1 H), 8.42 (br s, 1 H), 7.19-7.26 (m, 3 H), 7.10 (br d, J = 6.0 Hz, 1 H), 6.80-6.91 (m, 1 H), 6.70 (d, J = 8.0 Hz, 1 H), 6.65 (t, J = 8.7 Hz, 1 H), 6.21 (br d, J = 15.8 Hz, 1 H), 5.74-5.79 (m, 1 H), 4.94 (br s, 1 H), 4.27 (br s, 2 H), 4.03 (br d, J = 12.4 Hz, 1 H), 3.61-3.86 (m, 2 H), 2.94-3.20 (m, 1 H), 1.85 (br s, 3 H), 1.32 (br d, J = 6.2 Hz, 3 H), 1.02-1.08 (m, 4 H), 0.92 (d, J = 6.8 Hz, 3 H). $^{19}$F NMR (376 MHz, CHLOROFORM-d) δ ppm −104.83- −103.96 (m, 1F). |
| 40-1 | 560.9 | $^1$H NMR (400 MHz, DMSO-d$_6$) δ ppm 8.45 (br d, J = 5.4 Hz, 1 H), 8.39 (d, J = 5.0 Hz, 1 H), 7.47-7.55 (m, 1 H), 7.17-7.34 (m, 4 H), 6.81-6.92 (m, 1 H), 6.16-6.26 (m, 1 H), 5.73-5.80 (m, 1 H), 4.95 (br s, 1 H), 3.99-4.45 (m, 3 H), 3.71-3.85 (m, 1 H), 3.60-3.69 (m, 0.5 H), 3.41-3.53 (m, 0.5 H), 3.06-3.27 (m, 1 H), 2.65-2.75 (m, 1 H), 1.94 (s, 3 H), 1.34 (d, J = 6.6 Hz, 3 H), 1.07 (d, J = 6.6 Hz, 3 H), 0.94 (d, J = 6.6 Hz, 3 H). |
| 40-2 | 560.9 | $^1$H NMR (400 MHz, DMSO-d$_6$) δ ppm 8.46 (br d, J = 4.6 Hz, 1 H), 8.39 (d, J = 4.8 Hz, 1 H), 7.47-7.55 (m, 1 H), 7.17-7.34 (m, 4 H), 6.81-6.92 (m, 1 H), 6.16-6.26 (m, 1 H), 5.73-5.80 (m, 1 H), 4.95 (br s, 1 H), 3.99-4.45 (m, 3 H), 3.71-3.85 (m, 1 H), 3.60-3.69 (m, 0.5 H), 3.41-3.53 (m, 0.5 H), 3.06-3.27 (m, 1 H), 2.65-2.75 (m, 1 H), 1.93 (s, 3 H), 1.34 (d, J = 6.6 Hz, 3 H), 1.07 (d, J = 6.6 Hz, 3 H), 0.94 (d, J = 6.6 Hz, 3 H). |
| 41-1 | 561.2 | $^1$H NMR (400 MHz, DMSO-d$_6$) δ ppm 10.20 (s, 1 H), 8.39 (d, J = 4.8 Hz, 1 H), 8.24-8.34 (m, 1 H), 7.23-7.32 (m, 1 H), 7.19 (d, J = 5.0 Hz, 1 H), 6.87 (td, J = 16.3, 11.0 Hz, 1 H), 6.74 (d, J = 8.6 Hz, 1 H), 6.69 (t, J = 8.6 Hz, 1 H), 6.21 (br d, J = 16.2 Hz, 1 H), 5.74-5.80 (m, 1 H), 4.91 (br s, 1 H), 4.23-4.45 (m, 2 H), 3.97-4.21 (m, 1 H), 3.44-3.79 (m, 2 H), 3.11-3.31 (m, 1 H), 2.67-2.77 (m, 1 H), 1.91 (s, 3 H), 1.35 (d, J = 6.8 Hz, 3 H), 1.08 (d, J = 6.6 Hz, 3 H), 0.94 (d, J = 6.8 Hz, 3 H). |
| 41-2 | 561.2 | $^1$H NMR (400 MHz, DMSO-d$_6$) δ ppm 10.20 (s, 1 H), 8.39 (d, J = 4.8 Hz, 1 H), 8.24-8.34 (m, 1 H), 7.23-7.32 (m, 1 H), 7.19 (d, J = 5.0 Hz, 1 H), 6.87 (td, J = 16.3, 11.0 Hz, 1 H), 6.74 (d, J = 8.6 Hz, 1 H), 6.69 (t, J = 8.6 Hz, 1 H), 6.21 (br d, J = 16.2 Hz, 1 H), 5.74-5.80 (m, 1 H), 4.91-4.99 (m, 1 H), 4.23-4.45 (m, 2 H), 3.97-4.21 (m, 1 H), 3.44-3.79 (m, 2 H), 3.11-3.31 (m, 1 H), 2.67-2.77 (m, 1 H), 1.91 (s, 3 H), 1.35 (d, J = 6.8 Hz, 3 H), 1.08 (d, J = 6.6 Hz, 3 H), 0.94 (d, J = 6.8 Hz, 3 H). |
| 42-1 | 559.0 | $^1$H NMR (400 MHz, DMSO-d$_6$) δ ppm 10.25 (br s, 1 H), 8.16-8.34 (m, 2 H), 7.22-7.34 (m, 1 H), 7.10 (d, J = 5.0 Hz, 1 H), 6.79-6.94 (m, 1 H), 6.58-6.77 (m, 2 H), 6.13-6.27 (m, 1 H), 5.70-5.83 (m, 1 H), 4.86 (br s, 1 H), 4.26-4.48 (m, 2 H), 3.95-4.20 (m, 1 H), 3.45-3.73 (m, 2 H), 3.11-3.27 (m, 1 H), 1.91 (s, 3 H), 1.68 (br d, J = 3.9 Hz, 1 H), 1.36 (d, J = 6.6 Hz, 3 H), 0.82-0.88 (m, 1 H), 0.71-0.82 (m, 2 H), 0.58-0.66 (m, 1 H). $^{19}$F NMR (376 MHz, DMSO-d$_6$) δ ppm −116.15 (s, 1 F), −127.30 (s, 1 F). |
| 42-2 | 559.0 | $^1$H NMR (400 MHz, DMSO-d$_6$) δ ppm 10.22 (s, 1 H), 8.28-8.35 (m, 1 H), 8.25 (br d, J = 4.4 Hz, 1 H), 7.28 (q, J = 7.6 Hz, 1 H), 7.11 (br d, J = 4.4 Hz, 1 H), 6.80-6.93 (m, 1 H), 6.65-6.78 (m, 2 H), 6.20 (br d, J = 16.8 Hz, 1 H), 5.76 (br d, J = 10.6 Hz, 1 H), 4.96 (br d, J = 3.1 Hz, 1 H), 4.20-4.46 (m, 2 H), 3.97-4.18 (m, 1 H), 3.39-3.83 (m, 2 H), 3.02-3.29 (m, 1 H), 1.92 (s, 3 H), 1.69 (br s, 1 H), 1.31 (br d, J = 6.0 Hz, 3 H), 0.71-0.90 (m, 3 H), 0.62 (br d, J = 6.4 Hz, 1 H). $^{19}$F NMR (376 MHz, DMSO-d$_6$) δ ppm −115.37 (s, 1 F), −128.36 (s, 1 F). |
| 43 | 590.2 | $^1$H NMR (400 MHz, DMSO-d$_6$) δ ppm 9.06 (s, 1 H), 8.46-8.52 (m, 1 H), 7.48-7.55 (m, 1 H), 7.26-7.34 (m, 2 H), 7.17 (td, J = 7.4, 1.6 Hz, 1 H), 6.82-6.93 (m, 1 H), 6.22 (br d, J = 16.6 Hz, 1 H), 5.75-5.80 (m, 1 H), 5.00 (br s, 1 H), 4.31-4.43 (m, 2 H), 4.02-4.21 (m, 1 H), 3.81 (br d, J = 8.9 Hz, 1 H), 3.45-3.70 (m, 1 H), 3.10-3.30 (m, 1 H), 2.73 (br d, J = 6.4 Hz, 2 H), 1.36 (d, J = 6.6 Hz, 3 H), 1.09 (d, J = 6.6 Hz, 6 H), 0.93 (d, J = 6.4 Hz, 6 H). |
| 44-1 | 574.9 | $^1$H NMR (400 MHz, DMSO-d$_6$) δ 10.07-10.22 (m, 1 H), 8.39 (br s, 1 H), 8.24 (d, J = 4.8 Hz, 1 H), 7.25 (q, J = 8.1 Hz, 1 H), 7.12 (br s, 1 H), 6.79-6.93 (m, 1 H), 6.62-6.75 (m, 2 H), 6.20 (br d, J = 15.8 Hz, 1 H), 5.71-5.83 (m, 1 H), 4.88 (br s, 1 H), 4.25-4.45 (m, 2 H), 3.98-4.21 (m, 1 H), 3.54 (br d, J = 5.8 Hz, 2 H), 3.09-3.32 (m, 1 H), 1.92 (br d, J = 15.8 Hz, 3 H), 1.62-1.82 (m, 1 H), 1.37 (br s, 3 H), 0.85 (br s, 1 H), 0.76 (br s, 2 H), 0.65 (br s, 1 H). |
| 44-2 | 574.9 | $^1$H NMR (400 MHz, DMSO-d$_6$) δ 10.07-10.21 (m, 1 H), 8.44 (br s, 1 H), 8.25 (d, J = 5.0 Hz, 1 H), 7.25 (q, J = 7.9 Hz, 1 H), 7.13 (br s, 1 H), 6.86 (dt, J = 16.9, 8.3 Hz, 1 H), 6.63-6.75 (m, 2 H), 6.21 (br d, J = 16.8 Hz, 1 H), 5.72-5.80 (m, 1 H), 4.99 (br d, J = 2.3 Hz, 1 H), 4.21-4.46 (m, 2 H), 4.01-4.18 (m, 1 H), 3.40-3.59 (m, 2 H), 3.02-3.34 (m, 1 H), 1.92 (br d, J = 18.5 Hz, 3 H), 1.62-1.81 (m, 1 H), 1.31 (br s, 3 H), 0.83-0.91 (m, 1 H), 0.77 (br s, 2 H), 0.65 (br s, 1 H). |
| 45-1 | 559.0 | $^1$H NMR (400 MHz, DMSO-d$_6$) δ ppm 8.44 (br s, 1 H), 8.25 (d, J = 5.0 Hz, 1 H), 7.49-7.57 (m, 1 H), 7.30-7.35 (m, 1 H), 7.24-7.30 (m, 2 H), 7.11 (d, J = 5.0 Hz, 1 H), 6.80-6.93 (m, 1 H), 6.15-6.25 (m, 1 H), 5.73-5.80 (m, 1 H), 4.94 (br d, J = 4.6 Hz, 1 H), 4.28 (br s, 1 H), 3.98-4.19 (m, 1 H), 3.70-3.82 (m, 2 H), 3.41-3.68 (m, 1 H), 3.05-3.29 (m, 1 H), 1.97 (s, 3 H), 1.64 (br d, J = 4.1 Hz, 1 H), 1.34 (d, J = 6.8 Hz, 3 H), 0.86-0.94 (m, 1 H), 0.77-0.84 |

TABLE 14(b)-continued

Analytical Data for Individual Examples

| Ex. # | LRMS: (ESI, +ve ion) m/z | NMR |
|---|---|---|
| 45-2 | 559.0 | (m, 1 H), 0.70-0.76 (m, 1 H), 0.67 (br d, J = 8.1 Hz, 1 H). $^{19}$F NMR (376 MHz, DMSO-$d_6$) δ ppm −13.35 (s, 1 F). $^1$H NMR (400 MHz, DMSO-$d_6$) δ ppm 8.44 (br d, J = 4.6 Hz, 1 H), 8.25 (d, J = 4.8 Hz, 1 H), 7.48-7.57 (m, 1 H), 7.25-7.35 (m, 3 H), 7.12 (d, J = 5.0 Hz, 1 H), 6.77-6.94 (m, 1 H), 6.20 (br d, J = 17.2 Hz, 1 H), 5.71-5.79 (m, 1 H), 4.95 (br s, 1 H), 4.24-4.44 (m, 2 H), 3.98-4.22 (m, 1 H), 3.71-3.87 (m, 1 H), 3.56-3.67 (m, 1 H), 3.20-3.30 (m, 1 H), 1.96 (s, 3 H), 1.68 (br s, 1 H), 1.34 (d, J = 6.6 Hz, 3 H), 0.86-0.93 (m, 1 H), 0.73-0.84 (m, 2 H), 0.61-0.72 (m, 1 H). $^{19}$F NMR (376 MHz, DMSO-$d_6$) δ ppm −113.48 (s, 1 F). |
| 46-1 | 547.2 | $^1$H NMR (400 MHz, DMSO-$d_6$) δ ppm 8.42-8.47 (m, 1 H), 8.39 (d, J = 5.0 Hz, 1 H), 7.48-7.55 (m, 1 H), 7.21-7.33 (m, 4 H), 6.80-6.91 (m, 1 H), 6.21 (br d, J = 17.0 Hz, 1 H), 5.74-5.79 (m, 1 H), 4.93 (br s, 1 H), 3.98-4.44 (m, 3 H), 3.53-3.88 (m, 3 H), 2.33-2.45 (m, 2 H), 1.97 (s, 3 H), 1.34 (d, J = 6.6 Hz, 3 H), 1.03-1.07 (m, 3 H). $^{19}$F NMR (376 MHz, DMSO-$d_6$) δ ppm −113.84 (s, 1 F). |
| 46-2 | 547.0 | $^1$H NMR (400 MHz, DMSO-$d_6$) δ ppm 8.48 (br s, 1 H), 8.39 (d, J = 5.0 Hz, 1 H), 7.47-7.56 (m, 1 H), 7.21-7.33 (m, 4 H), 6.80-6.92 (m, 1 H), 6.21 (br d, J = 16.4 Hz, 1 H), 5.77 (br d, J = 11.4 Hz, 1 H), 4.97 (br s, 1 H), 4.00-4.48 (m, 3 H), 3.77 (td, J = 12.2, 6.1 Hz, 2 H), 3.04-3.33 (m, 1 H), 2.35-2.47 (m, 2 H), 1.97 (s, 3 H), 1.33 (br d, J = 6.6 Hz, 3 H), 1.00-1.08 (m, 3 H). $^{19}$F NMR (376 MHz, DMSO-$d_6$) δ ppm −113.86 (s, 1 F). |
| 47 | 562.1 | $^1$H NMR (400 MHz, DMSO-$d_6$) δ ppm 9.01 (s, 1 H), 8.48 (br d, J = 5.0 Hz, 1 H), 7.50-7.57 (m, 1 H), 7.27-7.35 (m, 3 H), 7.20-7.27 (m, 1 H), 6.79-6.93 (m, 1 H), 6.17-6.26 (m, 1 H), 5.65-5.80 (m, 1 H), 4.92-5.02 (m, 1 H), 4.23-4.44 (m, 2 H), 3.99-4.20 (m, 1 H), 3.72-3.88 (m, 1 H), 3.40-3.71 (m, 1 H), 2.35-2.48 (m, 4 H), 1.36 (d, J = 6.6 Hz, 3 H), 1.06 (t, J = 7.5 Hz, 6 H). $^{19}$F NMR (377 MHz, DMSO-$d_6$) δ ppm −114.01 (s, 1 F). |
| 48 | 569.2 | $^1$H NMR (400 MHz, DMSO-$d_6$) δ ppm 10.10 (s, 1 H), 9.01 (s, 1 H), 8.37 (br s, 1 H), 7.22-7.32 (m, 1 H), 6.80-6.93 (m, 1 H), 6.66-6.77 (m, 2 H), 6.20 (br d, J = 16.6 Hz, 1 H), 5.71-5.81 (m, 1 H), 4.83-5.04 (m, 1 H), 3.98-4.45 (m, 3 H), 3.56-3.87 (m, 2 H), 3.07 (br dd, J = 4.1, 2.9 Hz, 1 H), 2.59-2.70 (m, 1 H), 1.33 (br d, J = 5.8 Hz, 3 H), 1.07-1.14 (m, 3 H), 1.01 (br d, J = 6.6 Hz, 3 H). $^{19}$F NMR (376 MHz, DMSO-$d_6$) δ ppm −115.41 (br s, 1 F). |
| 49-1 | 576.2 | $^1$H NMR (400 MHz, DMSO-$d_6$) δ ppm 10.05 (s, 1 H), 8.40 (br s, 1 H), 7.54 (br d, J = 7.7 Hz, 1 H), 7.17-7.33 (m, 3 H), 6.78-7.01 (m, 2 H), 6.61-6.75 (m, 2 H), 6.20 (br d, J = 15.6 Hz, 1 H), 5.76 (br d, J = 10.8 Hz, 1 H), 4.86 (br s, 1 H), 4.26-4.52 (m, 1 H), 3.96-4.25 (m, 2 H), 3.36-3.74 (m, 2 H), 2.93-3.13 (m, 1 H), 1.28 (br s, 3 H), 1.11 (br s, 9 H). |
| 49-2 | 576.2 | $^1$H NMR (400 MHz, DMSO-$d_6$) δ ppm 10.07 (br s, 1 H), 8.37 (br s, 1 H), 7.54 (br d, J = 7.9 Hz, 1 H), 7.25-7.33 (m, 1 H), 7.17-7.25 (m, 2 H), 6.96 (br d, J = 6.0 Hz, 1 H), 6.77-6.90 (m, 1 H), 6.71 (d, J = 8.3 Hz, 1 H), 6.65 (br t, J = 8.7 Hz, 1 H), 6.20 (br d, J = 16.6 Hz, 1 H), 5.72-5.80 (m, 1 H), 4.85 (br s, 1 H), 4.18-4.43 (m, 2 H), 3.96-4.17 (m, 1 H), 3.70 (br s, 1 H), 3.41-3.64 (m, 1 H), 3.22 (br s, 1 H), 1.33 (br d, J = 6.2 Hz, 3 H), 1.08-1.14 (m, 9 H). |
| 50-1 | 546.8 | $^1$H NMR (400 MHz, DMSO-$d_6$) δ ppm 7.51-7.61 (m, 1 H), 7.43 (dd, J = 7.9, 1.0 Hz, 1 H), 7.33-7.39 (m, 2 H), 7.28-7.33 (m, 2 H), 7.24 (td, J = 7.6, 1.4 Hz, 1 H), 7.12 (dd, J = 7.9, 1.0 Hz, 1 H), 6.90 (br dd, J = 16.3, 10.5 Hz, 1 H), 6.21 (br d, J = 16.6 Hz, 1 H), 5.76 (dd, J = 8.7, 1.4 Hz, 1 H), 5.13-5.59 (m, 1 H), 4.64-4.94 (m, 1 H), 3.99-4.41 (m, 3 H), 3.47-3.90 (m, 2 H), 2.75 (quin, J = 6.8 Hz, 1 H), 1.25 (br s, 3 H), 1.11 (d, J = 6.8 Hz, 3 H), 0.99 (d, J = 6.8 Hz, 3 H). |
| 50-2 | 546.8 | $^1$H NMR (400 MHz, DMSO-$d_6$) δ ppm 7.50-7.61 (m, 1 H), 7.44 (dd, J = 7.7, 0.8 Hz, 1 H), 7.33-7.39 (m, 2 H), 7.28-7.33 (m, 2 H), 7.24 (td, J = 7.5, 1.3 Hz, 1 H), 7.13 (dd, J = 7.9, 0.8 Hz, 1 H), 6.89 (br dd, J = 16.3, 10.7 Hz, 1 H), 6.21 (br d, J = 16.6 Hz, 1 H), 5.76 (dd, J = 9.9, 1.2 Hz, 1 H), 5.13-5.59 (m, 1 H), 4.69-4.92 (m, 1 H), 3.97-4.39 (m, 3 H), 3.61-3.75 (m, 1 H), 3.44-3.60 (m, 1 H), 2.64-2.73 (m, 1 H), 1.25 (br s, 3 H), 1.09 (d, J = 6.8 Hz, 3 H), 1.00 (d, J = 6.8 Hz, 3 H). |
| 51-1 | 526.8 | $^1$H NMR (400 MHz, DMSO-$d_6$) δ ppm 7.48-7.59 (m, 1 H), 7.43 (dd, J = 8.3, 1.0 Hz, 1 H), 7.32-7.39 (m, 2 H), 7.25-7.32 (m, 2 H), 7.22 (dd, J = 7.5, 1.7 Hz, 1 H), 7.12 (dd, J = 7.7, 1.0 Hz, 1 H), 6.82-6.94 (m, 1 H), 6.21 (br d, J = 16.0 Hz, 1 H), 5.76 (dd, J = 10.4, 2.1 Hz, 1 H), 4.70-5.56 (m, 1 H), 3.95-4.41 (m, 3 H), 3.45-3.79 (m, 3 H), 2.55-2.65 (m, 1 H), 2.43 (d, J = 1.0 Hz, 3 H), 1.25 (br s, 3 H), 1.08 (d, J = 6.8 Hz, 3 H), 0.98 (d, J = 6.8 Hz, 3 H). |
| 51-2 | 526.8 | $^1$H NMR (400 MHz, DMSO-$d_6$) δ ppm 7.49-7.60 (m, 1 H), 7.42 (dd, J = 7.7, 1.7 Hz, 1 H), 7.30-7.38 (m, 2 H), 7.26-7.30 (m, 2 H), 7.23 (td, J = 7.5, 1.3 Hz, 1 H), 7.10 (dd, J = 7.8, 0.9 Hz, 1 H), 6.70-6.97 (m, 1 H), 6.21 (br d, J = 16.6 Hz, 1 H), 5.76 (dd, J = 10.5, 2.2 Hz, 1 H), 4.73-5.50 (m, 1 H), 3.89-4.79 (m, 3 H), 3.31-3.73 (m, 3 H), 2.63-2.73 (m, 1 H), 2.43 (d, J = 1.0 Hz, 3 H), 1.25 (br s, 3 H), 1.10 (d, J = 6.8 Hz, 3 H), 0.97 (d, J = 6.8 Hz, 3 H). |
| 52-1 | 541.8 | $^1$H NMR (400 MHz, DMSO-$d_6$) δ ppm 9.94 (br s, 1 H), 8.12 (br s, 1 H), 7.38 (dd, J = 7.5, 1.7 Hz, 1 H), 7.31 (td, J = 7.7, 1.5 Hz, 1 H), 7.15-7.24 (m, 2 H), 7.06 (dd, J = 6.0, 1.0 Hz, 1 H), 6.78-6.95 (m, 1 H), 6.70 (d, J = 8.3 Hz, 1 H), 6.64 (t, J = 8.8 Hz, 1 H), 6.21 (dd, J = 16.7, 5.3 Hz, 1 H), 5.77 (dd, J = 10.4, 2.3 Hz, 1 H), 4.80 (br s, 1 H), 4.11-4.48 (m, 4 H), 3.45-3.67 (m, 2 H), 3.07-3.25 (m, 1 H), 2.12 (s, 3 H), 1.36 (d, J = 6.6 Hz, 3 H), 1.05 (d, J = 6.6 Hz, 3 H), 0.95 (d, J = 6.8 Hz, 3 H). |
| 52-2 | 541.8 | $^1$H NMR (400 MHz, DMSO-$d_6$) δ ppm 9.94 (s, 1 H), 8.15 (s, 1 H), 7.38 (dd, J = 8.5, 1.0 Hz, 1 H), 7.32 (td, J = 6.6, 1.7 Hz, 1 H), 7.16-7.25 (m, 2 H), 7.06 (dd, J = 6.8, 1.2 Hz, 1 H), 6.81-6.93 (m, 1 H), 6.70 (d, J = 8.3 Hz, 1 H), 6.63 (t, J = 8.8 Hz, 1 H), 6.20 (br dd, J = 15.8, 5.4 Hz, 1 |

TABLE 14(b)-continued

Analytical Data for Individual Examples

| Ex. # | LRMS: (ESI, +ve ion) m/z | NMR |
|---|---|---|
|  |  | H), 5.77 (dd, J = 10.2, 2.5 Hz, 1 H), 4.87-4.98 (m, 1 H), 3.98-4.47 (m, 3 H), 3.57-3.80 (m, 3H), 2.97-3.11 (m, 1 H), 2.12 (s, 3 H), 1.30 (br d, J = 6.4 Hz, 3 H), 1.06 (d, J = 6.8 Hz, 3 H), 0.96 (d, J = 6.6 Hz, 3H). |
| 53-1 | 550.2 | $^1$H NMR (400 MHz, DMSO-$d_6$) δ ppm 8.45 (br s, 1 H), 7.49-7.60 (m, 1 H), 7.22-7.41 (m, 4 H), 6.78-6.93 (m, 1 H), 6.21 (br d, J = 16.2 Hz, 1 H), 5.72-5.81 (m, 1 H), 4.98 (br s, 1 H), 4.22-4.46 (m, 2 H), 3.99-4.21 (m, 2 H), 3.37-3.90 (m, 2 H), 2.99-3.28 (m, 1 H), 1.71 (s, 3 H), 1.33 (br d, J = 6.6 Hz, 3 H), 1.21 (br dd, J = 33.2, 6.4 Hz, 6 H). $^{19}$F NMR (376 MHz, DMSO-$d_6$) δ ppm −113.97 (s, 1 F). |
| 53-2 | 550.2 | $^1$H NMR (400 MHz, DMSO-$d_6$) δ ppm 8.43 (br s, 1 H), 7.55 (q, J = 6.2 Hz, 1 H), 7.24-7.40 (m, 4 H), 6.79-6.93 (m, 1 H), 6.21 (br d, J = 16.2 Hz, 1 H), 5.77 (br d, J = 11.8 Hz, 1 H), 4.95 (br s, 1 H), 4.23-4.47 (m, 2 H), 3.98-4.21 (m, 2 H), 3.39-3.89 (m, 2 H), 3.04-3.28 (m, 1 H), 1.71 (s, 3 H), 1.35 (br d, J = 6.6 Hz, 3 H), 1.21 (br dd, J = 35.5, 6.4 Hz, 6 H). $^{19}$F NMR (376 MHz, DMSO-$d_6$) δ ppm −113.94 (s, 1 F). |

Biological Assay Data

For compounds in Table 15, the following assay conditions were employed:

Coupled Nucleotide Exchange Assay: Purified GDP-bound KRAS protein (aa 1-169), containing both G12C and C118A amino acid substitutions and an TV-terminal His-tag, was pre-incubated with a compound dose-response titration for 2 hours in assay buffer (25 mM HEPES pH 7.4, 10 mM $MgCl_2$, and 0.01% Triton X-100). Following compound pre-incubation, purified SOS protein (aa 564-1049) and GTP (Roche 10106399001) were added to the assay wells and incubated for an additional hour. To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 10 minutes. The assay plates were then read on a PerkinElmer EnVision Multilabel Reader, using AlphaScreen® technology, and data were analyzed using a 4-parameter logistic model to calculate $IC_{50}$ values.

Phospho-ERK1/2 MSD Assay: MIA PaCa-2 (ATCC® CRL-1420™) and A549 (ATCC® CCL-185™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 or A549 cells were seeded in 96-well cell culture plates at a density of 25,000 cells/well and incubated at 37° C., 5% $CO_2$. A compound dose-response titration was diluted in growth media, added to appropriate wells of a cell culture plate, and then incubated at 37° C., 5% $CO_2$ for 4 hours. Following compound treatment, cells were stimulated with 10 ng/mL EGF (Roche 11376454001) for 10 min, washed with ice-cold Dulbecco's phosphate-buffered saline, no $Ca^{2+}$ or $Mg^{2+}$ (ThermoFisher Scientific 14190144), and then lysed in RIPA buffer (50 mM Tris-HCl pH 7.5, 1% Igepal, 0.5% sodium deoxycholate, 150 mM NaCl, and 0.5% sodium dodecyl sulfate) containing protease inhibitors (Roche 4693132001) and phosphatase inhibitors (Roche 4906837001). Cell lysates were stored frozen at −80° C. overnight. Phosphorylation of ERK1/2 in compound-treated lysates was assayed using Phospho-ERK1/2 Whole Cell Lysate kits (Meso Scale Discovery K151DWD) according to the manufacturer's protocol. Assay plates were read on a Meso Scale Discovery Sector Imager 6000, and data were analyzed using a 4-parameter logistic model to calculate $IC_{50}$ values.

TABLE 15

Biochemical and cellular activity of compounds

| Ex.# | Coupled exchange $IC_{50}$ (μM) | p-ERK $IC_{50}$ (MIA PaCa-2, μM) | p-ERK $IC_{50}$ (A549, μM) |
|---|---|---|---|
| 1-1 | 0.355 | 2.55 | >33.3 |
| 1-2 | 2.38 | 6.08 | >100 |
| 1-3 | 0.610 | 3.84 | >100 |
| 1-4 | >10 | >100 | >100 |
| 1-5 | 6.66 | — | — |
| 1-6 | 2.88 | 36.2 | >100 |
| 1-7 | 0.209 | 1.86 | >100 |
| 1-8 | 0.894 | 6.07 | >100 |
| 1-9 | 5.92 | — | — |
| 1-10 | 0.381 | 1.09 | 11.1 |
| 1-11 | 0.695 | 8.2 | >100 |
| 1-12 | 11.8 | — | — |
| 1-13 | >10 | — | — |
| 1-14 | 1.78 | 5.03 | >100 |
| 1-15 | 0.562 | 4.7 | >100 |
| 1-16 | 0.492 | 4.83 | >100 |
| 1-17 | 63.5 | — | — |
| 1-18 | 0.370 | 0.559 | >33.3 |
| 1-19 | 0.297 | 1.33 | >100 |
| 1-19-1 | 0.115 | 0.368 | >100 |
| 1-19-2 | 5.10 | >100 | >100 |
| 1-20 | 0.683 | 4.99 | >100 |
| 1-21 | 1.30 | 4.89 | >100 |
| 1-22 | >250 | — | — |
| 1-23 | >250 | — | — |
| 1-28 | 2.20 | — | >100 |
| 2-1 | 0.341 | 1.89 | 3.7 |
| 2-2 | 12.7 | — | — |
| 2-3 | 4.05 | 6.53 | >100 |
| 2-4 | >250 | — | — |
| 2-5 | 0.684 | 5.46 | 3.7 |
| 2-5-1 | 0.308 | 1.14 | >100 |
| 2-5-2 | 1.35 | 7.48 | 3.7 |
| 2-6 | 1.59 | 2.97 | 3.7 |
| 2-6-1 | 13.0 | — | — |
| 2-6-2 | 1.25 | 1.29 | 3.7 |
| 2-7 | 1.08 | 3.87 | >33.3 |
| 2-8 | 0.361 | 0.258 | >100 |
| 2-9 | 0.301 | 0.747 | >100 |
| 2-10 | 1.73 | 3.07 | >100 |
| 3-1 | 0.266 | 3.23 | >100 |
| 3-1-1 | 3.00 | >100 | >100 |
| 3-1-2 | 0.302 | 2.35 | >100 |
| 3-2 | >250 | — | — |
| 3-3 | 11.3 | — | — |
| 3-4 | >250 | — | — |
| 3-5 | 0.693 | 5.26 | 3.7 |
| 3-6 | 1.05 | 11.8 | >100 |
| 3-7 | 6.98 | — | — |
| 3-8 | 1.07 | 7.05 | >100 |
| 3-9 | 3.37 | 9.25 | >33.3 |
| 3-10 | 4.74 | 66.4 | 11.1 |
| 3-11 | 0.457 | 3.06 | 11.1 |
| 3-12 | 2.56 | 7.66 | >100 |
| 3-13 | 6.49 | — | — |
| 3-14 | 5.64 | — | — |
| 3-15 | 4.03 | 20.1 | >100 |
| 3-16 | 2.60 | 21.3 | >100 |
| 3-17 | 5.48 | — | — |
| 3-18 | 2.60 | >100 | >100 |

TABLE 15-continued

Biochemical and cellular activity of compounds

| Ex.# | Coupled exchange IC$_{50}$ (μM) | p-ERK IC$_{50}$ (MIA PaCa-2, μM) | p-ERK IC$_{50}$ (A549, μM) |
|---|---|---|---|
| 3-19 | 0.954 | 2.03 | >33.3 |
| 3-20 | 2.99 | 9.65 | >100 |
| 3-21 | 32.0 | — | — |
| 3-22 | 0.249 | 1.12 | >33.3 |
| 3-23 | 4.65 | 13.6 | >100 |
| 3-24 | 9.07 | 23.7 | >100 |
| 3-25 | >250 | — | — |
| 4-1 | 0.529 | 2.34 | >100 |
| 4-2 | >250 | — | — |
| 4-3 | >250 | — | — |
| 4-4 | >250 | — | — |
| 4-5 | >250 | — | — |
| 4-6 | 0.630 | 10.3 | >100 |
| 4-7 | 125 | — | — |
| 4-8 | 177 | — | — |
| 4-9 | >250 | — | — |
| 5-1 | 0.875 | 2.86 | >100 |
| 5-2 | 14.2 | — | — |
| 5-3 | 14.2 | — | — |
| 5-4 | 0.610 | 3.25 | >100 |
| 5-5 | 0.341 | 2.53 | >100 |
| 5-6 | 0.883 | 5.9 | >100 |
| 5-7 | 0.815 | 3.79 | >100 |
| 5-8 | 0.433 | 1.2 | >33.3 |
| 5-9 | 0.139 | 0.822 | >100 |
| 6-1 | 0.537 | 1.3 | 3.7 |
| 6-2 | 5.31 | — | — |
| 7-1 | 0.299 | 0.43 | >100 |
| 7-2 | 0.180 | 0.222 | >100 |
| 7-3 | 1.73 | 5.83 | >100 |
| 8-1 | 0.542 | 0.211 | 62.3 |
| 8-1-1 | 0.172 | 0.046 | 69.8 |
| 8-1-2 | 0.322 | 0.811 | >100 |
| 8-2 | 0.152 | 0.050 | >100 |
| 8-3 | 0.283 | 0.061 | >100 |
| 8-3-1 | 0.282 | 0.408 | >100 |
| 8-3-2 | 0.340 | 0.028 | >100 |
| 8-4 | 0.095 | 0.017 | >33.3 |
| 8-5 | 0.400 | 2.41 | >100 |
| 8-6 | 0.100 | 0.012 | 69.9 |
| 8-6-2 | 0.185 | 0.128 | >100 |
| 8-6-1 | 0.066 | 0.01 | >33.3 |
| 9-1 | 0.155 | 0.052 | 57.4 |
| 9-2 | 0.289 | 1.11 | 74.4 |
| 9-3 | 0.113 | 0.035 | 66.1 |
| 9-4 | 0.198 | 0.023 | 13 |
| 9-5 | 1.33 | 3.92 | >100 |
| 9-6 | 0.237 | 3.51 | >100 |
| 9-7-2 | — | 0.232 | 62.0 |
| 9-7-1 | — | 0.023 | 14.9 |
| 9-9 | 0.147 | 0.136 | 65.6 |
| 9-10 | 0.101 | 0.117 | 66.5 |
| 9-11 | 0.093 | 0.147 | 64 |
| 9-12 | 1.32 | 1.29 | >100 |
| 9-13 | 0.306 | 0.078 | 12.8 |
| 9-14 | 0.129 | 0.344 | >100 |
| 10-1 | 24.5 | — | — |
| 10-2 | 1.93 | 36.1 | >100 |
| 10-3 | 1.10 | 9.33 | >100 |
| 10-4 | 0.235 | 3.47 | >100 |
| 10-5 | 0.297 | 3.41 | >100 |
| 10-6 | 1.20 | 6.07 | >100 |
| 10-7 | 0.533 | 9.2 | >100 |
| 10-8 | 1.34 | 12.9 | >100 |
| 10-9 | 1.68 | 33.6 | >100 |
| 10-10 | 0.359 | 6.85 | >100 |
| 10-11 | 0.516 | 14.7 | >100 |
| 10-12 | 0.912 | 22.6 | >100 |
| 10-13 | 15.1 | — | — |
| 11-1-1 | 0.231 | 0.247 | 42.9 |
| 11-1-2 | 0.151 | 0.016 | 21.7 |
| 11-2-1 | 0.219 | 0.054 | 10 |
| 11-2-2 | 0.256 | 0.006 | 26.4 |
| 12 | 3.34 | 25.9 | >100 |
| 13 | 5.20 | >100 | >100 |
| 14 | 2.69 | — | — |
| 15 | 2.56 | — | — |
| 16 | 2.93 | 8.62 | 33.3 |
| 17-1 | 20.6 | — | — |
| 17-2 | 1.02 | 2.6 | 49.1 |
| 18-1 | 23.0 | — | — |
| 18-2 | 0.760 | >100 | >100 |
| 18-3 | 24.6 | — | — |
| 19-1 | 15.2 | — | — |
| 19-2 | 1.62 | 4.69 | 3.7 |
| 19-3 | 115 | — | — |
| 20 | 78.8 | — | — |
| 21 | 9.41 | — | — |
| 22 | 0.927 | 56.1 | >100 |
| 23 | 3.29 | 3.21 | >33.3 |
| 24 | 6.20 | — | — |
| 25 | 0.251 | 0.786 | >100 |
| 26 | 3.90 | 30.3 | >100 |
| 27 | 1.28 | 12.8 | >33.3 |
| 28 | 8.17 | — | — |
| 29 | 3.76 | >100 | >100 |
| 30 | 7.51 | 58 | >100 |
| 31 | 123 | — | — |
| 32 | 28.6 | — | — |
| 33 | 103 | — | — |
| 34 | 34.2 | — | — |
| 35 | 8.01 | 79.7 | >100 |
| 36 | 39.8 | — | — |
| 37 | 9.07 | 14.7 | >100 |
| 38 | 0.484 | 1.39 | >33.3 |

For compounds in Table 16, the following assay conditions were employed:

Coupled Nucleotide Exchange Assay: Purified GDP-bound KRAS protein (aa 1-169), containing both G12C and C118A amino acid substitutions and an TV-terminal His-tag, was pre-incubated with a compound dose-response titration for 5 min in assay buffer (25 mM HEPES pH 7.4, 10 mM MgCl$_2$, and 0.01% Triton X-100). Following compound pre-incubation, purified SOS protein (aa 564-1049) and GTP (Roche 10106399001) were added to the assay wells and incubated for an additional 30 min. To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 5 minutes. The assay plates were then read on a PerkinElmer EnVision Multilabel Reader, using AlphaScreen® technology, and data were analyzed using a 4-parameter logistic model to calculate IC$_{50}$ values.

Phospho-ERK1/2 MSD Assay: MIA PaCa-2 (ATCC® CRL-1420™) and A549 (ATCC® CCL-185™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 or A549 cells were seeded in 96-well cell culture plates at a density of 25,000 cells/well and incubated at 37° C., 5% CO$_2$. A compound dose-response titration was diluted in growth media, added to appropriate wells of a cell culture plate, and then incubated at 37° C., 5% CO$_2$ for 2 hours. Following compound treatment, cells were stimulated with 10 ng/mL EGF (Roche 11376454001) for 10 min, washed with ice-cold Dulbecco's phosphate-buffered saline, no $Ca^{2+}$ or $Mg^{2+}$ (ThermoFisher Scientific 14190144), and then lysed in RIPA buffer (50 mM Tris-HCl pH 7.5, 1% Igepal, 0.5% sodium deoxycholate, 150 mM NaCl, and 0.5% sodium dodecyl sulfate) containing protease inhibitors (Roche 4693132001) and phosphatase inhibitors (Roche 4906837001). Phosphorylation of ERK1/2 in compound-treated lysates was assayed using Phospho-ERK1/2 Whole Cell Lysate kits (Meso Scale Discovery K151DWD) according to the manufacturer's protocol. Assay plates were read on a Meso Scale Discovery Sector Imager 6000, and data were analyzed using a 4-parameter logistic model to calculate $IC_{50}$ values.

TABLE 16

Biochemical and cellular activity of compounds

| Ex.# | Coupled exchange $IC_{50}$ (μM) | p-ERK $IC_{50}$ (MIA PaCa-2, μM) | p-ERK $IC_{50}$ (A549, μM) |
|---|---|---|---|
| 39 | 0.063 | 0.029 | >100 |
| 39-1 | 0.025 | 0.028 | — |
| 39-2 | 0.222 | 0.195 | — |
| 40 | 0.063 | 0.029 | — |
| 40-1 | 0.057 | 0.022 | — |
| 40-2 | 0.597 | 0.321 | — |
| 41 | 0.136 | 0.085 | — |
| 41-1 | 0.093 | 0.072 | — |
| 41-2 | 1.39 | 1.66 | — |
| 42 | 0.335 | 0.362 | — |
| 42-1 | 0.150 | 0.103 | — |
| 42-2 | 1.56 | — | — |
| 43 | 0.038 | 0.034 | — |
| 44 | 0.103 | 0.065 | — |
| 44-1 | 0.033 | 0.025 | — |
| 44-2 | 0.208 | 0.138 | — |
| 45 | 0.319 | 0.062 | — |
| 45-1 | 0.089 | 0.049 | — |
| 45-2 | 0.727 | 0.435 | — |
| 46 | 0.493 | 0.169 | — |
| 46-1 | 0.170 | 0.126 | — |
| 46-2 | 0.971 | 0.552 | — |
| 47 | 0.409 | 0.152 | — |
| 48 | 0.081 | 0.063 | >10 |
| 49 | 0.177 | 0.154 | — |
| 49-1 | 2.58 | — | — |
| 49-2 | 0.117 | 0.051 | — |
| 50 | 0.276 | 0.188 | — |
| 50-1 | 0.117 | 0.097 | — |
| 50-2 | 3.69 | — | — |
| 51 | 0.538 | 0.440 | — |
| 51-1 | 11.2 | — | — |
| 51-2 | 0.221 | 0.089 | — |
| 52 | 0.338 | 0.215 | — |
| 52-1 | 5.99 | — | — |
| 52-2 | 0.146 | 0.177 | — |
| 53 | 0.125 | 0.071 | — |
| 53-1 | 0.098 | 0.093 | — |
| 53-2 | 0.320 | 0.229 | — |

(—) = not tested

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A compound, wherein the compound is selected from:

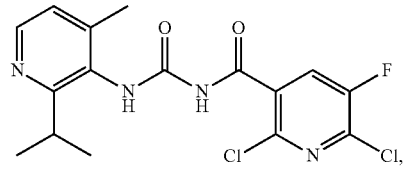

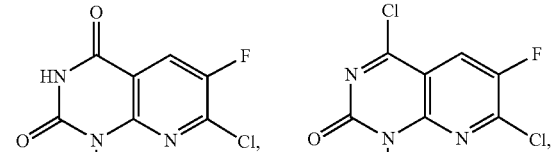

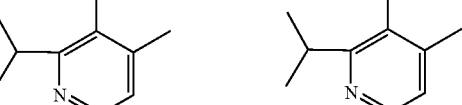

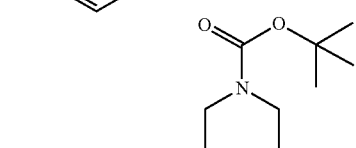

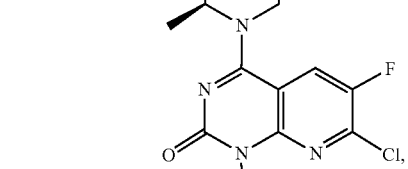

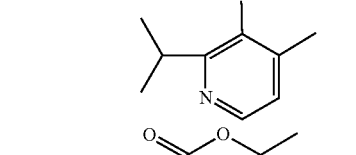

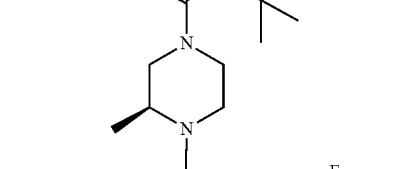

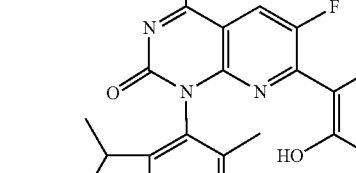, and

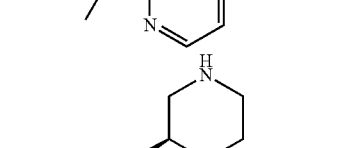

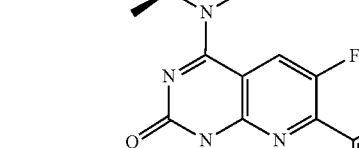

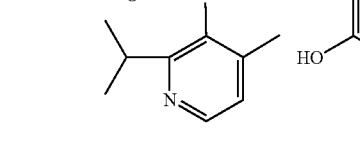.

2. The compound of claim 1, wherein the compound is

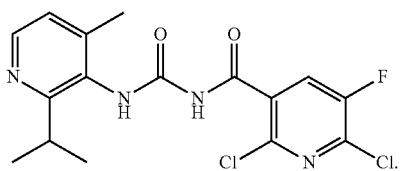 [SMILES: Cc1ccnc(C(C)C)c1NC(=O)NC(=O)c1cc(F)c(Cl)nc1Cl]

3. The compound of claim 1, wherein the compound is

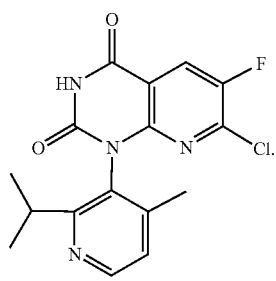 [SMILES: Cc1ccnc(C(C)C)c1-n1c(=O)[nH]c(=O)c2cc(F)c(Cl)nc21]

4. The compound of claim 1, wherein the compound is

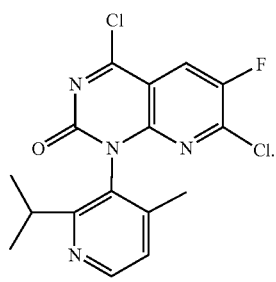 [SMILES: Cc1ccnc(C(C)C)c1-n1c(=O)nc(Cl)c2cc(F)c(Cl)nc21]

5. The compound of claim 1, wherein the compound is

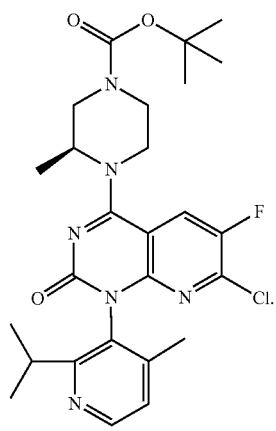 [SMILES: Cc1ccnc(C(C)C)c1-n1c(=O)nc(N2CCN(C(=O)OC(C)(C)C)C[C@@H]2C)c2cc(F)c(Cl)nc21]

6. The compound of claim 1, wherein the compound is

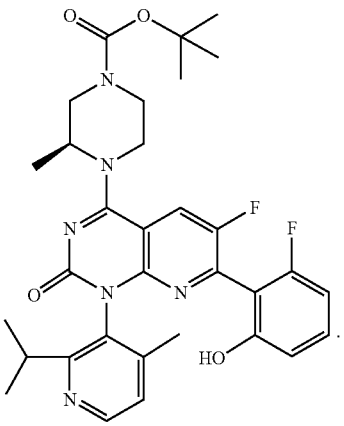 [SMILES: Cc1ccnc(C(C)C)c1-n1c(=O)nc(N2CCN(C(=O)OC(C)(C)C)C[C@@H]2C)c2cc(F)c(-c3c(O)cccc3F)nc21]

7. The compound of claim 1, wherein the compound is

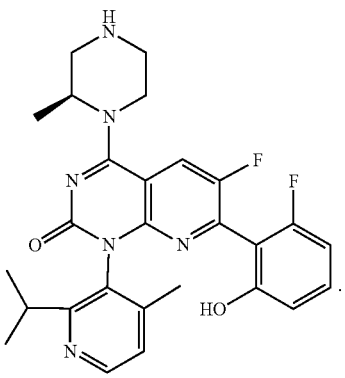 [SMILES: Cc1ccnc(C(C)C)c1-n1c(=O)nc(N2CCNC[C@@H]2C)c2cc(F)c(-c3c(O)cccc3F)nc21]

8. A process of making a compound, wherein the compound is

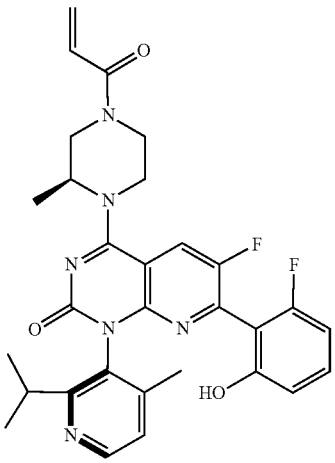

or a pharmaceutically acceptable salt thereof, and wherein the process comprises
(a) transforming 2,6-dichloro-5-fluoro-nicotinic acid into 2,6-dichloro-5-fluoronicotinamide;
(b) transforming 2,6-dichloro-5-fluoronicotinamide into the compound of claim 2;

(c) transforming the compound of claim 2 into the compound of claim 3;

(d) transforming the compound of claim 3 into the compound of claim 4;

(e) transforming the compound of claim 4 into the compound of claim 5;

transforming the compound of claim 5 into the compound of claim 6; or (g) transforming the compound of claim 6 into the compound of claim 7.

9. The process of claim 8, wherein the process comprises transforming 2,6-dichloro-5-fluoro-nicotinic acid into 2,6-dichloro-5-fluoronicotinamide.

10. The process of claim 8, wherein the process comprises transforming 2,6-dichloro-5-fluoronicotinamide into the compound of claim 3.

11. The process of claim 8, wherein the process comprises transforming the compound of claim 2 into the compound of claim 3.

12. The process of claim 8, wherein the process comprises transforming the compound of claim 3 into the compound of claim 4.

13. The process of claim 8, wherein the process comprises transforming the compound of claim 4 into the compound of claim 5.

14. The process of claim 8, wherein the process comprises transforming the compound of claim 5 into the compound of claim 6.

15. The process of claim 8, wherein the process comprises transforming the compound of claim 6 into the compound of claim 7.

16. A compound, wherein the compound is

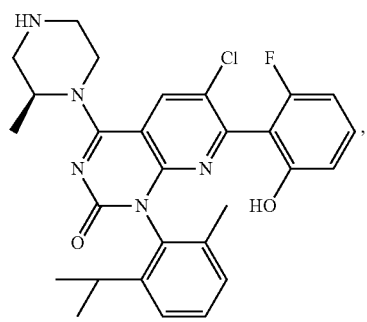

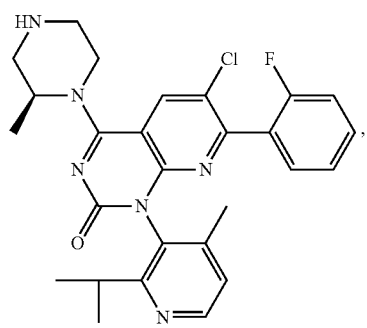

-continued

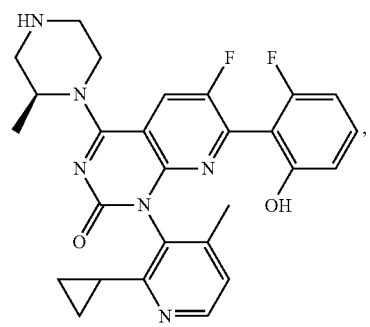

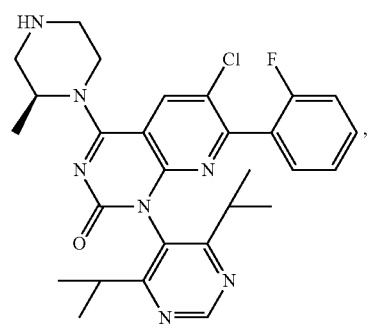

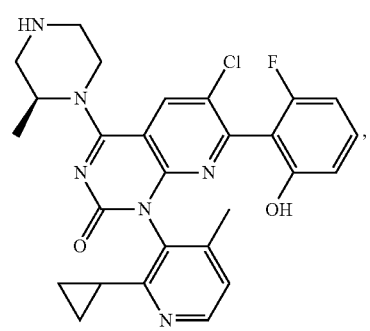

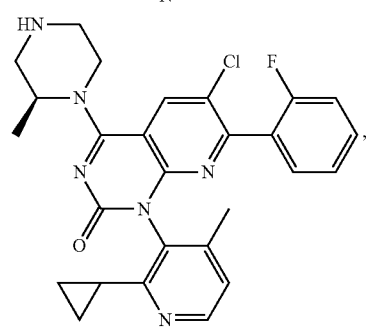

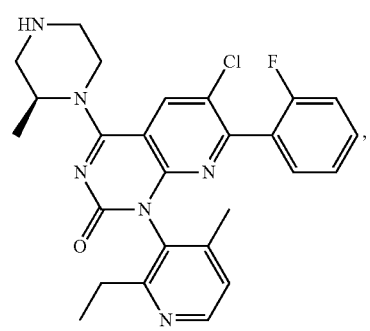

511
-continued
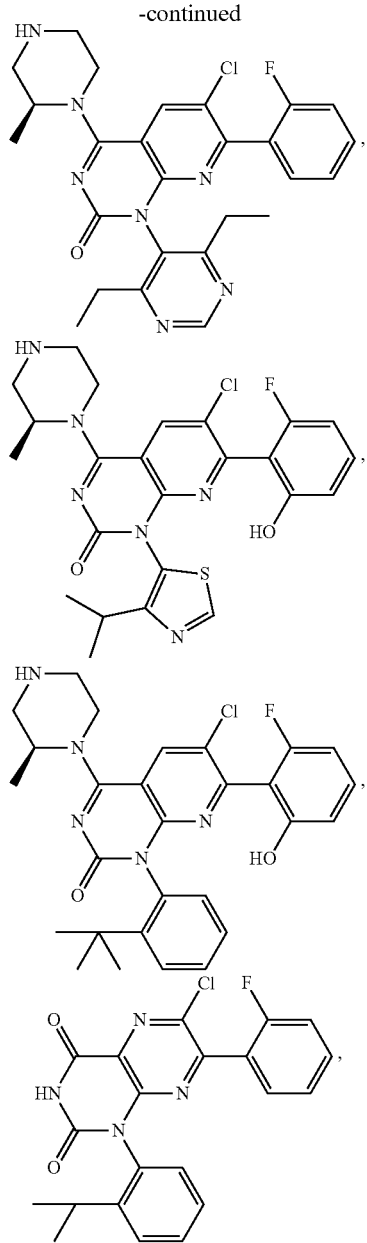
512
-continued
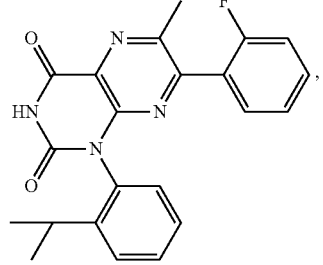
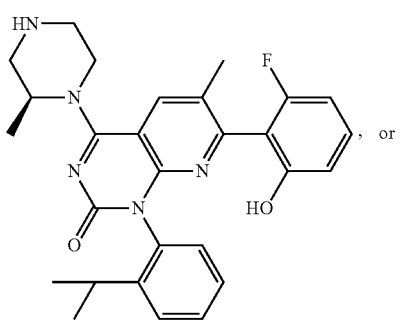
* * * * *

UNITED STATES PATENT AND TRADEMARK OFFICE
CERTIFICATE OF CORRECTION

PATENT NO. : 11,905,281 B2
APPLICATION NO. : 17/031607
DATED : February 20, 2024
INVENTOR(S) : Brian Alan Lanman et al.

Page 1 of 22

It is certified that error appears in the above-identified patent and that said Letters Patent is hereby corrected as shown below:

In the Specification

At Column 1, Lines 48-55, " 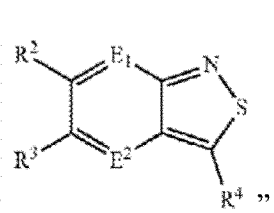 " should be -- 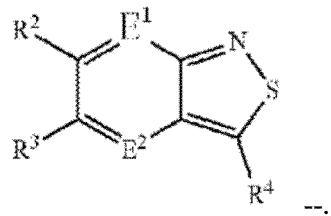 --.

At Column 2, Line 29, "$R^4$"" should be -- $R^{4'}$ --.

At Column 2, Line 29, "$C_{3-6}$alkyl," should be -- $C_{1-6}$alkyl, --.

At Column 2, Line 30, "cycloalklyl," should be -- cycloalkyl, --.

At Column 3, Lines 60-61, "$C_{1-8}$alkyl. $C_{2-5}$alkynyl," should be -- $C_{1-8}$alkyl, $C_{2-8}$alkynyl, --.

At Column 4, Lines 27-28, "$C_{0-5}$alkylene-$C_{6-14}$aryl," should be -- $C_{0-3}$alkylene-$C_{6-14}$aryl, --.

At Column 4, Line 63, "$C_{2-5}$alkynyl," should be -- $C_{2-8}$alkynyl, --.

At Column 5, Line 33, "CM alkylene-O—$C_{1-4}$alkyl," should be -- $C_{1-6}$ alkylene-O—$C_{1-4}$alkyl, --.

At Column 5, Line 48, "$C_{1-8}$alkyl." should be -- $C_{1-8}$alkyl, --.

At Column 5, Line 52, "O—$C_{0-3}$ alkylene-$C_{5-14}$cycloalkyl," should be -- O—$C_{0-3}$ alkylene-$C_{3-14}$cycloalkyl, --.

Signed and Sealed this
Twenty-seventh Day of May, 2025

Coke Morgan Stewart
*Acting Director of the United States Patent and Trademark Office*

CERTIFICATE OF CORRECTION (continued)
U.S. Pat. No. 11,905,281 B2

At Columns 5 & 6, Lines 67 & 1, "$C_{1-8}$alkylenearyl, $C_{1-8}$alkyleneheteroaryl," should be -- $C_{1-3}$alkylenearyl, $C_{1-3}$alkyleneheteroaryl, --.

At Column 6, Line 32, "$C_{1-6}$alkenyl," should be -- $C_{2-3}$alkenyl, --.

At Column 6, Lines 56-58, "$C_{1-6}$alkylene, —O—$C_{1-8}$alkylene, —S—$C_{1-8}$alkylene, and NH—$C_{20}$alkylene," should be -- $C_{2-6}$alkylene, —O—$C_{2-5}$alkylene, —S—$C_{2-5}$alkylene, and NH—$C_{2-5}$alkylene, --.

At Column 6, Line 61, "$C_{1-6}$alkynyl," should be -- $C_{2-6}$alkynyl, --.

At Column 7, Line 10, "$C_{0-5}$alkylene-$C_{6-14}$aryl," should be -- $C_{0-3}$alkylene-$C_{6-14}$aryl, --.

At Column 7, Lines 15-16, "NH—$C_{0-5}$alkylene-$C_{6-14}$aryl," should be -- NH—$C_{0-3}$alkylene-$C_{6-14}$aryl, --.

At Column 7, Lines 25-26, "$C_{1-8}$alkylenearyl. $C_{1-8}$alkyleneheteroaryl." should be -- $C_{1-3}$alkylenearyl, $C_{1-3}$alkyleneheteroaryl, --.

At Column 7, Line 31, "(HE)," should be -- (III'), --.

At Column 7, Lines 58-59, "C0-5alkylene-C6-14aryl," should be -- C0-3alkylene-C6-14aryl, --.

At Column 7, Line 65, "$C_{1-6}$alkyl," should be -- $C_{1-3}$alkyl, --.

At Column 8, Line 27, "$R^4$" should be -- $R^{4'}$ --.

At Column 9, Line 16, "$C_{0-5}$alkylene-$C_{6-14}$aryl," should be -- $C_{0-3}$alkylene-$C_{6-14}$aryl, --.

At Column 9, Line 22, "NH—$C_{0-5}$alkylene-$C_{6-14}$aryl," should be -- NH—$C_{0-3}$alkylene-$C_{6-14}$aryl, --.

At Column 10, Lines 30-31, "$C_{0-5}$alkylene-$C_{3-14}$cycloalkyl," should be -- $C_{0-3}$alkylene-$C_{3-14}$cycloalkyl, --.

At Column 10, Line 32, "$C_{0-5}$alkylene-$C_{6-14}$aryl," should be -- $C_{0-3}$alkylene-$C_{6-14}$aryl, --.

At Column 10, Line 45, "$C_{1-8}$alkyl. $C_{0-5}$alkylene-$C_{6-14}$aryl," should be -- $C_{1-8}$alkyl, $C_{0-3}$alkylene-$C_{6-14}$aryl, --.

At Column 10, Line 51, "NH—$C_{0-5}$alkylene-$C_{6-14}$aryl," should be -- NH—$C_{0-3}$alkylene-$C_{6-14}$aryl, --.

At Column 10, Line 52, "NH—$C_{0-5}$alkylene-$C_{3-14}$cycloalkyl," should be -- NH—$C_{0-3}$alkylene-$C_{3-14}$cycloalkyl, --.

At Column 11, Lines 28-29, "$C_{0-5}$alkylene-$C_{6-14}$aryl," should be -- $C_{0-3}$alkylene-$C_{6-14}$aryl, --.

At Column 11, Lines 35-36, "$C_{1-6}$alkoxy, cycloalkyl, $C_{2-3}$alkenyl." should be -- $C_{1-3}$alkoxy, $C_{3-4}$cycloalkyl, $C_{2-3}$alkenyl, --.

At Column 11, Line 63, "$R^4$" should be -- $R^{4'}$ --.

At Column 11, Line 63, "$C_{2-5}$alkynyl," should be -- $C_{2-8}$alkynyl, --.

At Column 12, Line 54, "$C_{0-5}$alkylene-$C_{6-14}$aryl," should be -- $C_{0-3}$alkylene-$C_{6-14}$aryl, --.

At Column 12, Line 55, "$C_{0-5}$alkylene-$C_{3-14}$cycloalkyl," should be -- $C_{0-3}$alkylene-$C_{3-14}$cycloalkyl, --.

At Column 12, Lines 56-57, "0-$C_{0-3}$alkylene-$C_{6-14}$aryl," should be -- O—$C_{0-3}$alkylene-$C_{6-14}$aryl, --.

At Column 12, Lines 57-58, "0-$C_{0-3}$alkylene-$C_{3-14}$ cycloalkyl," should be -- O—$C_{0-3}$alkylene-$C_{3-14}$ cycloalkyl, --.

At Column 12, Lines 58-59, "0-$C_{0-3}$alkylene-$C_{2-14}$heterocycloalkyl," should be -- O—$C_{0-3}$alkylene-$C_{2-14}$heterocycloalkyl, --.

At Column 12, Line 59, "N($C_{1-5}$alkyl)$_2$," should be -- N($C_{1-8}$alkyl)$_2$, --.

At Column 14, Line 18, "N($C_{1-5}$alkyl)$_2$," should be -- N($C_{1-8}$alkyl)$_2$, --.

At Column 14, Line 19, "NH—$C_{0-5}$alkylene-$C_{6-14}$aryl," should be -- NH—$C_{0-3}$alkylene-$C_{6-14}$aryl, --.

At Column 15, Line 19, "$R^4$" should be -- $R^{4'}$ --.

At Column 15, Line 21, "$C_{0-3}$alkylene-$C_{6-14}$cycloalkyl," should be -- $C_{0-3}$alkylene-$C_{3-14}$cycloalkyl, --.

At Column 15, Line 22, "$C_{0-5}$alkylene-$C_{6-14}$aryl," should be -- $C_{0-3}$alkylene-$C_{6-14}$aryl, --.

At Column 16, Line 1, "$C_{1-8}$alkyl." should be -- $C_{1-8}$alkyl, --.

At Column 16, Lines 7-8, "NH—$C_{0-5}$alkylene-$C_{2-14}$heteroaryl," should be -- NH—$C_{0-3}$alkylene-$C_{2-14}$heteroaryl, --.

At Column 16, Line 39, "$C_{2-5}$alkenyl," should be -- $C_{2-8}$alkenyl, --.

At Column 17, Line 24, "(HE)," should be -- (III'), --.

At Column 17, Line 29, "O—$C_{0-6}$alkylene-$C_{6-14}$cycloalkyl," should be -- O—$C_{0-6}$alkylene-$C_{3-14}$cycloalkyl, --.

At Column 17, Line 39, "z-Pr," should be -- i-Pr, --.

At Column 18, Line 11, "  ".

At Column 27, Line 60, "$C_1$." should be -- Cl. --.

At Column 32, Line 10, "$R^4$" should be -- $R^{4'}$ --.

At Column 41, Line 50, "$CH_2CO_2CH_3$, $CH_2C(O)NHCH_3$," should be -- $CH_2CO_2CH_3$, $CH_2NHC(O)CH_3$, $CH_2C(O)NHCH_3$, --.

At Column 41, Line 65, "$C_{0-5}$alkylene-$C_{6-14}$aryl." should be -- $C_{0-3}$alkylene-$C_{6-14}$aryl. --.

At Column 41, Line 67, "$C_{0-5}$alkylene-amide" should be -- $C_{0-3}$alkylene-amide --.

At Column 42, Line 4, "$CH_2NH(CH_3)CH_2C_{o2}CH_3$," should be -- $CH_2NH(CH_3)CH_2CO_2CH_3$, --.

At Column 47, Line 67, "$C_{m-n}$" should be -- $C_{m-n}$ --.

At Column 48, Lines 9-10, "$C_5$-$C_{14}$aryl, and $C_5$-$C_{14}$ heteroaryl." should be -- $C_5$-$C_{10}$aryl, and $C_5$-$C_{10}$ heteroaryl. --.

At Column 48, Line 40, "$CH_2NH(CH_3)CH_2C_{o2}CH_3$," should be -- $CH_2NH(CH_3)CH_2CO_2CH_3$, --.

At Column 50, Line 33, "$C_{M-M}$" should be -- $C_{10-14}$ --.

At Column 50, Line 44, "$C_{2-5}$alkynyl," should be -- $C_{2-8}$alkynyl, --.

At Column 50, Line 47, "$C_5$-$C_{14}$ heteroaryl." should be -- $C_5$-$C_{10}$ heteroaryl. --.

At Column 51, Lines 2-3, "$C_{2-5}$alkenyl. $C_{2-5}$alkynyl." should be -- $C_{2-8}$alkenyl, $C_{2-8}$alkynyl, --.

At Column 51, Line 6, "$C_5$-$C_{14}$ heteroaryl." should be -- $C_5$-$C_{10}$ heteroaryl. --.

At Column 51, Line 36, "—$C_{o2}C_1$-$C_8$alkyl," should be -- —$CO_2C_1$-$C_8$alkyl, --.

At Column 51, Line 38, "$C_5$-$C_{14}$aryl, and $C_5$-$C_{14}$ heteroaryl." should be -- $C_5$-$C_{10}$aryl, and $C_5$-$C_{10}$ heteroaryl. --.

At Column 52, Line 46, "Teoc" should be -- Alloc --.

At Column 52, Line 56, "Alloc" should be -- Fmoc --.

At Column 53, Lines 1-2, "As used herein, the term Fmoc refers to the structure Compounds of the Disclosure" should be -- Compounds of the Disclosure --.

CERTIFICATE OF CORRECTION (continued)
U.S. Pat. No. 11,905,281 B2

At Column 54, Lines 38-39, "$C_{0-5}$alkylenearyl, or $C_{0-5}$alkyleneheteroaryl," should be -- $C_{0-3}$alkylenearyl, or $C_{0-3}$alkyleneheteroaryl, --.

At Column 55, Line 3, "$R^4$" should be -- $R^{4'}$ --.

At Column 55, Line 3, "$C_{2-5}$alkynyl," should be -- $C_{2-8}$alkynyl, --.

At Column 55, Line 5, "$C_{0-5}$alkylene" should be -- $C_{0-3}$alkylene --.

At Column 55, Line 6, "$C_{0-5}$alkylenearyl," should be -- $C_{0-3}$alkylenearyl, --.

At Column 55, Line 48, "$C_{0-5}$alkylenearyl," should be -- $C_{0-3}$alkylenearyl, --.

At Column 55, Line 50, "$C_{1-8}$alkyl," should be -- $C_{1-3}$alkyl, --.

At Column 56, Line 41, "$C_{1-6}$alkyl," should be -- $C_{1-4}$alkyl, --.

At Column 56, Line 51, "$C_{1-8}$alkyl," should be -- $C_{1-3}$alkyl, --.

At Column 57, Line 13, "$R^4$" should be -- $R^{4'}$ --.

At Column 57, Line 15, "$C_{0-5}$alkylene-$C_{3-8}$cycloalkyl," should be -- $C_{0-3}$alkylene-$C_{3-8}$cycloalkyl, --.

At Column 57, Line 16, "$C_{0-5}$alkylenearyl," should be -- $C_{0-3}$alkylenearyl, --.

At Column 57, Line 55, "$C_{0-5}$alkylene-$C_{3-8}$cycloalkyl," should be -- $C_{0-3}$alkylene-$C_{3-8}$cycloalkyl, --.

At Column 57, Lines 55-56, "$C_{0-5}$alkylene-$C_{2-7}$heterocycloalkyl, $C_{0-5}$alkylenearyl," should be -- $C_{0-3}$alkylene-$C_{2-7}$heterocycloalkyl, $C_{0-3}$alkylenearyl, --.

At Column 57, Line 58, "$C_{1-8}$alkyl," should be -- $C_{1-3}$alkyl, --.

At Column 57, Line 61, "$C_{1-8}$alkyl," should be -- $C_{1-3}$alkyl, --.

At Column 57, Line 62, "$C_{1-8}$alkoxy," should be -- $C_{1-3}$alkoxy, --.

At Column 58, Line 7, "$C_{3-8}$cycloalkyl," should be -- $C_{3-5}$cycloalkyl, --.

At Column 60, Line 42, "(HE):" should be -- (III'): --.

At Column 61, Line 5, "$C_{1-6}$alkyl," should be -- $C_{1-3}$alkyl, --.

At Column 61, Line 34, "$R^4$" should be -- $R^{4'}$ --.

At Column 61, Line 36, "$C_{0-5}$alkylene-$C_{3-8}$cycloalkyl," should be -- $C_{0-3}$alkylene-$C_{3-8}$cycloalkyl, --.

CERTIFICATE OF CORRECTION (continued)
U.S. Pat. No. 11,905,281 B2

At Column 61, Line 37, "$C_{0-5}$alkylenearyl," should be -- $C_{0-3}$alkylenearyl, --.

At Column 62, Line 13, "$C_{2-5}$alkynyl," should be -- $C_{2-8}$alkynyl, --.

At Column 62, Line 17, "$C_{0-5}$alkylene-$C_{3-8}$cycloalkyl," should be -- $C_{0-3}$alkylene-$C_{3-8}$cycloalkyl, --.

At Column 62, Lines 17-18, "$C_{0-5}$alkylene-$C_{2-7}$heterocycloalkyl, $C_{0-5}$alkylenearyl," should be -- $C_{0-3}$alkylene-$C_{2-7}$heterocycloalkyl, $C_{0-3}$alkylenearyl, --.

At Column 62, Line 27, "$C_{1-8}$alkyl. $C_{0-5}$alkylenearyl," should be -- $C_{1-8}$alkyl, $C_{0-3}$alkylenearyl, --.

At Column 62, Lines 27-28, "$C_{0-3}$alkylene-$C_{3-5}$cycloalkyl," should be -- $C_{0-3}$alkylene-$C_{3-8}$cycloalkyl, --.

At Column 62, Line 30, "$C_1$alkoxy, $C_{1-6}$alkoxy," should be -- $C_{1-6}$alkoxy, --.

At Column 62, Lines 30-31, "O—$C_{0-5}$alkylenearyl, O—$C_{0-5}$alkyleneheteroaryl," should be -- O—$C_{0-3}$alkylenearyl, O—$C_{0-3}$alkyleneheteroaryl, --.

At Column 62, Line 31, "O—$C_{0-5}$alkylene-$C_5$-8 cycloalkyl," should be -- O—$C_{0-3}$alkylene-$C_{3-8}$cycloalkyl, --.

At Column 62, Lines 33-34, "NH—$C_{0-5}$alkylenearyl, NH—$C_{0-5}$alkyleneheteroaryl," should be -- NH—$C_{0-3}$alkylenearyl, NH—$C_{0-3}$alkyleneheteroaryl, --.

At Column 62, Line 34, "NH—$C_{0-5}$alkylene-$C_{3-8}$cycloalkyl," should be -- NH—$C_{0-3}$alkylene-$C_{3-8}$cycloalkyl, --.

At Column 62, Lines 34-35, "NH—$C_{0-5}$alkylene-$C_{2-7}$heterocycloalkyl," should be -- NH—$C_{0-3}$alkylene-$C_{2-7}$heterocycloalkyl, --.

At Column 64, Line 50, "$R^4$" should be -- $R^{4'}$ --.

At Column 64, Line 50, "$C_{2-5}$alkynyl," should be -- $C_{2-8}$alkynyl, --.

At Column 64, Line 51, "$C_1$alkylene-OH," should be -- $C_{1-6}$alkylene-OH, --.

At Column 64, Line 52, "$C_{0-3}$alkylene-$C_{3-5}$cycloalkyl," should be -- $C_{0-3}$alkylene-$C_{3-8}$cycloalkyl, --.

At Column 65, Line 27, "$C_{0-3}$alkylene-$C_{3-5}$cycloalkyl," should be -- $C_{0-3}$alkylene-$C_{3-8}$cycloalkyl, --.

At Column 65, Lines 35-36, "$C_{0-5}$alkylenearyl, $C_{0-5}$alkyleneheteroaryl, $C_{0-5}$alkylene-$C_{3-8}$cycloalkyl," should be -- $C_{0-3}$alkylenearyl, $C_{0-3}$alkyleneheteroaryl, $C_{0-3}$alkylene-$C_{3-8}$cycloalkyl, --.

CERTIFICATE OF CORRECTION (continued)
U.S. Pat. No. 11,905,281 B2

At Column 65, Lines 37-38, "$C_1$alkoxy, O—$C_{0-5}$alkylenearyl, O—$C_{0-5}$alkyleneheteroaryl, O—$C_{0-5}$alkylene-$C_{1-8}$cycloalkyl," should be -- $C_{1-6}$alkoxy, O—$C_{0-3}$alkylenearyl, O—$C_{0-3}$alkyleneheteroaryl, O—$C_{0-3}$alkylene-$C_{3-8}$cycloalkyl, --.

At Column 65, Line 40, "NH—$C_{0-5}$alkylenearyl," should be -- NH—$C_{0-3}$alkylenearyl, --.

At Column 65, Line 41, "NH—$C_{0-5}$alkylene-$C_{3-8}$cycloalkyl," should be -- NH—$C_{0-3}$alkylene-$C_{3-8}$cycloalkyl, --.

At Column 67, Line 38, "$R^4$" should be -- $R^{4'}$ --.

At Column 68, Line 12, "$C_{2-5}$alkynyl," should be -- $C_{2-8}$alkynyl, --.

At Column 68, Line 27, "NH—$C_{0-5}$alkylenearyl," should be -- NH—$C_{0-3}$alkylenearyl, --.

At Column 68, Line 46, "$C_{0-5}$alkylenearyl," should be -- $C_{0-3}$alkylenearyl, --.

At Column 68, Line 50, "$C_{0-1}$alkylene-$C_{1-8}$cycloalkyl," should be -- $C_{0-1}$alkylene-$C_{3-8}$cycloalkyl, --.

At Column 68, Line 52, "$C_{0-5}$alkylene-$C_{3-8}$heterocycloalkyl" should be -- $C_{0-3}$alkylene-$C_{3-8}$heterocycloalkyl --.

At Column 73, Line 1, "embodiment," should be -- In another embodiment, --.

At Column 78, Line 43, "Chalky 1" should be -- $C_{1-2}$alkyl --.

At Column 111, Line 12, "carfdzomib." should be -- carfilzomib. --.

At Column 157, Lines 25-43, " " should be -- --. 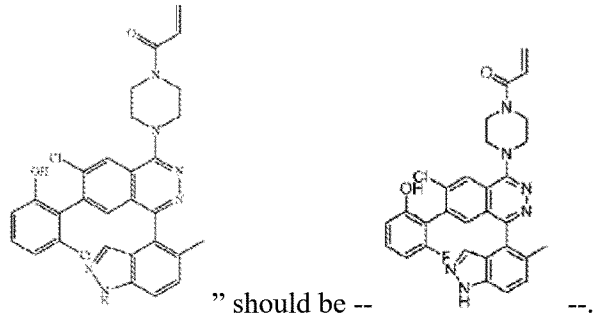

At Column 157, Lines 48-65, " " should be -- --. 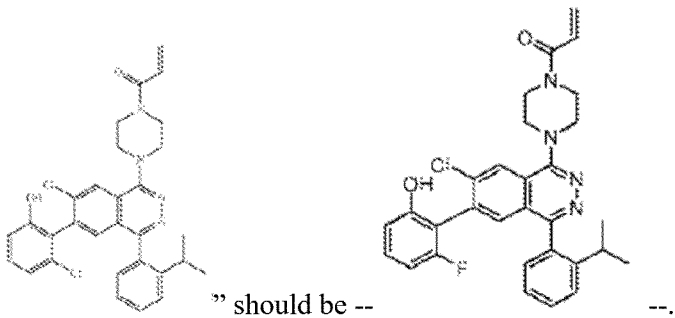

CERTIFICATE OF CORRECTION (continued)
U.S. Pat. No. 11,905,281 B2

At Column 182, Line 44, "Step t," should be -- Step 1, --.

At Column 185, Line 48, "R$^4$ (PG) reagent," should be -- R$^2$ (PG) reagent, --.

At Column 186, Line 62, "R$^4$ (PG) reagent," should be -- R$^2$ (PG) reagent, --.

At Column 198, Line 50, "mi dime" should be -- midline --.

At Column 198, Lines 62-63, "blastema," should be -- blastoma, --.

At Column 201, Lines 47-48, "Sabnosporamide A," should be -- Salinosporamide A, --.

At Column 202, Lines 13-14, "1-125 or 1-131," should be -- I-125 or I-131, --.

At Column 202, Line 35, "EPOS 18442," should be -- EP0818442, --.

At Column 203, Line 16, "barozole," should be -- liarozole, --.

At Column 203, Line 48, "EDI" should be -- LDI --.

At Column 203, Line 57, "RE" should be -- RL --.

At Column 205, Line 1, "TEC ELL-12," should be -- TLC ELL-12, --.

At Column 205, Line 42, "Sobering" should be -- Schering --.

At Column 205, Line 44, "(Finn)," should be -- (Pinn), --.

At Column 205, Line 55, "(Aetema," should be -- (Aeterna, --.

At Column 205, Line 58, "HIF-1alfa" should be -- HIF-1alfa --.

At Column 206, Line 8, "MAh," should be -- MAb, --.

At Column 206, Line 8, "MAh," should be -- MAb, --.

At Column 206, Line 16, "T etrathiomoly bdate," should be -- Tetrathiomolybdate, --.

At Column 206, Line 19, "MAh," should be -- MAb, --.

At Column 206, Line 23, "(Sima," should be -- Sima, --.

At Column 206, Line 40, "bafdomycin A1," should be -- bafilomycin A1, --.

At Column 206, Line 53, "pegfdgrastim;" should be -- pegfilgrastim; --.

CERTIFICATE OF CORRECTION (continued)
U.S. Pat. No. 11,905,281 B2

At Column 206, Line 64, "anthracydines," should be -- anthracyclines, --.

At Column 207, Line 10, "antiprobferative/antimitotic antimetabobtes" should be -- antiproliferative/antimitotic antimetabolites --.

At Column 207, Line 22, "sirobmus)," should be -- sirolimus), --.

At Column 207, Line 29, "BAFF-neutrabzing" should be -- BAFF-neutralizing --.

At Column 207, Line 31, "CNT0328)," should be -- CNTO328), --.

At Column 207, Line 34, "anti-CSI" should be -- anti-CS1 --.

At Column 207, Line 38, "Torcl/2" should be -- Torc1/2 --.

At Column 209, Line 20, "Xraxler," should be -- Traxler, --.

At Column 209, Line 20, "Exp. Opin. Xher." should be -- Exp. Opin. Ther. --.

At Column 209, Lines 41-42, "morphobne" should be -- morpholine --.

At Column 209, Line 44, "(quinobn-3-yl)" should be -- (quinolin-3-yl) --.

At Column 209, Line 45, "quinobn-1-yl]" should be -- quinolin-1-yl] --.

At Column 209, Lines 58-59, "quinazobn-5-yl)-nicotinamide" should be -- quinazolin-5-yl)-nicotinamide --.

At Column 209, Line 64, "thiazobdine" should be -- thiazolidine --.

At Column 210, Line 11, "Biochem. J" should be -- Br. J. Cancer --.

At Column 211, Line 44, "BC1-2 inhibitor," should be -- BCl-2 inhibitor, --.

At Column 212, Line 8, "BC1-2 inhibitor," should be -- BCl-2 inhibitor, --.

At Column 212, Line 40, "BC1-2 inhibitor," should be -- BCl-2 inhibitor, --.

At Column 213, Line 4, "BC1-2 inhibitor," should be -- BCl-2 inhibitor, --.

At Column 213, Line 36, "BC1-2 inhibitor," should be -- BCl-2 inhibitor, --.

At Column 214, Line 3, "lenalidomide." should be -- lenalidomide, --.

At Column 214, Line 33, "MCl-r inhibitor," should be -- MCl-1 inhibitor, --.

At Column 214, Line 63, "BC1-2 inhibitor," should be -- BCl-2 inhibitor, --.

At Column 215, Line 28, "BC1-2 inhibitor," should be -- BCl-2 inhibitor, --.

At Column 215, Line 63, "BC1-2 inhibitor," should be -- BCl-2 inhibitor, --.

At Column 216, Line 29, "BC1-2 inhibitor," should be -- BCl-2 inhibitor, --.

At Column 216, Line 63, "BC1-2 inhibitor," should be -- BCl-2 inhibitor, --.

At Column 217, Line 29, "BC1-2 inhibitor," should be -- BCl-2 inhibitor, --.

At Column 217, Line 63, "BC1-2 inhibitor," should be -- BCl-2 inhibitor, --.

At Column 221, Line 36, "(1° F., s)." should be -- (1 F, s). --.

At Column 221, Line 57, "(1° F., s)." should be -- (1 F, s). --.

At Column 222, Line 14, "(L6 mL)" should be -- (1.6 mL) --.

At Column 222, Line 62, "DMSO-de)" should be -- DMSO-$d_6$) --.

At Column 222, Line 62, "(hr s, 1H)," should be -- (br s, 1H), --.

At Column 222, Line 65, "(hr t, J=5.1 Hz, 4H)." should be -- (br t, J=5.1 Hz, 4H). --.

At Column 245, Line 30, "THE" should be -- THF --.

At Column 245, Line 41, "(hr. s, 2H)," should be -- (br. s, 2H), --.

At Column 245, Line 48, "THE" should be -- THF --.

At Column 246, Line 9, "in z" should be -- m/z --.

At Column 246, Line 21, "TEA" should be -- TFA --.

At Column 246, Line 30, "(TEA" should be -- (TFA --.

At Column 246, Line 62, "(hr. s, 1H)," should be -- (br. s, 1H), --.

At Column 246, Line 64, "0.7=2.1" should be -- J=2.1 --.

At Columns 247 & 248, in TABLE 2, under "Name", Lines 12-13, "[1,2]thiazolo[2,3-b]pyridin-3-yl)-" should be -- [1,2]thiazolo[3,4-b]pyridin-3-yl)- --.

At Columns 277 & 278, in TABLE 3-continued, under "Reagent", Lines 21-22, "5-Phos" should be

CERTIFICATE OF CORRECTION (continued)
U.S. Pat. No. 11,905,281 B2

-- S-Phos --.

At Column 297, Line 30, "((3A)-4-(5-chloro" should be -- ((3S)-4-(5-chloro --.

At Column 298, Line 64, "Step 3" should be -- Step 5 --.

At Column 300, Line 29, "((3A)-4-(5-chloro" should be -- ((3S)-4-(5-chloro --.

At Column 305, Lines 13-14, "DMSO-de) 5-113.6" should be -- DMSO-$d_6$) δ-113.6 --.

At Column 305, Line 28, "CDCl₆)" should be -- CDCl₃) --.

At Column 305, Line 48, "0.7=0.7," should be -- J=0.7, --.

At Column 305, Line 51, "0.7=7.1 Hz," should be -- J=7.1 Hz, --.

At Column 306, Line 26, "(5)-1-(3-methylpiperazin" should be -- (S)-1-(3-methylpiperazin --.

At Column 306, Line 62, "(A)-tert-Butyl" should be -- (S)-tert-Butyl --.

At Column 306, Line 64, "(S)-1-boc-2-methy 1-piperazine" should be -- (S)-1-boc-2-methyl-piperazine --.

At Column 307, Line 5, "(3/)," should be -- (3x), --.

At Column 307, Line 13, "2113" should be -- 277.3 --.

At Column 307, Line 14, "(A)-1-(3-Methylpiperazin" should be -- (S)-1-(3-Methylpiperazin --.

At Column 307, Line 17, "TEA" should be -- TFA --.

At Column 307, Line 30, "TEA" should be -- TFA --.

At Column 308, Line 19, "BBn" should be -- BBr₃ --.

At Column 308, Line 34, "(hr. d, J=15.1 Hz, 1H)" should be -- (br. d., J=15.1 Hz, 1H) --.

At Column 311, Line 63, "acryloyo" should be -- acryloyl --.

At Column 313, Line 40, "(A)-4-(4-Acryloyl" should be -- (S)-4-(4-Acryloyl --.

At Column 313, Lines 44-45, "(S)-4-iV-boc-2-methyl" should be -- (S)-4-N-boc-2-methyl --.

At Column 313, Line 56, "(5)-tert-butyl" should be -- (S)-tert-butyl --.

At Column 313, Lines 61-62, "(5)-7-bromo-6-chloro" should be -- (S)-7-bromo-6-chloro --.

CERTIFICATE OF CORRECTION (continued)
U.S. Pat. No. 11,905,281 B2

At Column 313, Line 67, "(5)-7-bromo-" should be -- (S)-7-bromo- --.

At Column 314, Line 12, "(hr s, 1H)," should be -- (br s, 1H), --.

At Column 314, Line 13, "(hr s, 1H)," should be -- (br s, 1H), --.

At Column 314, Line 17, "(hr s, 3H)." should be -- (br s, 3H). --.

At Column 314, Line 20, "(A)-4-(4-Acryloyl" should be -- (S)-4-(4-Acryloyl --.

At Column 314, Lines 34-35, "(5)-4-(4-acryloyl" should be -- (S)-4-(4-acryloyl --.

At Column 314, Line 40, "((2A)-2-methyl" should be -- ((2S)-2-methyl --.

At Column 314, Lines 55-56, "4-((25)-2-methyl" should be -- 4-((2S)-2-methyl --.

At Column 314, Line 58, "0.1=" should be -- J= --.

At Column 314, Line 60, "0.7=2.3" should be -- J=2.3 --.

At Column 329, Line 31, "in z" should be -- m/z --.

At Column 330, Line 26, "THE," should be -- THF, --.

At Column 330, Line 30, "THE" should be -- THF --.

At Column 330, Lines 46-47, "(Intermediate 1.25 mg," should be -- (Intermediate I, 25 mg, --.

At Column 342, Line 49, "(1H, hr s)" should be -- (1H, br s) --.

At Column 342, Line 61, "(1H, hr s)" should be -- (1H, br s) --.

At Column 349, Line 23, "chloro-1N-phenyl" should be -- chloro-N-phenyl --.

At Column 349, Line 61, "5:" should be -- δ: --.

At Column 359, Line 40, "BBr" should be -- $BBr_3$ --.

At Column 360, Line 45, "(hr. s, 1H)," should be -- (br. s, 1H), --.

At Column 360, Line 45, "(hr. s, 1H)," should be -- (br. s, 1H), --.

At Column 361, Line 4, "(hr. s, 1H)," should be -- (br. s, 1H), --.

At Column 361, Line 12, "(hr. s, 1H)," should be -- (br. s, 1H), --.

At Column 361, Line 14, "(hr. s, 1H)," should be -- (br. s, 1H), --.

At Column 361, Line 14, "(hr. s, 1H)," should be -- (br. s, 1H), --.

At Column 362, Line 1, "(hr. s, 2H)," should be -- (br. s, 2H), --.

At Column 366, Line 53, "DMSO-A)" should be -- DMSO-$d_6$) --.

At Column 366, Line 53, "(hr. s, 1H)," should be -- (br. s, 1H), --.

At Column 368, Line 1, "DMSO-d$^6$)" should be -- DMSO-$d_6$) --.

At Column 368, Line 61, "methyl-2h-indazol" should be -- methyl-2H-indazol --.

At Column 376, Line 55, "amine, in z" should be -- amine. m/z --.

At Column 378, Line 52, "TEA" should be -- TFA --.

At Column 378, Line 55, "SEC" should be -- SFC --.

At Column 378, Line 62, "(t, J=1F Hz, 1H)," should be -- (t, J=7.6 Hz, 1H), --.

At Column 383, Line 18, "4.30 Hz)," should be -- 4.30 Hz). --.

At Column 383, Lines 21-22, "A-Chlorosuccinimide" should be -- N-Chlorosuccinimide --.

At Column 383, Line 26, "A-Chlorosuccinimide" should be -- N-Chlorosuccinimide --.

At Column 383, Line 29, "Additional/V-chlorosuccinimide" should be -- Additional N-chlorosuccinimide --.

At Column 385, Lines 7-8, "CHLOROFORM-tit)" should be -- CHLOROFORM-d) --.

At Column 391, Line 64, "TEA" should be -- TFA --.

At Column 391, Line 64, "TEA" should be -- TFA --.

At Column 392, Line 20, "(1H, hr td, J=8.22, 6.65 Hz)" should be -- (1H, br td, J=8.22, 6.65 Hz) --.

At Column 394, Line 61, "THE," should be -- THF, --.

At Column 395, Line 7, "tot-butyl" should be -- tert-butyl --.

At Column 395, Line 15, "0.7=16.82," should be -- J=16.82, --.

At Column 395, Line 16, "0.7=16.82," should be -- J=16.82, --.

At Column 395, Line 16, "0.7=10.56," should be -- J=10.56, --.

At Column 402, Line 28, "(hr s, 1H)," should be -- (br s, 1H), --.

At Column 403, Line 1, "(hr s, 1H)," should be -- (br s, 1H), --.

At Column 403, Line 3, "(hr s, 1H)," should be -- (br s, 1H), --.

At Column 403, Line 7, "(5S)-tert-butyl" should be -- (3S)-tert-butyl --.

At Column 403, Line 28, "(35)-tert-butyl" should be -- (3S)-tert-butyl --.

At Column 403, Line 32, "(hr s, 1H)," should be -- (br s, 1H), --.

At Column 403, Line 32, "(hr s, 1H)," should be -- (br s, 1H), --.

At Column 403, Line 34, "(hr s, 1H)," should be -- (br s, 1H), --.

At Column 403, Line 34, "(hr s, 2H)," should be -- (br s, 2H), --.

At Column 403, Line 37, "(hr s, 1F)." should be -- (br s, 1F). --.

At Column 403, Line 39, "4-((2A)-2-methyl" should be -- 4-((2S)-2-methyl --.

At Column 403, Line 41, "(35)-tert-butyl" should be -- (3S)-tert-butyl --.

At Column 403, Line 61, "((25)-2-methyl" should be -- ((2S)-2-methyl --.

At Column 403, Line 62, "DMSO-4)" should be -- DMSO-$d_6$) --.

At Column 403, Line 63, "(hr s, 1H)," should be -- (br s, 1H), --.

At Column 403, Line 66, "(hr s, 1H)," should be -- (br s, 1H), --.

At Column 404, Line 1, "(hr s, 3H)," should be -- (br s, 3H), --.

At Column 406, Line 50, "(hr s, 2H)," should be -- (br s, 2H), --.

At Column 406, Line 56, "THE" should be -- THF --.

At Column 407, Line 8, "pyrido[2,3-d]yrimidine" should be -- pyrido[2,3-d]pyrimidine --.

At Column 407, Line 11, "THE" should be -- THF --.

At Column 407, Line 11, "THE," should be -- THF, --.

CERTIFICATE OF CORRECTION (continued)
U.S. Pat. No. 11,905,281 B2

At Column 407, Line 22, "(hr s, 1H)," should be -- (br s, 1H), --.

At Column 407, Line 27, "pyrido[2,3-d]yrimidin" should be -- pyrido[2,3-d]pyrimidin --.

At Column 407, Line 38, "(A)-tert-Butyl" should be -- (S)-tert-Butyl --.

At Column 407, Line 45, "(5)-4-N-Boc-2-methyl" should be -- (S)-4-N-Boc-2-methyl --.

At Column 407, Line 61, "(hr t, J=5.7 Hz, 3H)," should be -- (br t, J=5.7 Hz, 3H), --.

At Column 407, Line 65, "(A)-tert-Butyl" should be -- (S)-tert-Butyl --.

At Column 408, Line 32, "0.7=6.6," should be -- J=6.6, --.

At Column 408, Line 36, "((2A)-2-methyl" should be -- ((2S)-2-methyl --.

At Column 408, Line 40, "dihydropyrido[2,3-<7]" should be -- dihydropyrido[2,3-d] --.

At Column 408, Line 56, "3-py ridinyl)-4-((25)-2-methyl" should be -- 3-pyridinyl)-4-((2S)-2-methyl --.

At Column 408, Line 61, "(hr s, 1H)," should be -- (br s, 1H), --.

At Column 410, Line 64, "(hr s, 1H)" should be -- (br s, 1H) --.

At Column 410, Line 65, "(hr s, 1H)." should be -- (br s, 1H). --.

At Column 411, Line 34, "(hr s, 1H)," should be -- (br s, 1H), --.

At Column 411, Line 52, "(A)-tert-Butyl" should be -- (S)-tert-Butyl --.

At Column 411, Line 58, "(<5)-4-N-Boc-2-methyl" should be -- (S)-4-N-Boc-2-methyl --.

At Column 412, Line 3, "2-fluoro-1,2-dihydropyrido[2,3-d]" should be -- 2-oxo-1,2-dihydropyrido[2,3-d] --.

At Column 412, Line 6, "(3A)-tert-Butyl" should be -- (3S)-tert-Butyl --.

At Column 412, Lines 10-11, "2-fluoro-1,2-dihydropyrido[2,3-d]" should be -- 2-oxo-1,2-dihydropyrido[2,3-d] --.

At Column 412, Line 29, "(hr s, 1H)," should be -- (br s, 1H), --.

At Column 412, Lines 32-33, "(hr t, J=14.2 Hz, 1H)," should be -- (br t, J=14.2 Hz, 1H), --.

At Column 412, Line 33, "0.7=12.9" should be -- J=12.9 --.

At Column 412, Line 60, "4-((25)-2-methyl" should be -- 4-((2S)-2-methyl --.

At Column 412, Line 65, "0.7=8.6" should be -- J=8.6 --.

At Column 412, Line 66, "0.7=16.2" should be -- J=16.2 --.

At Column 413, Line 2, "0.7=6.8" should be -- J=6.8 --.

At Column 413, Line 2, "0.7=6.8" should be -- J=6.8 --.

At Column 415, Line 2, "THE" should be -- THF --.

At Column 415, Line 6, "THE" should be -- THF --.

At Column 415, Line 22, "6-fluoropyrido[2,3-</]pyrimidine" should be -- 6-fluoropyrido[2,3-d]pyrimidine --.

At Column 415, Line 35, "step," should be -- step. --.

At Column 415, Line 47, "step, in z" should be -- step. m/z --.

At Column 415, Line 49, "(A)-tert-Butyl" should be -- (S)-tert-Butyl --.

At Column 415, Line 55, "(5)-4-N-Boc-2-methyl" should be -- (S)-4-N-Boc-2-methyl --.

At Column 415, Line 66, "0.7=4.8" should be -- J=4.8 --.

At Column 415, Line 66, "(hr s, 1H)," should be -- (br s, 1H), --.

At Column 415, Line 67, "(hr s, 1H)," should be -- (br s, 1H), --.

At Column 416, Line 5, "(3A)-tert-Butyl" should be -- (3S)-tert-Butyl --.

At Column 416, Line 26, "(35)-tert-butyl" should be -- (3S)-tert-butyl --.

At Column 416, Line 42, "(35)-tert-butyl" should be -- (3S)-tert-butyl --.

At Column 416, Line 57, "4-((25)-2-methyl" should be -- 4-((2S)-2-methyl --.

At Column 418, Line 58, "step, in z" should be -- step. m/z --.

At Column 419, Lines 10-11, "(hr s, 1H)," should be -- (br s, 1H), --.

At Column 419, Line 17, "THE" should be -- THF --.

At Column 419, Line 18, "THE," should be -- THF, --.

CERTIFICATE OF CORRECTION (continued)
U.S. Pat. No. 11,905,281 B2

At Column 419, Line 37, "(A)-tert-Butyl" should be -- (S)-tert-Butyl --.

At Column 419, Line 49, "(5)-4-N-Boc-2-methyl" should be -- (S)-4-N-Boc-2-methyl --.

At Column 419, Line 65, "(hr s, 1H)," should be -- (br s, 1H), --.

At Column 419, Line 65, "0.7=14.1" should be -- J=14.1 --.

At Column 420, Line 3, "(A)-tert-Butyl" should be -- (S)-tert-Butyl --.

At Column 420, Line 7, "(5)-tert-butyl" should be -- (S)-tert-butyl --.

At Column 420, Line 25, "dihydropyrido[2,3-<7]" should be -- dihydropyrido[2,3-d] --.

At Column 420, Line 35, "4-((2A)-2-methyl" should be -- 4-((2S)-2-methyl --.

At Column 420, Line 40, "dihydropyrido[2,3-<7]" should be -- dihydropyrido[2,3-d] --.

At Column 420, Line 57, "((25)-2-methyl" should be -- ((2S)-2-methyl --.

At Column 420, Line 58, "piperazinyl)pyrido[2,3-<7]pyrimidin-2" should be
-- piperazinyl)pyrido[2,3-d]pyrimidin-2 --.

At Column 421, Line 5, "4-((2A)-2-methyl" should be -- 4-((2S)-2-methyl --.

At Column 422, Line 49, "(hr s, 1H)," should be -- (br s, 1H), --.

At Column 422, Line 66, "(hr s, 1H)," should be -- (br s, 1H), --.

At Column 423, Line 4, "pyrido[2,3-</]pyrimidin" should be -- pyrido[2,3-d]pyrimidin --.

At Column 423, Line 16, "(A)-tert-Butyl" should be -- (S)-tert-Butyl --.

At Column 423, Line 31, "dihydropyrido[2,3-<7]" should be -- dihydropyrido[2,3-d] --.

At Column 423, Line 35, "0.7=3.4," should be -- J=3.4, --.

At Column 423, Line 41, "(3A)-tert-Butyl" should be -- (3S)-tert-Butyl --.

At Column 423, Line 64, "(35)-tert-butyl" should be -- (3S)-tert-butyl --.

At Column 424, Line 11, "4-((2A)-2-methyl" should be -- 4-((2S)-2-methyl --.

At Column 424, Line 14, "(35)-tert-butyl" should be -- (3S)-tert-butyl --.

At Column 424, Line 31, "4-((25)-2-methyl" should be -- 4-((2S)-2-methyl --.

CERTIFICATE OF CORRECTION (continued)
U.S. Pat. No. 11,905,281 B2

At Column 424, Line 47, "4-((2A)-2-methyl" should be -- 4-((2S)-2-methyl --.

At Column 425, Line 31, "(A)-tert-Butyl" should be -- (S)-tert-Butyl --.

At Column 425, Line 34, "(5)-tert-butyl" should be -- (S)-tert-butyl --.

At Column 425, Line 59, "0.7=13.9" should be -- J=13.9 --.

At Column 425, Line 65, "4-((2A)-2-methyl" should be -- 4-((2S)-2-methyl --.

At Column 426, Line 16, "((25)-2-methyl" should be -- ((2S)-2-methyl --.

At Column 426, Line 17, "piperazinyl)pyrido[2,3-(7]" should be -- piperazinyl)pyrido[2,3-d] --.

At Column 426, Line 20, "0.7=5.0" should be -- J=5.0 --.

At Column 428, Line 10, "(hr s, 2H)," should be -- (br s, 2H), --.

At Column 428, Line 11, "0.7=7.6" should be -- J=7.6 --.

At Column 428, Line 11, "7=7.6" should be -- J=7.6 --.

At Column 428, Line 15, "THE" should be -- THF --.

At Column 428, Line 49, "(A)-tert-Butyl" should be -- (S)-tert-Butyl --.

At Column 429, Lines 3-4, "(hr s, 1H)," should be -- (br s, 1H), --.

At Column 429, Line 4, "(hr s, 1H)," should be -- (br s, 1H), --.

At Column 429, Line 9, "(A)-tert-Butyl" should be -- (S)-tert-Butyl --.

At Column 429, Line 34, "(hr s, 1H)," should be -- (br s, 1H), --.

At Column 429, Line 35, "(hr s, 1H)," should be -- (br s, 1H), --.

At Column 429, Line 35, "(hr s, 1H)," should be -- (br s, 1H), --.

At Column 429, Line 61, "4-((25)-2-methyl" should be -- 4-((2S)-2-methyl --.

At Column 432, Line 52, "(5)-4-N-Boc-2-methyl" should be -- (S)-4-N-Boc-2-methyl --.

At Column 432, Line 63, "(hr s, 1H)," should be -- (br s, 1H), --.

At Column 432, Line 64, "0.7=13.7" should be -- J=13.7 --.

At Column 433, Line 1, "(A)-tert-Butyl" should be -- (S)-tert-Butyl --.

At Column 433, Line 4, "(5)-tert-butyl" should be -- (S)-tert-butyl --.

At Column 433, Line 56, "4-((25)-2-methyl" should be -- 4-((2S)-2-methyl --.

At Column 435, Line 46, "(hr s, 1H)," should be -- (br s, 1H), --.

At Column 435, Line 46, "(hr s, 1H)," should be -- (br s, 1H), --.

At Column 436, Lines 23-24, "(5)-tert-butyl" should be -- (S)-tert-butyl --.

At Column 436, Line 27, "(hr s, 1H)," should be -- (br s, 1H), --.

At Column 436, Line 30, "0.7=13.3," should be -- J=13.3, --.

At Column 436, Line 30, "0.7=6.4," should be -- J=6.4, --.

At Column 436, Line 33, "(3A)-tert-butyl" should be -- (3S)-tert-butyl --.

At Column 436, Line 36, "(5)-tert-butyl" should be -- (S)-tert-butyl --.

At Column 436, Line 53, "(35)-tert-butyl" should be -- (3S)-tert-butyl --.

At Column 436, Line 57, "DMSO-4)" should be -- DMSO-$d_6$) --.

At Column 436, Line 58, "(hr s, 1H)," should be -- (br s, 1H), --.

At Column 436, Line 60, "(hr s, 1H)," should be -- (br s, 1H), --.

At Column 436, Line 61, "(hr s, 1H)," should be -- (br s, 1H), --.

At Column 436, Line 61, "(hr s, 3H)," should be -- (br s, 3H), --.

At Column 436, Line 62, "0.7=6.8" should be -- J=6.8 --.

At Column 436, Line 63, "(hr s, 1F)." should be -- (br s, 1F). --.

At Column 436, Lines 65-66, "4-((2A)-2-methyl" should be -- 4-((2S)-2-methyl --.

At Column 437, Line 19, "((25)-2-methyl" should be -- ((2S)-2-methyl --.

At Column 437, Line 20, "pyrido[2,3-<7]" should be -- pyrido[2,3-d] --.

At Column 437, Line 22, "(hr s, 1H)," should be -- (br s, 1H), --.

At Column 437, Line 25, "(hr dd," should be -- (br dd, --.

At Column 437, Line 28, "(hr s, 1F)." should be -- (br s, 1F). --.

At Column 439, Line 15, "(hr s, 1H)," should be -- (br s, 1H), --.

At Column 439, Line 16, "(hr dd," should be -- (br dd, --.

At Column 439, Line 39, "(A)-tert-Butyl" should be -- (S)-tert-Butyl --.

At Column 440, Line 1, "(3A)-tert-Butyl" should be -- (3S)-tert-Butyl --.

At Column 440, Line 4, "(5)-tert-butyl" should be -- (S)-tert-butyl --.

At Column 440, Line 22, "(35)-tert-butyl" should be -- (3S)-tert-butyl --.

At Column 440, Lines 25-26, "DMSO-fife)" should be -- DMSO-$d_6$) --.

At Column 440, Line 30, "(hr d," should be -- (br d, --.

At Column 440, Line 36, "4-((25)-2-methyl" should be -- 4-((2S)-2-methyl --.

At Column 440, Line 39, "(35)-tert-butyl" should be -- (3S)-tert-butyl --.

At Column 440, Line 57, "((25)-2-methyl" should be -- ((2S)-2-methyl --.

At Column 440, Lines 57-58, "pyrido[2,3-<7]pyrimidin" should be -- pyrido[2,3-d]pyrimidin --.

At Column 440, Line 61, "(hr dd," should be -- (br dd, --.

At Column 442, Line 52, "Z-BuOH" should be -- t-BuOH --.

At Column 442, Line 64, "THE" should be -- THF --.

At Column 443, Line 5, "(hr s, 1H)," should be -- (br s, 1H), --.

At Column 443, Line 6, "(hr s, 1H)," should be -- (br s, 1H), --.

At Column 443, Line 24, "THE," should be -- THF, --.

At Column 443, Line 27, "THE" should be -- THF --.

At Column 443, Line 37, "(hr s, 1H)," should be -- (br s, 1H), --.

At Column 443, Lines 60-61, "((25)-2-methyl" should be -- ((2S)-2-methyl --.

At Column 443, Line 65, "(hr dt," should be -- (br dt, --.

At Column 444, Line 6, "4-((2A)-2-methyl" should be -- 4-((2S)-2-methyl --.

At Column 445, Line 7, "CHLOROFORM-<7)" should be -- CHLOROFORM-d) --.

At Column 445, Line 7, "(hr s, 1H)," should be -- (br s, 1H), --.

At Column 445, Line 13, "4-((2A)-2-methyl" should be -- 4-((2S)-2-methyl --.

At Column 445, Line 23, "(5)-1-(3-methylpiperazin" should be -- (S)-1-(3-methylpiperazin --.

At Column 445, Line 33, "((25)-2-methyl" should be -- ((2S)-2-methyl --.

At Column 445, Line 35, "0.7=7.7," should be -- J=7.7, --.

At Column 445, Line 37, "0.7=7.1," should be -- J=7.1, --.

At Column 445, Line 38, "0.7=16.6" should be -- J=16.6 --.

At Column 448, Line 3, "0.7=7.9," should be -- J=7.9, --.

At Column 448, Line 3, "0.7=6.8" should be -- J=6.8 --.

At Column 448, Line 33, "0.7=6.8," should be -- J=6.8, --.

At Column 448, Line 53, "(35)-4-(7-(2-fluoro-6-hydroxyphenyl)" should be -- (3S)-4-(7-(2-fluoro-6-hydroxyphenyl) --.

At Column 448, Line 61, "(35)-4-(7-(2-fluoro-6-hydroxyphenyl)" should be -- (3S)-4-(7-(2-fluoro-6-hydroxyphenyl) --.

At Column 449, Line 10, "4-((25)-2-methyl" should be -- 4-((2S)-2-methyl --.

At Column 451, Line 17, "(hr s, 1H)," should be -- (br s, 1H), --.

At Column 451, Line 17, "(hr s, 1H)," should be -- (br s, 1H), --.

At Column 451, Line 22, "THE," should be -- THF, --.

At Column 451, Line 36, "(hr s, 1H)," should be -- (br s, 1H), --.

At Column 451, Line 51, "(A)-tert-Butyl" should be -- (S)-tert-Butyl --.

At Column 451, Line 57, "(5)-4-N-Boc-2-methyl" should be -- (S)-4-N-Boc-2-methyl --.

At Column 452, Line 7, "(A)-4-(6-chloro" should be -- (S)-4-(6-chloro --.

At Column 452, Line 36, "((2A)-2-methyl" should be -- ((2S)-2-methyl --.

At Column 452, Line 40, "(5)-4-(6-chloro" should be -- (S)-4-(6-chloro --.

At Column 482, Line 39, "(2, 1H)," should be -- (s, 1H), --.

At Column 485, Line 19, "2.4-2.64" should be -- 2.49-2.64 --.

At Column 487, Line 22, "(m, 1 H," should be -- (m, 1 H), --.

At Column 487, Line 24, "(m, 1 H," should be -- (m, 1 H), --.

At Column 490, Line 57, "(7.27" should be -- 7.27 --.

At Column 491, Line 49, "1 H," should be -- (1 H, --.

At Column 501, Line 35, "TV-terminal" should be -- N-terminal --.

At Column 504, Line 38, "TV-terminal" should be -- N-terminal --.

In the Claims

At Column 509, Line 8, "transforming" should be -- (f) transforming --.

At Column 509, Line 19, "claim 3." should be -- claim 2. --.